US012760028B2

(12) United States Patent
Yue et al.

(10) Patent No.: US 12,760,028 B2
(45) Date of Patent: Oct. 13, 2026

(54) ORGANIC COMPOUND, ORGANIC ELECTROLUMINESCENT DEVICE AND ELECTRONIC APPARATUS THEREOF

(71) Applicant: SHAANXI LIGHTE OPTOELECTRONICS MATERIAL CO., LTD., Xi'an (CN)

(72) Inventors: Na Yue, Xi'an (CN); Zhengshen Hua, Xi'an (CN); Youngkook Kim, Xi'an (CN); Yingwen Li, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 958 days.

(21) Appl. No.: 18/003,918

(22) PCT Filed: Mar. 22, 2022

(86) PCT No.: PCT/CN2022/082341

§ 371 (c)(1),
(2) Date: Dec. 30, 2022

(87) PCT Pub. No.: WO2022/218112

PCT Pub. Date: Oct. 20, 2022

(65) Prior Publication Data

US 2023/0301184 A1 Sep. 21, 2023

(30) Foreign Application Priority Data

Apr. 16, 2021 (CN) ........................ 202110414338.1

(51) Int. Cl.
*C07D 487/06* (2006.01)
*C07D 519/00* (2006.01)
(Continued)

(52) U.S. Cl.
CPC ......... *C07D 487/06* (2013.01); *C07D 519/00* (2013.01); *C09K 11/06* (2013.01);
(Continued)

(58) Field of Classification Search
CPC .. C07D 487/06; C07D 519/00; C07D 471/04; C07D 487/10; C07D 487/16;
(Continued)

(56) References Cited

U.S. PATENT DOCUMENTS

2020/0006668 A1 1/2020 Sun et al.
2021/0043848 A1 2/2021 Kim et al.

FOREIGN PATENT DOCUMENTS

CN 108727398 A 11/2018
CN 111868210 A 10/2020
(Continued)

OTHER PUBLICATIONS

Machine translation of WO 2020/262853 A1. (Year: 2020).*
(Continued)

*Primary Examiner* — Alan D Diamond
(74) *Attorney, Agent, or Firm* — ANOVA LAW GROUP, PLLC

(57) ABSTRACT

The present application relates to an organic compound, and there are electron transport and injection groups and a conjugated fused heteroaromatic ring in a structure of the organic compound. The organic compound can be used in a functional layer of an organic light-emitting device (OLED). When used in an OLED, the organic compound of the present application can improve the light-emitting efficiency and service life of the OLED.

16 Claims, 1 Drawing Sheet

(51) Int. Cl.
*C09K 11/06* (2006.01)
*H10K 50/11* (2023.01)
*H10K 85/00* (2023.01)
*H10K 85/60* (2023.01)

(52) U.S. Cl.
CPC ........... *H10K 85/00* (2023.02); *H10K 85/615* (2023.02); *H10K 85/624* (2023.02); *H10K 85/626* (2023.02); *H10K 85/654* (2023.02); *H10K 85/657* (2023.02); *H10K 85/6572* (2023.02); *H10K 85/6574* (2023.02); *H10K 85/6576* (2023.02); *C09K 2211/1018* (2013.01); *H10K 50/11* (2023.02)

(58) Field of Classification Search
CPC .. C07D 491/16; C07D 493/16; C07D 495/16; C09K 11/06; C09K 2211/1018; H10K 85/00; H10K 85/615; H10K 85/624; H10K 85/626; H10K 85/654; H10K 85/657; H10K 85/6572; H10K 85/6574; H10K 85/6576; H10K 50/11; H10K 50/16
See application file for complete search history.

(56) References Cited

FOREIGN PATENT DOCUMENTS

| | | | | | |
|---|---|---|---|---|---|
| CN | 114085228 | A | * | 2/2022 | ........... C07D 513/16 |
| KR | 20210023223 | A | | 3/2021 | |
| WO | 2020000827 | A | | 1/2020 | |
| WO | 2020262853 | A | | 12/2020 | |

OTHER PUBLICATIONS

The World Intellectual Property Organization (WIPO) International Search Report for PCT/CN2022/082341 Jun. 27, 2022 4 Pages (with translation).

The China National Intellectual Property Administration (CNIPA) Notice of the first review comments for CN Application No. 2021104143381 Mar. 23, 2023 8 Pages (Including English translation).

* cited by examiner

ORGANIC COMPOUND, ORGANIC ELECTROLUMINESCENT DEVICE AND ELECTRONIC APPARATUS THEREOF

CROSS REFERENCE TO RELATED APPLICATION

The present application is a national phase entry under 35 U.S.C § 371 of International Application No. PCT/CN2022/082341, filed on Mar. 22, 2022, which claims priority to Chinese Patent Application CN202110414338.1 filed on Apr. 16, 2021, all of which is incorporated into the present application by reference in their entirety.

TECHNICAL FIELD

The present application belongs to the technical field of organic materials, and specifically provides an organic compound, and an organic electroluminescent device (OLED) and electronic apparatus thereof.

BACKGROUND

OLEDs are thin-film devices manufactured from organic optoelectronic functional materials, and can emit light under the excitation of an electric field. Currently, OLEDs (organic electroluminescent devices) have been widely used in mobile phones, computers, lighting, and other fields due to their advantages such as high luminance, fast response, and wide adaptability.

In addition to an electrode material film layer, an OLED needs to have different organic functional materials. π-bond or anti-π-bond orbitals of organic functional materials lead to shifted valences and conductivity, and the overlap of the orbitals leads to a highest occupied molecular orbital (HOMO) and a lowest unoccupied molecular orbital (LUMO), which achieves charge transfer through intermolecular transition.

In order to improve the luminance, efficiency, and life span of OLEDs, a multi-layer structure is generally adopted, including a hole injection layer (HIL), a hole transport layer (HTL), a light-emitting layer, and an electron transport layer (ETL). These organic layers can improve the injection efficiency of carriers (holes and electrons) at an interface between the layers, and balance the ability to transport carriers between the layers, thereby improving the luminance and efficiency of a device.

SUMMARY

The present application is intended to provide an organic compound, and an OLED and electronic apparatus thereof. When the organic compound of the present application is used as an ETL and/or light-emitting layer material for an electronic device, the light-emitting efficiency and service life of the electronic device can be improved.

In a first aspect of the present application, an organic compound with a structure shown in formula 1 is provided:

formula 1

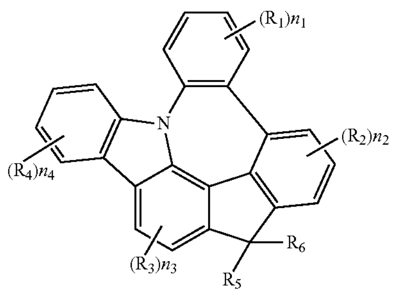

wherein $R_5$ and $R_6$ are the same or different, and are each independently selected from the group consisting of alkyl with 1 to 6 carbon atoms, haloalkyl with 1 to 6 carbon atoms, cycloalkyl with 3 to 10 carbon atoms, substituted or unsubstituted aryl with 6 to 15 carbon atoms, and substituted or unsubstituted heteroaryl with 3 to 12 carbon atoms; or $R_5$ and $R_6$ are optionally connected to each other to form a 5- to 18-membered aliphatic ring or a substituted or unsubstituted 5- to 18-membered aromatic ring together with carbon atom to which they are jointly connected, and a substituent on the 5- to 18-membered aromatic ring is independently selected from the group consisting of deuterium, halogen, and alkyl with 1 to 6 carbon atoms;

$R_1$, $R_2$, $R_3$, and $R_4$ are the same or different, and are each independently selected from the group consisting of a group shown in formula 2, aryl with 6 to 20 carbon atoms, heteroaryl with 3 to 20 carbon atoms, hydrogen, deuterium, halogen, cyano, alkyl with 1 to 10 carbon atoms, haloalkyl with 1 to 10 carbon atoms, deuterated alkyl with 1 to 10 carbon atoms, alkoxy with 1 to 10 carbon atoms, cycloalkyl with 3 to 10 carbon atoms, and trialkylsilyl with 3 to 12 carbon atoms, and any one or two of $R_1$, $R_2$, $R_3$, and $R_4$ are the group shown in formula 2, formula 2

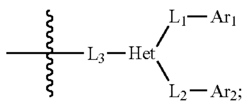

wherein Het is electron-deficient 6- to 18-membered nitrogen-containing heteroarylene;

$L_1$, $L_2$, and $L_3$ are each independently selected from the group consisting of a single bond, substituted or unsubstituted arylene with 6 to 30 carbon atoms, and substituted or unsubstituted heteroarylene with 3 to 30 carbon atoms;

$Ar_1$ and $Ar_2$ are the same or different, and are each independently selected from the group consisting of hydrogen, deuterium, substituted or unsubstituted aryl with 6 to 30 carbon atoms, and substituted or unsubstituted heteroaryl with 3 to 30 carbon atoms;

$n_1$ and $n_4$ are the same or different, represent a number of $R_1$ and a number of $R_4$ respectively, and are each independently selected from the group consisting of 1, 2, 3, and 4; $n_3$ represents a number of $R_3$ and is selected from the group consisting of 1 and 2; and $n_2$ represents a number of $R_2$ and is selected from the group consisting of 1, 2, and 3;

substituents in $L_1$, $L_2$, $L_3$, $Ar_1$, $Ar_2$, $R_5$, and $R_6$ are the same or different, and are each independently selected from the group consisting of deuterium, cyano, halogen, alkyl with 1 to 10 carbon atoms, haloalkyl with 1 to 10 carbon atoms, deuterated alkyl with 1 to 10 carbon atoms, cycloalkyl with 3 to 10 carbon atoms, aryl with 6 to 20 carbon atoms, heteroaryl with 3 to 20 carbon atoms, alkoxy with 1 to 10 carbon atoms, alkylthio with 1 to 10 carbon atoms, trialkylsilyl with 1 to 12 carbon atoms, arylsilyl with 6 to 18 carbon atoms, aryloxy with 6 to 20 carbon atoms, and arylthio with 6 to 20 carbon atoms; and optionally, in $Ar_1$ and $Ar_2$, any two adjacent substituents connected to each other to form a substituted or unsubstituted 5- to 15-membered ring, and a substituent on the 5- to 15-membered ring is independently selected from the group consisting of deuterium, cyano, halogen, alkyl with 1 to 4 carbon atoms, haloalkyl with 1 to 4 carbon atoms, deuterated alkyl with 1 to 4 carbon atoms, trialkylsilyl with 3 to 6 carbon atoms, aryl with 6 to 12 carbon atoms, and heteroaryl with 5 to 12 carbon atoms.

In a second aspect of the present application, an OLED is provided, including: an anode and a cathode that are arranged oppositely, and a functional layer arranged between the anode and the cathode, wherein the functional layer includes the organic compound provided in the first aspect of the present application.

Preferably, the functional layer may include an ETL and/or a light-emitting layer, and the ETL and/or the light-emitting layer may include the organic compound.

In a third aspect of the present application, an electronic apparatus is provided, which includes the OLED in the second aspect of the present application.

The organic compound of the present application has a fused-ring parent nucleus of carbazolo-fluorene, and a nitrogen-containing electron transport group is linked to the parent nucleus. The parent nucleus structure has a large conjugated system, and the electron density distribution of the system is conducive to improving the hole mobility. Carbon atoms of a fluorene ring on the parent nucleus have two substituents, which can adjust a spatial structure of the parent nucleus, effectively avoid the stacking of molecules, and improve the stability of film formation. Electron-deficient nitrogen-containing groups with high electron mobility are used as electron transport and injection groups, and are linked to a benzene ring of the parent nucleus through a conjugated single bond, such that the dipole moment on both sides of the organic compound molecule is increased and a triplet-state energy level is increased, thereby improving the stability of carrier migration. When used as a host material for an ETL and/or a light-emitting layer of an OLED, the organic compound of the present application can effectively improve the service life and light-emitting efficiency of the OLED.

Other features and advantages of the present application will be described in detail in the following DETAILED DESCRIPTION section.

BRIEF DESCRIPTION OF THE DRAWINGS

The accompanying drawings are provided for further understanding the present application, and constitute a part of the specification. The accompanying drawings and the following specific embodiments are intended to explain the present application, but do not limit the present application. In the accompanying drawings.

REFERENCE NUMERALS

Figure 1:
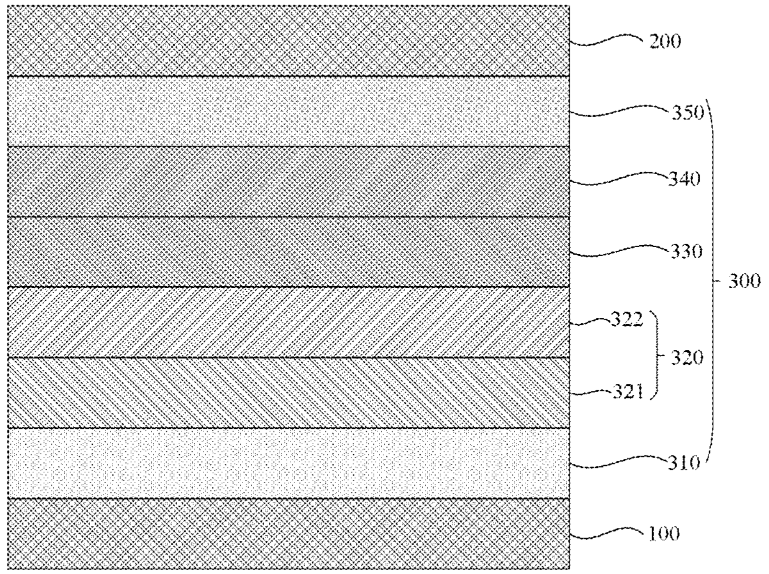
FIG. 1 is a schematic structural diagram of an OLED according to an embodiment of the present application.

| | | | |
|---|---|---|---|
| 100 anode; | 200 cathode; | 300 functional layer; | 310 HIL; |
| 320 HTL; | 321 first HTL; | 322 hole adjustment layer; | 330 light-emitting layer; |
| 340 ETL; | 350 electron injection layer (EIL); and | 400 electronic apparatus. | |

DETAILED DESCRIPTION

The specific embodiments of the present application are described in detail below with reference to the accompanying drawings. It should be understood that the specific embodiments described herein are merely intended to illustrate and explain the present application rather than to limit the present application.

The terms "a" and "the" are used to indicate that there are one or more elements, components, and the like. The terms "include", "comprise" and "having" are used to indicate open-ended inclusion, which means that there may be additional elements, components, and the like in addition to the listed elements, components, and the like.

In a first aspect of the present application, an organic compound with a structure shown in formula 1 is provided:

formula 1

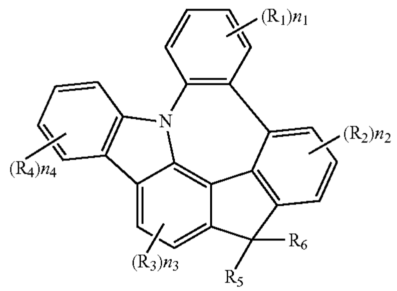

wherein $R_5$ and $R_6$ are the same or different, and are each independently selected from the group consisting of alkyl with 1 to 6 carbon atoms, haloalkyl with 1 to 6 carbon atoms, cycloalkyl with 3 to 10 carbon atoms, substituted or unsubstituted aryl with 6 to 15 carbon atoms, and substituted or unsubstituted heteroaryl with 3 to 12 carbon atoms; or $R_5$ and $R_6$ are optionally connected to each other to form a 5- to 18-membered aliphatic ring or a substituted or unsubstituted 5- to 18-membered aromatic ring together with carbon atom to which they are jointly connected, and a substituent on the 5- to 18-membered aromatic ring is independently selected from the group consisting of deuterium, halogen, and alkyl with 1 to 6 carbon atoms;

$R_1$, $R_2$, $R_3$, and $R_4$ are the same or different, and are each independently selected from the group consisting of a group shown in formula 2, aryl with 6 to 20 carbon atoms, heteroaryl with 3 to 20 carbon atoms, hydrogen, deuterium, halogen, cyano, alkyl with 1 to 10 carbon atoms, haloalkyl with 1 to 10 carbon atoms, deuterated alkyl with 1 to 10 carbon atoms, alkoxy with 1 to 10 carbon atoms, cycloalkyl with 3 to 10 carbon atoms, and trialkylsilyl with 3 to 12 carbon atoms, and any one or two of $R_1$, $R_2$, $R_3$, and $R_4$ are the group shown in formula 2, formula 2

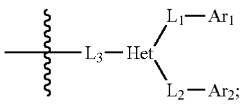

wherein Het is electron-deficient 6- to 18-membered nitrogen-containing heteroarylene;

$L_1$, $L_2$, and $L_3$ are each independently selected from the group consisting of a single bond, substituted or unsubstituted arylene with 6 to 30 carbon atoms, and substituted or unsubstituted heteroarylene with 3 to 30 carbon atoms;

$Ar_1$ and $Ar_2$ are the same or different, and are each independently selected from the group consisting of hydrogen, deuterium, substituted or unsubstituted aryl with 6 to 30 carbon atoms, and substituted or unsubstituted heteroaryl with 3 to 30 carbon atoms;

$n_1$ and $n_4$ are the same or different, represent a number of $R_1$ and a number of $R_4$ respectively, and are each independently selected from the group consisting of 1, 2, 3, and 4; $n_3$ represents a number of $R_3$ and is selected from the group consisting of 1 and 2; and $n_2$ represents a number of $R_2$ and is selected from the group consisting of 1, 2, and 3;

substituents in $L_1$, $L_2$, $L_3$, $Ar_1$, $Ar_2$, $R_5$ and $R_6$ are the same or different, and are each independently selected from the group consisting of deuterium, cyano, halogen, alkyl with 1 to 10 carbon atoms, haloalkyl with 1 to 10 carbon atoms, deuterated alkyl with 1 to 10 carbon atoms, cycloalkyl with 3 to 10 carbon atoms, aryl with 6 to 20 carbon atoms, heteroaryl with 3 to 20 carbon atoms, alkoxy with 1 to 10 carbon atoms, alkylthio with 1 to 10 carbon atoms, trialkylsilyl with 1 to 12 carbon atoms, arylsilyl with 6 to 18 carbon atoms, aryloxy with 6 to 20 carbon atoms, and arylthio with 6 to 20 carbon atoms; and optionally, in $Ar_1$ and $Ar_2$, any two adjacent substituents connected to each other to form a substituted or unsubstituted 5- to 15-membered ring, and a substituent on the 5- to 15-membered ring is independently selected from the group consisting of deuterium, cyano, halogen, alkyl with 1 to 4 carbon atoms, haloalkyl with 1 to 4 carbon atoms, deuterated alkyl with 1 to 4 carbon atoms, trialkylsilyl with 3 to 6 carbon atoms, aryl with 6 to 12 carbon atoms, and heteroaryl with 5 to 12 carbon atoms.

The organic compound of the present application has a fused ring structure of carbazolo-fluorene, and thus a large rigid planar structure can be formed, which can effectively improve the hole mobility of a material; and a structure in which there are double substituents at position 9 of fluorene can effectively avoid the stacking of compounds and improve the film formation stability and thermal stability, thereby effectively improving the service life of the OLEDs. Electron-deficient nitrogen-containing heteroaryl is linked to the fused ring structure, which can greatly improve the ability of a material to attract electrons and improve the electron mobility. In addition, the electron and hole transport ability can be further adjusted by adjusting substituents in the nitrogen-containing heteroaryl. When used as a host material for an ETL or a light-emitting layer of an OLED, the organic compound of the present application can improve the light-emitting efficiency and service life of the OLED.

The description manners used in this application such as " . . . is(are) each independently" "each of . . . is independently selected from" and " . . . each is(are) independently selected from the group consisting of" can be used interchangeably, and should be understood in a broad sense, which can mean that, in different groups, specific options expressed by the same symbols do not affect each other, or in the same group, specific options expressed by the same symbols do not affect each other. For example,

Q-1

"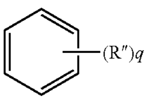

Q-2

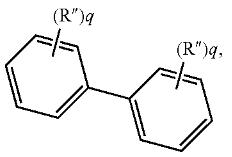

wherein q is independently 0, 1, 2, or 3 and each of substituents R" is independently selected from hydrogen, deuterium, fluorine, and chlorine" means that, in formula Q-1, there are q substituents R" on the benzene ring, the substituents R" can be the same or different, and options for each substituent R" do not affect each other; and in formula Q-2, there are q substituents R" on each benzene ring of the biphenyl, the numbers q of substituents R" on the two benzene rings can be the same or different, the substituents R" can be the same or different, and options for each substituent R" do not affect each other.

In the present application, the term "substituted or unsubstituted" means that a functional group after the term may have or may not have a substituent (hereinafter, for ease of description, substituents are collectively referred to as Rc). For example, the "substituted or unsubstituted aryl" refers to an aryl having one or more substituent Rc or a non-substituent aryl. For example, the substituents Rc are each selected from the group consisting of deuterium, cyano, halogen, alkyl with 1 to 10 carbon atoms, haloalkyl with 1 to 10 carbon atoms, deuterated alkyl with 1 to 10 carbon atoms, cycloalkyl with 3 to 10 carbon atoms, aryl with 6 to 20 carbon atoms, heteroaryl with 3 to 20 carbon atoms, alkoxy with 1 to 10 carbon atoms, alkylthio with 1 to 10 carbon atoms, trialkylsilyl with 1 to 12 carbon atoms, arylsilyl with 6 to 18 carbon atoms, aryloxy with 6 to 20 carbon atoms, and arylthio with 6 to 20 carbon atoms. A substituted functional group may have one or more of the above-mentioned substituents Rc, wherein when two substituents Rc are attached to the same atom, these two substituents Rc exist independently or connected to form a ring; and when there are two adjacent substituents Rc on the group, the two adjacent substituents Rc exist independently or form a fused ring with the group. When two adjacent substituents Rc are attached to the same atom, the two adjacent substituents Rc can exist independently or form a spiro-ring with the group to which they are jointly connected.

In the present application, the number of carbon atoms in a substituted or unsubstituted functional group refers to the number of all carbon atoms. For example, if $Ar_1$ is substituted aryl with 20 carbon atoms, the number of all carbon atoms in the aryl and substituents thereon is 20.

In the present application, the number of carbon atoms in each of $L_1$, $L_2$, $L_3$, $Ar_1$, $Ar_2$, $R_1$, $R_2$, $R_3$, $R_4$, $R_5$, and $R_6$ refers to the number of all carbon atoms. For example, if $L_1$ is substituted arylene with 12 carbon atoms, the number of carbon atoms in the arylene and substituents thereon is 12. For example, if $Ar_1$ is

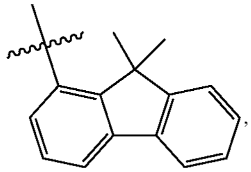 [SMILES: *c1cccc2c1C(C)(C)c1ccccc1-2], the number of carbon atoms in $Ar_1$ is 15; and if $L_1$ is

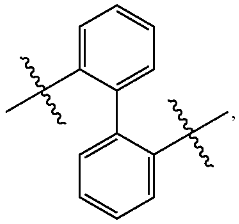 [SMILES: *c1ccccc1-c1ccccc1*], the number of carbon atoms in $L_1$ is 12.

In the present application, the case of consecutively naming with a prefix means that substituents are listed in a writing order. For example, aryloxy indicates alkoxy substituted by aryl.

In the present application, the aryl refers to any functional group or substituent derived from an aromatic carbocyclic ring. The aryl may refer to a monocyclic aryl group or a polycyclic aryl group. In other words, the aryl may refer a monocyclic aryl group, a fused-ring aryl group, two or more monocyclic aryl groups that are conjugated through carbon-carbon bonds, a monocyclic aryl group and a fused-ring aryl group that are conjugated through carbon-carbon bonds, and two or more fused-ring aryl groups that are conjugated through carbon-carbon bonds. The fused-ring aryl group refers to a ring system of two or more rings in which two adjacent rings share two carbon atoms, wherein for example, at least one of the rings is aromatic and the remaining rings may be cycloalkyl, cycloalkenyl, or aryl. Examples of the aryl in the present application may include, but are not limited to, phenyl, naphthyl, anthracenyl, phenanthryl, biphenyl, terphenyl, tetraphenyl, pentaphenyl, benzo[9,10]phenanthryl, pyrenyl, benzofluoranthenyl, chrysenyl, pyrylo, fluorenyl, triphenylene, tetraphenyl, and triphenylenyl. In the present application, the fused aryl ring refers to a polyaromatic ring formed by two or more aromatic or heteroaromatic rings that share ring edges, such as naphthalene, anthracene, phenanthrene, and pyrene.

In the present application, the fluorenyl may be substituted, and two substituents are connected to form a spiro-ring structure. In the case where the fluorenyl is substituted, the substituted fluorenyl may be, but is not limited to,

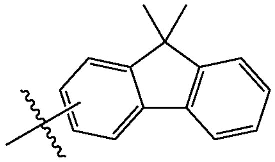

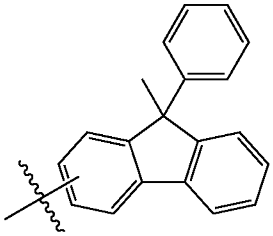

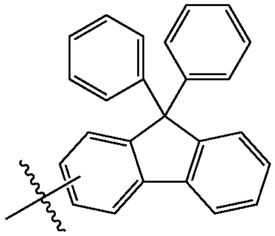

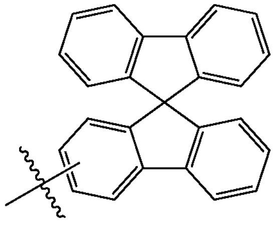

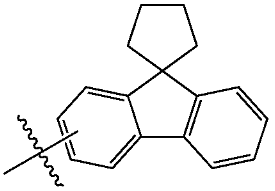

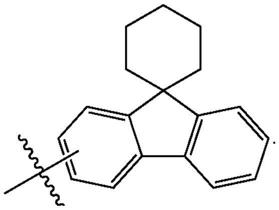.

In the present application, the substituted aryl refers to aryl in which one or more hydrogen atoms are substituted by groups such as deuterium, halogen, cyano, aryl, heteroaryl, alkylsilyl, arylsilyl, alkyl, haloalkyl, cycloalkyl, alkoxy, and alkylthio. It should be understood that the number of carbon atoms in the substituted aryl refers to the total number of carbon atoms in the aryl and substituents thereon. For example, in substituted aryl with 18 carbon atoms, there are a total of 18 carbon atoms in the aryl and substituents thereon.

In the present application, examples of aryl as a substituent may include, but are not limited to, phenyl, naphthyl, anthracenyl, phenanthryl, biphenyl, terphenyl, fluorenyl, dimethylfluorenyl, pyrenyl, and pyrylo.

In some embodiments, the aryl may be substituted or unsubstituted aryl with 6 to 30 carbon atoms; in some embodiments, the aryl may be substituted or unsubstituted aryl with 6 to 25 carbon atoms; in some embodiments, the aryl may be substituted or unsubstituted aryl with 6 to 20 carbon atoms; in some embodiments, the aryl may be substituted or unsubstituted aryl with 6 to 18 carbon atoms; in some embodiments, the aryl may be substituted or unsubstituted aryl with 6 to 15 carbon atoms; in some embodiments, the aryl may be substituted or unsubstituted aryl with 6 to 13 carbon atoms; and in some embodiments, the aryl may be substituted or unsubstituted aryl with 6 to 12 carbon atoms. In the present application, there can be 6, 10, 12, 13, 14, 15, 16, 18, 20, 24, 25, or 30 carbon atoms in the substituted or unsubstituted aryl, and there can also be any other number of carbon atoms in the substituted or unsubstituted aryl, which will not be listed here. In the present application, the biphenyl can be construed as phenyl-substituted aryl, and can also be construed as unsubstituted aryl.

In the present application, the arylene may be a divalent group, which is applicable to the above-mentioned description about the aryl.

In the present application, the heteroaryl refers to a monocyclic or polycyclic system with 1, 2, 3, 4, 5, 6, or 7 heteroatoms independently selected from the group consisting of O, N, P, Si, Se, B, and S, wherein at least one ring system is aromatic. Each ring system in heteroaryl includes a ring formed by 5 to 7 ring atoms and has one or more attachment points linked to the remaining part of the molecule. The heteroaryl can be monocyclic heteroaryl or polycyclic heteroaryl. In other words, the heteroaryl may refer to a single aromatic ring system or multiple aromatic ring systems conjugated through carbon-carbon bonds, wherein each aromatic ring system is an aromatic monocyclic ring or an aromatic fused ring. The fused-ring heteroaryl refers to a ring system of two or more rings in which two adjacent rings share two atoms, wherein for example, at least one of the rings is aromatic and the remaining rings may be cycloalkyl, heterocyclyl, cycloalkenyl, or aryl. For example, the heteroaryl may include, but is not limited to, thienyl, furyl, pyrrolyl, imidazolyl, thiazolyl, oxazolyl, isothiazolyl, oxadiazolyl, triazolyl, pyridyl, bipyridyl, phenanthridinyl, pyrimidinyl, triazinyl, acridinyl, pyridazinyl, pyrazinyl, quinolinyl, quinazolinyl, quinoxalinyl, phenoxazinyl, phthalazinyl, pyridopyrimidinyl, pyridopyrazinyl, pyrazinopyrazinyl, isoquinolinyl, indolyl, carbazolyl, benzoxazolyl, benzimidazolyl, benzocarbazolyl, benzothienyl, dibenzothienyl, thienothienyl, benzofuranyl, phenanthrolinyl, isoxazolyl, thiadiazolyl, benzothiazolyl, phenothiazinyl, silylfluorenyl, dibenzofuranyl, N-arylcarbazolyl (such as N-phenyl carbazolyl), N-heteroarylcarbazolyl (such as N-pyridylcarbazolyl), and N-alkylcarbazolyl (such as N-methylcarbazolyl). The thienyl, furyl, phenanthrolinyl, and the like are heteroaryl with a single aromatic ring system; and the N-arylcarbazolyl, N-heteroarylcarbazolyl, and the like are heteroaryl with multiple ring systems conjugated through carbon-carbon bonds.

In the present application, substituted heteroaryl may refer to heteroaryl in which one or more hydrogen atoms are substituted by groups such as deuterium, halogen, cyano, aryl, heteroaryl, trialkylsilyl, alkyl, cycloalkyl, alkoxy, and alkylthio. It should be understood that the number of carbon atoms in the substituted heteroaryl refers to the total number of carbon atoms in the heteroaryl and substituents thereon. For example, substituted heteroaryl with 14 carbon atoms means that there are a total of 14 carbon atoms in the heteroaryl and substituents thereon.

In the present application, examples of heteroaryl as a substituent may include, but are not limited to, dibenzothienyl, dibenzofuranyl, carbazolyl, N-phenylcarbazolyl, pyridyl, bipyridyl, pyrimidinyl, triazinyl, quinolinyl, isoquinolinyl, quinazolinyl, benzimidazolyl, indolyl, and phenanthrolinyl.

In some embodiments, the substituted or unsubstituted heteroaryl may be substituted or unsubstituted heteroaryl with 3 to 12 carbon atoms; in some embodiments, the substituted or unsubstituted heteroaryl may be substituted or unsubstituted heteroaryl with 3 to 15 carbon atoms; in some embodiments, the substituted or unsubstituted heteroaryl may be substituted or unsubstituted heteroaryl with 5 to 12 carbon atoms; and in some embodiments, the substituted or unsubstituted heteroaryl may be substituted or unsubstituted heteroaryl with 5 to 18 carbon atoms. In substituted or unsubstituted heteroaryl with 3 to 30 carbon atoms, there can be 3, 4, 5, 7, 12, 13, 14, 15, 16, 18, 20, 24, 25, or 30 carbon atoms, and there can also be any other number of carbon atoms, which will not be listed here.

In the present application, electron-deficient nitrogen-containing heteroaryl (heteroarylene) refers to heteroaryl (heteroarylene) with at least one $sp^2$ hybridized nitrogen atom, and lone pair electrons in the nitrogen atom in such heteroaryl do not participate in conjugation, such that the overall electron density is low. The "electron-deficient 6- to 18-membered nitrogen-containing heteroarylene" is a heteroaromatic ring that is formed by 6 to 18 atoms and includes a $sp^2$ hybridized nitrogen atom, which includes, but is not limited to, pyridyl, pyrimidinyl, triazinyl, pyridazinyl, pyrazinyl, benzoxazolyl, benzimidazolyl, benzothiazolyl, quinolinyl, quinazolinyl, quinoxalinyl, pyridopyrimidinyl, pyridopyrazinyl, pyrazinopyrazinyl, isoquinolinyl, benzimidazolyl, benzothiazolyl, and phenanthrolinyl.

In the present application, the heteroarylene may be a divalent or multivalent group, which is applicable to the above-mentioned description about the heteroaryl.

In the present application, the alkyl may include saturated linear or branched monovalent or multivalent hydrocarbyl with 1 to 10 carbon atoms. In some embodiments, the alkyl may include 1 to 10 carbon atoms; in some embodiments, the alkyl may include 1 to 8 carbon atoms; in some embodiments, the alkyl may include 1 to 6 carbon atoms; in some embodiments, the alkyl may include 1 to 4 carbon atoms; and in some embodiments, the alkyl may include 1 to 3 carbon atoms. Examples of alkyl with 1 to 4 carbon atoms as a substituent may include, but are not limited to, methyl, ethyl, n-propyl, isopropyl, n-butyl, isobutyl, sec-butyl, and tert-butyl.

In the present application, the halogen can be fluorine, chlorine, bromine, or iodine.

In the present application, the alkoxy means that alkyl is attached to the remaining part of the molecule through an oxygen atom, wherein the alkyl has the meaning defined in the present application. Examples of alkoxy as a substituent may include, but are not limited to, methoxy, ethoxy, 1-propoxy, 2-propoxy, 1-butoxy, 2-methyl-1-propoxy, 2-butoxy, and 2-methyl-2-propoxy.

In the present application, the trialkylsilyl refers to

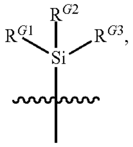

wherein $R^{G1}$, $R^{G2}$, and $R^{G3}$ are each independently alkyl; and specific examples of the trialkylsilyl may include, but are not limited to, trimethylsilyl, triethylsilyl, tert-butyldimethylsilyl, and propyl dimethylsilyl.

In the present application, the haloalkyl refers to alkyl substituted by one or more halogen atoms, wherein the alkyl has the meaning defined in the present application. In an embodiment, the haloalkyl with 1 to 4 carbon atoms may include fluorine-substituted alkyl with 1 to 4 carbon atoms, and such examples may include, but are not limited to, trifluoromethyl, difluoromethyl, and 1-fluoro-2-chloroethyl.

The "ring" in the present application may include a saturated ring and an unsaturated ring, wherein the saturated ring refers to cycloalkyl and heterocycloalkyl and the unsaturated ring refers to cycloalkenyl, heterocycloalkenyl, aryl, and heteroaryl.

In the present application, a ring system formed by n ring atoms is an n membered ring. For example, phenyl is 6-membered aryl. A 5- to 10-membered aromatic ring refers to aryl or heteroaryl with 5 to 10 ring atoms; and a 5-10 membered aliphatic ring refers to cycloalkyl or cycloalkenyl with 5 to 10 ring atoms. A 5- to 15-membered ring is a ring system with 5 to 15 ring atoms, and the ring system can be an aliphatic ring or an aromatic ring, including, but not limited to, cyclopentane, cyclohexane, and a fluorene ring.

In the present application, a 5- to 18-membered aromatic ring is a ring system that includes 5 to 18 ring atoms and an aromatic ring. For example, the fluorene ring is a 13-membered aromatic ring.

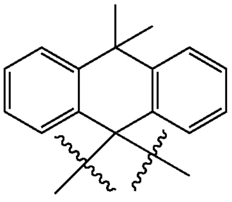 [SMILES: *C1(*)c2ccccc2C(C)(C)c2ccccc21]

is a substituted 14-membered aromatic ring.

In the present application, the term “optional” or “optionally” means that the event or environment subsequently described may, but not necessarily, occur, which includes situations where the event or environment occurs or does not occur. For example, the phrase “optionally, any two adjacent substituents connected to each other to form a ring” means that two adjacent substituents may or may not connected to each other to form a ring, and this solution includes the situation where the two substituents are connected to each other to form a ring and the situation where the two substituents exist independently of each other. For example, the two adjacent substituents may exist in the form of forming a saturated or unsaturated ring, and may also exist independently of each other. When two adjacent substituents attached to the same atom form a ring, the formed ring is linked to the remaining part of the molecule in a spiro mode. When two adjacent substituents respectively attached to two adjacent atoms form a ring, the formed ring is linked to the remaining part of the molecule in a fused mode.

In the present application, a non-positional bond refers to a single bond

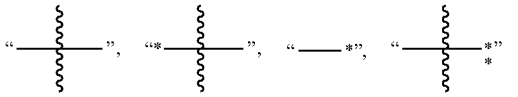

or

extending from a ring system, which means that one end of the bond can be attached to any position in the ring system through which the bond penetrates, and the other end is attached to the remaining part of the compound molecule. For example, as shown in the following formula (X'), the dibenzofuranyl represented by the formula (X') is attached to the remaining part of the molecule through a non-positional bond extending from the middle of a benzene ring at a side, which indicates any possible attachment modes shown in formula (X'-1) to formula (X'-4).

(X')

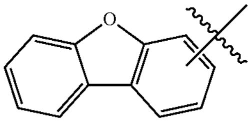

-continued (X'-1)

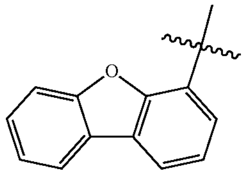

(X'-2)

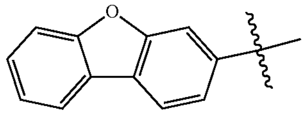

(X'-3)

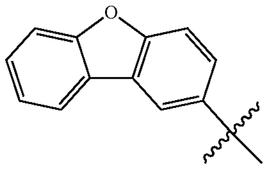

(X'-4)

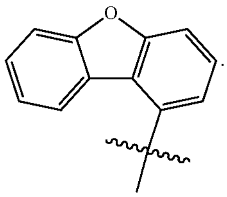

In some embodiments, the organic compound may have a structure shown in the following formula 1-1, 1-2, 1-3, or 1-4:

formula 1-1

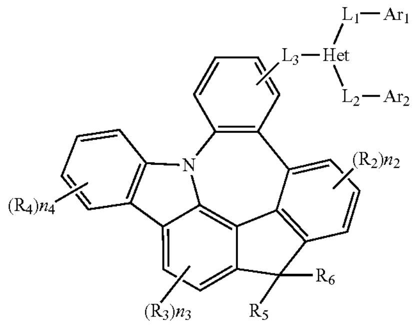

formula 1-2

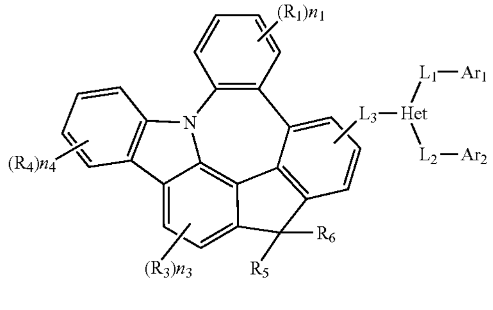

-continued formula 1-3

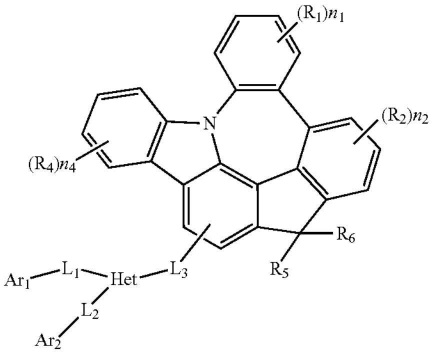

formula 1-4

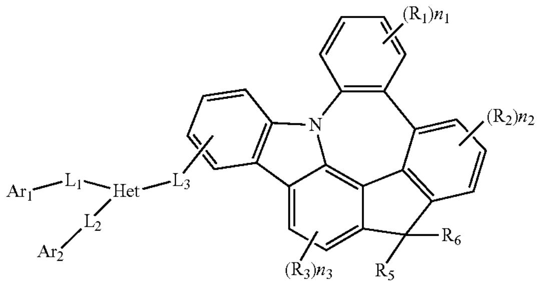

wherein $R_1$, $R_2$, $R_3$, and $R_4$ are the same or different, and are each independently selected from the group consisting of hydrogen, deuterium, fluorine, cyano, phenyl, naphthyl, pyridyl, methyl, ethyl, tert-butyl, isopropyl, trifluoromethyl, trideuteromethyl, and trimethylsilyl.

In some embodiments of the present application, only one of $R_1$, $R_2$, $R_3$, and $R_4$ is the group shown in chemical formula 2, and the rest may all be hydrogen.

In some embodiments of the present application, $R_5$ and $R_6$ are each independently selected from the group consisting of methyl, ethyl, n-propyl, isopropyl, tert-butyl, trifluoromethyl, trideuteromethyl, phenyl, naphthyl, biphenyl, fluorenyl, dimethylfluorenyl, anthracenyl, phenanthryl, pyridyl, dibenzothienyl, dibenzofuranyl, and carbazolyl; or $R_5$ and $R_6$ are connected to each other to form a fluorene ring, cyclopentane, cyclohexane, or

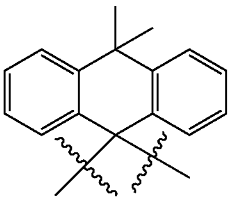

together with the carbon atom to which they are jointly connected.

In some specific embodiments of the present application, $R_5$ and $R_6$ are each independently selected from the group consisting of methyl and the following groups:

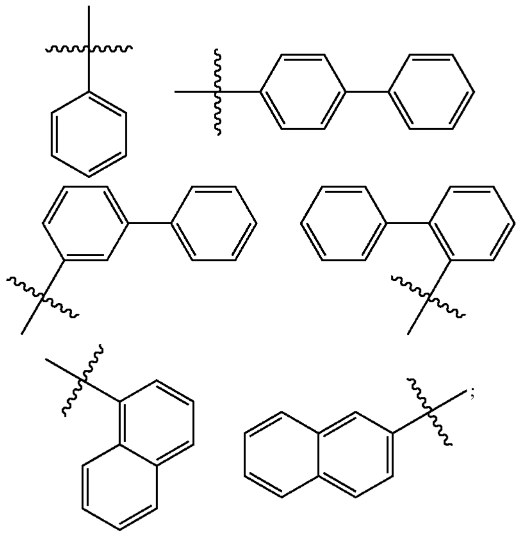

;

or $R_5$ and $R_6$ connected to each other to form a spiro-ring together with carbon atom to which they are jointly connected, the spiro-ring is selected from the group consisting of the following spiro-ring:

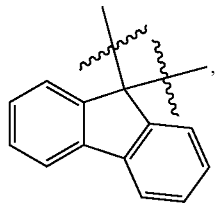

,

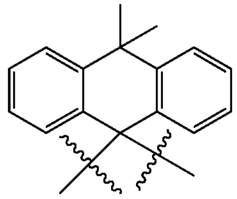 [SMILES: *C1(*)c2ccccc2C(C)(C)c2ccccc21]

,

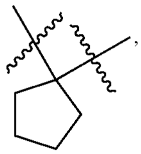

, and

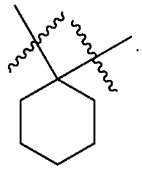

.

Optionally, any one or two of $R_1$, $R_2$, $R_3$, and $R_4$ in the organic compound shown in formula 1 is a group shown in formula 2:

formula 2

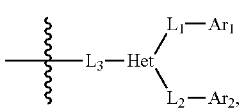

wherein Het is electron-deficient 6- to 18-membered nitrogen-containing heteroarylene. The $sp^2$ hybridized nitrogen atom on Het can reduce an electron cloud density of the conjugated system of the heteroarylene as a whole instead of increasing an electron cloud density of the conjugated system of the heteroarylene, lone pair electrons on a heteroatom do not participate in the conjugated system, and the heteroatom reduces the electron cloud density of the conjugated system due to its strong electronegativity. In this way, the Het group can form an electron transport core group of the compound, such that the compound can effectively realize the electron transport and can effectively balance the transport rates of electrons and holes in a light-emitting layer. In this way, the compound can be used as a host material for a bipolar organic light-emitting layer to simultaneously transport electrons and holes, can also be used as a host material for an electron-type organic light-emitting layer in combination with a host material for a hole-type organic light-emitting layer, and can also be used as an electron transport material.

In some embodiments of the present application, the Het group is selected from the group consisting of triazinylene, pyridylene, pyrimidinylene, quinolinylene, quinoxalinylene, quinazolinylene, isoquinolinylene, benzimidazolylene, benzothiazolylene, benzoxazolylene, phenanthrolinylene, benzoquinazolinylene, phenanthroimidazolylene, benzofuranopyrimidinylene, benzothienopyrimidinylene, and the following groups:

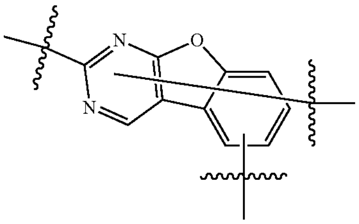

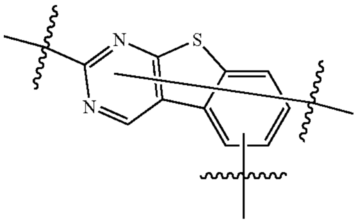

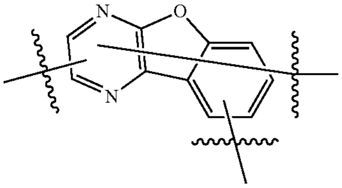

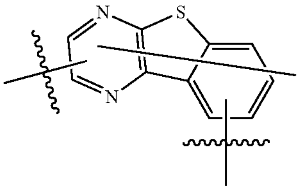

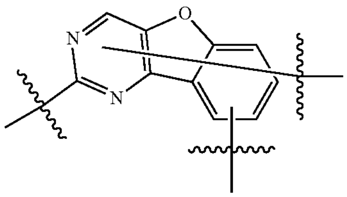

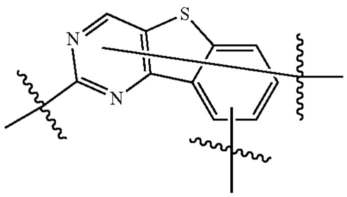

-continued

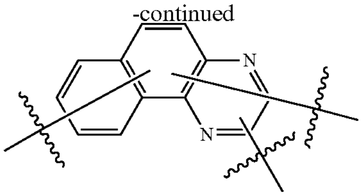

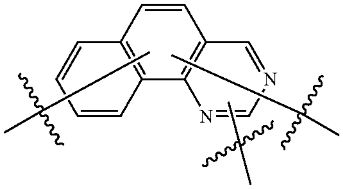

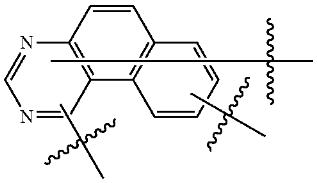

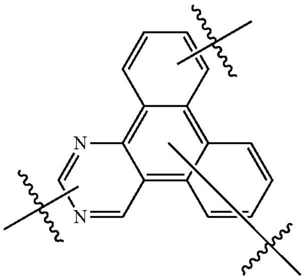

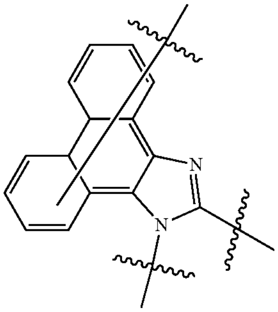

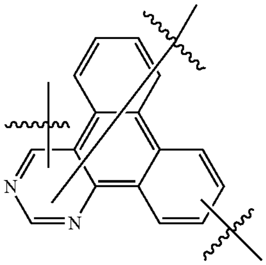

.

In some embodiments, the Het is selected from the group consisting of the following groups:

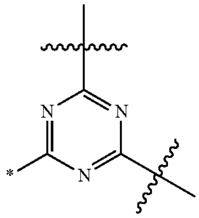

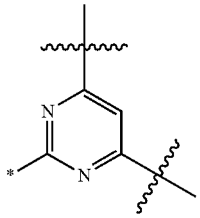

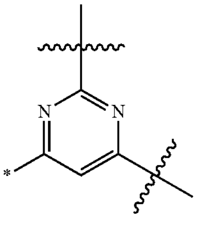

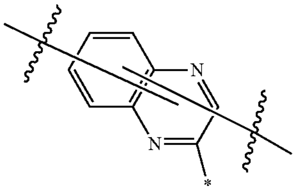

-continued
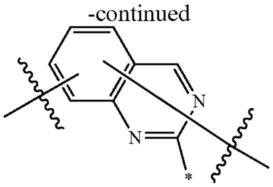
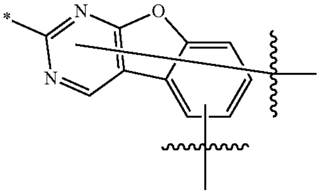
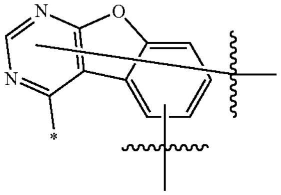
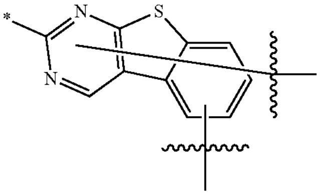
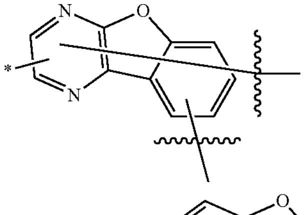
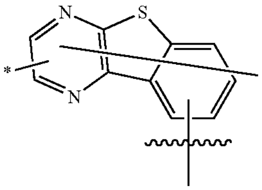
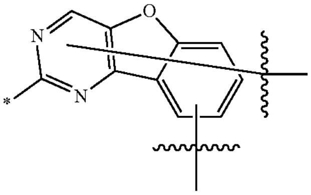
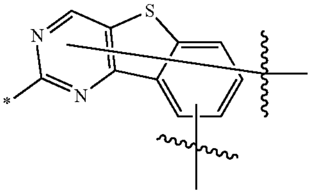
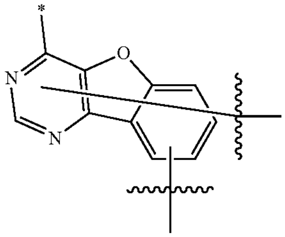
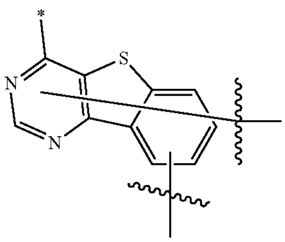
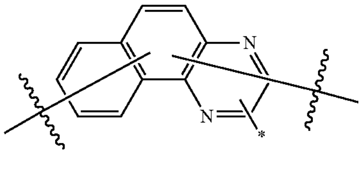
-continued
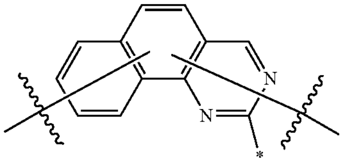
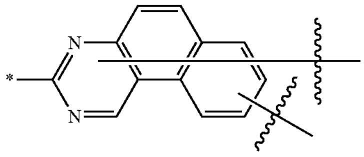
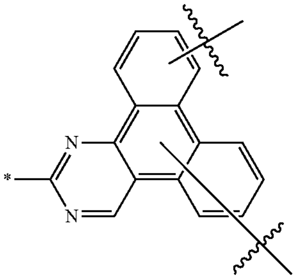
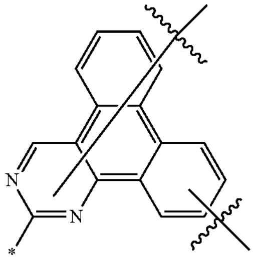
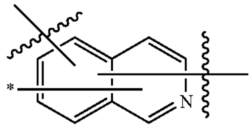
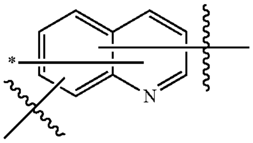
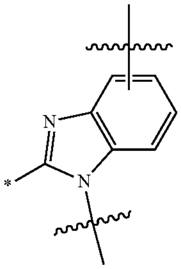
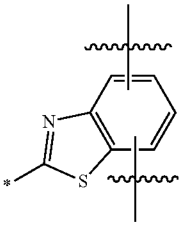
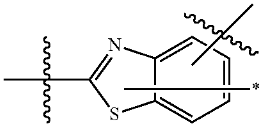
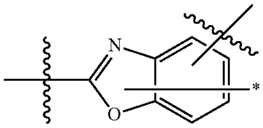
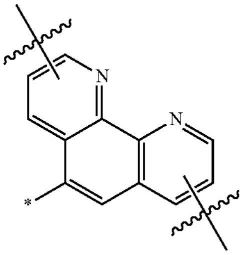
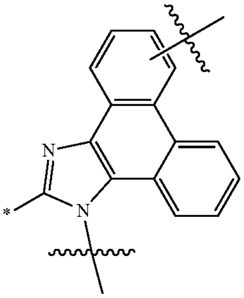

-continued
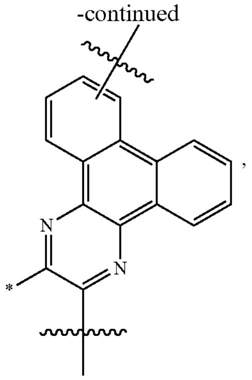
,
wherein * represents a bond linked to $L_3$ and the remaining two bonds
are linked to $L_1$ and $L_2$, respectively.
In some specific embodiments, the Het is selected from the group consisting of the following nitrogen-containing heteroarylene groups:
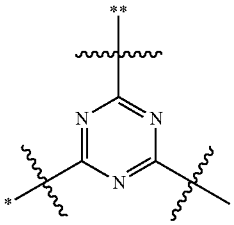
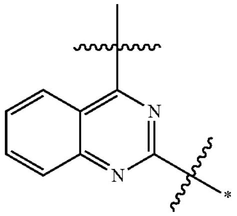
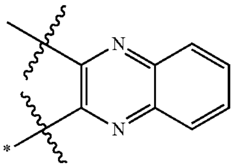
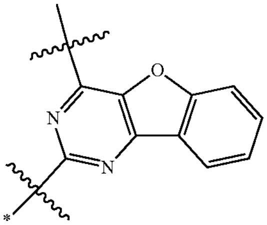
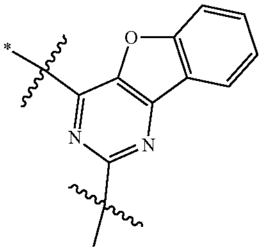
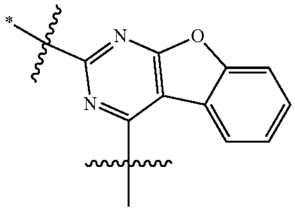
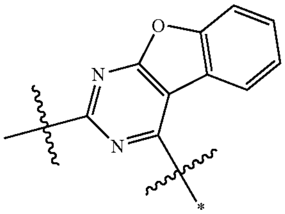
-continued
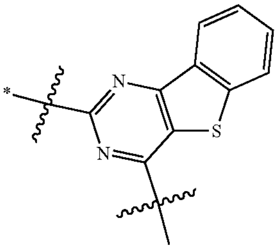
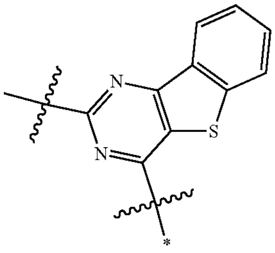
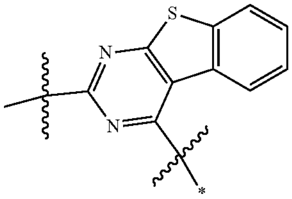
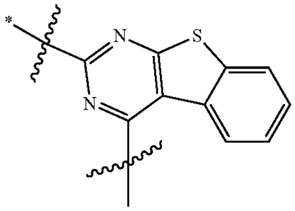
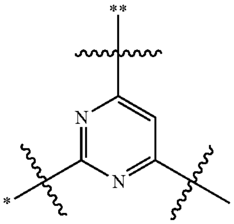
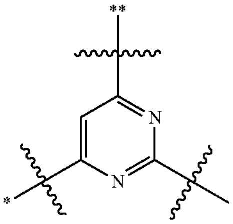
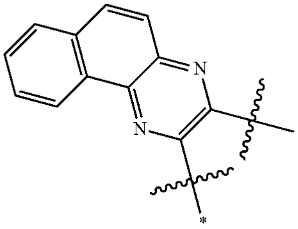
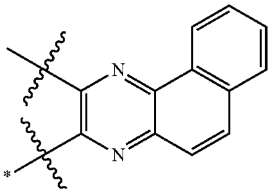
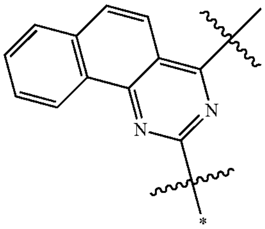
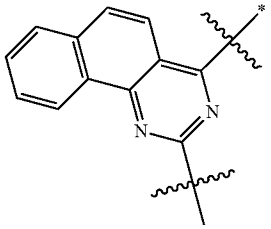
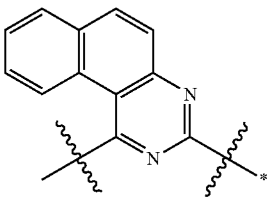
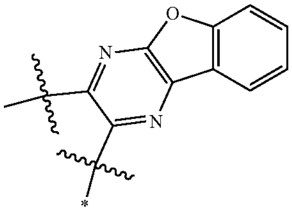

-continued

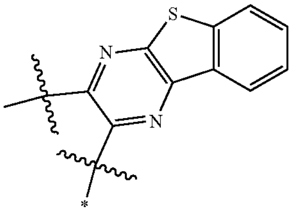

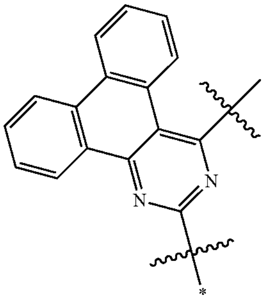

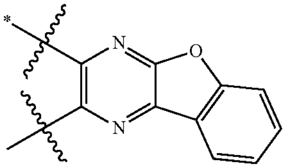

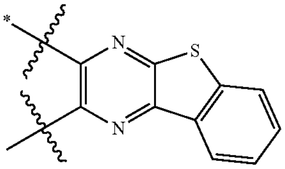

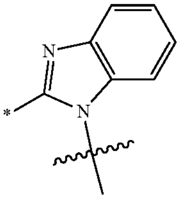

wherein

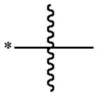 [SMILES: **]

represents a position at which Het is linked to $L_3$,

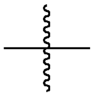

represents a position at which Het is linked to $L_1$,

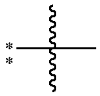

represents a position at which Het is linked to $L_2$; if there is no

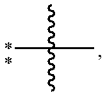

, it represents that

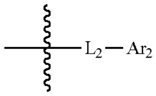

at which the Het is linked to, $L_2$ is a single bond and $Ar_2$ is hydrogen.

In the present application, when the Het group in formula 1 is triazinyl, a balance is well achieved between the hole mobility and electron mobility of the compound, such that the compound can improve the efficiency of a device when used in a light-emitting layer of the device.

In some embodiments of the present application, $L_1$, $L_2$, and $L_3$ are each independently selected from the group consisting of a single bond, substituted or unsubstituted arylene with 6 to 18 carbon atoms, and substituted or unsubstituted heteroarylene with 5 to 12 carbon atoms.

Optionally, substituents in $L_1$, $L_2$, and $L_3$ are each independently selected from the group consisting of deuterium, cyano, fluorine, alkyl with 1 to 5 carbon atoms, haloalkyl with 1 to 5 carbon atoms, deuterated alkyl with 1 to 5 carbon atoms, aryl with 6 to 12 carbon atoms, and pyridyl.

In some embodiments of the present application, $L_1$, $L_2$, and $L_3$ are each independently selected from the group consisting of a single bond, substituted or unsubstituted phenylene, substituted or unsubstituted naphthylene, substituted or unsubstituted biphenylene, substituted or unsubstituted anthracenylene, substituted or unsubstituted phenanthrylene, substituted or unsubstituted fluorenylene, substituted or unsubstituted dibenzothienylene, substituted or unsubstituted dibenzofuranylene, and substituted or unsubstituted carbazolylene; and substituents in $L_1$, $L_2$, and $L_3$ are each independently selected from the group consisting of deuterium, cyano, fluorine, methyl, ethyl, n-propyl, isopropyl, n-butyl, tert-butyl, trifluoromethyl, trideuteromethyl, phenyl, naphthyl, and pyridyl.

In some specific embodiments, $L_1$, $L_2$, and $L_3$ are each independently selected from the group consisting of a single bond and a substituted or unsubstituted group W; an unsubstituted group W is selected from the group consisting of the following groups:

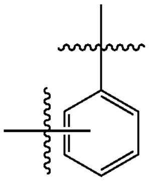

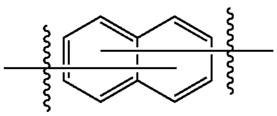

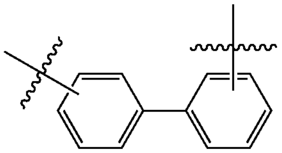

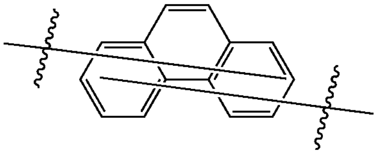

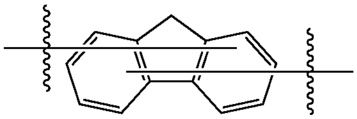

-continued

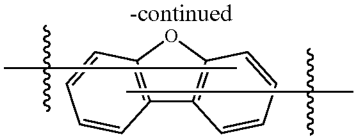

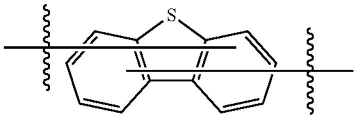

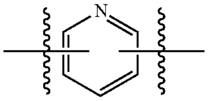

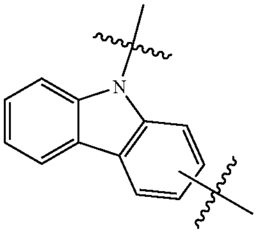

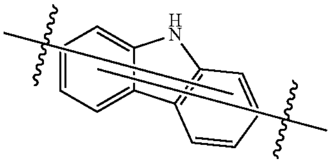

, wherein represents a chemical bond; when the group W is substituted by one or more substituents, the one or more substituents are each independently selected from the group consisting of deuterium, fluorine, cyano, methyl, ethyl, n-propyl, isopropyl, n-butyl, tert-butyl, trifluoromethyl, trideuteromethyl, phenyl, naphthyl, and pyridyl.

In some specific embodiments of the present application, $L_1$, $L_2$, and $L_3$ are each independently selected from the group consisting of a single bond and the following groups:

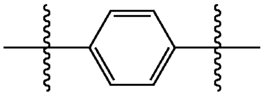

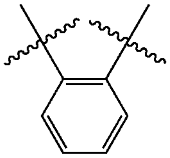

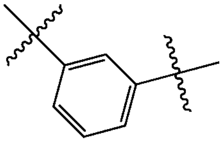

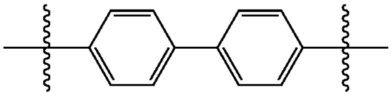

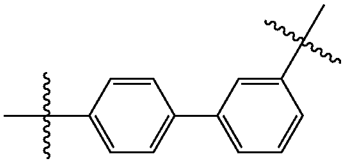

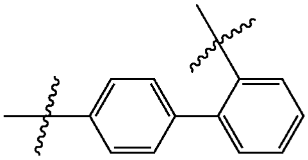

-continued

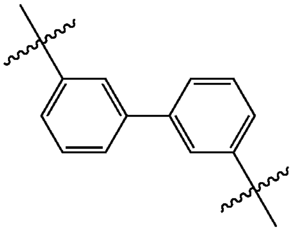

.

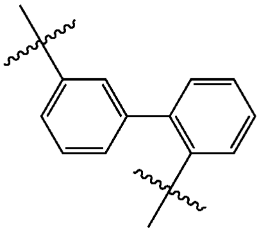

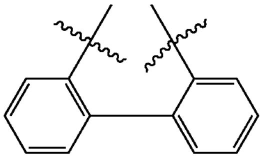

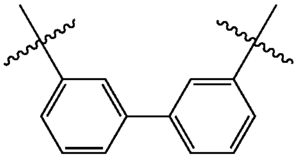

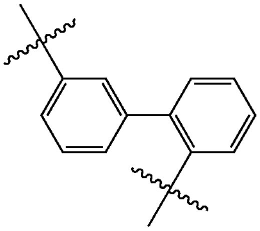

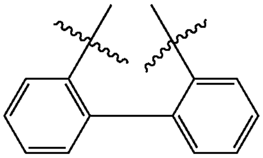

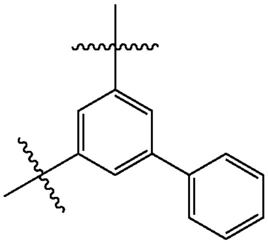

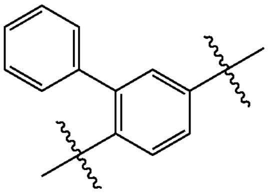

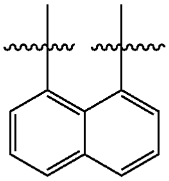

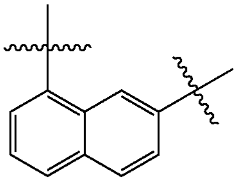

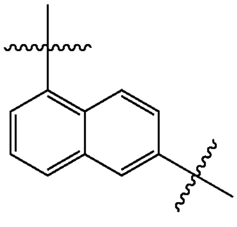

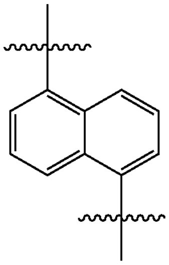

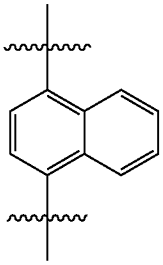

-continued
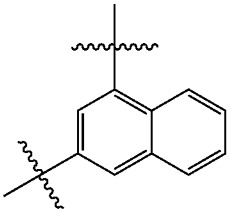
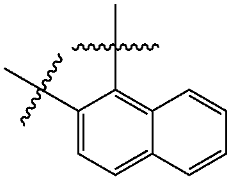
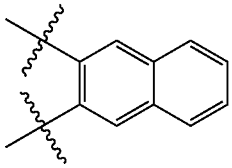
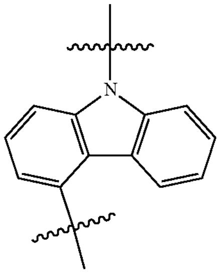
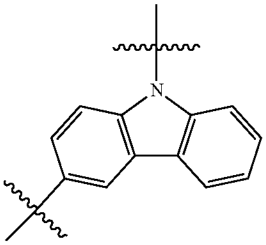
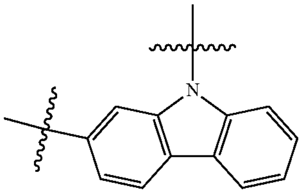
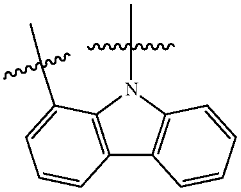
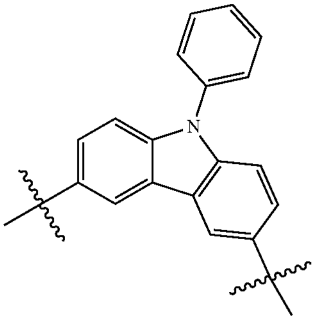
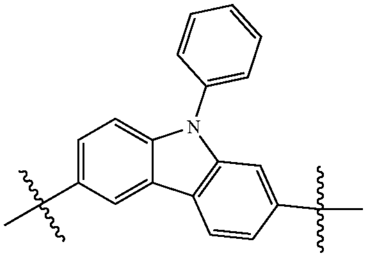
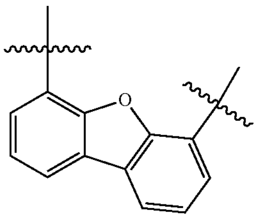
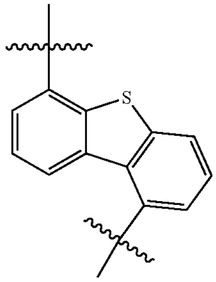
-continued
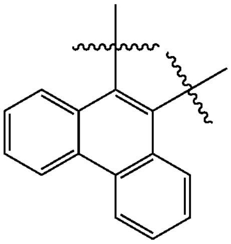
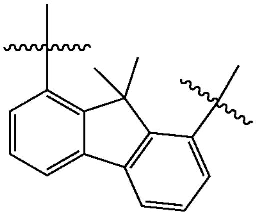
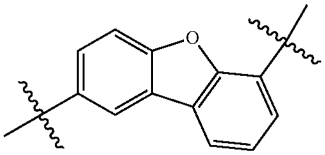
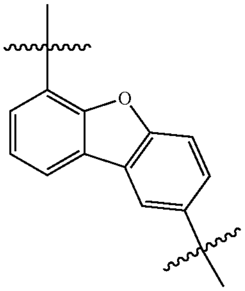
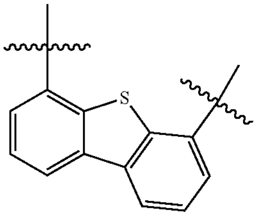
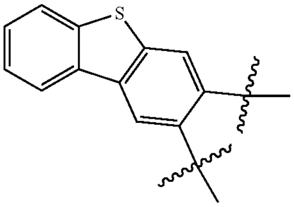
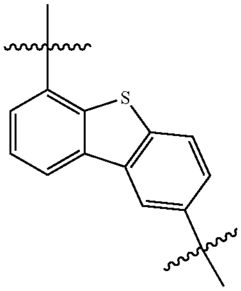
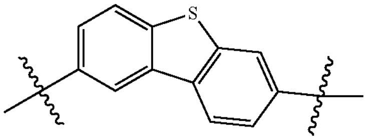
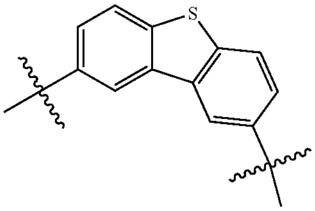
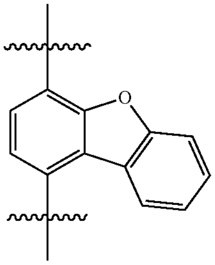
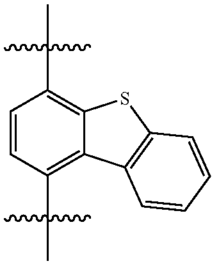
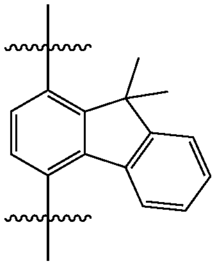

-continued

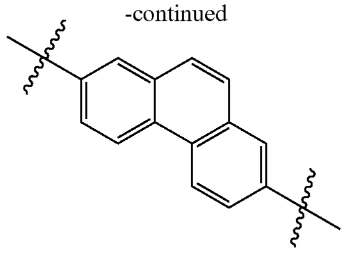

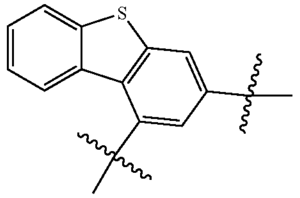

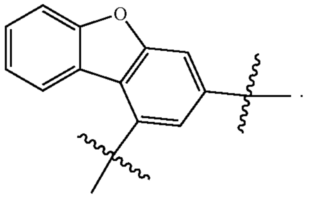

In some embodiments of the present application, $Ar_1$ and $Ar_2$ are the same or different, and are each independently selected from the group consisting of hydrogen, deuterium, substituted or unsubstituted aryl with 6 to 25 carbon atoms, and substituted or unsubstituted heteroaryl with 5 to 20 carbon atoms. Optionally, substituents in $Ar_1$ and $Ar_2$ are each independently selected from the group consisting of deuterium, cyano, fluorine, alkyl with 1 to 5 carbon atoms, haloalkyl with 1 to 5 carbon atoms, deuterated alkyl with 1 to 5 carbon atoms, aryl with 6 to 15 carbon atoms, and heteroaryl with 5 to 12 carbon atoms. Optionally, in $Ar_1$ and $Ar_2$, any two adjacent substituents connected to each other to form a substituted or unsubstituted 5- to 13-membered ring, and a substituent on the 5- to 13-membered ring is selected from the group consisting of deuterium, cyano, halogen, alkyl with 1 to 4 carbon atoms, haloalkyl with 1 to 4 carbon atoms, deuterated alkyl with 1 to 4 carbon atoms, trialkylsilyl with 3 to 6 carbon atoms, aryl with 6 to 12 carbon atoms, and heteroaryl with 5 to 12 carbon atoms.

In some embodiments, the substituted or unsubstituted aryl may have 6, 10, 12, 13, 14, 15, 16, 17, 18, 20, 25, or 30 carbon atoms.

In some embodiments, the substituted or unsubstituted heteroaryl may have 3, 4, 5, 6, 7, 8, 9, 10, 11, 12, 13, 14, 15, 16, 17, 18, 20, 21, 22, 23, 24, 25, 26, 27, 28, 29, or 30 carbon atoms.

In some embodiments of the present application, $Ar_1$ and $Ar_2$ are the same or different, and are each independently selected from the group consisting of hydrogen, deuterium, substituted or unsubstituted phenyl, substituted or unsubstituted biphenyl, substituted or unsubstituted naphthyl, substituted or unsubstituted terphenyl, substituted or unsubstituted fluorenyl, substituted or unsubstituted pyrenyl, substituted or unsubstituted perylenyl, substituted or unsubstituted anthracenyl, substituted or unsubstituted phenanthryl, substituted or unsubstituted pyridyl, substituted or unsubstituted dibenzothienyl, substituted or unsubstituted dibenzofuranyl, substituted or unsubstituted carbazolyl, and substituted or unsubstituted spirobifluorenyl; and substituents in $Ar_1$ and $Ar_2$ are the same or different, and are each independently selected from the group consisting of methyl, ethyl, n-propyl, isopropyl, n-butyl, tert-butyl, trifluoromethyl, trideuteromethyl, phenyl, naphthyl, phenanthryl, fluorenyl, dibenzothienyl, dibenzofuranyl, carbazolyl, and pyridyl.

In a specific embodiment of the present application, $Ar_1$ and $Ar_2$ are the same or different, and are each independently selected from the group consisting of hydrogen, deuterium, and a substituted or unsubstituted group Y; an unsubstituted group Y is selected from the group consisting of the following groups:

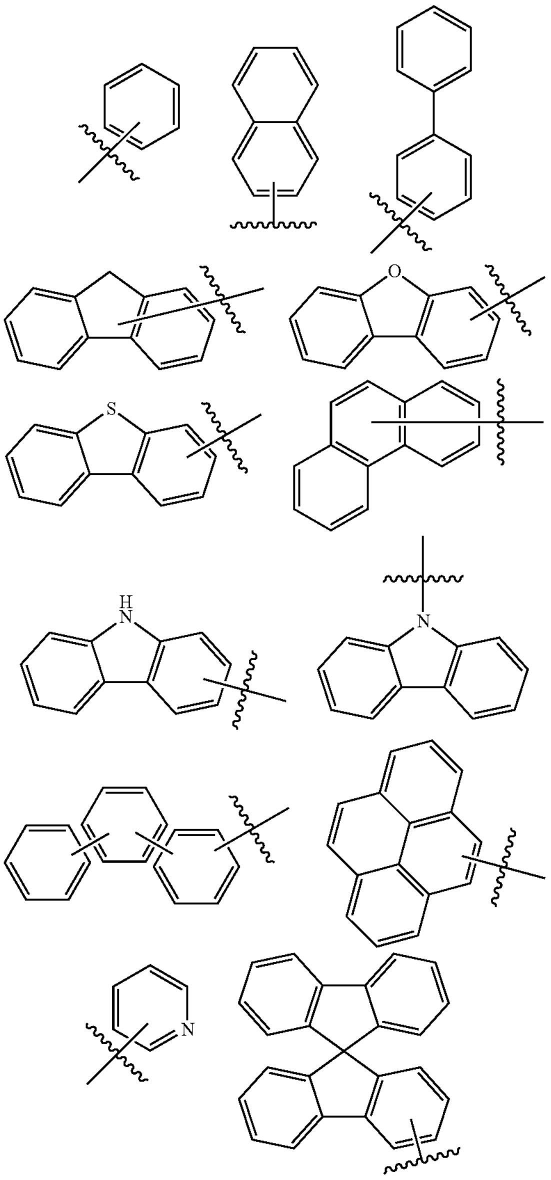

wherein

represents a chemical bond; and when the group Y is substituted by one or more substituents, the one or more substituents are each independently selected from the group consisting of deuterium, cyano, fluorine, methyl, ethyl, n-propyl, isopropyl, n-butyl, tert-butyl, trifluoromethyl, trideuteromethyl, trimethylsilyl, phenyl, naphthyl, and pyridyl.

In a specific embodiment of the present application, $Ar_1$ and $Ar_2$ are the same or different, and are each independently selected from the group consisting of hydrogen, deuterium, and the following groups:

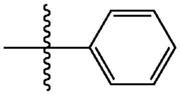
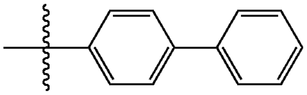
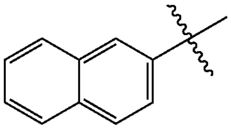
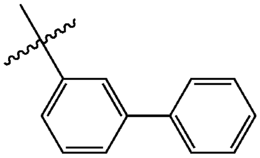
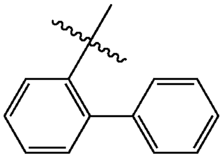
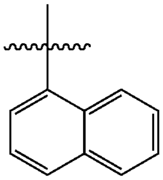
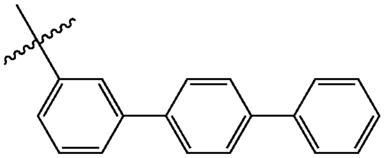
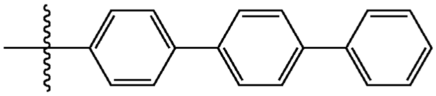
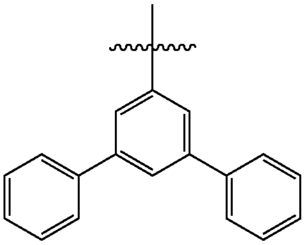
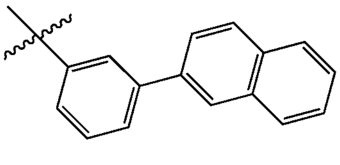
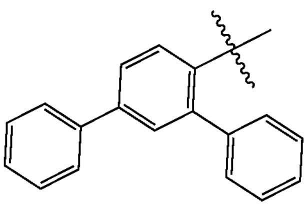

-continued

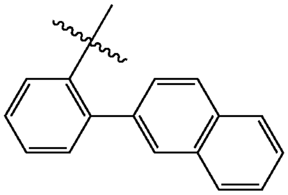
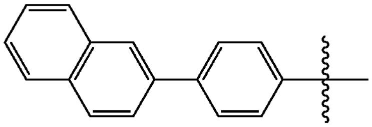
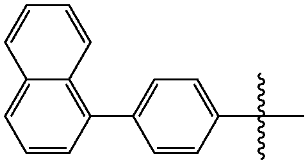
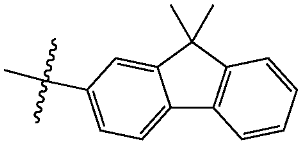
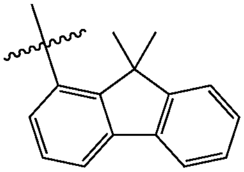
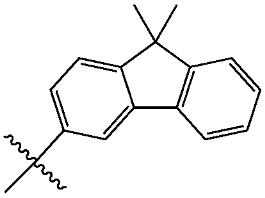
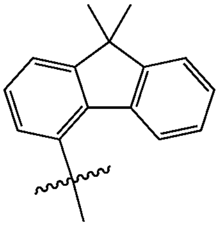
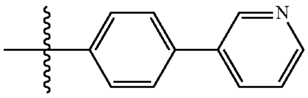
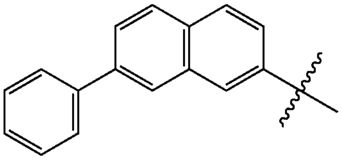
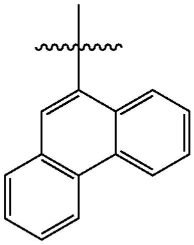
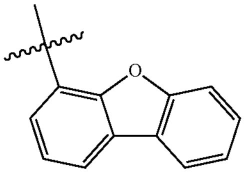
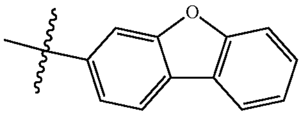
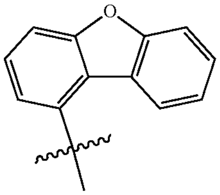
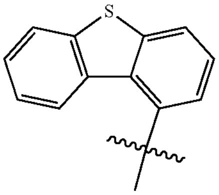

-continued
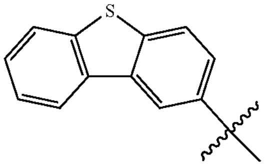
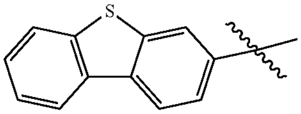
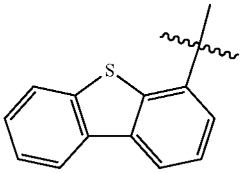
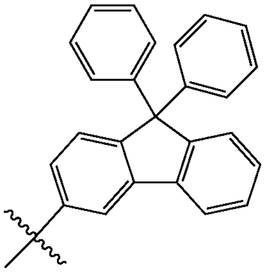
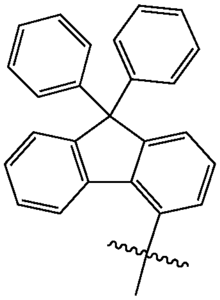
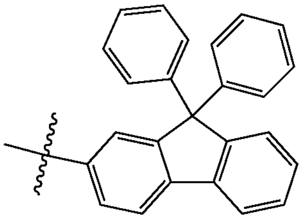
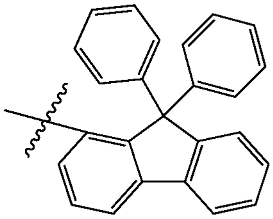
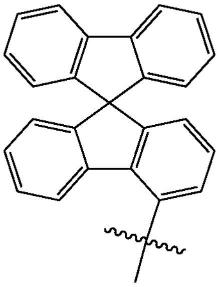
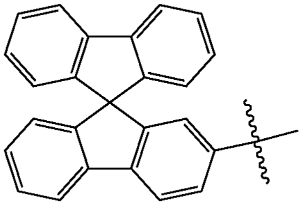
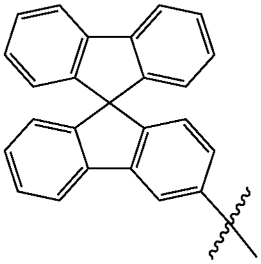
-continued
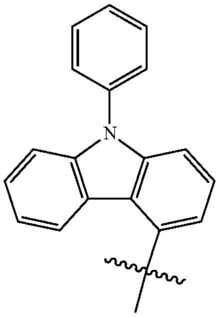
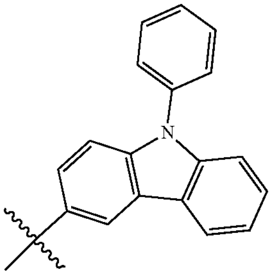
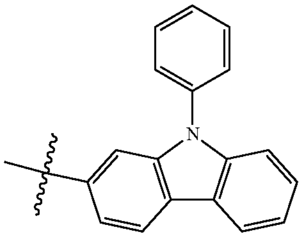
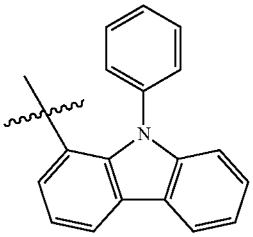
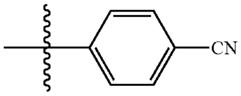
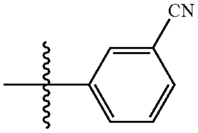
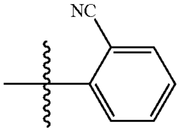
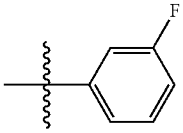
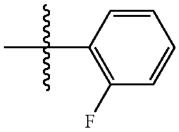
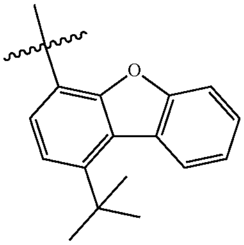
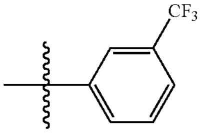
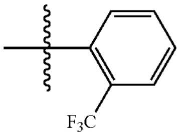
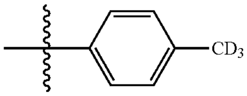
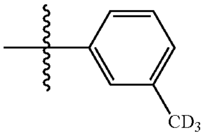
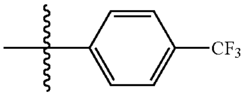
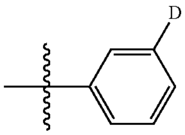
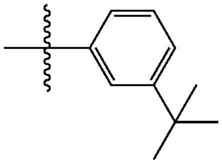

-continued
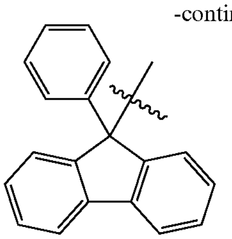
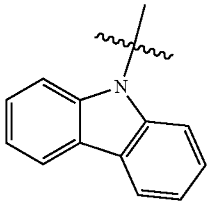
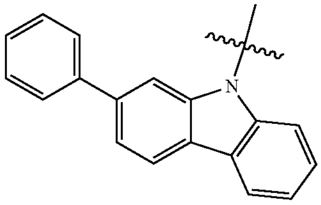
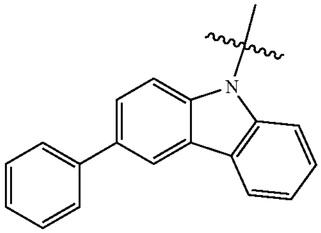
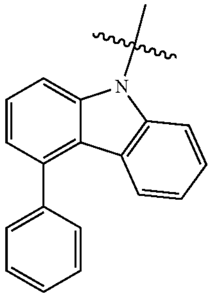
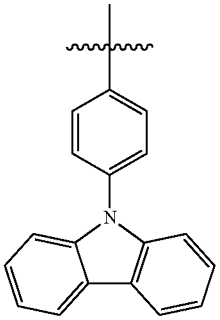
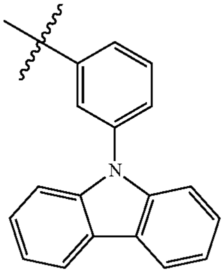
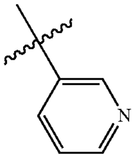
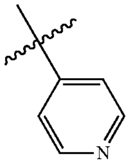
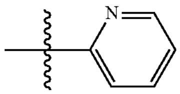
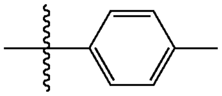
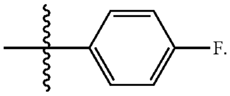
In a specific embodiment of the present application,
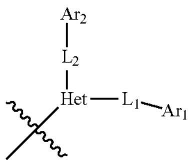
is selected from the group consisting of the following structures:
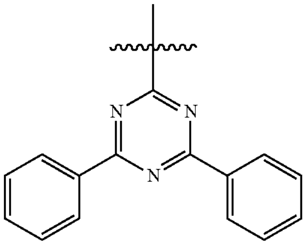
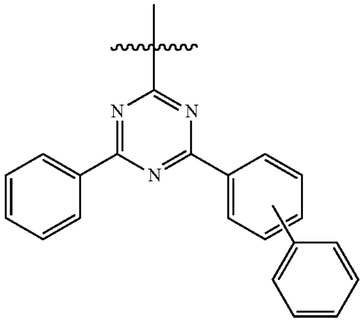
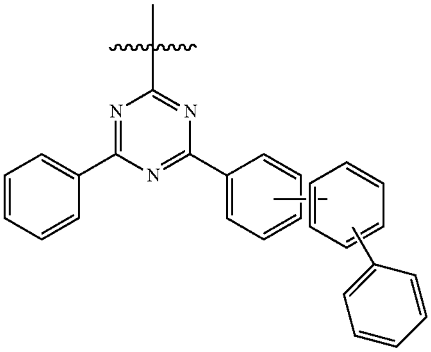
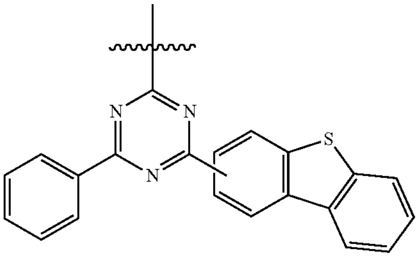
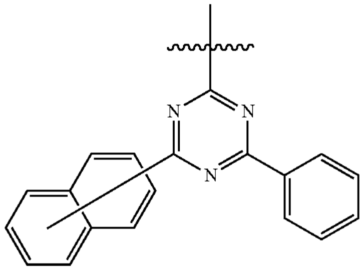

-continued
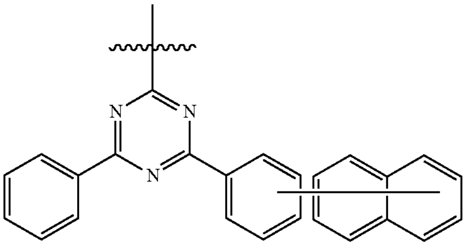
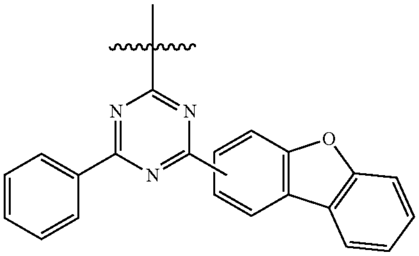
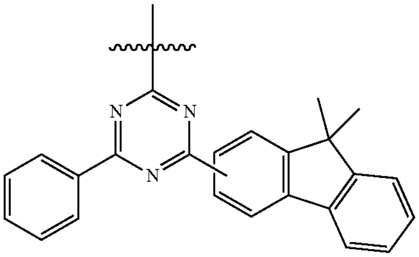
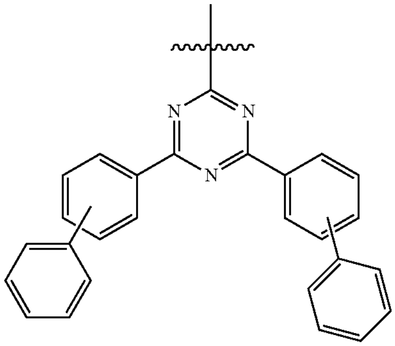
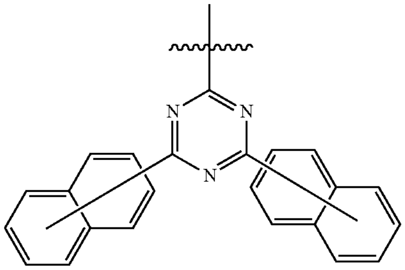
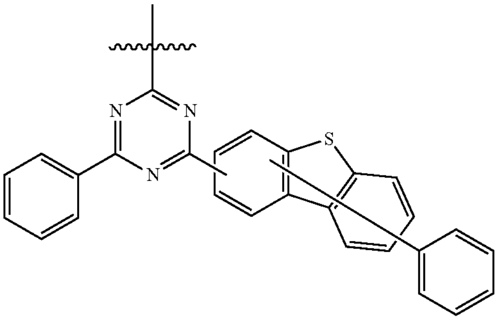
-continued
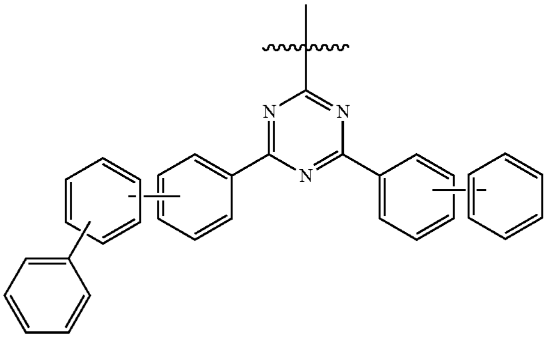
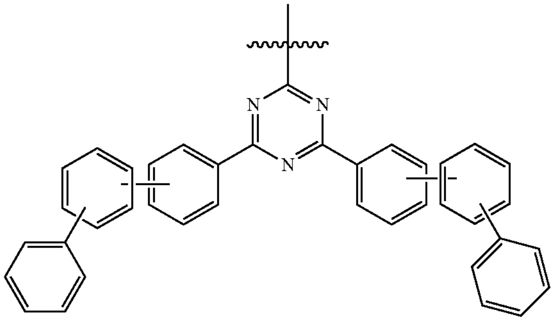
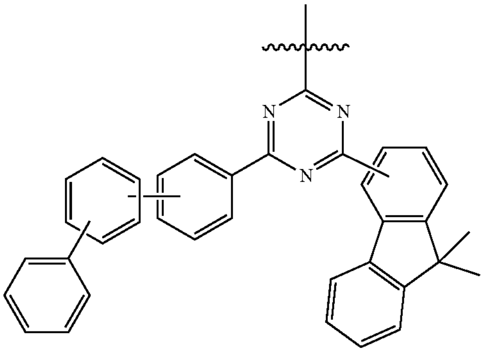
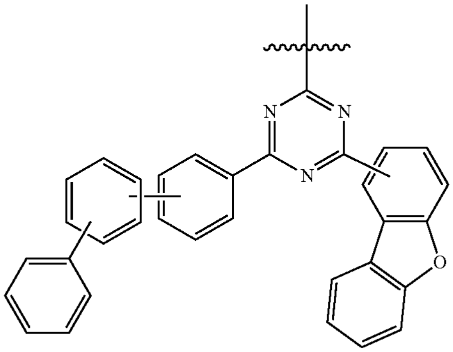
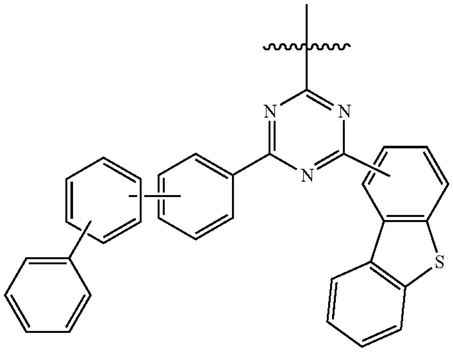

-continued
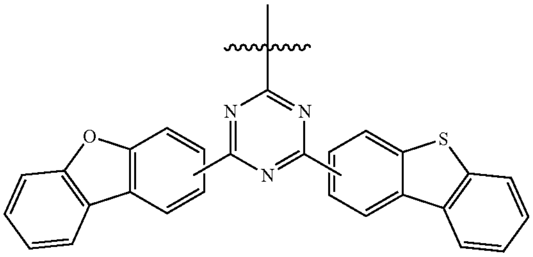
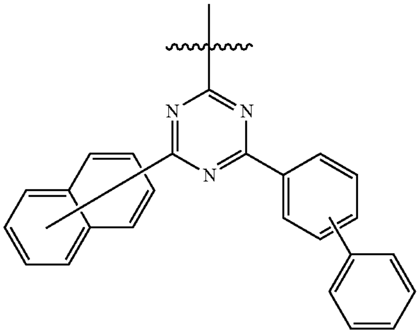
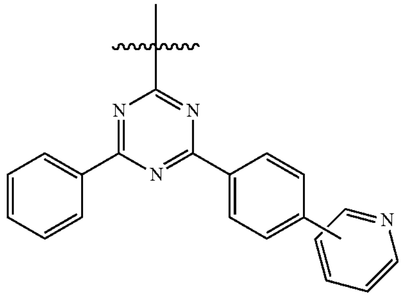
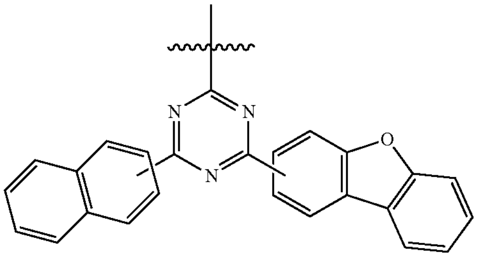
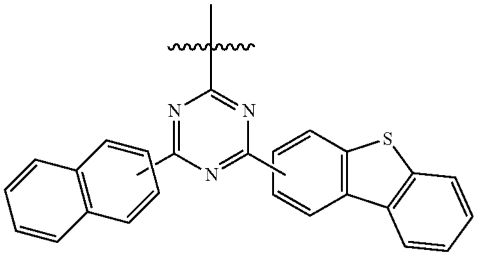
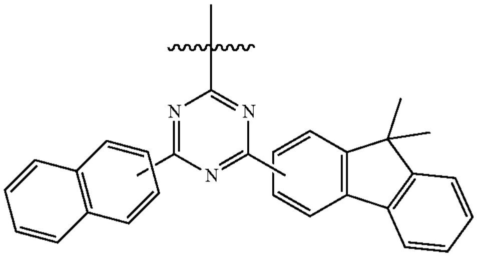
-continued
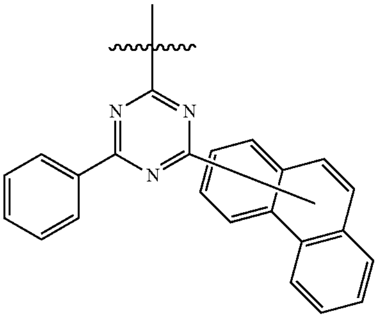
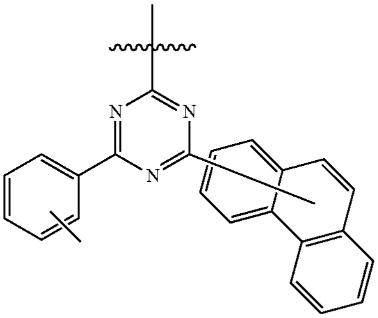
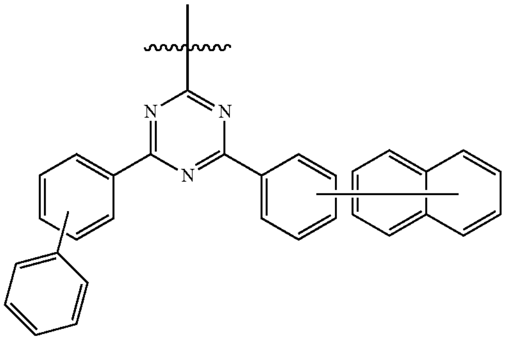
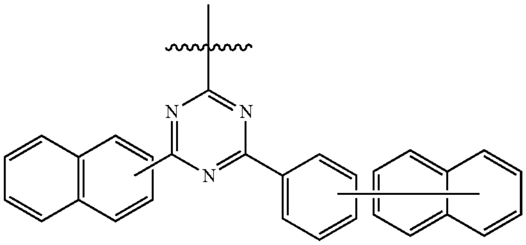
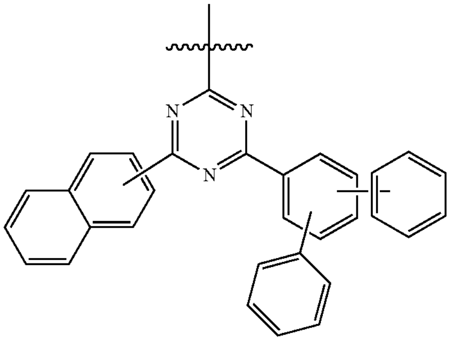

-continued
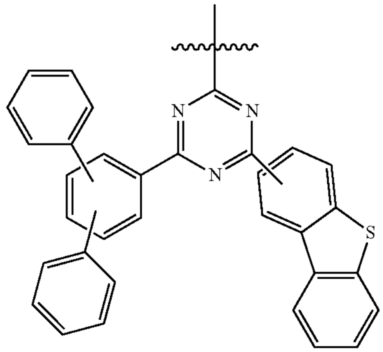
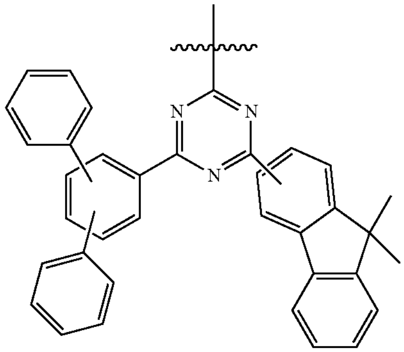
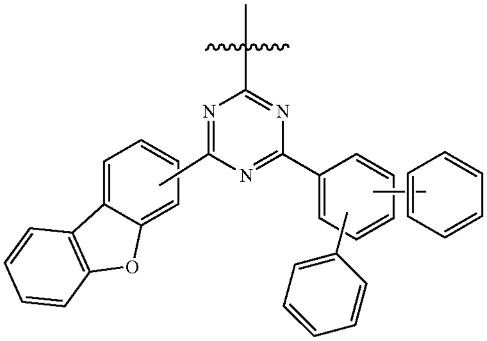
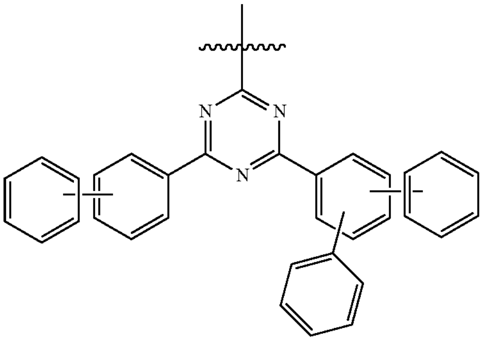
-continued
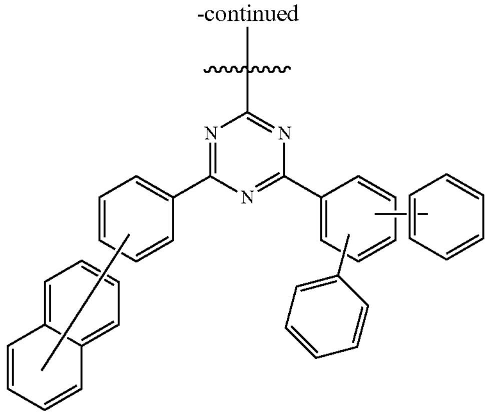
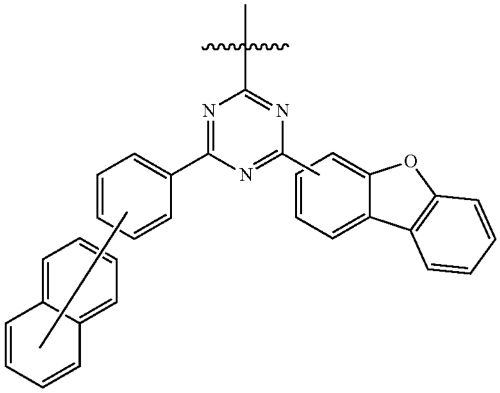
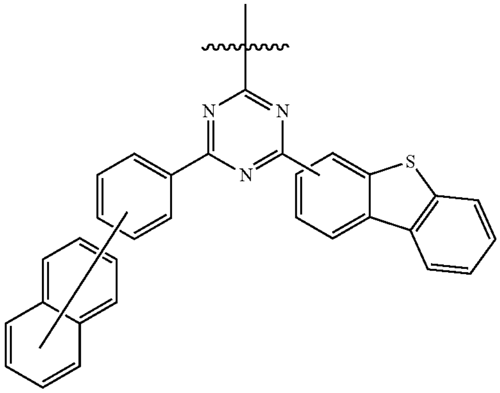
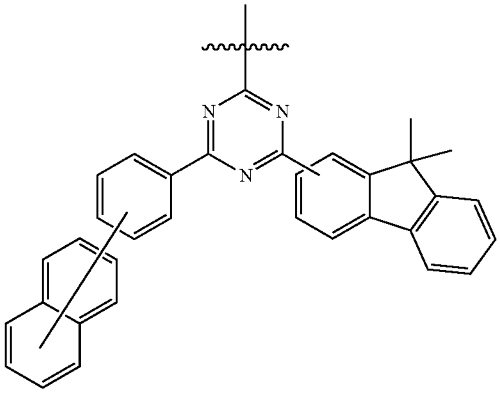

-continued
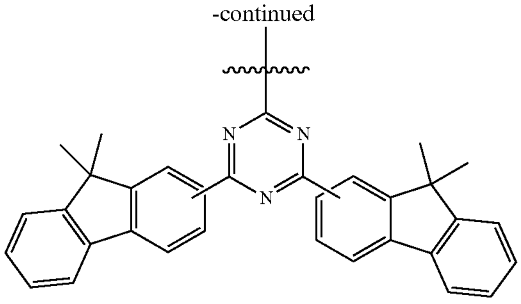
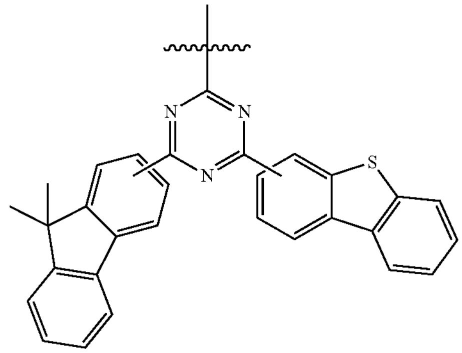
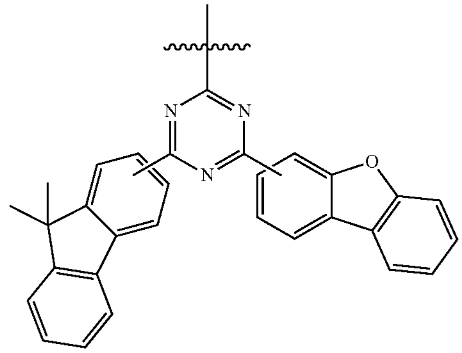
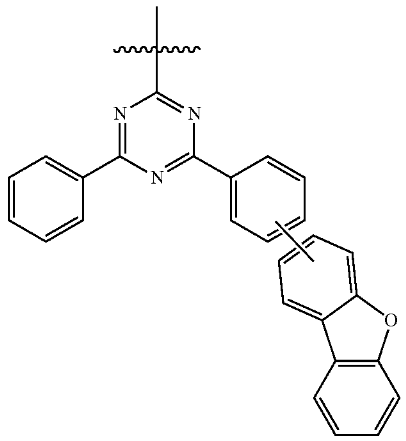
-continued
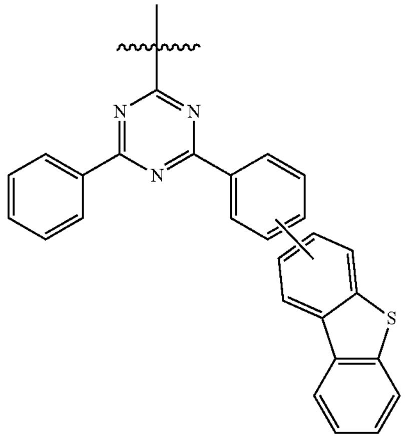
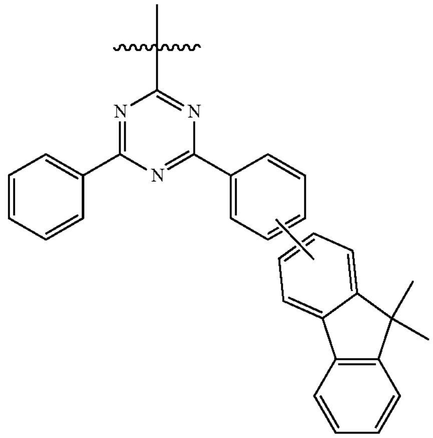
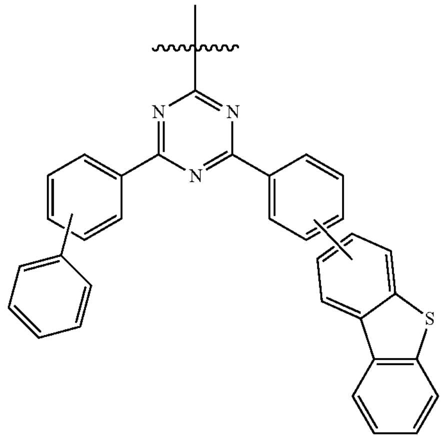
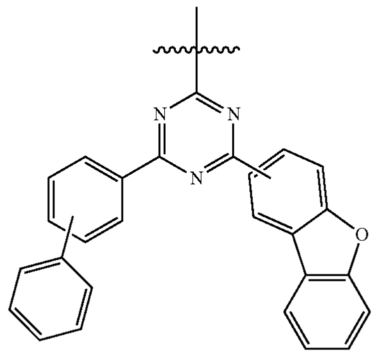

-continued
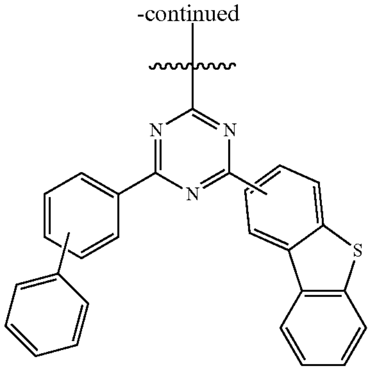
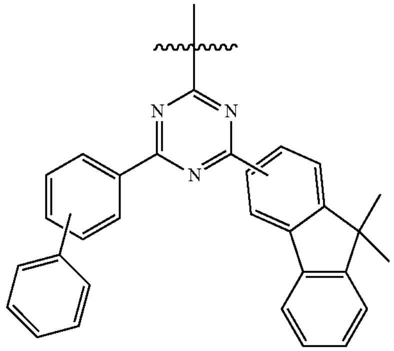
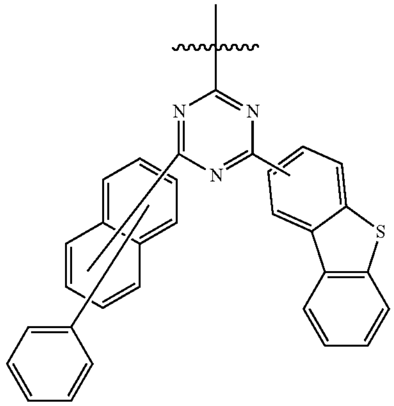
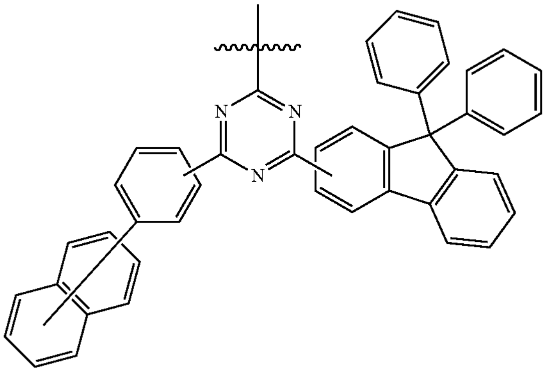
-continued
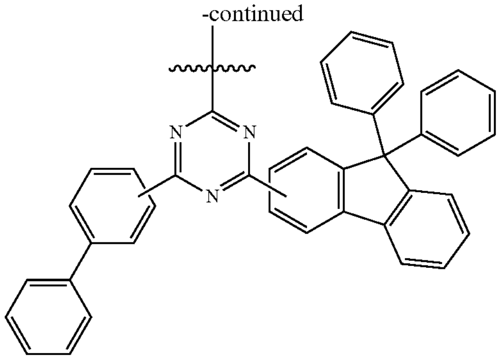
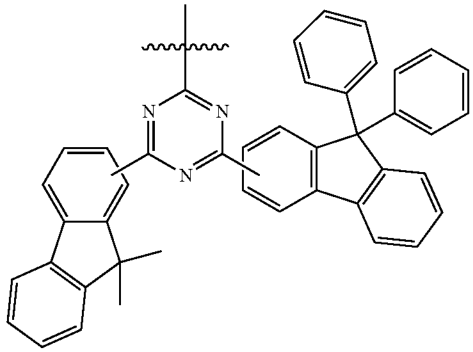
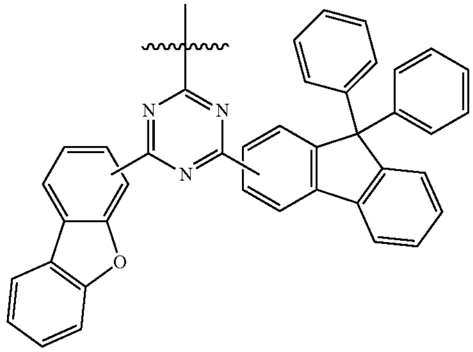
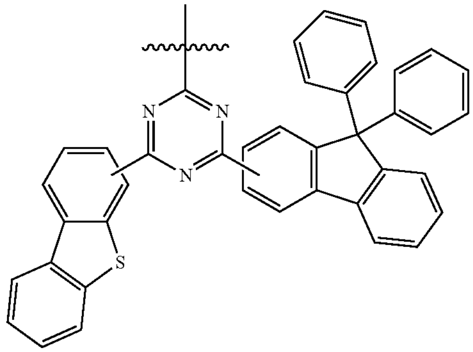
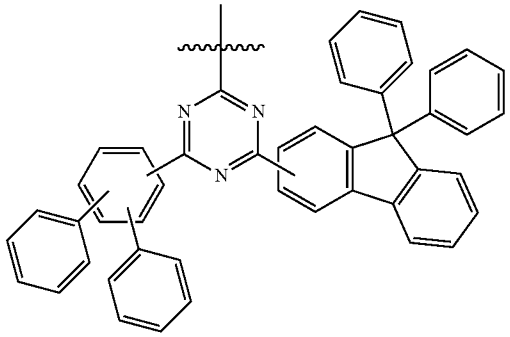

-continued
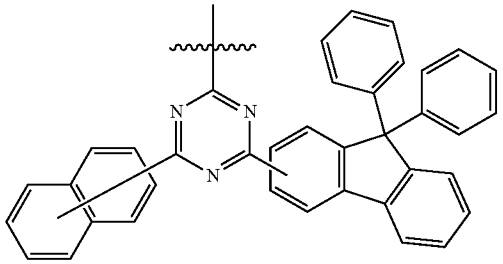
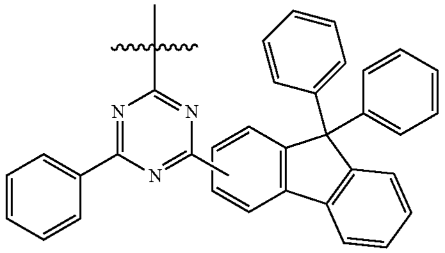
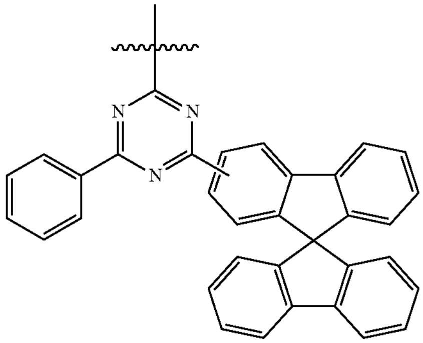
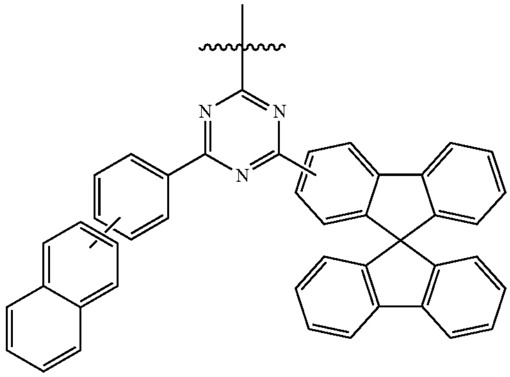
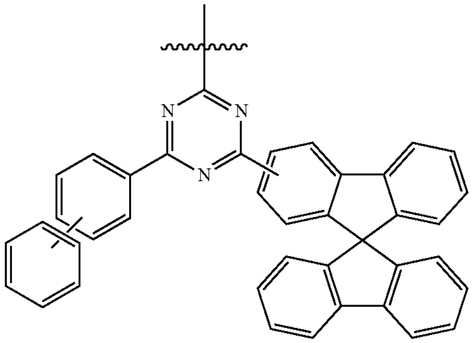
-continued
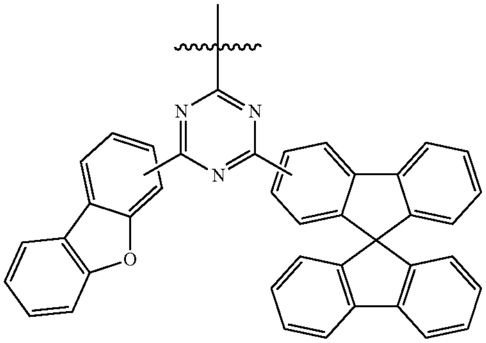
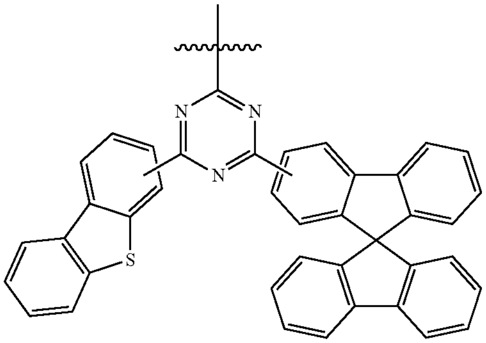
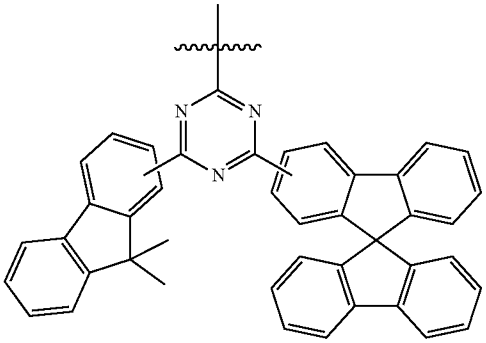
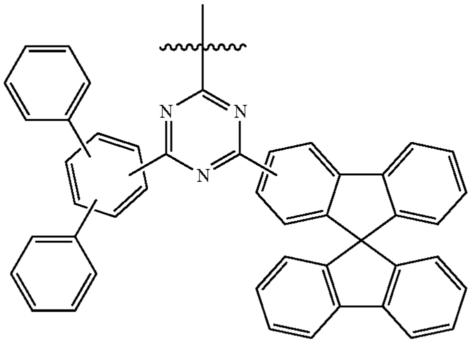
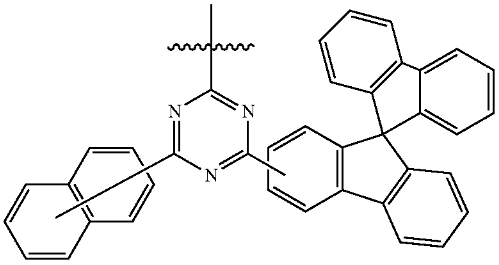

-continued
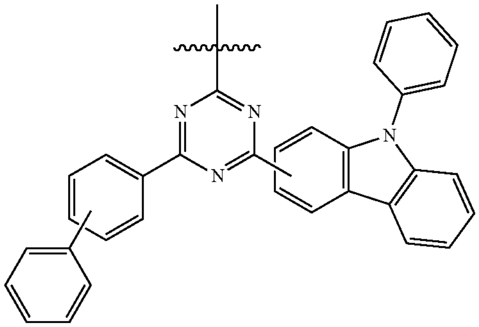
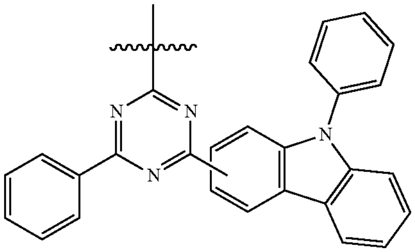
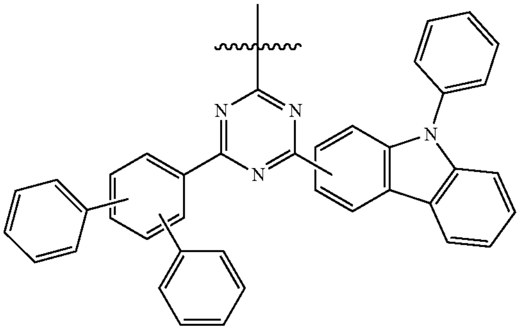
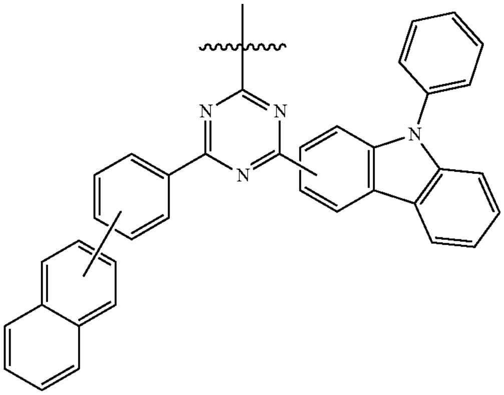
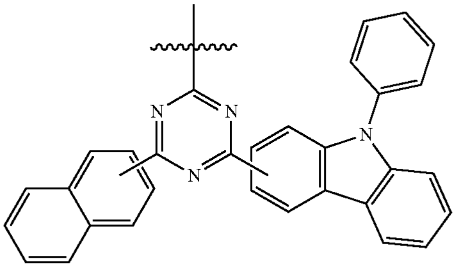
-continued
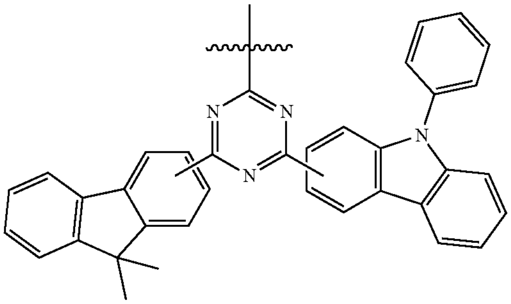
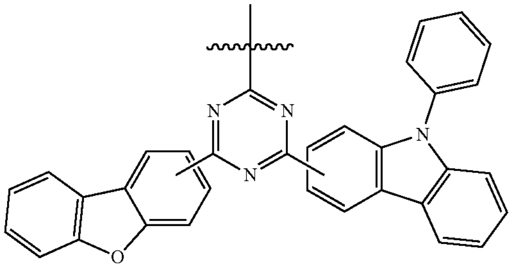
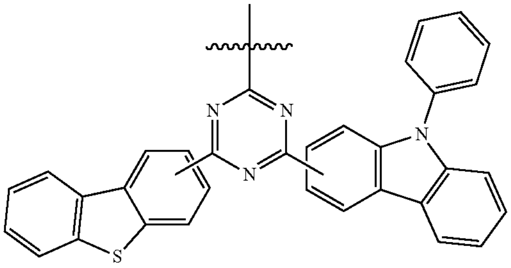
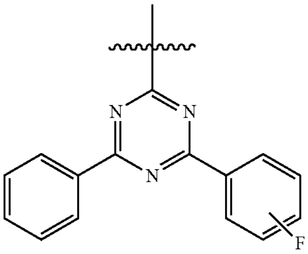
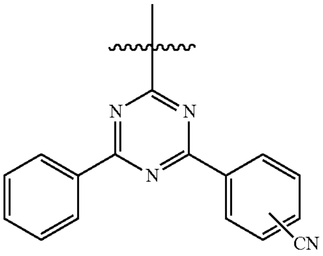
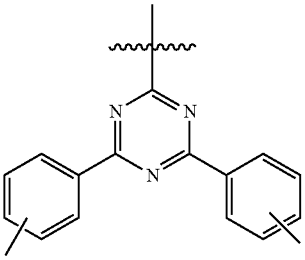

-continued
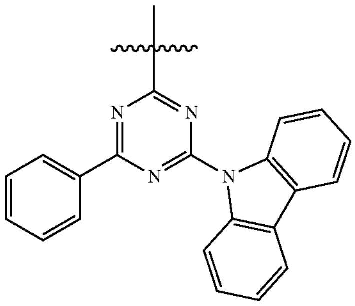
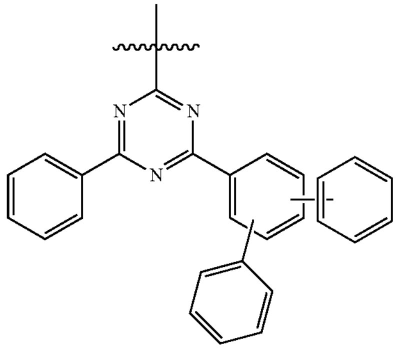
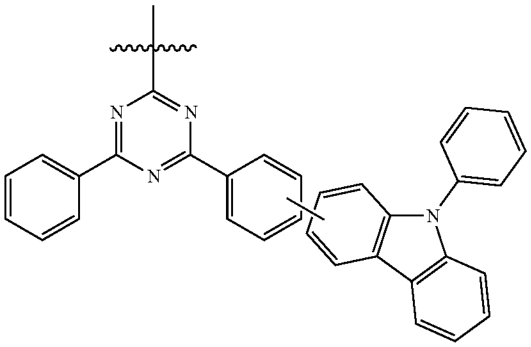
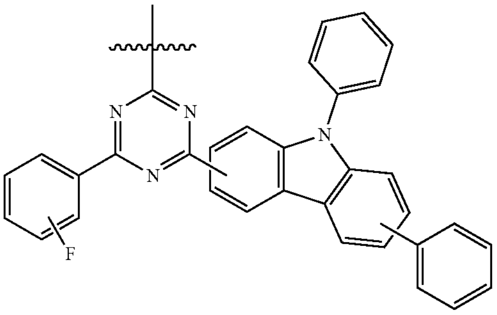
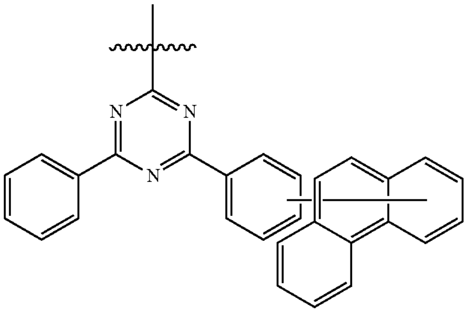
-continued
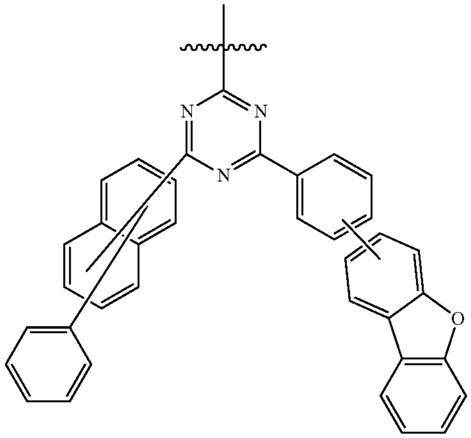
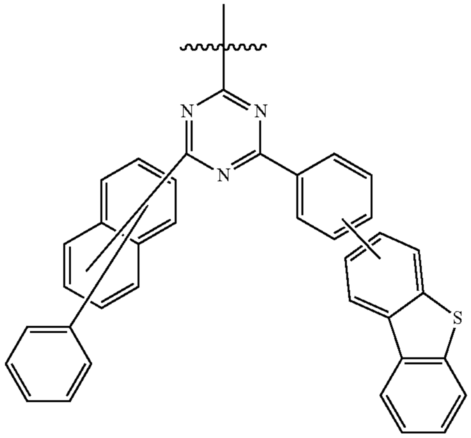
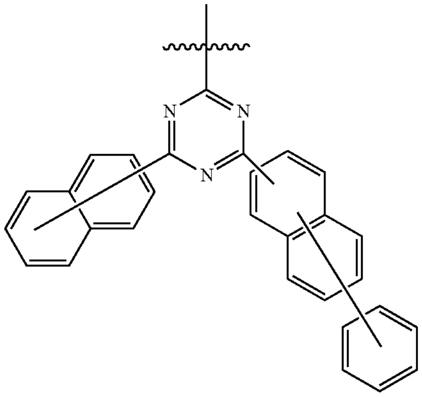
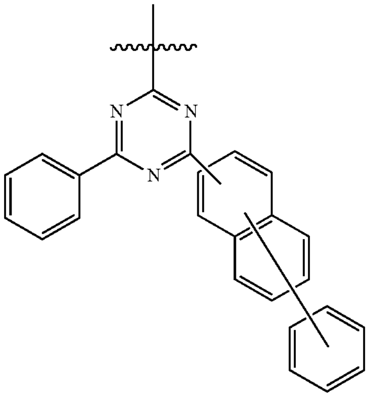

-continued
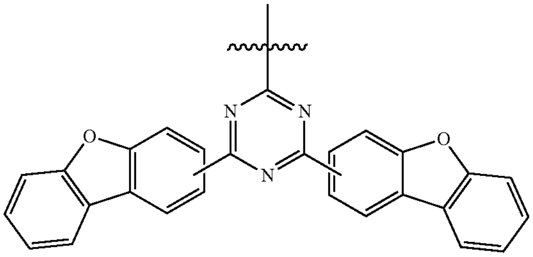
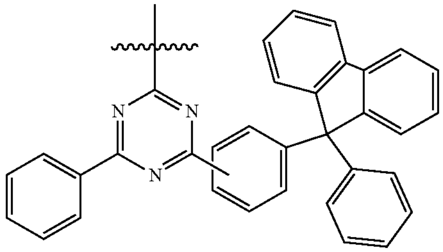
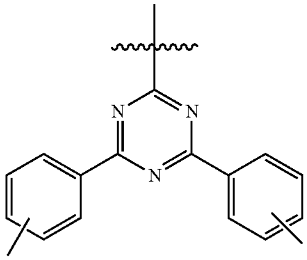
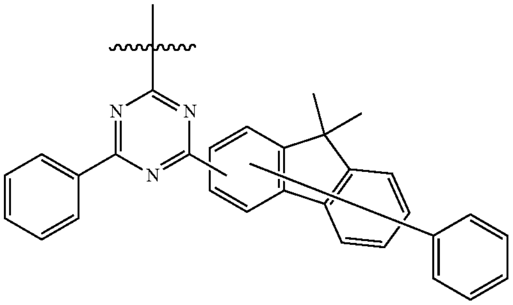
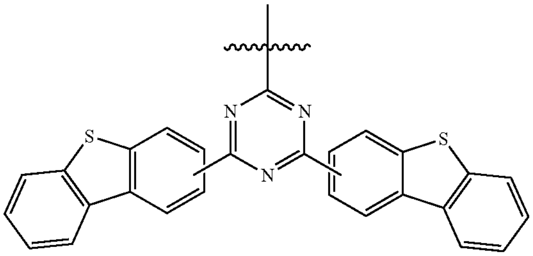
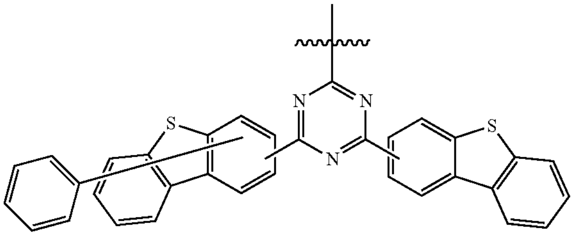
-continued
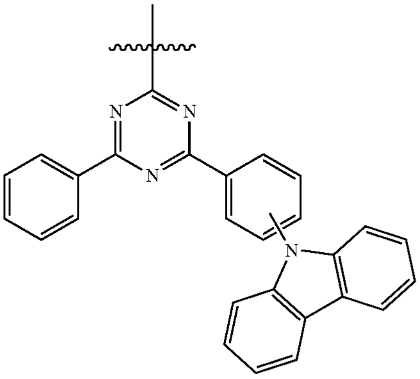
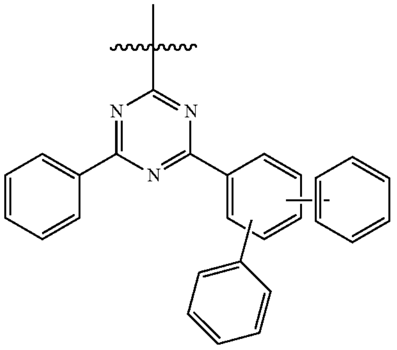
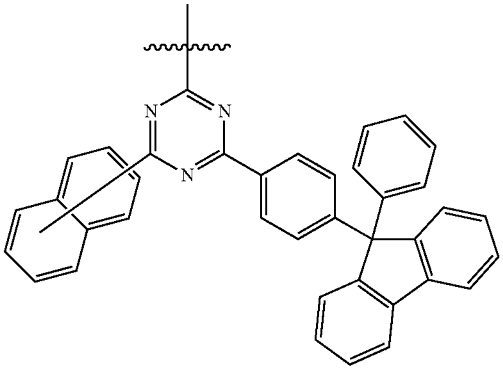
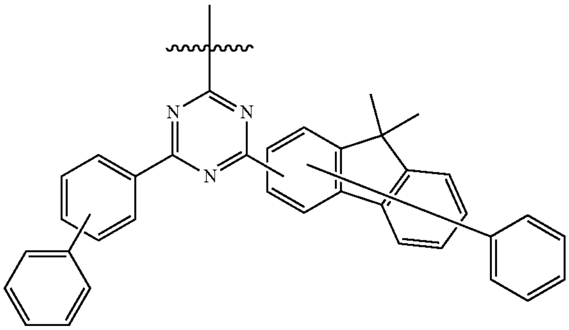
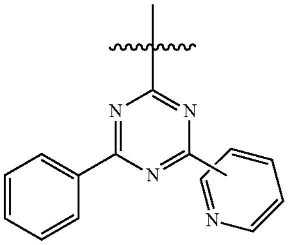

-continued
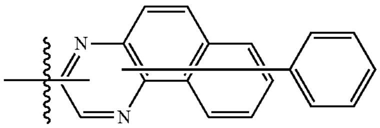
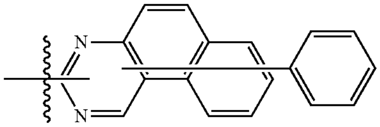
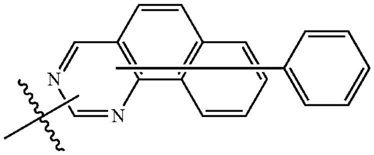
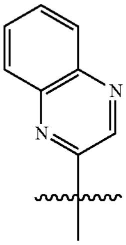
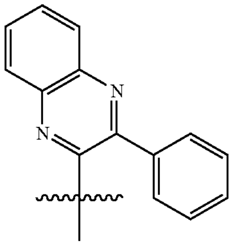
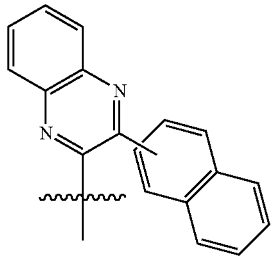
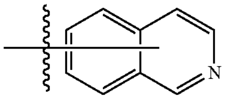
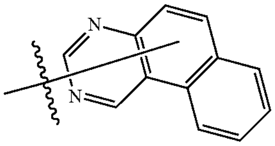
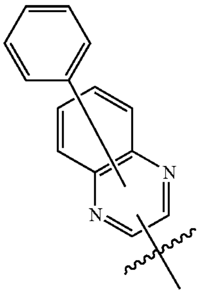
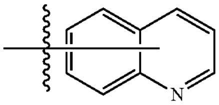
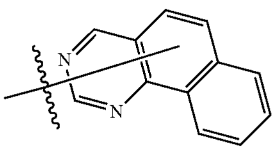
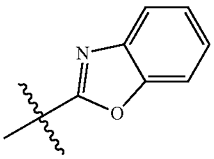
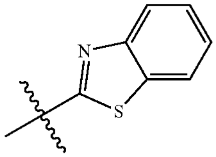
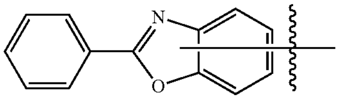
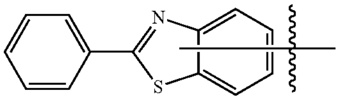
-continued
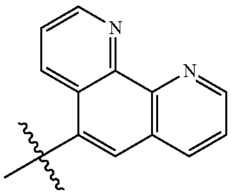
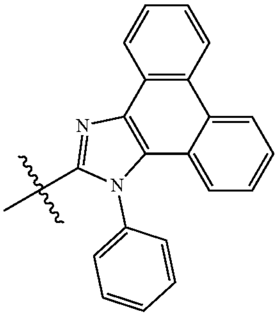
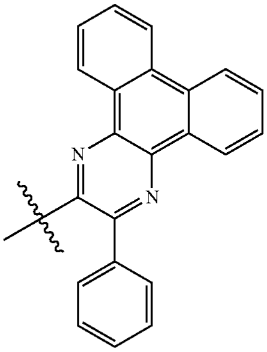
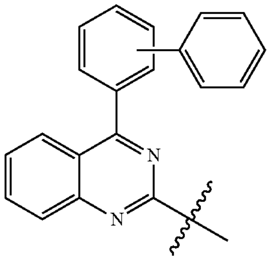
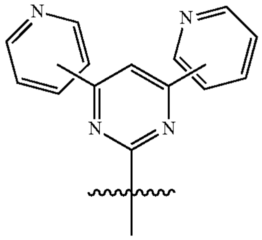
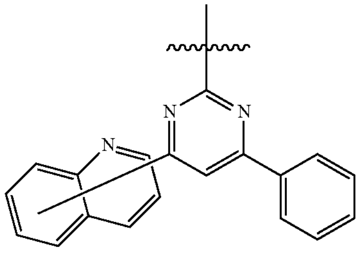
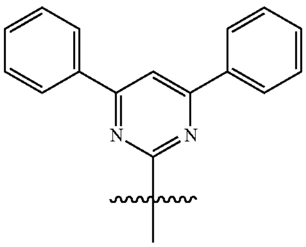
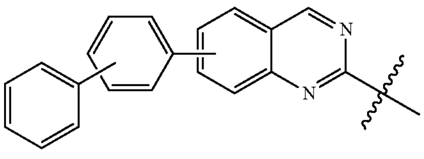

-continued
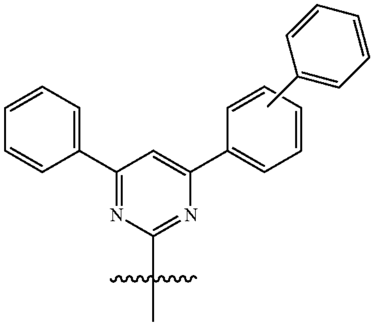
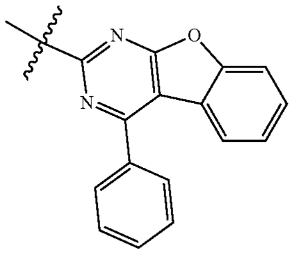
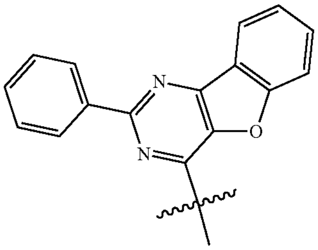
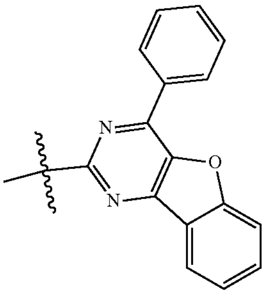
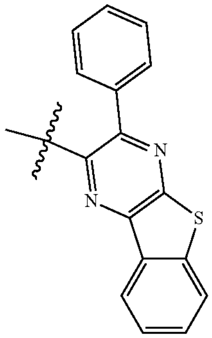
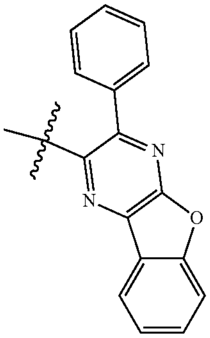
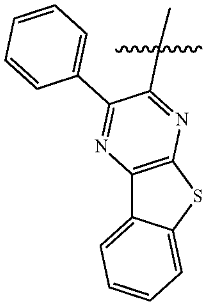
-continued
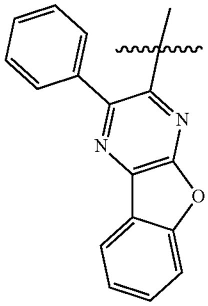
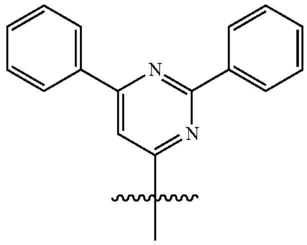
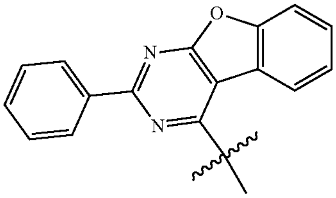
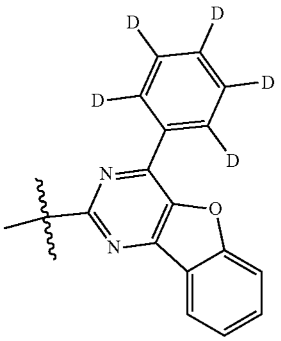
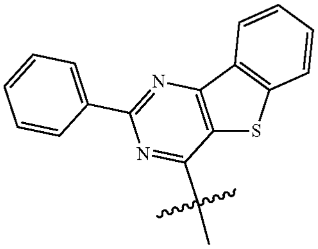
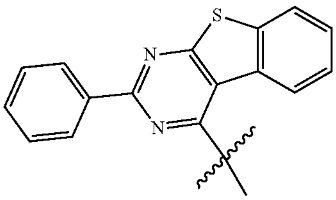
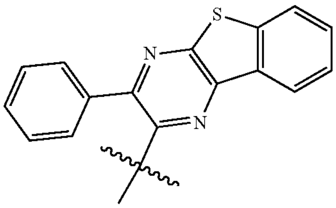

-continued
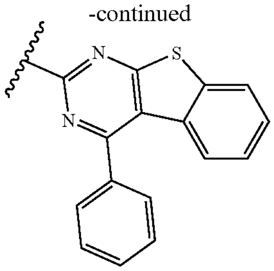
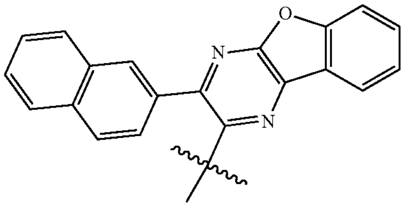
-continued
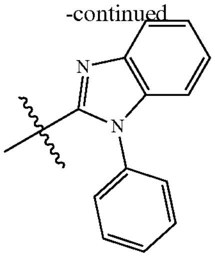
.
In a specific embodiment of the present application, the organic compound is selected from the group consisting of the following organic compounds.
1
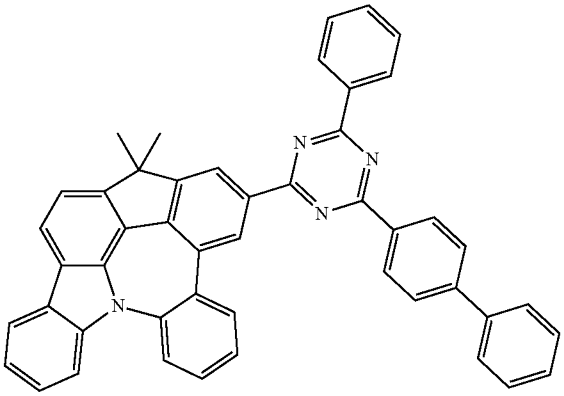
2
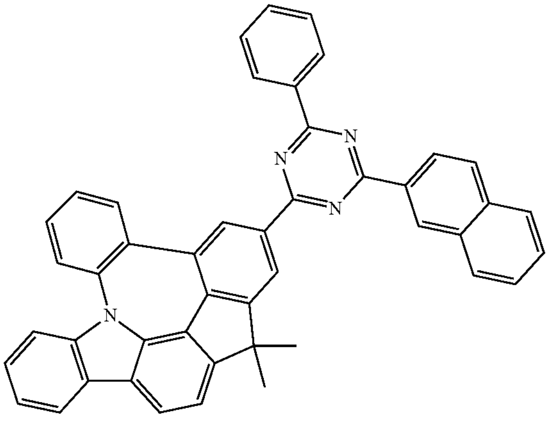
3
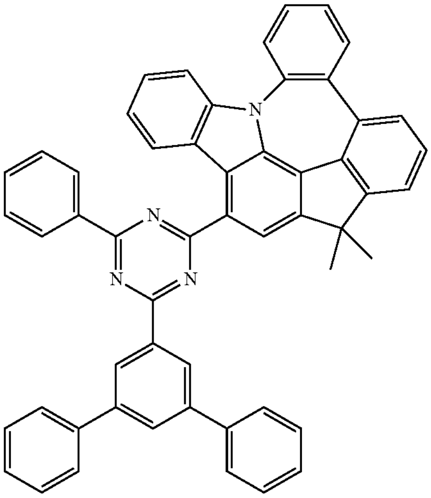
4
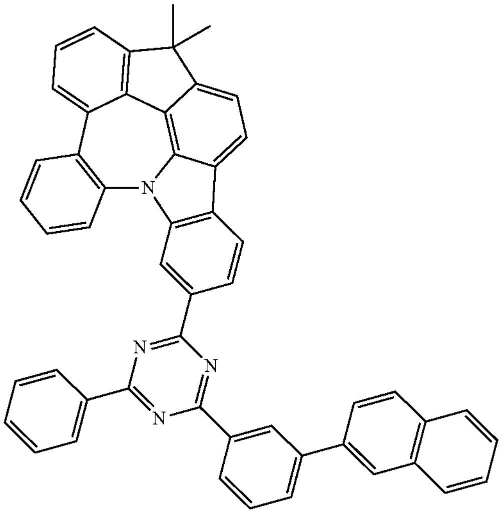

-continued
5
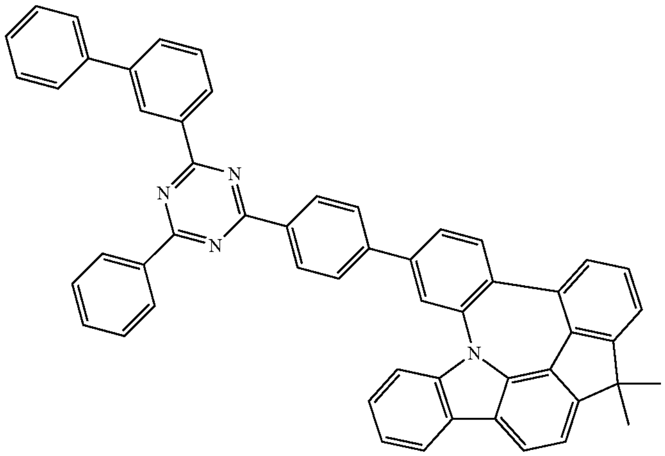
6
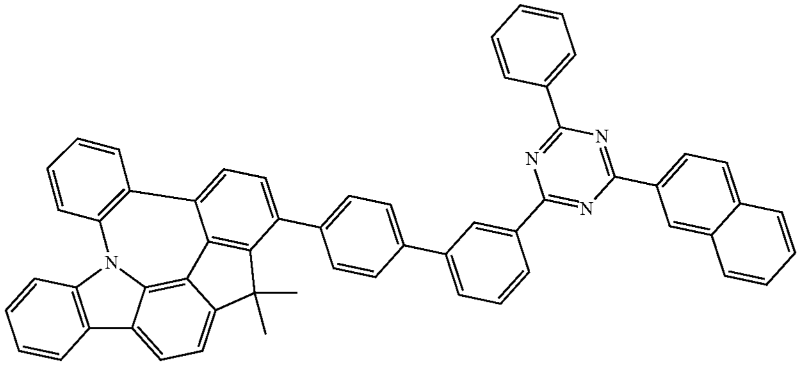
7
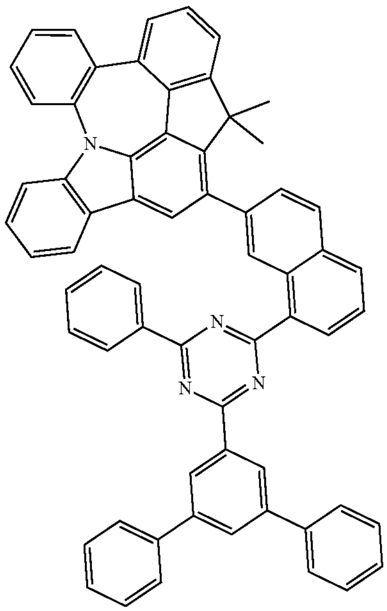
8
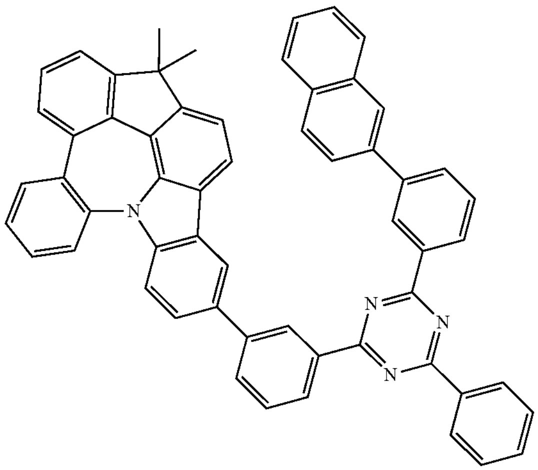

-continued
9
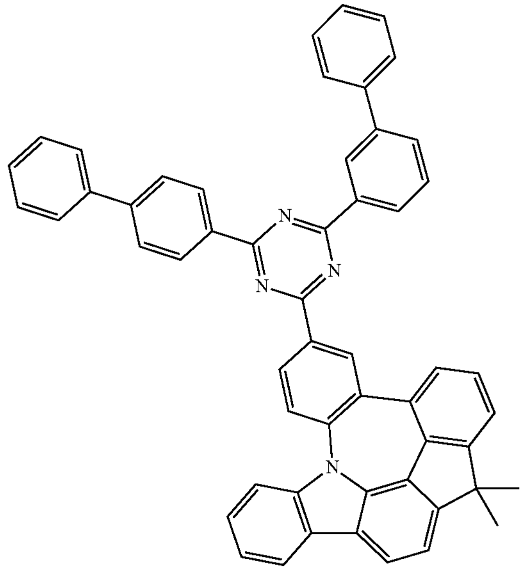
10
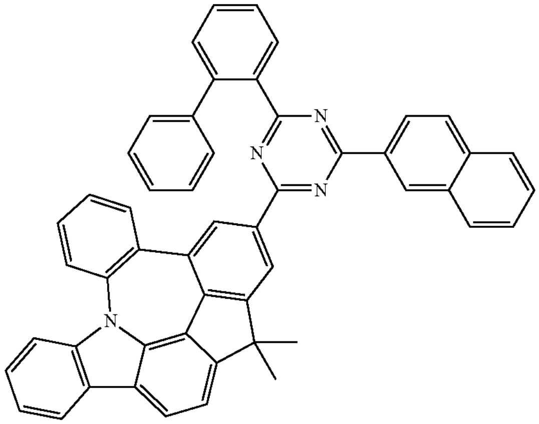
11
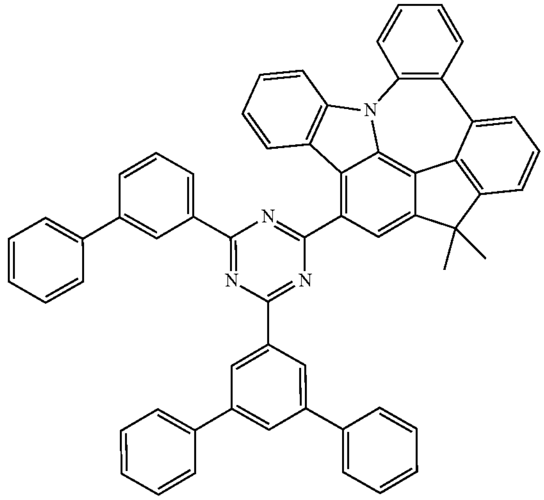
12
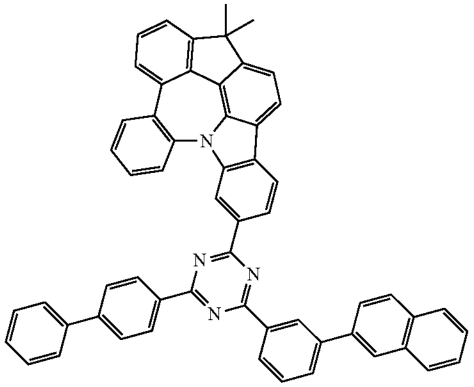
13
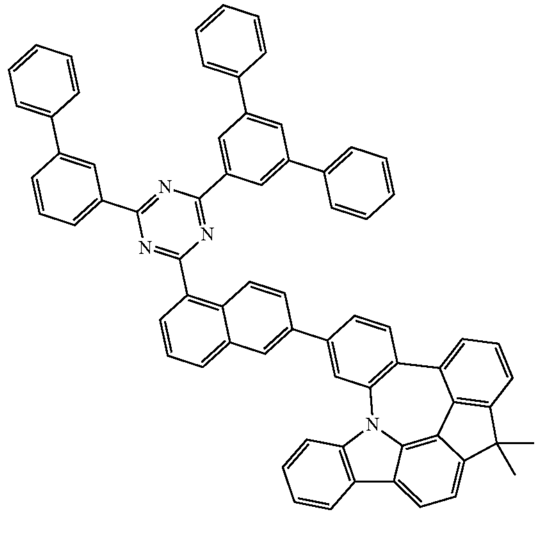
14
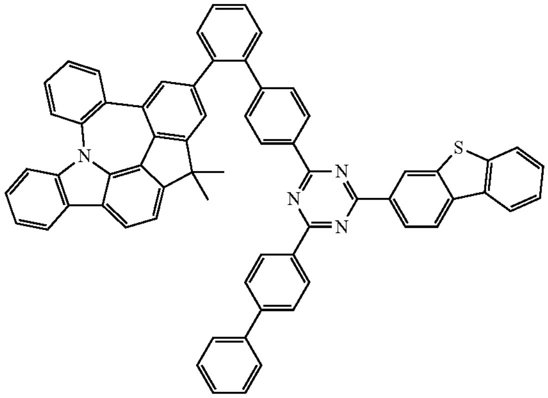

-continued
15
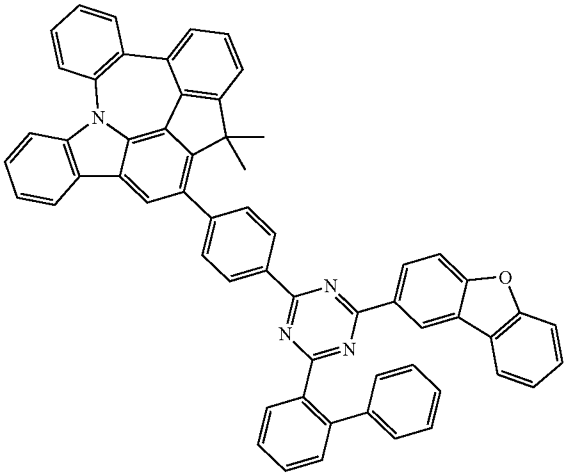
16
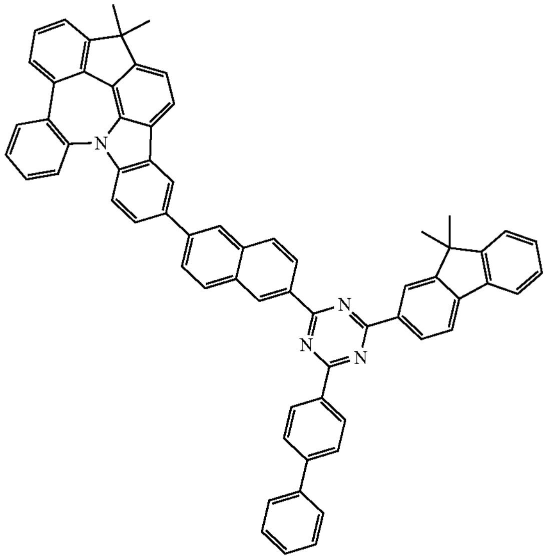
17
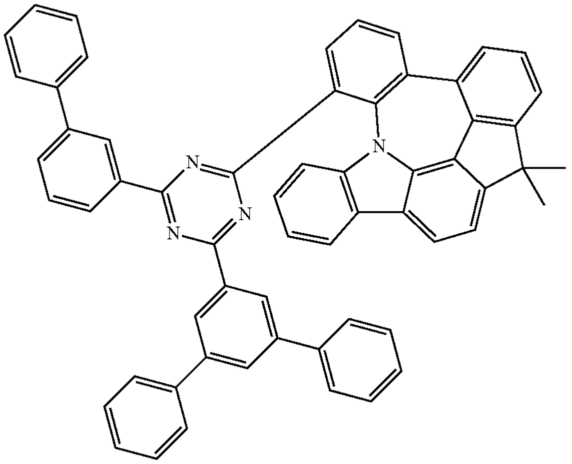
18
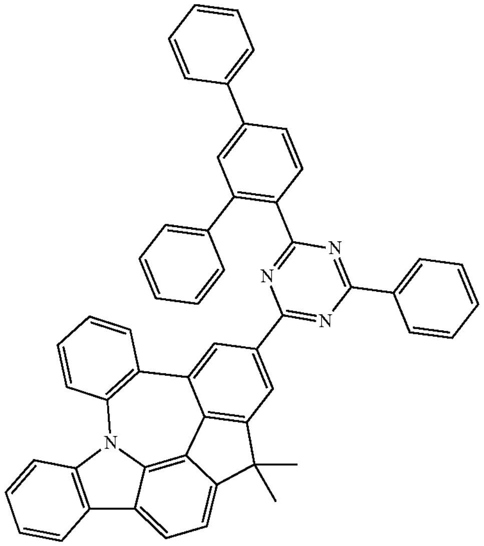

-continued
19
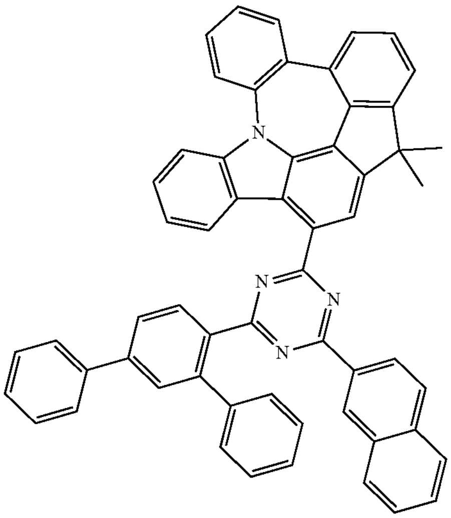
20
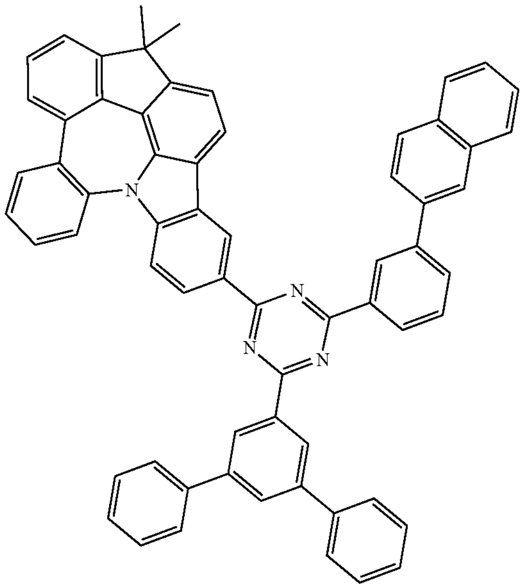
21
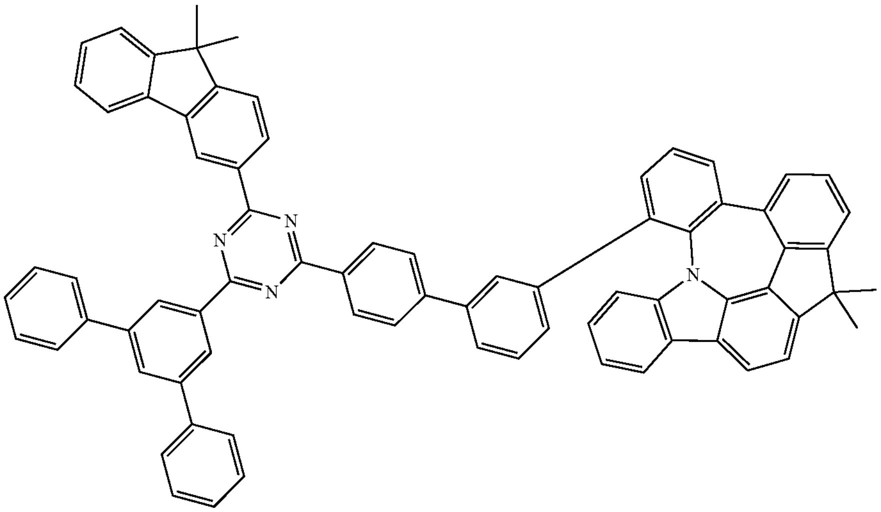
22
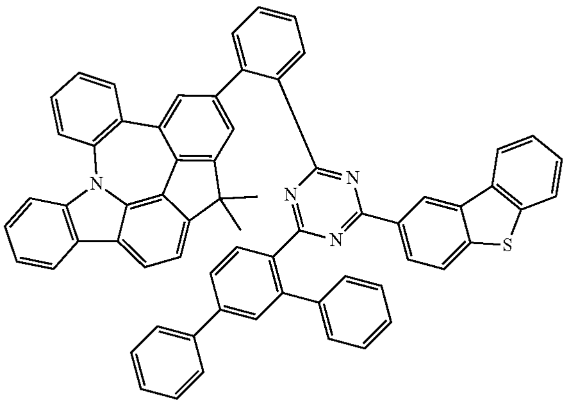
23
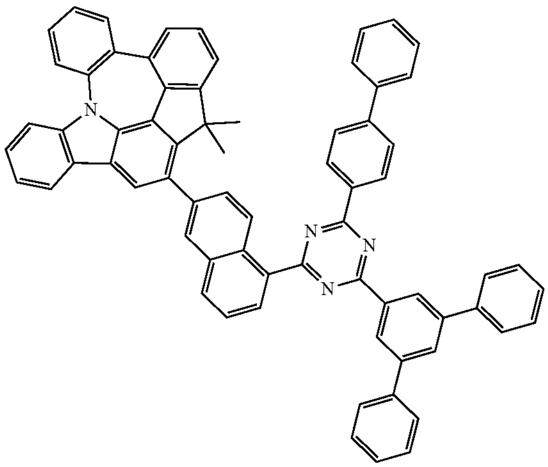

-continued
24
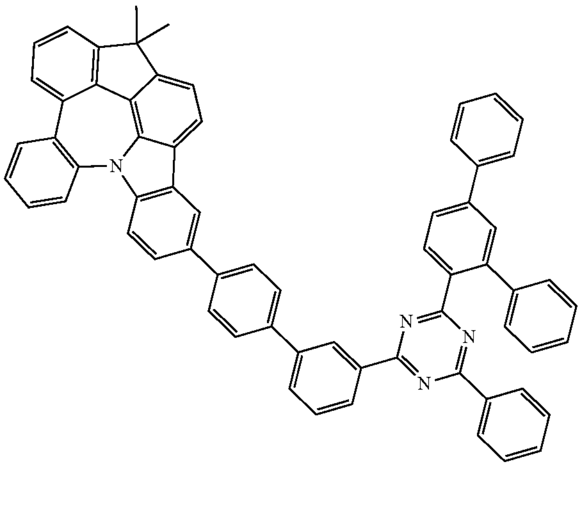
25
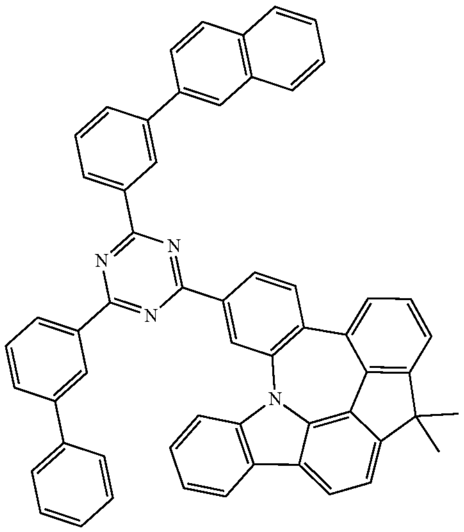
26
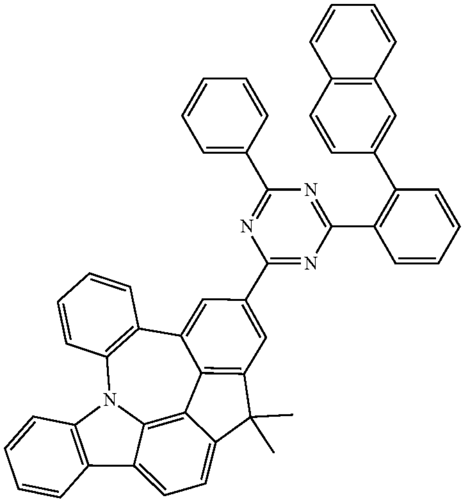
27
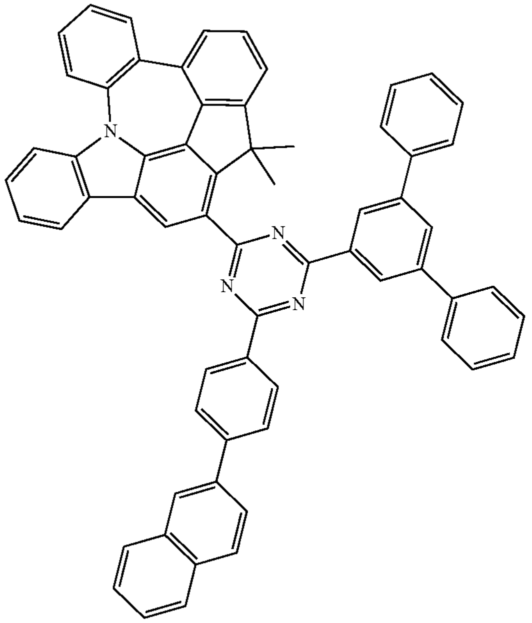

-continued
28
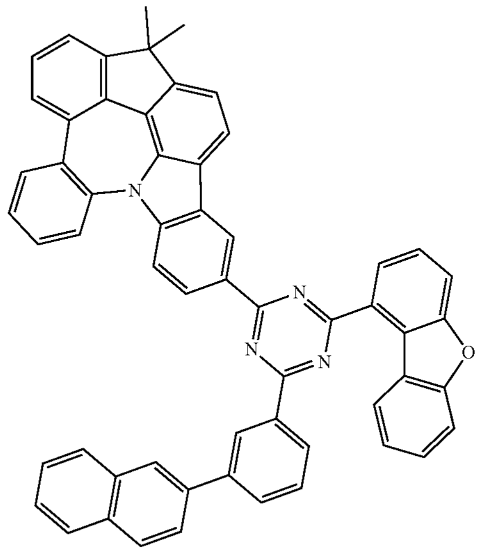
29
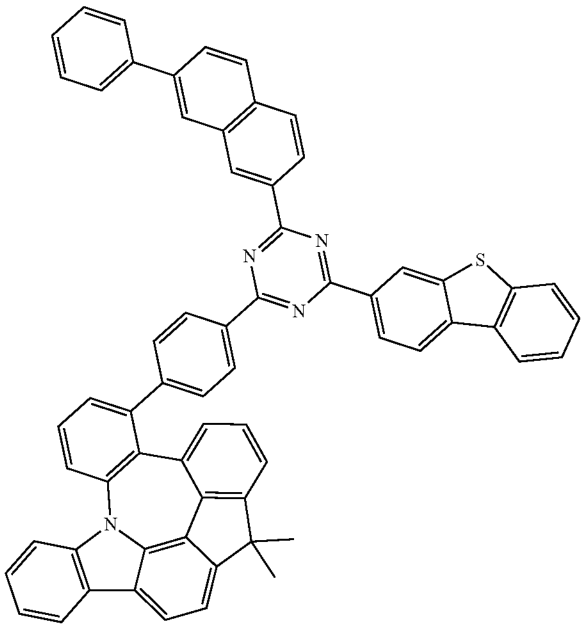
30
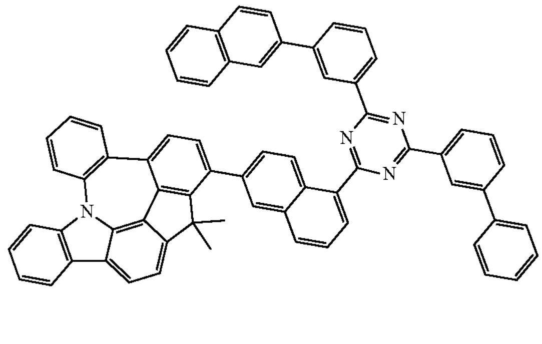
31
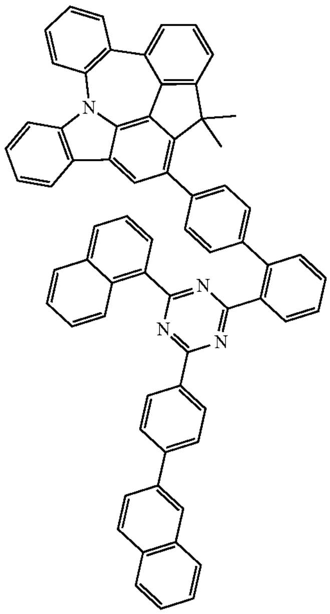

-continued
32
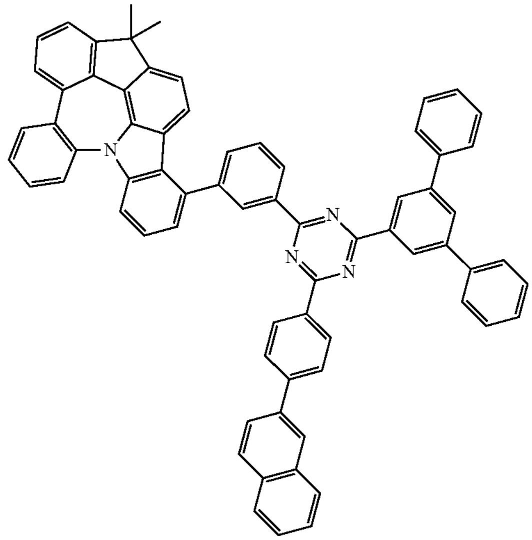
33
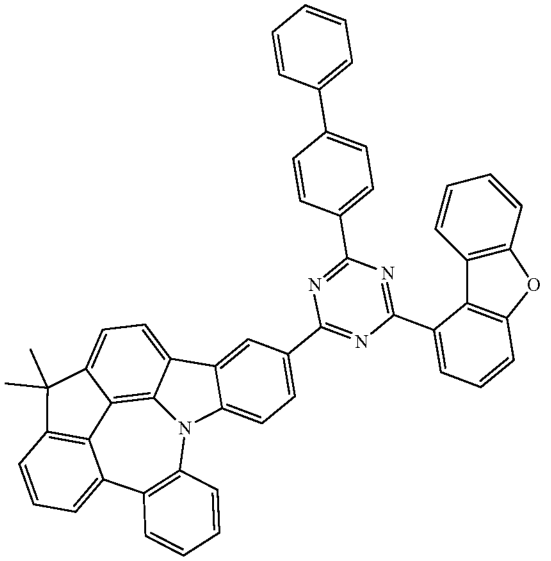
34
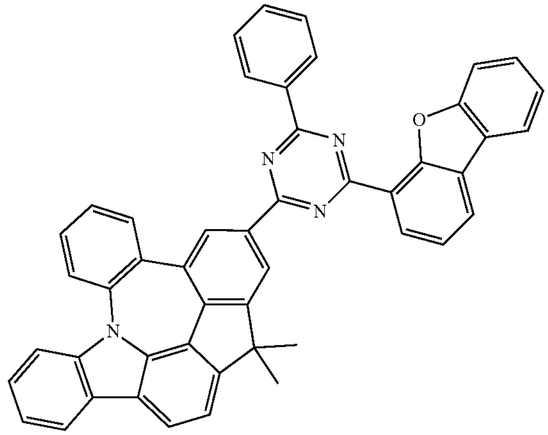
35
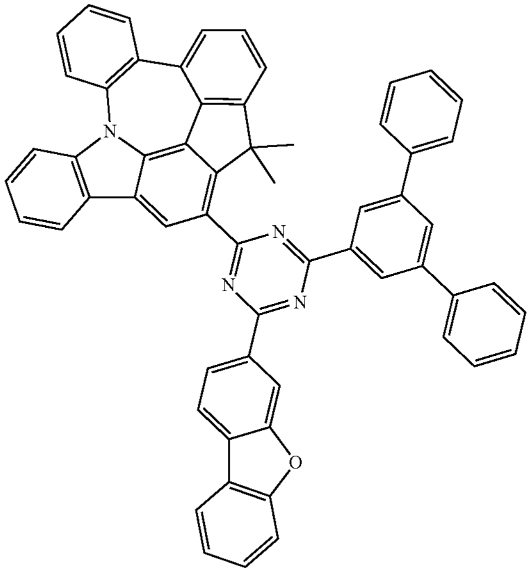
36
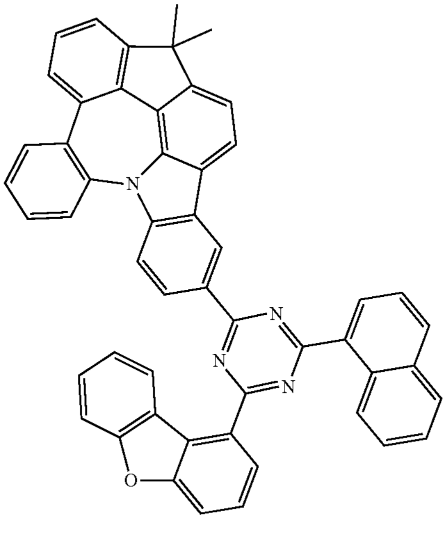
37
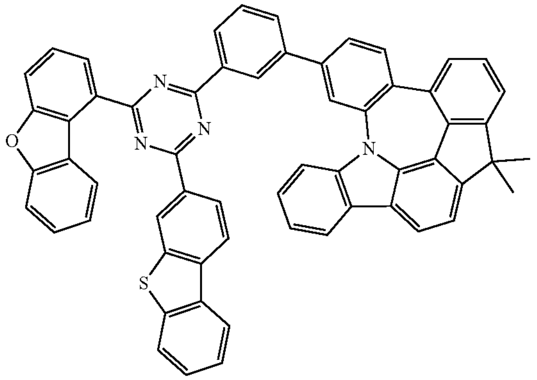

-continued
38
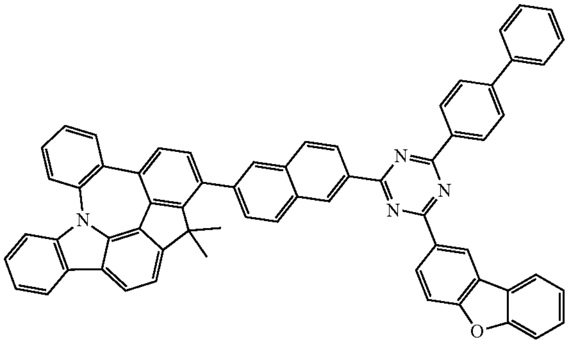
39
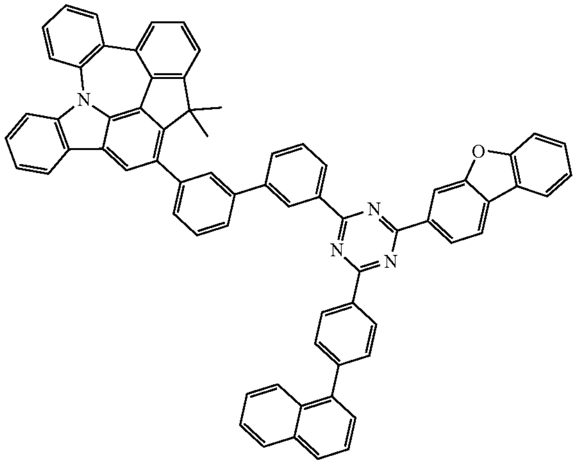
40
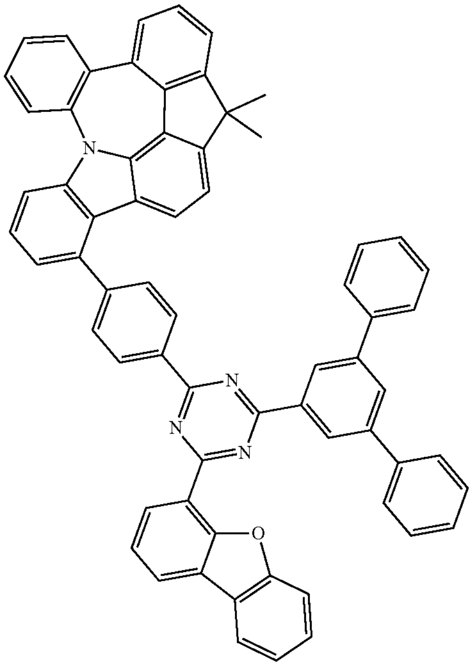
41
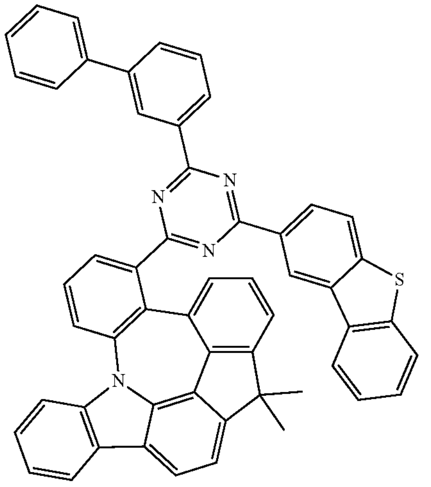

-continued
42
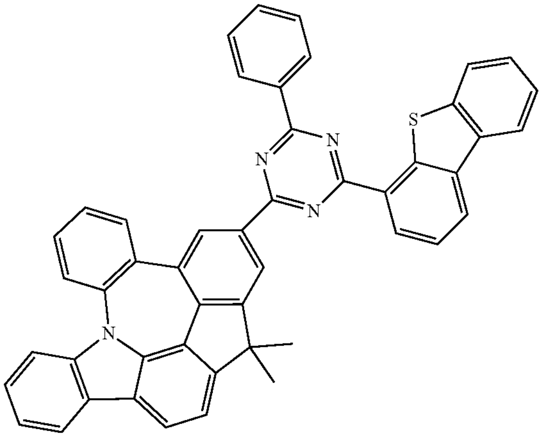
43
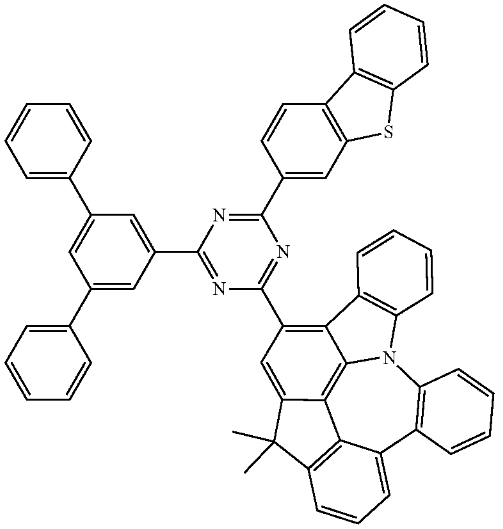
44
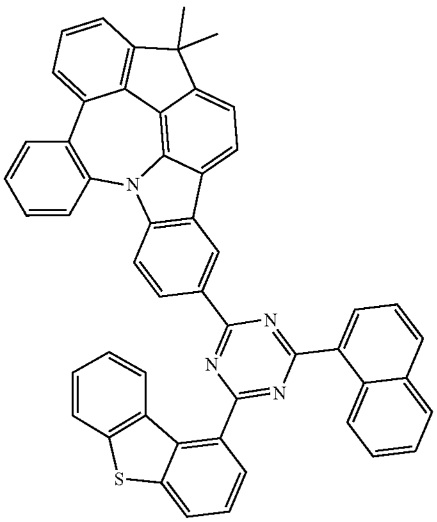
45
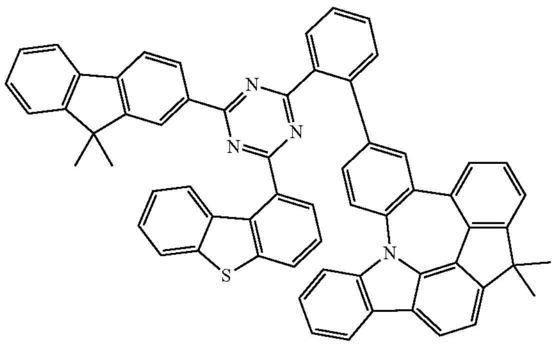

-continued
46
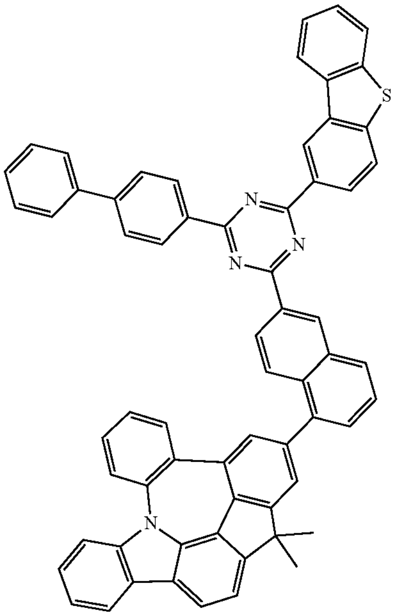
47
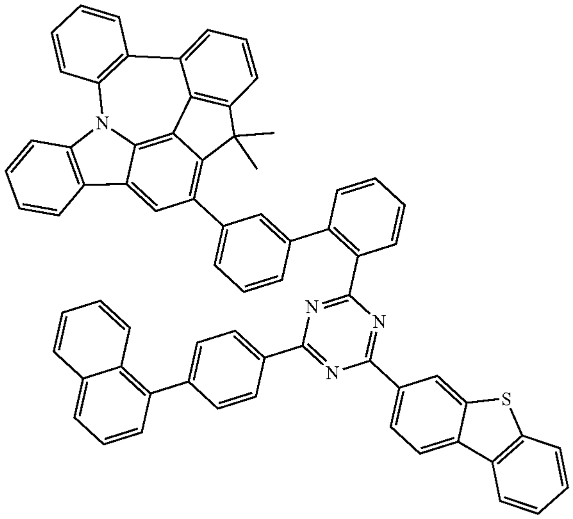
48
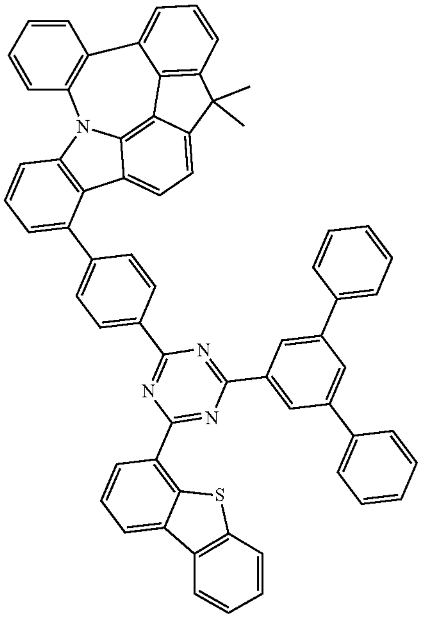
49
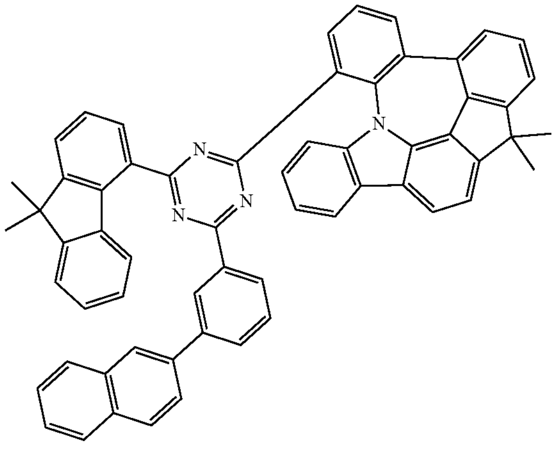

-continued
50
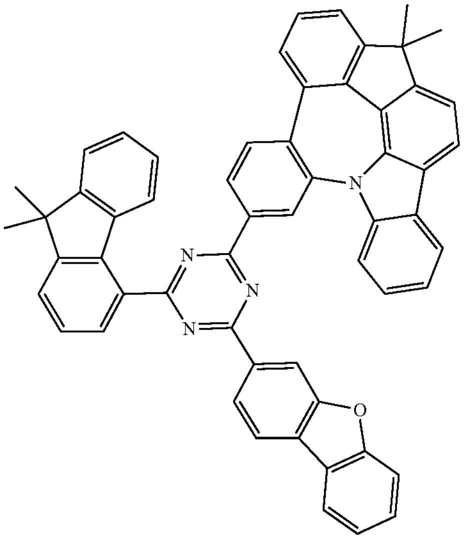
51
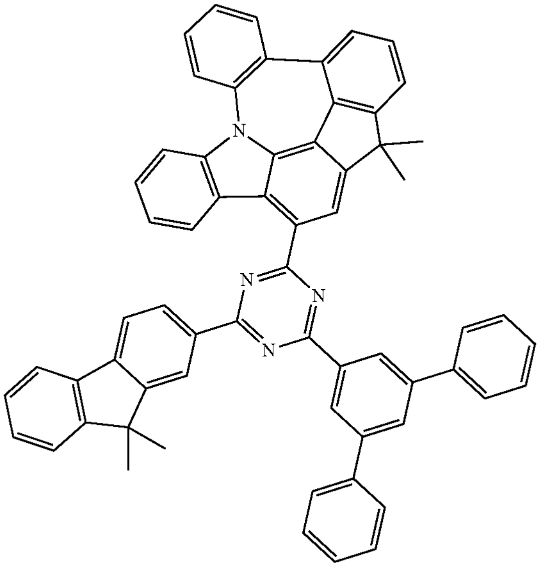
52
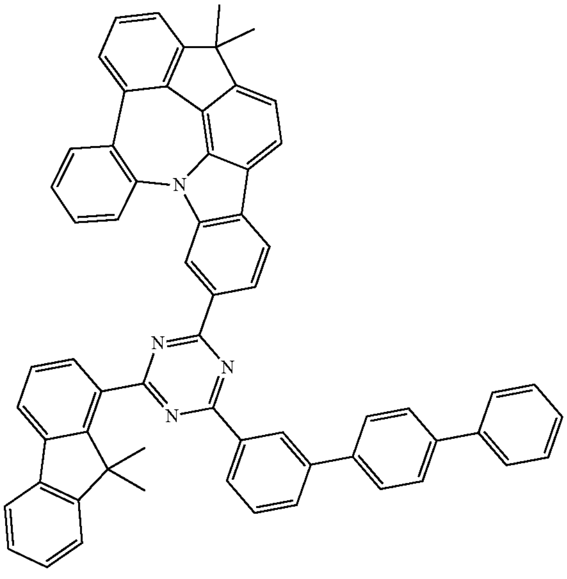
53
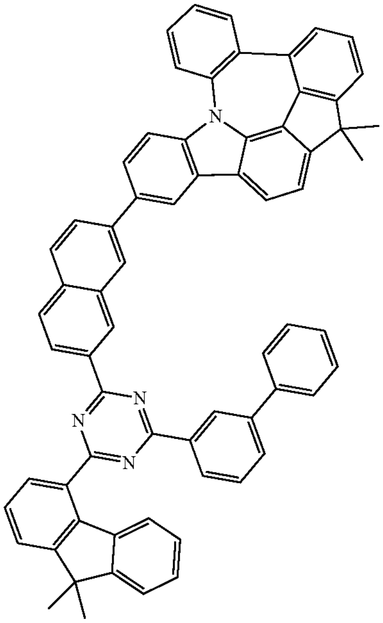

-continued
54
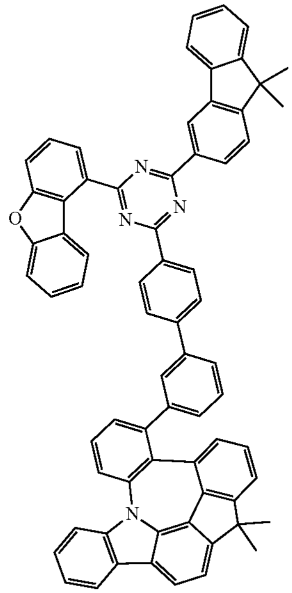
55
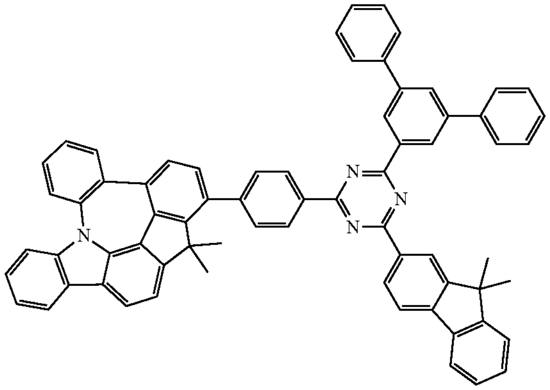
56
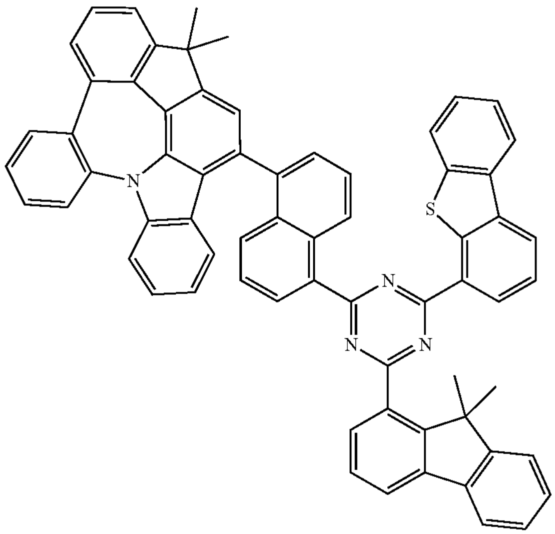
57
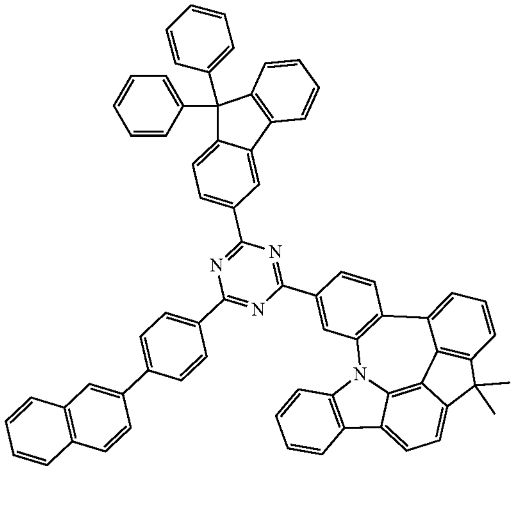

-continued
58
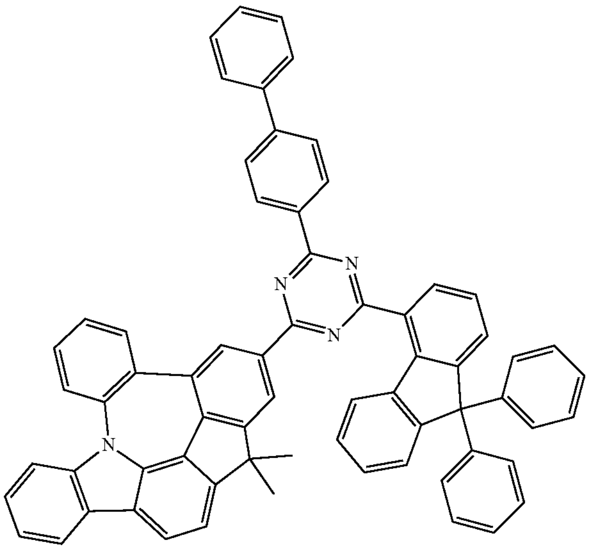
59
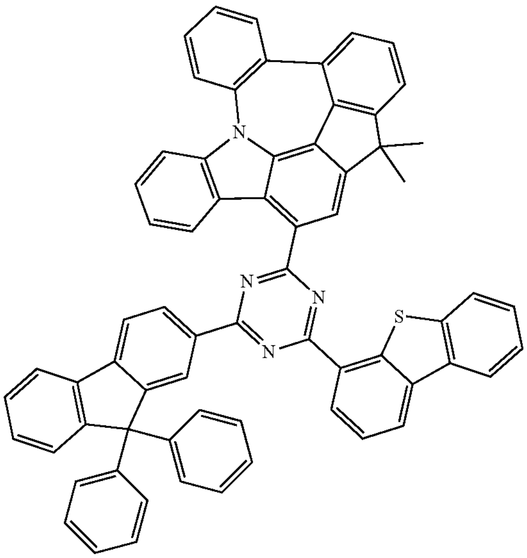
60
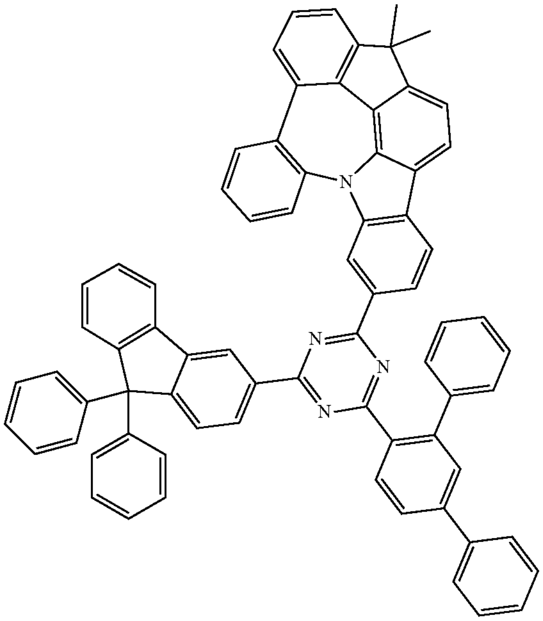
61
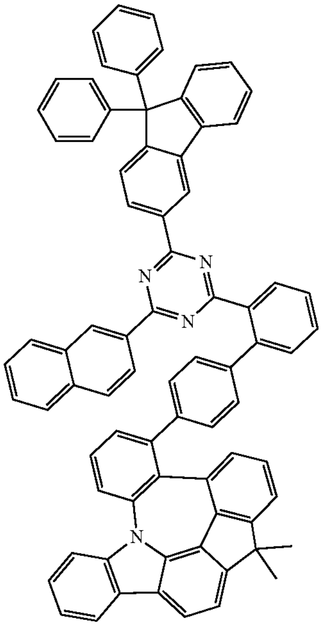
62
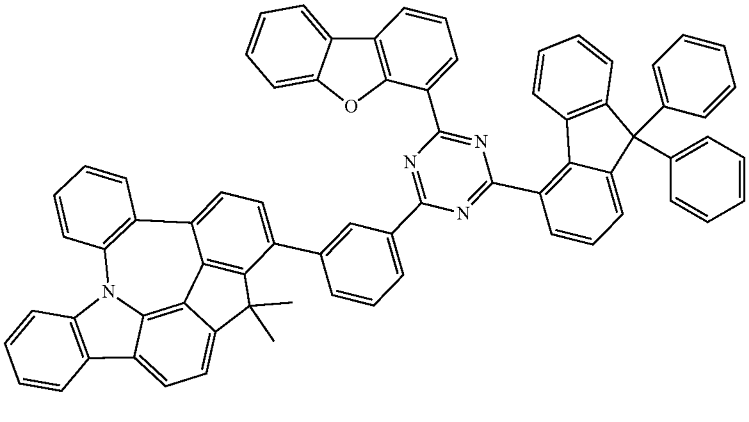

-continued
63
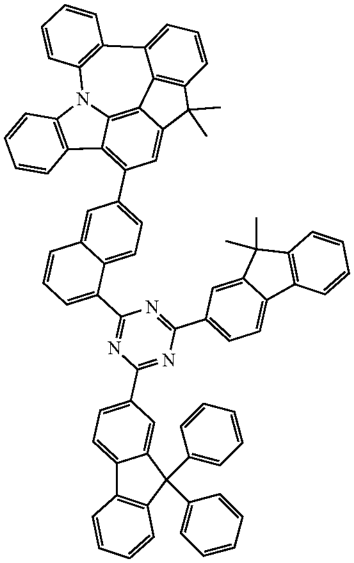
64
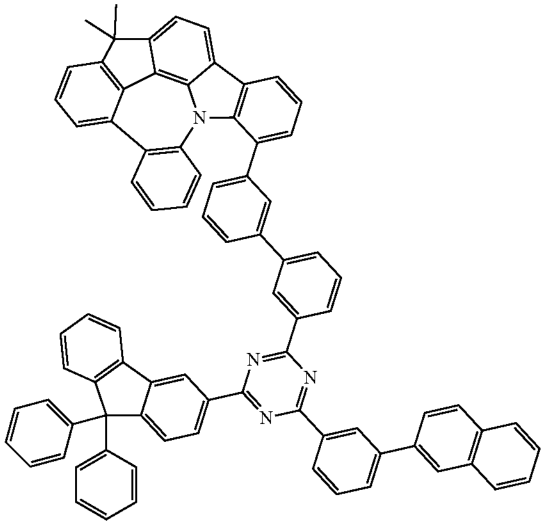
65
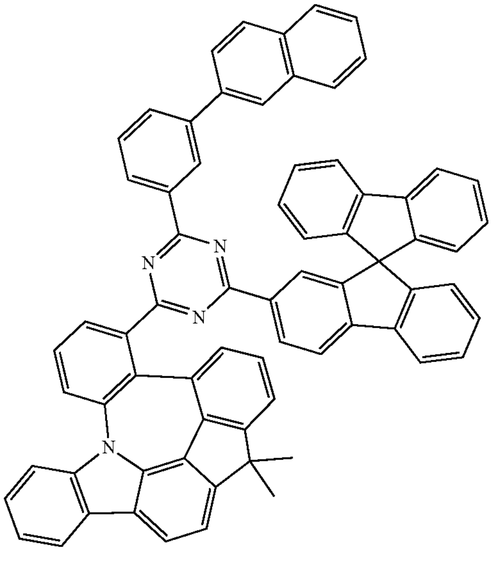
66
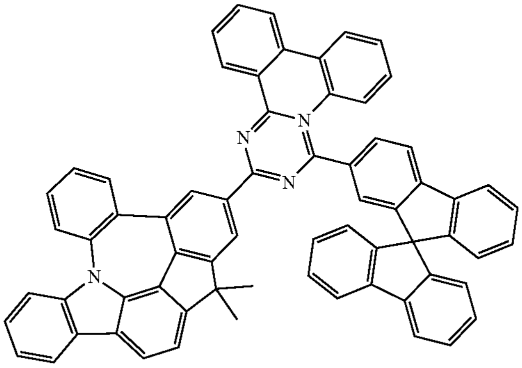

-continued
67
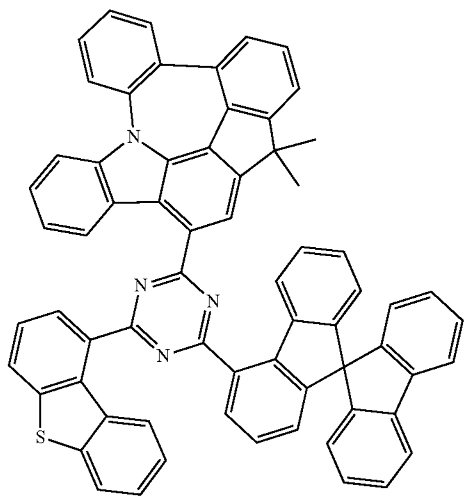
68
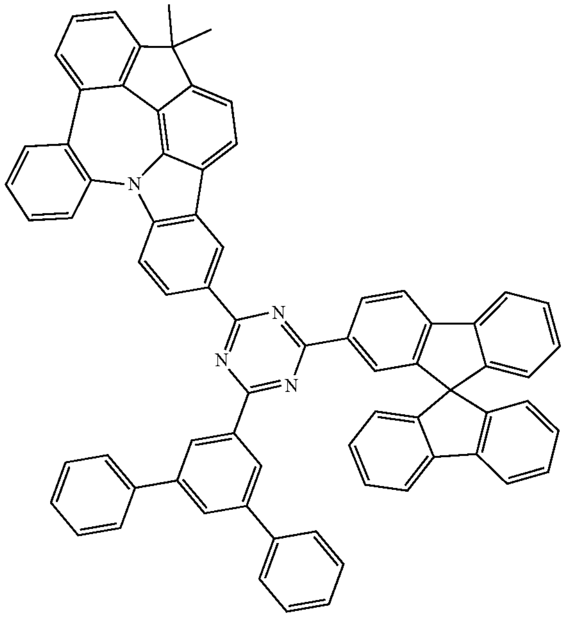
69
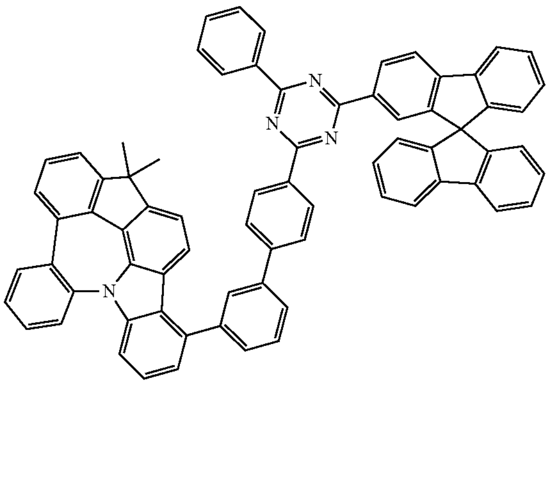
70
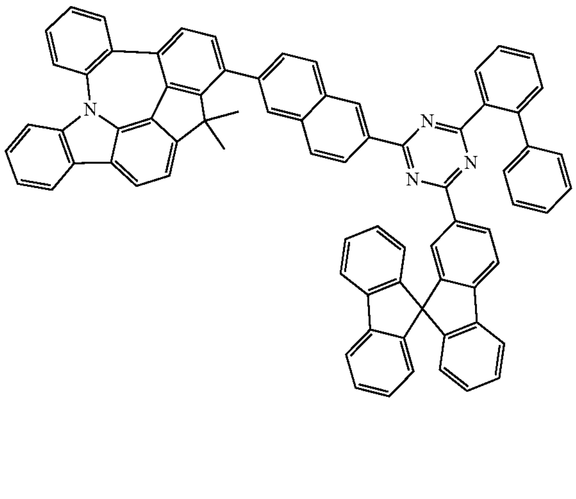

-continued
71
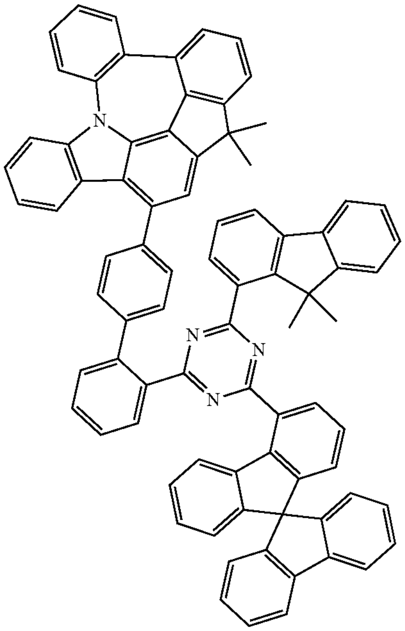
72
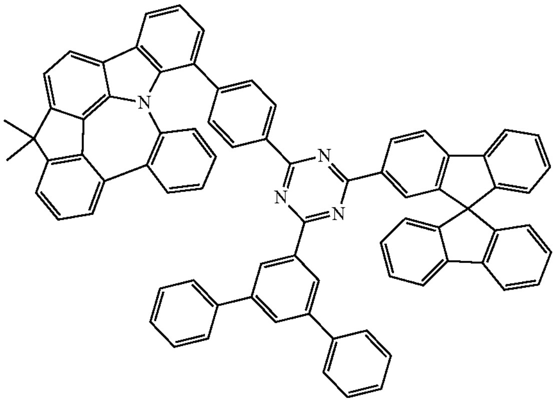
73
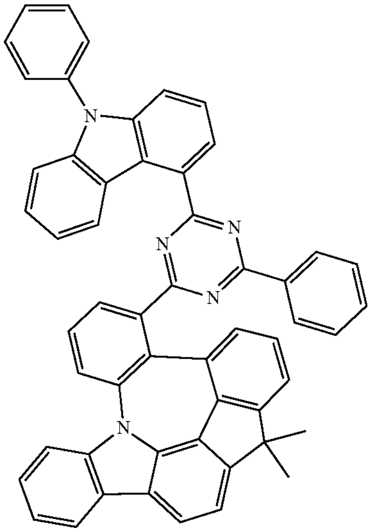
74
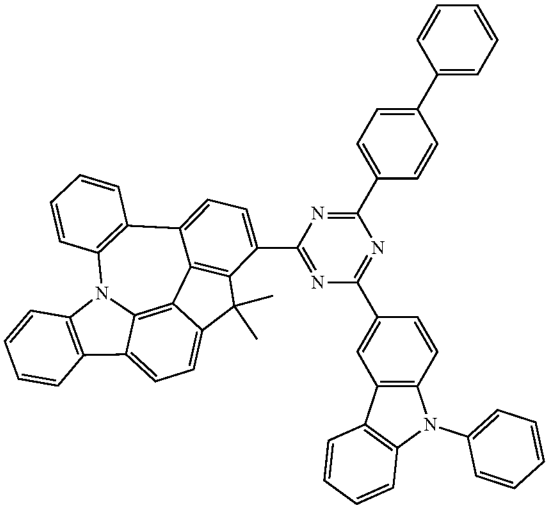

-continued
75
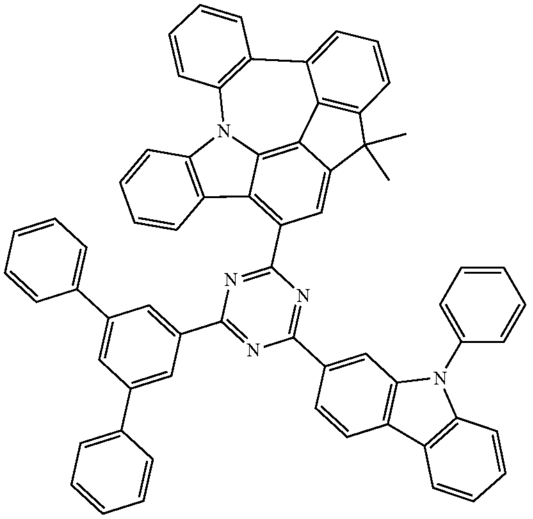
76
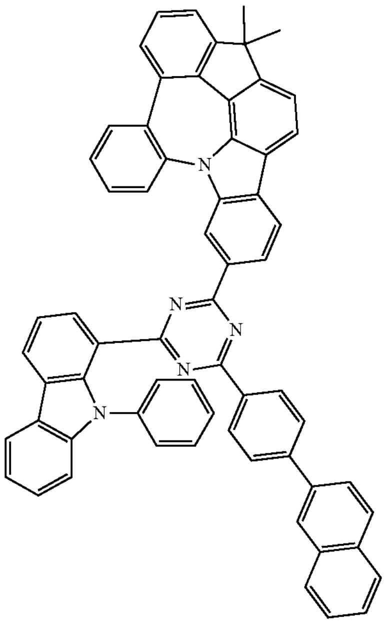
77
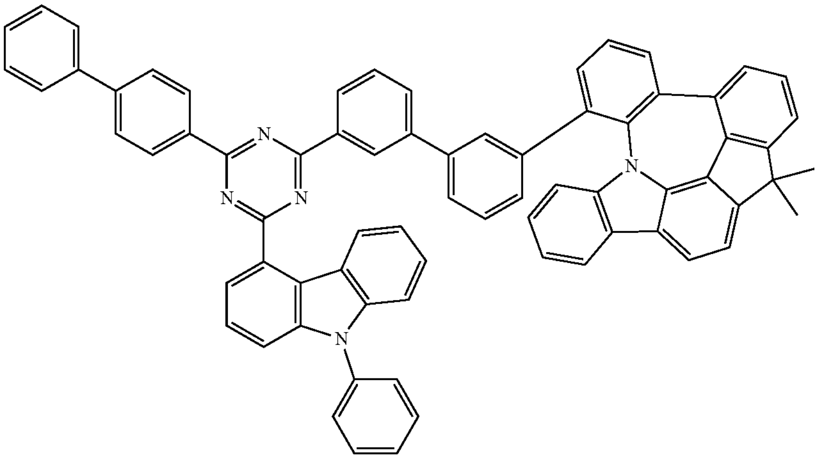

-continued
78
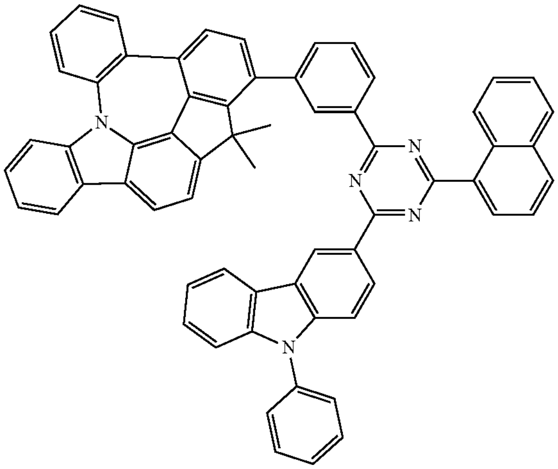
79
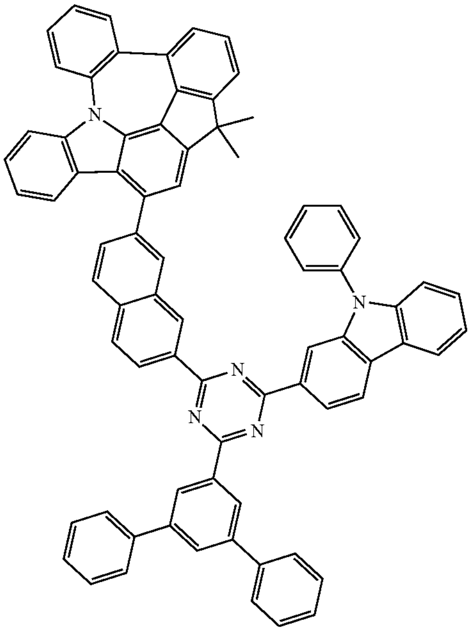
80
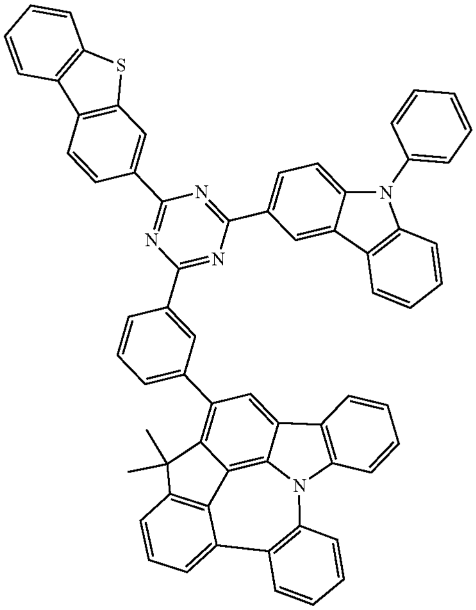
81
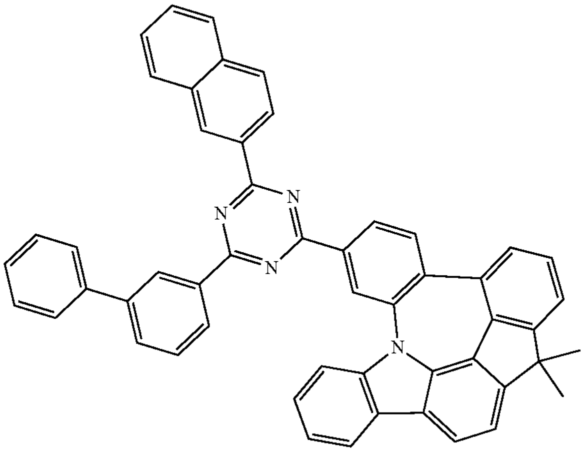

-continued
82
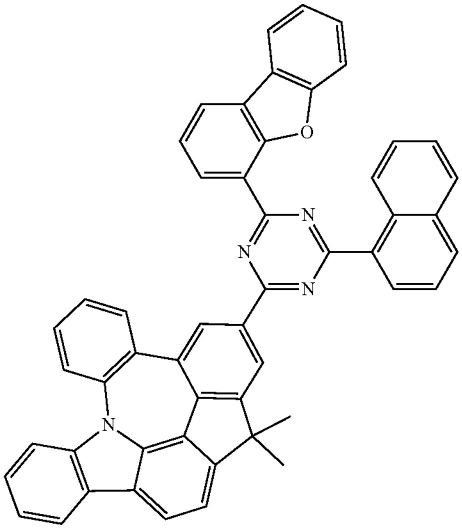
83
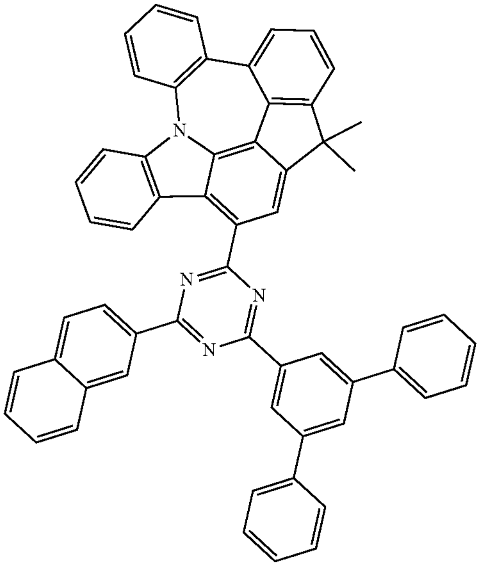
84
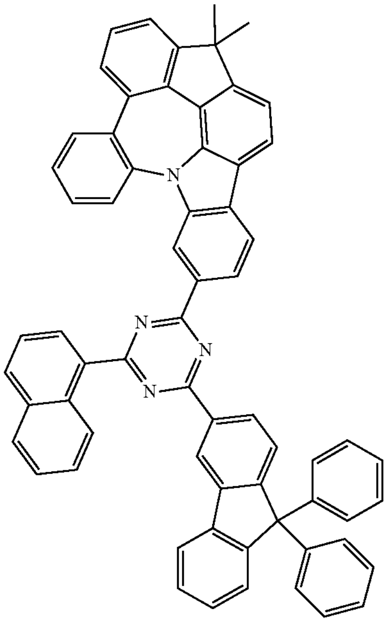
85
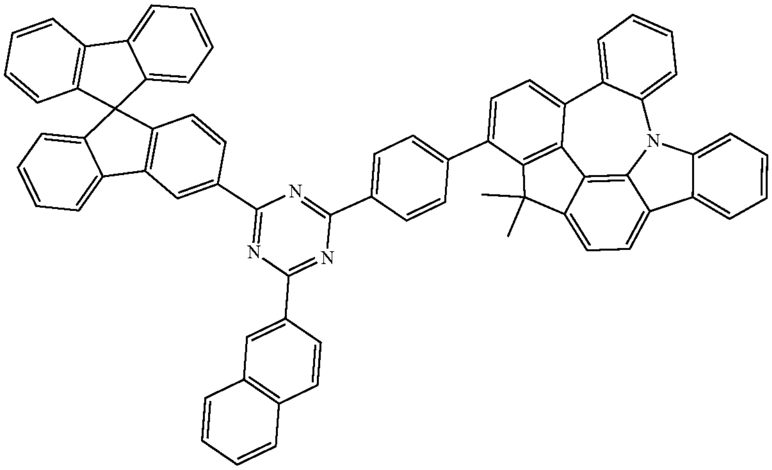

-continued
86
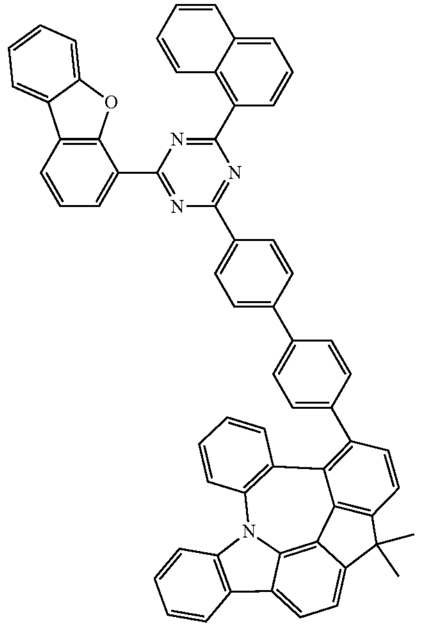
87
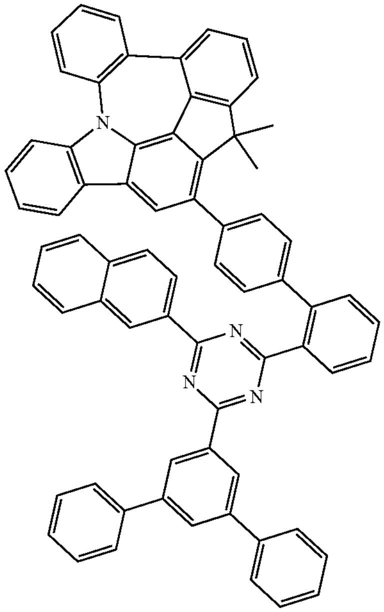
88
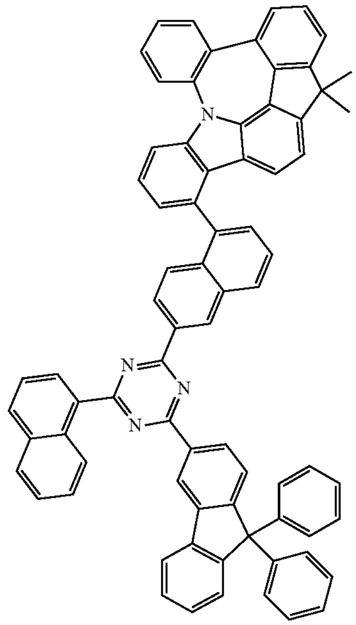
89
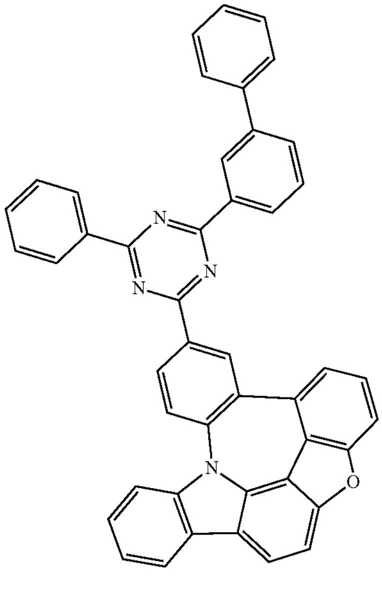

-continued
90
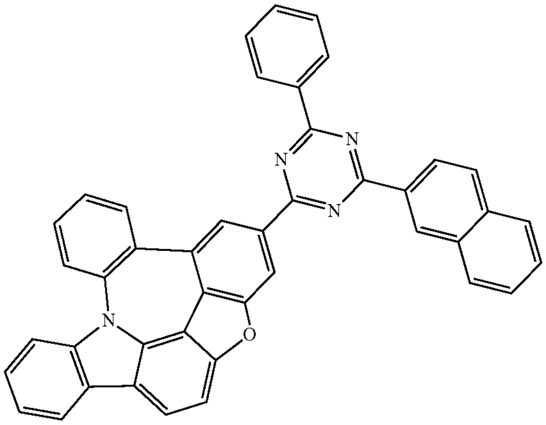
91
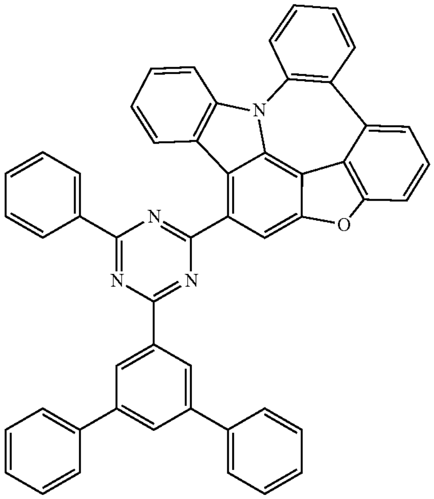
92
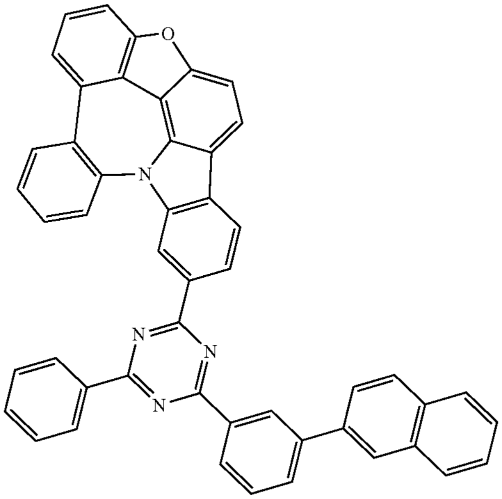
93
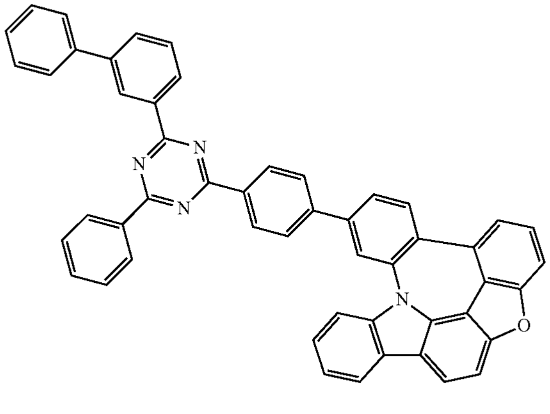
94
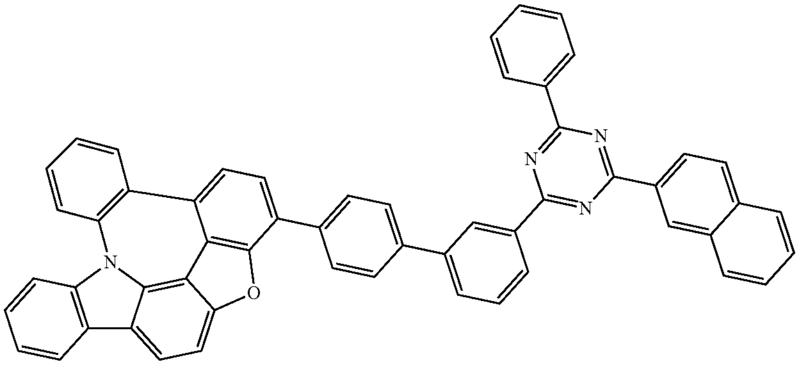

-continued
95
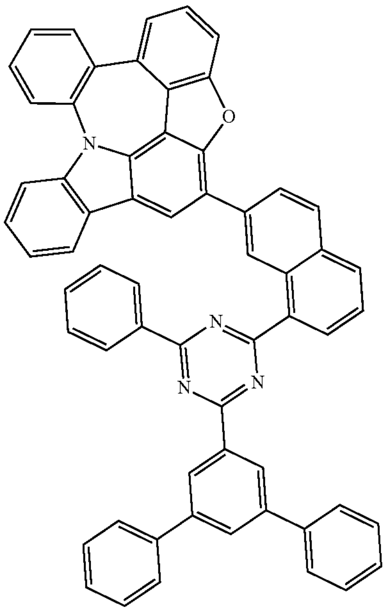
96
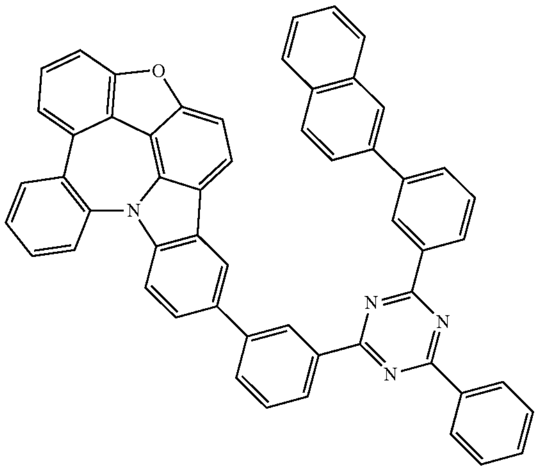
97
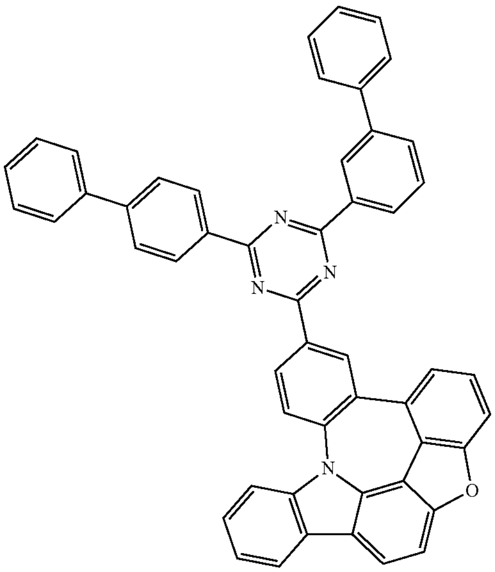
98
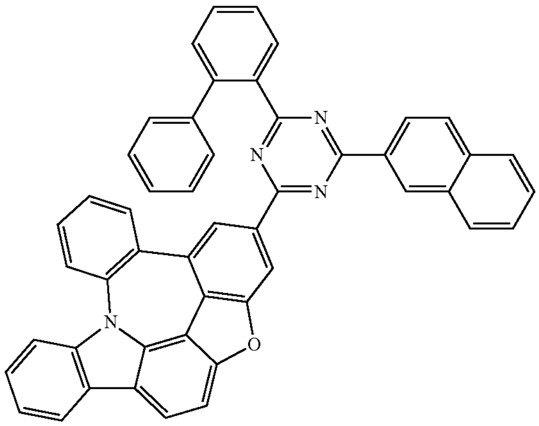

-continued
99
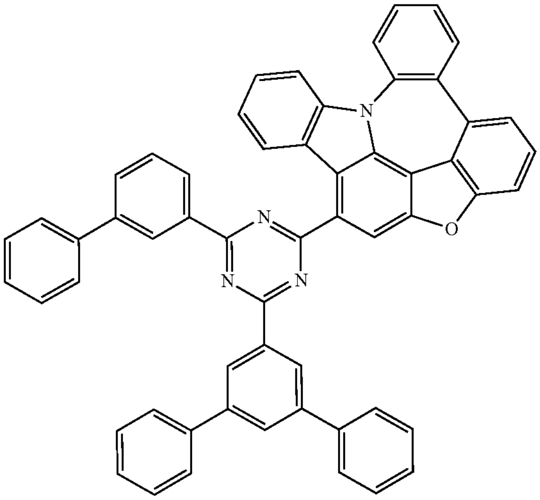
100
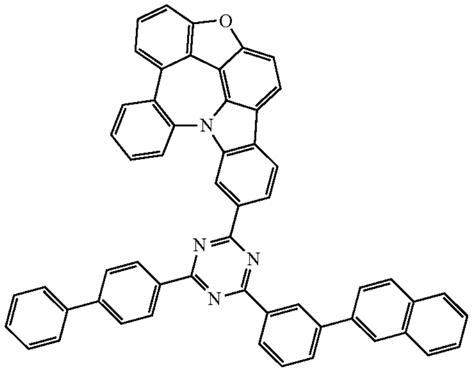
101
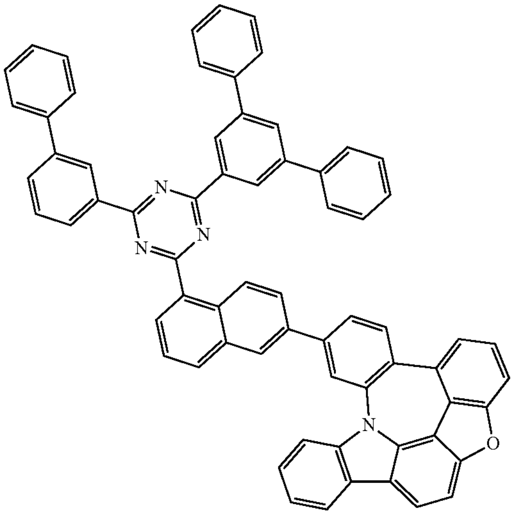
102
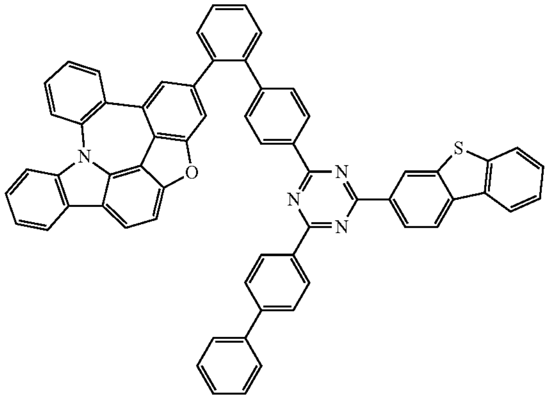
103
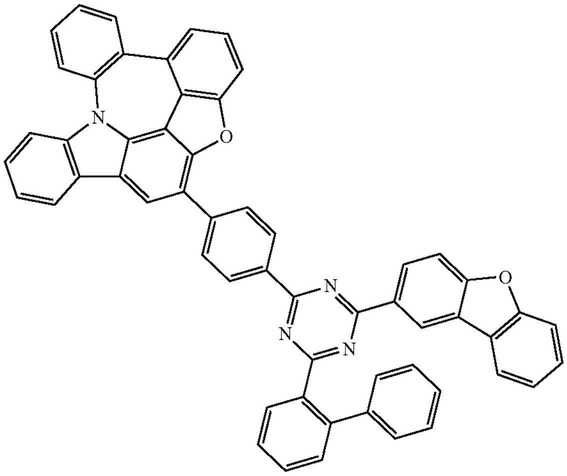
104
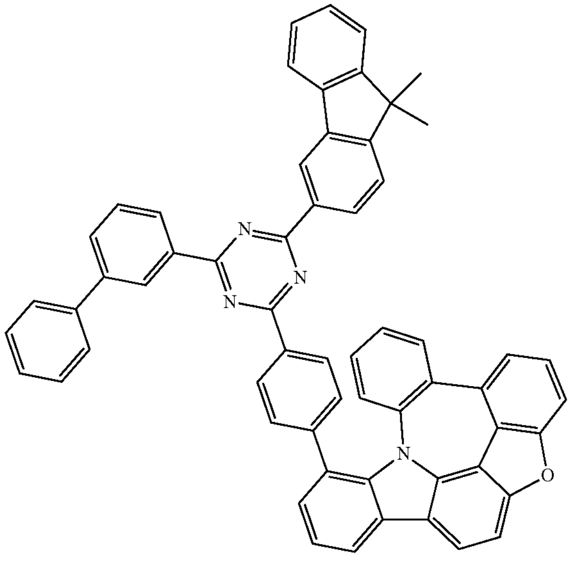

-continued
105
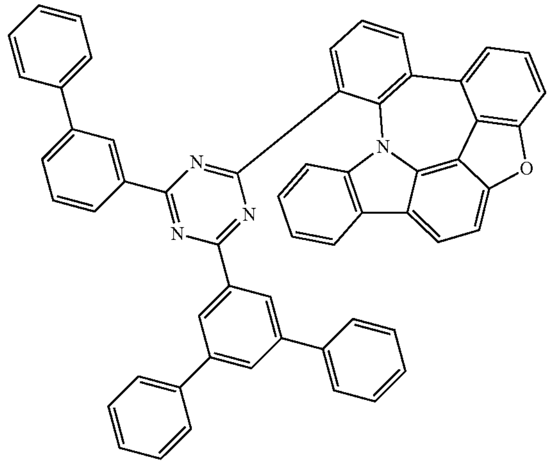
106
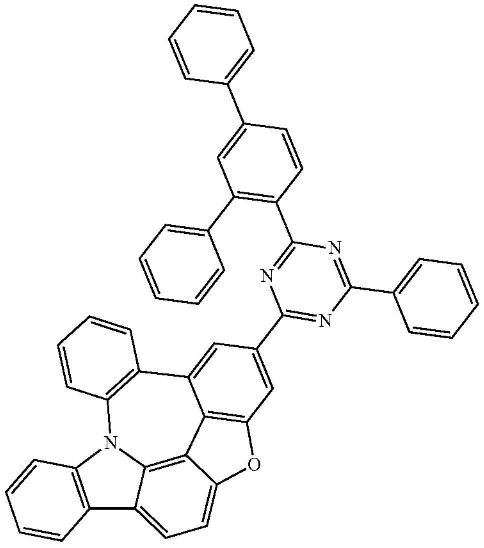
107
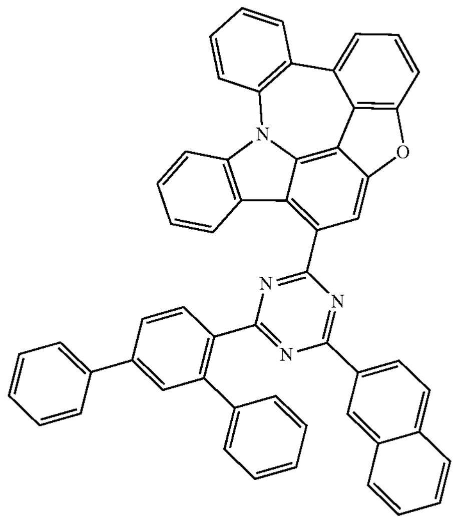
108
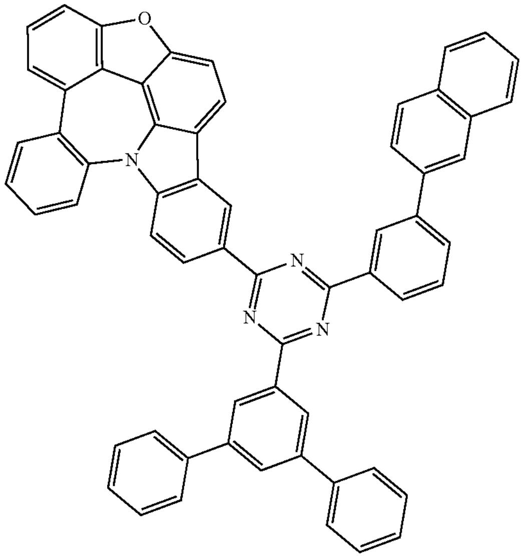
109
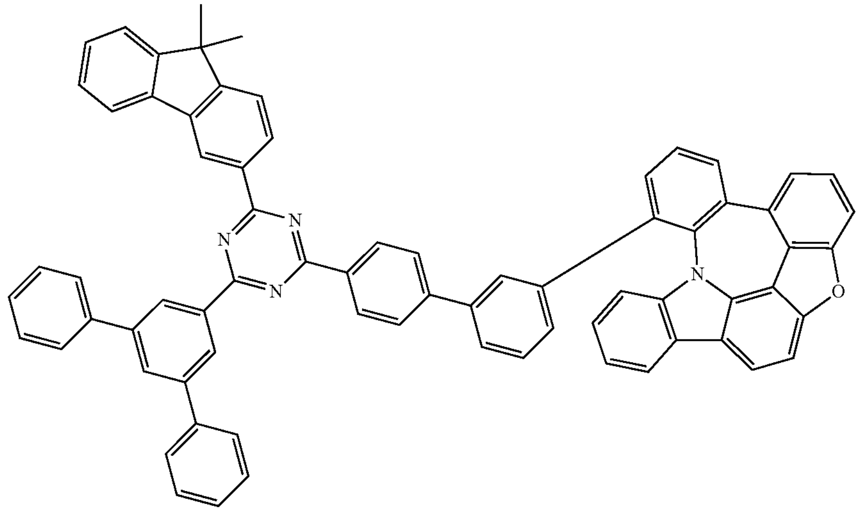

-continued
110
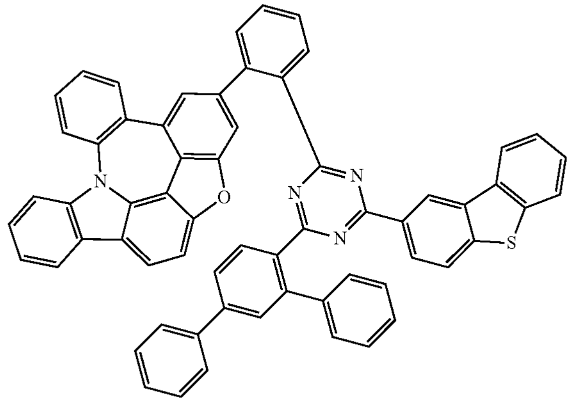
111
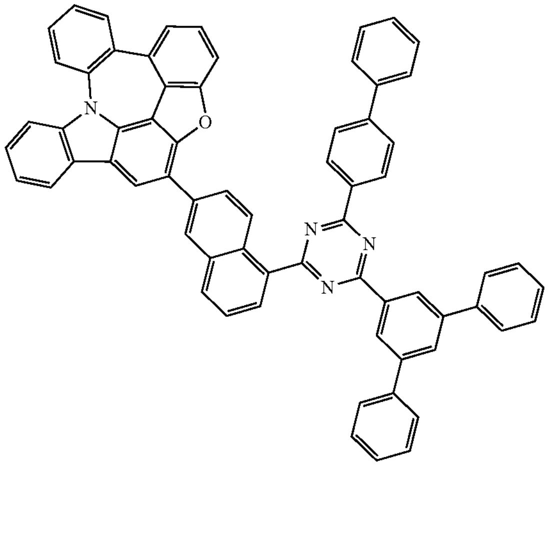
112
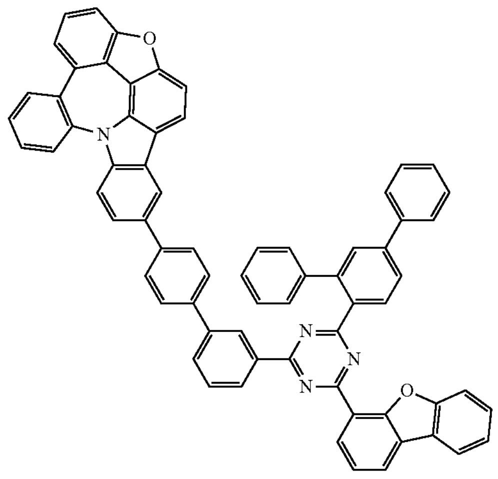
113
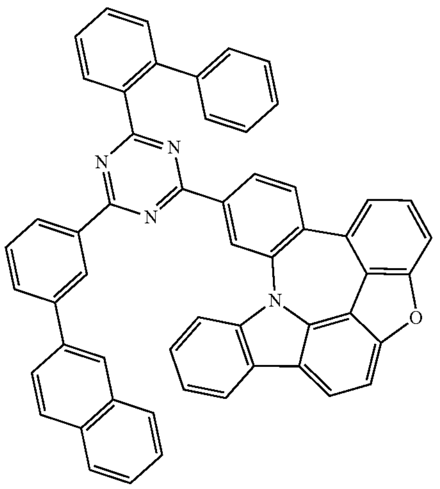
114
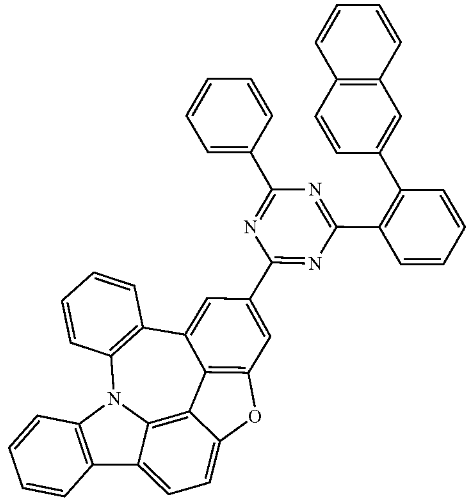
115
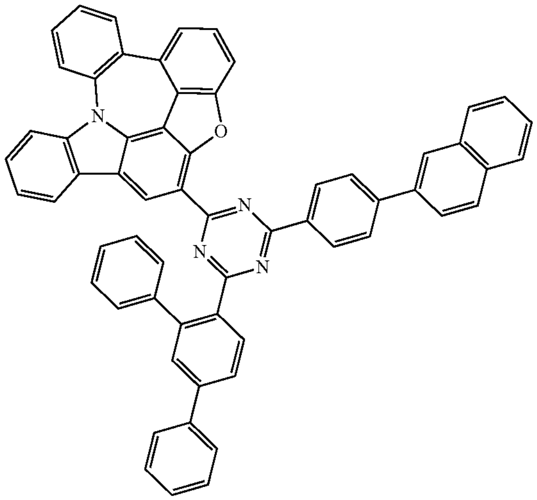

-continued
116
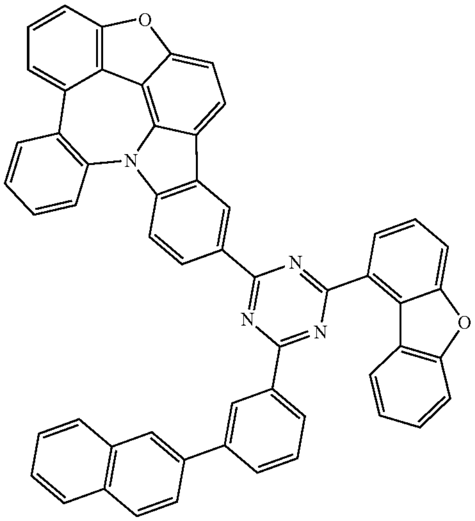
117
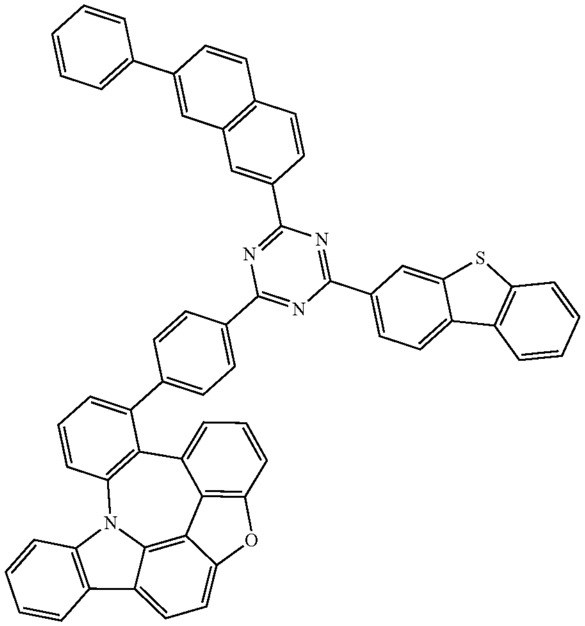
118
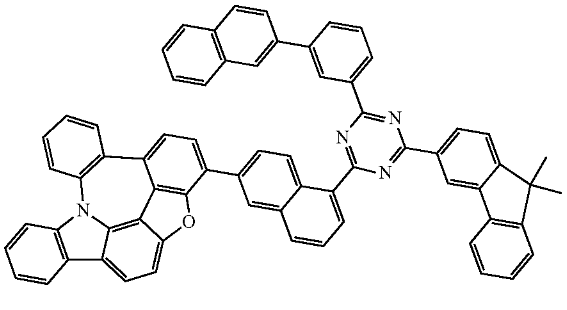
119
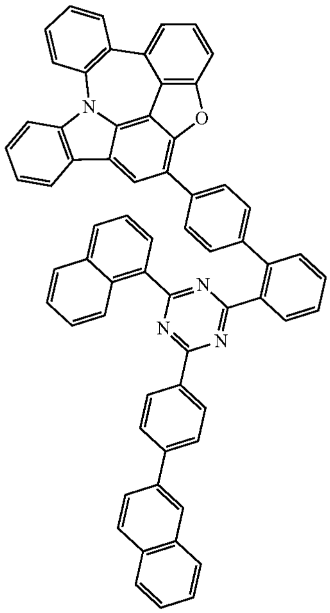

-continued
120
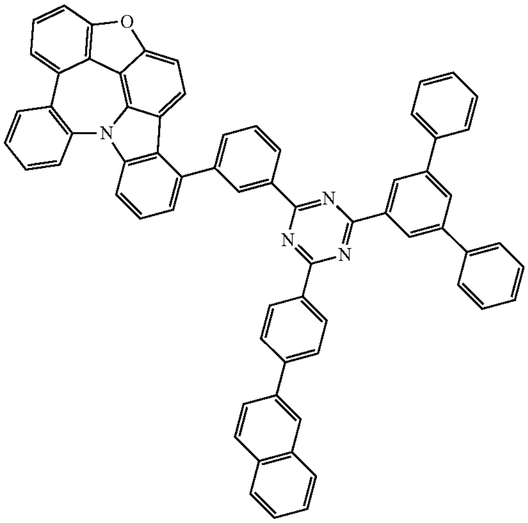
121
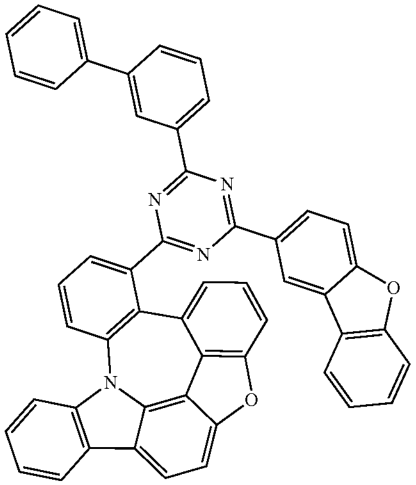
122
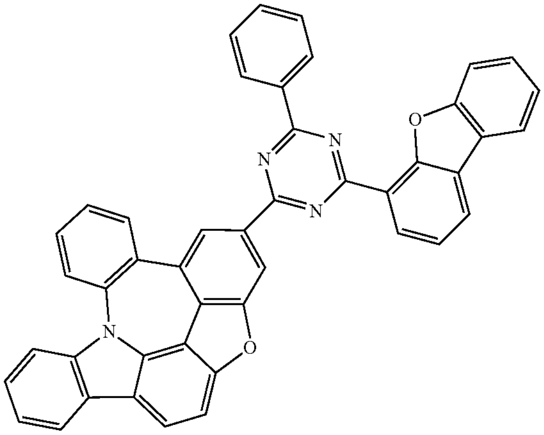
123
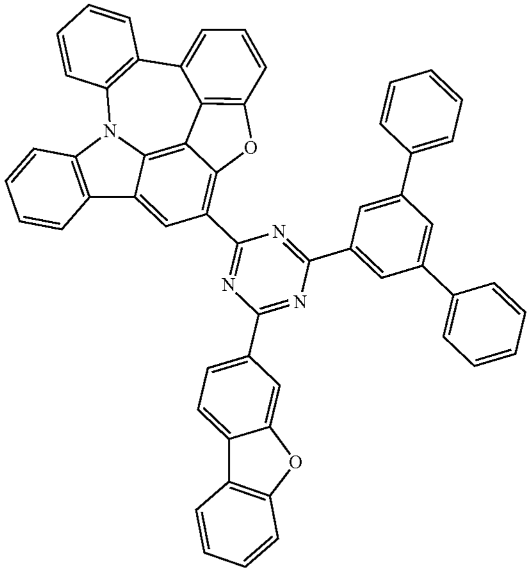

-continued
124
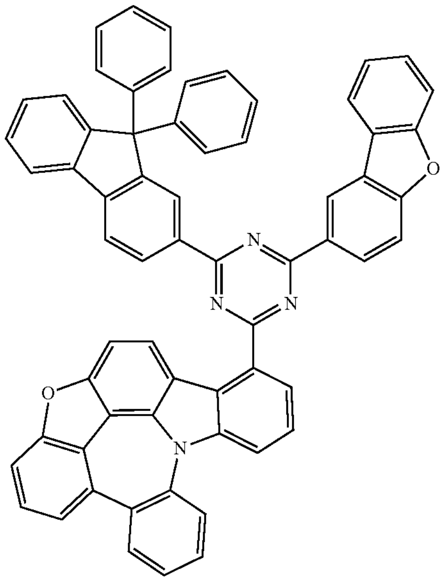
125
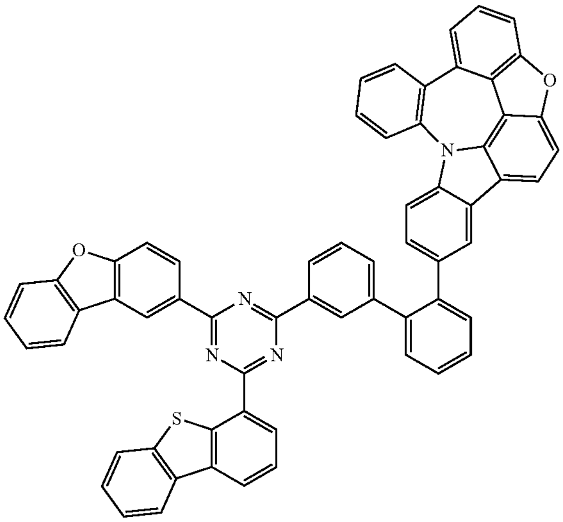
126
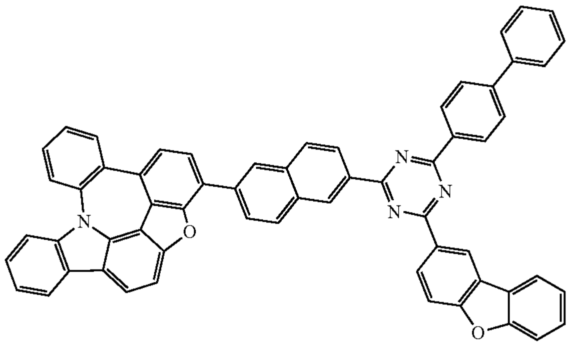
127
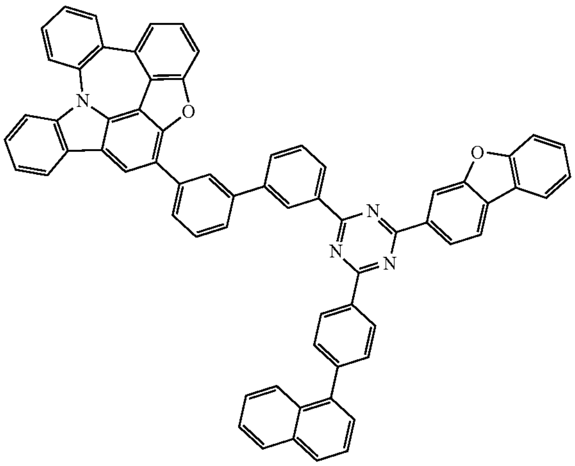

-continued
128
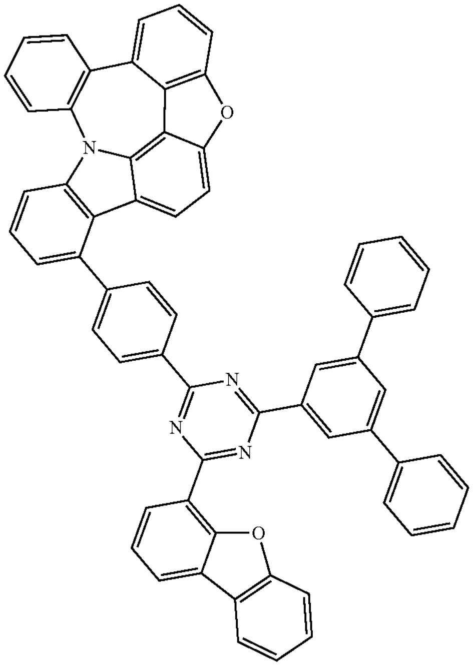
129
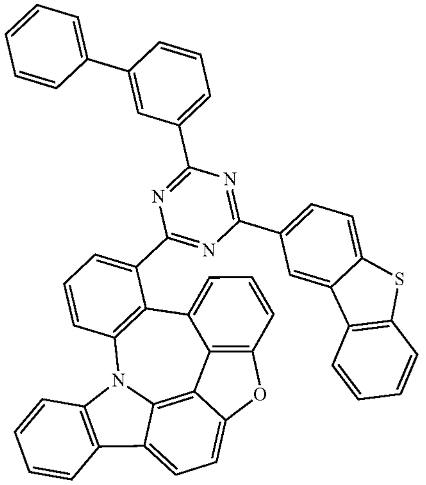
130
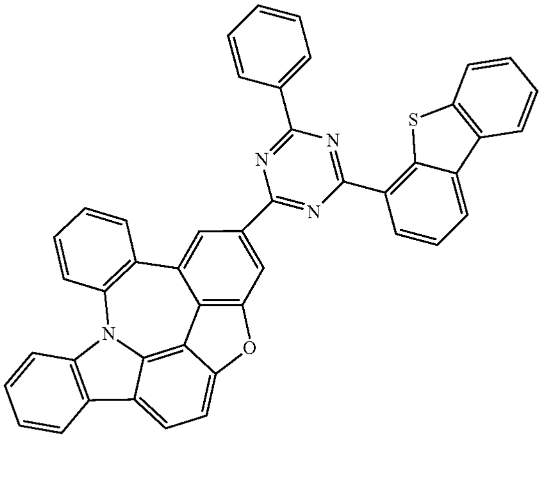
131
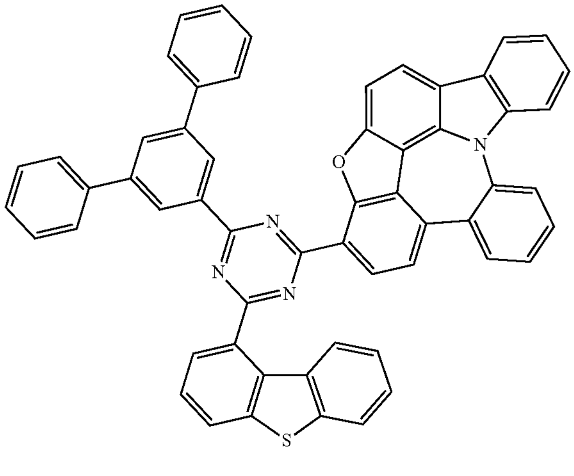

-continued
132
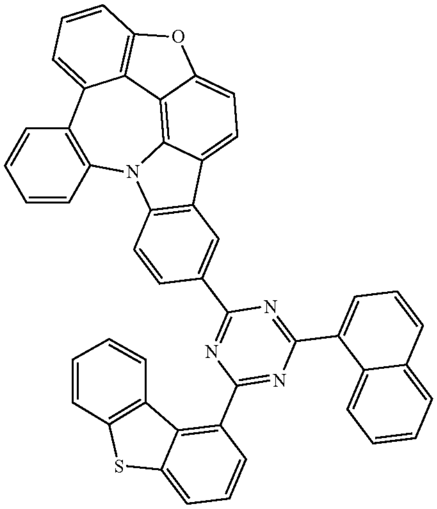
133
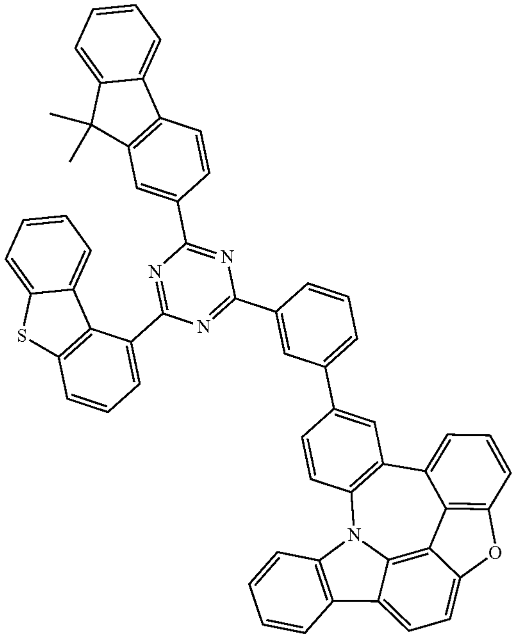
134
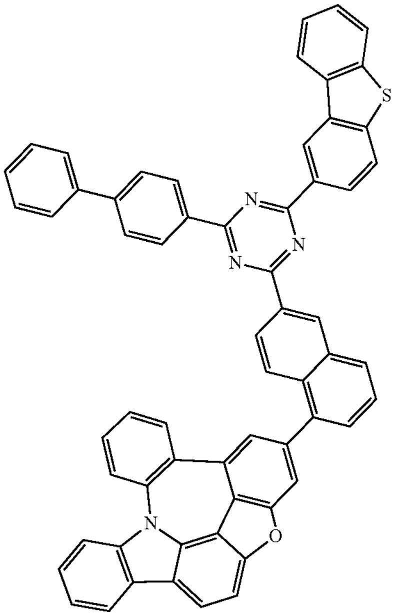
135
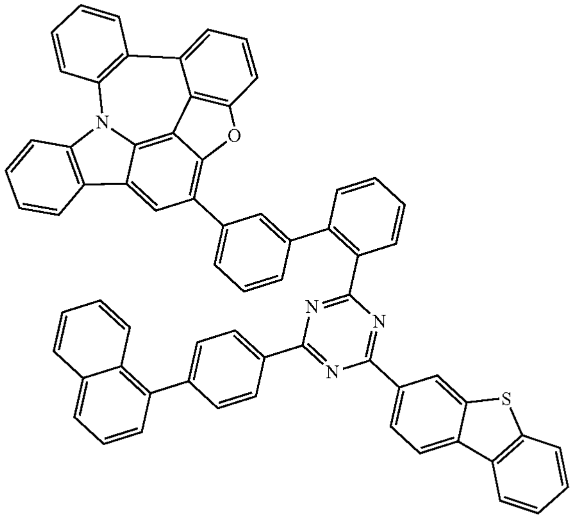

-continued
136
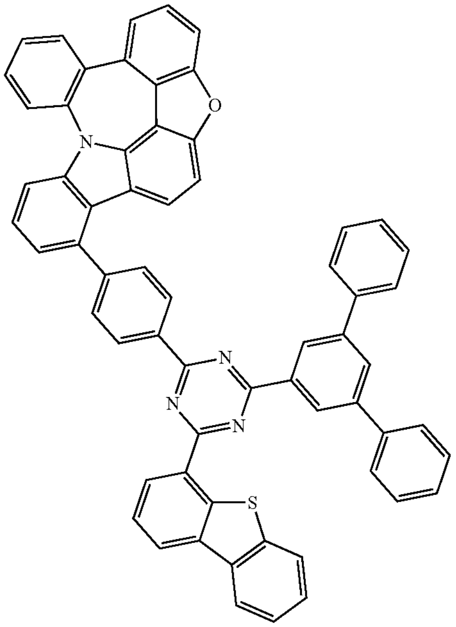
137
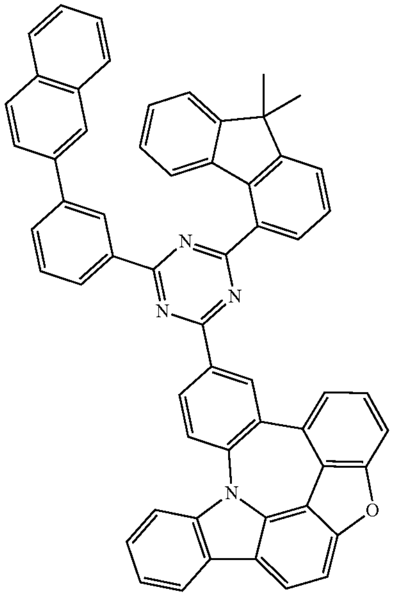
138
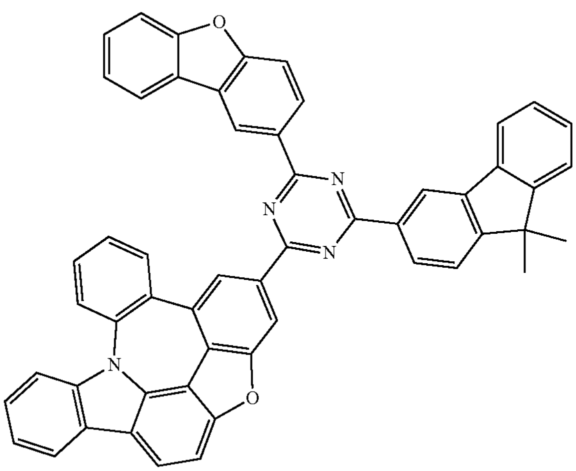
139
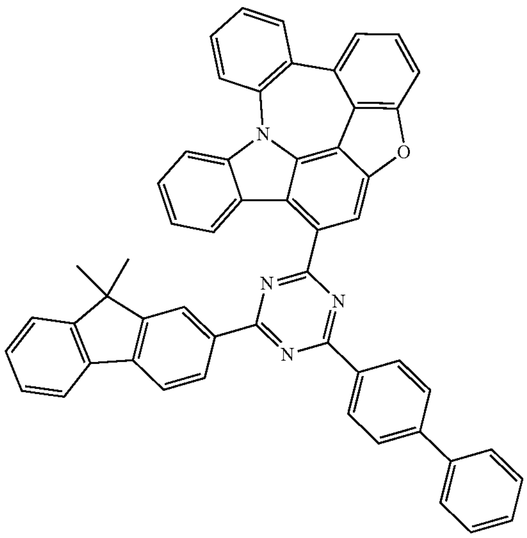

-continued
140
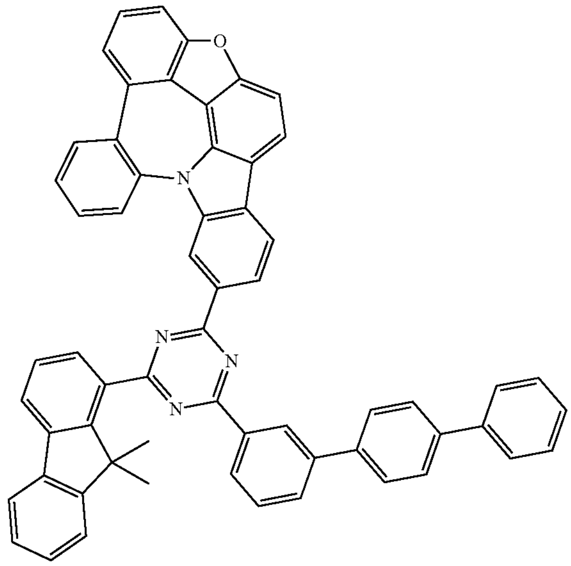
141
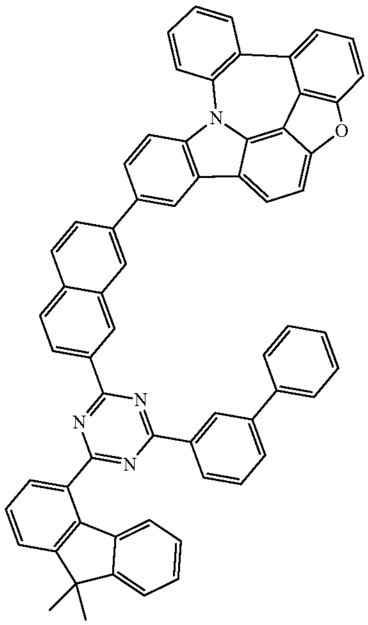
142
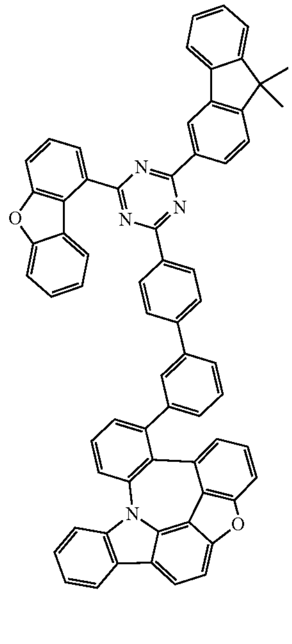
143
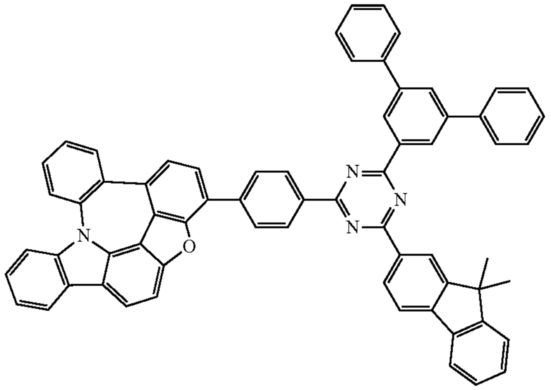

-continued
144
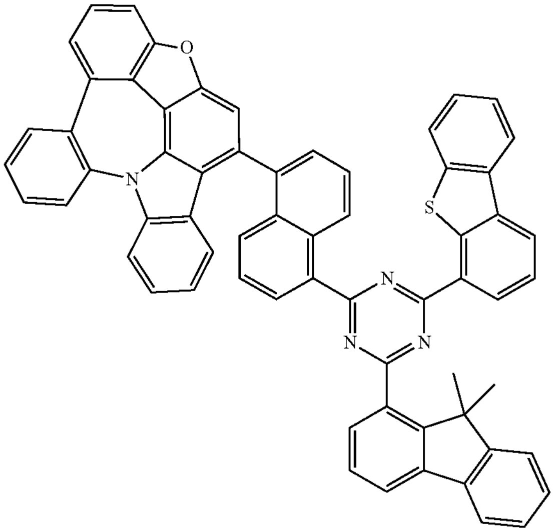
145
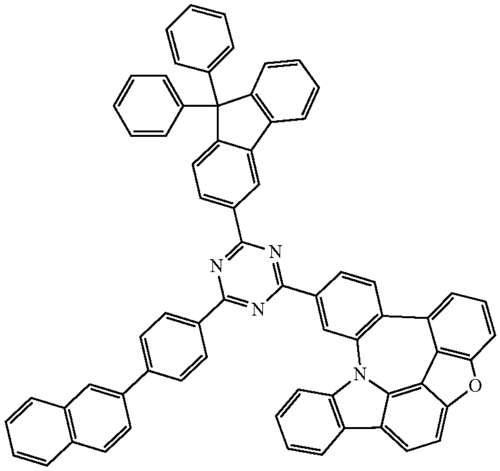
146
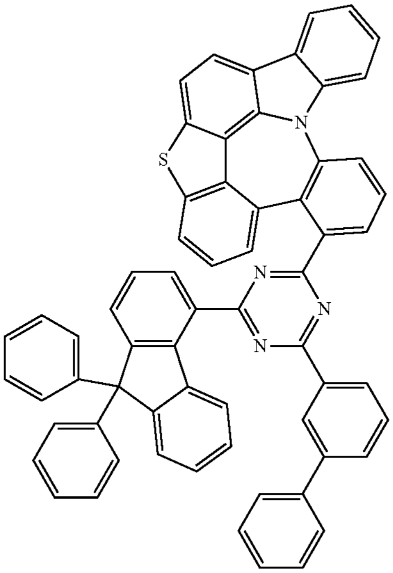
147
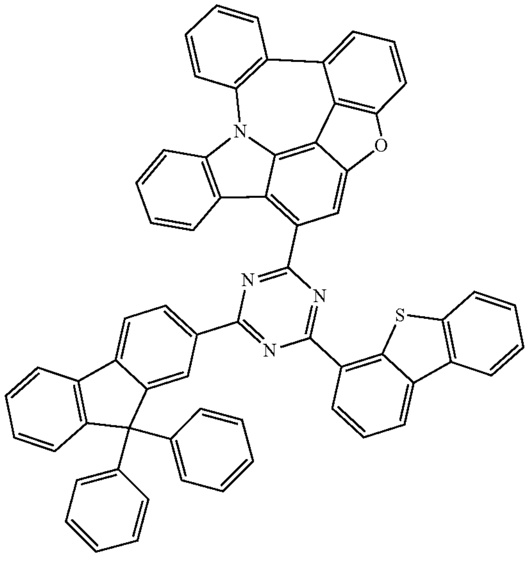

-continued
148
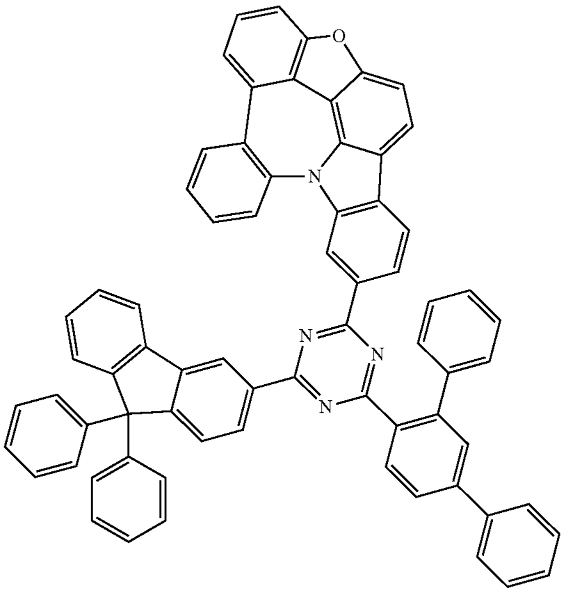
145
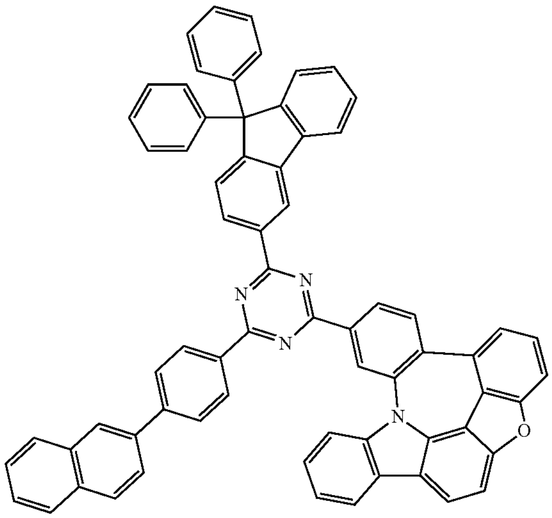
150
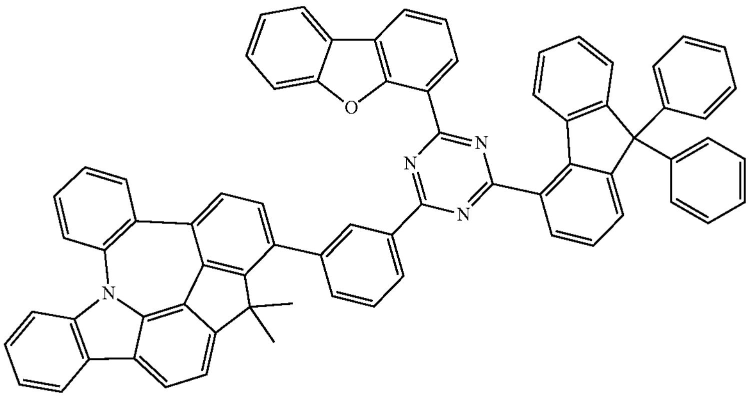
146
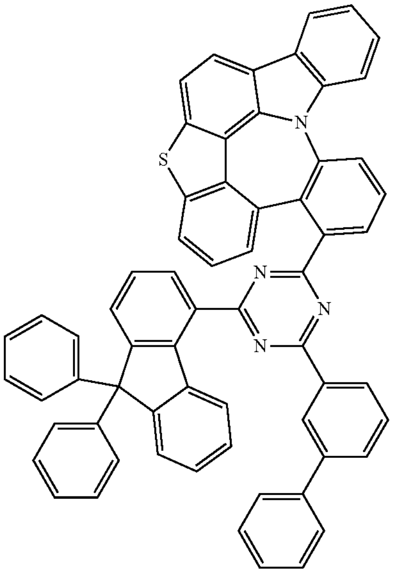
147
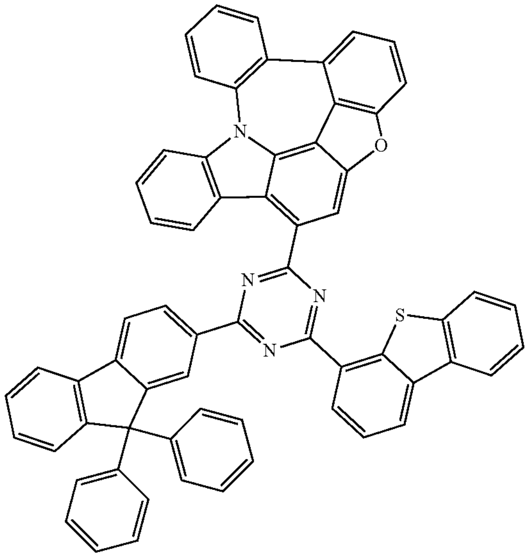

-continued
148
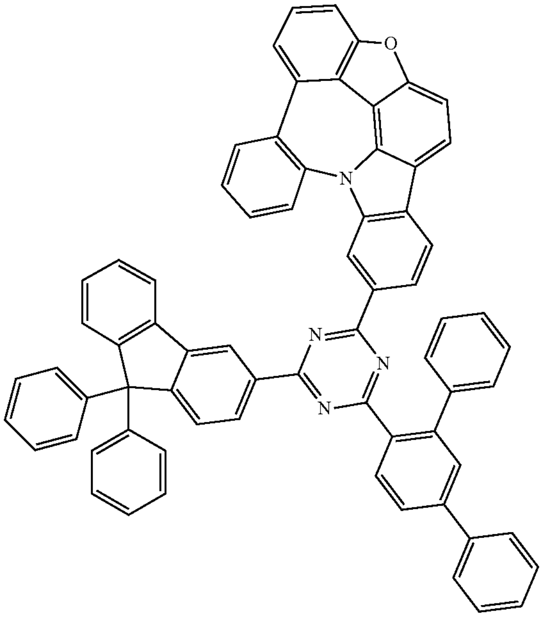
149
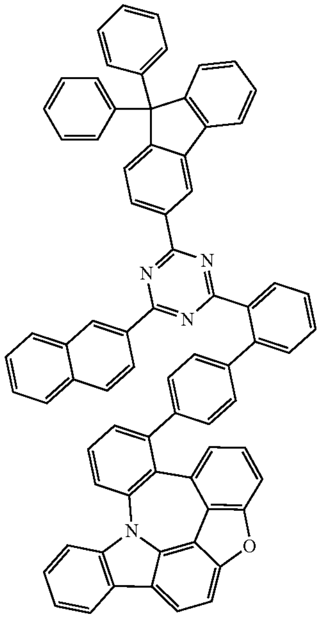
150
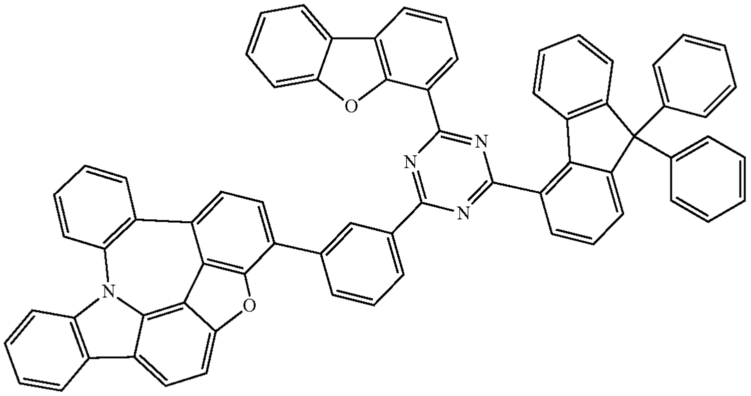
151
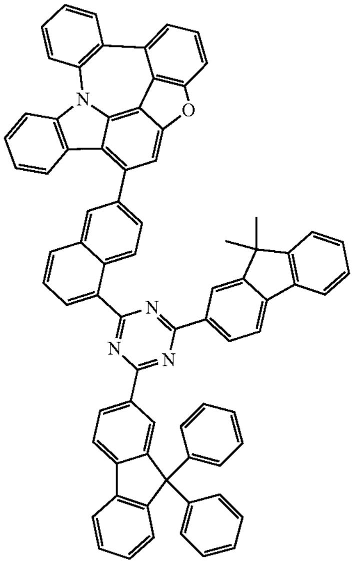
152
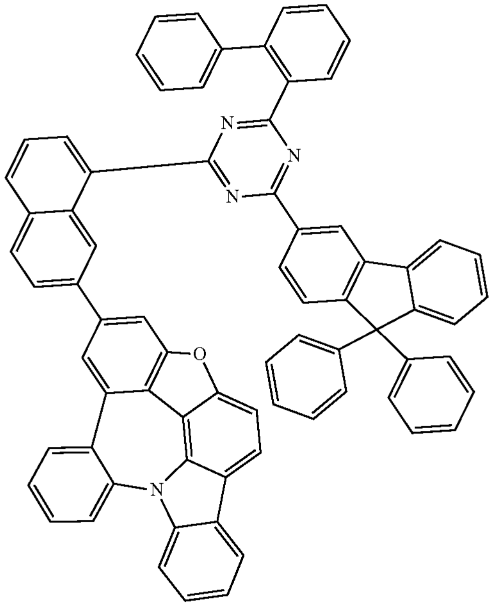

-continued
153
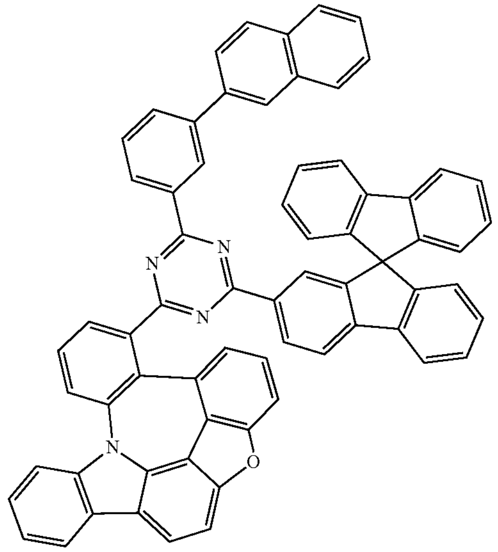
154
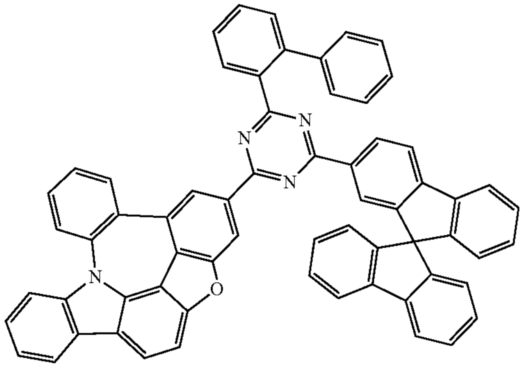
155
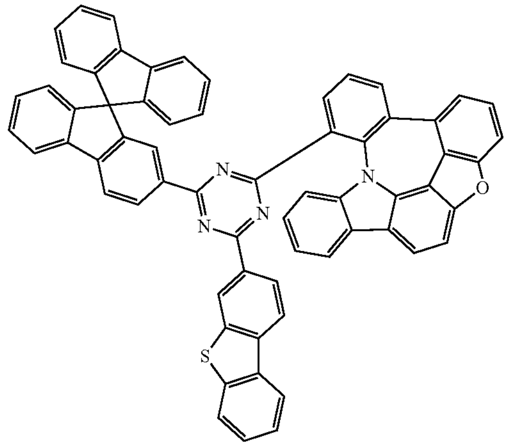
156
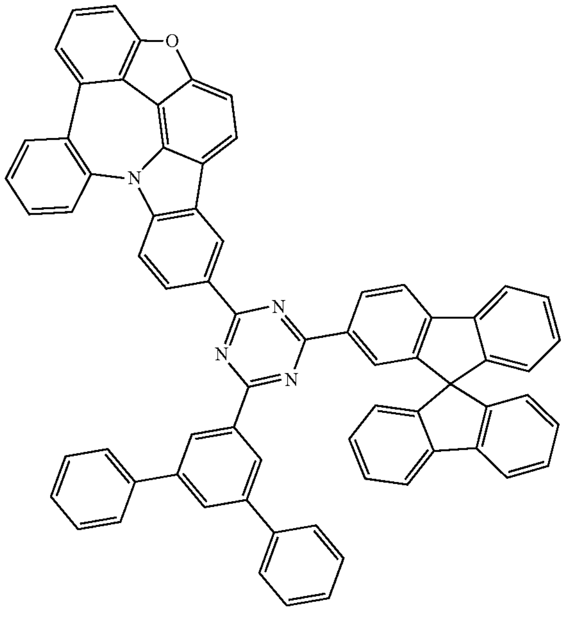

-continued
157
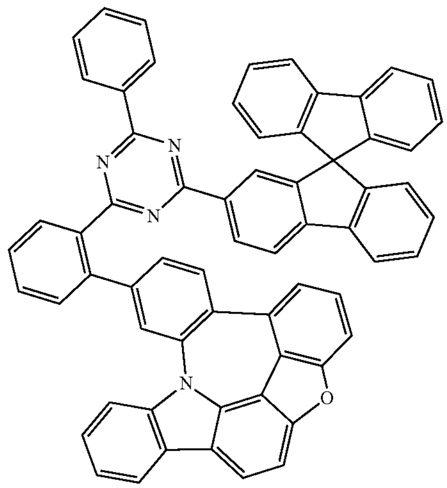
158
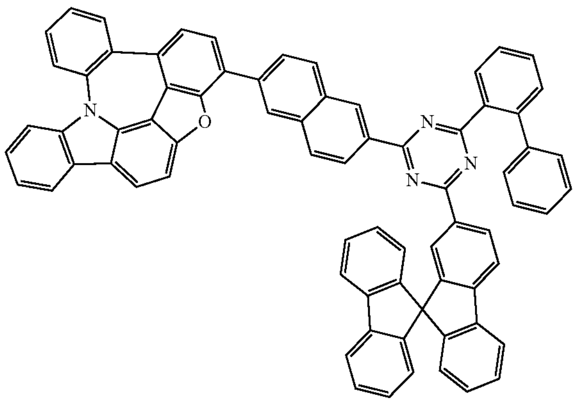
159
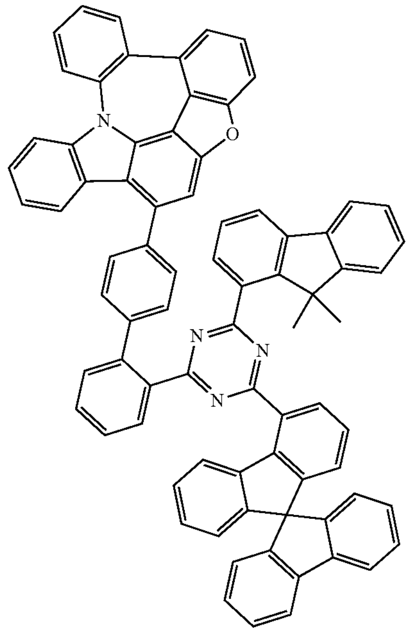
160
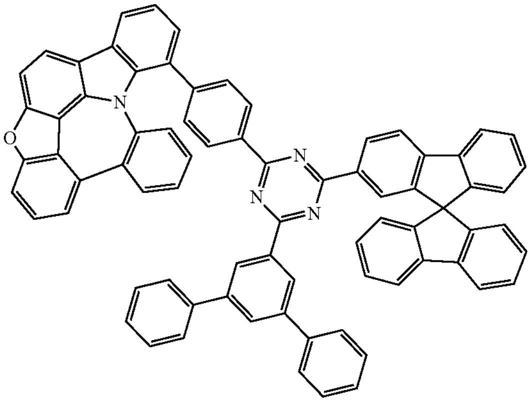

-continued
161
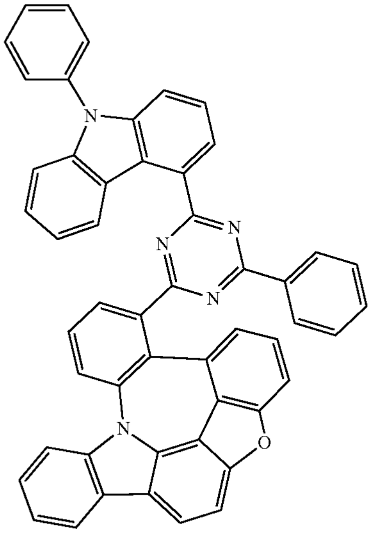
162
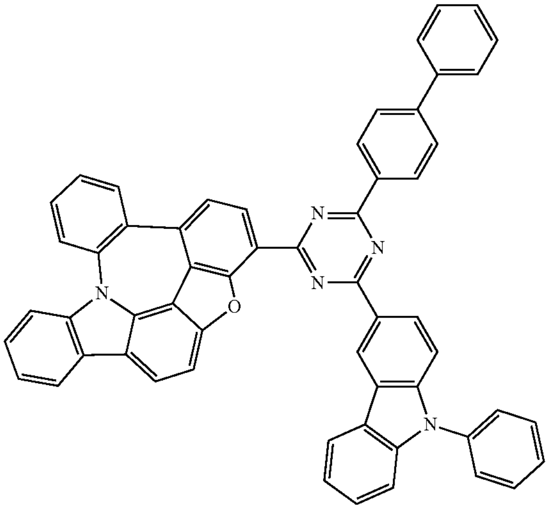
163
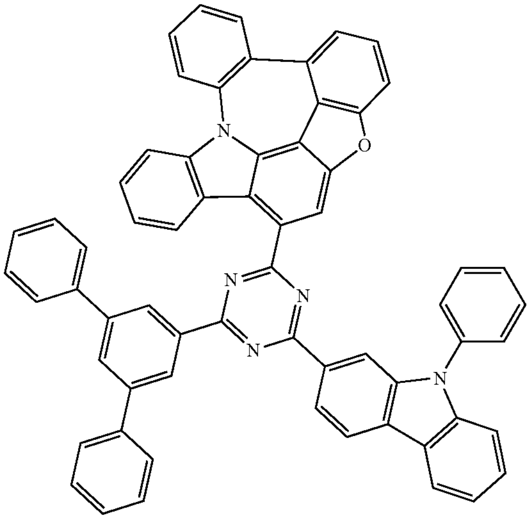
164
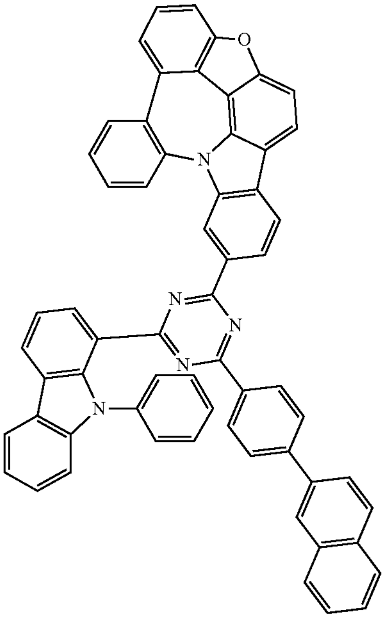

165
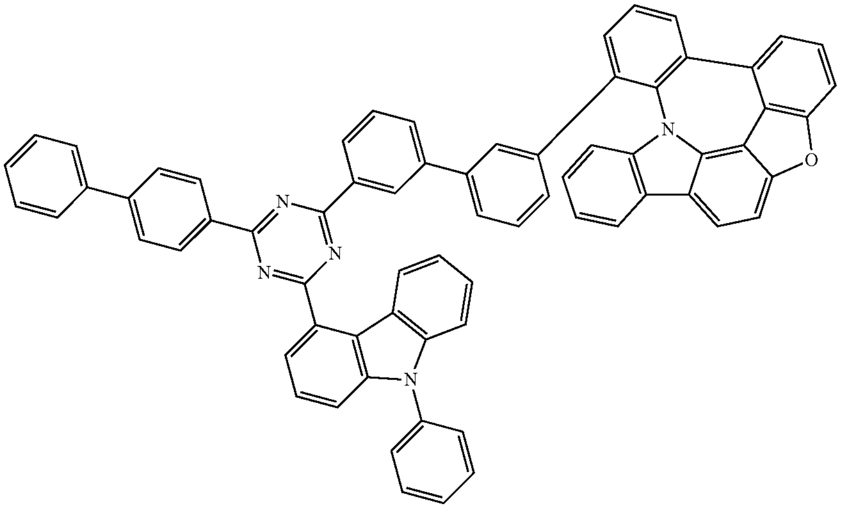
166
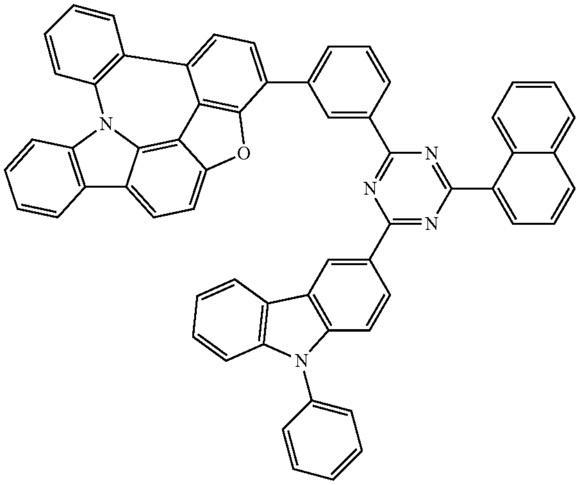
167
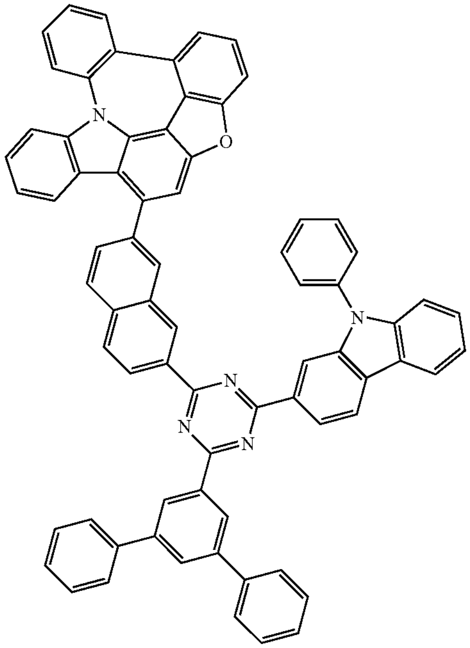

-continued
168
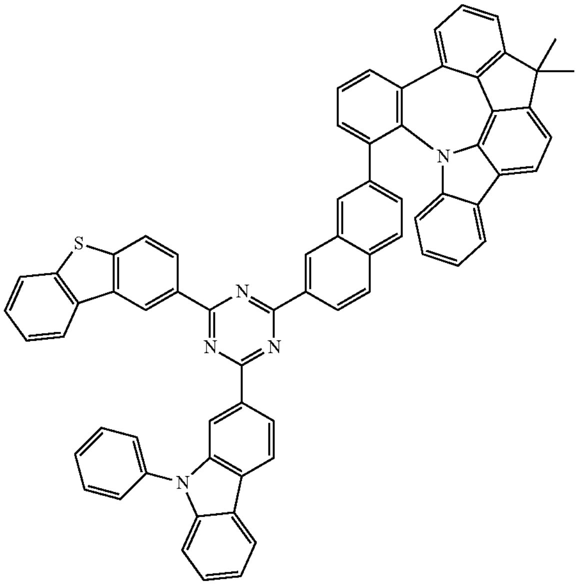
169
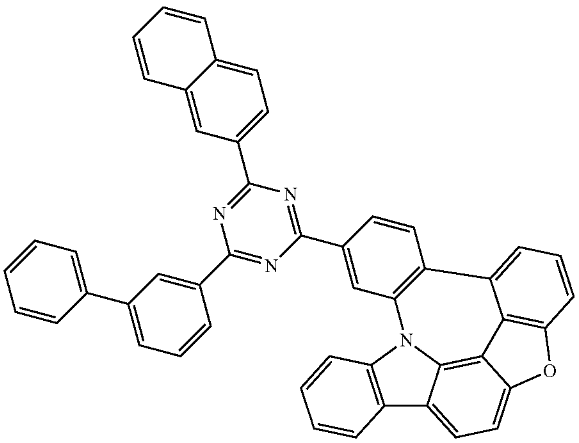
170
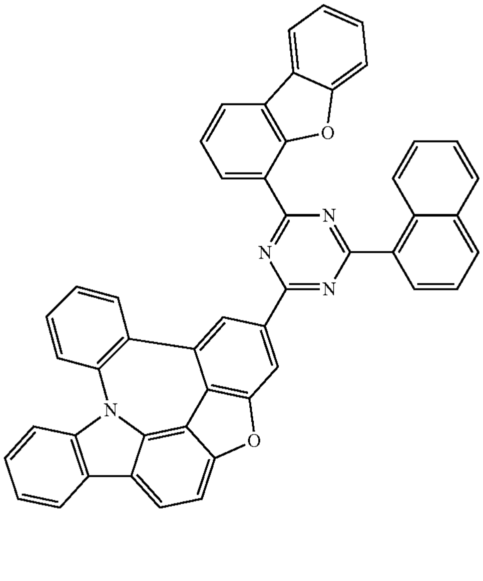
171
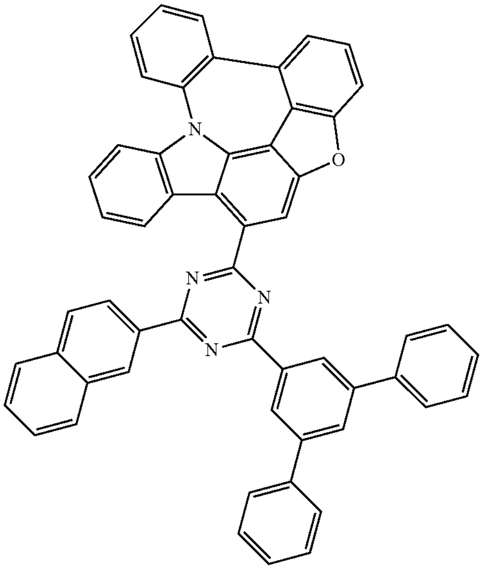

-continued
172
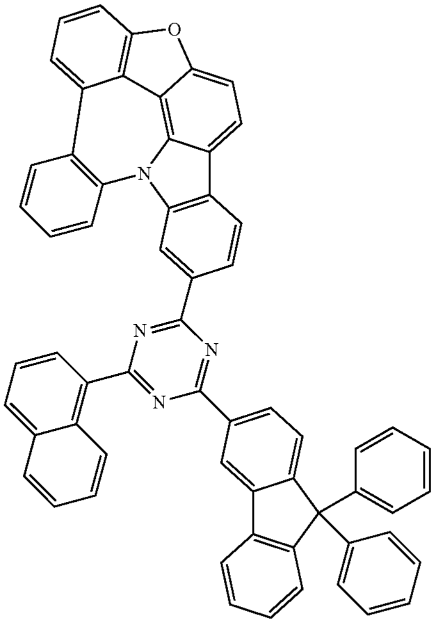
173
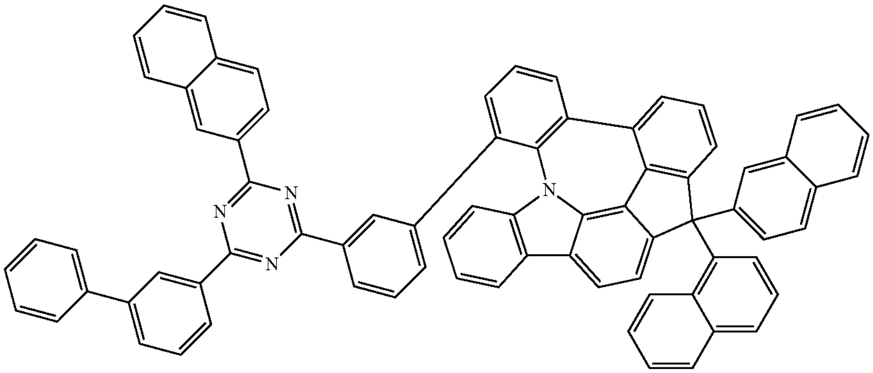
174
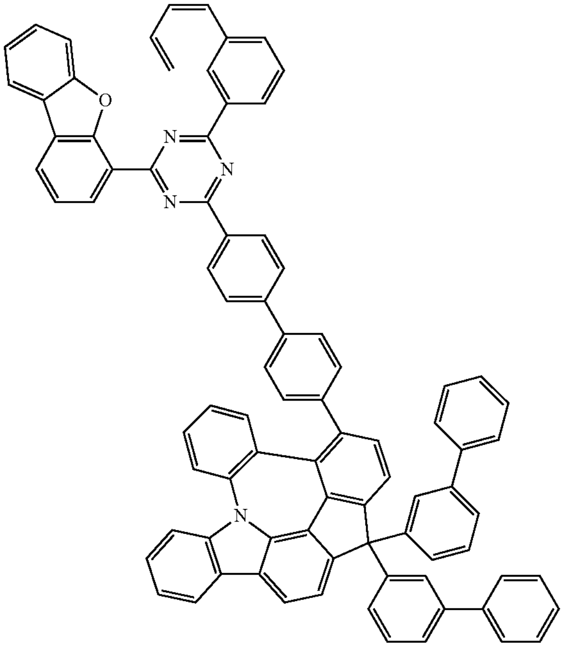
175
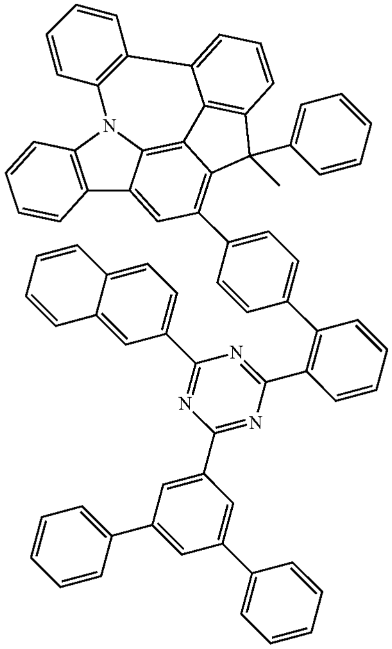

-continued
176
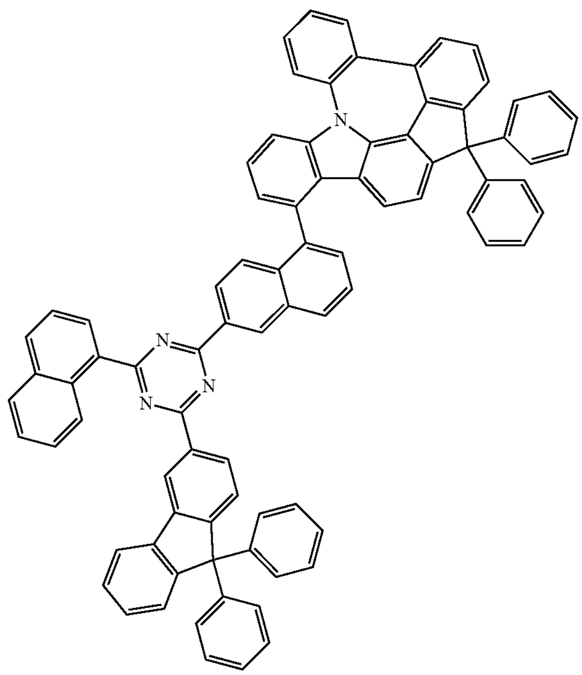
177
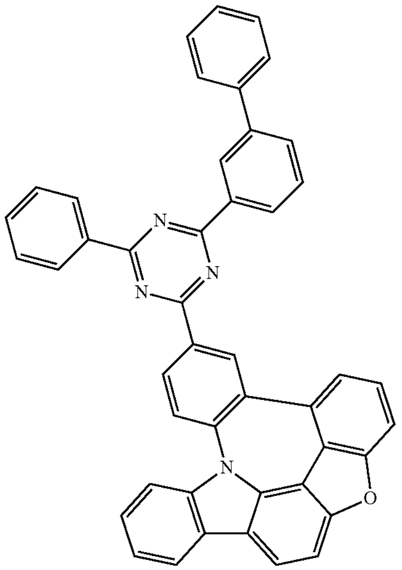
178
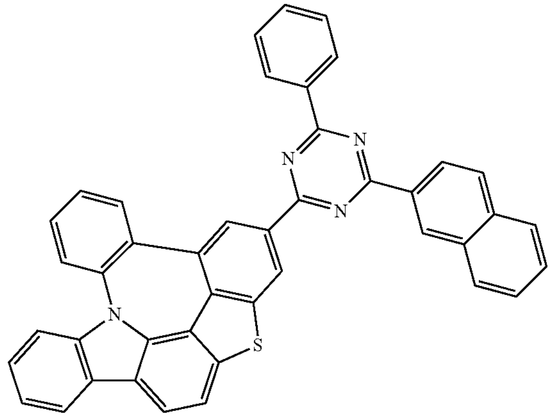
179
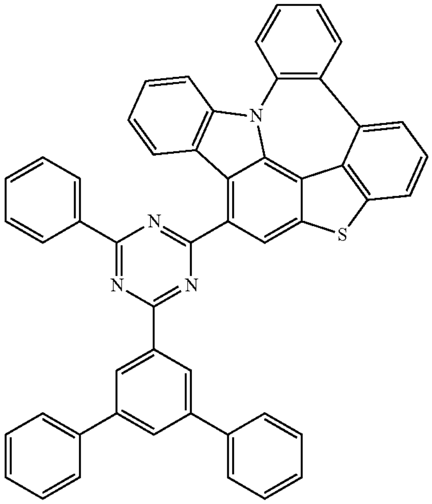

-continued
180
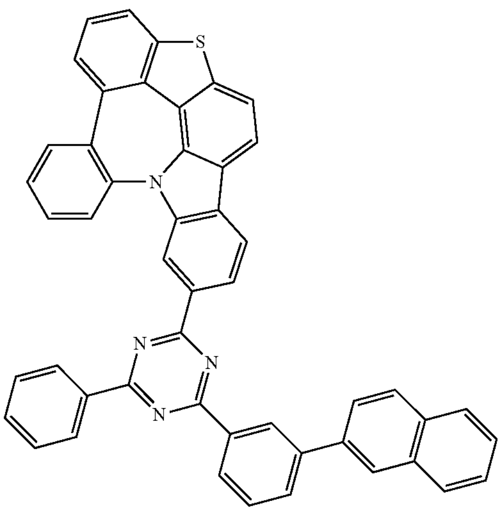
181
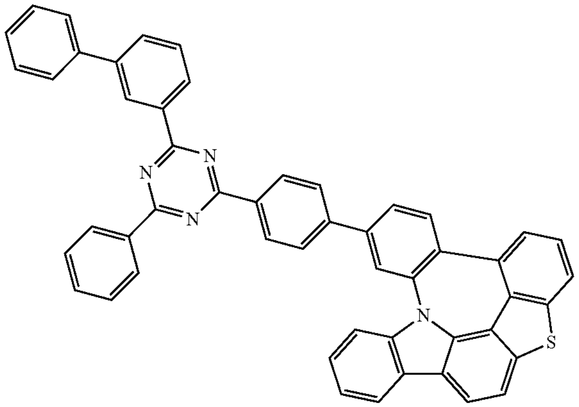
182
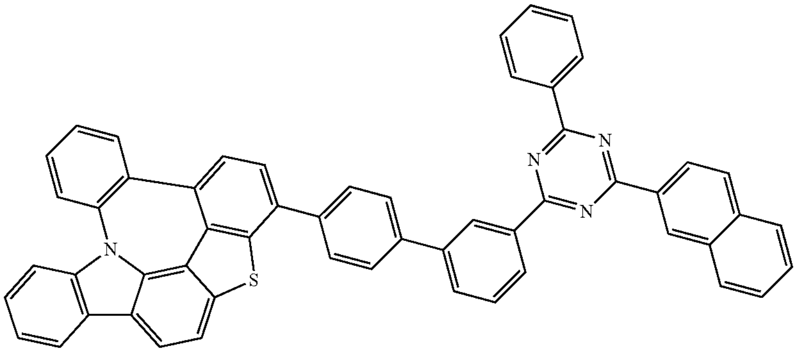
183
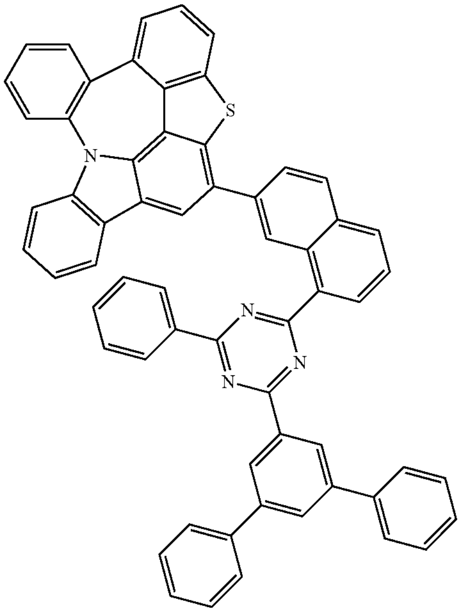
184
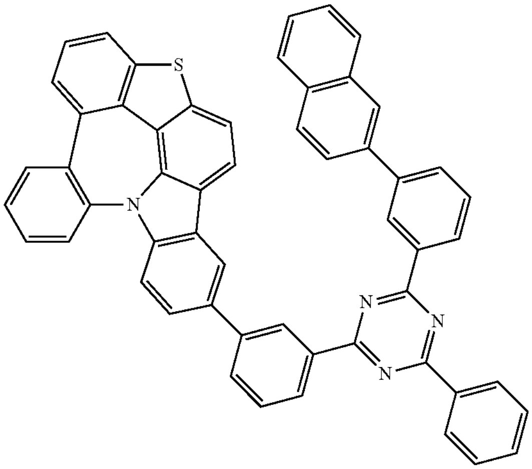

-continued
185
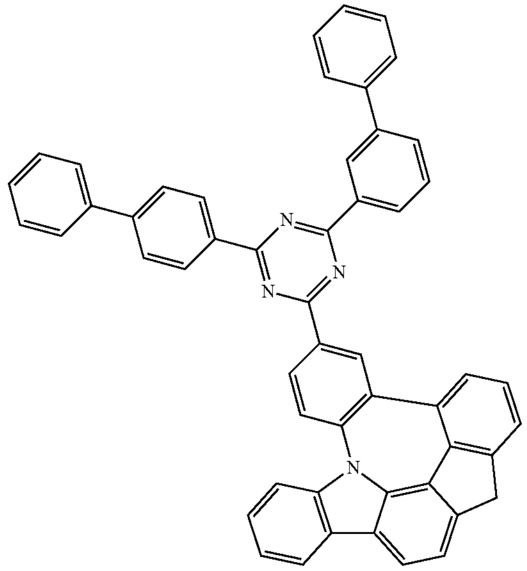
186
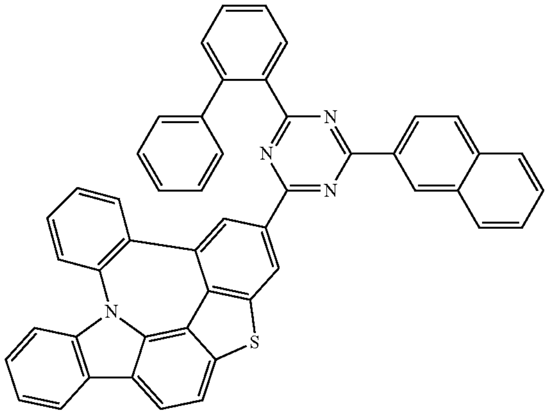
187
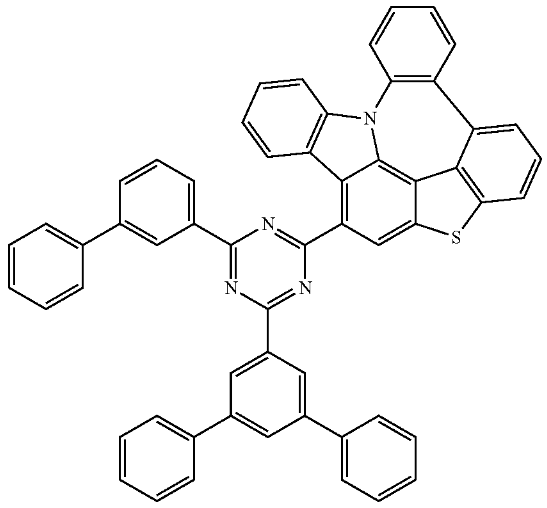
188
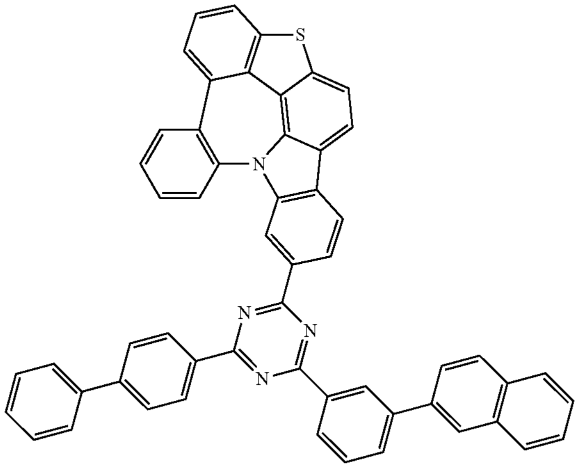
189
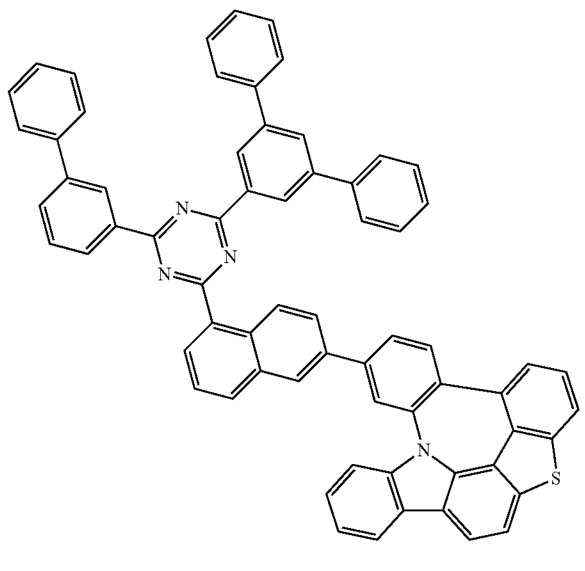
190
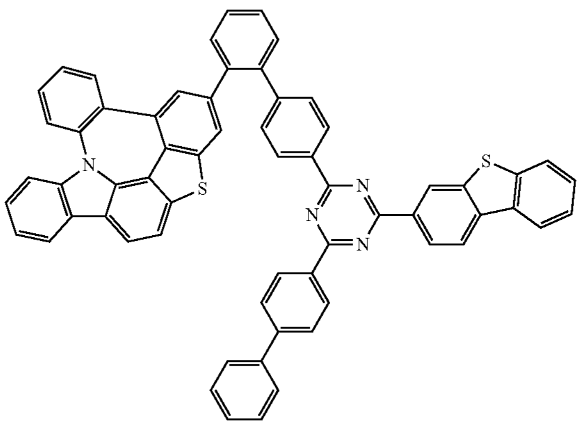

-continued
191
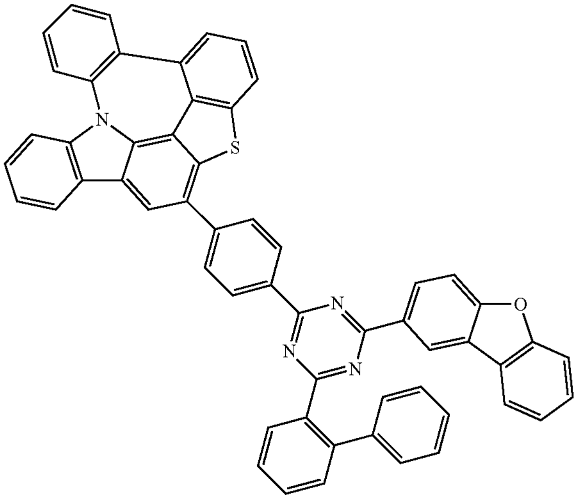
192
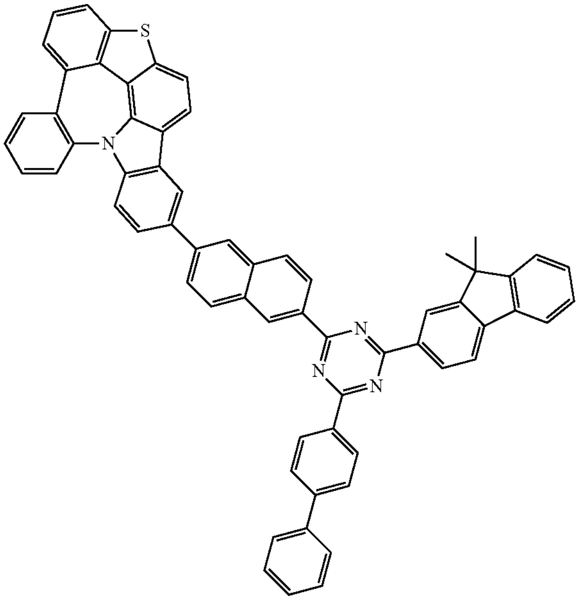
193
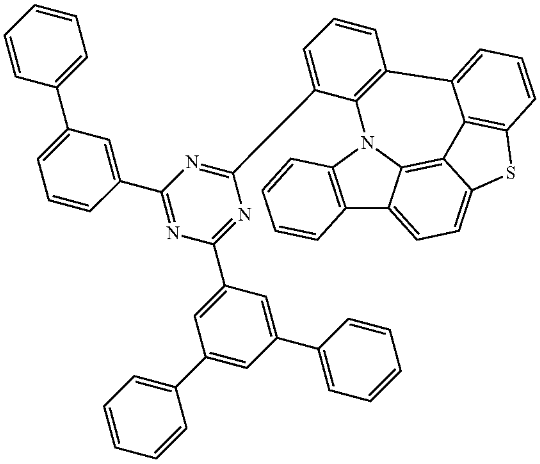
194
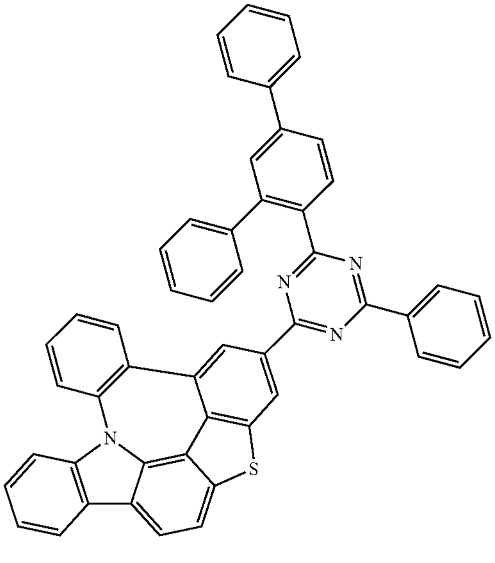

-continued
195
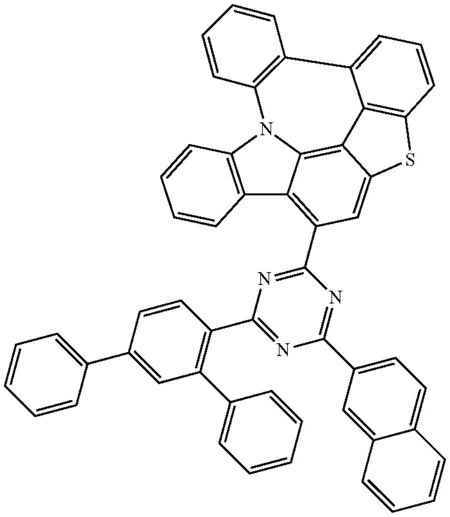
196
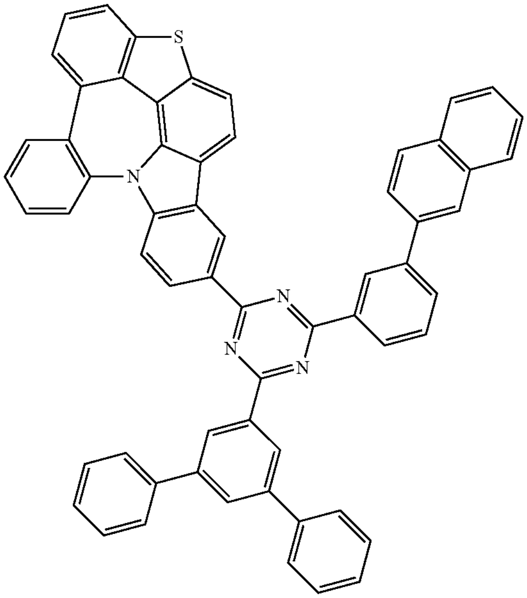
197
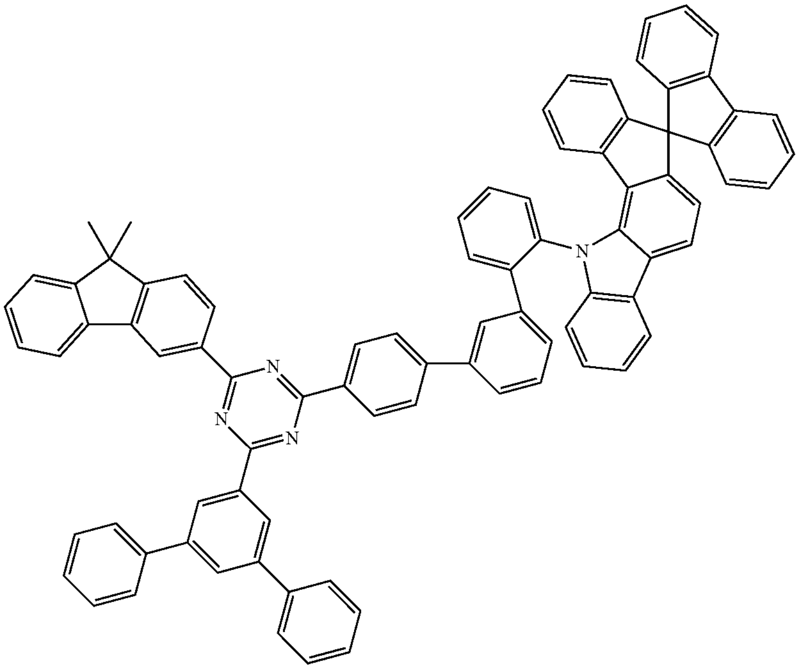

-continued
198
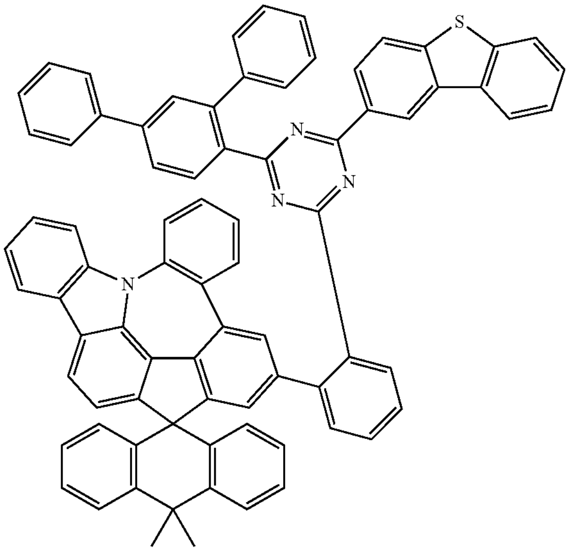
199
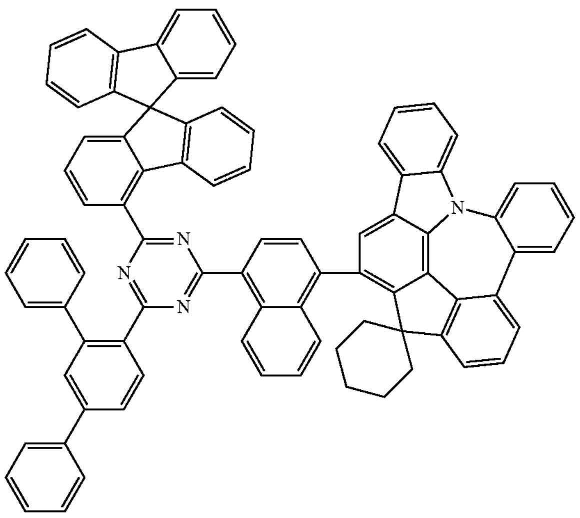
200
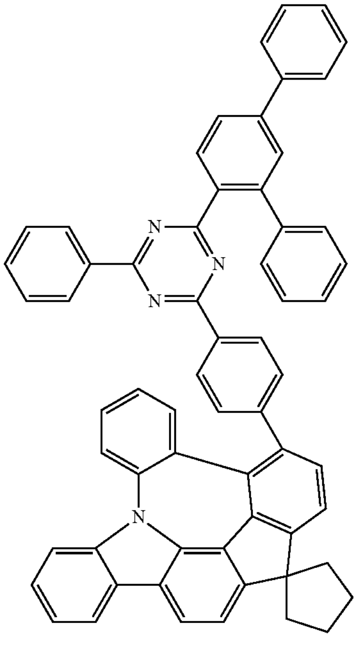
201
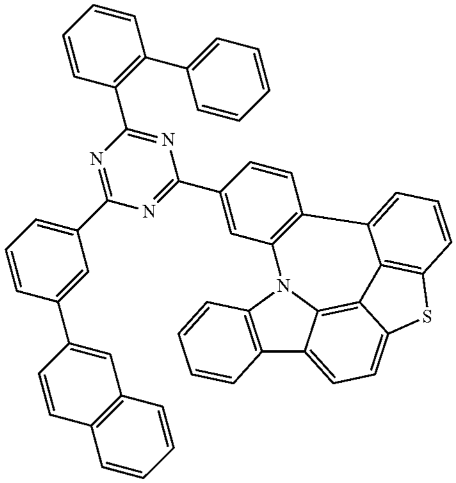

-continued
202
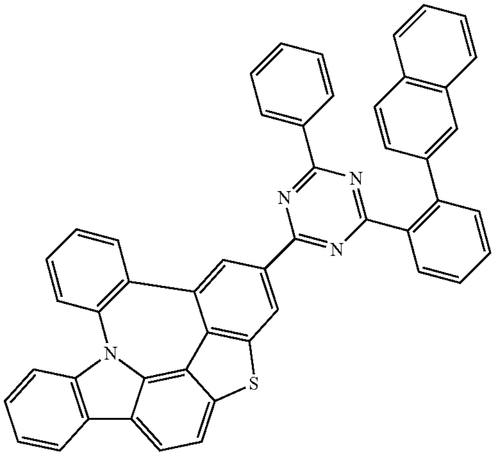
203
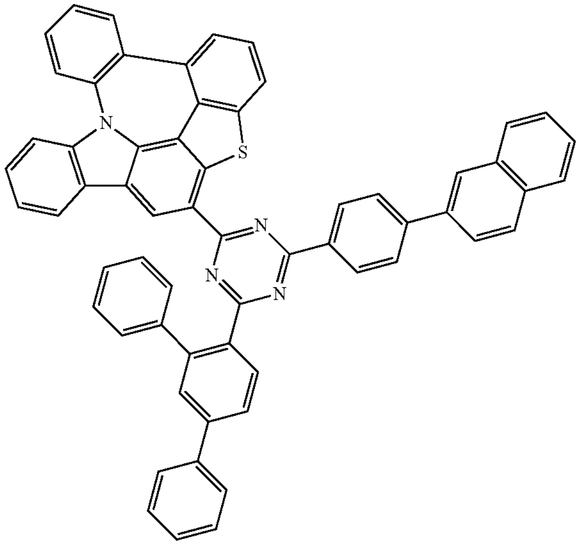
204
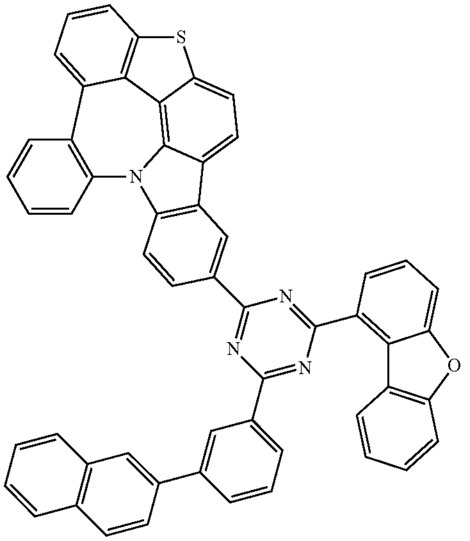
205
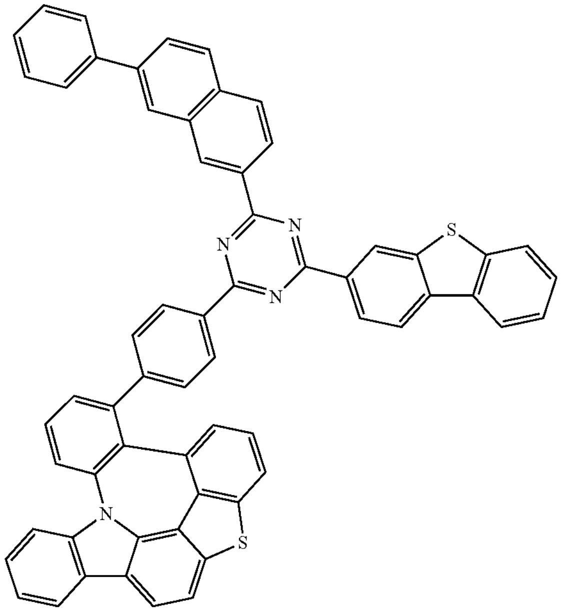

-continued
206
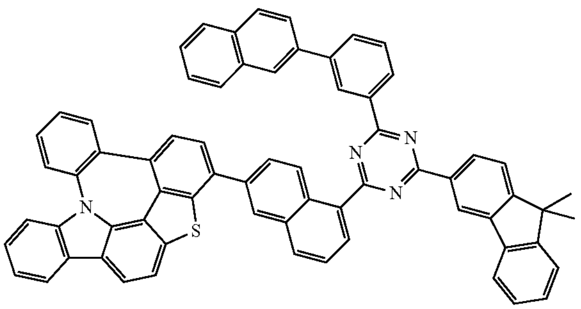
207
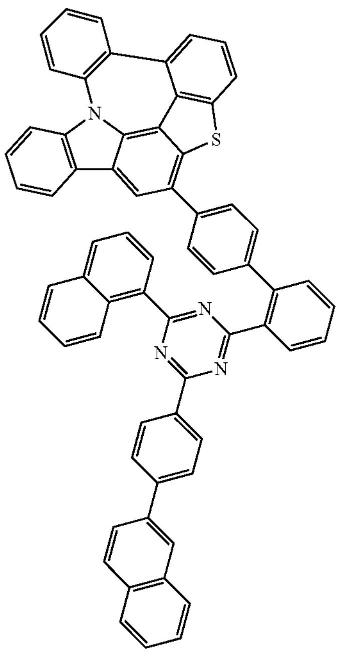
208
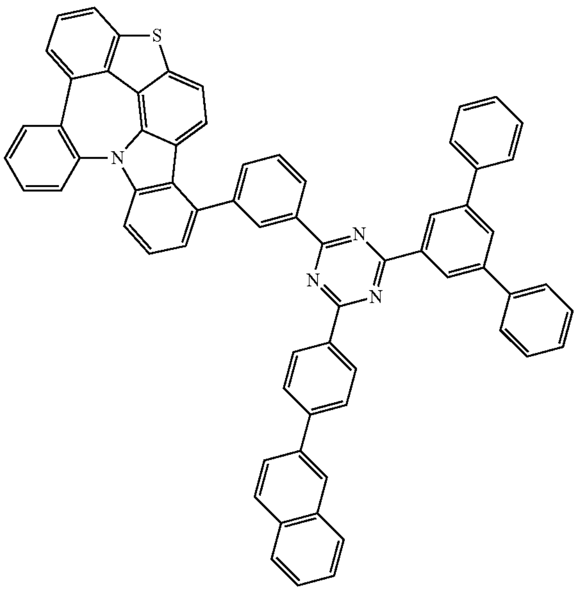
209
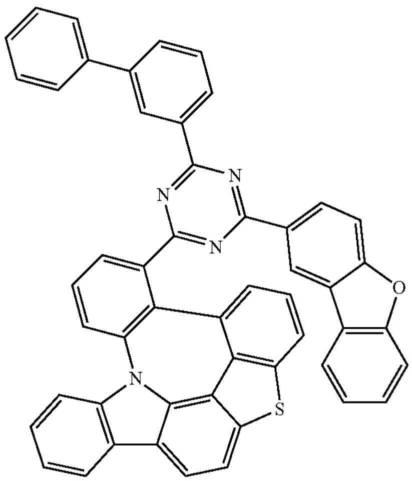

-continued
210
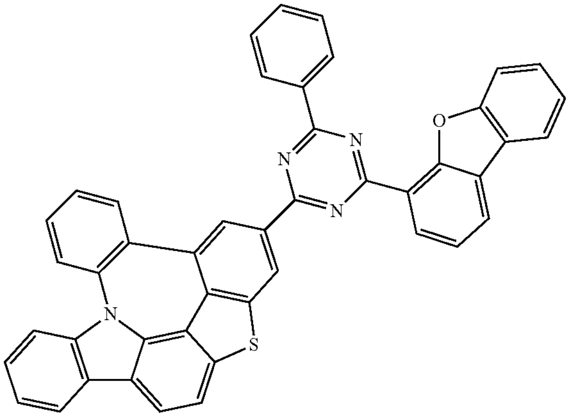
211
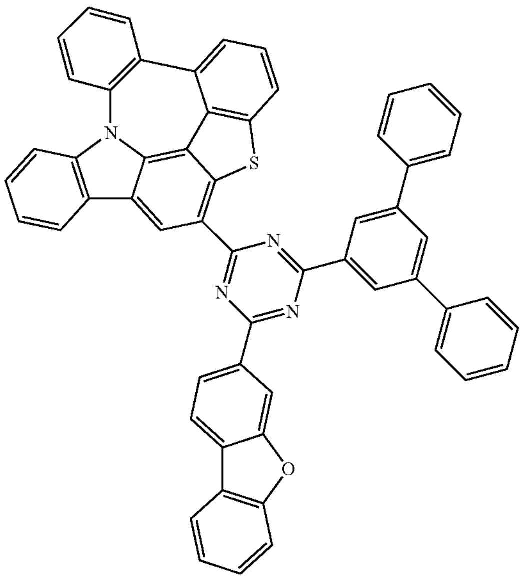
212
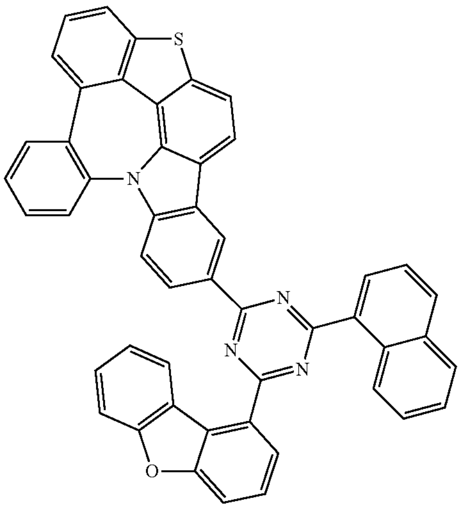
213
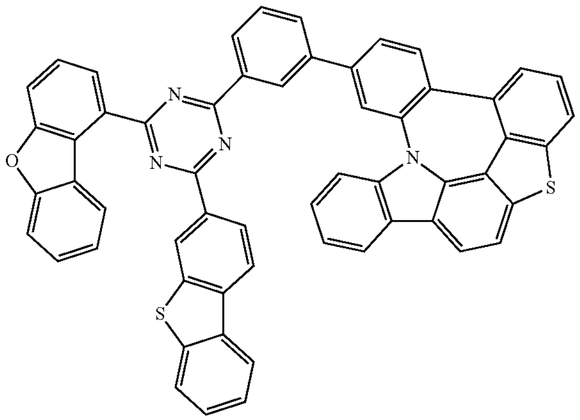
214
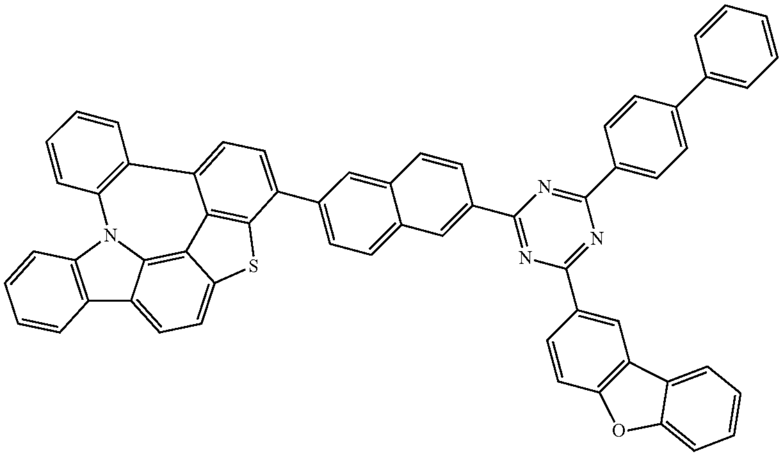

-continued
215
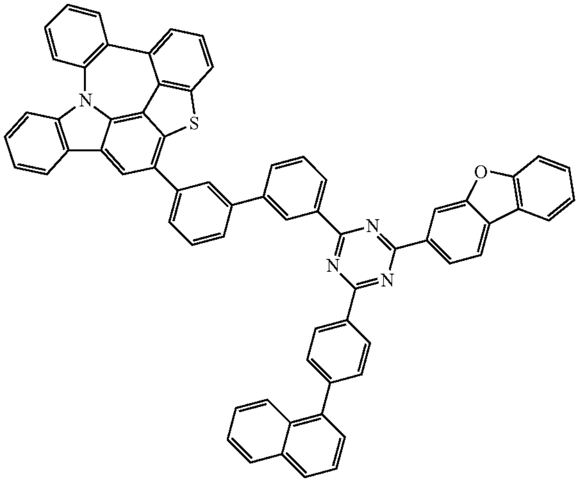
216
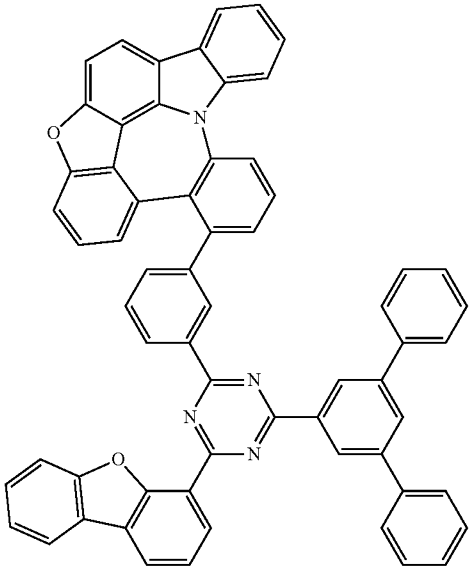
217
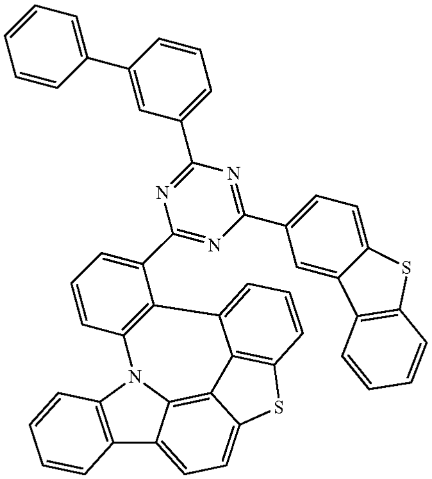
218
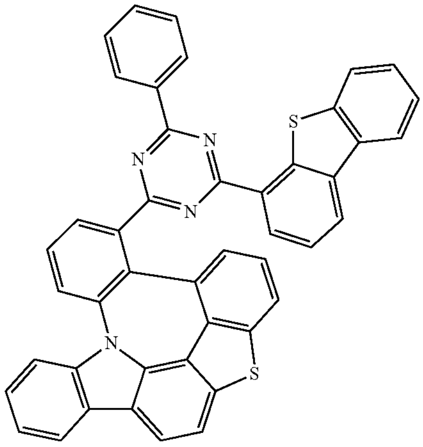
219
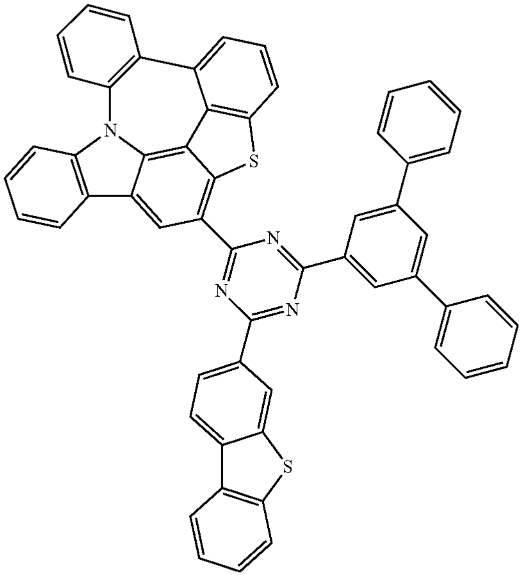
220
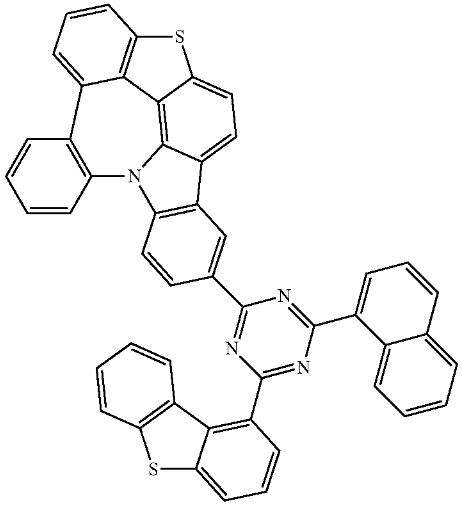

-continued
221
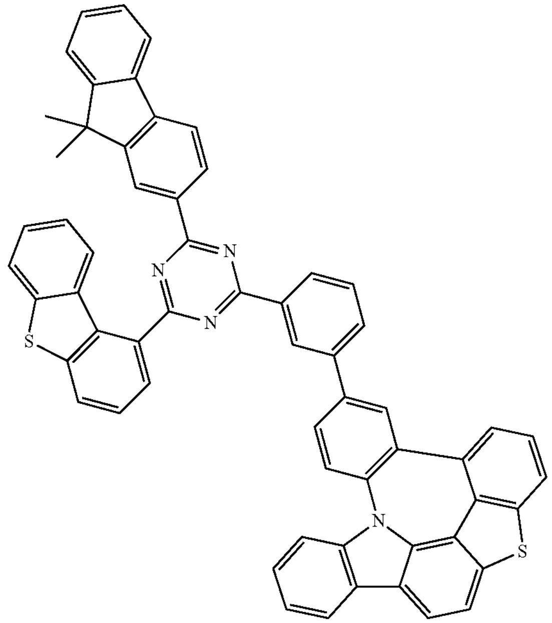
222
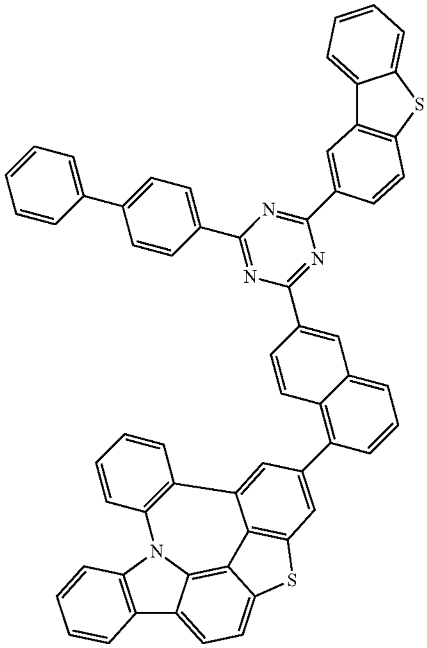
223
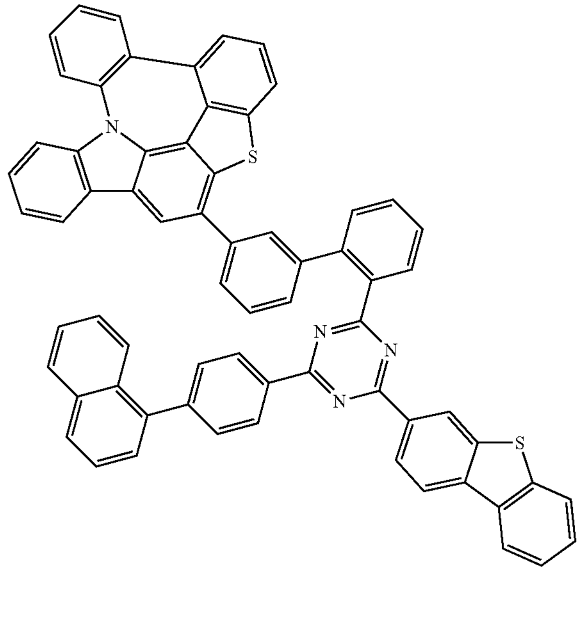
224
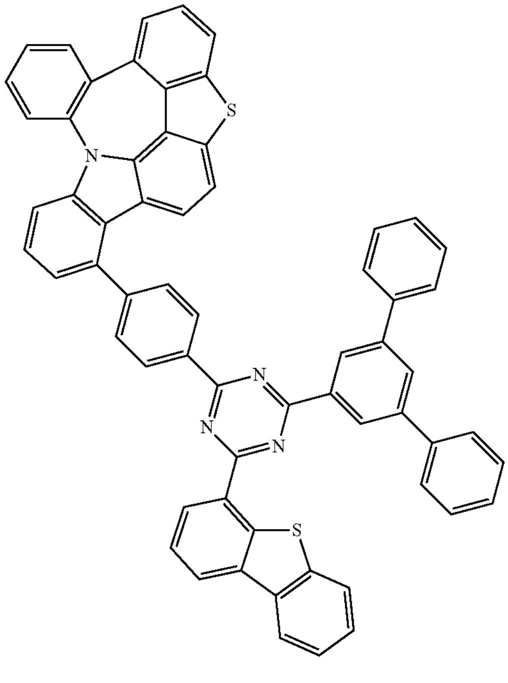

-continued
225
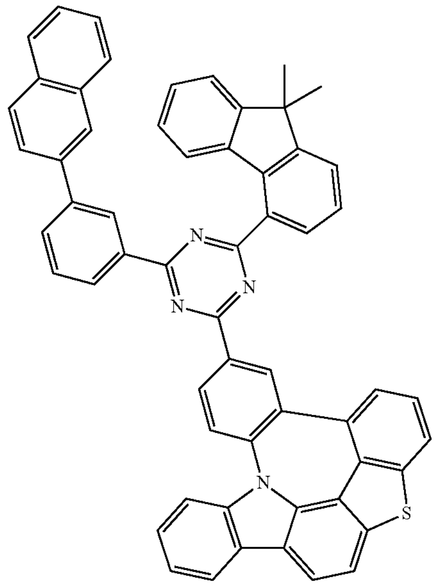
226
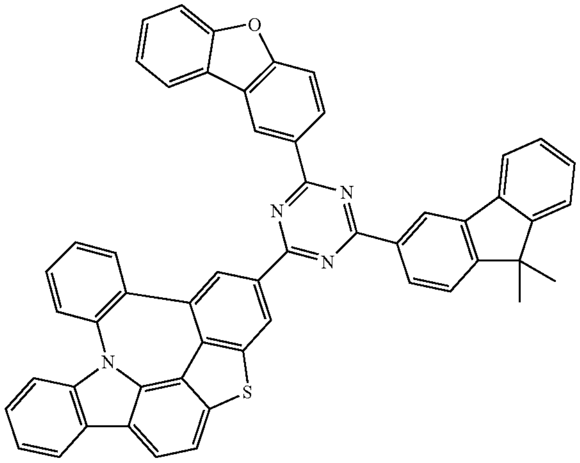
227
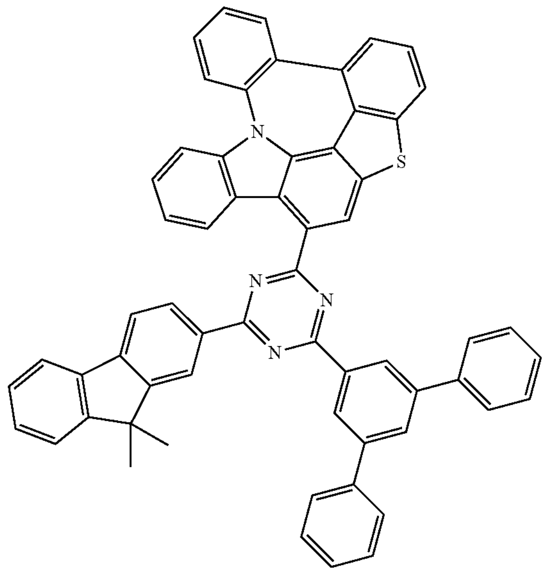
228
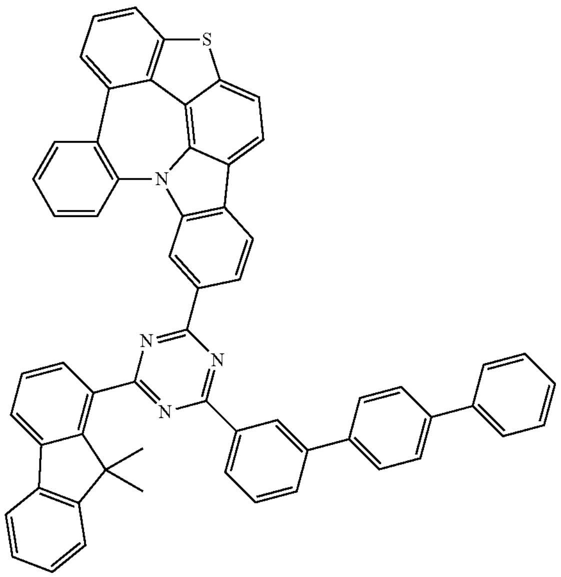

-continued
229
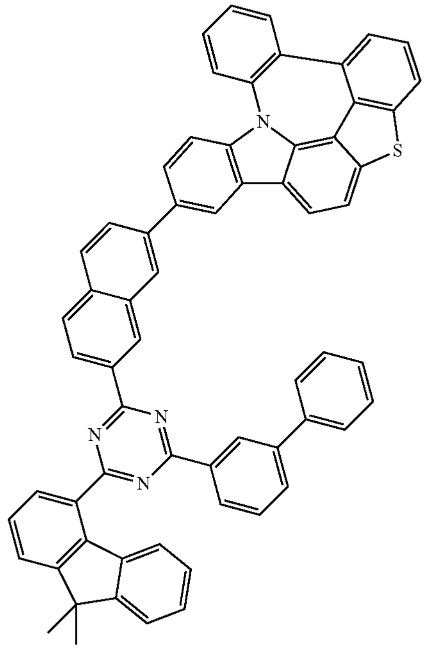
230
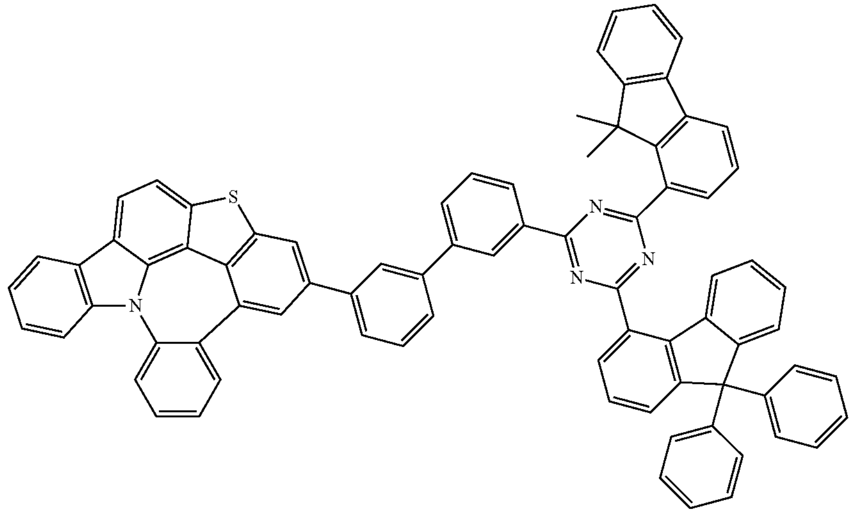

-continued
231
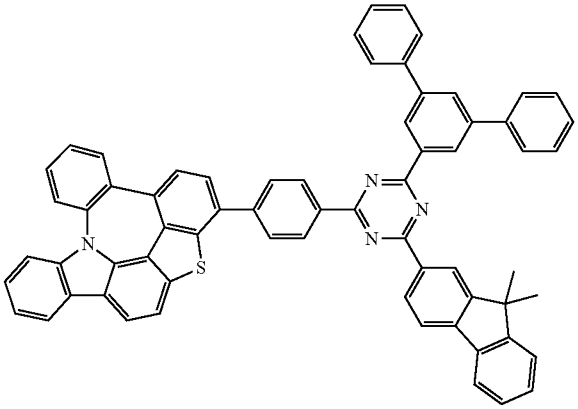
232
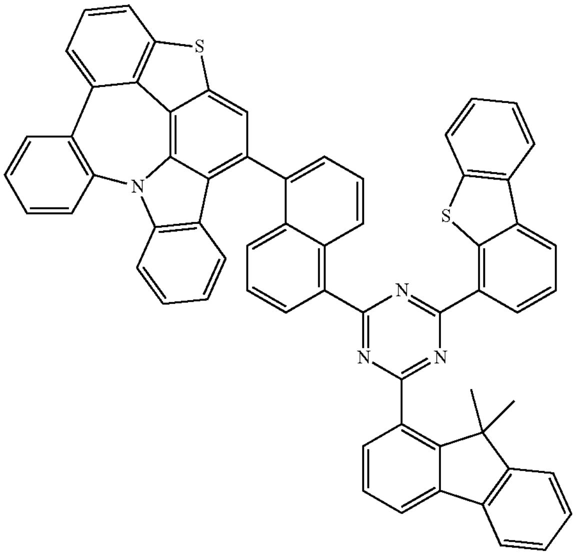
233
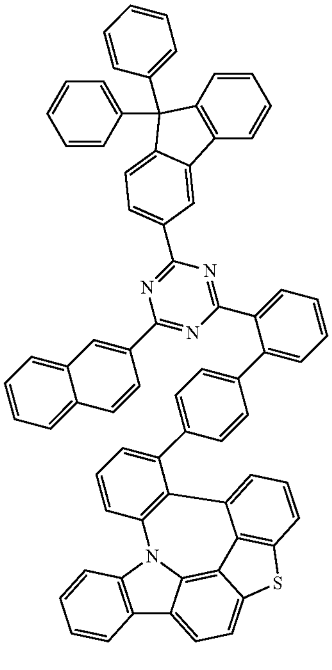
234
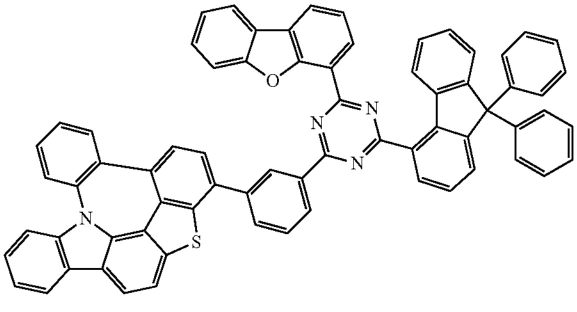

-continued
235
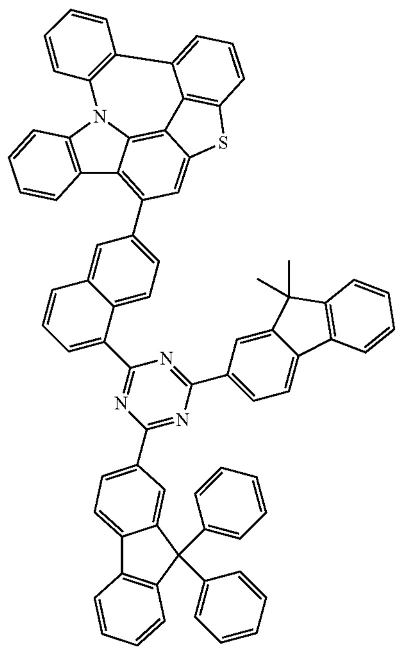
236
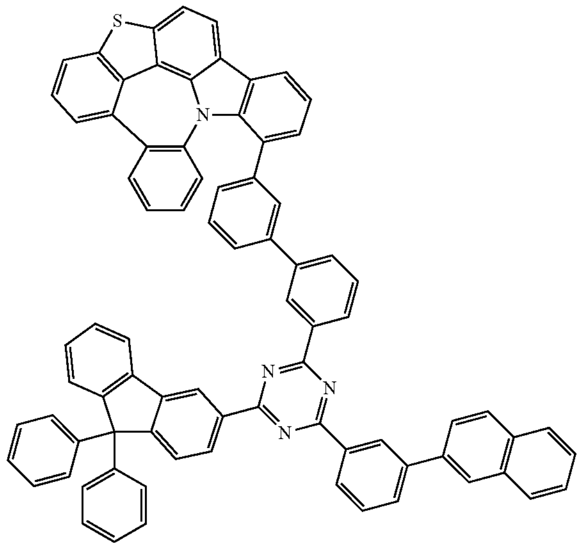
237
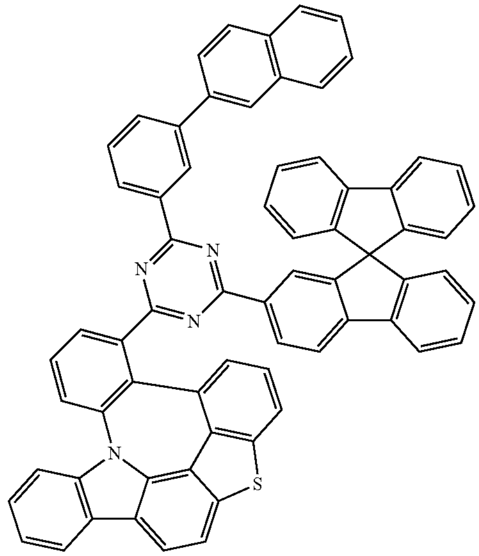
238
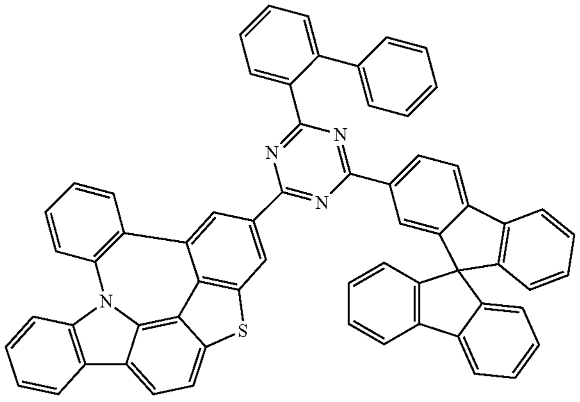

-continued
239
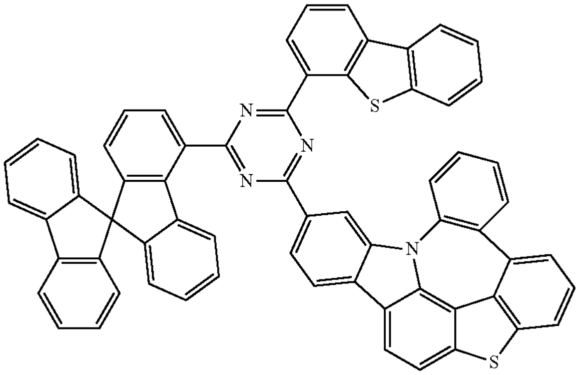
240
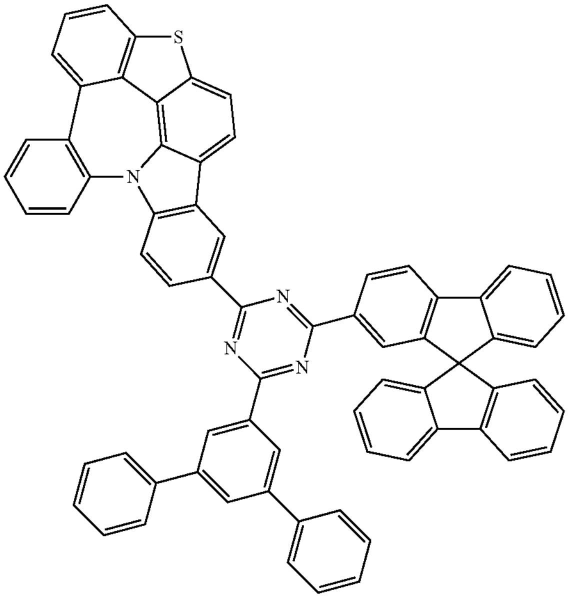
241
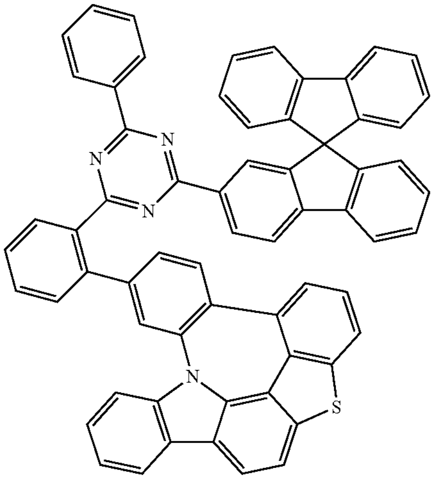
242
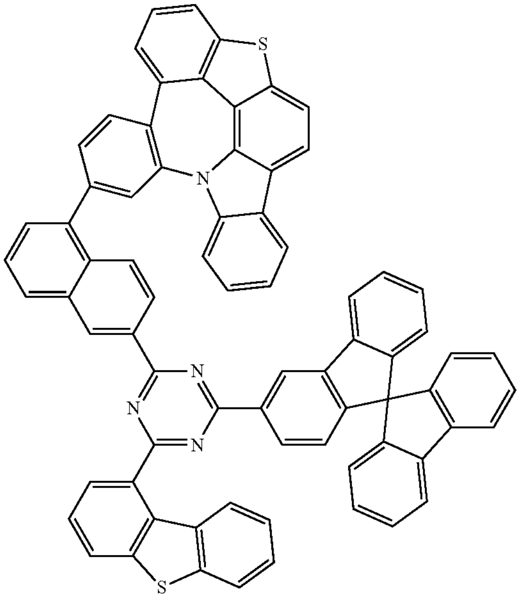

-continued
243
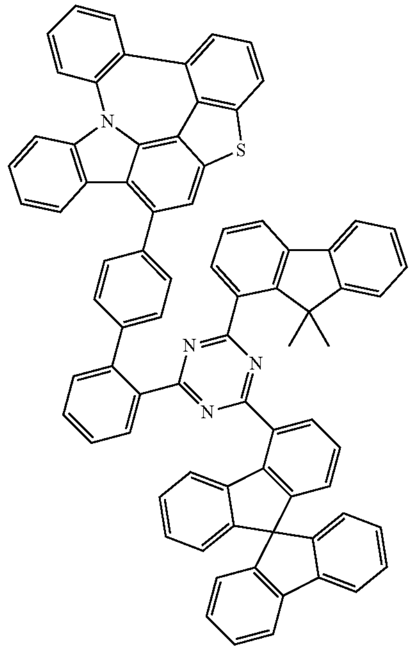
244
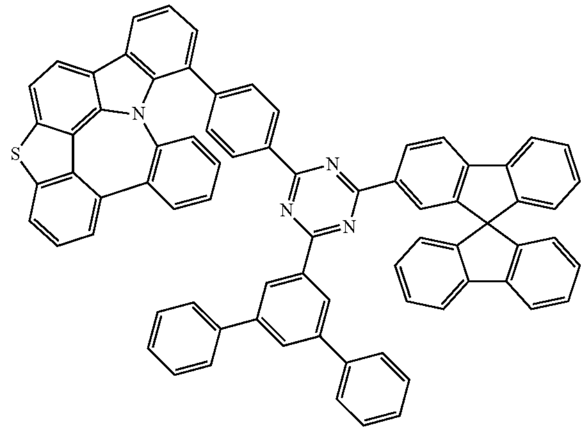
245
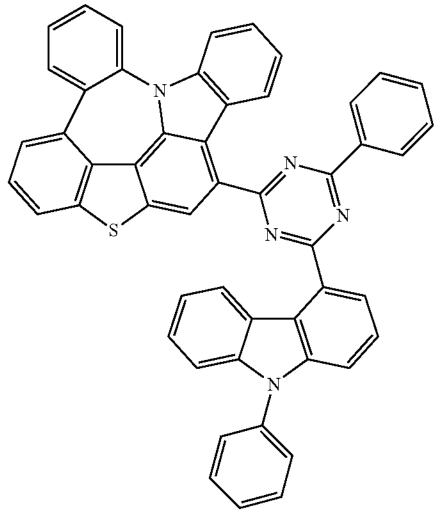
246
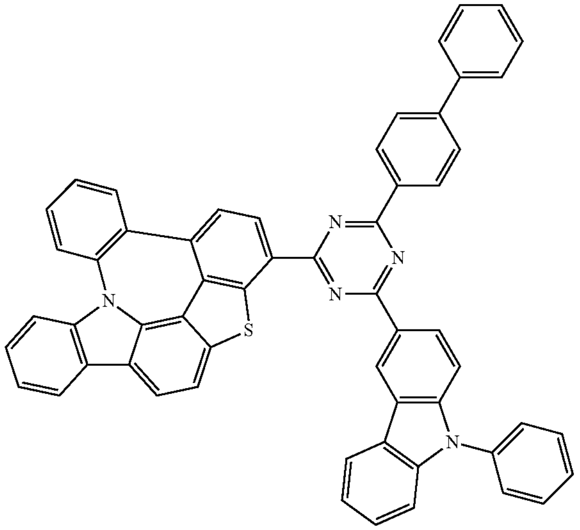

-continued
247
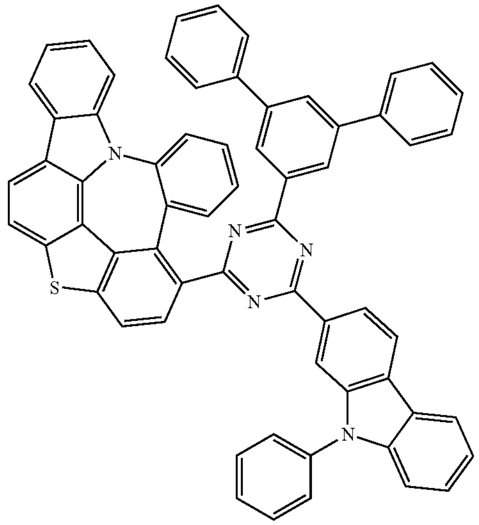
248
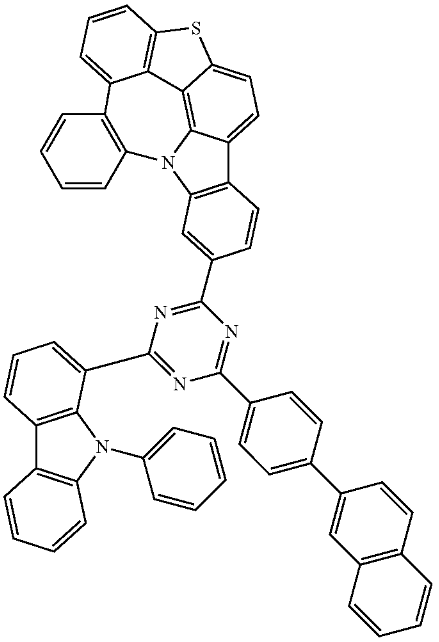
249
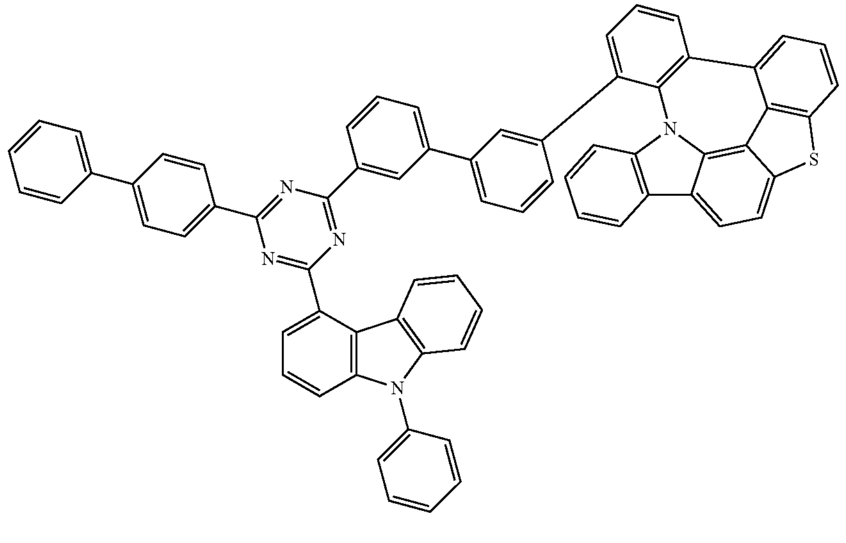

-continued
250
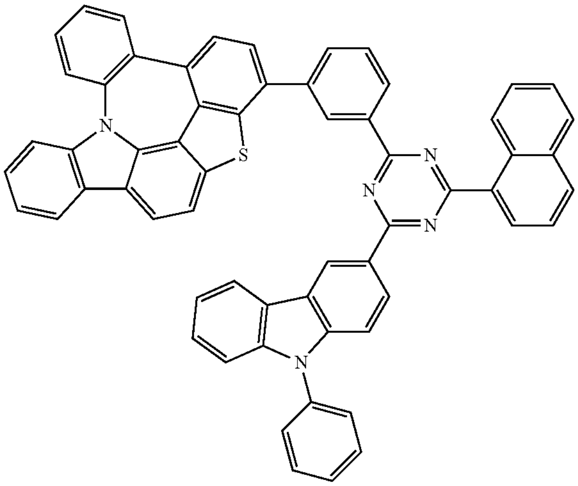
251
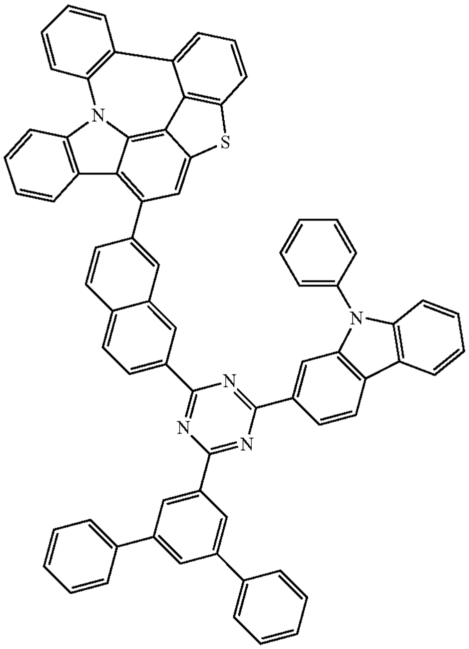
252
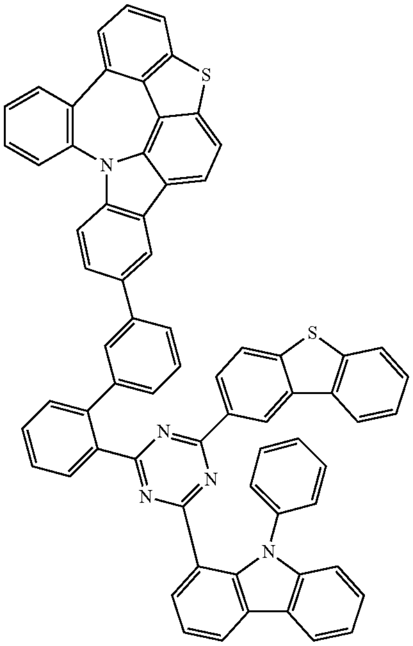
253
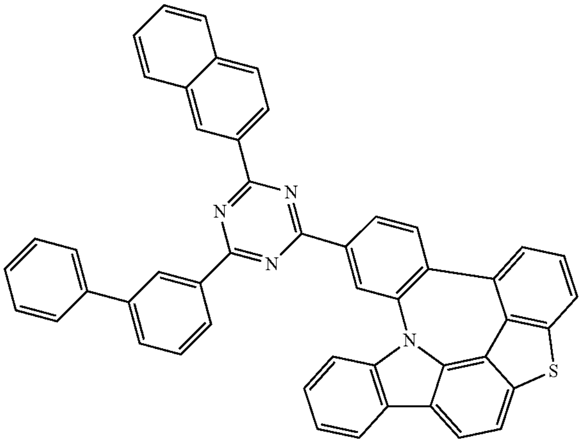

-continued
254
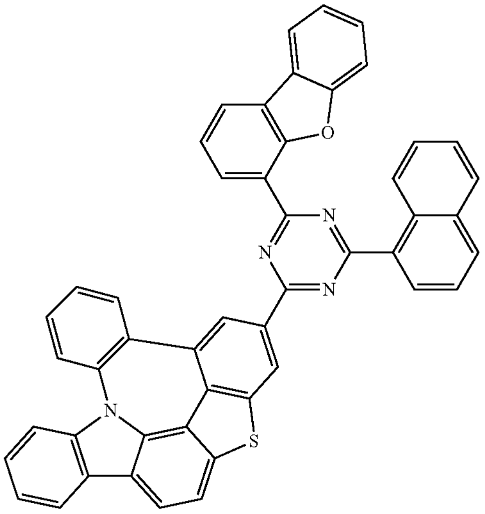
255
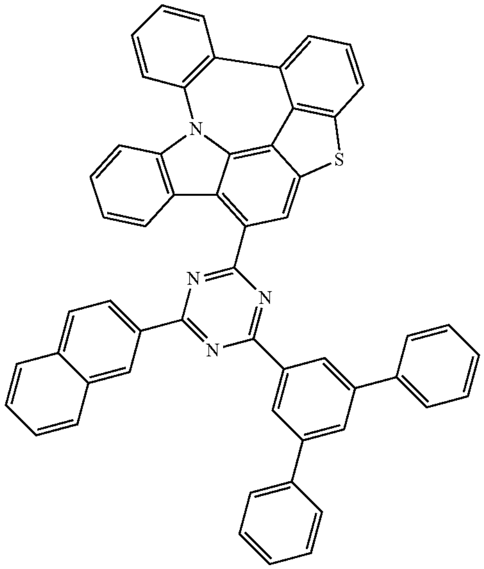
256
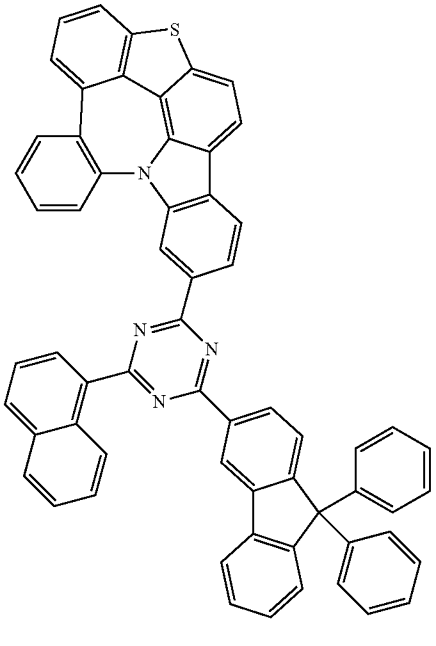
257
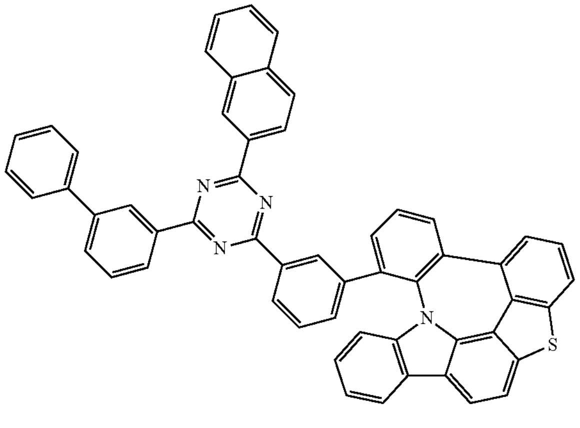

-continued
258
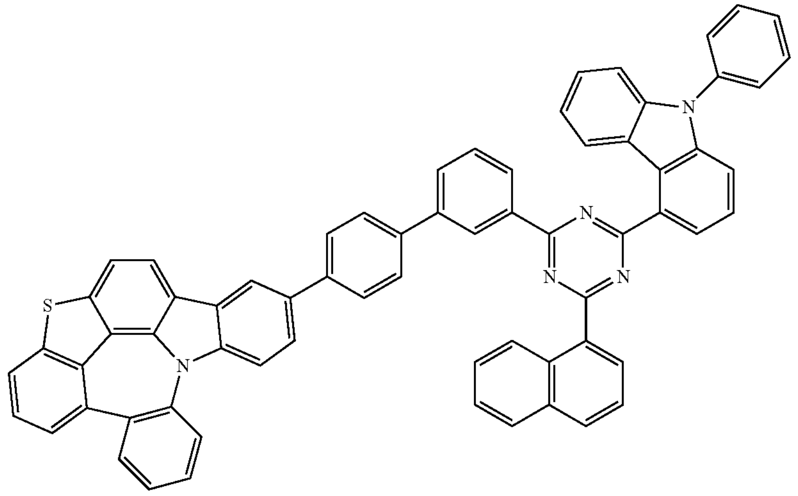
259
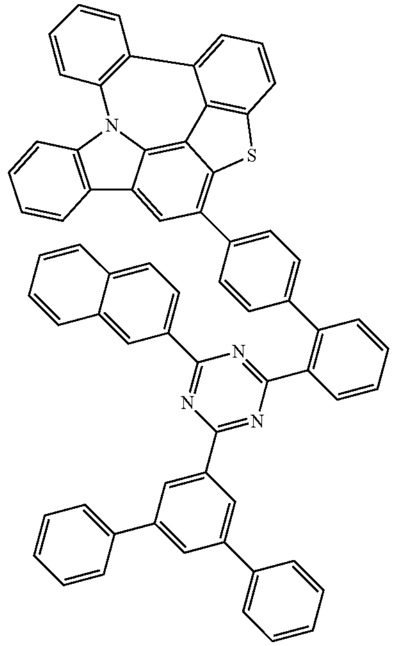
300
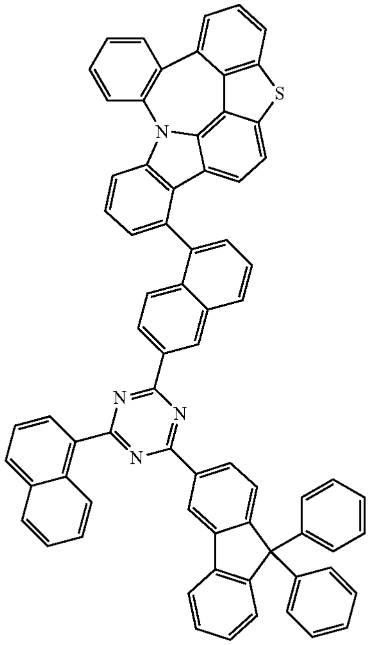

-continued
301
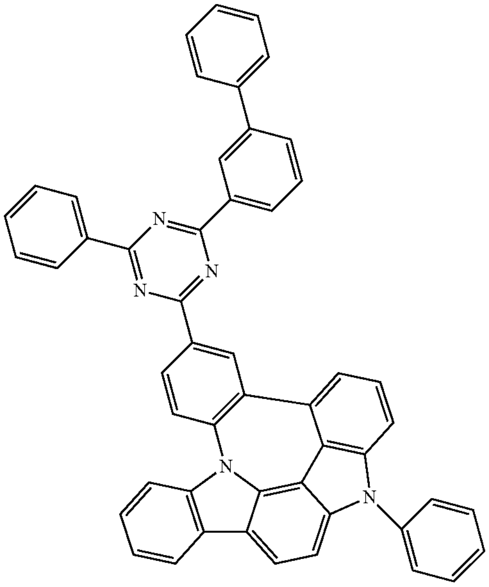
302
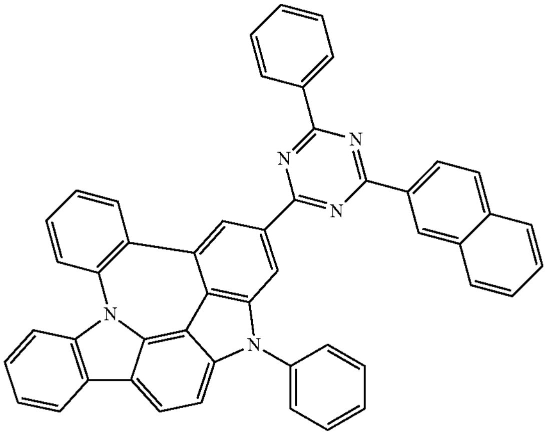
303
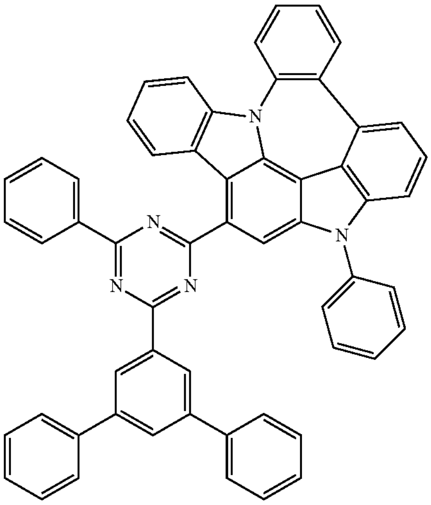
304
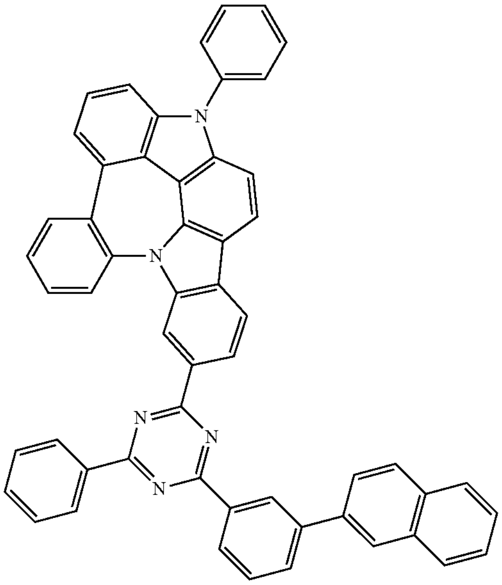
305
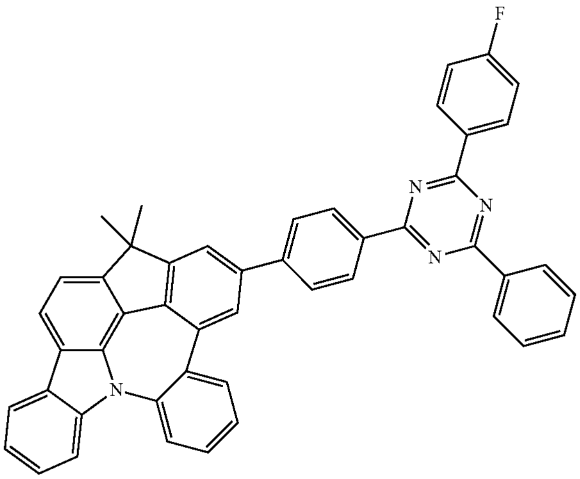
306
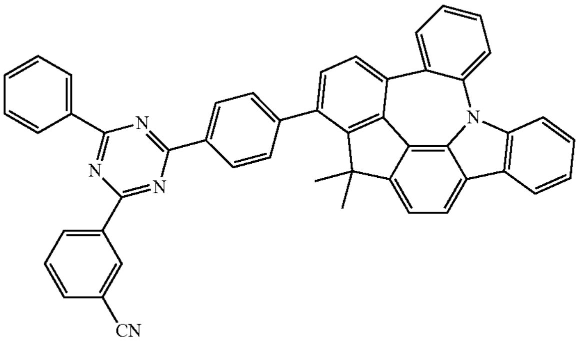

-continued
307
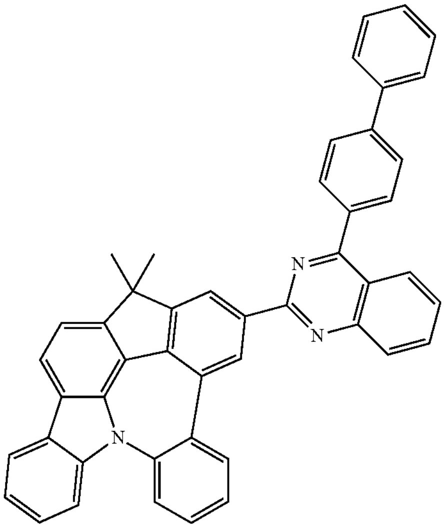
308
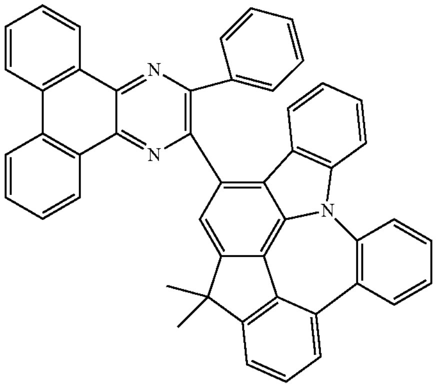
309
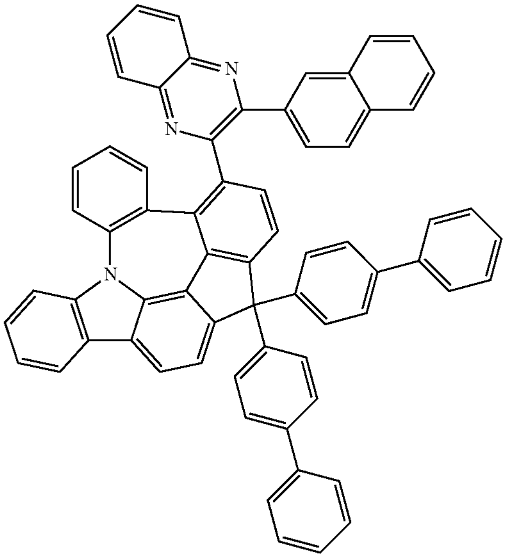
310
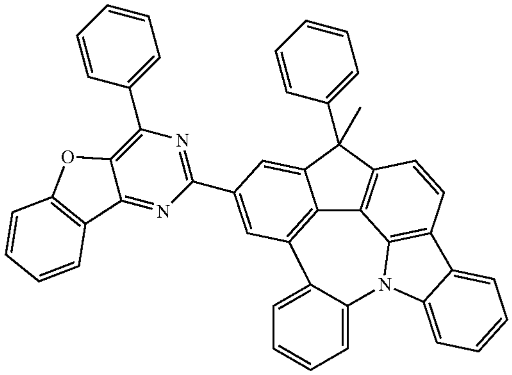
311
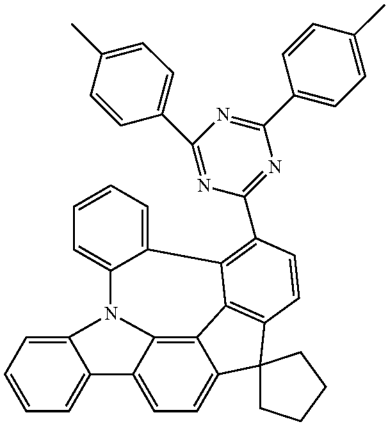
312
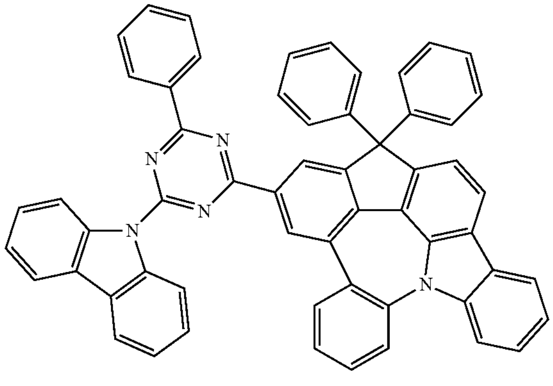

-continued
313
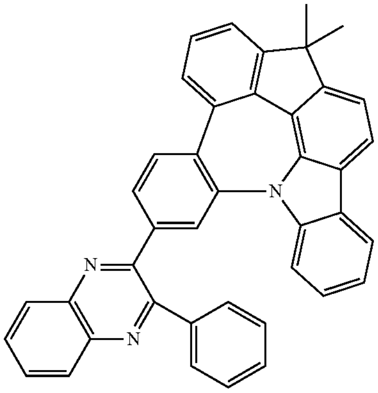
314
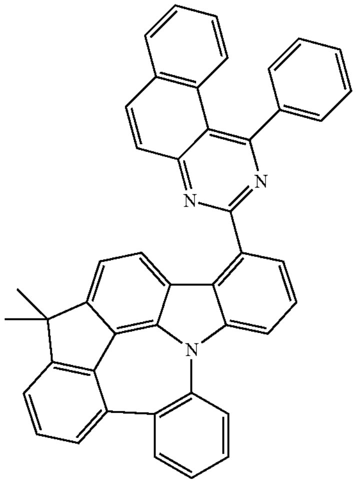
315
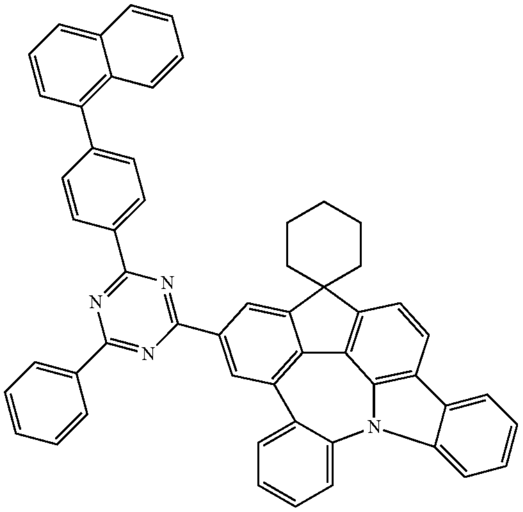
316
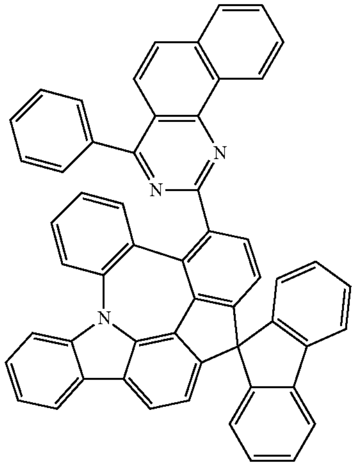
317
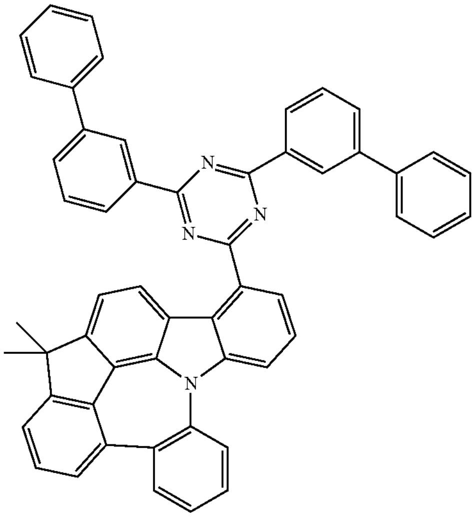
318
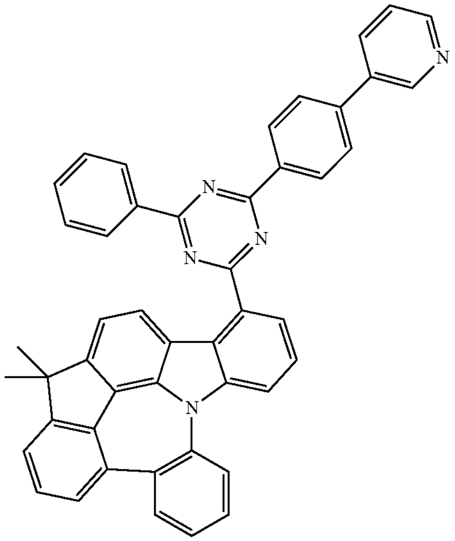

-continued
319
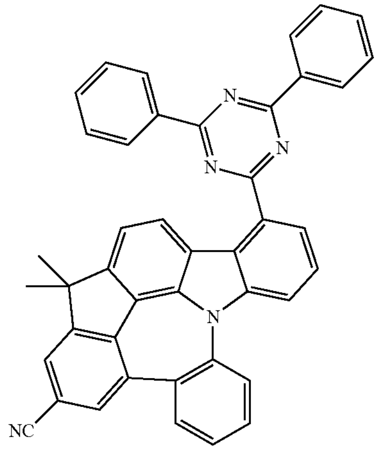
320
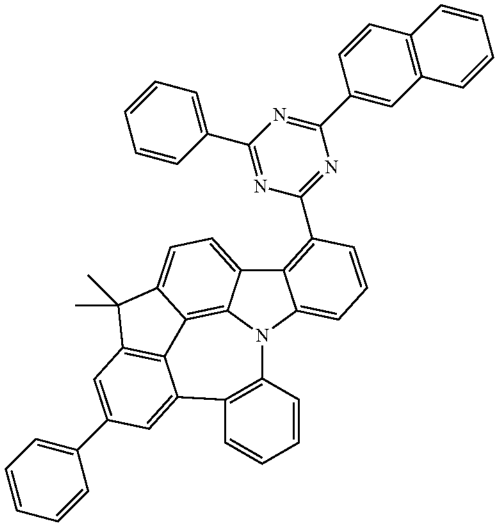
321
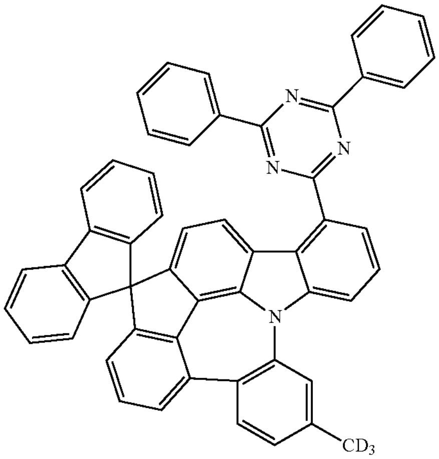
322
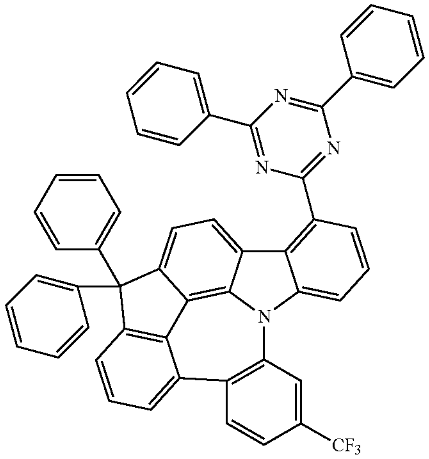
323
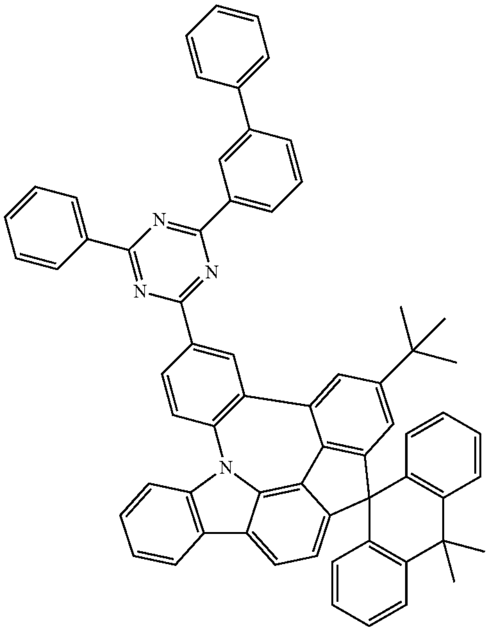
324
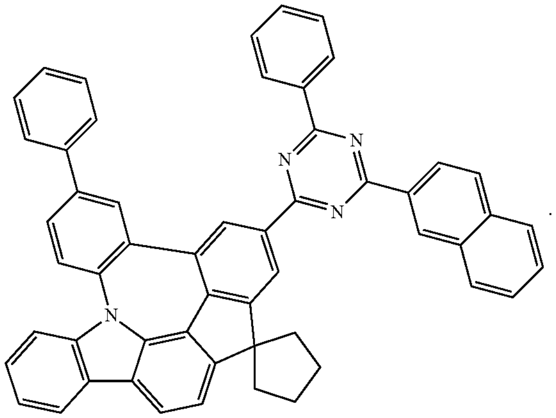

In a second aspect of the present application, an OLED is provided, including: an anode and a cathode that are arranged oppositely, and a functional layer arranged between the anode and the cathode, wherein the functional layer includes the organic compound provided in the first aspect of the present application.

In a specific embodiment, the functional layer may include an ETL, and the ETL may include the organic compound. The ETL may include the organic compound provided in the present application, or may include both the organic compound provided in the present application and other materials, and there may be one or more ETLs.

In a specific embodiment, the functional layer may include a light-emitting layer, and the light-emitting layer may include the organic compound. A host material for the light-emitting layer may include the organic compound provided in the present application, or may include the organic compound provided in the present application and other materials.

As shown in FIG. 1, the OLED may include an anode 100, a first HTL 321, a hole adjustment layer 322, a light-emitting layer 330 as an energy conversion layer, an ETL 340, and a cathode 200 that are successively stacked.

Optionally, the anode 100 may be preferably made of a material with a large work function that facilitates the injection of holes into the functional layer. Specific examples of the anode material may include, but are not limited to: metals such as nickel, platinum, vanadium, chromium, copper, zinc, and gold or alloys thereof; metal oxides such as zinc oxide, indium oxide, indium tin oxide (ITO), and indium zinc oxide (IZO); a combination of a metal and an oxide such as ZnO:Al or $SnO_2$:Sb; or conductive polymers such as poly(3-methylthiophene), poly[3,4-(ethylene-1,2-dioxy)thiophene] (PEDT), polypyrrole (PPy), and polyaniline (PANI). Preferably, an electronic device may include a transparent electrode with ITO as an anode.

Optionally, the first HTL 321 may include one or more hole transport materials, and the hole transport materials may be carbazole polymers, carbazole-linked triarylamine compounds, or other compounds, which is not particularly limited in the present application. For example, the first HTL 321 may include the compound PAPB.

Optionally, the hole adjustment layer 322 (also referred to as "second HTL") may include a triarylamine compound or another type of a compound. In an embodiment, the hole adjustment layer may include PAPB.

Optionally, the light-emitting layer 330 may include a single light-emitting material, or may include a host material and a dopant material. Optionally, the light-emitting layer 330 may include a host material and a dopant material, wherein holes injected into the light-emitting layer 330 and electrons injected into the light-emitting layer 330 can be recombined in the light-emitting layer 330 to form excitons, the excitons transfer energy to the host material, and then the host material transfers energy to the dopant material, such that the dopant material can emit light. The host material for the light-emitting layer 330 may be a metal chelate compound, a bisstyryl derivative, an aromatic amine derivative, a dibenzofuran derivative, or the like. In a specific embodiment of the present application, the host material for the light-emitting layer may include the organic compound in the present application.

The dopant material for the light-emitting layer 330 may be a compound with a condensed aryl ring or a derivative thereof, a compound with a heteroaryl ring or a derivative thereof, an aromatic amine derivative, or the like, which is not particularly limited in the present application. In a specific embodiment of the present application, the light-emitting layer 330 may include the compound $Ir(piq)_2(acac)$ and the organic compound of the present application as a host of the light-emitting layer.

Optionally, the ETL 340 may have a single-layer structure or a multi-layer structure, which may include one or more electron transport materials. The electron transport materials may include, but are not limited to, the organic compound of the present application, benzimidazole derivatives, oxadiazole derivatives, quinoxaline derivatives, or other electron transport materials. In an embodiment of the present application, the ETL 340 may include ET-06 and 8-hydroxyquinolinolato-lithium (LiQ).

In the present application, the cathode 200 may include a cathode material with a small work function that facilitates the injection of electrons into the functional layer. Specific examples of the cathode material may include, but are not limited to: metals such as magnesium, calcium, sodium, potassium, titanium, indium, yttrium, lithium, gadolinium, aluminum, silver, tin, and lead or alloys thereof; or multilayer materials such as LiF/Al, Liq/Al, $LiO_2$/Al, LiF/Ca, LiF/Al, and $BaF_2$/Ca. Preferably, a metal electrode with magnesium and silver may be adopted as the cathode.

Optionally, as shown in FIG. 1, an EIL 350 may be further arranged between the cathode 200 and the ETL 340 to enhance the ability to inject electrons into the ETL 340. The EIL 350 may include an inorganic material such as an alkali metal sulfide and an alkali metal halide, or may include a complex of an alkali metal and an organic substance. For example, the EIL 350 may include LiQ.

Optionally, as shown in FIG. 1, an HIL 310 may be further arranged between the anode 100 and the first HTL 321 to enhance the ability to inject holes into the first HTL 321. The HIL 310 can be made of a benzidine derivative, a starburst arylamine compound, a phthalocyanine derivative, or another material, which is not particularly limited in the present application. For example, the HIL 310 may include F4-TCNQ.

In a third aspect of the present application, an electronic apparatus is provided, which includes the OLED provided in the second aspect of the present application.

Figure 2:
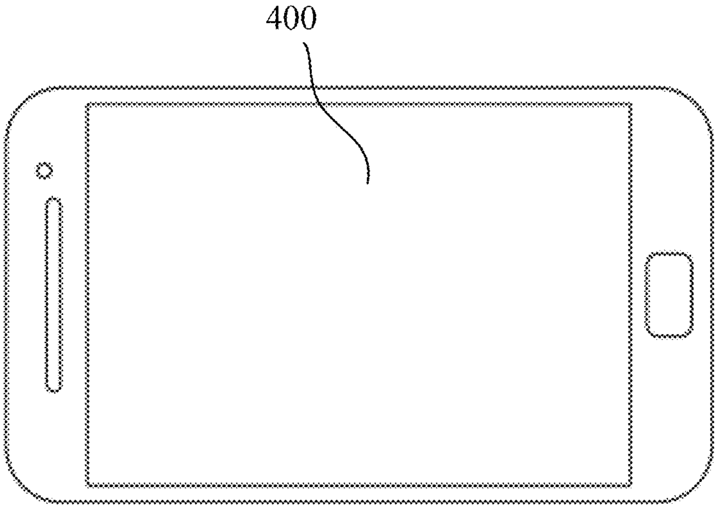
FIG. 2 is a schematic structural diagram of an electronic apparatus according to an embodiment of the present application.

According to an embodiment, as shown in FIG. 2, the present disclosure provides an electronic apparatus 400, and the electronic apparatus 400 includes the OLED. For example, the electronic apparatus 400 may be a display apparatus, a lighting apparatus, an optical communication apparatus, or another electronic apparatus, including but not limited to computer screen, mobile phone screen, television set, electronic paper, emergency light, and optical module.

Synthesis Examples

In the synthesis examples described below, unless otherwise stated, all temperatures are in degrees Celsius (° C.). Some reagents are purchased from commodity suppliers such as Aldrich Chemical Company, Arco Chemical Company, and Alfa Chemical Company, and some intermediates that cannot be directly purchased are prepared from commercially-available raw materials through simple reactions. The compounds of the synthesis methods not mentioned in the present application are all commercially-available raw materials.

Unless otherwise stated, these materials are used without further purification. The remaining conventional reagents are purchased from Shantou Xilong Chemical Co., Ltd., Guangdong Guanghua Chemical Reagent Factory, Guangzhou Chemical Reagent Factory, Tianjin Haoyuyu Chemical Co., Ltd., Tianjin Fuchen Chemical Reagent Factory, Wuhan Xinhuayuan Technology Development Co., Ltd., Qingdao Tenglong Chemical Reagent Co., Ltd., and Qingdao Haiyang Chemical Co., Ltd. The reactions in the synthesis examples are generally conducted under a positive pressure of nitrogen or argon or in a drying tube with an anhydrous solvent (unless otherwise stated); and during the reactions, a reaction flask is plugged with a suitable rubber plug, a substrate is injected into the reaction flask through a syringe, and all glass wares involved are dry.

During purification, a chromatographic column is a silica gel column, and silica gel (100 to 200 mesh) is purchased from Qingdao Haiyang Chemical Co., Ltd.

In each synthesis example, low-resolution mass spectrometry (MS) data are obtained under the following conditions: Agilent 6120 quadrupole HPLC-M (column model: Zorbax SB-C18, 2.1×30 mm, 3.5 μm, 6 min, flow rate: 0.6 mL/min; and mobile phase: a proportion of (acetonitrile with 0.1% formic acid) in (water with 0.1% formic acid): 5% to 95%, electrospray ionization (ESI), and ultraviolet (UV) detection at 210 nm/254 nm.

$^1$H nuclear magnetic resonance (NMR) spectroscopy: Through a Bruker 400 MHz NMR spectrometer, the NMR spectroscopy is conducted at room temperature with $CDCl_3$ (in ppm) as a solvent and tetramethylsilane (TMS) (0 ppm) as a reference standard. When multiplets appear, the following abbreviations will be adopted: s: singlet, d: doublet, t: triplet, and m: multiplet.

Synthesis Examples

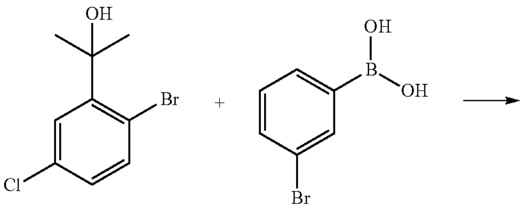

SA-1-1 SA-2-1

-continued

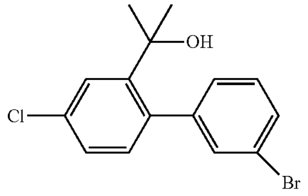

SA-3-1

Under nitrogen atmosphere, the raw materials SA-1-1 (232.8 g, 933.07 mmol) and SA-2-1 (187.36 g, 933.07 mmol), tetrahydrofuran (THF) (1,397 mL), and water (464 mL) were added to a three-necked flask, and a resulting mixture was heated to reflux and stirred until a resulting solution was clear; $Pd_2(PPh_3)_4$ (10.78 g, 9.33 mmol) and $K_2CO_3$ (193.15 g, 1399.61 mmol) were added, a resulting mixture was stirred until a resulting solution was clear, and then heated to reflux and stirred for 24 h. After the reaction was completed, the resulting reaction solution was cooled to room temperature, dichloromethane (DCM) was added for extraction, the separated organic phase was washed with water until neutral and dried with anhydrous magnesium sulfate, filtered, and a resulting filtrate was concentrated in vacuum to obtain a residue; and the residue was purified by silica gel column chromatography to obtain an intermediate SA-3-1 (206.59 g, yield: 68%).

The intermediates SA-3-X (X was a variable, which was an integer of 1 to 20, the same below) listed in Table 1 were each synthesized with reference to the synthesis method of the intermediate SA-3-1, except that SA-1-X was used instead of the raw material SA-1-1 and SA-2-X was used instead of the raw material SA-2-1.

TABLE 1

| SA-1-X | SA-2-X | SA-3-X | Yield (%) |
|---|---|---|---|
| 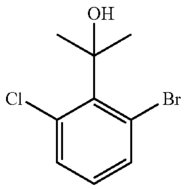 SA-1-2 | 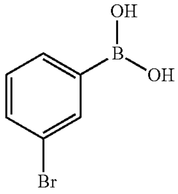 SA-2-1 | 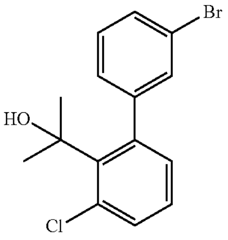 SA-3-2 | 62 |
| 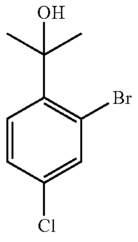 SA-1-3 | | 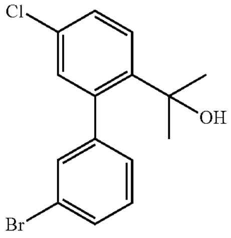 SA-3-3 | 67 |

TABLE 1-continued

| SA-1-X | SA-2-X | SA-3-X | Yield (%) |
|---|---|---|---|
| 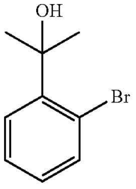 SA-1-4 | 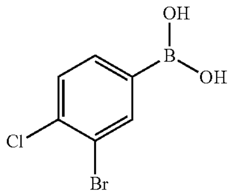 SA-2-2 | 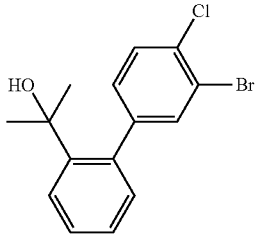 SA-3-4 | 63 |
| | 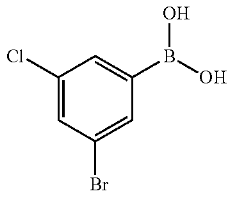 SA-2-3 | 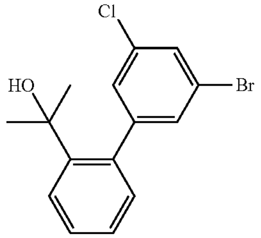 SA-3-5 | 67 |

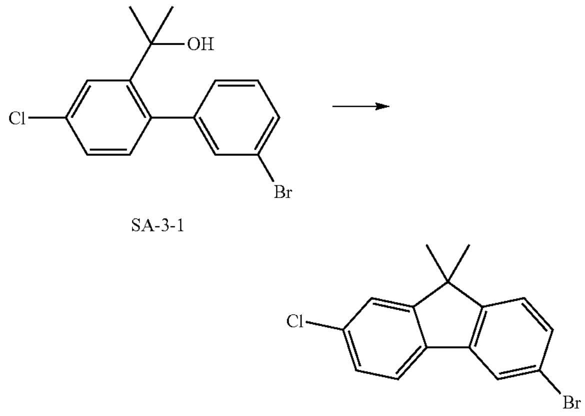

SA-3-1

SA-4-1

The intermediate SA-3-1 (209 g, 641.44 mmol), acetic acid (990 mL), and phosphoric acid (55 mL) were added to a three-necked flask, a resulting mixture was heated to 50° C. and stirred until a resulting solution was clear, and the reaction mixture was stirred for 4 h. After the reaction was completed, a resulting reaction solution was cooled to room temperature, a NaOH aqueous solution was added for neutralization, and ethyl acetate was added for extraction. The combined organic phases were dried with anhydrous magnesium sulfate, and filtered, a filtrate was concentrated in vacuum to obtain a residue, and the residue was purified by silica gel column chromatography to obtain an intermediate SA-4-1 (132.20 g, yield: 67%).

The intermediates SA-4-X listed in Table 2 were each synthesized with reference to the synthesis method of the intermediate SA-4-1, except that an intermediate SA-3-X was used instead of the intermediate SA-3-1.

TABLE 2

| SA-3-X | SA-4-X | Yield (%) |
|---|---|---|
| 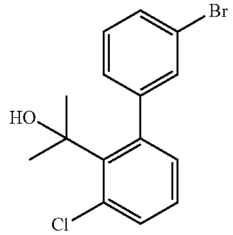 SA-3-2 | 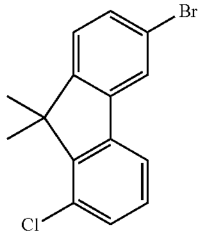 SA-4-2 | 68 |
| 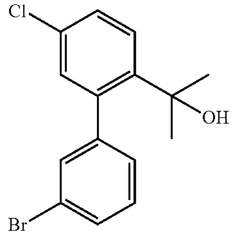 SA-3-3 | 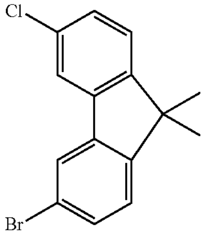 SA-4-3 | 69 |

TABLE 2-continued

| SA-3-X | SA-4-X | Yield (%) |
|---|---|---|
| 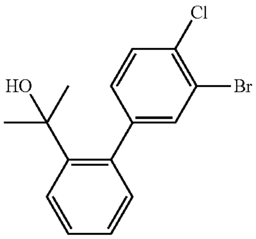 SA-3-4 | 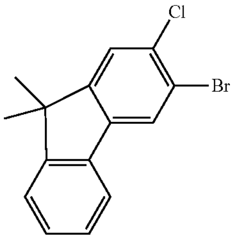 SA-4-4 | 66 |
| 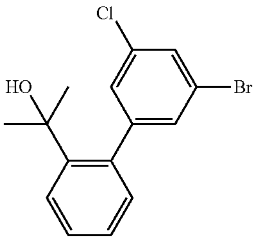 SA-3-5 | 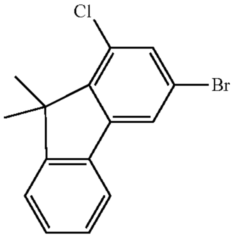 SA-4-5 | 63 |

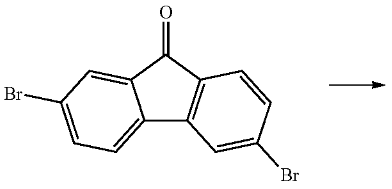

SB-1-1

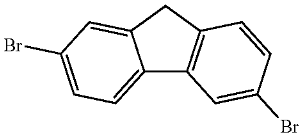

SB-2-1

Raney nickel (8 g), hydrazine hydrate (105 mL, 2,166 mmol), a raw material SB-1-1 (183 g, 541.42 mmol), toluene (1,098 mL), and ethanol (366 mL) were added to a three-necked flask, a resulting mixture was quickly stirred and heated to reflux, and a reaction was conducted for 2 h; and after the reaction was completed, the reaction solution was concentrated in vacuum to obtain a residue, and the residue was purified by silica gel column chromatography to obtain an intermediate SB-2-1 (128.08 g, yield: 73%).

The intermediates SB-2-X listed in Table 3 below were each synthesized with reference to the synthesis method of the intermediate SB-2-1, except that SB-1-X was used instead of the SB-1-1.

TABLE 3

| SB-1-X | SB-2-X | Yield (%) |
|---|---|---|
| 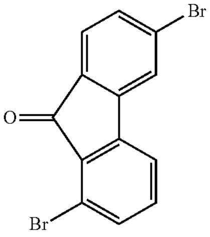 SB-1-2 | 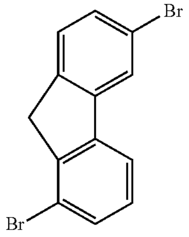 SB-2-2 | 75.1 |
| 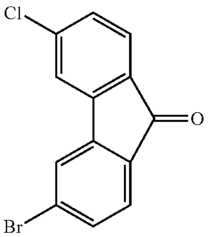 SB-1-3 | 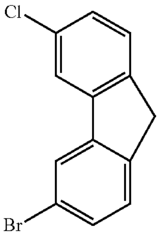 SB-2-3 | 77.6 |
| 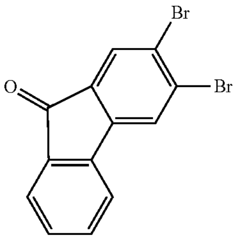 SB-1-4 | 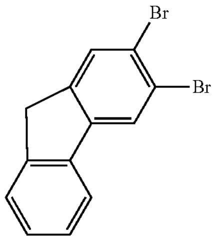 SB-2-4 | 70.8 |
| 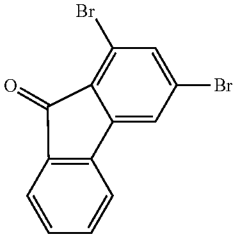 SB-1-5 | 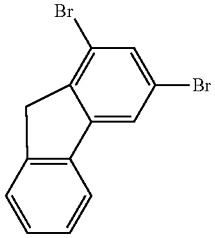 SB-2-5 | 74.7 |

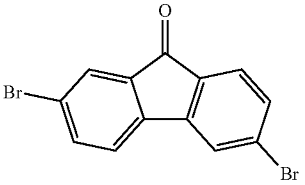

SB-1-1

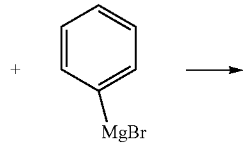

SB-3-1

-continued

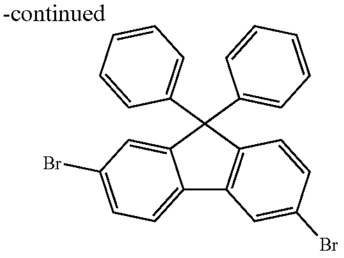

SB-4-1

The SB-1-1 (124 g, 366.86 mmol) and anhydrous THF (744 mL) were added to a three-necked flask, a resulting mixture was cooled to −10° C., then the SB-3-1 (69.84 g, 385.20 mmol) was added, and a resulting mixture was continuously stirred until it was warmed to room temperature; then a saturated $NH_4Cl$ solution (500 mL) was added for quenching, and ethyl acetate was added to a resulting reaction solution for extraction. The combined organic phases were washed with water, dried with anhydrous sodium sulfate, and filtered, a filtrate was concentrated in vacuum to obtain a residue, and the residue was purified by recrystallization with toluene and n-heptane; benzene was added to a resulting crystal, a resulting mixture was heated to 50° C., then trifluoromethanesulfonic acid (100 mL) was added dropwise, after the dropwise addition, the reaction mixture was conducted for another 30 min; and a resulting reaction mixture was washed with water and the separated organic phase was dried with anhydrous sodium sulfate, concentrated in vacuum to obtain a residue, and the residue was purified by silica gel column chromatography with a mixture of n-heptane and ethyl acetate to obtain an intermediate SB-4-1 (130.7 g, yield: 75%).

The intermediates SB-4-X listed in Table 4 below were each synthesized with reference to the synthesis method of the intermediate SB-4-1, except that SB-1-X was used instead of the SB-1-1 and SB-3-X was used instead of the SB-3-1.

TABLE 4

| SB-1-X | SB-3-X | SB-4-X | Yield (%) |
|---|---|---|---|
| 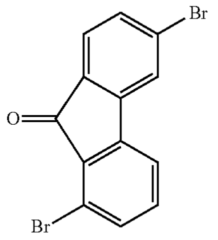 SB-1-2 | 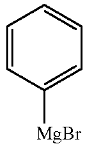 SB-3-1 | 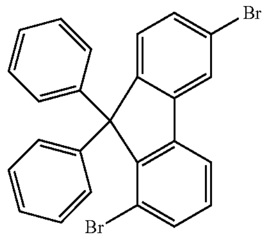 SB-4-2 | 75.7 |
| 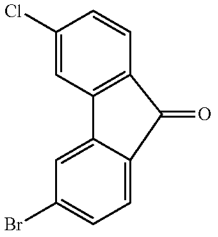 SB-1-3 | 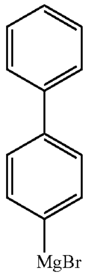 SB-3-2 | 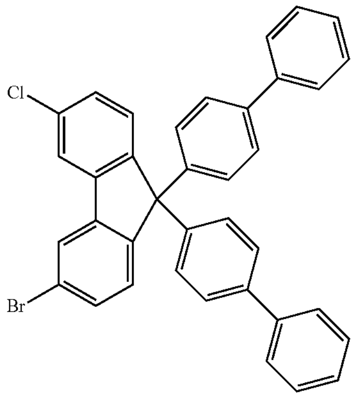 SB-4-3 | 73.5 |

TABLE 4-continued
| SB-1-X | SB-3-X | SB-4-X | Yield (%) |
|---|---|---|---|
| 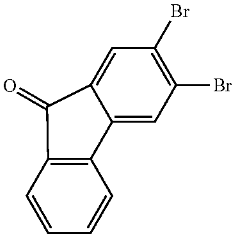 SB-1-4 | 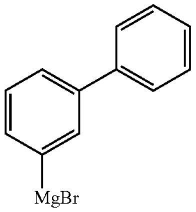 SB-3-3 | 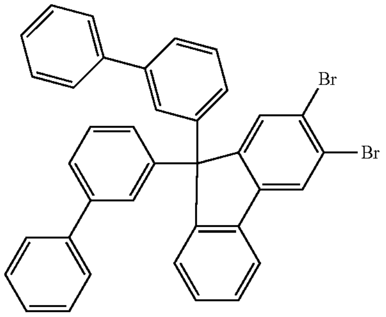 SB-4-4 | 66.3 |
| 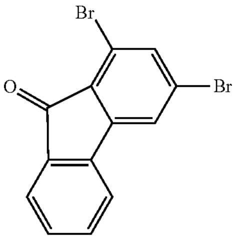 SB-1-5 | 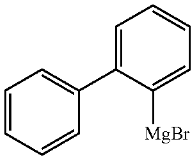 SB-3-4 | 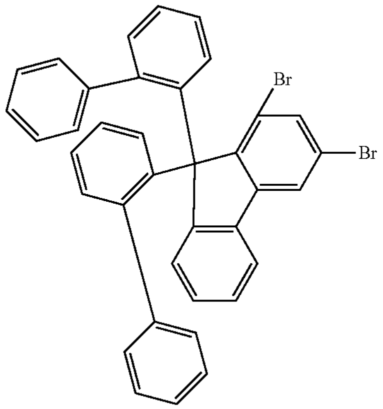 SB-4-5 | 61.8 |
| 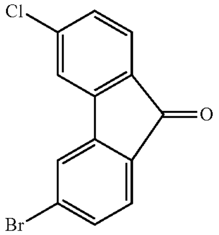 SB-1-3 | 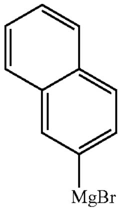 SB-3-5 | 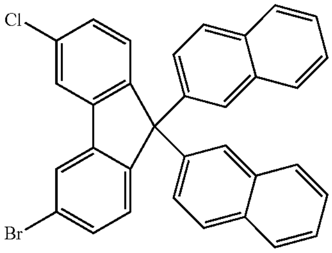 SB-4-6 | 71.2 |
| 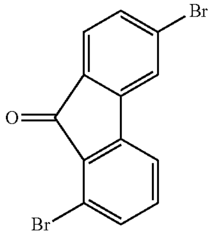 SB-1-2 | 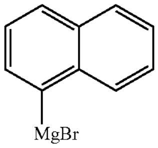 SB-3- 6 | 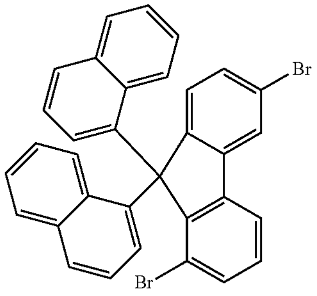 SB-4-7 | 65.2 |

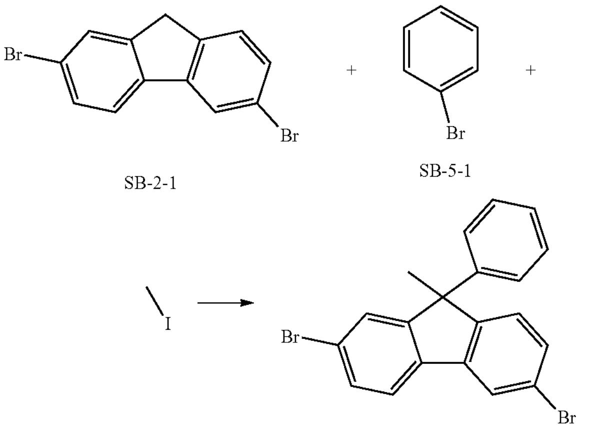

SB-2-1 SB-5-1 SB-6-1

Under nitrogen atmosphere, SB-2-1 (130 g, 401.21 mmol), SB-5-1 (56.83 g, 401.21 mmol), dioxane, potassium tert-butoxide (112.34 g, 1,003.03 mmol), and $Pd_2(dba)_3$ (3.82 g, 4.01 mmol) were added to a three-necked flask, a resulting mixture was heated to 120° C., and stirred for 12 h; iodomethane (56.95 g, 401.21 mmol) was added, and a resulting mixture was stirred at room temperature for 6 h. After the reaction was completed, a resulting reaction mixture was washed with water until neutral and a separated organic phase was concentrated in vacuum to obtain a residue; and the residue was purified by silica gel column chromatography and eluted with a mixture of petroleum ether (PE) and ethyl acetate (in a volume ratio of 10:1) to obtain an intermediate SB-6-1 (126.3 g, yield: 76%).

The intermediates SB-6-X listed in Table 5 below were each synthesized with reference to the synthesis method of the intermediate SB-6-1, except that SB-2-X was used instead of the intermediate SB-2-1 and SB-5-X was used instead of the intermediate SB-5-1.

TABLE 5

| SB-2-X | SB-5-X | SB-6-X | Yield (%) |
|---|---|---|---|
| 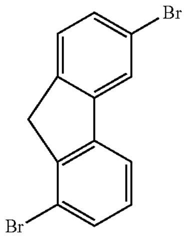 SB-2-2 | 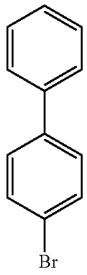 SB-5-2 | 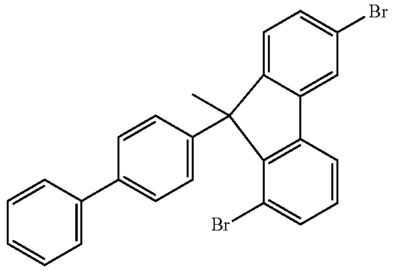 SB-6-2 | 75.4 |
| 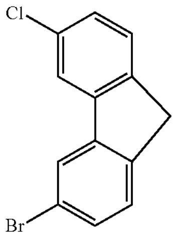 SB-2-3 | 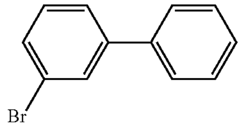 SB-5-3 | 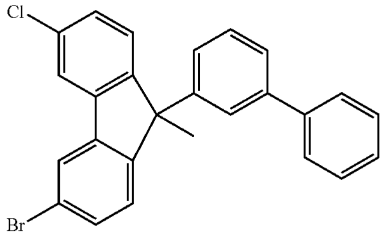 SB-6-3 | 76.8 |
| 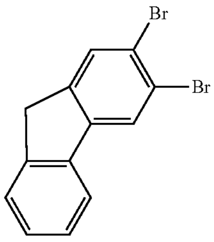 SB-2-4 | 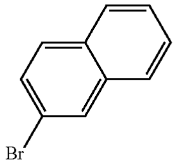 SB-5-4 | 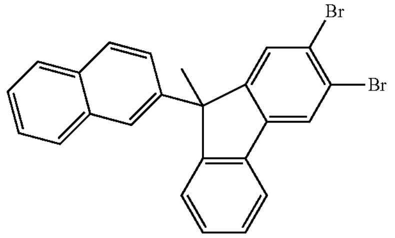 SB-6-4 | 71.5 |

TABLE 5-continued

| SB-2-X | SB-5-X | SB-6-X | Yield (%) |
|---|---|---|---|
| 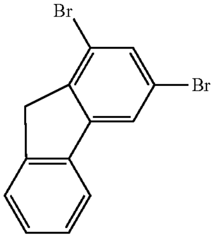 SB-2-5 | 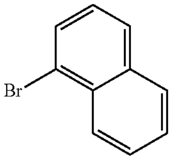 SB-5-5 | 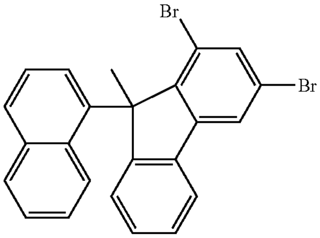 SB-6-5 | 77.3 |

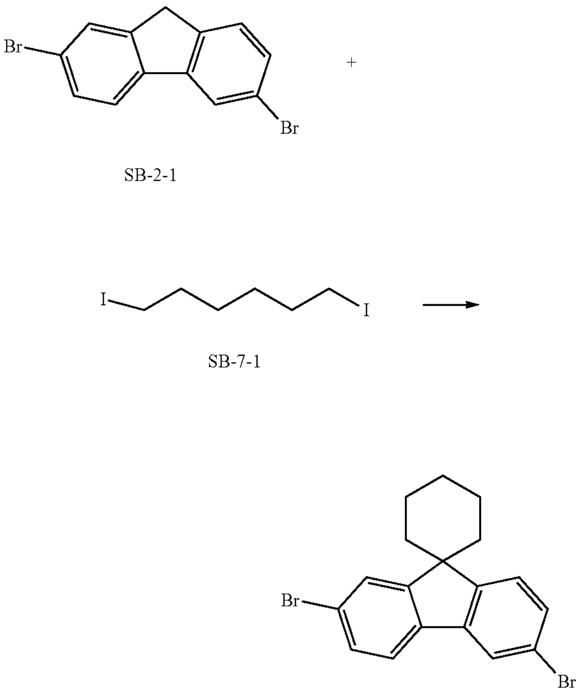

SB-2-1 + SB-7-1 → SB-8-1

SB-2-1 (141 g, 435.19 mmol) was dissolved in anhydrous dimethylsulfoxide (DMSO) (845 mL) in a three-necked flask, then sodium tert-butoxide (62.73 g, 652.79 mmol) was added at room temperature, and a resulting mixture was stirred and heated to 65° C.; then a raw material SB-7-1 (161.79 g, 478.71 mmol) was dissolved in anhydrous DMSO and then added dropwise to the three-necked flask, after the dropwise addition, a resulting mixture was kept at 65° C. and stirred for 30 min. After a reaction was completed, 300 mL of a $NH_4OH$ aqueous solution was added, a resulting mixture was stirred for 20 min and filtered, and a filter cake was washed with methanol and water to obtain a crude product; and the crude product was purified by silica gel column chromatography to obtain an intermediate SB-8-1 (126.28 g, yield: 74%).

The intermediates SB-8-X listed in Table 6 below were each synthesized with reference to the synthesis method of the intermediate SB-8-1, except that an intermediate SB-2-X was used instead of the SB-2-1 and a raw material SB-7-X was used instead of the SB-7-1.

TABLE 6

| SB-2-X | SB-7-X | SB-8-X | Yield (%) |
|---|---|---|---|
| 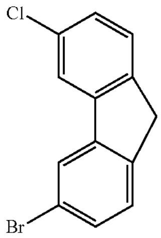 SB-2-3 | 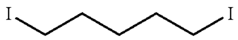 SB-7-2 | 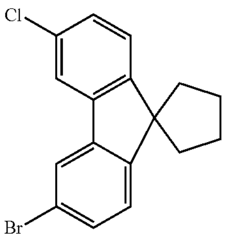 SB-8-3 | 75.4 |

TABLE 6-continued

| SB-2-X | SB-7-X | SB-8-X | Yield (%) |
|---|---|---|---|
| 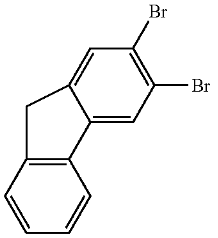 SB-2-4 | 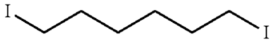 SB-7-1 | 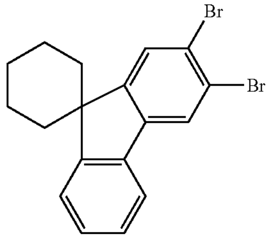 SB-8-4 | 76.7 |
| 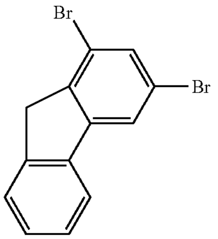 SB-2-5 | 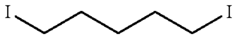 SB-7-2 | 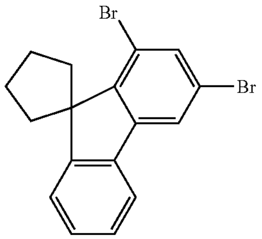 SB-6-5 | 75.8 |

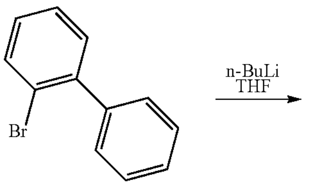

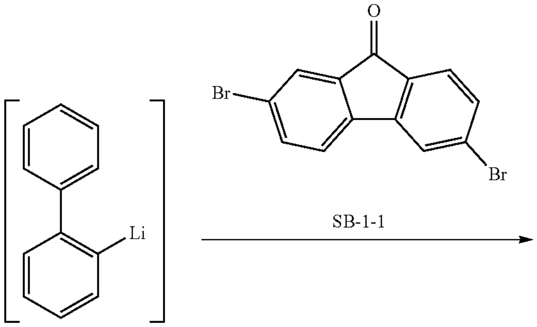
SB-1-1

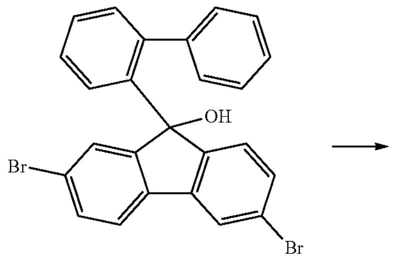
SB-3-2a

-continued

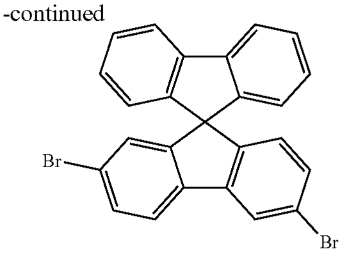
SB-9-1

Under the fully-dry condition and the nitrogen atmosphere, 2-bromo-1,1-biphenyl (105.5 g, 452.58 mmol) and 600 mL of anhydrous THF were added to a 1 L four-necked flask, a resulting mixture was stirred for dissolution and then cooled with liquid nitrogen to −78° C. or lower, 120 mL of a solution of n-BuLi in n-hexane (452.58 mmol) was slowly added dropwise, after the dropwise addition, a resulting mixture was stirred at −78° C. for 1 h; then SB-1-1 (152.97 g, 452.58 mmol) was added in batches at this temperature, and a resulting mixture was kept at −78° C. for 1 h, then warmed to room temperature, and stirred at room temperature for 12 h. After the reaction was completed, 8 mL of a hydrochloric acid solution was added dropwise for quenching, ethyl acetate was added for extraction, and a separated organic phase was washed with saturated brine, and concentrated in vacuum to obtain an intermediate SB-3-2a; the intermediate SB-3-2a was directly added to a 2 L dry three-necked flask without any purification, then 1,335 mL of acetic acid and 20 g of hydrochloric acid with a mass fraction of 36% were added, a resulting mixture was heated to reflux and stirred for 3 h, and then the reaction was completed; a resulting reaction mixture was cooled to room temperature and filtered, and a filter cake was washed twice with water, then dried, and purified by silica gel column chromatography to obtain an intermediate SB-9-1 (123.40 g, yield: 57.5%).

The intermediates SB-9-X listed in Table 7 below were each synthesized with reference to the synthesis method of the intermediate SB-9-1, except that SB-1-X was used instead of the SB-1-1.

TABLE 7

| SB-1-X | SB-9-X | Yield (%) |
|---|---|---|
| 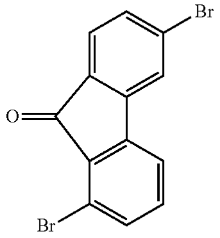 SB-1-2 | 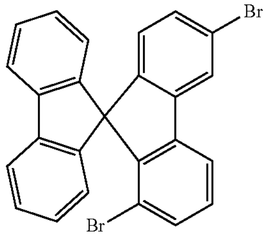 SB-9-2 | 75.1 |
| 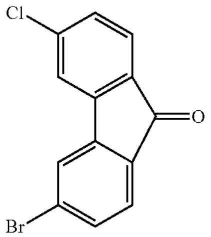 SB-1-3 | 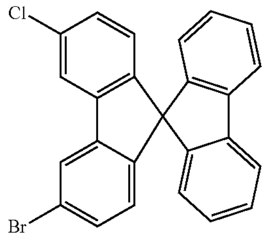 SB-9-3 | 76.5 |
| 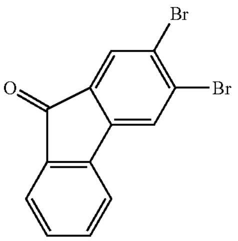 SB-1-4 | 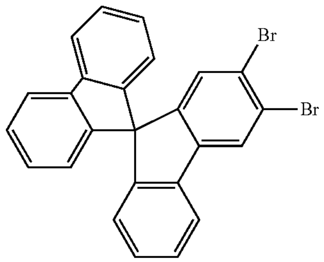 SB-9-4 | 74.8 |

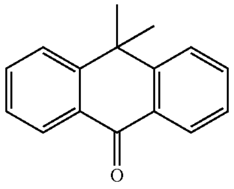
SC-1-1

+

-continued

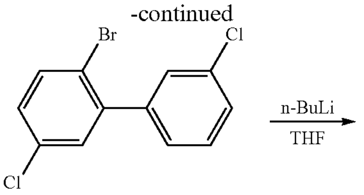

SC-2-1

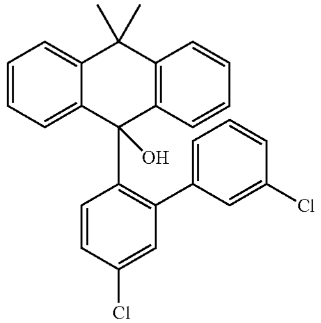

SC-3-1

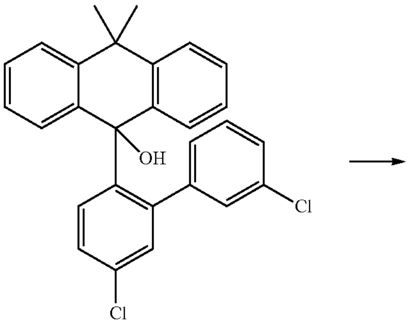

SC-3-1

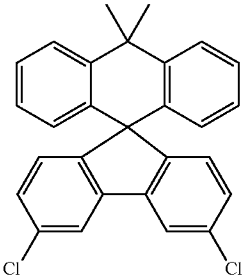

SC-4-1

Under the nitrogen atmosphere, SC-1-1 (151 g, 679.3 mmol) and THF (906 mL) were added to a three-necked flask, a resulting mixture was thoroughly stirred and cooled to −78° C., then n-butyllithium (10.87 g, 169.83 mmol) was added dropwise, after the dropwise addition, a resulting mixture was stirred at −78° C. for 1 h; then a raw material SC-2-1 (215.40 g, 713.27 mmol) was diluted with THF (430 mL) and then added dropwise, after the dropwise addition, a resulting mixture was stirred at −78° C. for another 1 h, then naturally warmed to 25° C., and stirred for 12 h. After the reaction was completed, a resulting reaction solution was poured into water (500 mL) and stirred for 10 min, and then extraction was conducted twice with DCM (500 mL); and combined organic phases were dried with anhydrous magnesium sulfate, and filtered by a silica gel funnel, and a filtrate was concentrated in vacuum to obtain an intermediate SC-3-1 (192.12 g, yield: 63.5%).

The intermediate SC-3-2 listed in Table 8 below was synthesized with reference to the synthesis method of the intermediate SC-3-1, except that SC-2-2 was used instead of the SC-2-1.

The intermediate SC-3-1 (191 g, 428.85 mmol) and trifluoroacetic acid (TFA) (1146 mL) were added to a single-necked flask, and a resulting mixture was heated to reflux at 80° C. and stirred for 11 h. After the reaction was completed, a resulting reaction solution was poured into water (1:20, v/v), a resulting mixture was stirred for 30 min and filtered, and a filter cake was rinsed with water and ethanol to obtain a crude product; and the crude product was purified by recrystallization with a mixture of DCM:n-heptane=1:2 (v/v) to obtain an intermediate SC-4-1 (130.13 g, yield: 71%).

The intermediate SC-4-2 listed in Table 9 below was synthesized with reference to the synthesis method of the intermediate SC-4-1, except that the intermediate SC-3-2 was used instead of the intermediate SC-3-1.

TABLE 8

| SC-1-1 | SC-2-2 | SC-3-2 | Yield (%) |
|---|---|---|---|
| 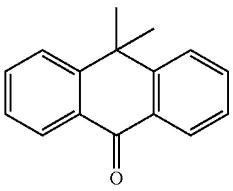 SC-1-1 | 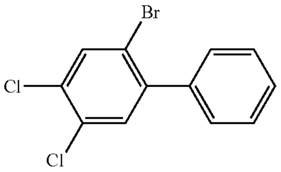 SC-2-2 | 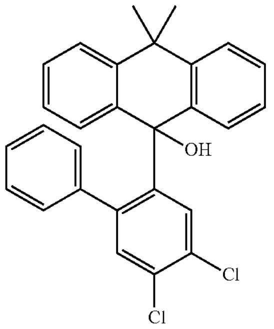 SC-3-2 | 64.5 |

TABLE 9

| SC-3-2 | SC-4-2 | Yield (%) |
|---|---|---|
| 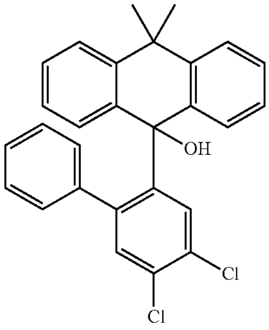 SC-3-2 | 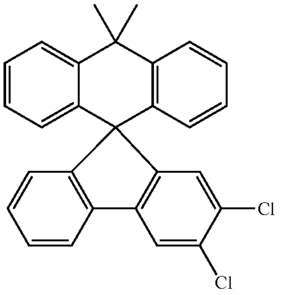 SC-4-2 | 72.3 |

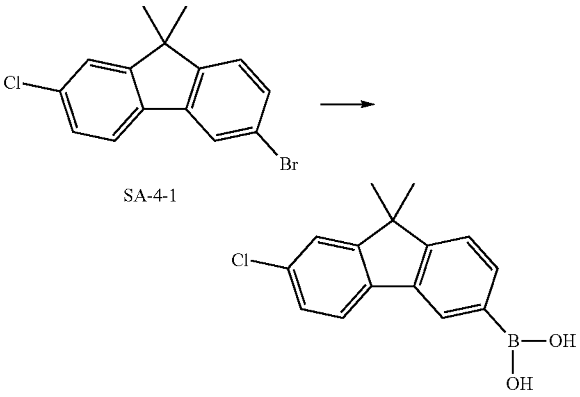

SA-4-1

A-1-1

SA-4-1 (128.65 g, 418.24 mmol) was dissolved in THF (772 mL), a resulting solution was cooled to −78° C., and then tert-butyllithium (t-BuLi) (60.83 mL, 627.36 mmol) was slowly added; a resulting mixture was stirred at the above temperature for 1 h, then triisopropyl borate (78.63 mL, 418.24 mmol) was added, and a resulting mixture was gradually warmed to room temperature and stirred for 3 h. A hydrochloric acid solution (300 mL) was added, and a resulting mixture was further stirred at room temperature for 1.5 h; and then a resulting precipitate was filtered out, then the filtrate was washed with water and diethyl ether successively, and then concentrated in vacuum to obtain an intermediate A-1-1 (98.01 g, yield: 86%).

The intermediates Y-1-X (Y was a variable, representing A, B, or C) listed in Table 10 were each synthesized with reference to the synthesis method of the intermediate A-1-1, except that SY-X-X was used instead of SA-4-1.

TABLE 10

| SY-X-X | Y-1-X | Yield (%) |
|---|---|---|
| 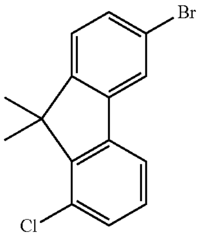 SA-4-2 | 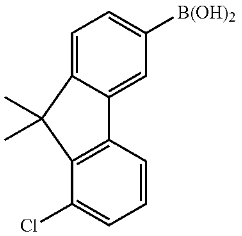 A-1-2 | 84.1 |
| 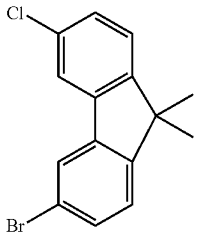 SA-4-3 | 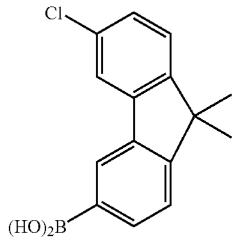 A-1-3 | 86.2 |

TABLE 10-continued
| SY-X-X | Y-1-X | Yield (%) |
|---|---|---|
| 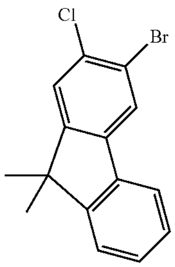 SA-4-4 | 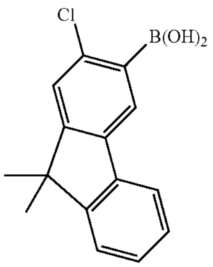 A-1-4 | 79.8 |
| 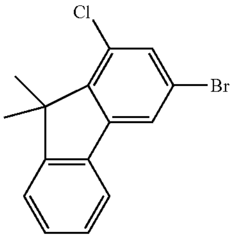 SA-4-5 | 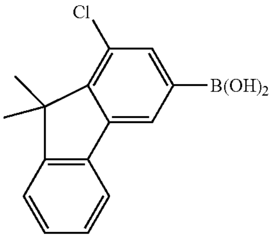 A-1-5 | 82.5 |
| 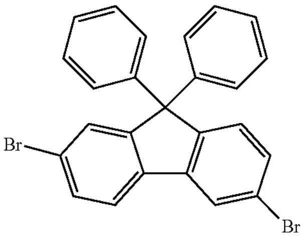 SB-4-1 | 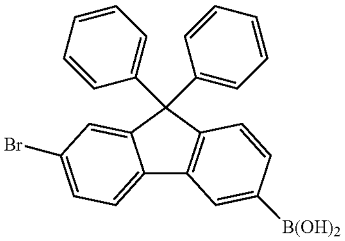 B-1-1 | 51.2 |
| 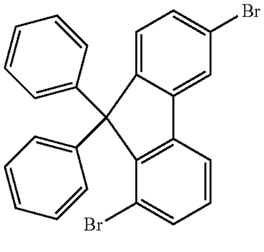 SB-4-2 | 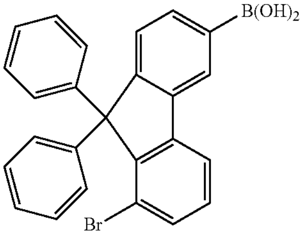 B-1-2 | 56.8 |

TABLE 10-continued
| SY-X-X | Y-1-X | Yield (%) |
| --- | --- | --- |
| 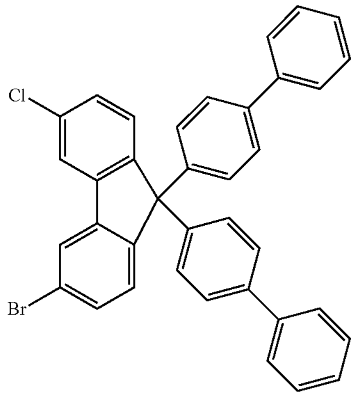 SB-4-3 | 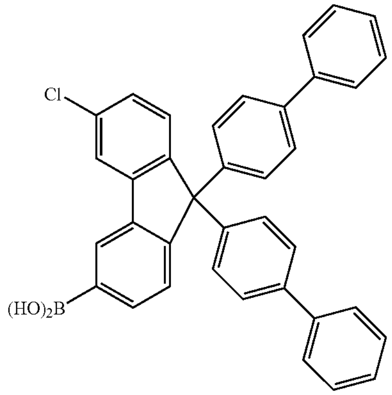 B-1-3 | 54.8 |
| 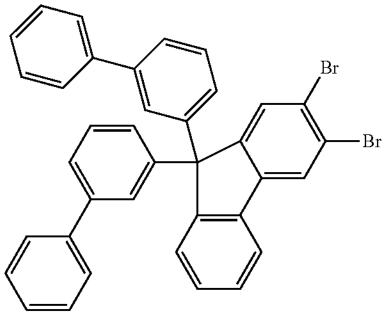 SB-4-4 | 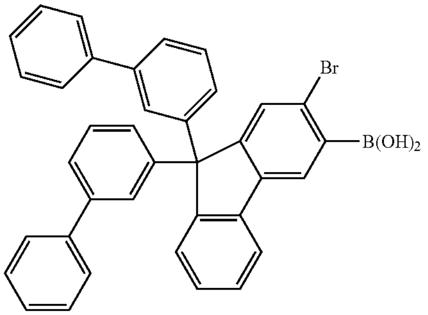 B-1-4 | 51.0 |
| 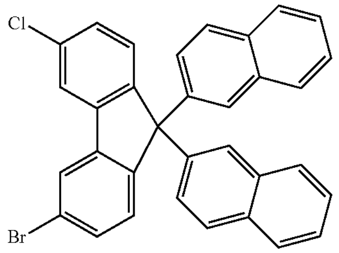 SB-4-6 | 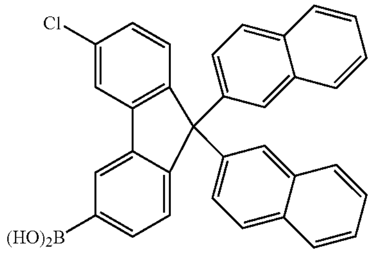 B-1-6 | 68.7 |
| 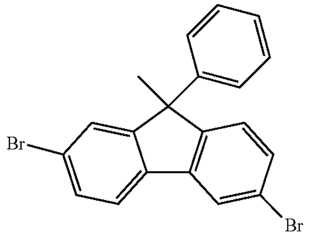 SB-6-1 | 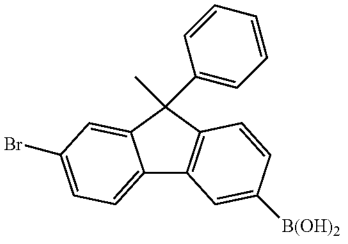 B-1-8 | 63.0 |

TABLE 10-continued
| SY-X-X | Y-1-X | Yield (%) |
|---|---|---|
| 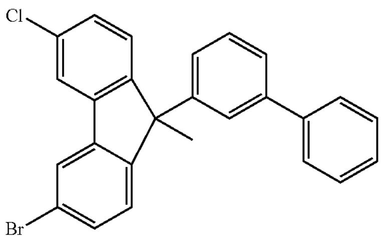 SB-6-3 | 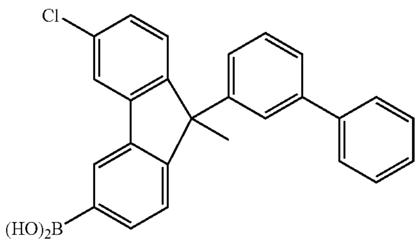 B-1-10 | 67.9 |
| 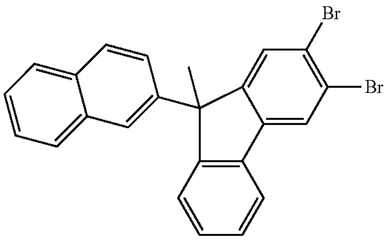 SB-6-4 | 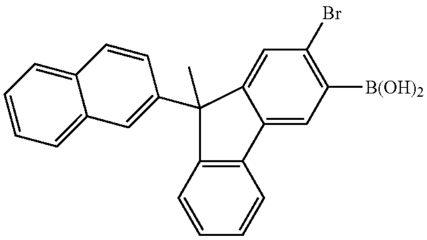 B-1-11 | 60.2 |
| 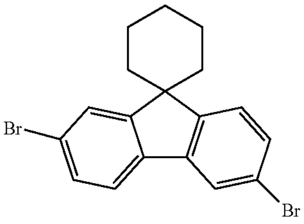 SB-8-1 | 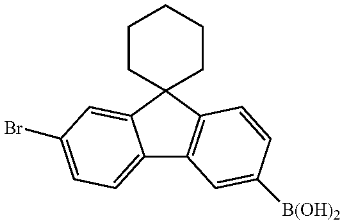 B-1-13 | 61.2 |
| 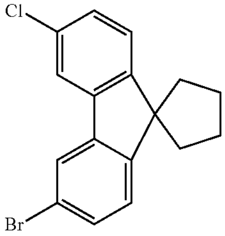 SB-8-3 | 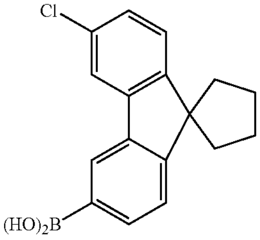 B-1-15 | 68.7 |
| 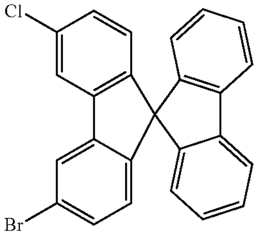 SB-9-3 | 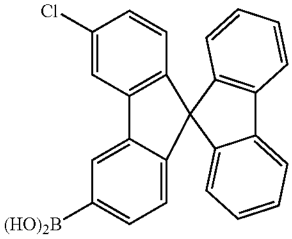 B-1-20 | 67.1 |

TABLE 10-continued

| SY-X-X | Y-1-X | Yield (%) |
| --- | --- | --- |
| 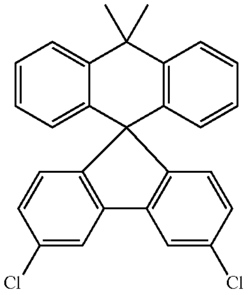 SC-4-1 | 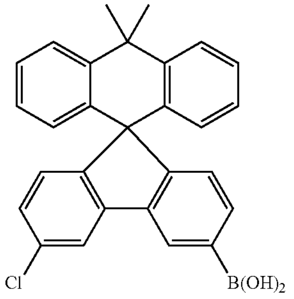 C-1-1 | 51.2 |

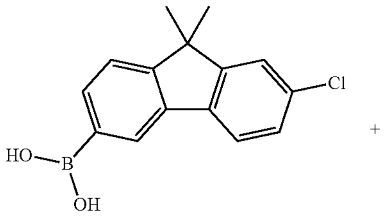

A-1-1

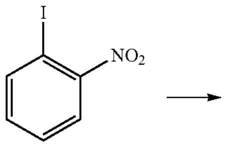

A-2-1

-continued

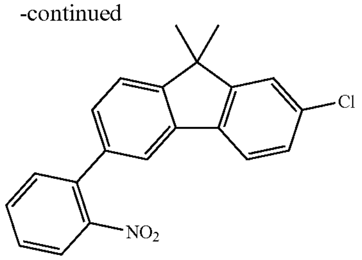

A-3-1

Under the nitrogen atmosphere, A-1-1 (97.5 g, 357.75 mmol), A-2-1 (89.08 g, 357.75 mmol), THF (582 mL), and $H_2O$ (194 mL) were added to a three-necked flask, and a resulting mixture was heated and stirred until a resulting solution was clear; then $Pd(PPh_3)_4$ (0.43 g, 3.76 mmol) and $K_2CO_3$ (77.78 g, 563.63 mmol) were added, and a resulting mixture was heated to reflux and stirred for 15 h; a resulting reaction mixture was cooled to room temperature and then washed with water until neutral, and a separated organic phase was concentrated in vacuum to obtain a residue; and the residue was purified by silica gel column chromatography to obtain an intermediate A-3-1 (85.01 g, yield: 68%).

The intermediates A-3-X, B-3-X, and C-3-X listed in Table 11 were each synthesized with reference to the synthesis method of the intermediate A-3-1, except that A-1-X, B-1-X, or C-1-X was used instead of the intermediate A-1-1 and A-2-X was used instead of the A-2-1.

TABLE 11

| A-1-X/B-1-X/C-1-X | A-2-X | A-3-X/B-3-X/C-3-X | Yield (%) |
| --- | --- | --- | --- |
| 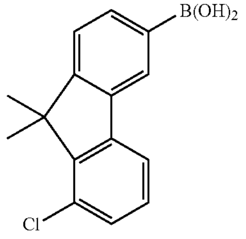 A-1-2 | 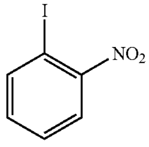 A-2-1 | 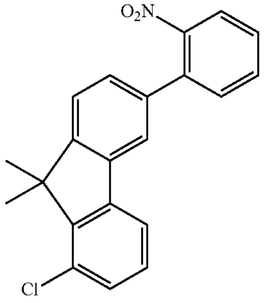 A-3-2 | 69.1 |

TABLE 11-continued
| A-1-X/B-1-X/C-1-X | A-2-X | A-3-X/B-3-X/C-3-X | Yield (%) |
|---|---|---|---|
| 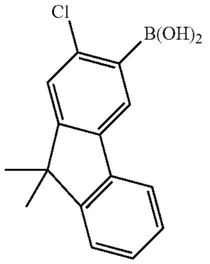 A-1-4 | | 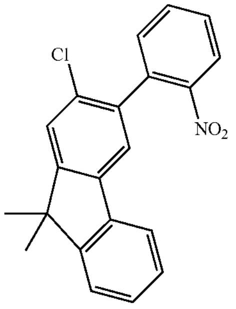 A-3-4 | 62.8 |
| 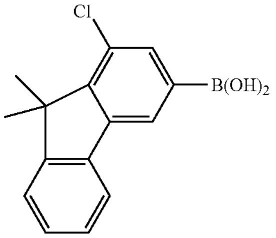 A-1-5 | | 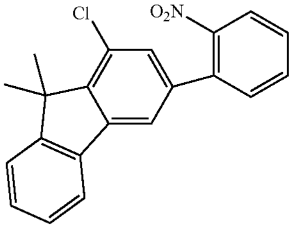 A-3-5 | 65.6 |
| 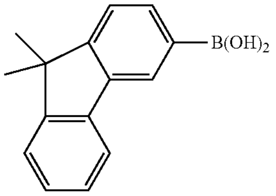 A-1-6 | 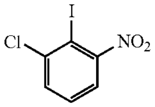 A-2-2 | 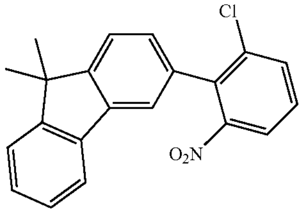 A-3-6 | 65.3 |
| | 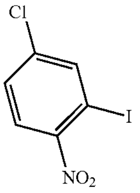 A-2-3 | 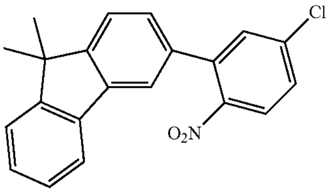 A-3-7 | 66.1 |
| | 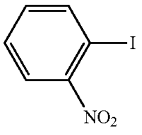 A-2-6 | 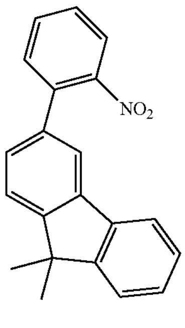 A-3-11 | 68.3 |

TABLE 11-continued
| A-1-X/B-1-X/C-1-X | A-2-X | A-3-X/B-3-X/C-3-X | Yield (%) |
|---|---|---|---|
| 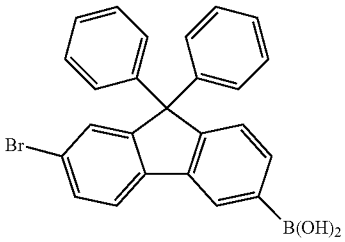 B-1-1 | 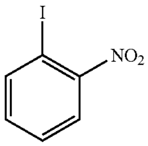 A-2-1 | 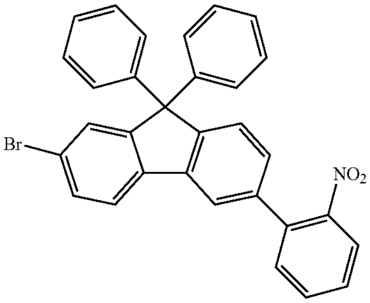 B-3-1 | 65.8 |
| 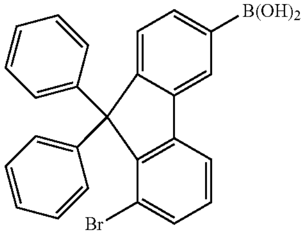 B-1-2 | | 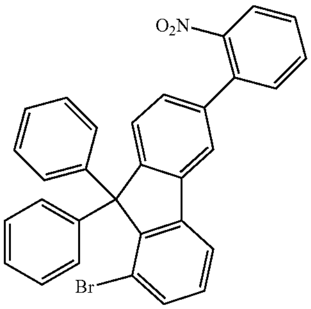 B-3-2 | 64.7 |
| 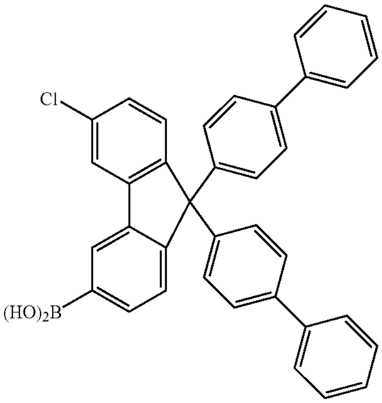 B-1-3 | | 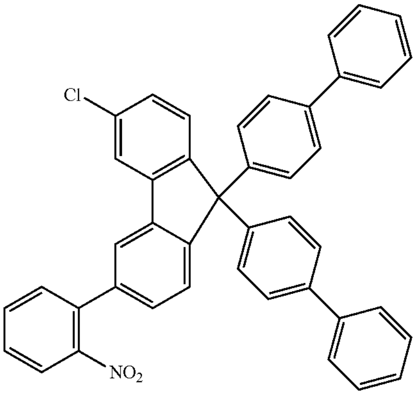 B-3-3 | 66.1 |

TABLE 11-continued
| A-1-X/B-1-X/C-1-X | A-2-X | A-3-X/B-3-X/C-3-X | Yield (%) |
| --- | --- | --- | --- |
| 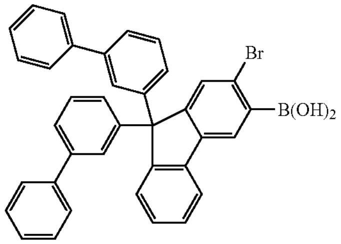 B-1-4 | | 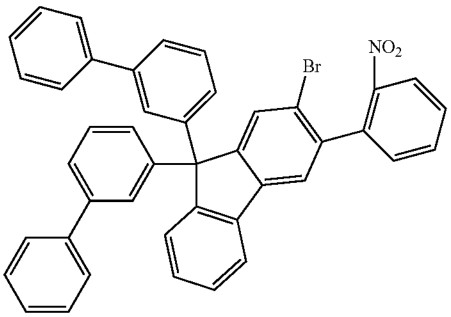 B-3-4 | 60.2 |
| 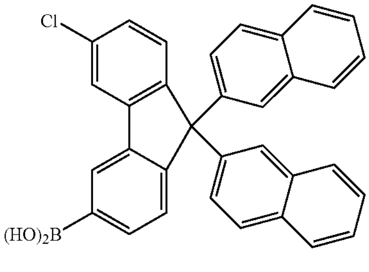 B-1-6 | | 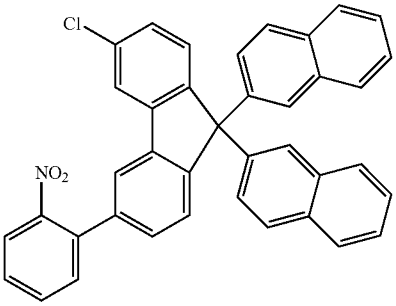 B-3-6 | 64.8 |
| 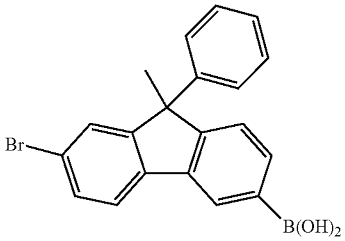 B-1-8 | | 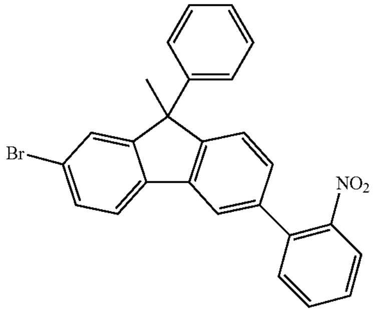 B-3-8 | 63.8 |
| 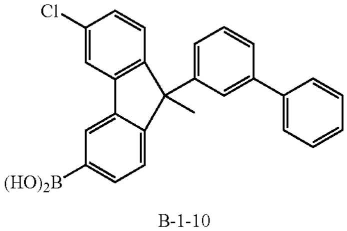 [SMILES: CC1(c2cccc(-c3ccccc3)c2)c2ccc(Cl)cc2-c2cc(B(O)O)ccc21] B-1-10 | | 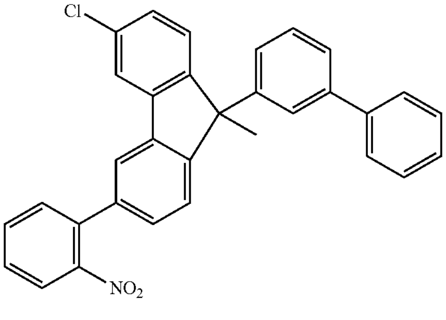 B-3-10 | 66.4 |

TABLE 11-continued
| A-1-X/B-1-X/C-1-X | A-2-X | A-3-X/B-3-X/C-3-X | Yield (%) |
|---|---|---|---|
| 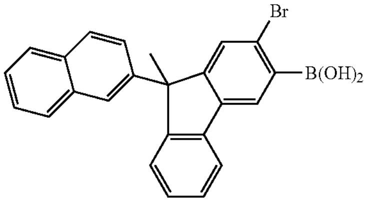 B-1-11 | | 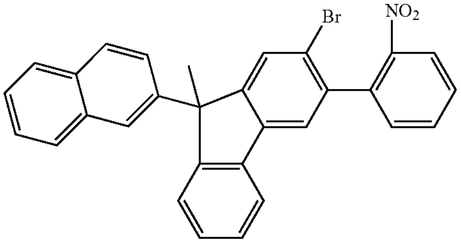 B-3-11 | 61.2 |
| 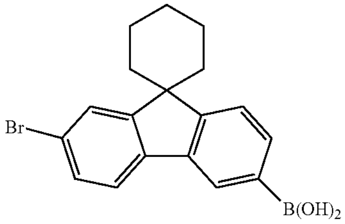 B-1-13 | | 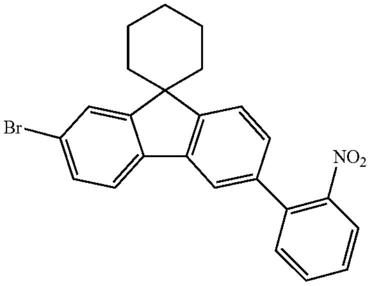 B-3-13 | 66.4 |
| 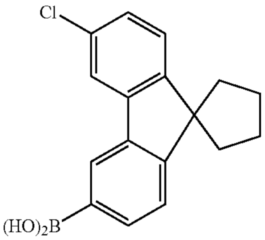 B-1-15 | | 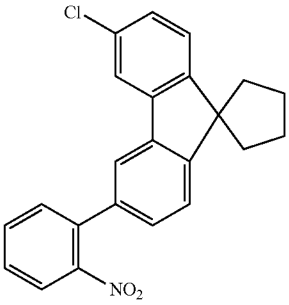 B-3-15 | 65.7 |
| 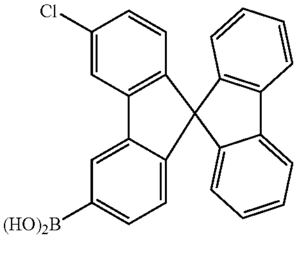 B-1-20 | | 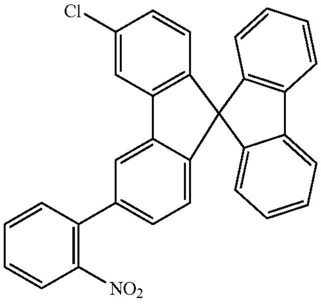 B-3-20 | 65.1 |

TABLE 11-continued

| A-1-X/B-1-X/C-1-X | A-2-X | A-3-X/B-3-X/C-3-X | Yield (%) |
|---|---|---|---|
| 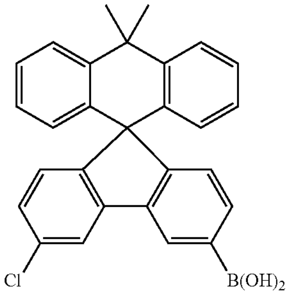 C-1-1 | | 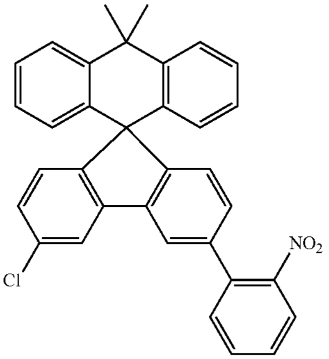 C-3-1 | 65.3 |

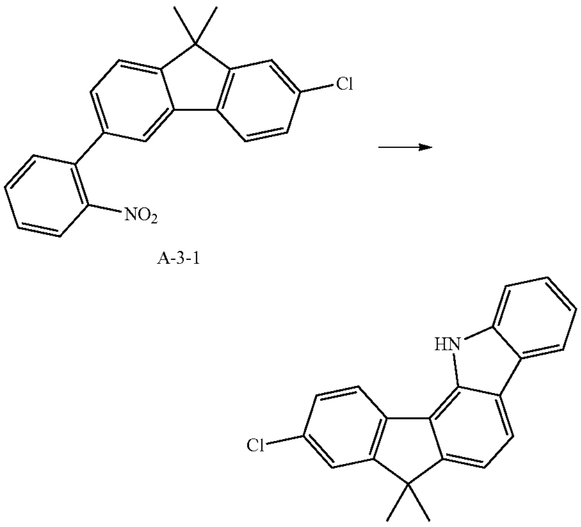

A-3-1

A-5-1

Under the nitrogen atmosphere, A-3-1 (84.67 g, 242.05 mmol) was added to a three-necked flask, 400 mL of o-dichlorobenzene was added for dissolution, triphenylphosphine (1.27 g, 4.84 mmol) was added, and a resulting mixture was heated to 170° C. to 190° C. and stirred for 12 h to 16 h. After the reaction was completed, a resulting reaction system was cooled to room temperature and filtered, a filtrate was concentrated in vacuum to obtain a residue, and the residue was purified by silica gel column chromatography to obtain an intermediate A-5-1 (50 g, yield: 65.1%).

The intermediates A-5-X, B-4-X, and C-4-X listed in Table 12 were each synthesized with reference to the synthesis method of the intermediate A-5-1, except that an intermediate A-3-X, B-3-X, or C-3-X was used instead of the intermediate A-3-1.

TABLE 12

| A-3-X/B-3-X/C-3-X | A-5-X/B-4-X/C-4-X | Yield (%) |
|---|---|---|
| 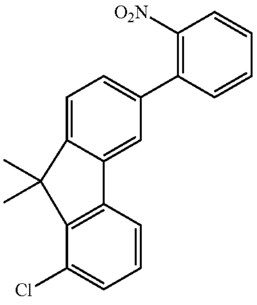 A-3-2 | 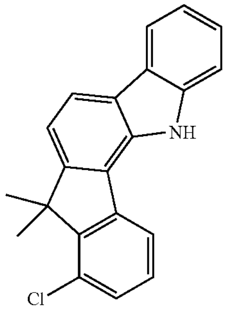 A-5-2 | 62.5 |

TABLE 12-continued
| A-3-X/B-3-X/C-3-X | A-5-X/B-4-X/C-4-X | Yield (%) |
|---|---|---|
| 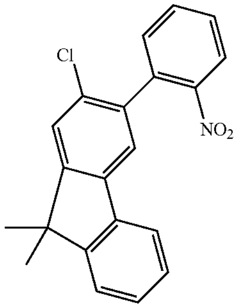 A-3-4 | 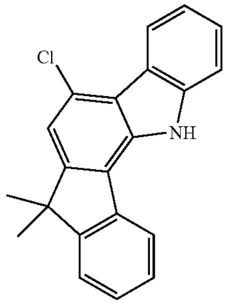 A-5-4 | 65.2 |
| 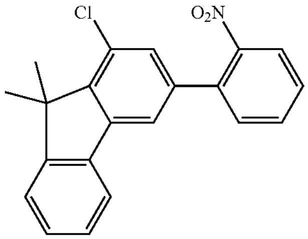 A-3-5 | 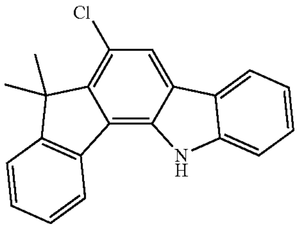 C-5-5 | 63.4 |
| 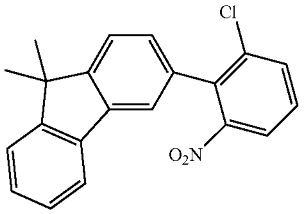 A-3-6 | 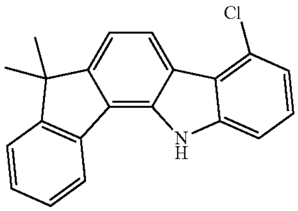 A-5-6 | 64.5 |
| 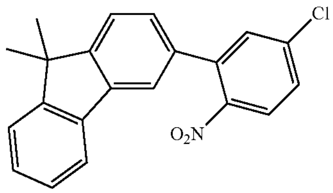 A-3-7 | 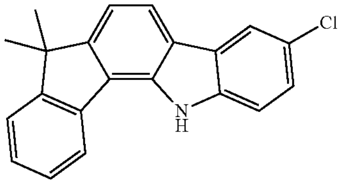 A-5-7 | 63.3 |
| 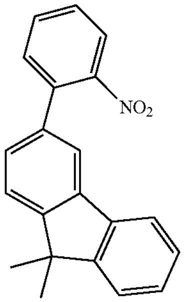 A-3-11 | 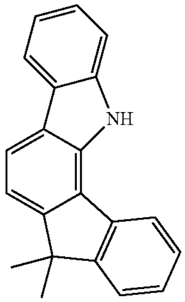 A-5-11 | 65.1 |

TABLE 12-continued
| A-3-X/B-3-X/C-3-X | A-5-X/B-4-X/C-4-X | Yield (%) |
|---|---|---|
| 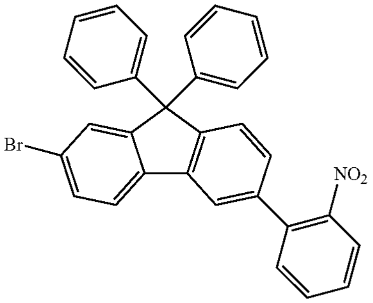 B-3-1 | 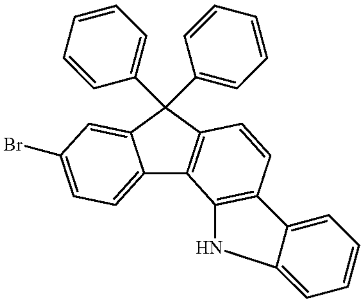 B-4-1 | 63.1 |
| 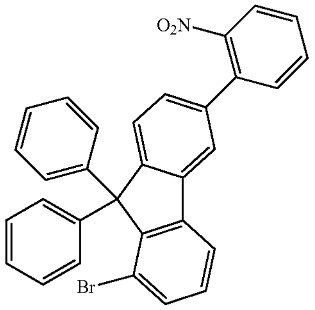 B-3-2 | 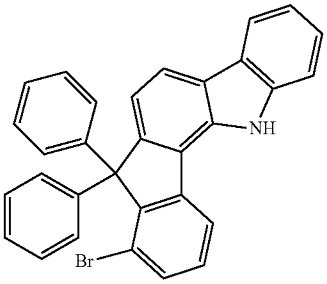 B-4-2 | 65.3 |
| 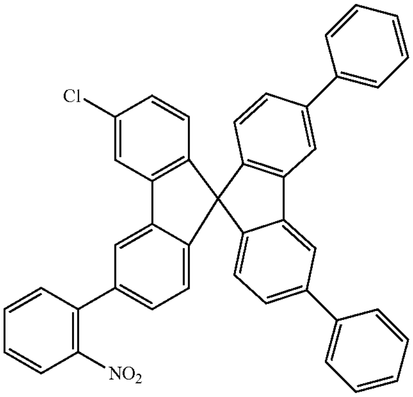 B-3-3 | 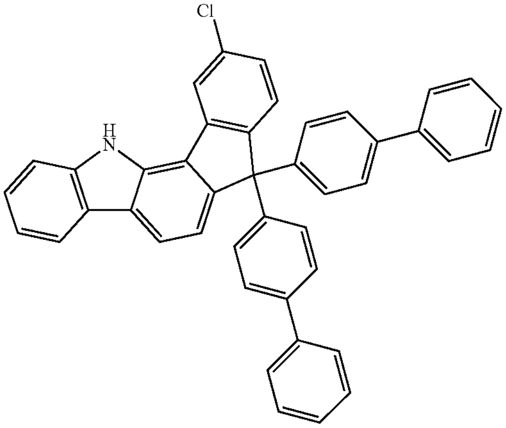 B-4-3 | 62.5 |
| 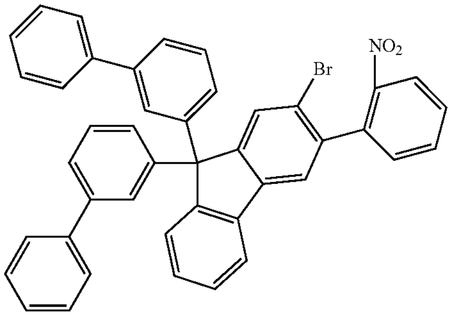 B-3-4 | 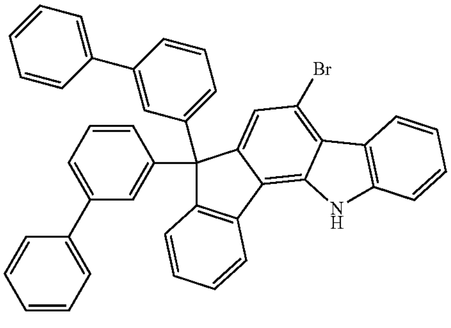 B-4-4 | 60.2 |

TABLE 12-continued
| A-3-X/B-3-X/C-3-X | A-5-X/B-4-X/C-4-X | Yield (%) |
|---|---|---|
| 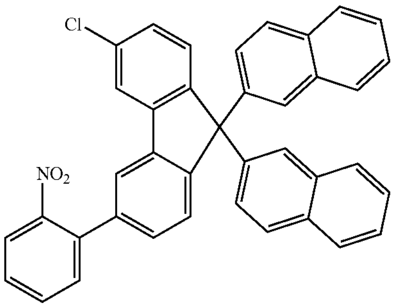 B-3-6 | 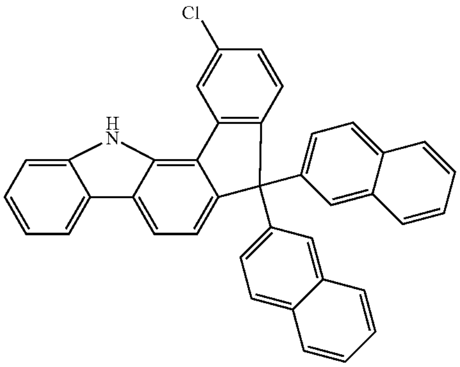 B-4-6 | 62.3 |
| 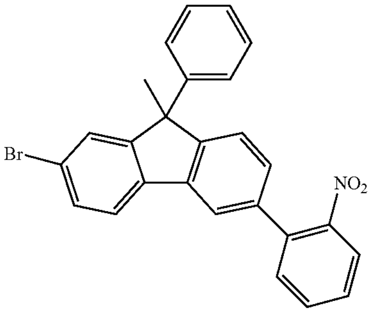 B-3-8 | 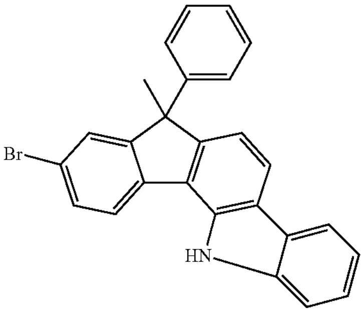 B-4-8 | 63.5 |
| 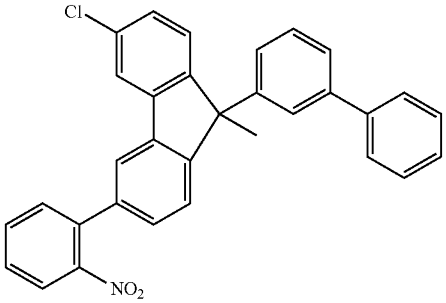 B-3-10 | 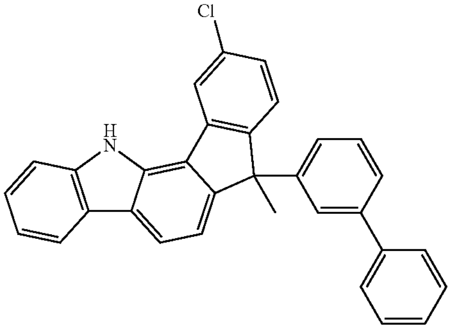 B-4-10 | 65.1 |
| 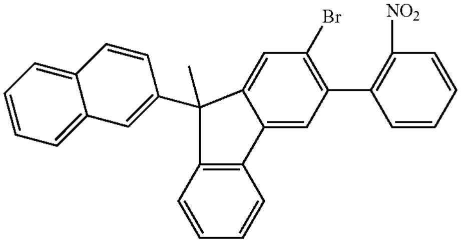 B-3-11 | 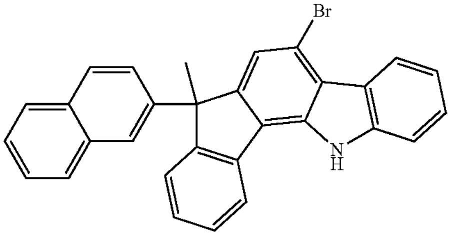 B-4-11 | 60.8 |

TABLE 12-continued
| A-3-X/B-3-X/C-3-X | A-5-X/B-4-X/C-4-X | Yield (%) |
|---|---|---|
| 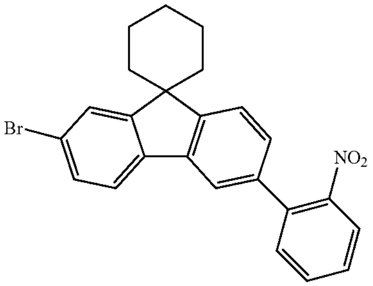 B-3-13 | 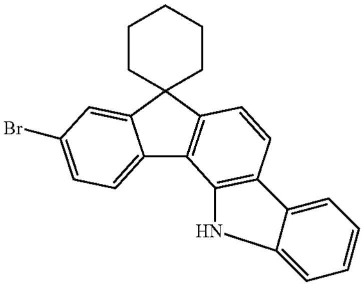 B-4-13 | 64.2 |
| 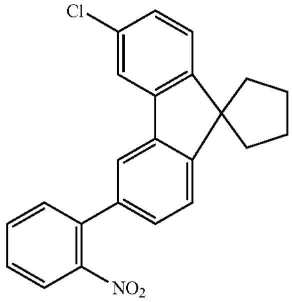 B-3-15 | 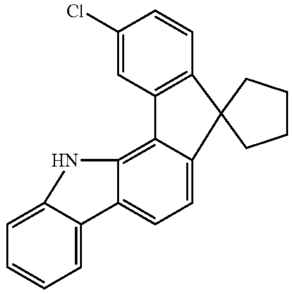 B-4-15 | 63.5 |
| 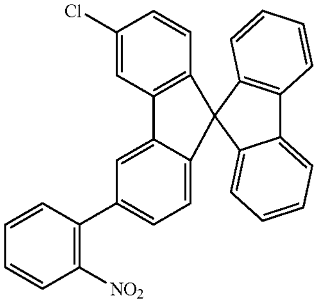 B-3-20 | 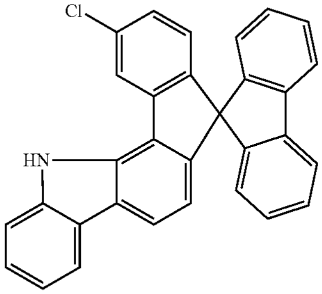 B-4-20 | 63.8 |
| 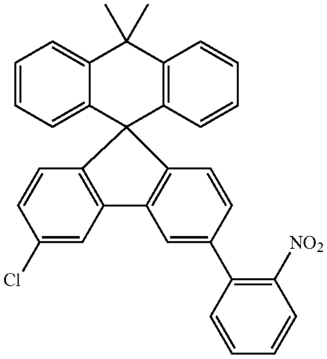 C-3-1 | 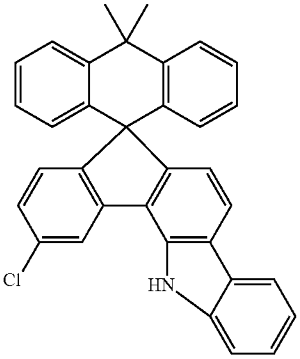 C-4-1 | 64.8 |

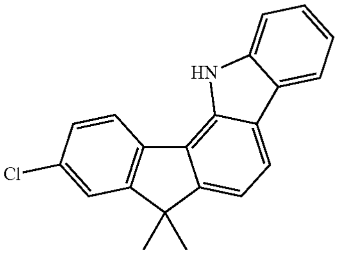

A-5-1

+

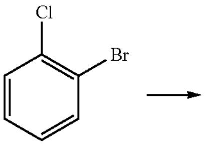

A-6-1

-continued

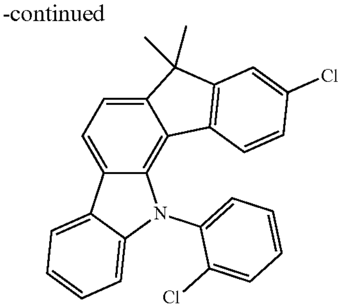

A-7-1

The intermediate A-5-1 (49.79 g, 156.66 mmol), a raw material A-6-1 (29.99 g, 156.66 mmol), and toluene (400 mL) were added to a three-necked round-bottomed flask, and a resulting mixture was heated to reflux under the nitrogen atmosphere; tris(dibenzylideneacetone)dipalladium (1.44 g, 1.57 mmol), 2-dicyclohexylphosphino-2,4,6-triisopropylbiphenyl (X-phos) (1.5 g, 3.13 mmol), and sodium tert-butoxide (22.58 g, 234.99 mmol) were added, and a resulting mixture was stirred for 3 h; the reaction mixture was cooled to room temperature, washed with water, dried with anhydrous magnesium sulfate, and filtered, and a filtrate was concentrated in vacuum to obtain a crude product; and the crude product was purified by recrystallization with a toluene to obtain a solid intermediate A-7-1 (51.0 g, yield: 76%).

The intermediates A-7-X, B-6-X, and C-6-X listed in Table 13 were each synthesized with reference to the synthesis method of the intermediate A-7-1, except that A-5-X, B-4-X, or C-4-X was used instead of the intermediate A-5-1 and A-6-X was used instead of the A-6-1.

TABLE 13

| A-5-X/B-4-X/C-4-X | A-6-X | A-7-X/B-6-X/C-6-X | Yield (%) |
|---|---|---|---|
| 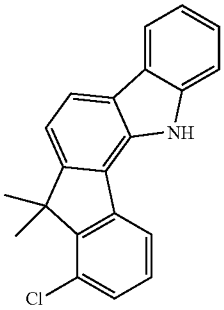 A-5-2 | 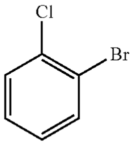 A-6-1 | 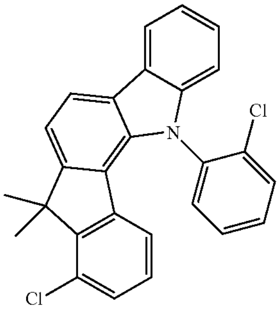 A-7-2 | 77.1 |
| 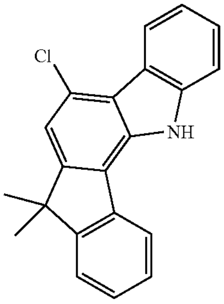 A-5-4 | | 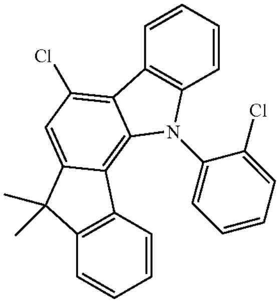 A-7-4 | 75.3 |

TABLE 13-continued
| A-5-X/B-4-X/C-4-X | A-6-X | A-7-X/B-6-X/C-6-X | Yield (%) |
| --- | --- | --- | --- |
| 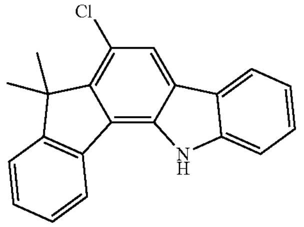 A-5-5 | | 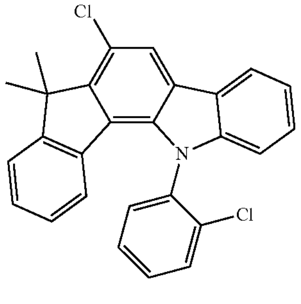 A-7-5 | 76.5 |
| 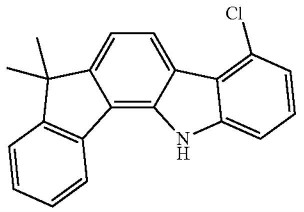 A-5-6 | | 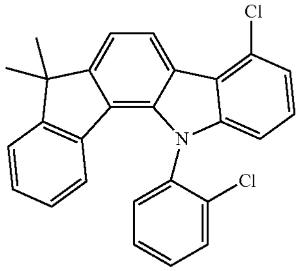 A-7-6 | 74.4 |
| 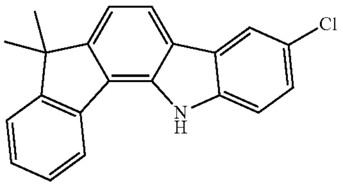 A-5-7 | | 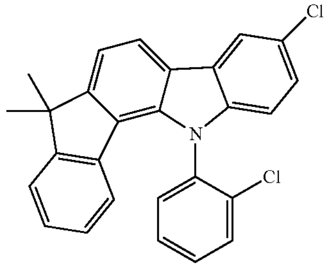 A-7-7 | 76.1 |
| 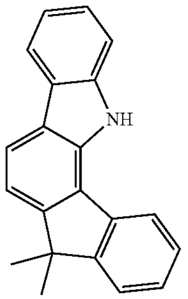 A-5-11 | 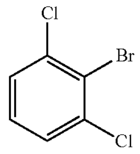 A-6-2 | 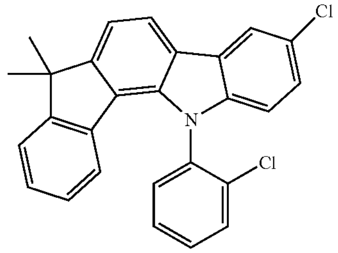 A-7-7 | 66.6 |

TABLE 13-continued
| A-5-X/B-4-X/C-4-X | A-6-X | A-7-X/B-6-X/C-6-X | Yield (%) |
|---|---|---|---|
| | 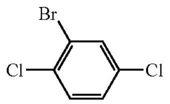 A-6-3 | 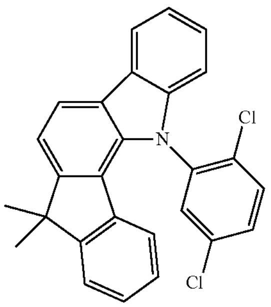 A-7-12 | 68.1 |
| 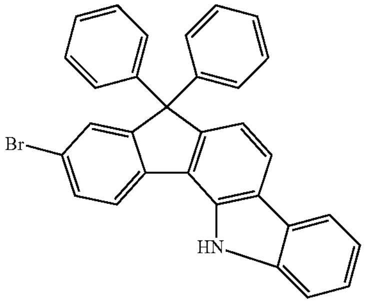 B-4-1 | 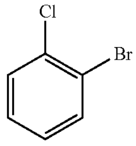 A-6-1 | 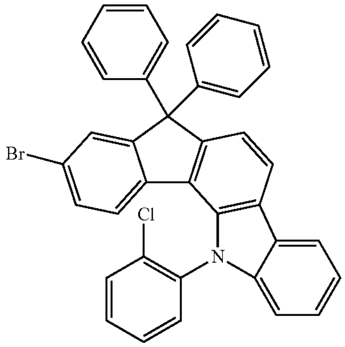 B-6-1 | 65.2 |
| 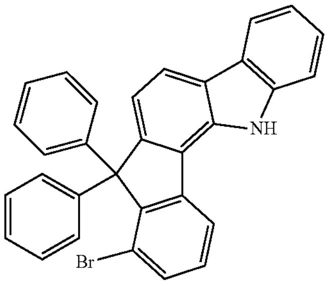 B-4-2 | | 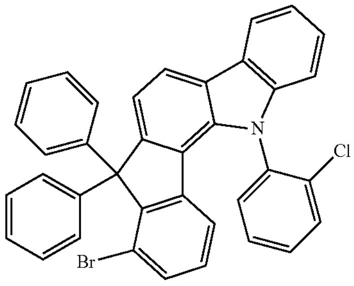 B-6-2 | 63.4 |
| 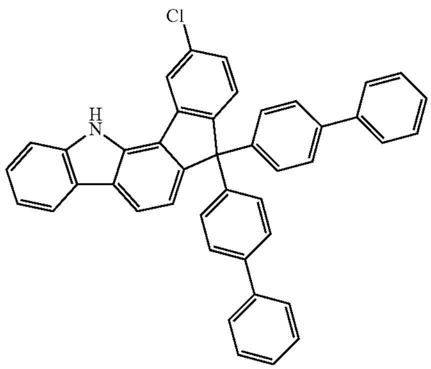 B-4-3 | | 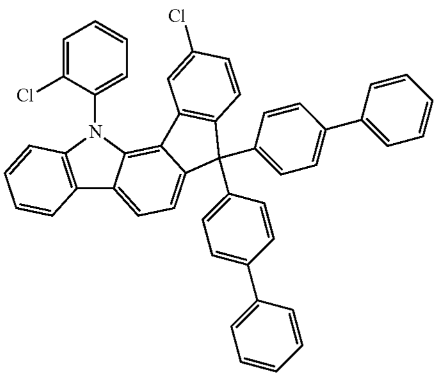 B-6-3 | 66.2 |

TABLE 13-continued
| A-5-X/B-4-X/C-4-X | A-6-X | A-7-X/B-6-X/C-6-X | Yield (%) |
|---|---|---|---|
| 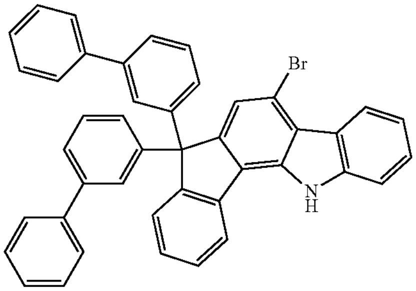 B-4-4 | | 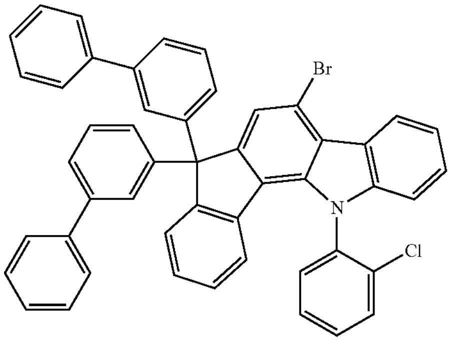 B-6-4 | 64.8 |
| 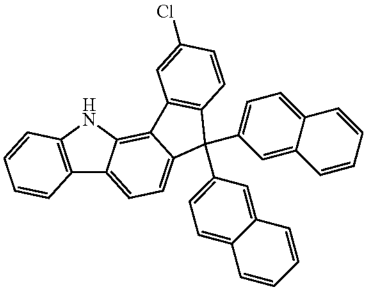 B-4-6 | | 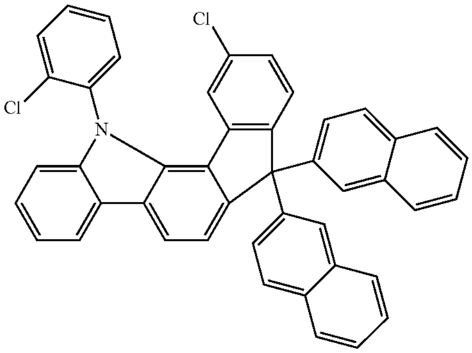 B-6-6 | 67.2 |
| 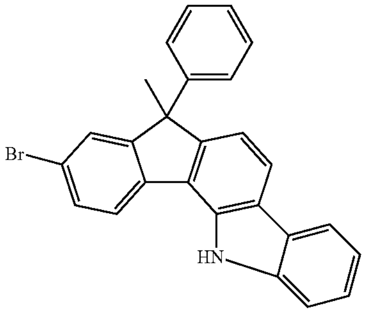 B-4-8 | | 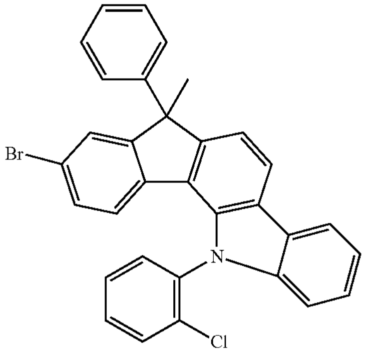 B-6-8 | 67.1 |

TABLE 13-continued
| A-5-X/B-4-X/C-4-X | A-6-X | A-7-X/B-6-X/C-6-X | Yield (%) |
|---|---|---|---|
| 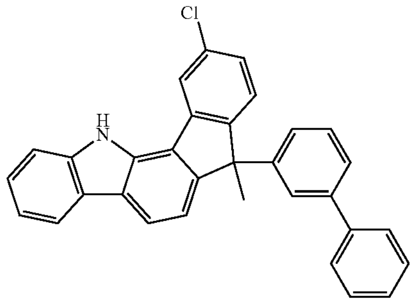 B-4-10 | | 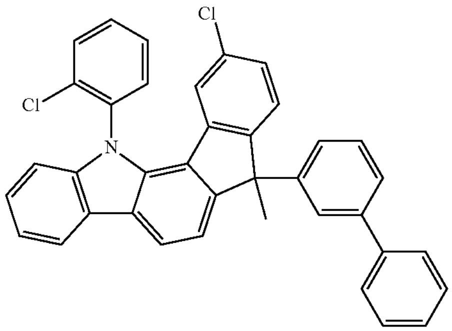 B-6-10 | 67.8 |
| 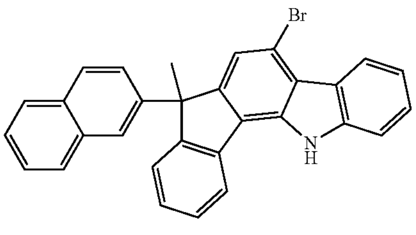 B-4-11 | | 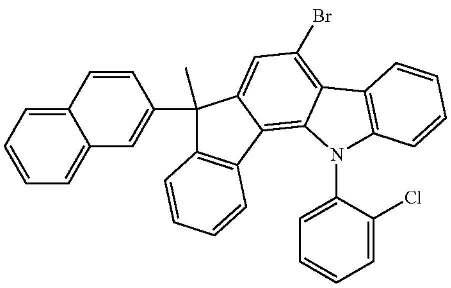 B-6-11 | 65.4 |
| 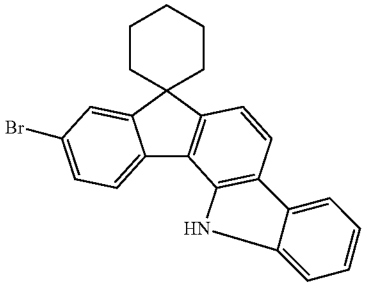 B-4-13 | | 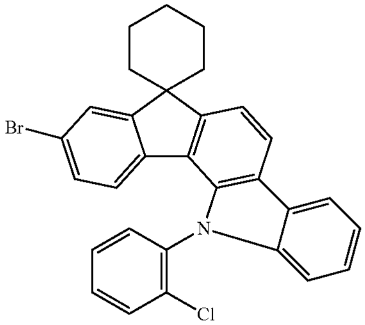 B-6-13 | 63.1 |
| 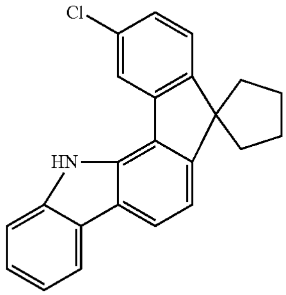 B-4-15 | | 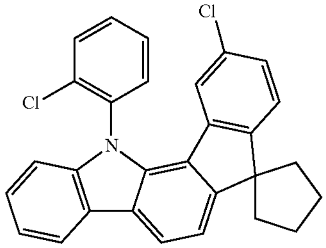 B-6-15 | 68.4 |

TABLE 13-continued
| A-5-X/B-4-X/C-4-X | A-6-X | A-7-X/B-6-X/C-6-X | Yield (%) |
|---|---|---|---|
| 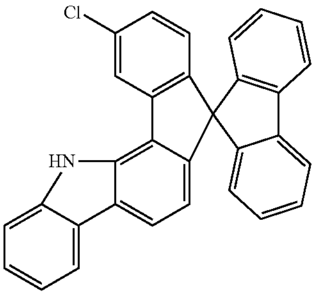 B-4-20 | | 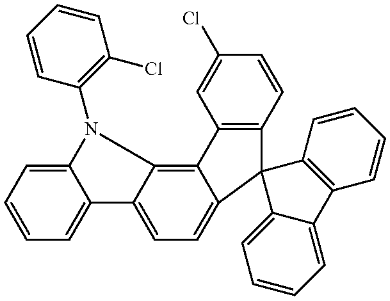 B-6-20 | 66.2 |
| 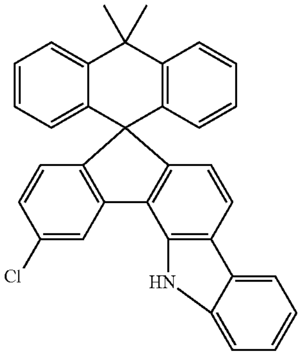 C-4-1 | | 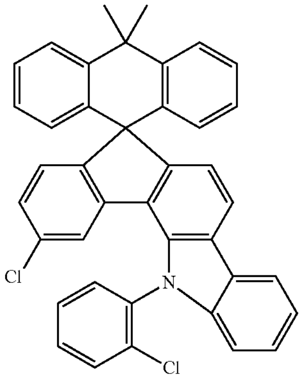 C-6-1 | 66.8 |
-continued
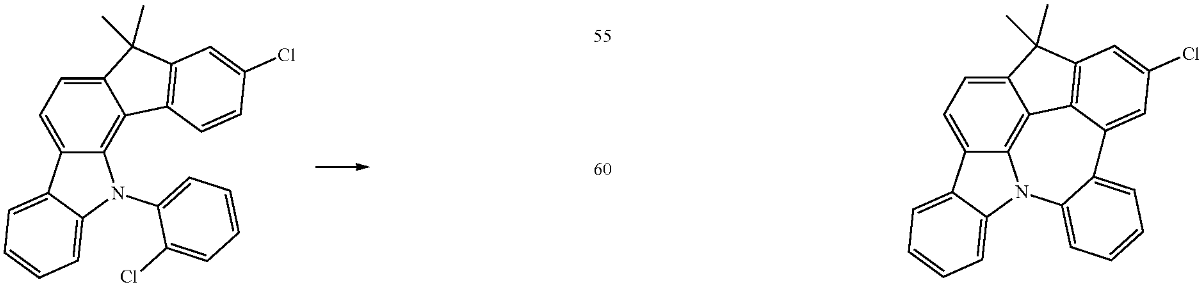
A-7-1 A-8-1

Under the nitrogen atmosphere, A-7-1 (50.50 g, 117.89 mmol), palladium acetate (0.26 g, 1.18 mmol), tricyclohexylphosphine tetrafluoroborate (0.87 g, 2.36 mmol), cesium carbonate (57.62 g, 176.84 mmol), and o-xylene (303 mL) were added to a three-necked flask, and a resulting mixture was heated to reflux and stirred for 2 h; and after the reaction was completed, chloroform was added for extraction, a separated organic phase was concentrated in vacuum to obtain a crude product, and the crude product was purified by silica gel column chromatography to obtain an intermediate A-8-1 (30.95 g, yield: 67%).

The intermediates A-8-X, B-7-X, and C-7-X listed in Table 14 were each synthesized with reference to the synthesis method of the intermediate A-8-1, except that an intermediate A-7-X, B-6-X, or C-6-X was used instead of the intermediate A-7-1.

TABLE 14

| A-7-X/B-6-X/C-6-X | A-8-X/B-7-X/C-7-X | Yield (%) |
|---|---|---|
| 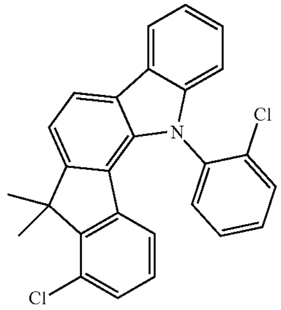 A-7-2 | 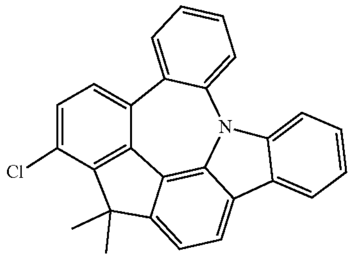 A-8-2 | 70.2 |
| 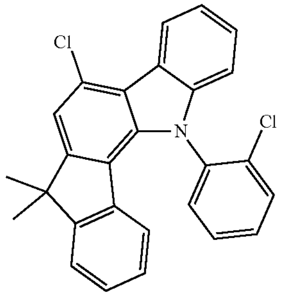 A-7-4 | 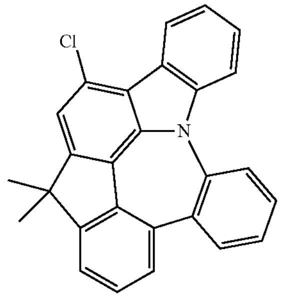 A-8-4 | 67.1 |
| 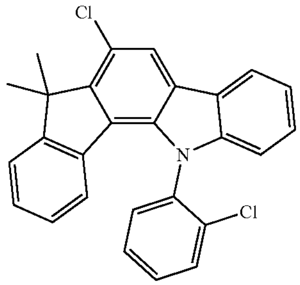 A-7-5 | 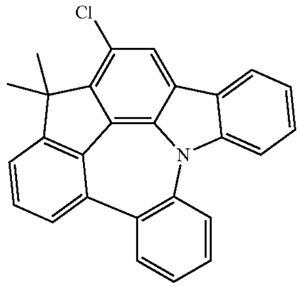 A-8-5 | 66.3 |
| 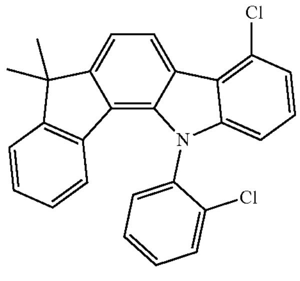 A-7-6 | 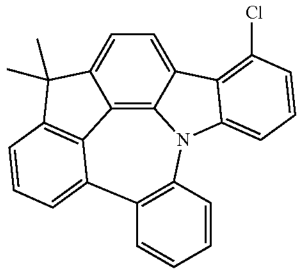 A-8-6 | 68.2 |

TABLE 14-continued
| A-7-X/B-6-X/C-6-X | A-8-X/B-7-X/C-7-X | Yield (%) |
| --- | --- | --- |
| 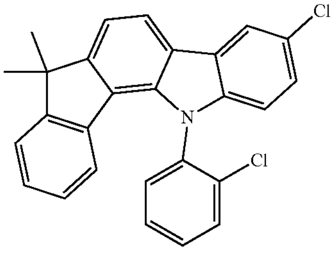 A-7-7 | 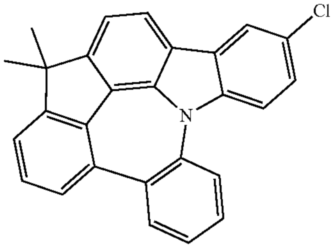 A-8-7 | 67.4 |
| 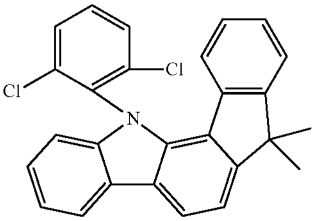 A-7-11 | 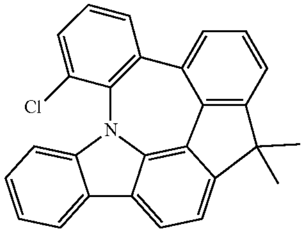 A-8-11 | 66.5 |
| 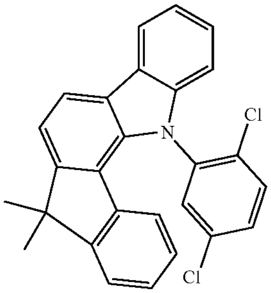 A-7-12 | 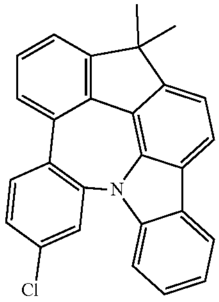 A-8-12 | 62.1 |
| 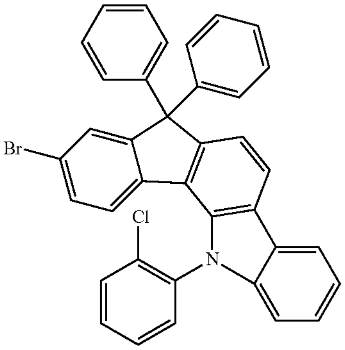 B-6-1 | 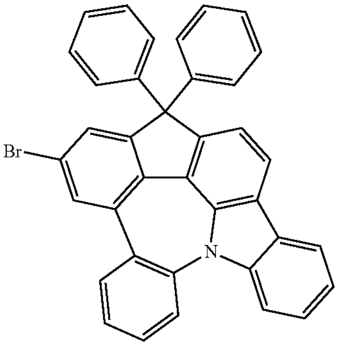 B-7-1 | 60.3 |

TABLE 14-continued
| A-7-X/B-6-X/C-6-X | A-8-X/B-7-X/C-7-X | Yield (%) |
|---|---|---|
| 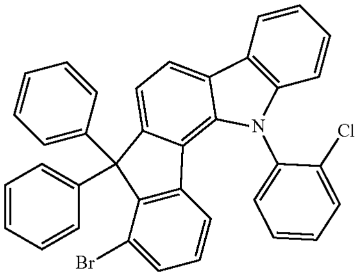 B-6-2 | 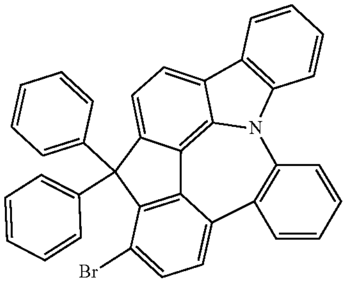 B-7-2 | 61.2 |
| 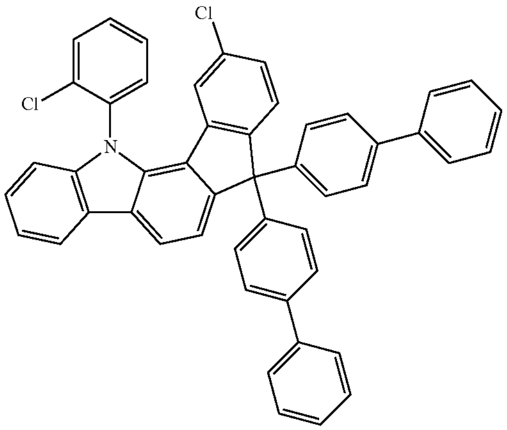 B-6-3 | 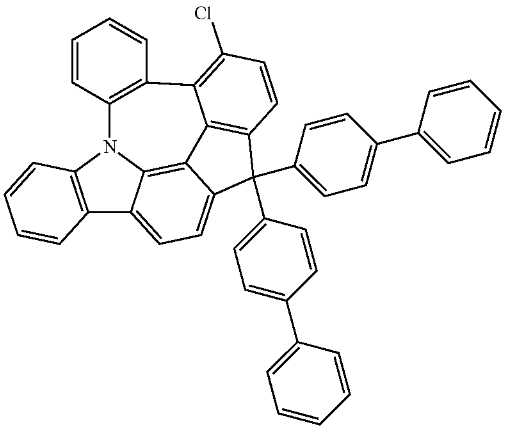 B-7-3 | 63.1 |
| 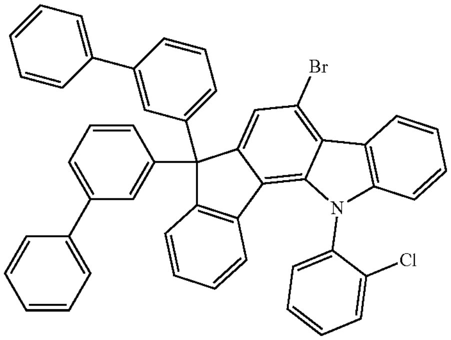 B-6-4 | 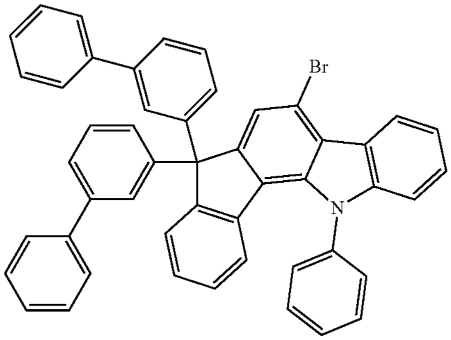 B-7-4 | 62.4 |
| 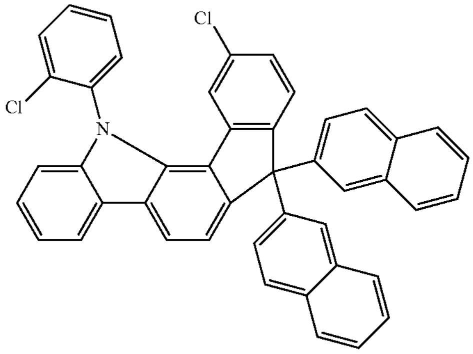 8-6-6 | 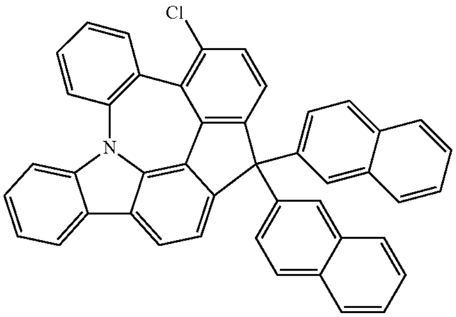 B-7-6 | 61.2 |

TABLE 14-continued
| A-7-X/B-6-X/C-6-X | A-8-X/B-7-X/C-7-X | Yield (%) |
|---|---|---|
| 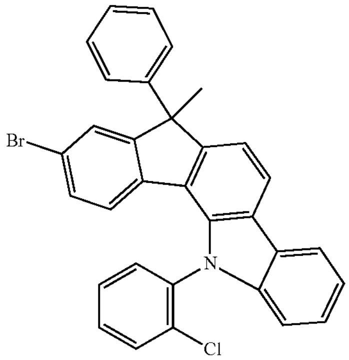 B-6-8 | 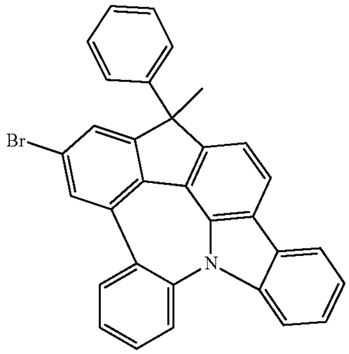 B-7-8 | 62.3 |
| 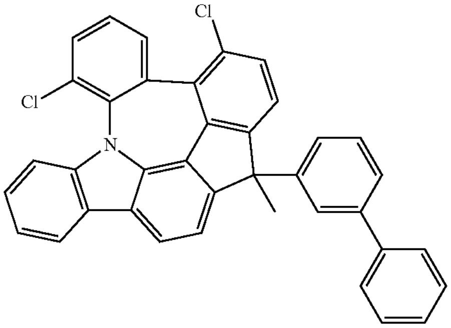 B-6-10 | 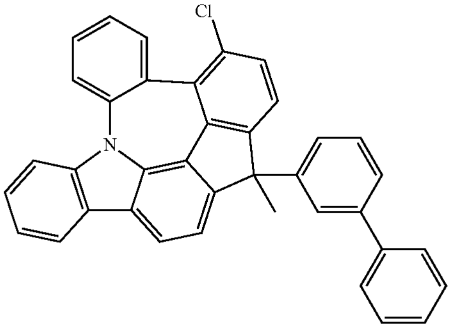 B-7-10 | 63.5 |
| 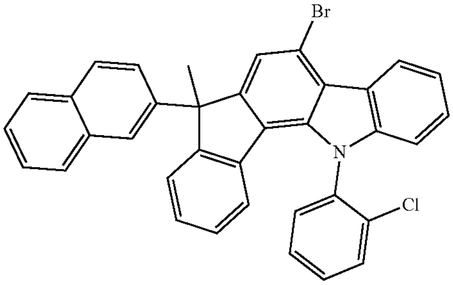 B-6-11 | 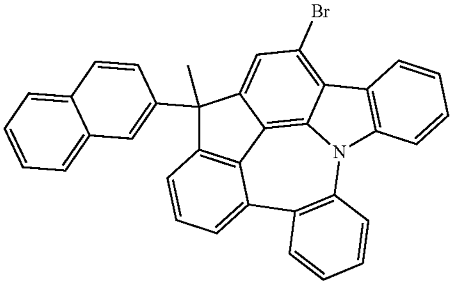 B-7-11 | 63.1 |
| 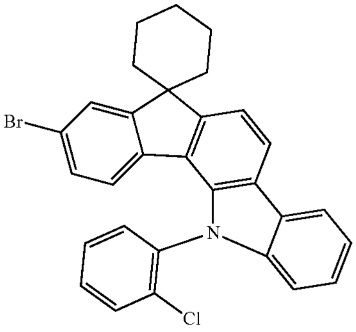 B-6-13 | 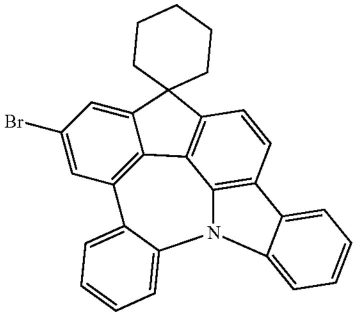 B-7-13 | 58.1 |

TABLE 14-continued
| A-7-X/B-6-X/C-6-X | A-8-X/B-7-X/C-7-X | Yield (%) |
|---|---|---|
| 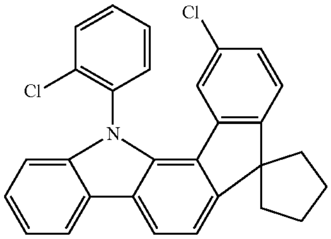 B-6-15 | 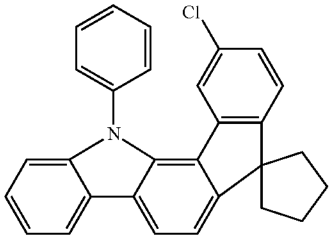 B-7-15 | 60.3 |
| 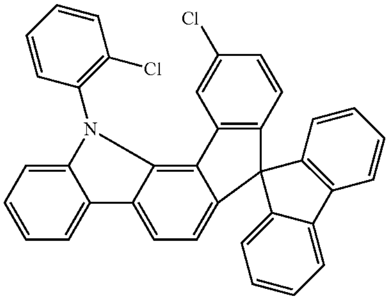 B-6-20 | 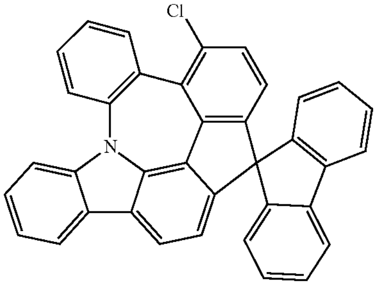 B-7-20 | 64.2 |
| 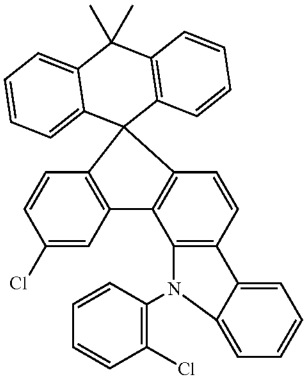 C-6-1 | 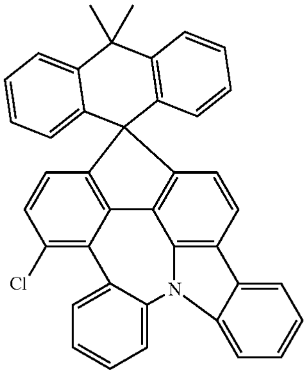 C-7-1 | 63.5 |
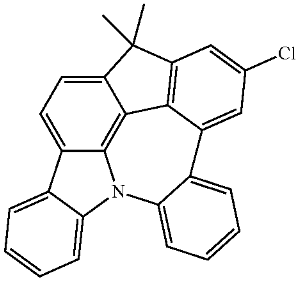
A-8-1
+
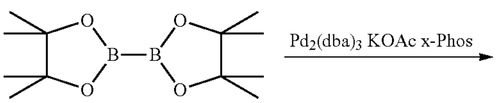
-continued
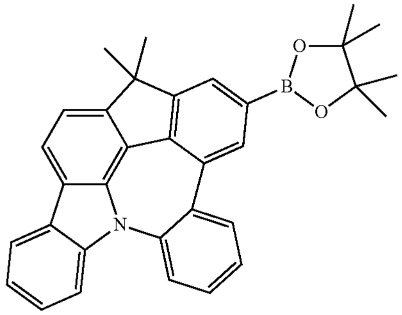
A-10-1
The intermediate A-8-1 (30 g, 76.55 mmol), bis(pinacolato)diboron (19.36 g, 76.55 mmol), tris(dibenzylideneacetone)dipalladium (0.71 g, 0.77 mmol), X-Phos (0.72 g, 1.53 mmol), potassium acetate (11.25 g, 114.83 mmol), and 1,4-dioxane (240 mL) were added to a three-necked round-bottomed flask, and a resulting mixture was heated to 80° C. under nitrogen atmosphere and stirred for 3 h; a resulting reaction mixture was cooled to room temperature, washed with water, dried with magnesium sulfate, and filtered, and a filtrate was concentrated in vacuum to obtain a crude product; and the crude product was purified by recrystallization with a toluene system to obtain a solid intermediate A-10-1 (28.12 g, yield: 76%).

The intermediates A-10-X, B-8-X, and C-8-1 listed in Table 15 were each synthesized with reference to the synthesis method of the intermediate A-10-1, except that an intermediate A-8-X, B-7-X, or C-7-1 was used instead of the intermediate A-8-1.

TABLE 15

| A-8-X/B-7-X/C-7-1 | A-10-X/B-8-X/C-8-1 | Yield (%) |
|---|---|---|
| 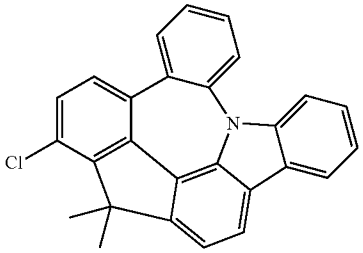 A-8-2 | 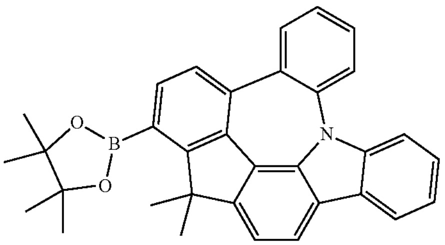 A-10-2 | 78.2 |
| 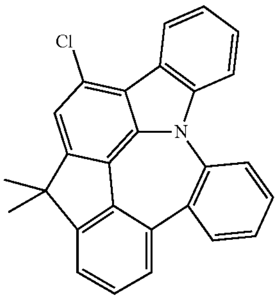 A-8-4 | 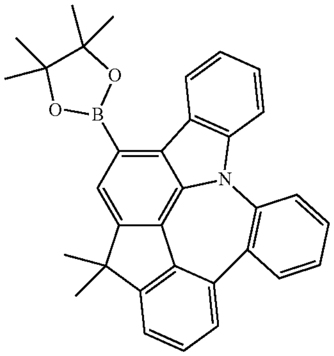 A-10-4 | 72.5 |
| 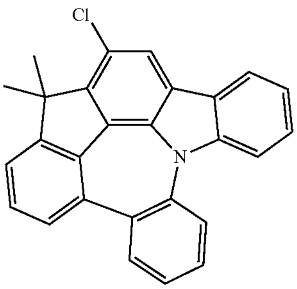 A-8-5 | 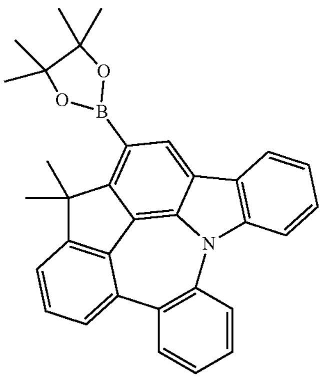 A-10-5 | 74.7 |

TABLE 15-continued
| A-8-X/B-7-X/C-7-1 | A-10-X/B-8-X/C-8-1 | Yield (%) |
|---|---|---|
| 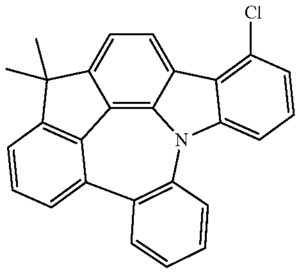 A-8-6 | 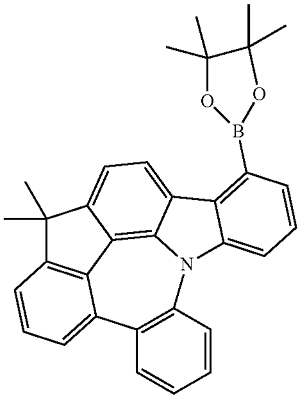 A-10-6 | 71.8 |
| 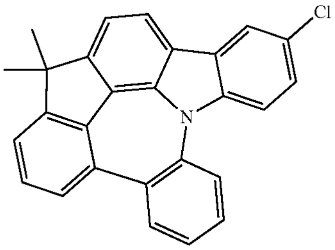 A-8-7 | 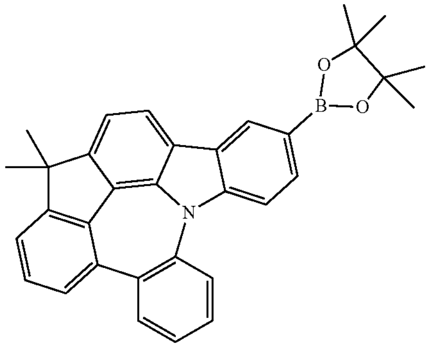 A-10-7 | 75.6 |
| 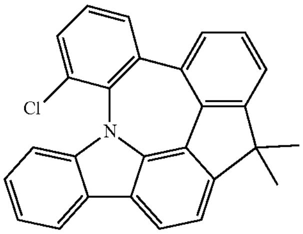 A-8-11 | 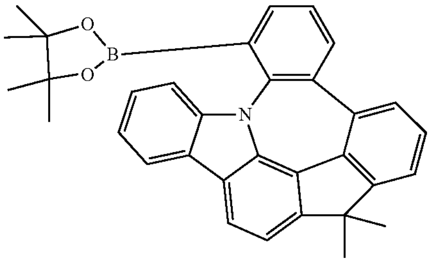 A-10-11 | 68.1 |
| 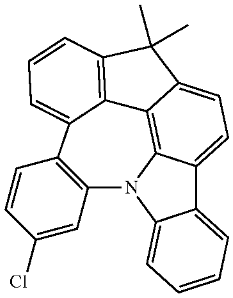 A-8-12 | 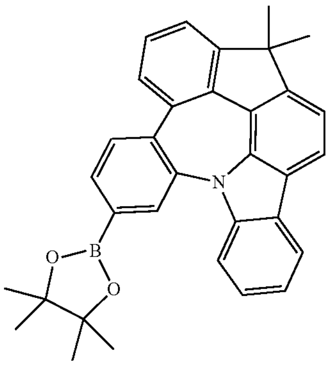 A-10-12 | 73.2 |

TABLE 15-continued
| A-8-X/B-7-X/C-7-1 | A-10-X/B-8-X/C-8-1 | Yield (%) |
|---|---|---|
| 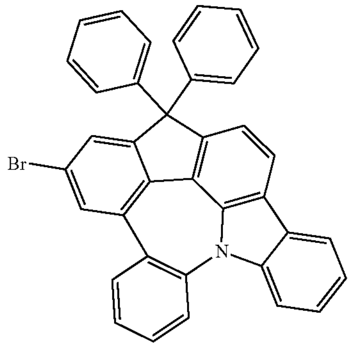 B-7-1 | 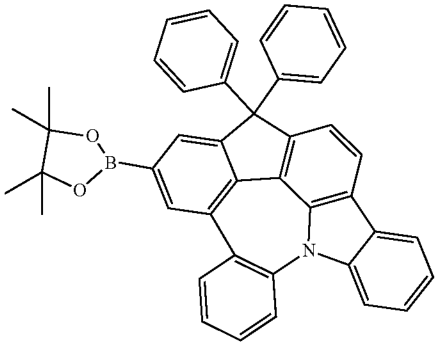 B-8-1 | 75.2 |
| 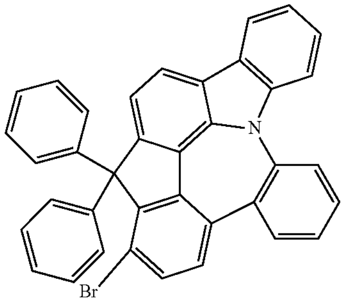 B-7-2 | 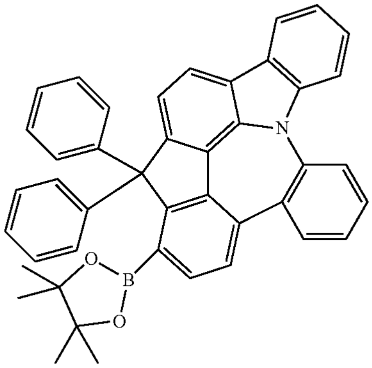 B-8-2 | 67.1 |
| 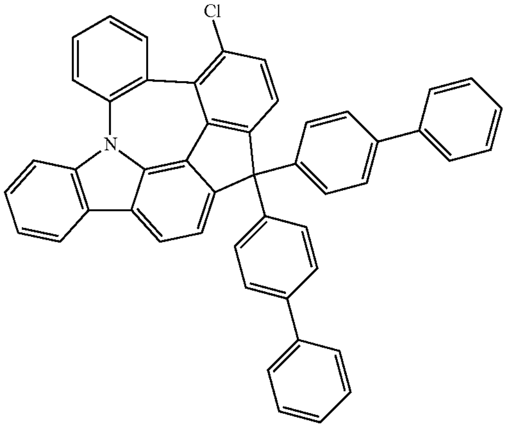 B-7-3 | 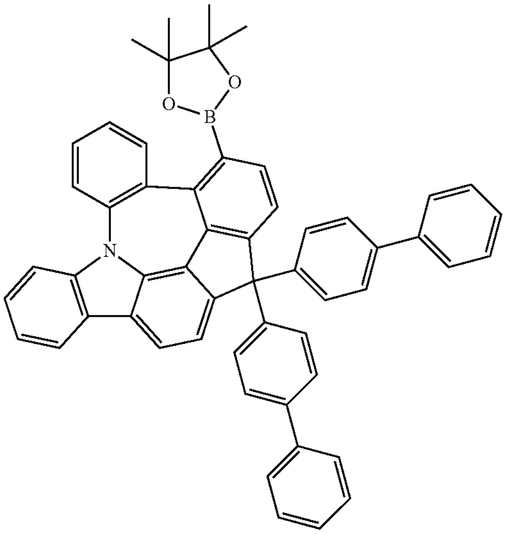 B-8-3 | 66.8 |

TABLE 15-continued
| A-8-X/B-7-X/C-7-1 | A-10-X/B-8-X/C-8-1 | Yield (%) |
| --- | --- | --- |
| 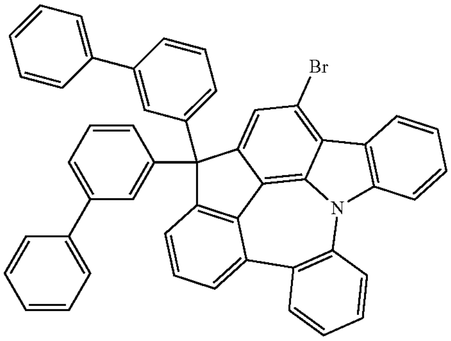 B-7-4 | 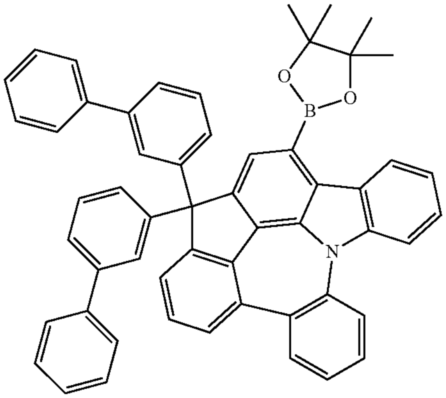 B-8-4 | 66.7 |
| 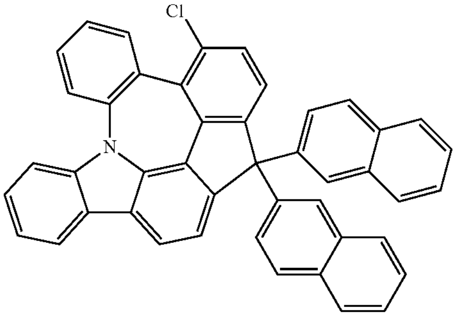 B-7-6 | 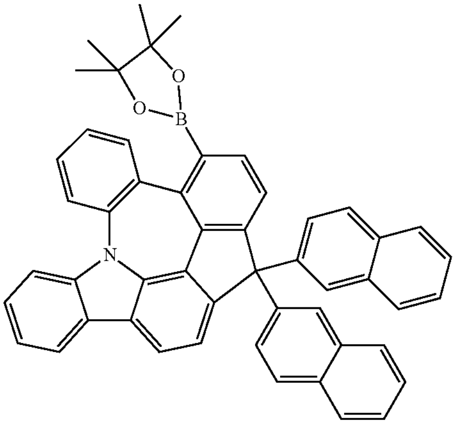 B-8-6 | 63.1 |
| 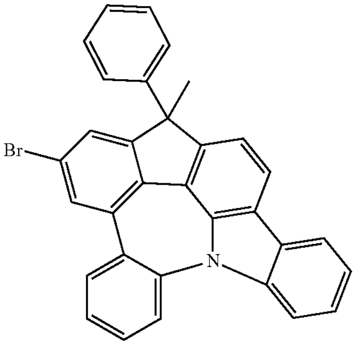 B-7-8 | 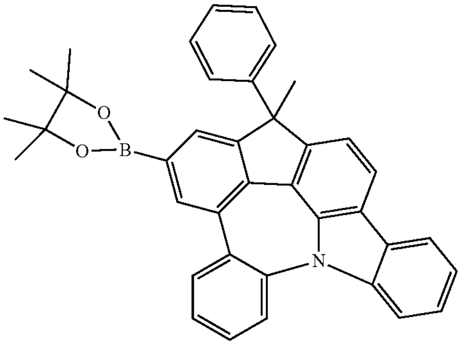 B-8-8 | 66.8 |

TABLE 15-continued
| A-8-X/B-7-X/C-7-1 | A-10-X/B-8-X/C-8-1 | Yield (%) |
|---|---|---|
| 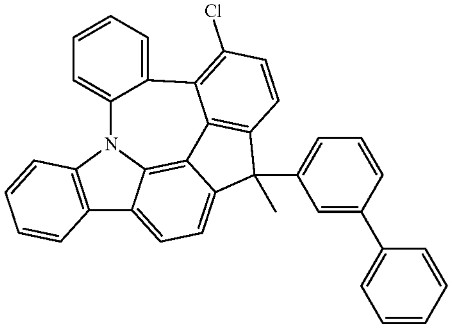 B-7-10 | 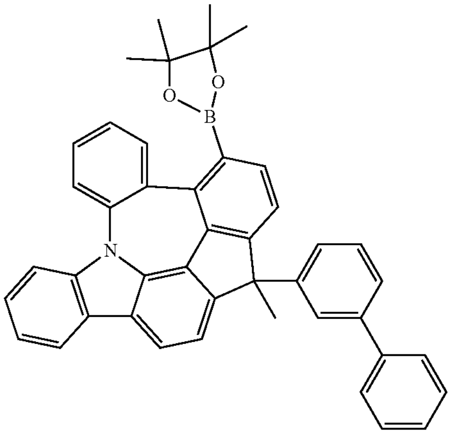 B-8-10 | 61.2 |
| 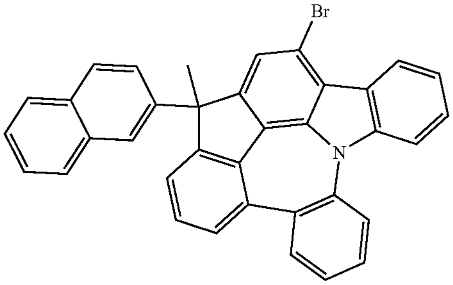 B-7-11 | 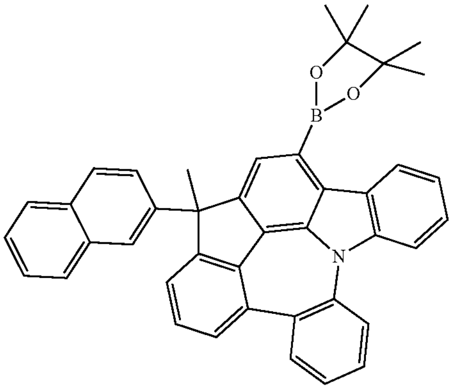 B-8-11 | 65.8 |
| 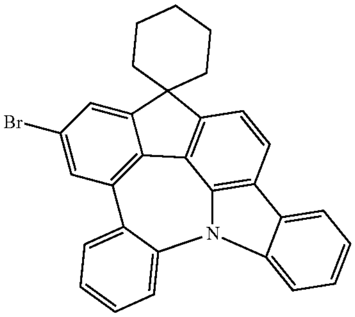 B-7-13 | 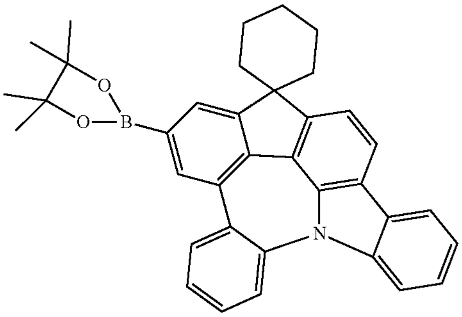 B-8-13 | 66.7 |

TABLE 15-continued
| A-8-X/B-7-X/C-7-1 | A-10-X/B-8-X/C-8-1 | Yield (%) |
|---|---|---|
| 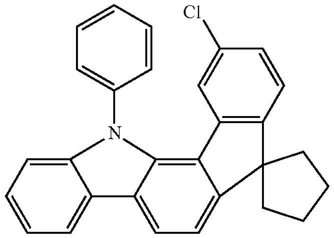 B-7-15 | 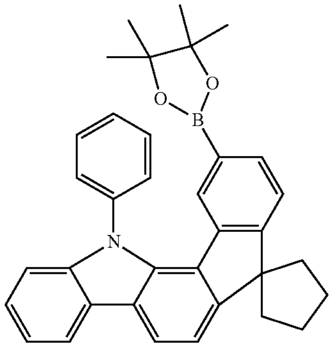 B-8-15 | 61.2 |
| 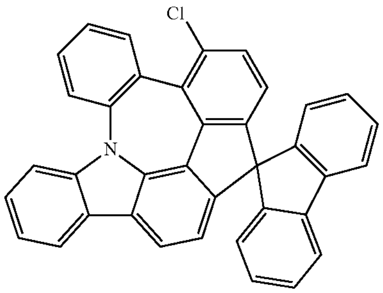 B-7-20 | 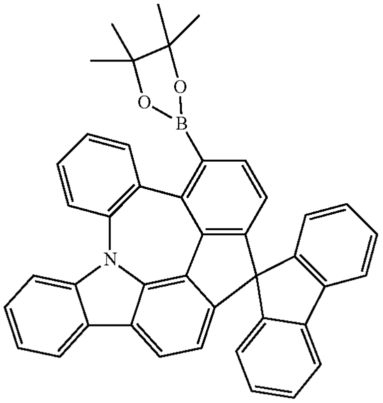 B-8-20 | 60.2 |
| 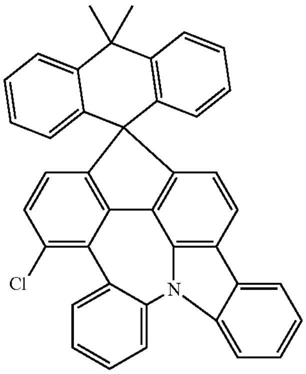 C-7-1 | 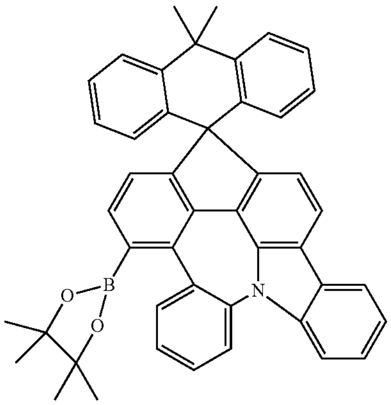 C-8-1 | 61.5 |

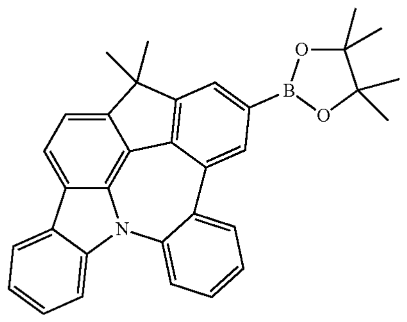

A-10-1

+

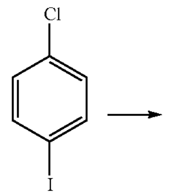

A-9-1

-continued

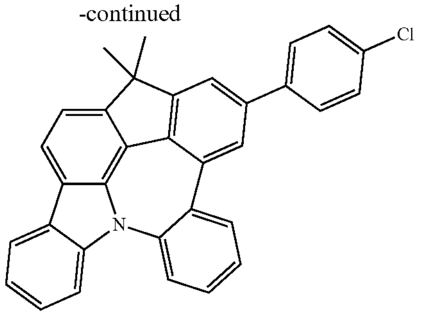

A-12-1

The intermediate A-10-1 (43.5 g, 89.98 mmol), a raw material A-9-1 (21.46 g, 89.98 mmol), palladium acetate (0.20 g, 0.90 mmol), X-Phos (0.86 g, 1.80 mmol), potassium carbonate (18.63 g, 134.8 mmol), toluene (261 mL), absolute ethanol (87 mL), and deionized water (87 mL) were added to a round-bottomed flask, and a resulting mixture was heated to 78° C. under nitrogen atmosphere and stirred for 4 h; a resulting reaction system was cooled to room temperature, washed with water, dried with anhydrous magnesium sulfate, and filtered, and a filtrate was concentrated in vacuum to obtain a crude product; and the crude product was purified by recrystallization with a DCM/n-heptane system to obtain a solid intermediate A-12-1 (32.0 g, yield: 76%).

The intermediates A-12-X, B-10-X, and C-10-1 listed in Table 16 were each synthesized with reference to the synthesis method of the intermediate A-12-1, except that an intermediate A-10-X, B-8-X, or C-8-1 was used instead of the intermediate A-10-1 and A-11-X or A-9-X was used instead of the A-9-1.

TABLE 16
| A-10-X/B-8-X/C-8-1 | A-11-X/A-9-X | A-12-X/B-10-X/C-10-1 | Yield (%) |
|---|---|---|---|
| 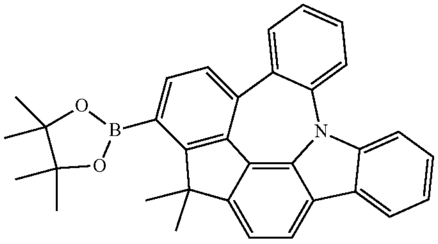 A-10-2 | 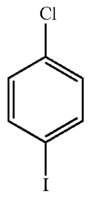 A-9-1 | 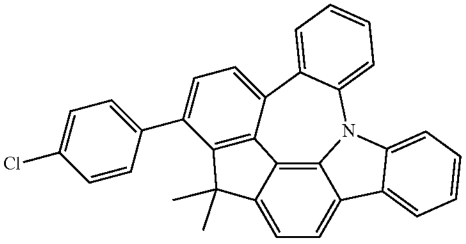 A-12-2 | 75.2 |
| 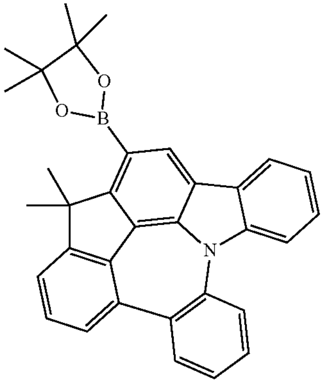 A-10-5 | 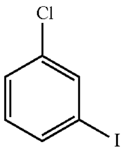 A-9-4 | 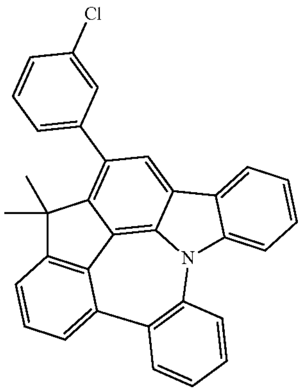 A-12-5 | 73.1 |

TABLE 16-continued
| A-10-X/B-8-X/C-8-1 | A-11-X/A-9-X | A-12-X/B-10-X/C-10-1 | Yield (%) |
|---|---|---|---|
| 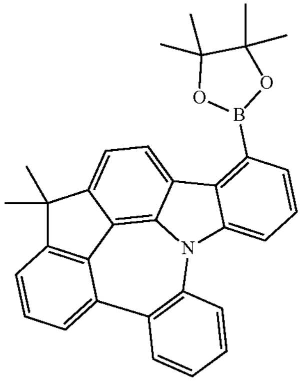 A-10-6 | 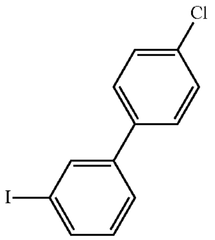 A-11-3 | 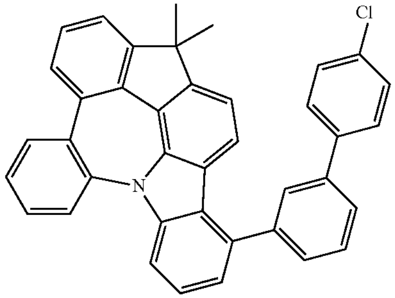 A-12-6 | 75.5 |
| 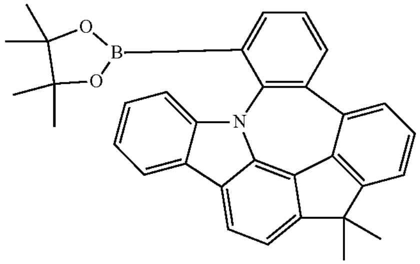 A-10-11 | 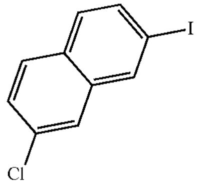 A-11-4 | 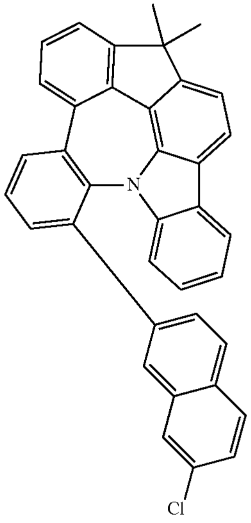 A-12-11 | 67.4 |

TABLE 16-continued
| A-10-X/B-8-X/C-8-1 | A-11-X/A-9-X | A-12-X/B-10-X/C-10-1 | Yield (%) |
|---|---|---|---|
| 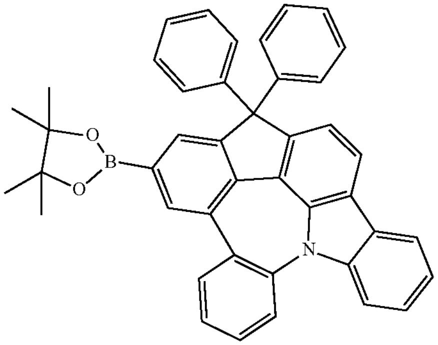 B-8-1 | 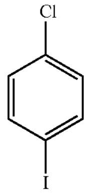 A-9-1 | 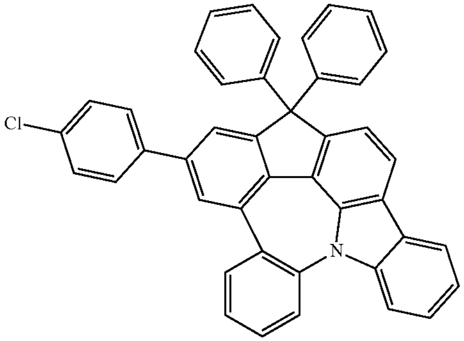 B-10-1 | 70.8 |
| 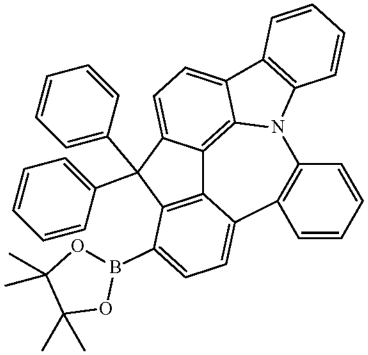 B-7-2 | 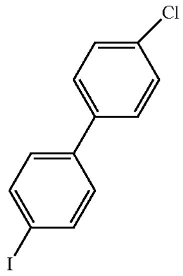 A-9-8 | 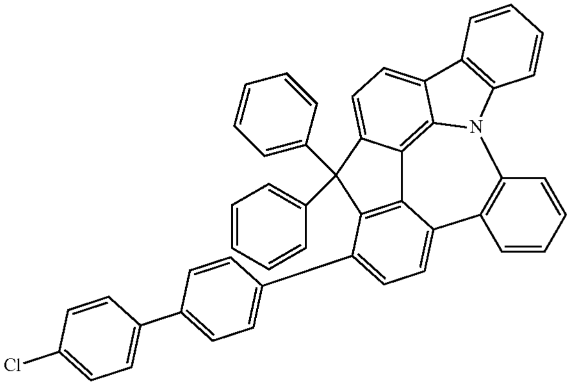 B-10-2 | 65.2 |

TABLE 16-continued
| A-10-X/B-8-X/C-8-1 | A-11-X/A-9-X | A-12-X/B-10-X/C-10-1 | Yield (%) |
|---|---|---|---|
| 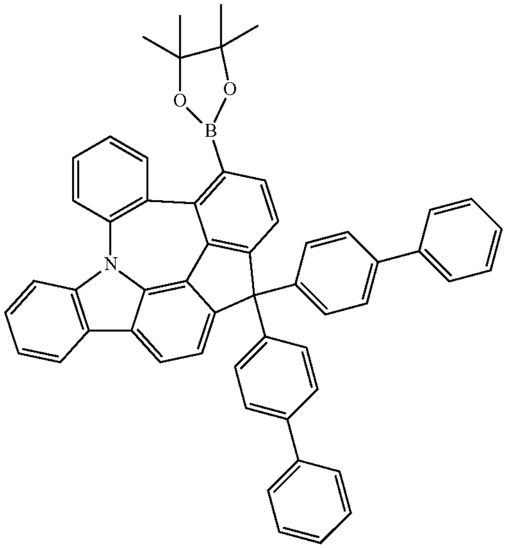 B-8-3 | 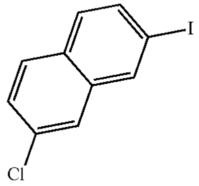 A-9-9 | 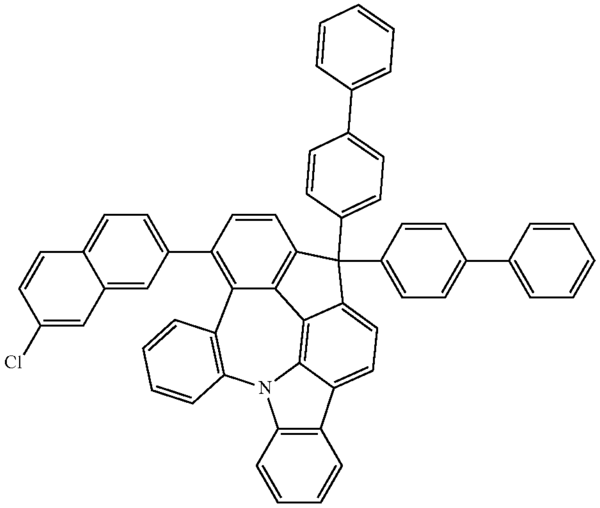 B-10-3 | 64.8 |
| 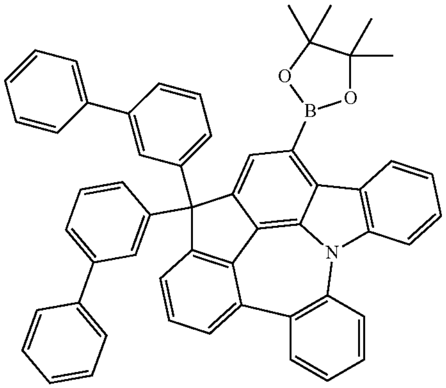 B-8-4 | 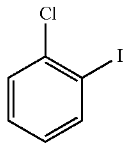 A-9-7 | 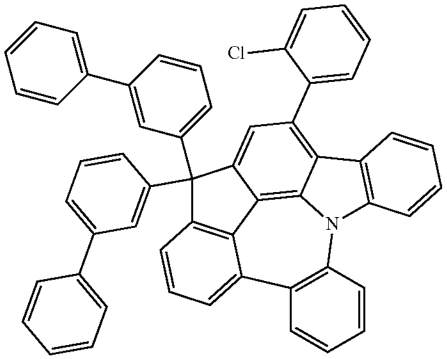 B-10-4 | 70.2 |

TABLE 16-continued
| A-10-X/B-8-X/C-8-1 | A-11-X/A-9-X | A-12-X/B-10-X/C-10-1 | Yield (%) |
|---|---|---|---|
| 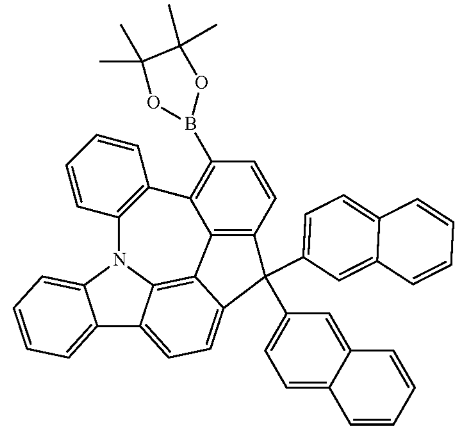 B-8-6 | 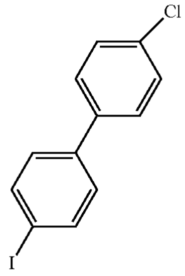 A-9-8 | 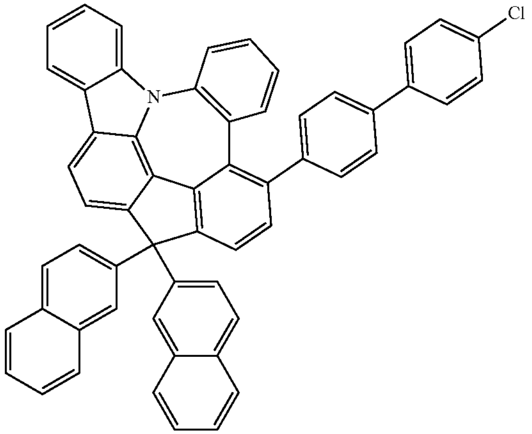 B-10-6 | 67.1 |
| 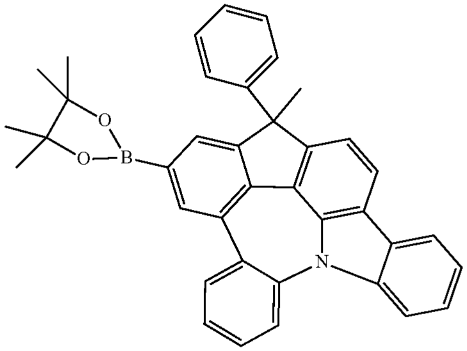 B-8-8 | 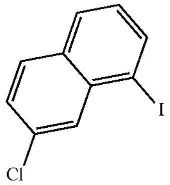 A-9-6 | 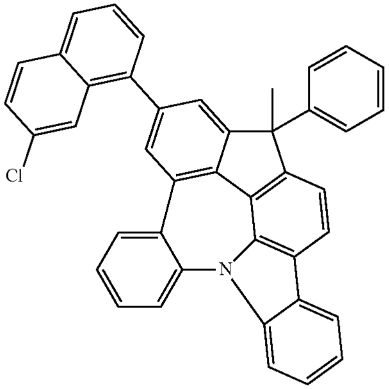 B-10-8 | 71.6 |

TABLE 16-continued
| A-10-X/B-8-X/C-8-1 | A-11-X/A-9-X | A-12-X/B-10-X/C-10-1 | Yield (%) |
|---|---|---|---|
| 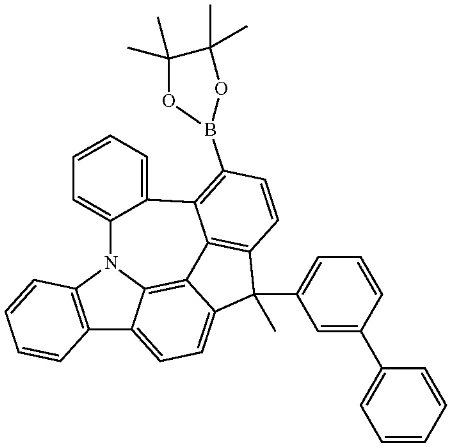 B-8-10 | 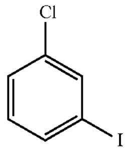 A-9-4 | 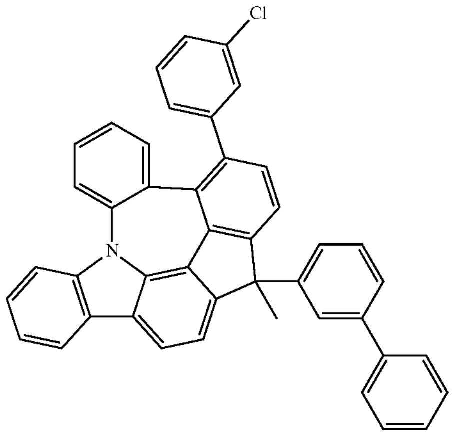 B-10-10 | 66.7 |
| 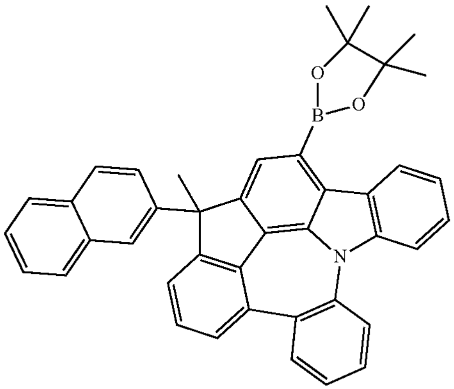 B-8-11 | 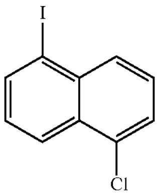 A-9-3 | 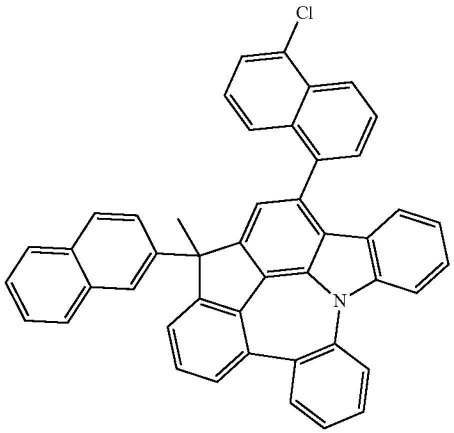 B-10-11 | 70.6 |

TABLE 16-continued
| A-10-X/B-8-X/C-8-1 | A-11-X/A-9-X | A-12-X/B-10-X/C-10-1 | Yield (%) |
|---|---|---|---|
| 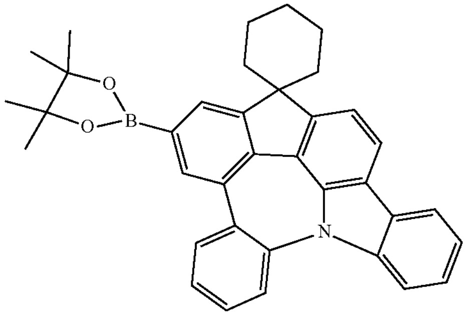 B-8-13 | 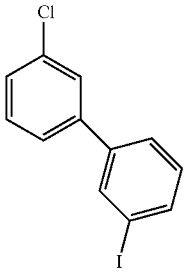 A-9-2 | 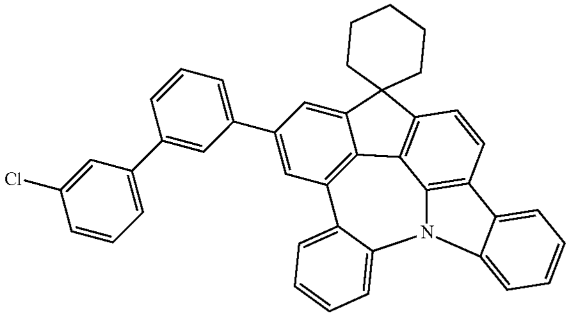 B-10-13 | 74.1 |
| 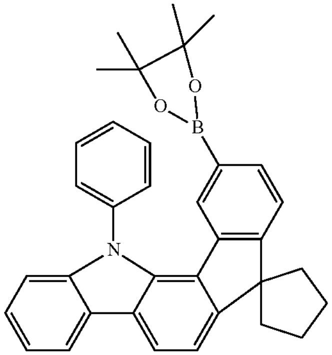 B-8-15 | 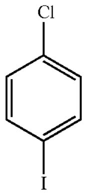 A-9-1 | 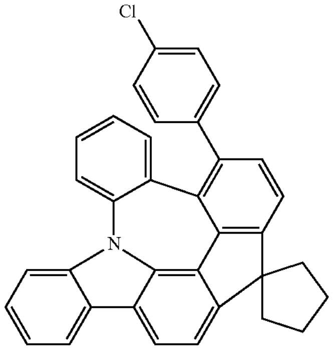 B-10-15 | 68.2 |

TABLE 16-continued
| A-10-X/B-8-X/C-8-1 | A-11-X/A-9-X | A-12-X/B-10-X/C-10-1 | Yield (%) |
|---|---|---|---|
| 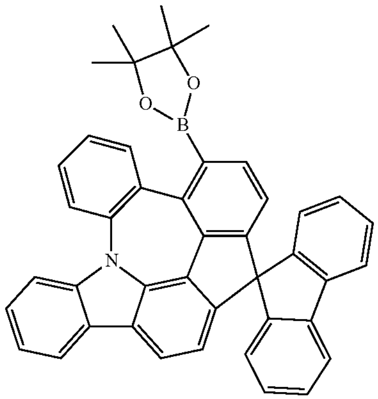 B-8-20 | 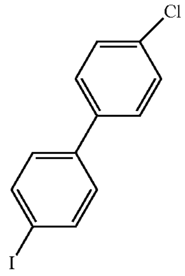 A-9-8 | 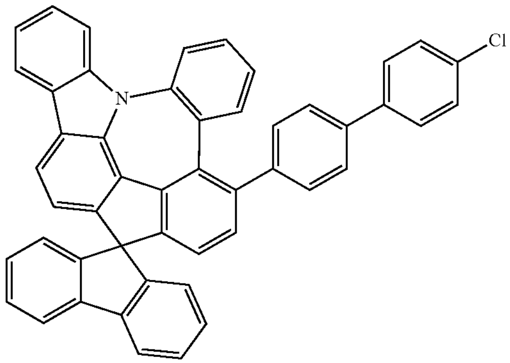 B-10-20 | 67.1 |
| 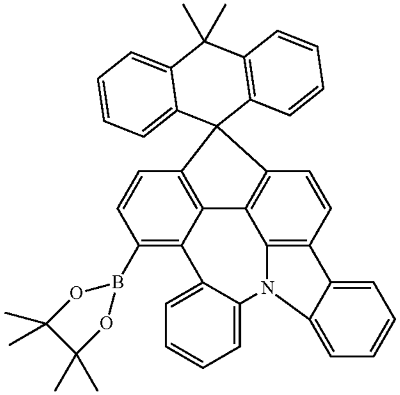 C-8-1 | 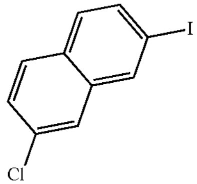 A-9-9 | 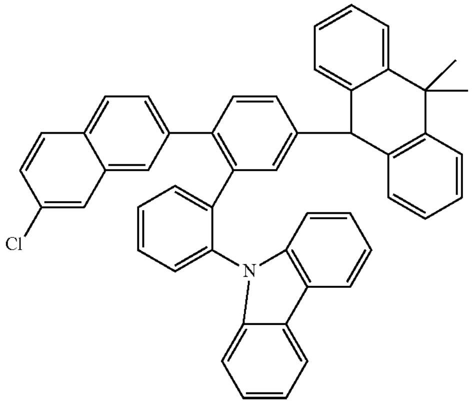 C-10-1 | 66.8 |

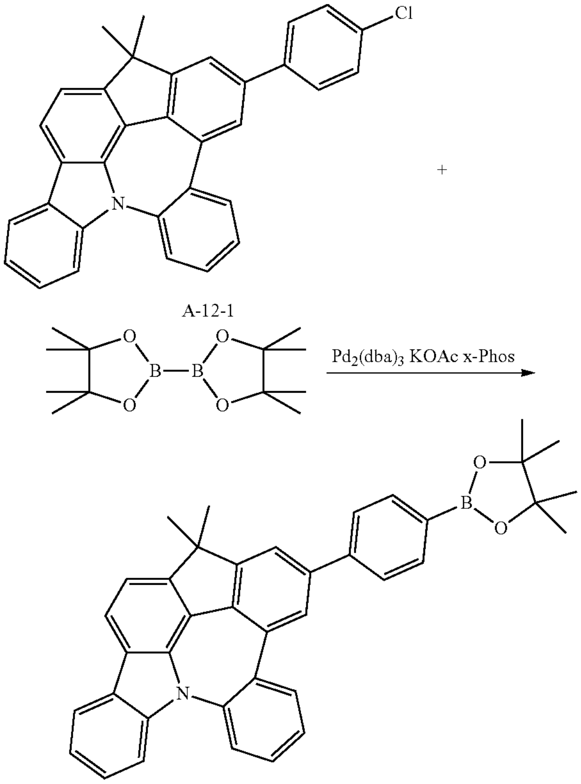

A-12-1

A-13-1

The intermediate A-12-1 (27.5 g, 58.76 mmol), bis(pinacolato)diboron (14.86 g, 58.76 mmol), tris(dibenzylideneacetone)dipalladium (0.54 g, 0.59 mmol), X-Phos (0.55 g, 1.18 mmol), potassium acetate (8.64 g, 88.14 mmol), and 1,4-dioxane (224 mL) were added to a three-necked round-bottomed flask, and a resulting mixture was heated to 80° C. under nitrogen atmosphere and stirred for 3 h; a resulting reaction system was cooled to room temperature, washed with water, dried with magnesium sulfate, and filtered, and a filtrate was concentrated in vacuum to obtain a crude product; and the crude product was purified by recrystallization with a toluene system to obtain a solid intermediate A-13-1 (26.3 g, yield: 80%).

The intermediates A-13-X, B-13-X, and C-13-1 listed in Table 17 were each synthesized with reference to the synthesis method of the intermediate A-13-1, except that an intermediate A-12-X, B-10-X, or C-10-1 was used instead of the intermediate A-12-1.

TABLE 17

| A-12-X/B-10-X/C-10-1 | A-13-X/B-13-X/C-13-1 | Yield (%) |
|---|---|---|
| 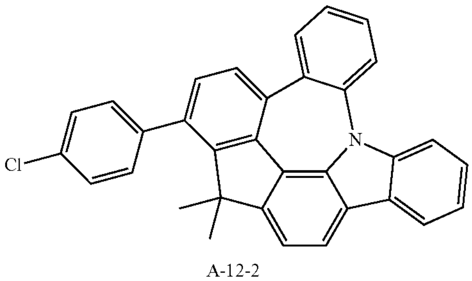 [SMILES: CC1(C)c2ccc3c4ccccc4n4c3c2-c2c(ccc(-c3ccc(Cl)cc3)c21)-c1ccccc1-4] A-12-2 | 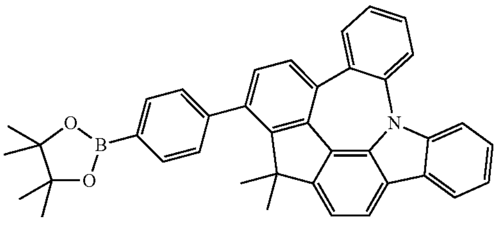 A-13-2 | 81.1 |

TABLE 17-continued
| A-12-X/B-10-X/C-10-1 | A-13-X/B-13-X/C-13-1 | Yield (%) |
|---|---|---|
| 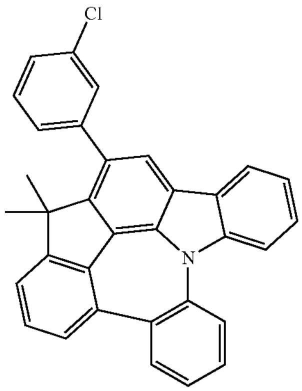 A-12-5 | 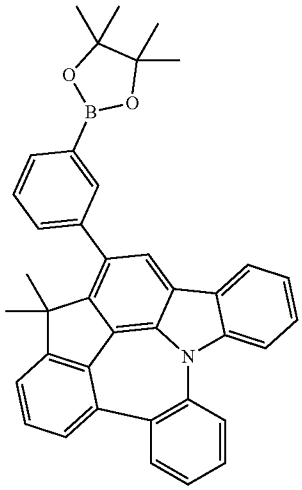 A-13-5 | 78.2 |
| 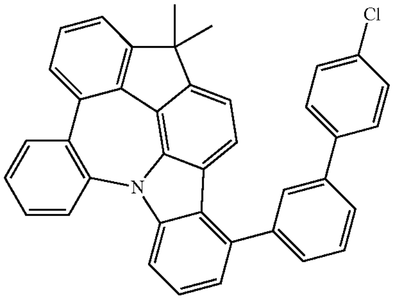 A-12-6 | 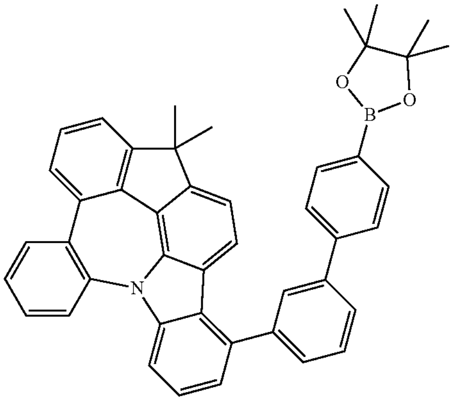 A-13-6 | 80.3 |

TABLE 17-continued
| A-12-X/B-10-X/C-10-1 | A-13-X/B-13-X/C-13-1 | Yield (%) |
|---|---|---|
| 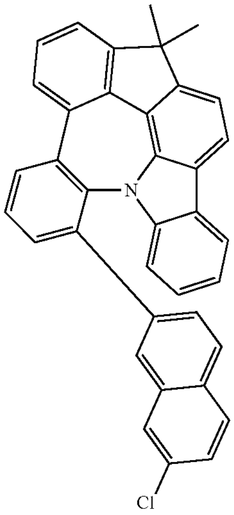 A-12-11 | 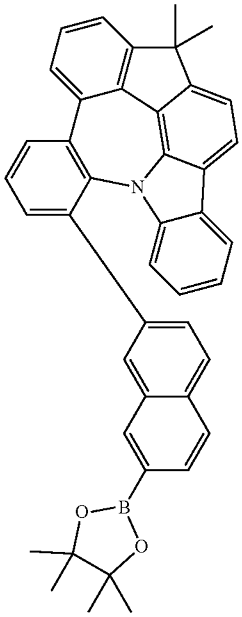 A-13-11 | 77.5 |
| 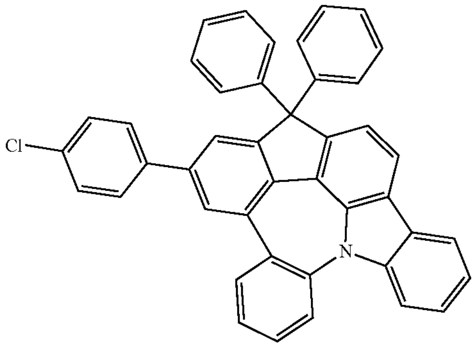 B-10-1 | 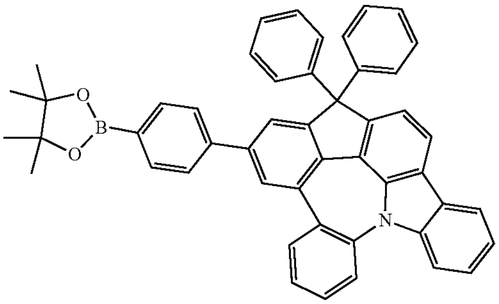 B-13-1 | 74.8 |
| 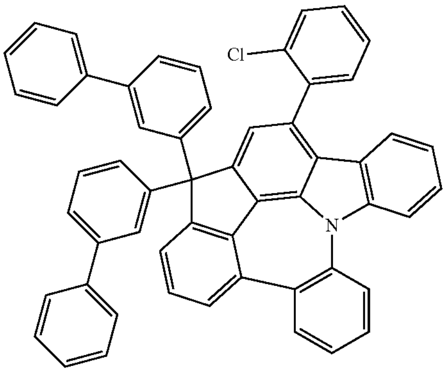 B-10-4 | 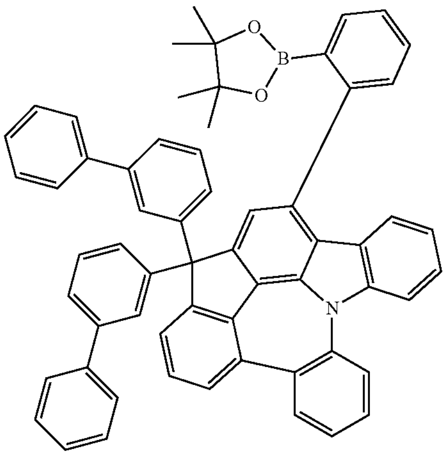 B-13-4 | 70.2 |

TABLE 17-continued
| A-12-X/B-10-X/C-10-1 | A-13-X/B-13-X/C-13-1 | Yield (%) |
| --- | --- | --- |
| 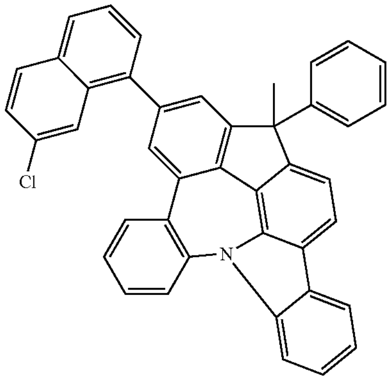 B-10-8 | 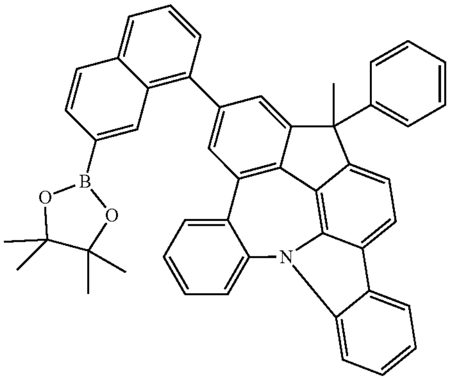 B-13-8 | 73.5 |
| 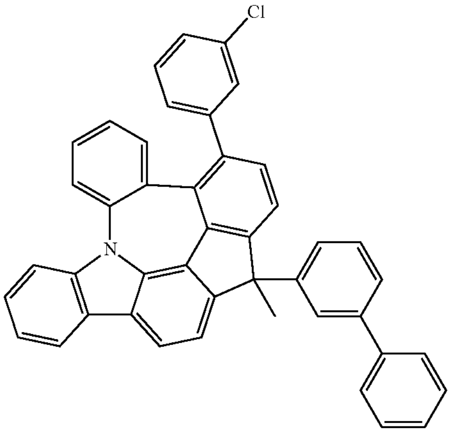 B-10-10 | 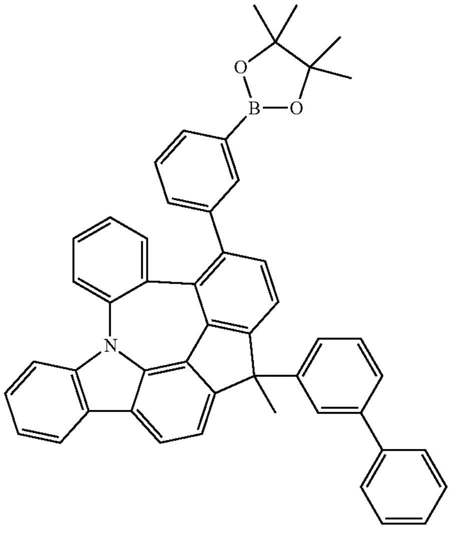 B-13-10 | 75.1 |

TABLE 17-continued
| A-12-X/B-10-X/C-10-1 | A-13-X/B-13-X/C-13-1 | Yield (%) |
|---|---|---|
| 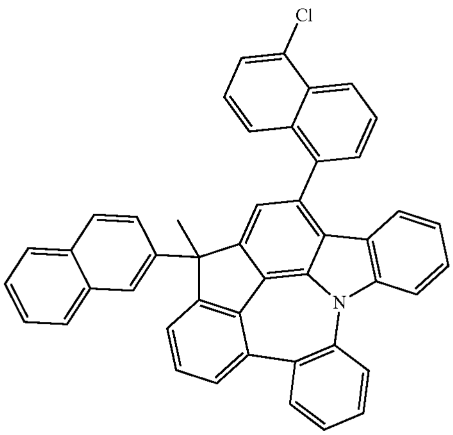 B-10-11 | 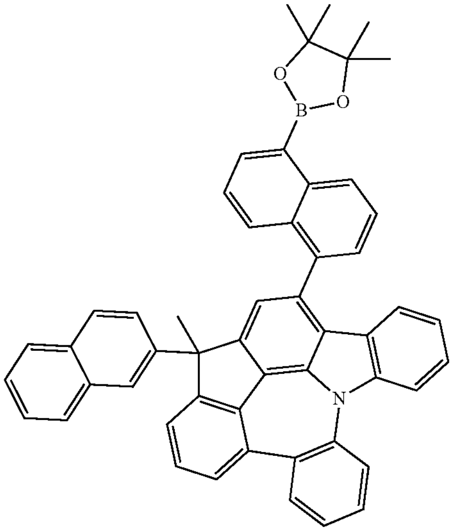 B-13-11 | 71.2 |
| 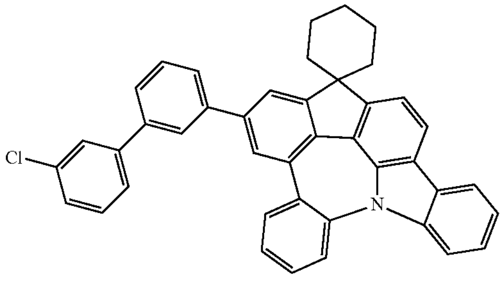 B-10-13 | 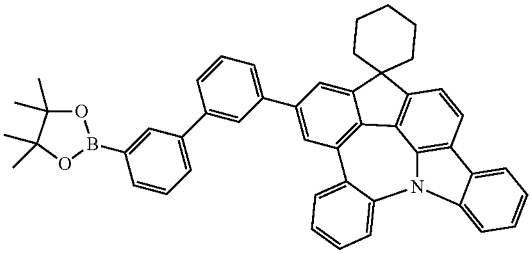 B-13-13 | 73.8 |
| 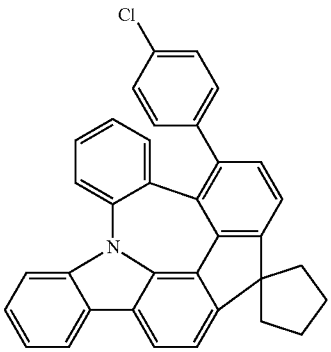 B-10-15 | 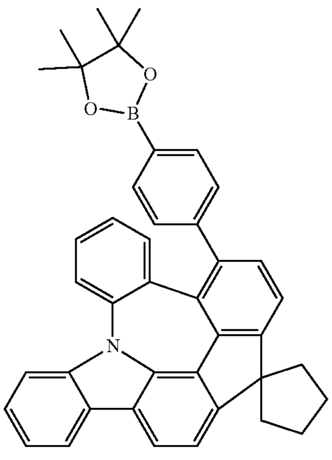 B-13-15 | 74.2 |

TABLE 17-continued

| A-12-X/B-10-X/C-10-1 | A-13-X/B-13-X/C-13-1 | Yield (%) |
|---|---|---|
| 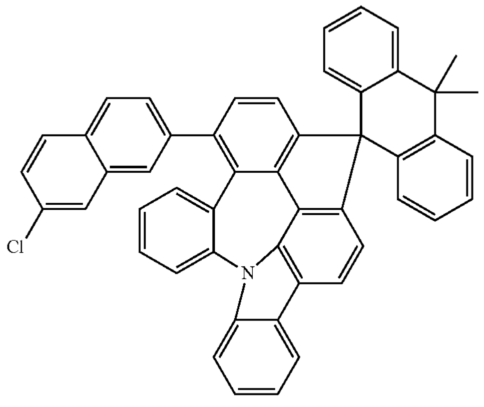 C-10-1 | 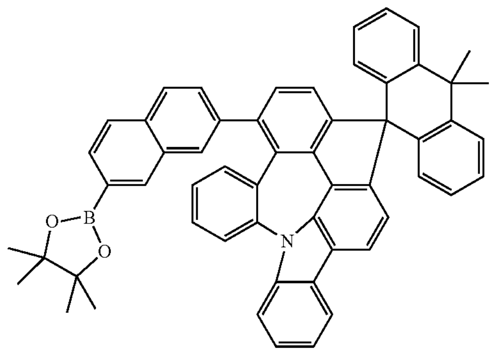 C-13-1 | 75.6 |

-continued

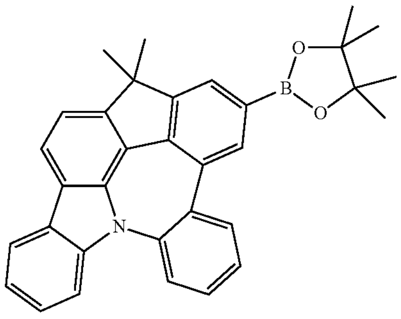

A-10-1

+

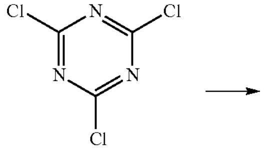

A-14-1

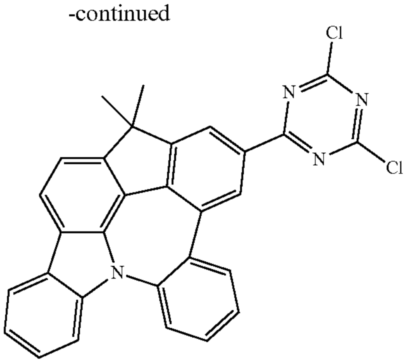

A-15-1

Nitrogen was introduced into a 250 mL three-necked flask, the intermediate A-10-1 (26.25 g, 54.3 mmol), a raw material A-14-1 (9.9 g, 54.3 mmol), THF (156 mL), and $H_2O$ (52 mL) were added, and a resulting mixture was heated to reflux and stirred; tetrakis(triphenylphosphine) palladium (0.42 g, 0.362 mmol) and potassium carbonate (7.5 g, 54.3 mmol) were added, and a resulting mixture was heated to reflux and stirred for 10 h; a resulting reaction system was naturally cooled to room temperature, 80 mL of dilute hydrochloric acid was added for quenching, and a resulting mixture was washed with water until neutral; and DCM was added for extraction, a separated organic phase was concentrated in vacuum to obtain a residue, and the residue was purified by silica gel column chromatography and dried to obtain an intermediate A-15-1 (18.30 g, yield: 67%).

The intermediates A-15-X, B-15-X, and C-15-1 listed in Table 18 were each synthesized with reference to the synthesis method of the intermediate A-15-1, except that a raw material A was used instead of the intermediate A-10-1.

TABLE 18
| Raw material A | A-15-X/B-15-X/C-15-1 | Yield (%) |
|---|---|---|
| 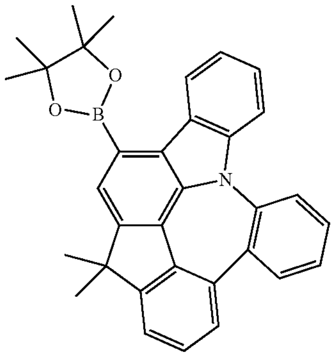 A-10-4 | 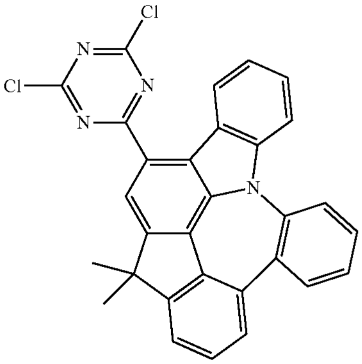 A-15-4 | 62.5 |
| 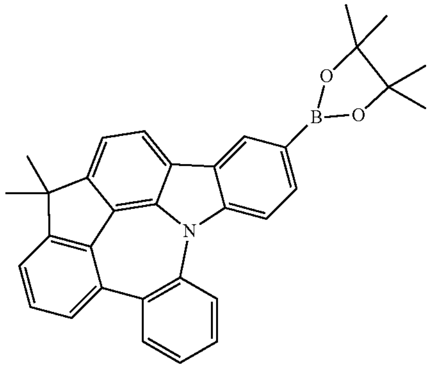 A-10-7 | 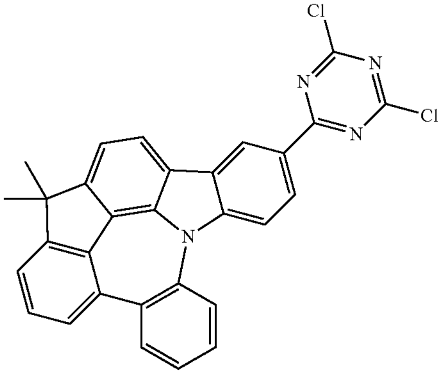 A-15-7 | 66.1 |
| 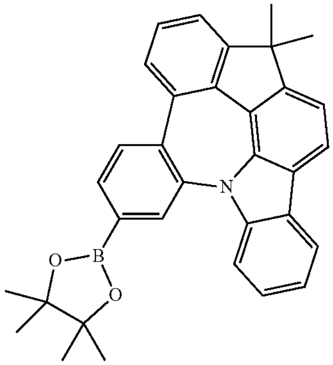 A-10-12 | 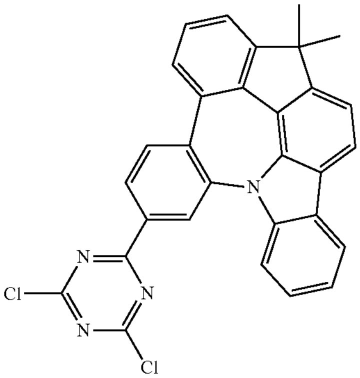 A-15-12 | 67.1 |
| 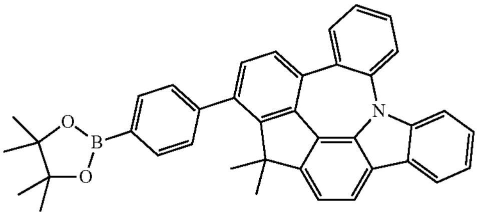 A-13-2 | 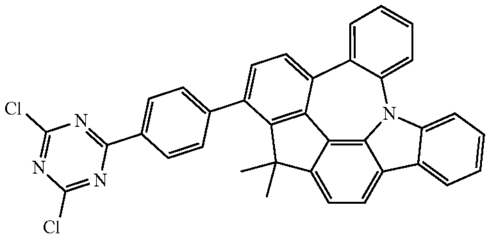 A-15-2 | 65.3 |

TABLE 18-continued
| Raw material A | A-15-X/B-15-X/C-15-1 | Yield (%) |
|---|---|---|
| 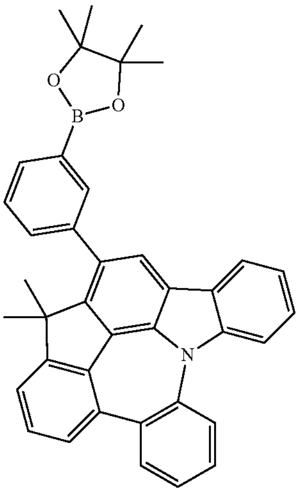 A-13-5 | 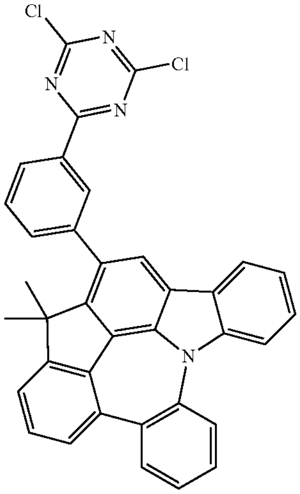 A-15-5 | 66.2 |
| 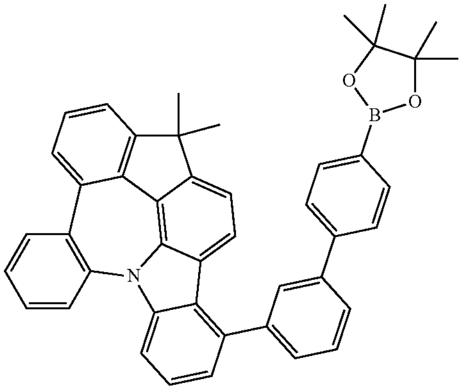 A-13-6 | 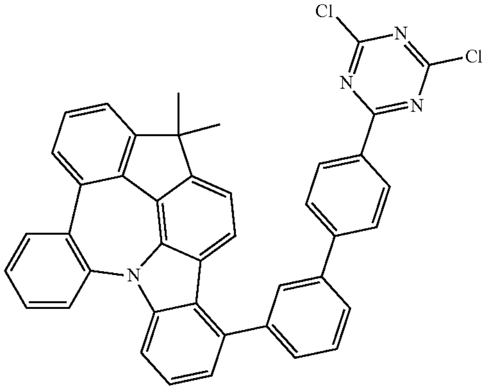 A-15-6 | 64.8 |
| 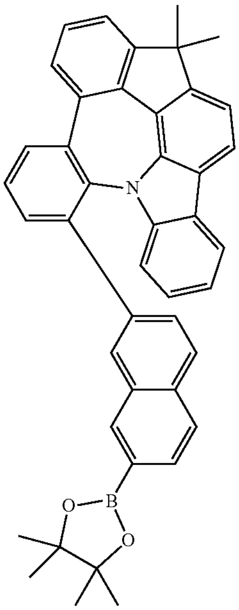 A-13-11 | 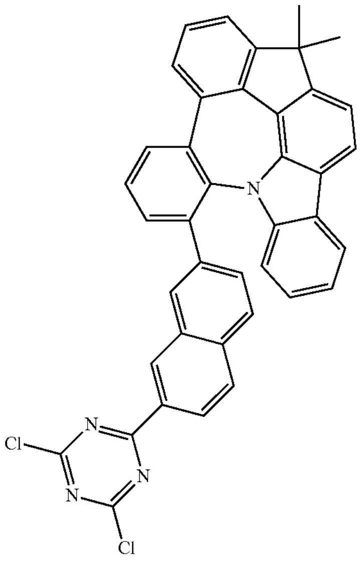 A-15-11 | 63.5 |

TABLE 18-continued
| Raw material A | A-15-X/B-15-X/C-15-1 | Yield (%) |
|---|---|---|
| 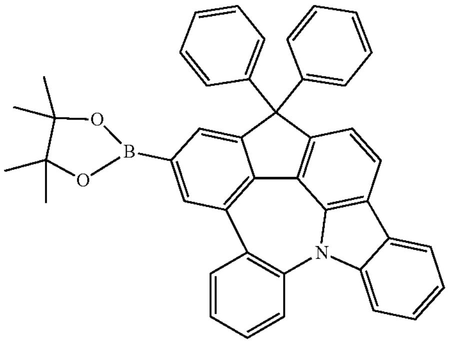 B-8-1 | 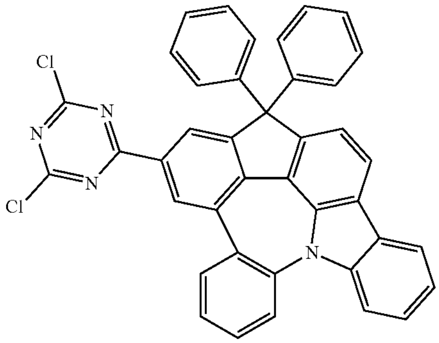 B-15-1 | 65.8 |
| 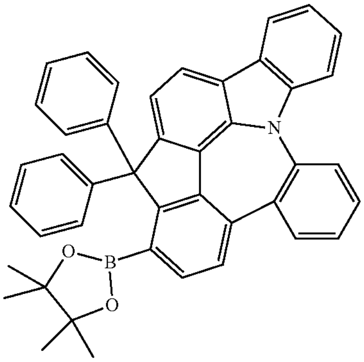 B-8-2 | 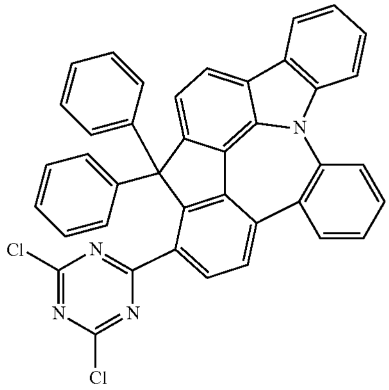 B-15-2 | 60.2 |
| 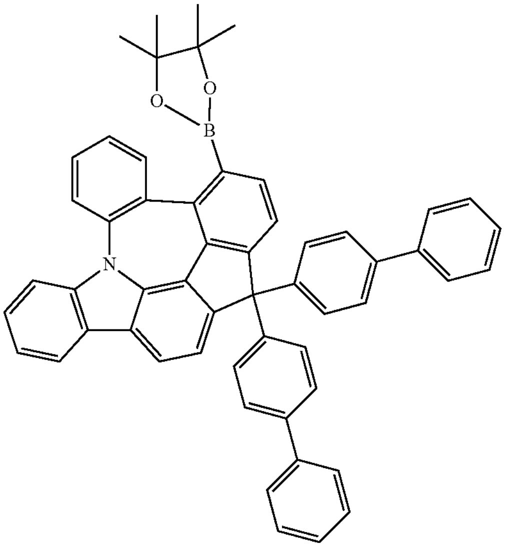 B-8-3 | 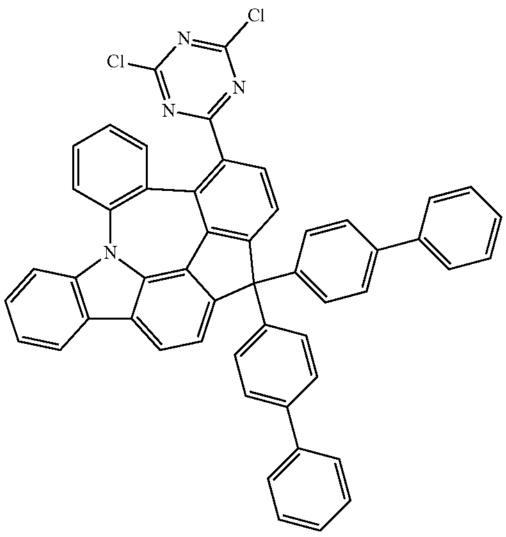 B-15-3 | 61.8 |

TABLE 18-continued
| Raw material A | A-15-X/B-15-X/C-15-1 | Yield (%) |
|---|---|---|
| 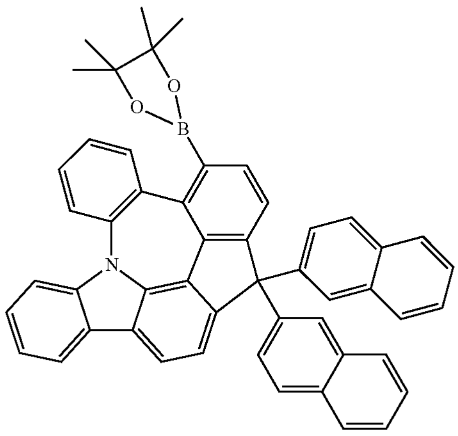 B-8-6 | 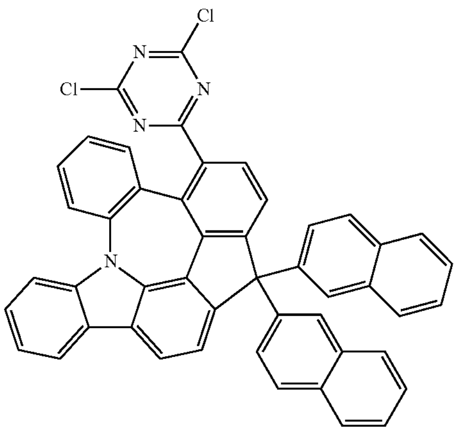 B-15-6 | 60.8 |
| 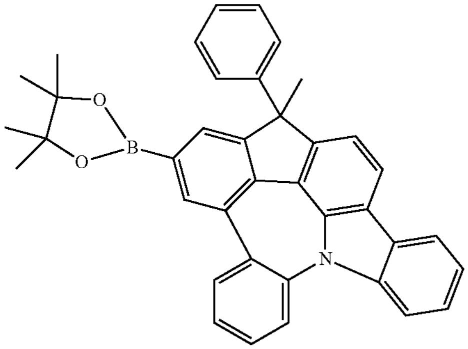 B-8-8 | 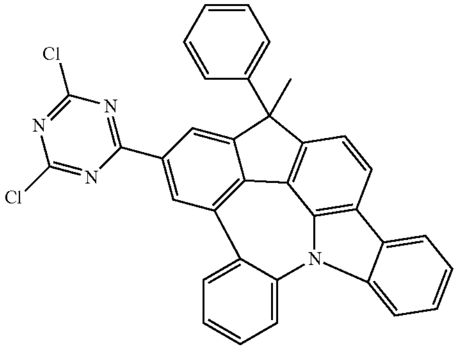 B-15-8 | 64.2 |
| 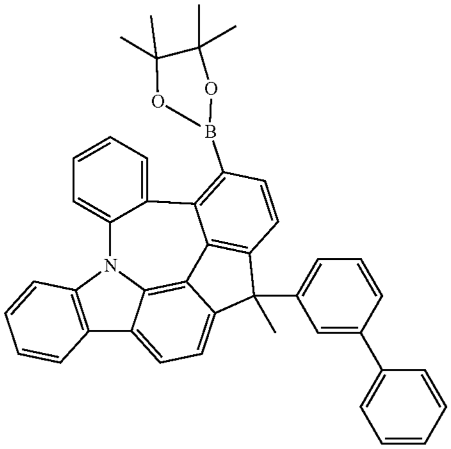 B-8-10 | 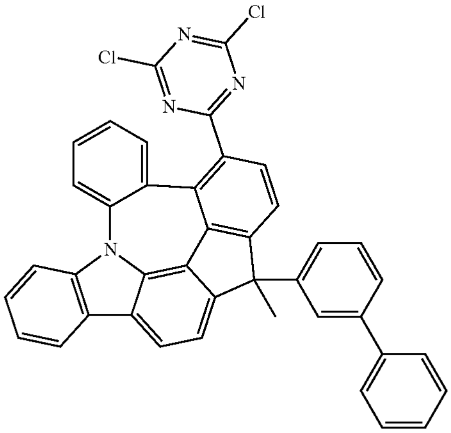 B-15-10 | 61.2 |

TABLE 18-continued
| Raw material A | A-15-X/B-15-X/C-15-1 | Yield (%) |
|---|---|---|
| 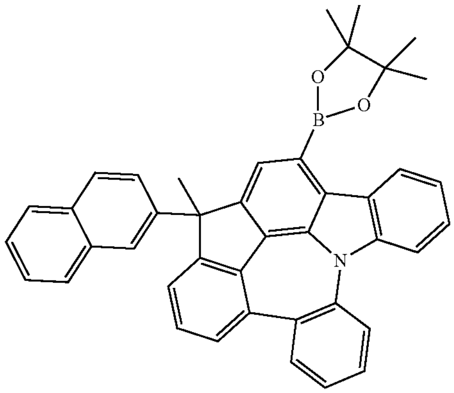 B-8-11 | 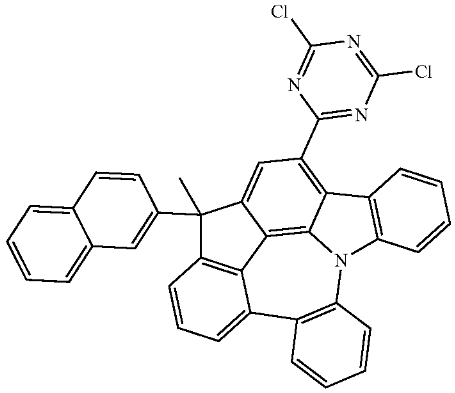 B-15-11 | 63.7 |
| 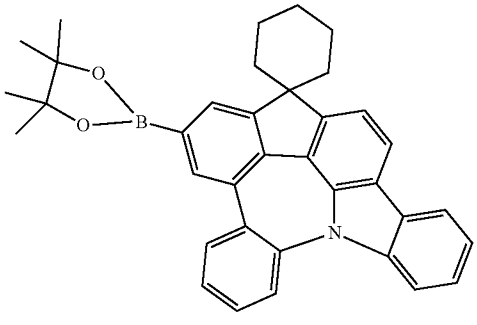 B-8-13 | 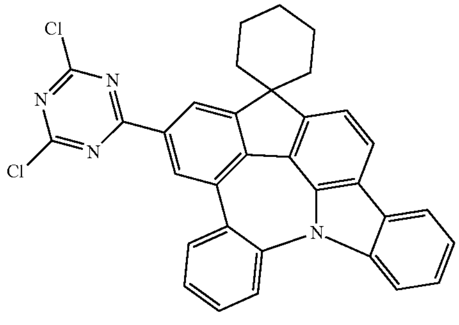 B-15-13 | 65.1 |
| 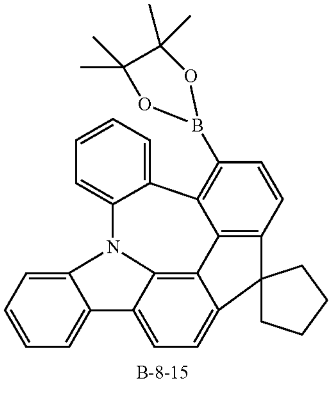 [SMILES: CC1(C)OB(c2ccc3c4c2-c2ccccc2-n2c5ccccc5c5ccc(c-4c52)C32CCCC2)OC1(C)C] B-8-15 | 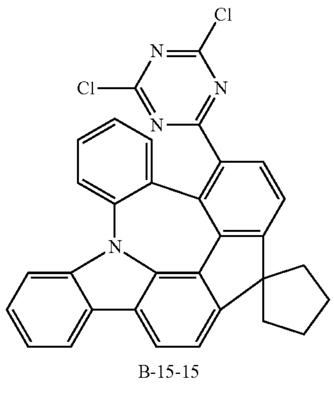 [SMILES: Clc1nc(Cl)nc(-c2ccc3c4c2-c2ccccc2-n2c5ccccc5c5ccc(c-4c52)C32CCCC2)n1] B-15-15 | 60.2 |

TABLE 18-continued
| Raw material A | A-15-X/B-15-X/C-15-1 | Yield (%) |
|---|---|---|
| 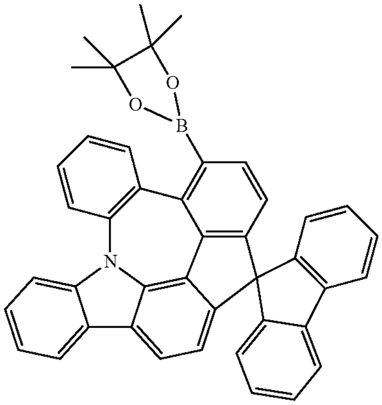 B-8-20 | 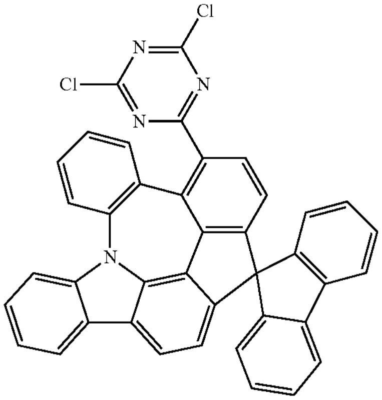 B-15-20 | 62.1 |
| 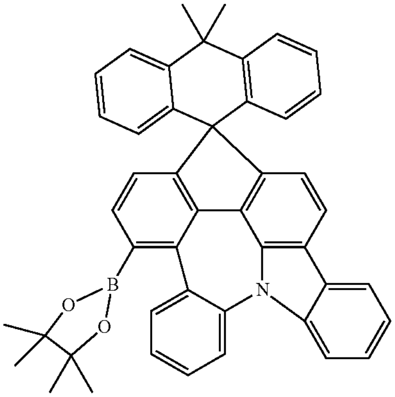 C-8-1 | 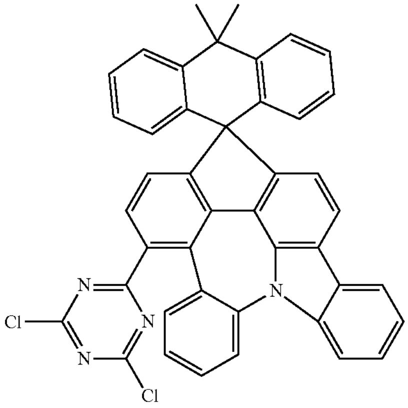 C-15-1 | 60.5 |
| 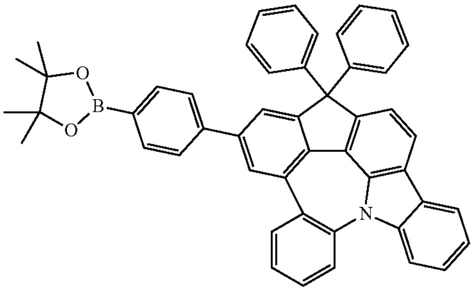 B-13-1 | 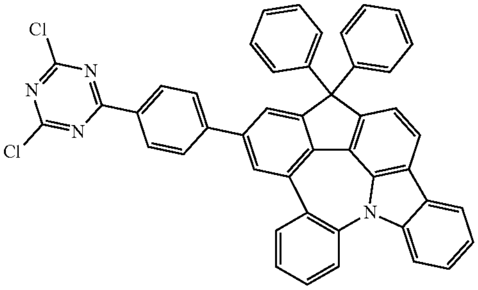 B-15-1 | 65.7 |

TABLE 18-continued
| Raw material A | A-15-X/B-15-X/C-15-1 | Yield (%) |
|---|---|---|
| 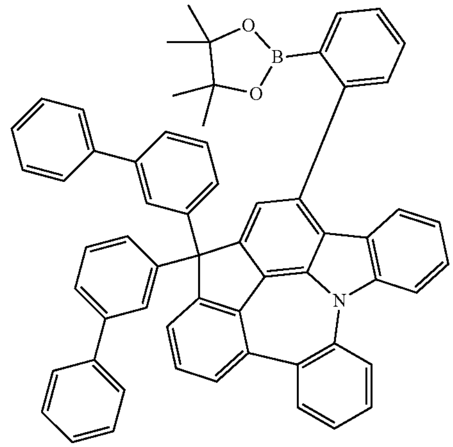<br>B-13-4 | 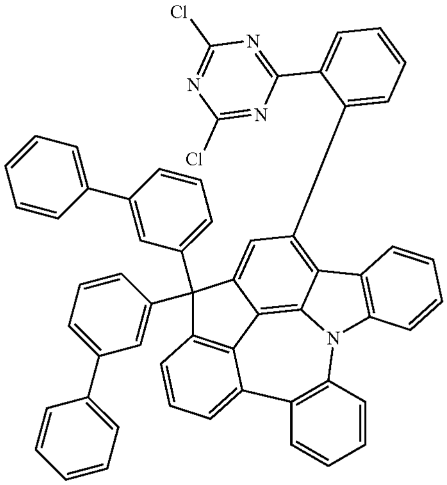<br>B-15-4 | 61.0 |
| 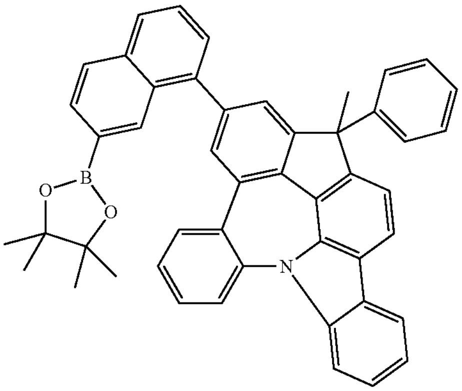<br>B-13-8 | 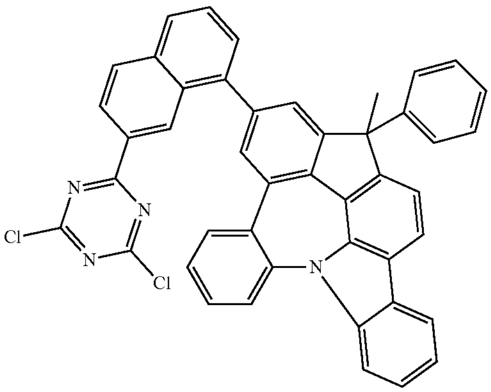<br>B-15-8 | 60.3 |
| 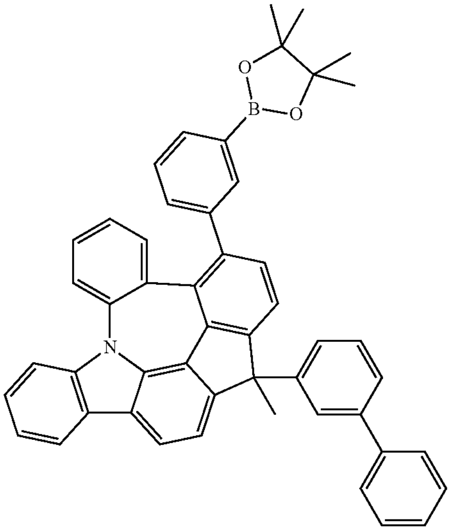<br>B-13-10 | 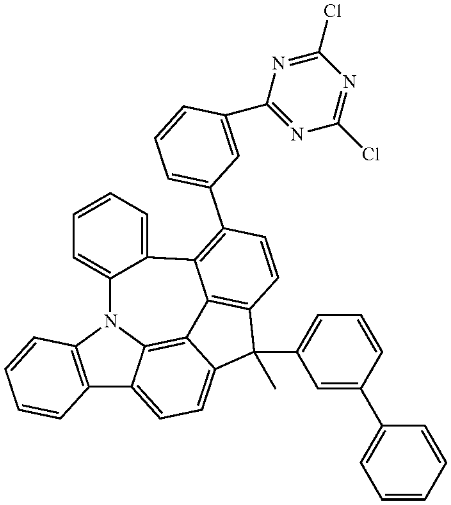<br>B-15-10 | 62.8 |

TABLE 18-continued
| Raw material A | A-15-X/B-15-X/C-15-1 | Yield (%) |
|---|---|---|
| 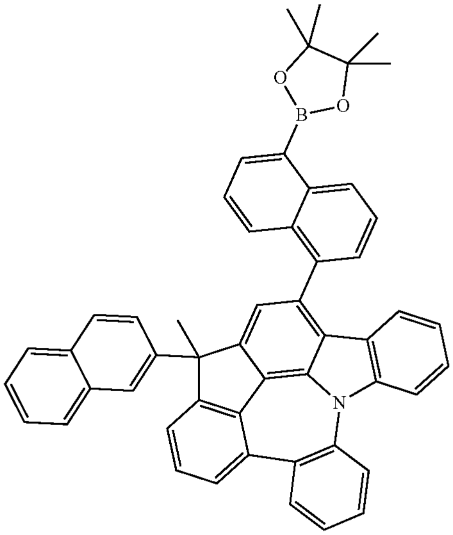 B-13-11 | 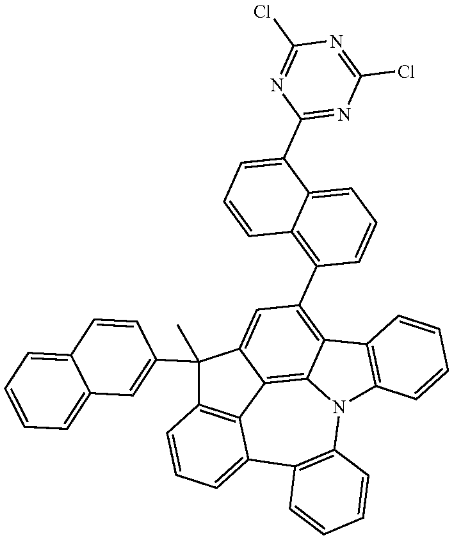 B-15-11 | 63.8 |
| 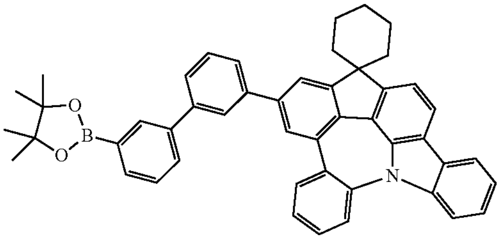 B-13-13 | 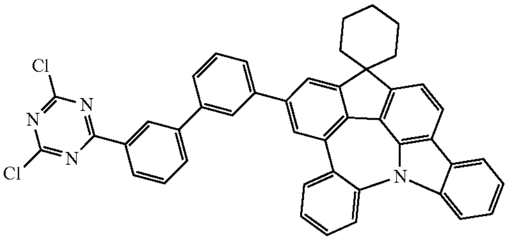 B-15-13 | 64.1 |
| 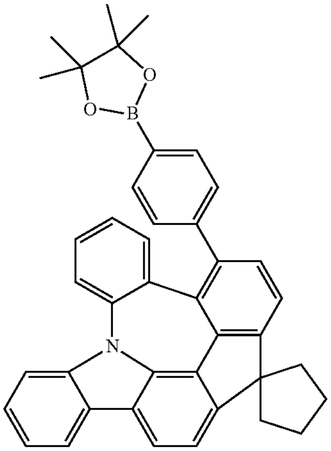 B-13-15 | 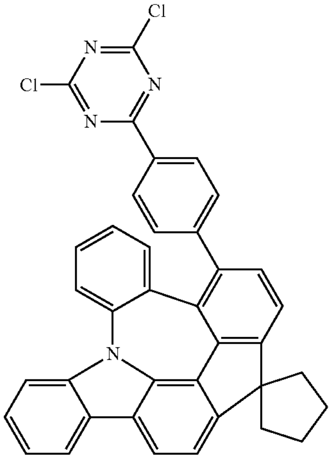 B-15-15 | 62.5 |

TABLE 18-continued

| Raw material A | A-15-X/B-15-X/C-15-1 | Yield (%) |
|---|---|---|
| 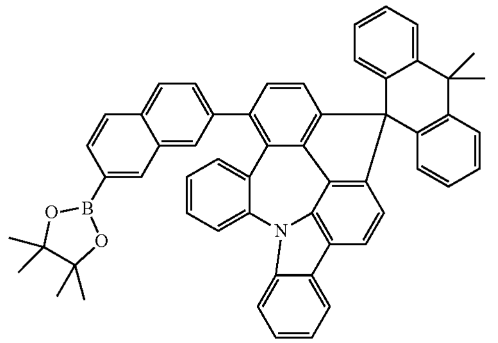 C-13-1 | 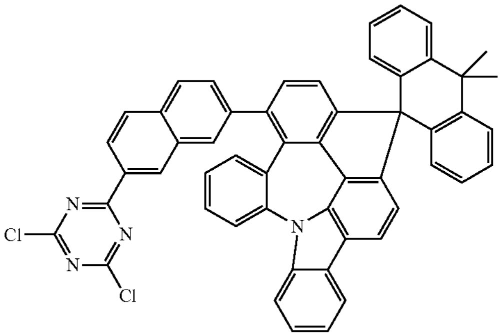 C-15-2 | 63.9 |

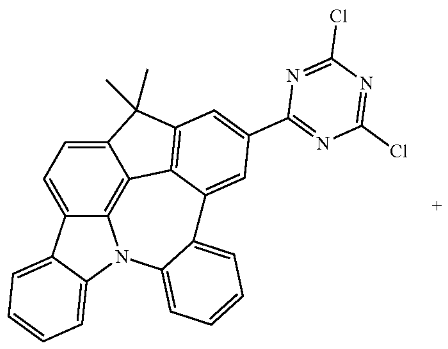

A-15-1

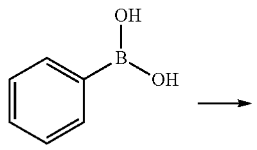

A-16-1

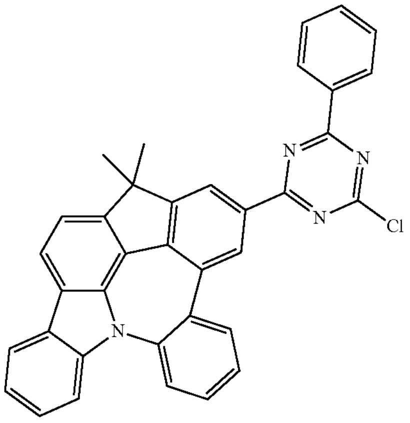

A-17-1

Nitrogen was introduced into a 250 mL three-necked flask, the intermediate A-15-1 (11.75 g, 23.25 mmol), a raw material A-16-1 (2.83 g, 23.25 mmol), THF (72 mL), and $H_2O$ (24 mL) were added, and a resulting mixture was heated to reflux and stirred; tetrakis(triphenylphosphine) palladium (0.27 g, 0.23 mmol) and potassium carbonate (4.77 g, 34.88 mmol) were added, a resulting mixture was heated to reflux and stirred for 10 h. A sample was taken for TLC to confirm that the reaction was complete; a resulting reaction system was naturally cooled, 80 mL of dilute hydrochloric acid was added for quenching, and a resulting mixture was washed with water until neutral; and DCM was added for extraction, a separated organic phase was concentrated in vacuum to obtain a residue, and the residue was purified by silica gel column chromatography and dried to obtain an intermediate A-17-1 (7.0 g, yield: 55%).

The intermediates A-17-X, B-17-X, and C-17-X listed in Table 19 were each synthesized with reference to the synthesis method of the intermediate A-17-1, except that an intermediate A-15-X, B-15-X, or C-15-X was used instead of the intermediate A-15-1 and a raw material A-16-X was used instead of the A-16-1.

TABLE 19
| A-15-X/B-15-X/C-15-X | A-16-X | A-17-X/B-17-X/ C-17-X | Yield (%) |
| --- | --- | --- | --- |
| 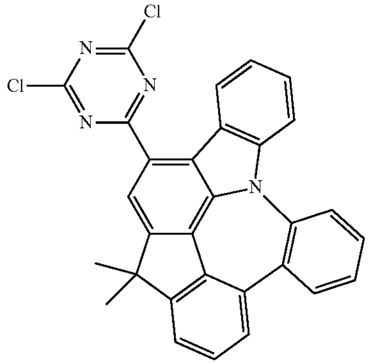 A-15-4 | 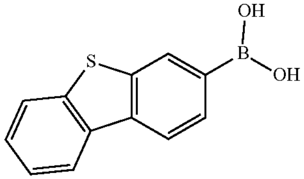 A-16-2 | 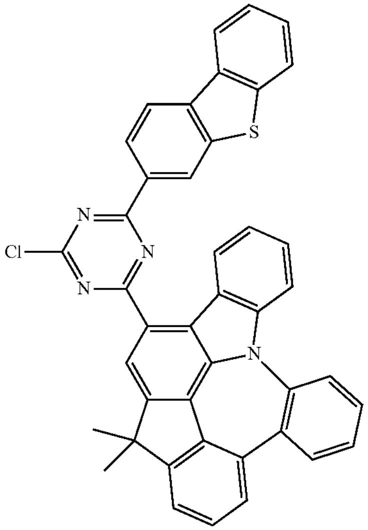 A-17-4 | 54.2 |

TABLE 19-continued
| A-15-X/B-15-X/C-15-X | A-16-X | A-17-X/B-17-X/ C-17-X | Yield (%) |
|---|---|---|---|
| 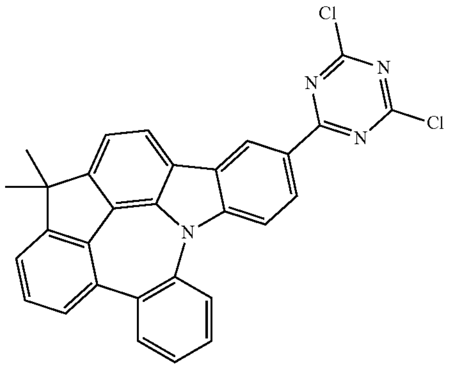 A-15-7 | 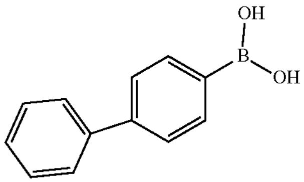 A-16-3 | 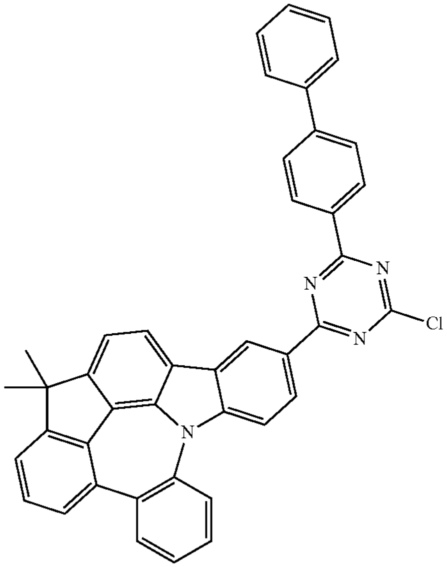 A-17-7 | 56.1 |
| 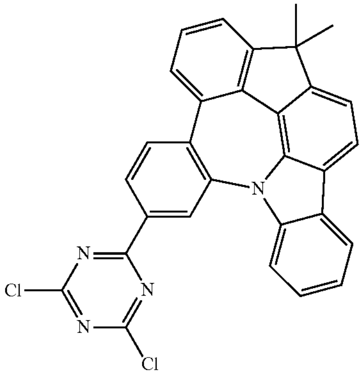 A-15-12 | 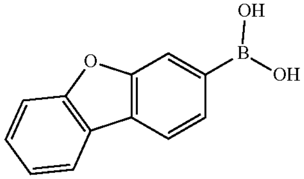 A-16-4 | 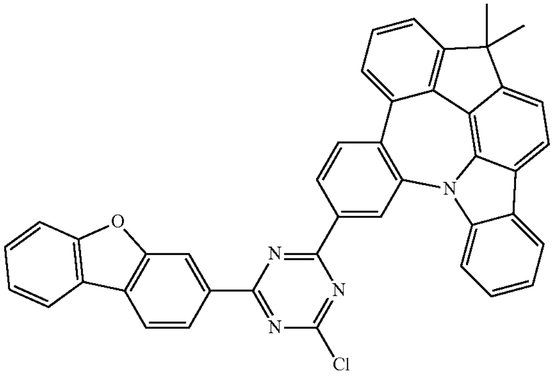 A-15-12 | 51.5 |

TABLE 19-continued
| A-15-X/B-15-X/C-15-X | A-16-X | A-17-X/B-17-X/ C-17-X | Yield (%) |
|---|---|---|---|
| 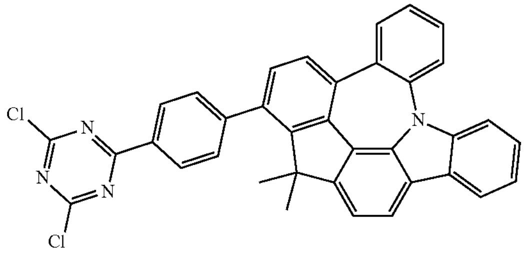 A-15-2 | 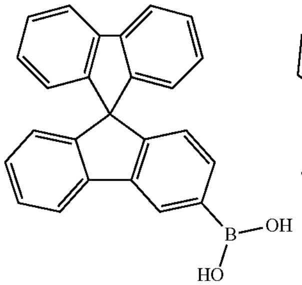 A-16-15 | 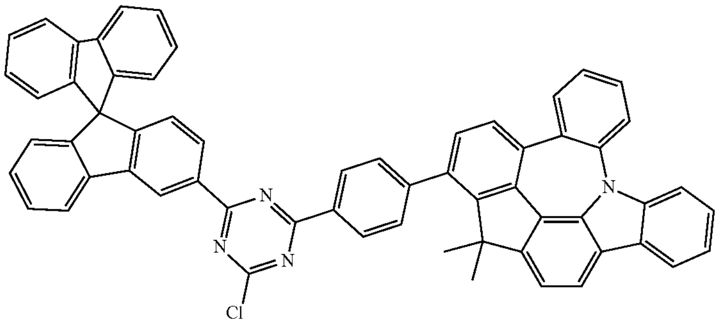 A-17-2 | 55.4 |
| 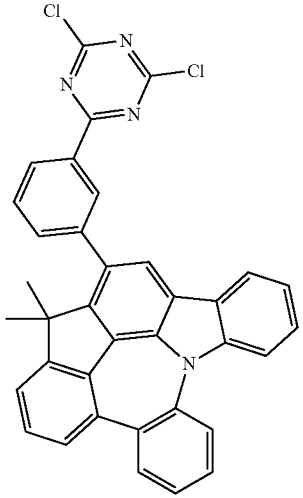 A-15-5 | 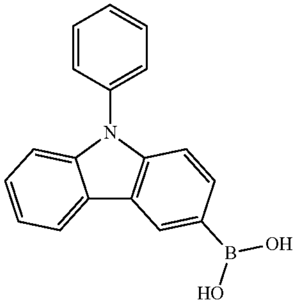 A-16-16 | 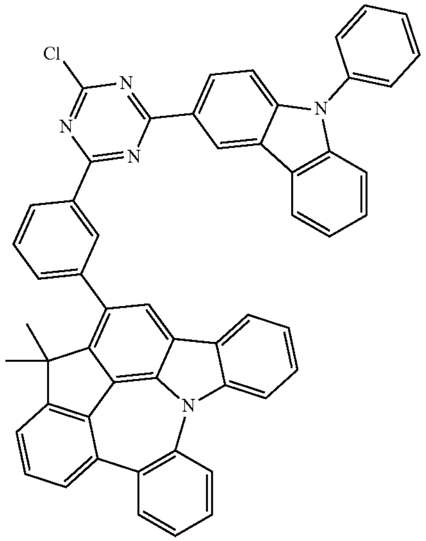 A-17-5 | 54.5 |

TABLE 19-continued
| A-15-X/B-15-X/C-15-X | A-16-X | A-17-X/B-17-X/ C-17-X | Yield (%) |
|---|---|---|---|
| 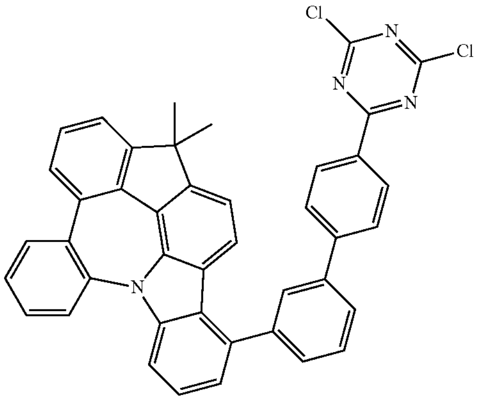 A-15-6 | 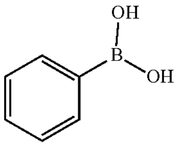 A-16-1 | 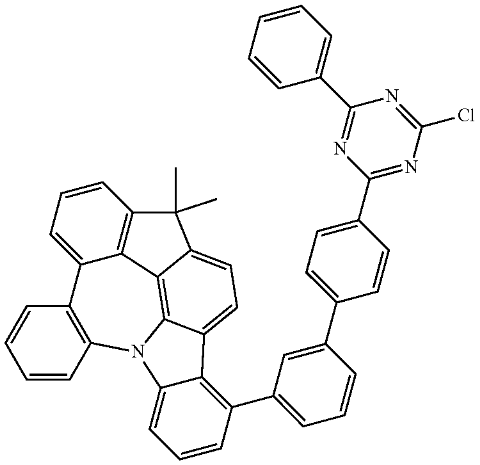 A-17-6 | 56.8 |

TABLE 19-continued
| A-15-X/B-15-X/C-15-X | A-16-X | A-17-X/B-17-X/ C-17-X | Yield (%) |
|---|---|---|---|
| 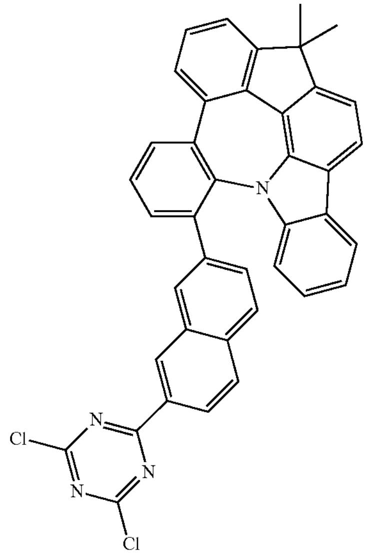 A-15-11 | 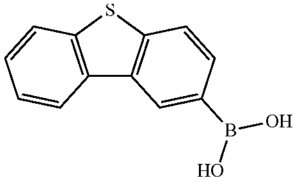 A-16-17 | 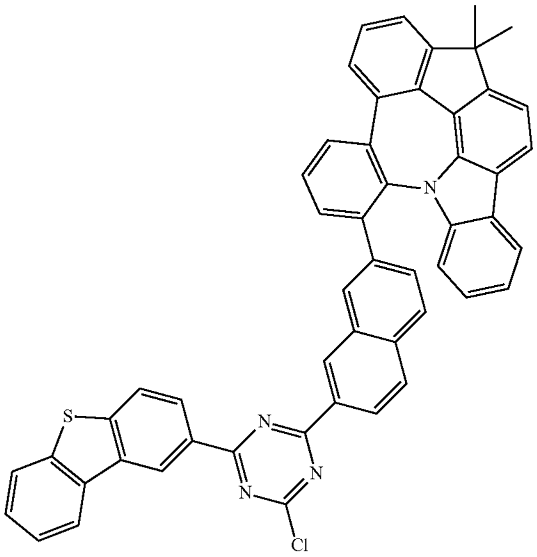 A-17-17 | 51.4 |
| 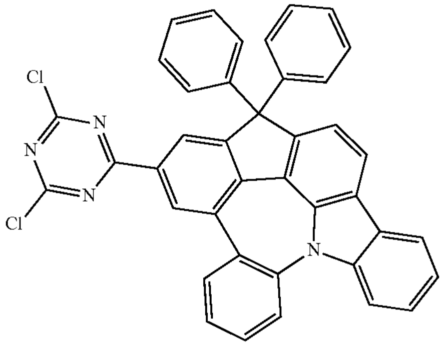 B-15-1 | 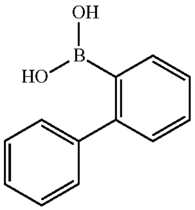 A-16-18 | 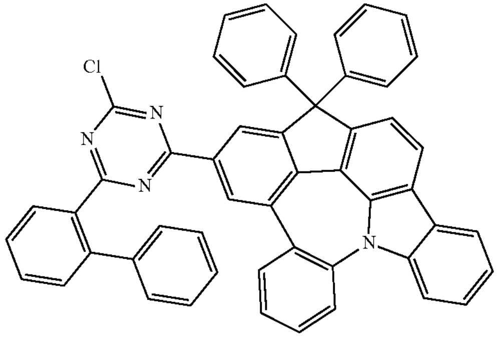 B-17-1 | 51.2 |

TABLE 19-continued
| A-15-X/B-15-X/C-15-X | A-16-X | A-17-X/B-17-X/ C-17-X | Yield (%) |
|---|---|---|---|
| 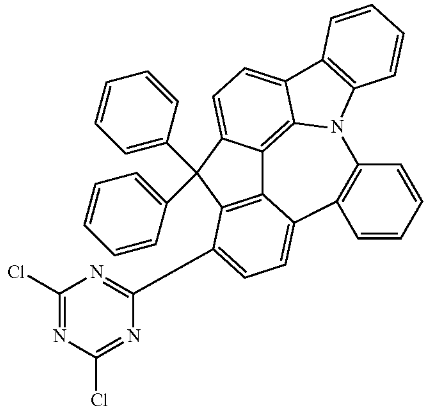 B-15-2 | 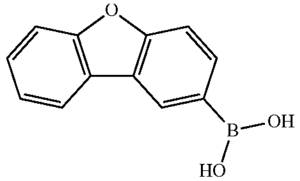 A-16-19 | 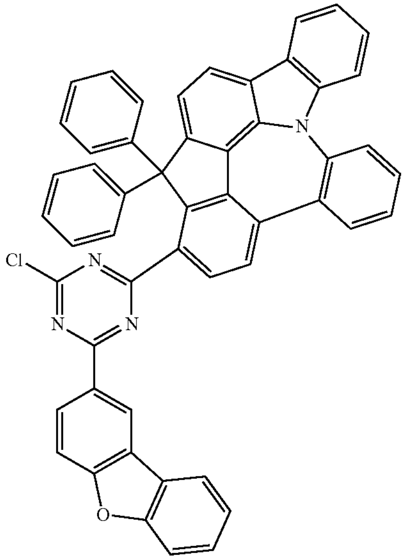 B-17-2 | 48.3 |

TABLE 19-continued
| A-15-X/B-15-X/C-15-X | A-16-X | A-17-X/B-17-X/ C-17-X | Yield (%) |
|---|---|---|---|
| 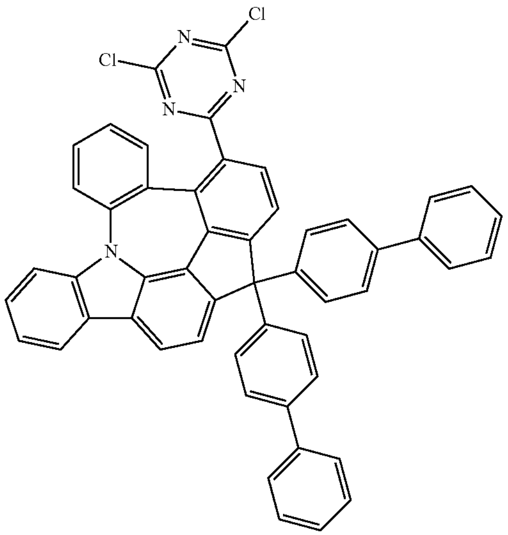 B-15-3 | 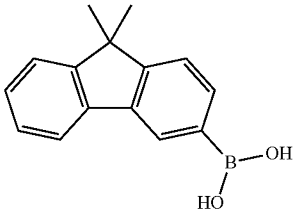 A-16-20 | 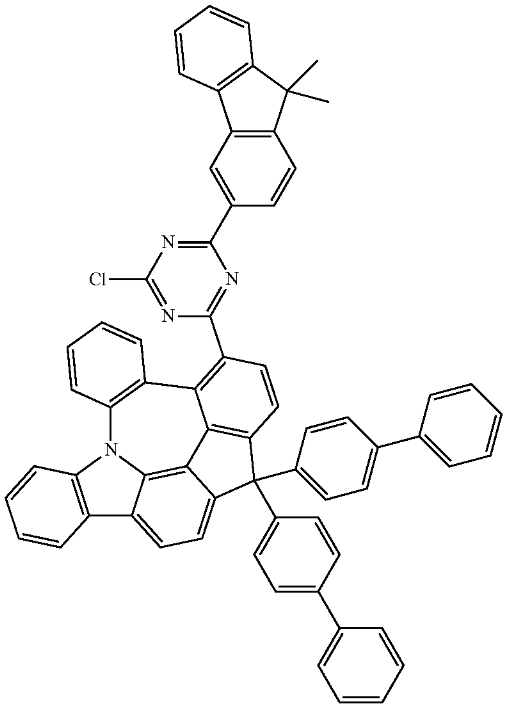 B-17-3 | 50.6 |

TABLE 19-continued
| A-15-X/B-15-X/C-15-X | A-16-X | A-17-X/B-17-X/ C-17-X | Yield (%) |
| --- | --- | --- | --- |
| 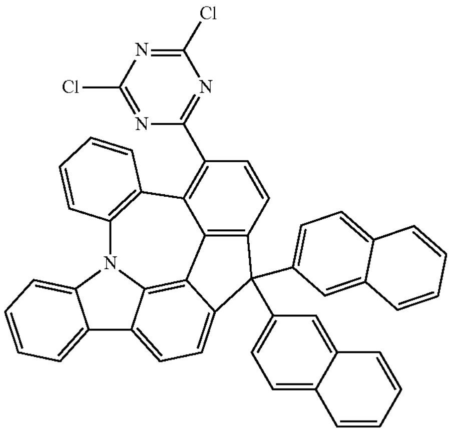 B-15-6 | 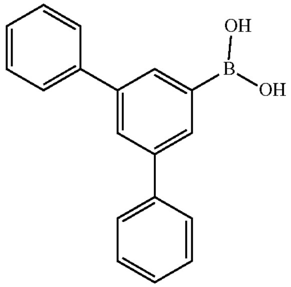 A-16-6 | 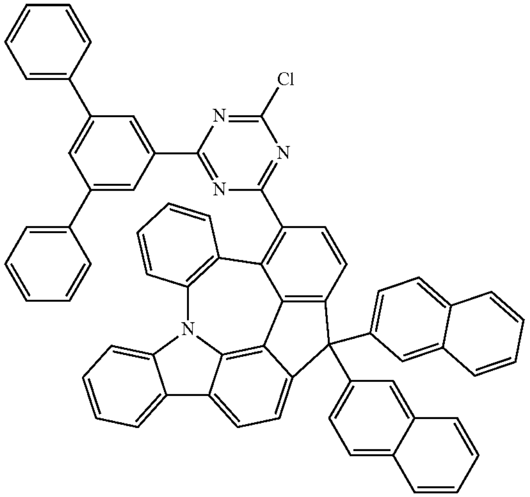 B-17-6 | 48.9 |
| 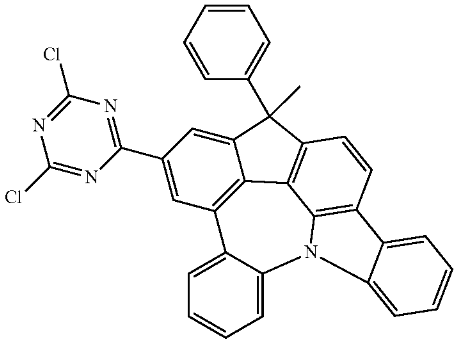 B-15-8 | 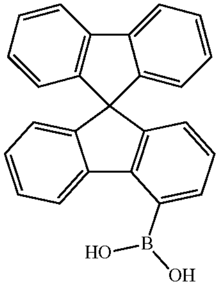 A-16-22 | 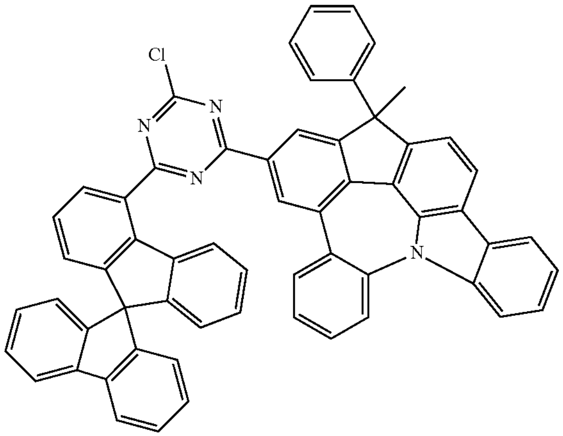 B-17-8 | 52.3 |

TABLE 19-continued
| A-15-X/B-15-X/C-15-X | A-16-X | A-17-X/B-17-X/ C-17-X | Yield (%) |
|---|---|---|---|
| 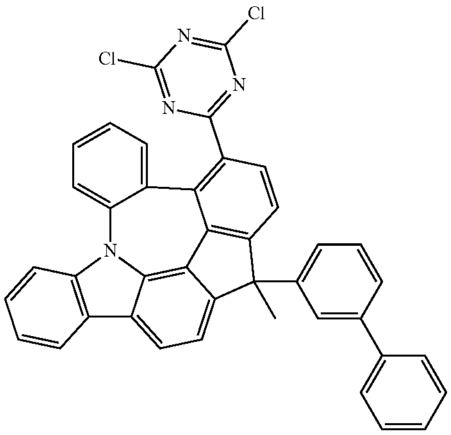 B-15-10 | 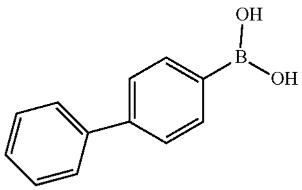 A-16-3 | 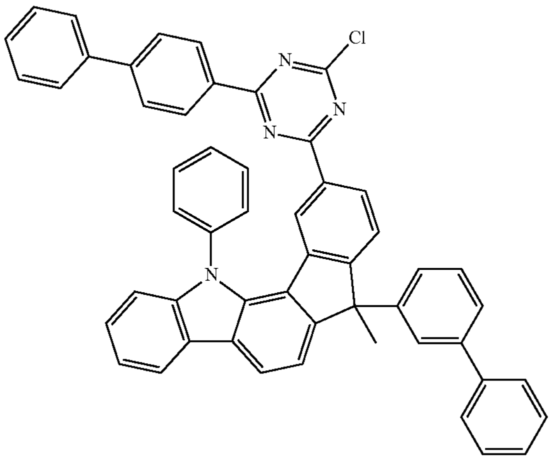 B-17-10 | 50.8 |
| 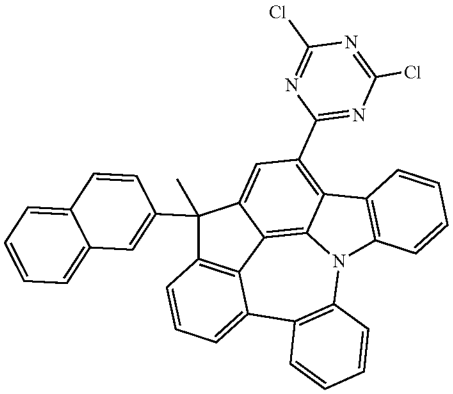 B-15-11 | 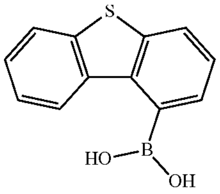 A-16-24 | 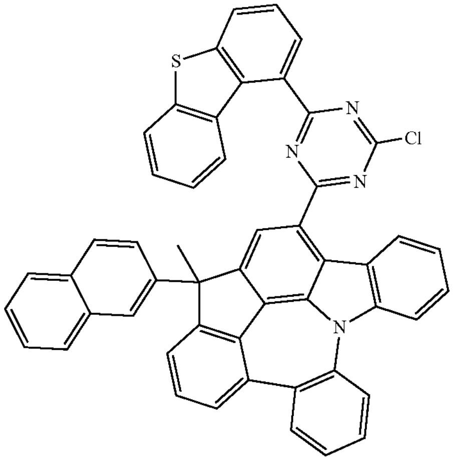 B-17-11 | 53.1 |

TABLE 19-continued
| A-15-X/B-15-X/C-15-X | A-16-X | A-17-X/B-17-X/ C-17-X | Yield (%) |
|---|---|---|---|
| 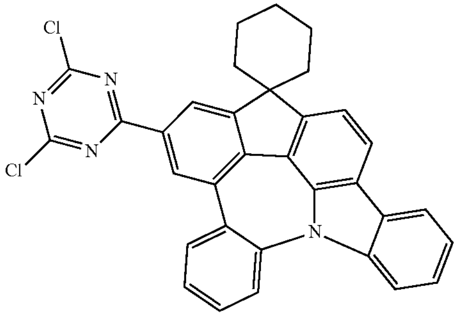 B-15-13 | 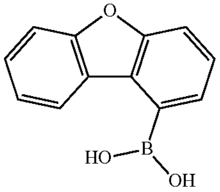 A-16-25 | 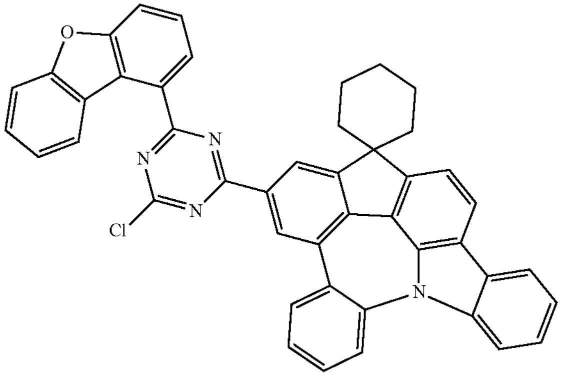 B-17-13 | 51.2 |
| 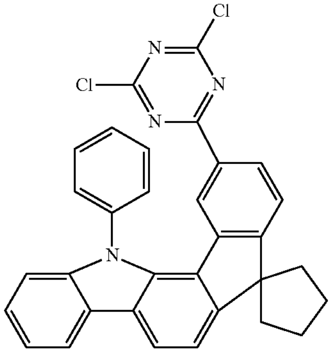 B-15-15 | 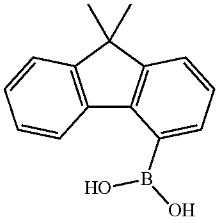 A-16-26 | 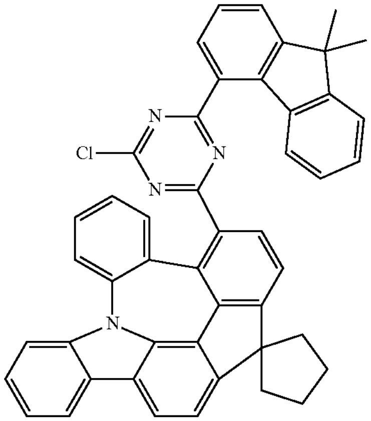 B-17-15 | 53.4 |

TABLE 19-continued
| A-15-X/B-15-X/C-15-X | A-16-X | A-17-X/B-17-X/ C-17-X | Yield (%) |
|---|---|---|---|
| 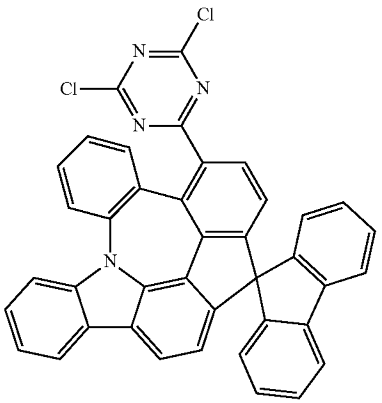 B-15-20 | 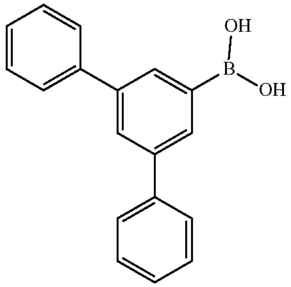 A-16-6 | 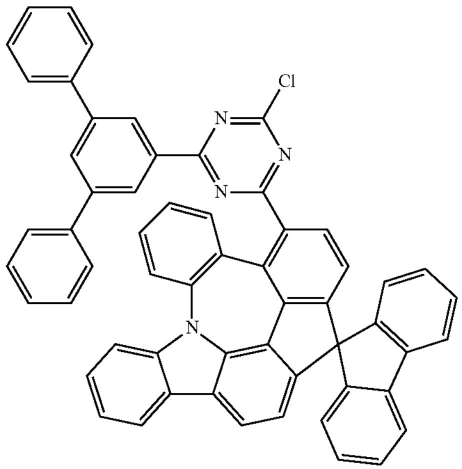 B-17-20 | 51.5 |
| 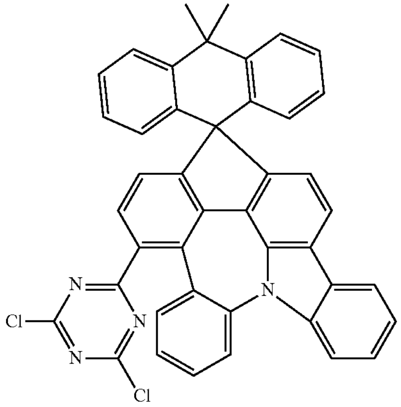 C-15-1 | 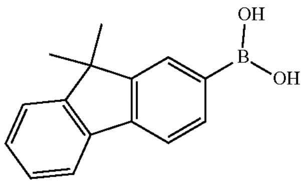 A-16-5 | 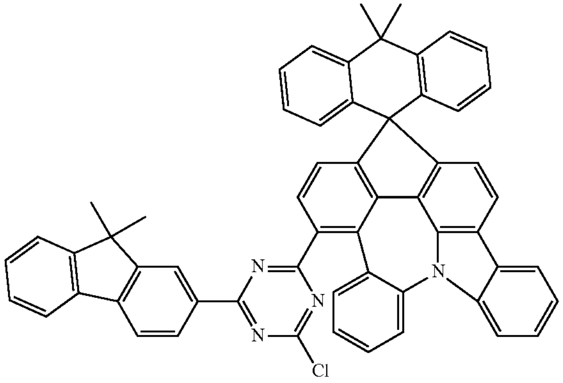 C-17-1 | 48.2 |

TABLE 19-continued
| A-15-X/B-15-X/C-15-X | A-16-X | A-17-X/B-17-X/ C-17-X | Yield (%) |
|---|---|---|---|
| 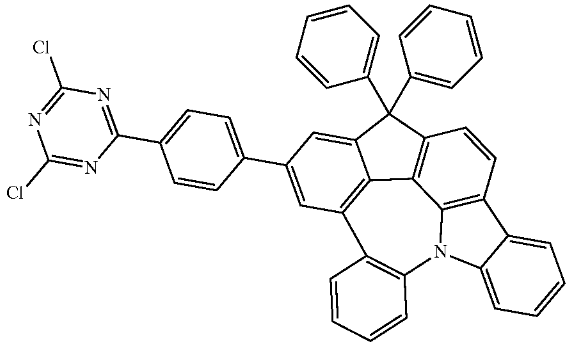 B-15-1 | 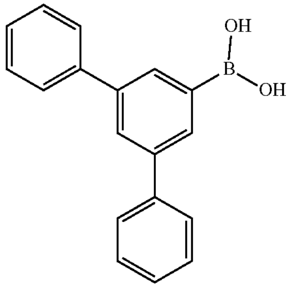 A-16-6 | 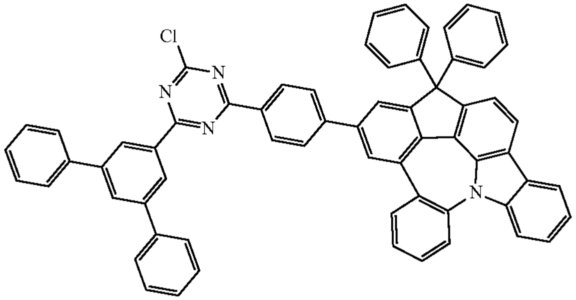 B-17-21 | 50.9 |
| 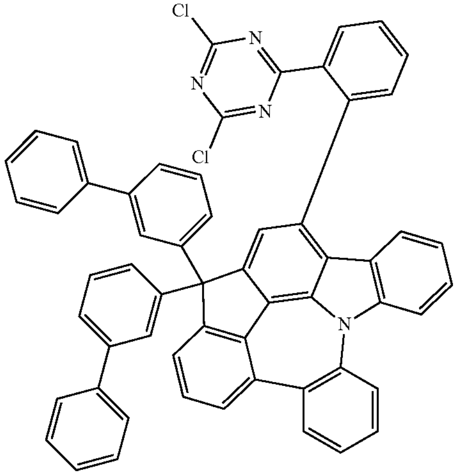 B-15-4 | 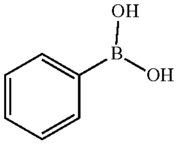 A-16-1 | 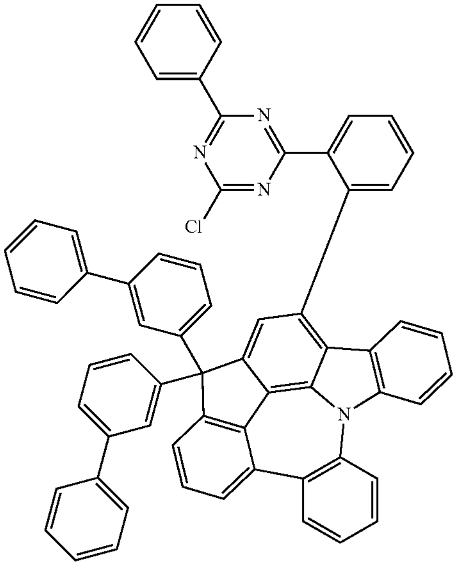 B-17-22 | 51.6 |

TABLE 19-continued
| A-15-X/B-15-X/C-15-X | A-16-X | A-17-X/B-17-X/ C-17-X | Yield (%) |
|---|---|---|---|
| 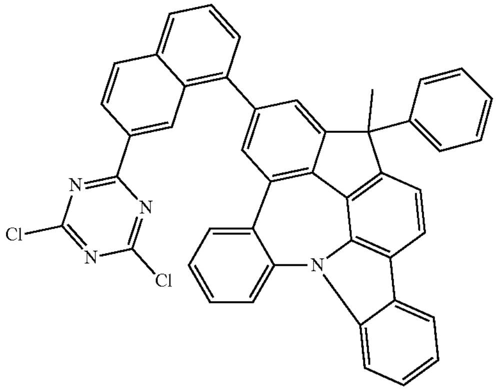 B-15-8 | 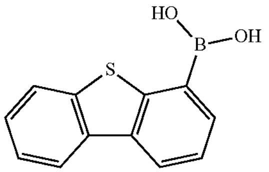 A-16-10 | 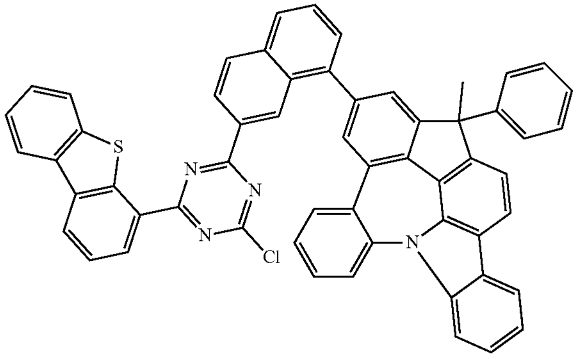 B-17-23 | 55.8 |

TABLE 19-continued
| A-15-X/B-15-X/C-15-X | A-16-X | A-17-X/B-17-X/ C-17-X | Yield (%) |
| --- | --- | --- | --- |
| 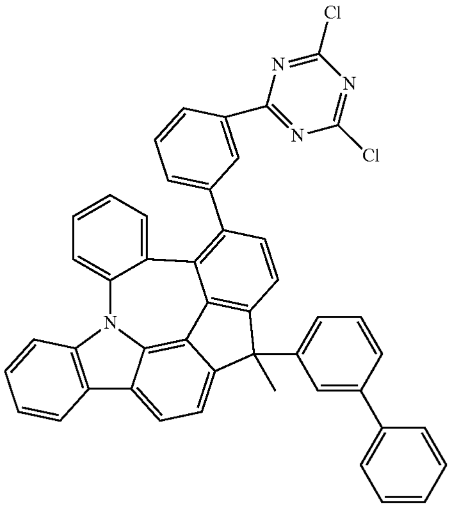 B-15-10 | 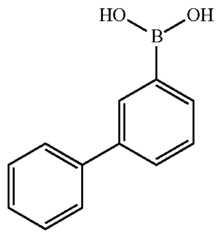 A-16-11 | 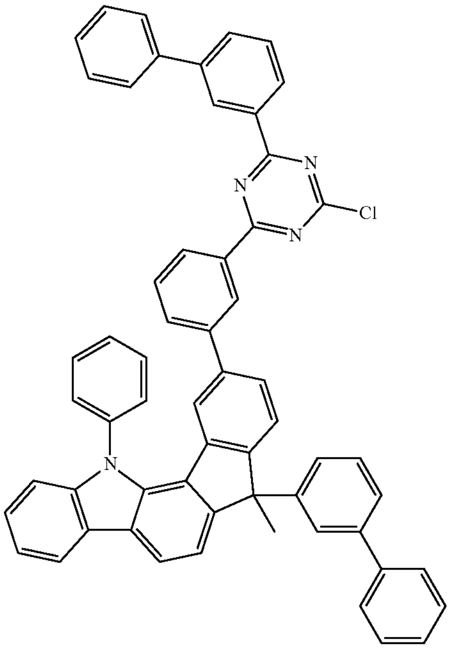 B-17-24 | 54.6 |

TABLE 19-continued
| A-15-X/B-15-X/C-15-X | A-16-X | A-17-X/B-17-X/ C-17-X | Yield (%) |
|---|---|---|---|
| 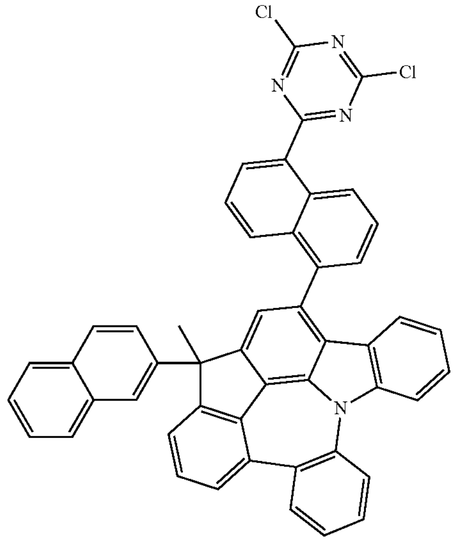 B-15-11 | 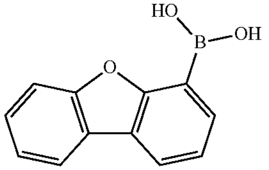 A-16-12 | 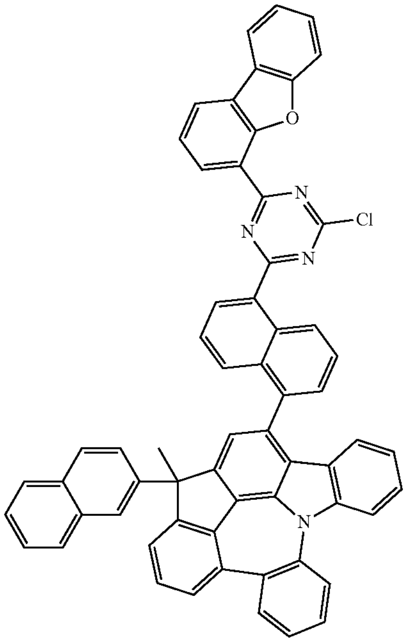 B-17-25 | 51.2 |
| 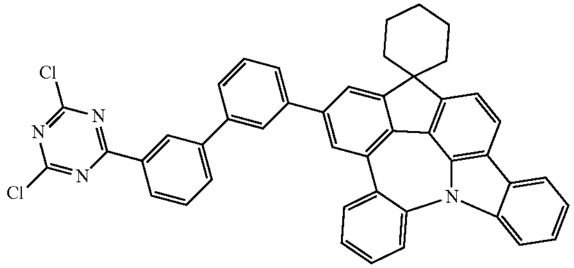 B-15-13 | 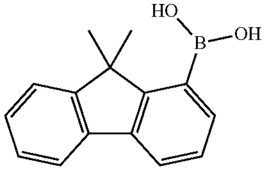 A-16-13 | 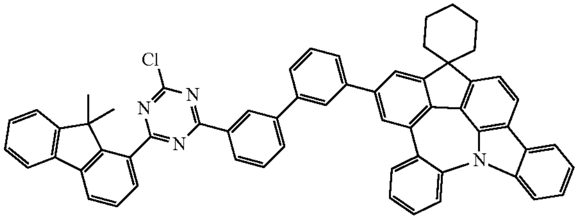 B-17-26 | 50.6 |

TABLE 19-continued
| A-15-X/B-15-X/C-15-X | A-16-X | A-17-X/B-17-X/ C-17-X | Yield (%) |
|---|---|---|---|
| 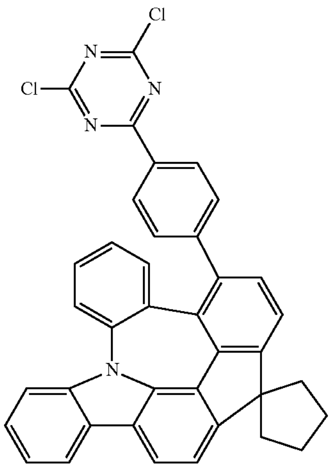 B-15-15 | 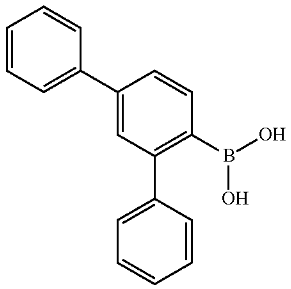 A-16-14 | 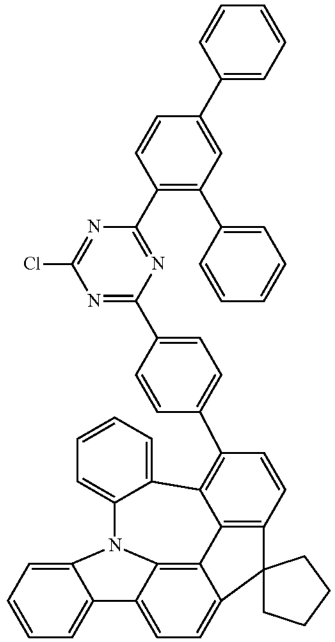 B-17-27 | 50.9 |

TABLE 19-continued
| A-15-X/B-15-X/C-15-X | A-16-X | A-17-X/B-17-X/ C-17-X | Yield (%) |
| --- | --- | --- | --- |
| 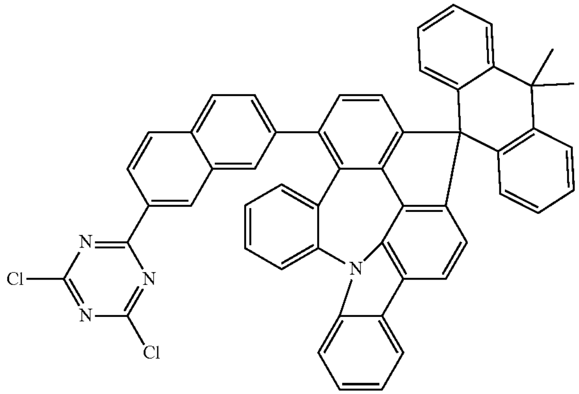 C-15-2 | 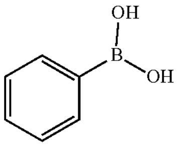 A-16-1 | 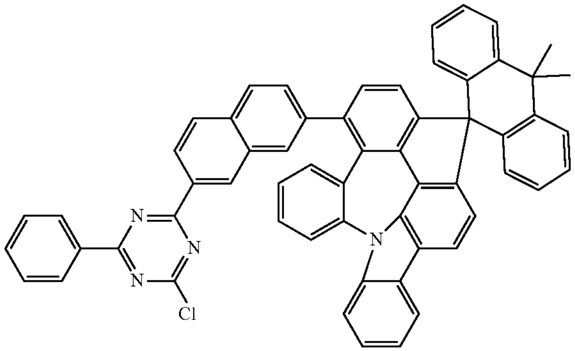 C-17-2 | 54.7 |

Compound Synthesis

Preparation Example 1: Compound 1

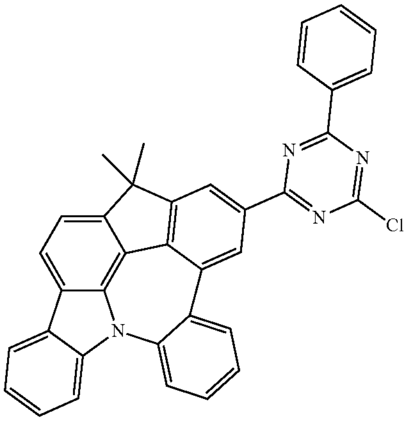

A-17-1

+

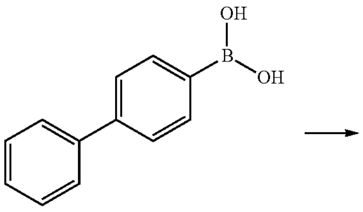

A-16-3

-continued

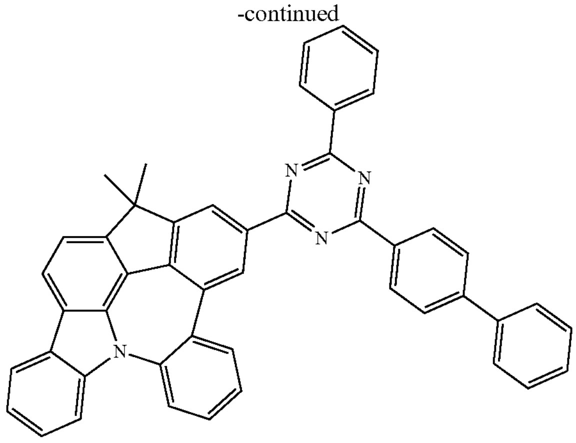

1

Nitrogen was introduced into a 250 mL three-necked flask, the intermediate A-17-1 (6.58 g, 12.03 mmol), a raw material A-16-3 (2.38 g, 12.03 mmol), 42 mL of THF, and 14 mL of $H_2O$ were added, and a resulting mixture was heated to reflux and stirred; tetrakis(triphenylphosphine) palladium (0.14 g, 0.12 mmol) and potassium carbonate (2.49 g, 18.05 mmol) were added, a resulting mixture was heated to reflux and stirred for 10 h. A sample was taken for TLC to confirm that the reaction was complete; a resulting reaction mixture was naturally cooled to room temperature, 80 mL of dilute hydrochloric acid was added for quenching, and a resulting solution was washed with water until neutral; DCM was added for extraction, a separated organic phase was concentrated in vacuum to obtain a residue, and the residue was purified by silica gel column chromatography to obtain a crude product; and the crude product was purified by recrystallization with DCM and n-heptane, and a product was filtered out and dried to obtain the compound 1 (5.36 g, yield: 67%, MS: m/z=665.3 $[M+H]^+$).

The compounds X listed in Table 20 were each synthesized with reference to the synthesis method of the compound 1, except that an intermediate A-17-X, B-17-X, or C-17-X was used instead of the intermediate A-17-1 and a raw material A-16-X was used instead of the A-16-3.

TABLE 20
| Preparation Example | A-17-X/B-17-X/C-17-X | A-16-X | Compound X | Yield (%) | MS $[M + H]^+$ |
|---|---|---|---|---|---|
| 2 | 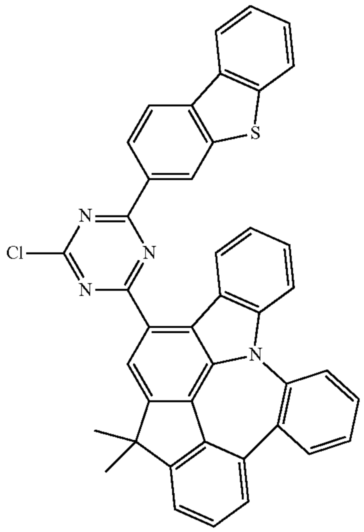 A-17-4 | 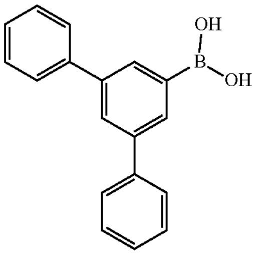 A-16-6 | 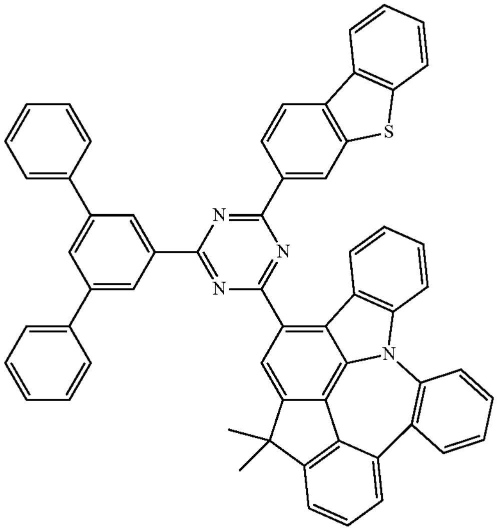 43 | 66.2 | 847.3 |

TABLE 20-continued
| Preparation Example | A-17-X/B-17-X/C-17-X | A-16-X | Compound X | Yield (%) | MS $[M + H]^+$ |
|---|---|---|---|---|---|
| 3 | 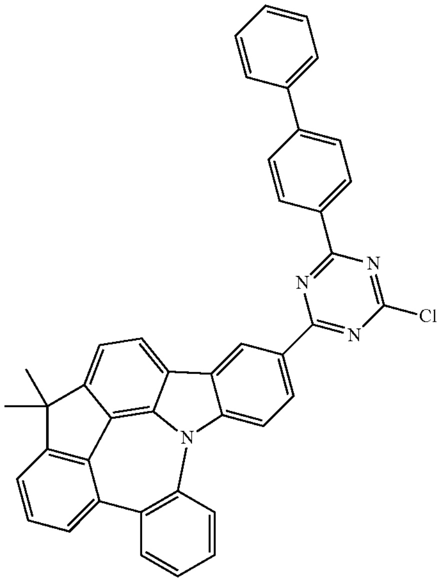 A-17-7 | 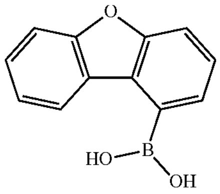 A-16-25 | 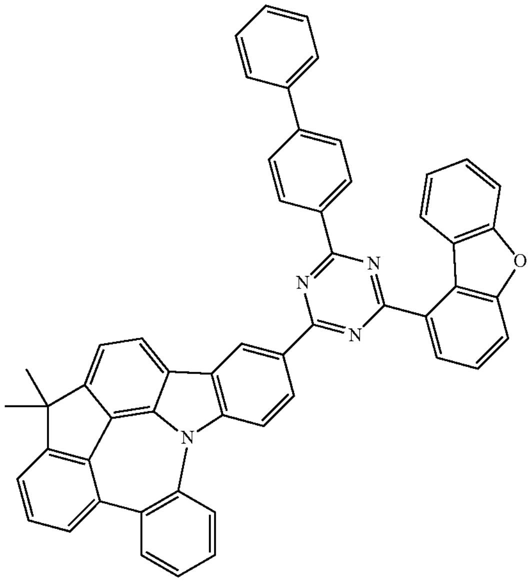 33 | 61.5 | 755.3 |

TABLE 20-continued
| Preparation Example | A-17-X/B-17-X/C-17-X | A-16-X | Compound X | Yield (%) | MS $[M + H]^+$ |
|---|---|---|---|---|---|
| 4 | 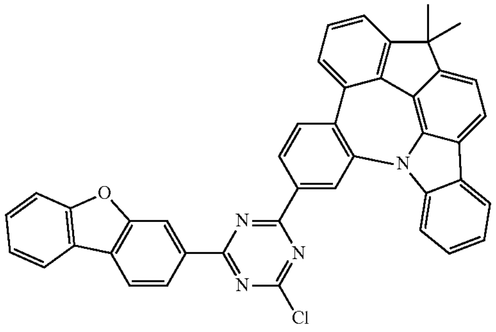 A-17-12 | 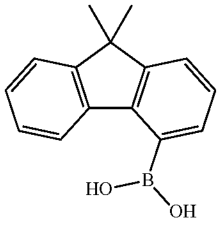 A-16-26 | 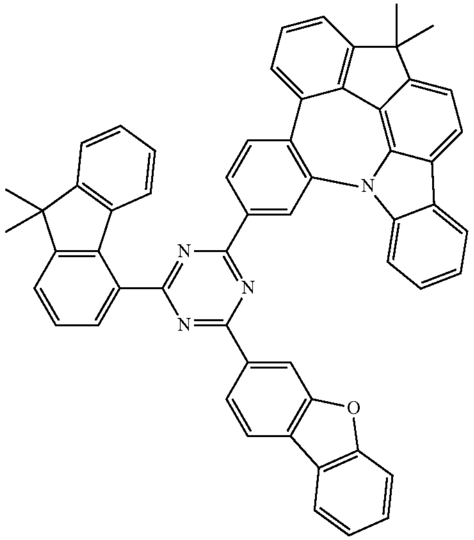 50 | 60.4 | 795.3 |
| 5 | 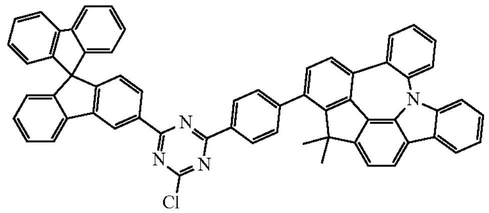 A-17-2 | 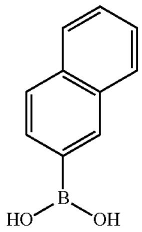 A-16-28 | 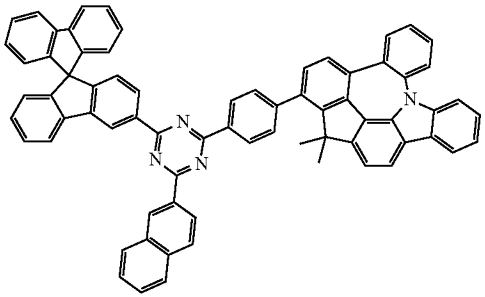 85 | 67.1 | 953.4 |

TABLE 20-continued
| Preparation Example | A-17-X/B-17-X/C-17-X | A-16-X | Compound X | Yield (%) | MS $[M + H]^+$ |
|---|---|---|---|---|---|
| 6 | 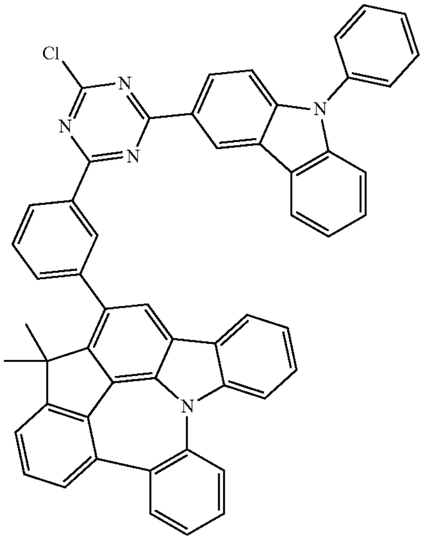 A-17-5 | 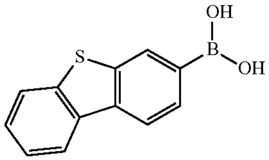 A-16-2 | 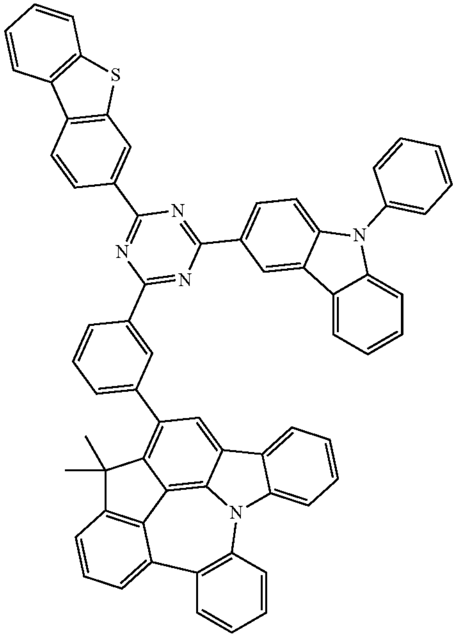 80 | 68.0 | 936.3 |

TABLE 20-continued
| Preparation Example | A-17-X/B-17-X/C-17-X | A-16-X | Compound X | Yield (%) | MS [M + H]+ |
|---|---|---|---|---|---|
| 7 | 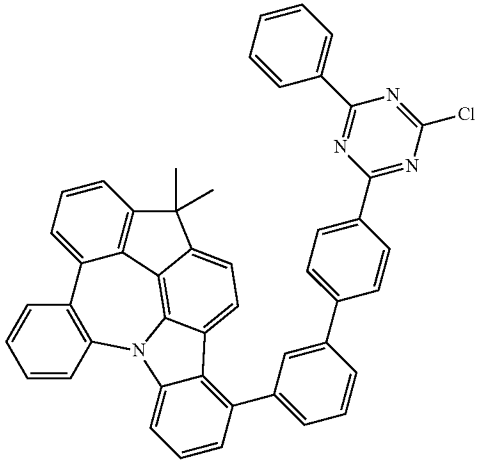 A-17-6 | 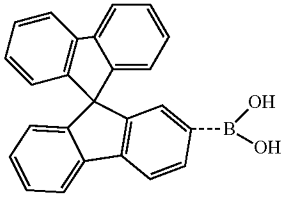 A-16-8 | 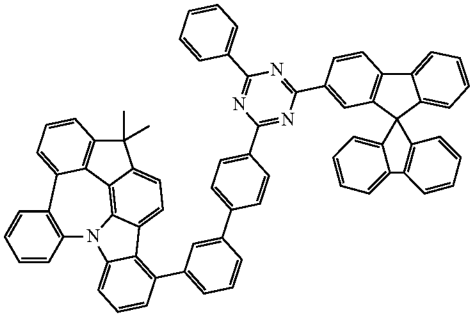 69 | 65.3 | 979.4 |

TABLE 20-continued
| Preparation Example | A-17-X/B-17-X/C-17-X | A-16-X | Compound X | Yield (%) | MS $[M + H]^+$ |
|---|---|---|---|---|---|
| 8 | 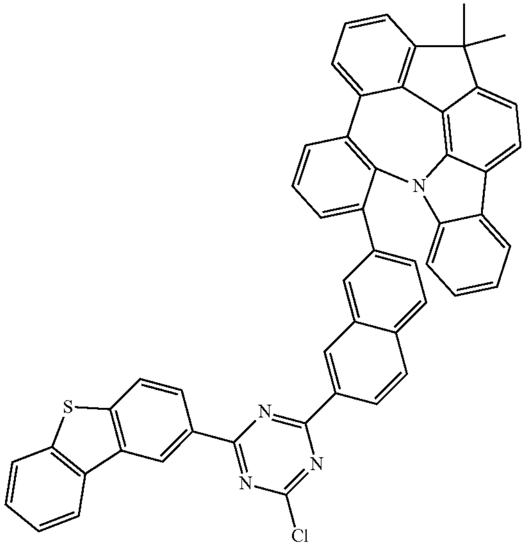 A-17-17 | 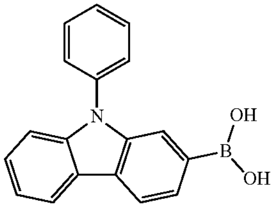 A-16-9 | 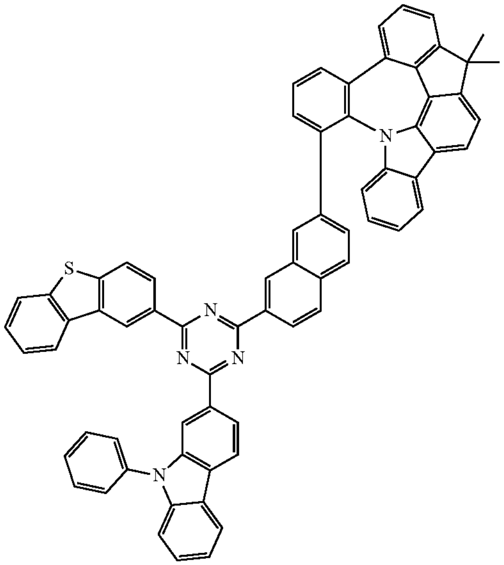 79 | 67.4 | 986.3 |

TABLE 20-continued
| Preparation Example | A-17-X/B-17-X/C-17-X | A-16-X | Compound X | Yield (%) | MS [M + H]$^+$ |
|---|---|---|---|---|---|
| 9 | 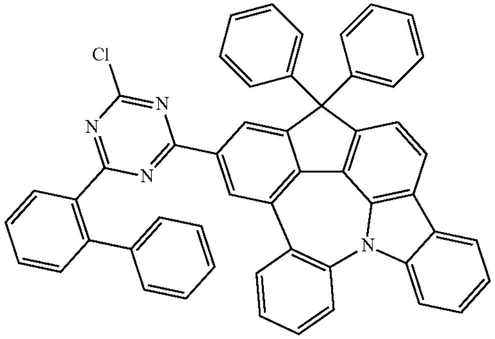 B-17-1 | 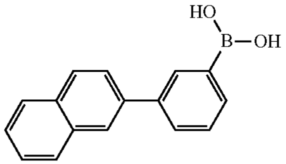 A-16-30 | 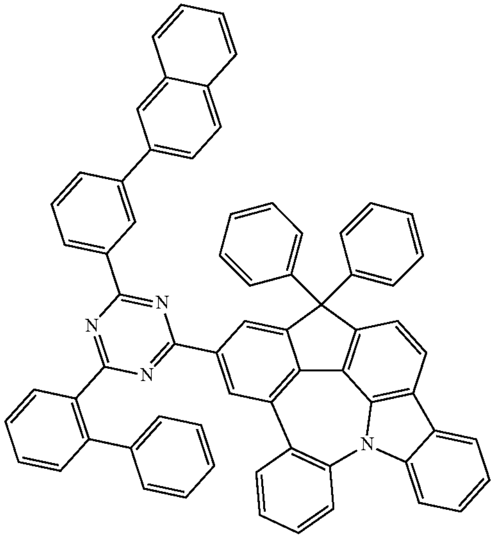 100 | 66.2 | 915.3 |

TABLE 20-continued
| Preparation Example | A-17-X/B-17-X/C-17-X | A-16-X | Compound X | Yield (%) | MS $[M + H]^+$ |
| --- | --- | --- | --- | --- | --- |
| 10 | 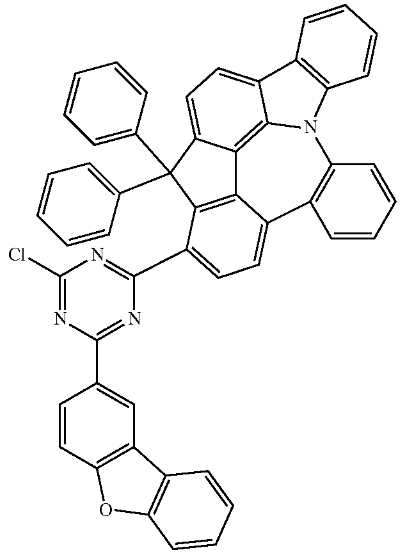 B-17-2 | 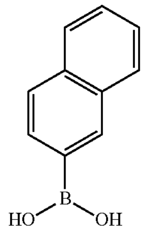 A-16-28 | 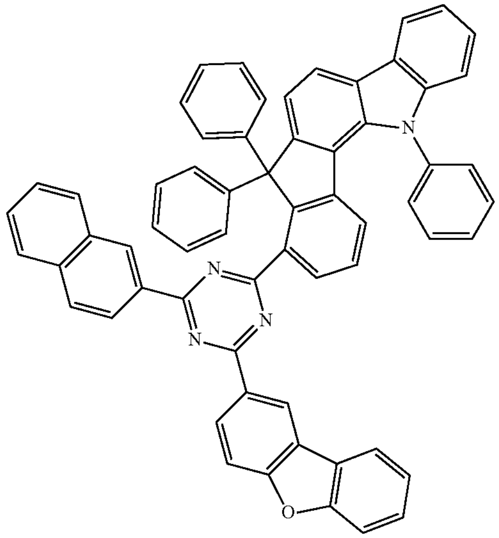 122 | 60.3 | 853.3 |

TABLE 20-continued
| Preparation Example | A-17-X/B-17-X/C-17-X | A-16-X | Compound X | Yield (%) | MS $[M + H]^+$ |
|---|---|---|---|---|---|
| 11 | 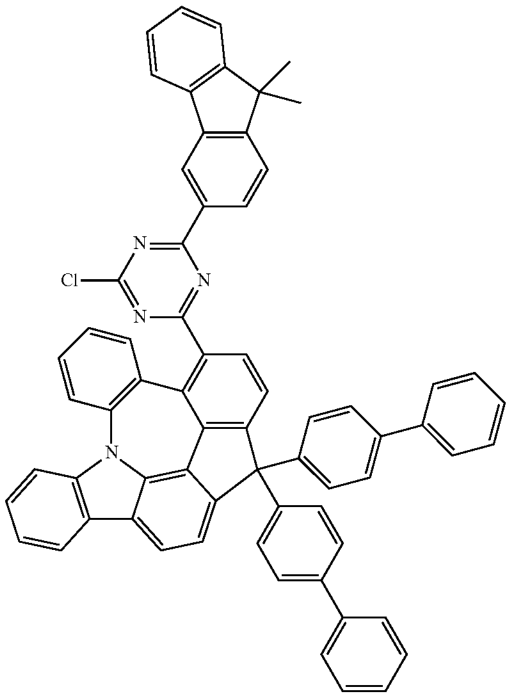 B-17-3 | 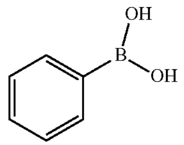 A-16-1 | 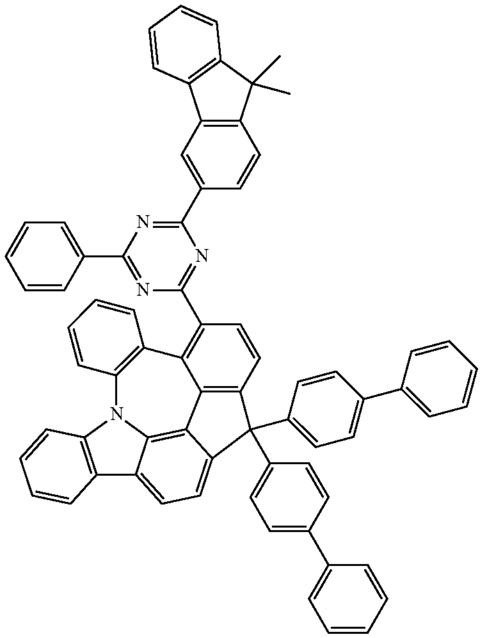 140 | 65.3 | 981.4 |

TABLE 20-continued
| Preparation Example | A-17-X/B-17-X/C-17-X | A-16-X | Compound X | Yield (%) | MS [M + H]+ |
|---|---|---|---|---|---|
| 12 | 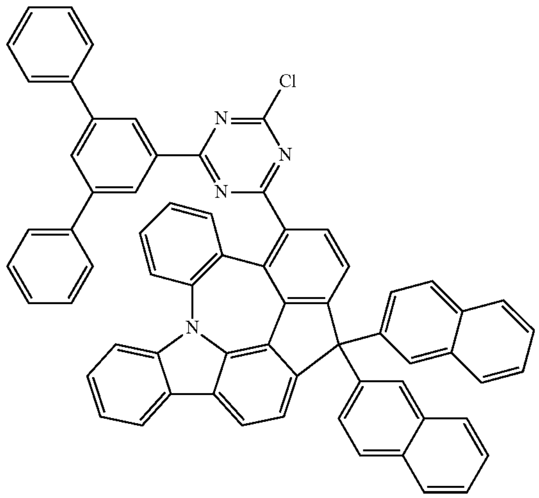 B-17-6 | 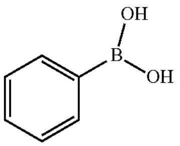 A-16-1 | 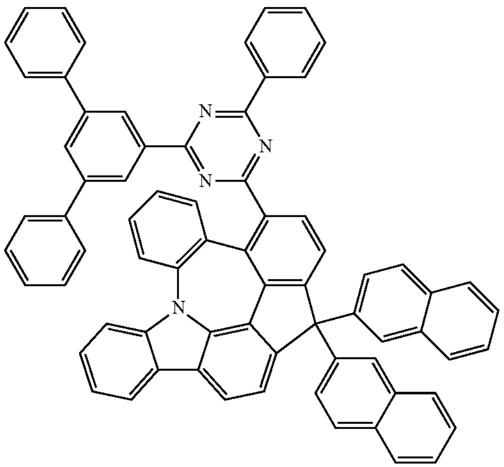 107 | 66.4 | 965.3 |
| 13 | 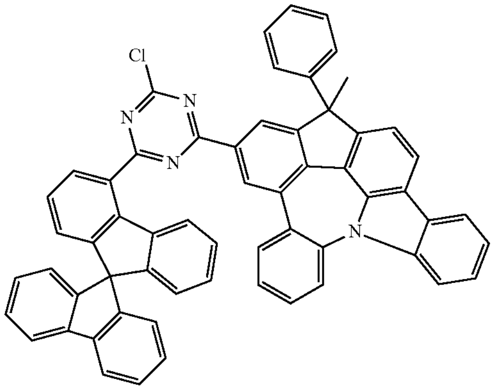 B-17-8 | 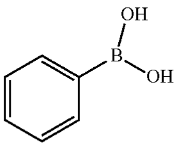 A-16-1 | 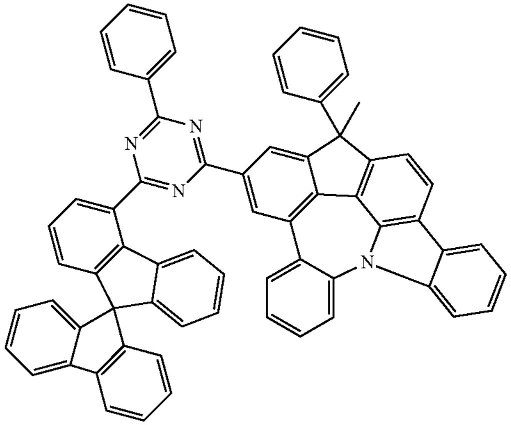 154 | 65.8 | 889.3 |

TABLE 20-continued
| Preparation Example | A-17-X/B-17-X/C-17-X | A-16-X | Compound X | Yield (%) | MS [M + H]$^+$ |
|---|---|---|---|---|---|
| 14 | 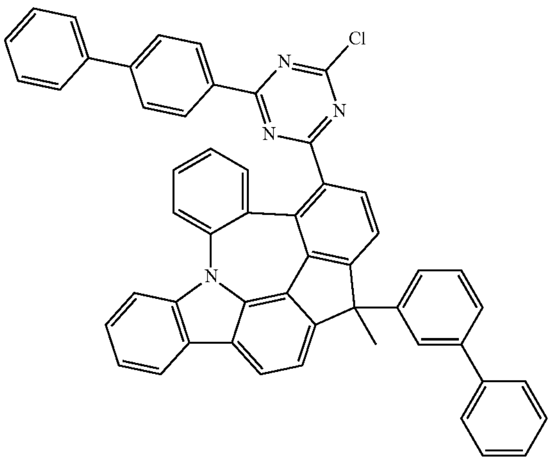 B-17-10 | 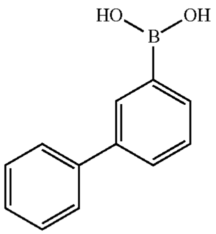 A-16-11 | 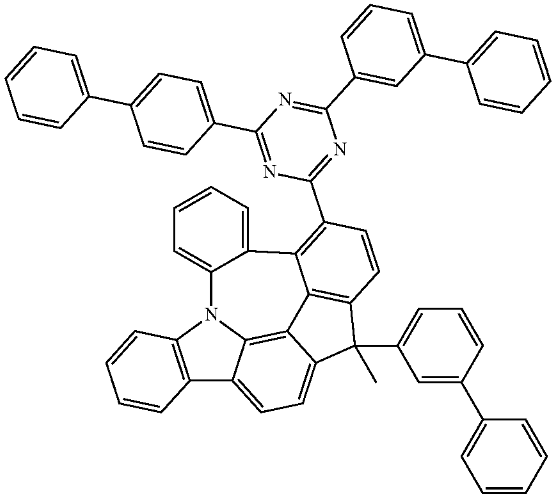 97 | 63.4 | 879.3 |

TABLE 20-continued
| Preparation Example | A-17-X/B-17-X/C-17-X | A-16-X | Compound X | Yield (%) | MS [M + H]+ |
|---|---|---|---|---|---|
| 15 | 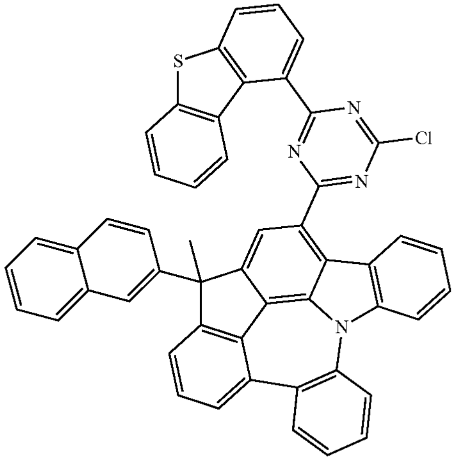 B-17-11 | 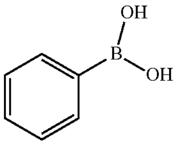 A-16-1 | 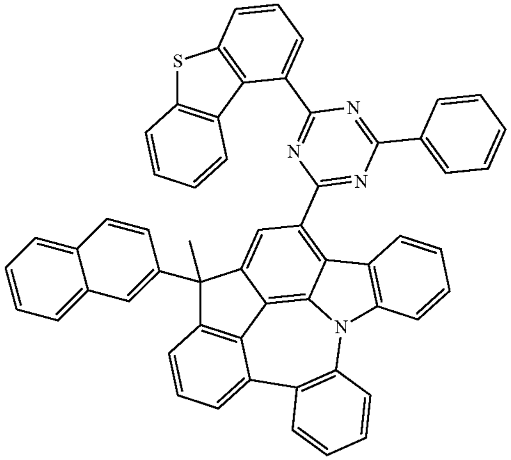 129 | 64.7 | 807.2 |
| 16 | 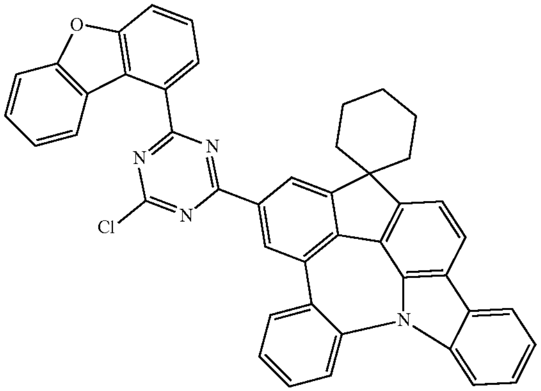 B-17-13 | 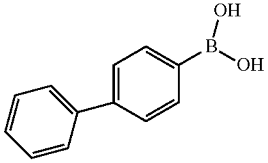 A-16-3 | 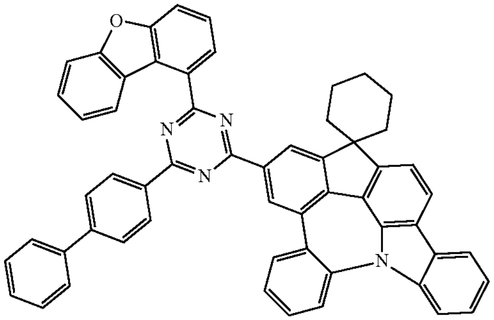 211 | 63.5 | 795.3 |

TABLE 20-continued
| Preparation Example | A-17-X/B-17-X/C-17-X | A-16-X | Compound X | Yield (%) | MS [M + H]$^+$ |
|---|---|---|---|---|---|
| 17 | 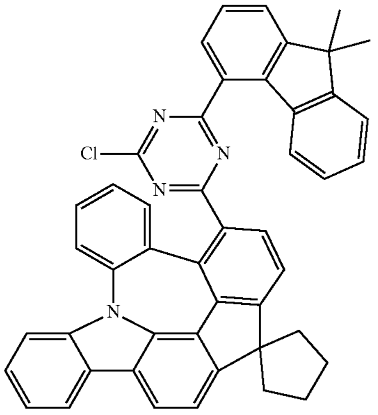 B-17-15 | 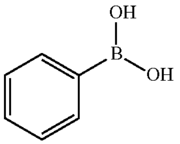 A-16-1 | 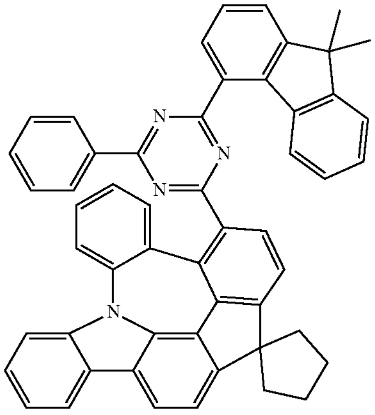 225 | 67.1 | 731.3 |
| 18 | 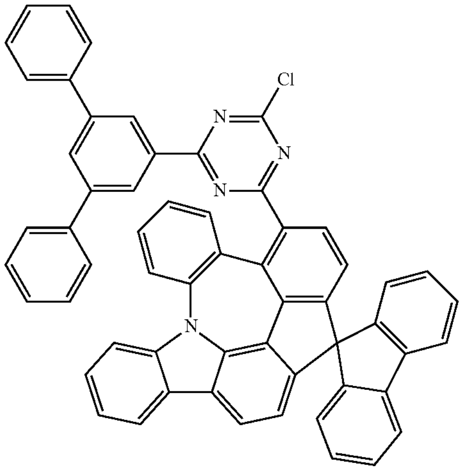 B-17-20 | 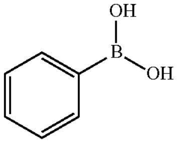 A-16-1 | 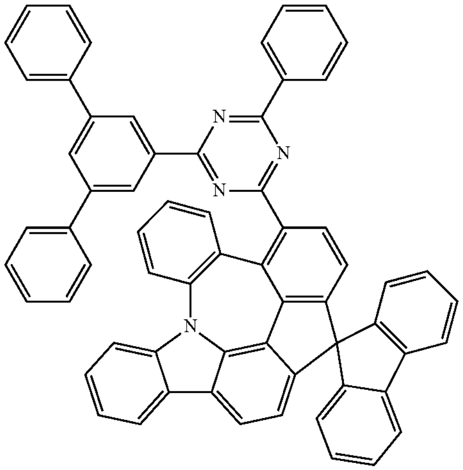 195 | 65.2 | 863.3 |

TABLE 20-continued
| Preparation Example | A-17-X/B-17-X/C-17-X | A-16-X | Compound X | Yield (%) | MS [M + H]$^+$ |
|---|---|---|---|---|---|
| 19 | 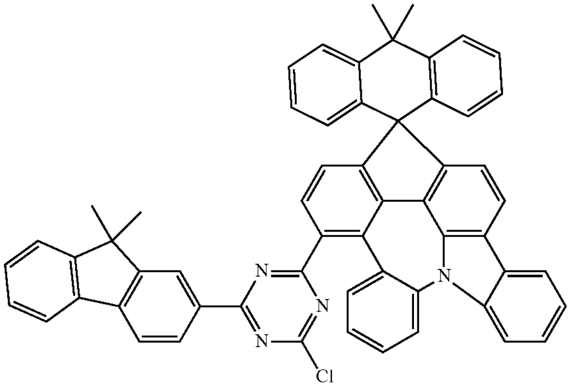 C-17-1 | 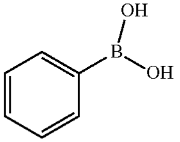 A-16-1 | 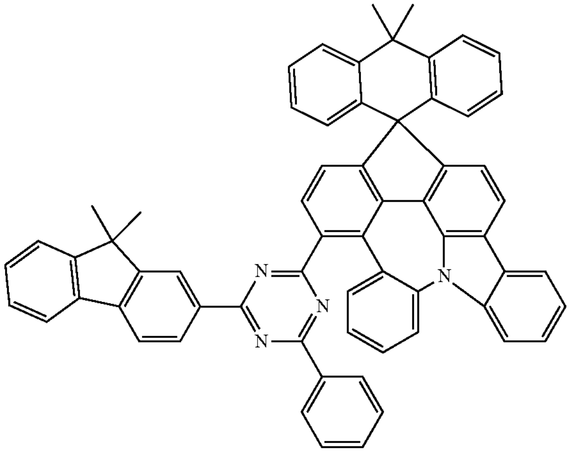 228 | 63.4 | 869.4 |
| 20 | 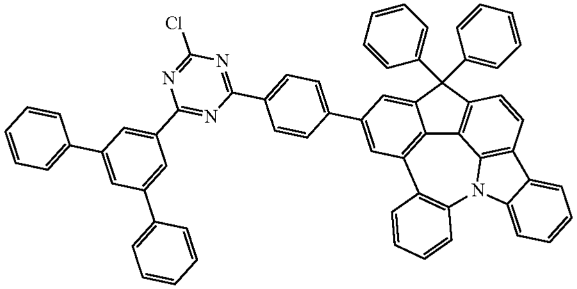 B-17-21 | 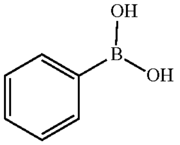 A-16-1 | 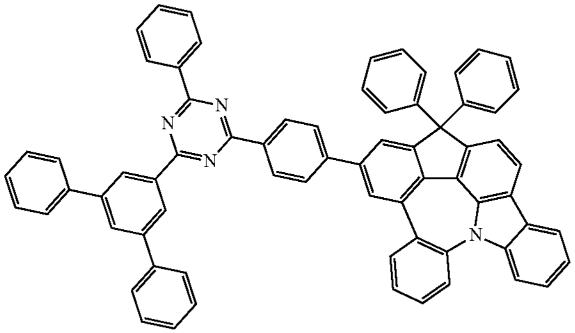 111 | 65.2 | 941.3 |

TABLE 20-continued
| Preparation Example | A-17-X/B-17-X/C-17-X | A-16-X | Compound X | Yield (%) | MS [M + H]$^+$ |
|---|---|---|---|---|---|
| 21 | 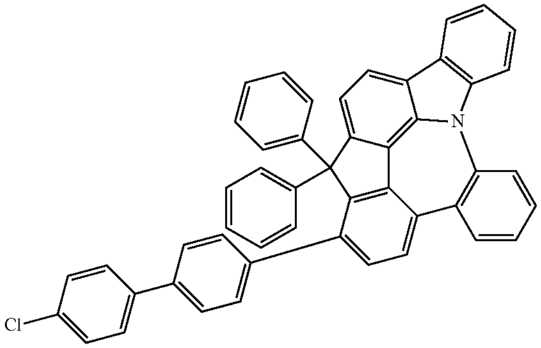 B-10-2 | 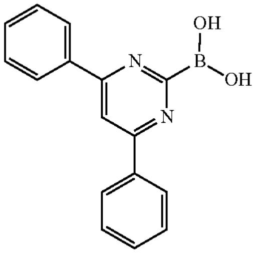 A-16-31 | 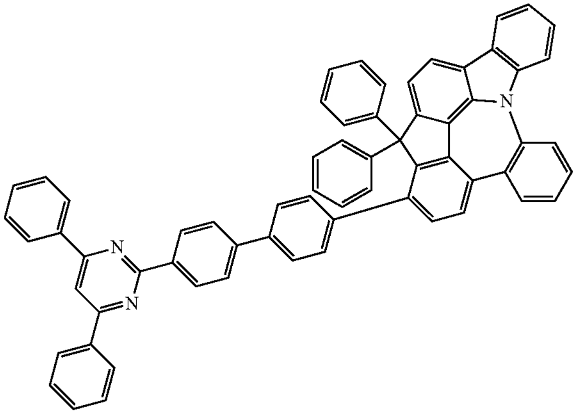 117 | 62.0 | 864.3 |
| 22 | 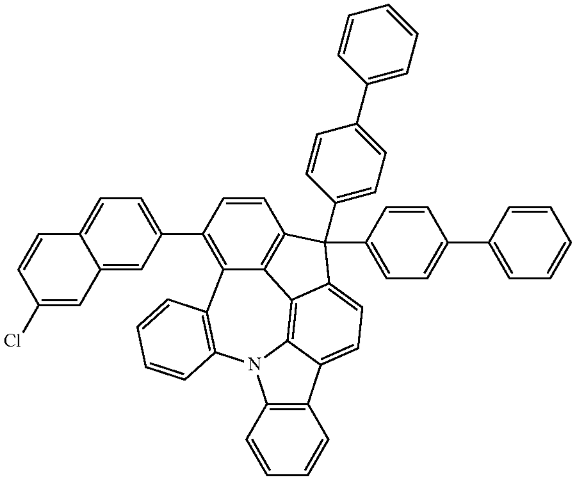 B-10-3 | 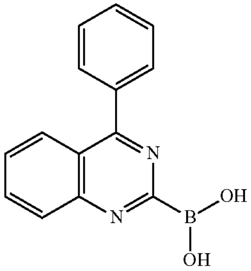 A-16-32 | 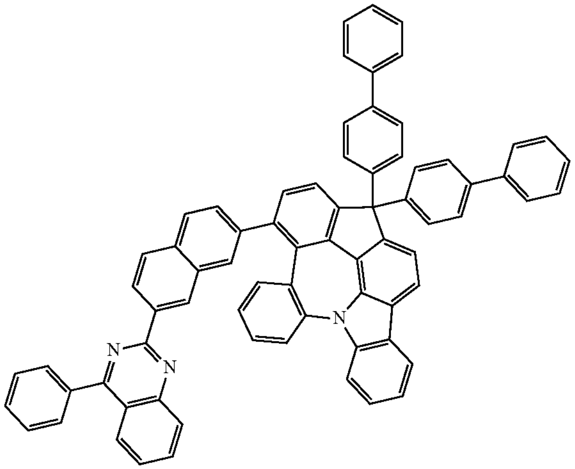 147 | 61.5 | 964.4 |

TABLE 20-continued
| Preparation Example | A-17-X/B-17-X/C-17-X | A-16-X | Compound X | Yield (%) | MS $[M + H]^+$ |
| --- | --- | --- | --- | --- | --- |
| 23 | 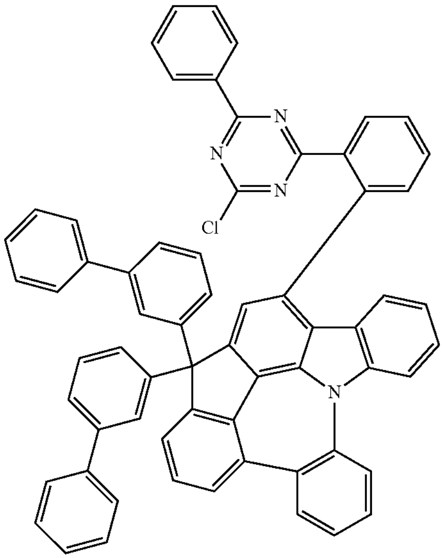 B-17-22 | 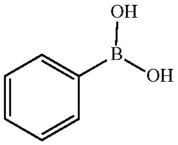 A-16-1 | 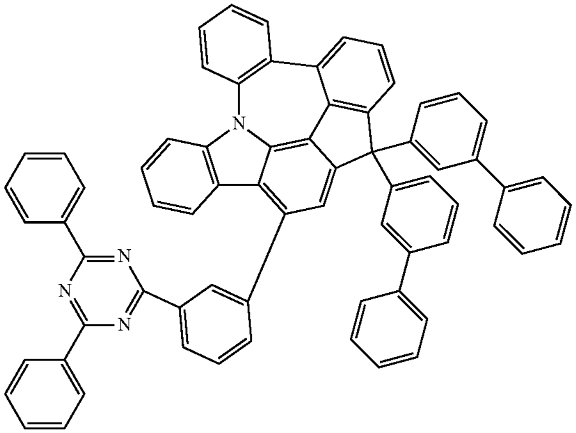 96 | 58.7 | 941.3 |

TABLE 20-continued
| Preparation Example | A-17-X/B-17-X/C-17-X | A-16-X | Compound X | Yield (%) | MS [M + H]+ |
|---|---|---|---|---|---|
| 24 | 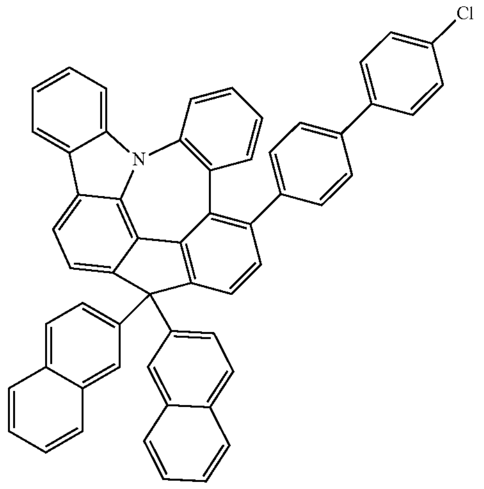 B-10-6 | 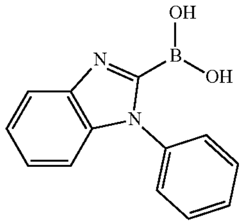 A-16-33 | 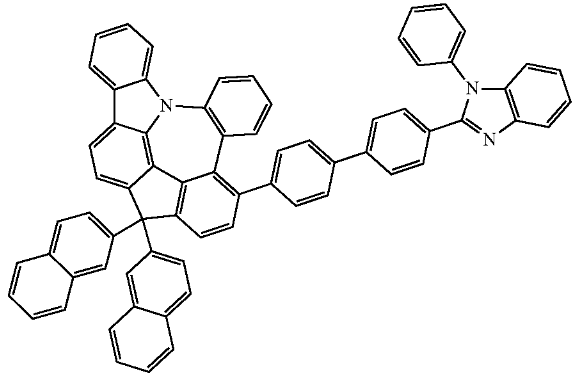 168 | 65.1 | 926.3 |
| 25 | 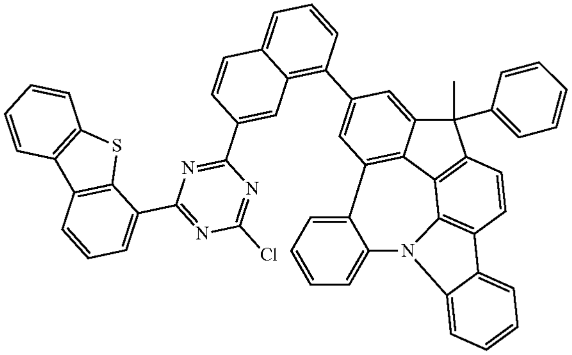 B-17-23 | 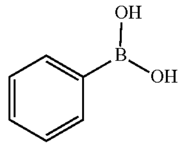 A-16-1 | 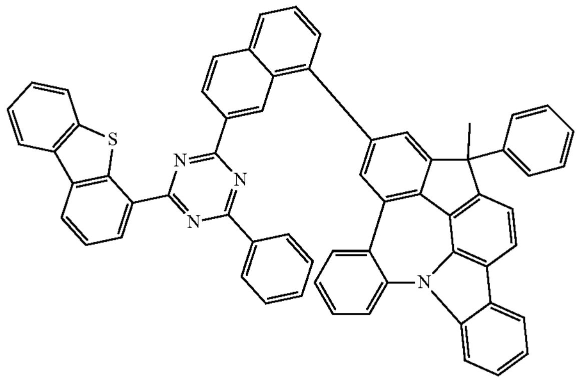 136 | 60.2 | 883.3 |

TABLE 20-continued
| Preparation Example | A-17-X/B-17-X/C-17-X | A-16-X | Compound X | Yield (%) | MS $[M + H]^+$ |
|---|---|---|---|---|---|
| 26 | 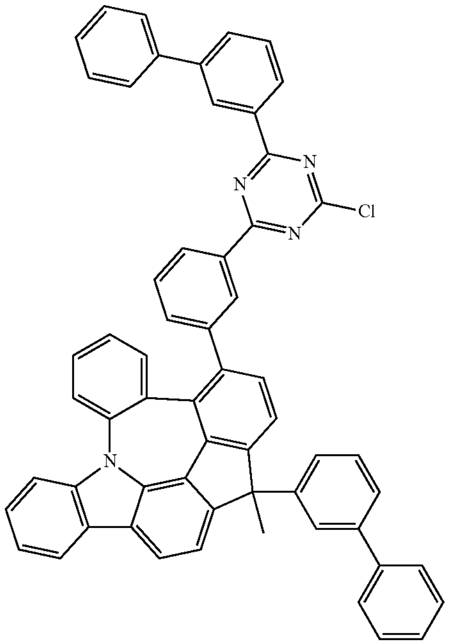 B-17-24 | 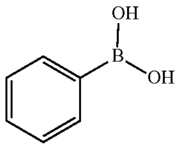 A-16-1 | 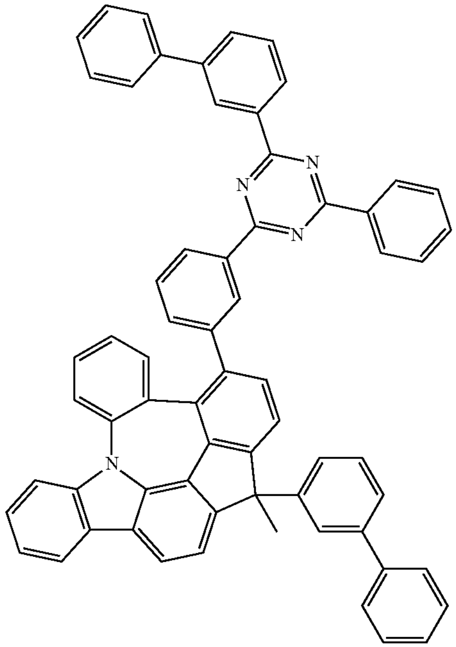 104 | 64.2 | 879.3 |

TABLE 20-continued
| Preparation Example | A-17-X/B-17-X/C-17-X | A-16-X | Compound X | Yield (%) | MS [M + H]+ |
| --- | --- | --- | --- | --- | --- |
| 27 | 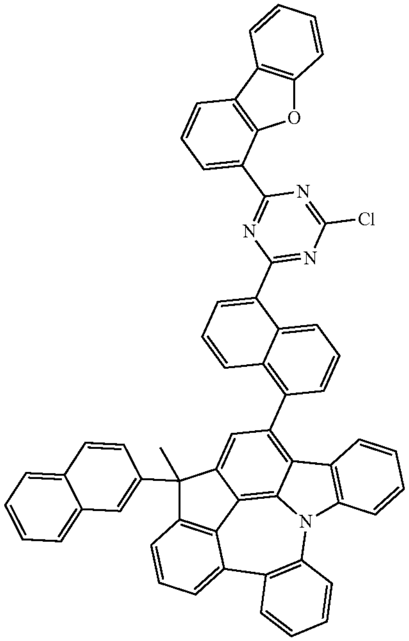 B-17-27 | 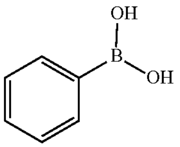 A-16-1 | 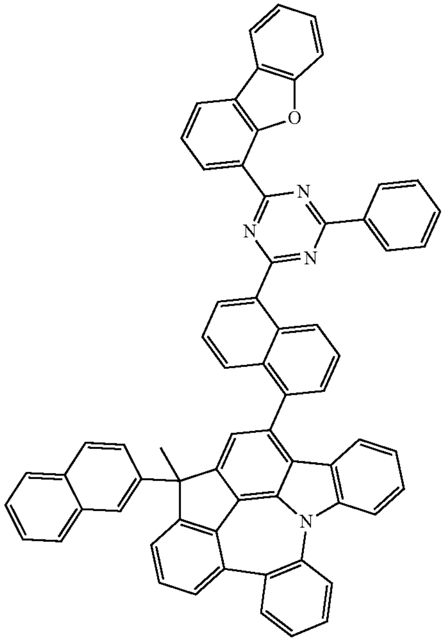 128 | 65.4 | 917.3 |
| 28 | 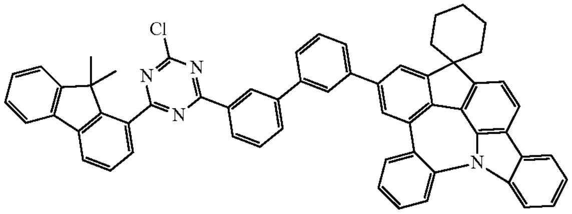 B-17-26 | 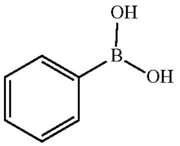 A-16-1 | 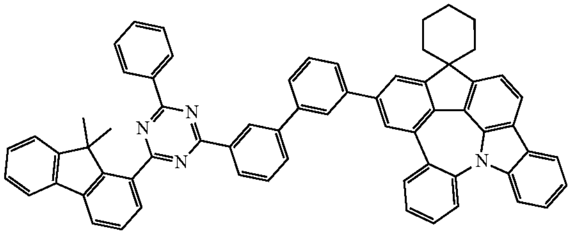 232 | 61.0 | 897.4 |

TABLE 20-continued
| Preparation Example | A-17-X/B-17-X/C-17-X | A-16-X | Compound X | Yield (%) | MS [M + H]+ |
|---|---|---|---|---|---|
| 29 | 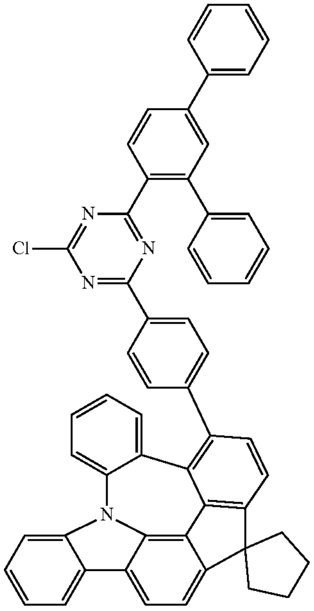 B-17-27 | 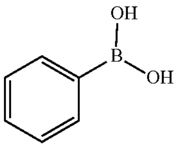 A-16-1 | 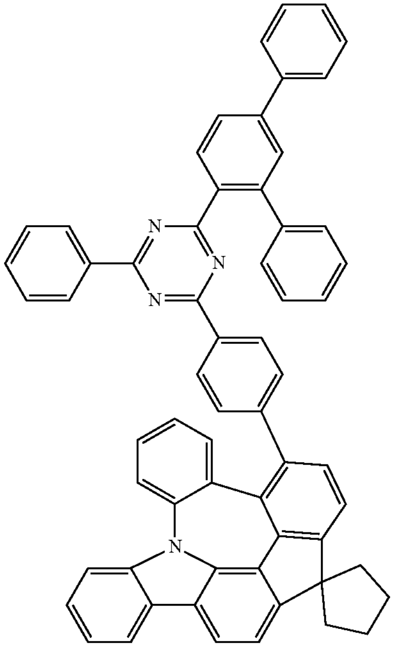 200 | 64.2 | 843.3 |

TABLE 20-continued
| Preparation Example | A-17-X/B-17-X/C-17-X | A-16-X | Compound X | Yield (%) | MS [M + H]+ |
|---|---|---|---|---|---|
| 30 | 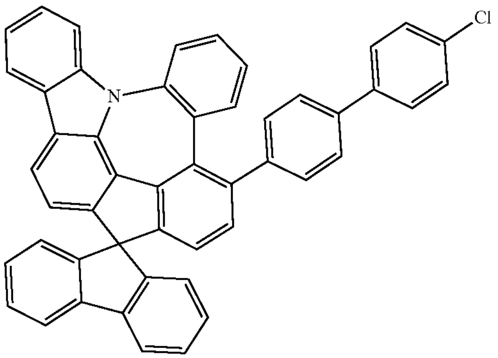 B-10-20 | 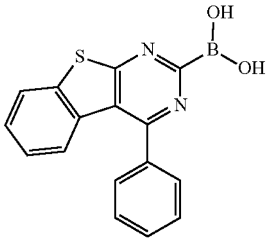 A-16-34 | 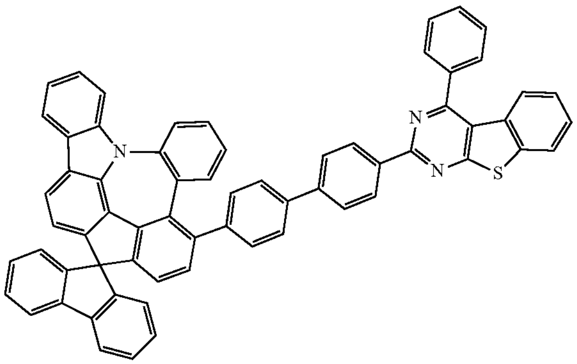 242 | 63.2 | 892.3 |
| 31 | 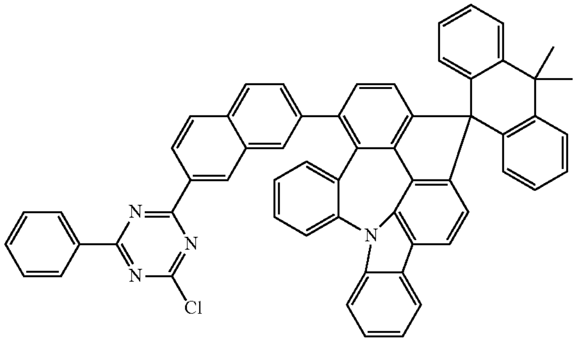 C-17-2 | 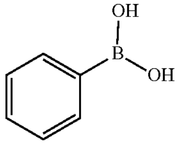 A-16-1 | 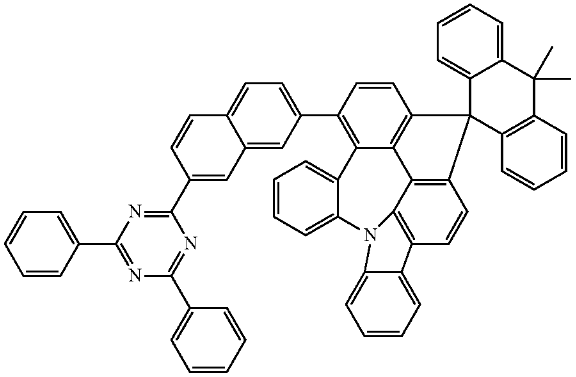 181 | 61.2 | 879.3 |

Preparation Example 32

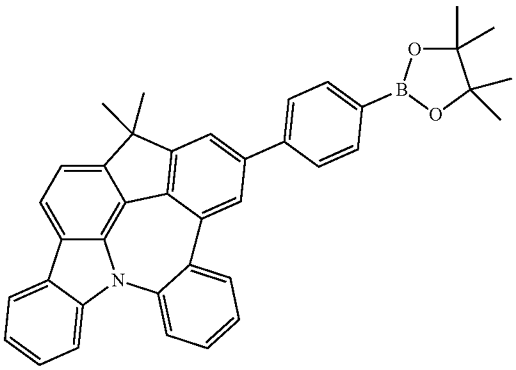

A-13-1

+

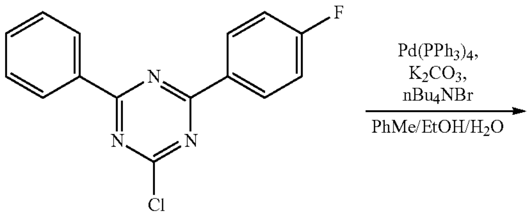

-continued

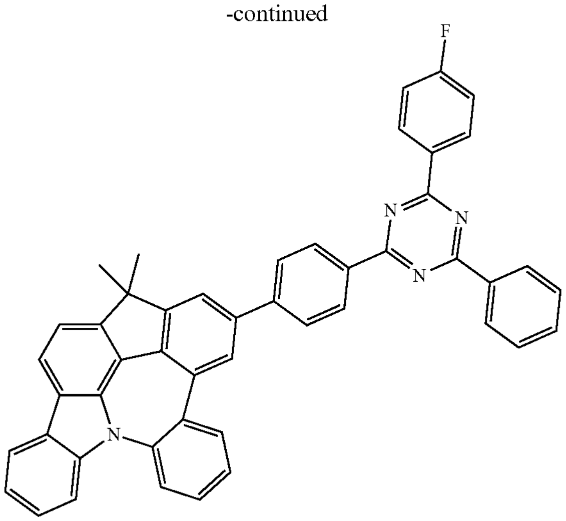

305

The intermediate A-13-1 (9.60 g, 17.3 mmol), 2-phenyl-4-(4-fluorophenyl)-6-chloro-1,3,5-triazine (4.7 g, 16.5 mmol), tetrakis(triphenylphosphine)palladium (0.19 g, 0.16 mmol), potassium carbonate (5.0 g, 36.3 mmol), and tetra-butylammonium bromide (TBAB) (1.1 g, 3.3 mmol) were added to a flask, then a mixed solvent of toluene (80 mL), ethanol (40 mL), and water (20 mL) was added, and a resulting mixture was heated to 80° C. under nitrogen atmosphere and stirred at the temperature for 8 h; then the resulting reaction mixture was cooled to room temperature, and then the stirring was stopped. The reaction solution was washed with water, a separated organic phase was dried with anhydrous magnesium sulfate, and concentrated in vacuum to obtain a crude product; and the crude product was purified by silica gel column chromatography with n-heptane as a mobile phase to obtain a white solid product, which was the compound 305 (9.4 g, yield: 80%, MS: m/z=683.2 $[M+H]^+$).

Preparation Examples 33 to 45

The compounds X listed in Table 21 were each synthesized with reference to the synthesis method in Preparation Example 32, except that a reactant I was used instead of the intermediate A-13-1 and a reactant J was used instead of 2-phenyl-4-(4-fluorophenyl)-6-chloro-1,3,5-triazine.

TABLE 21
| Preparation Example | Reactant I | Reactant J | Compound X | Yield (%) | MS [M + H]$^+$ |
|---|---|---|---|---|---|
| 33 | 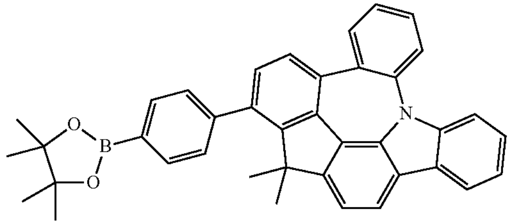 A-13-2 | 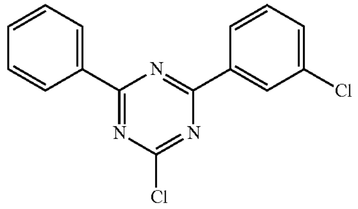 [SMILES: Clc1cccc(-c2nc(Cl)nc(-c3ccccc3)n2)c1] | 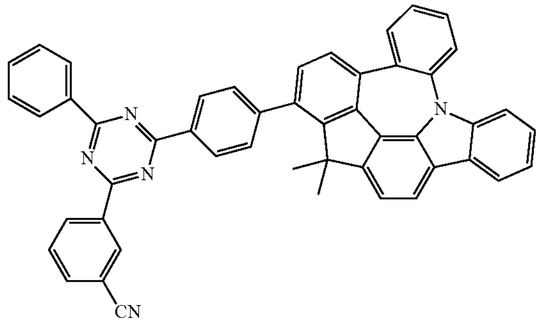 306 | 65 | 690.3 |

TABLE 21-continued
| Preparation Example | Reactant I | Reactant J | Compound X | Yield (%) | MS [M + H]+ |
|---|---|---|---|---|---|
| 34 | 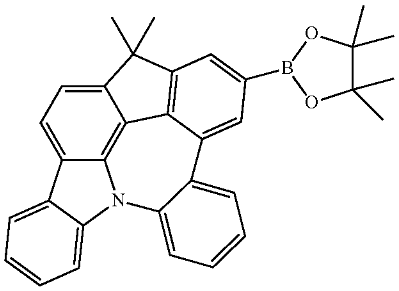 A-10-1 | 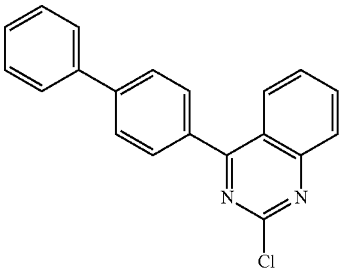 [SMILES: Clc1nc(-c2ccc(-c3ccccc3)cc2)c2ccccc2n1] | 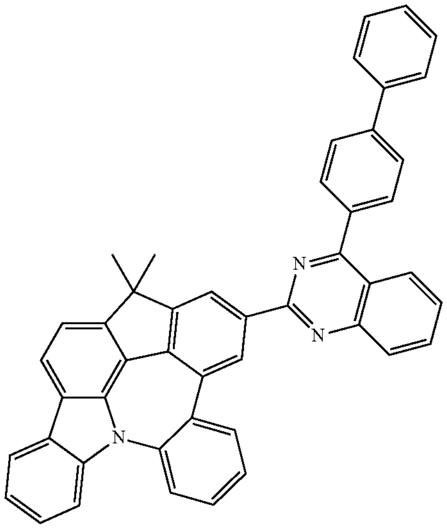 307 | 62 | 638.2 |

TABLE 21-continued
| Preparation Example | Reactant I | Reactant J | Compound X | Yield (%) | MS [M + H]$^+$ |
|---|---|---|---|---|---|
| 35 | 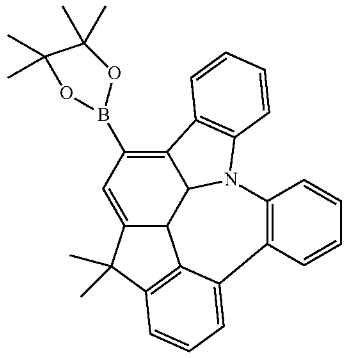 A-10-4 | 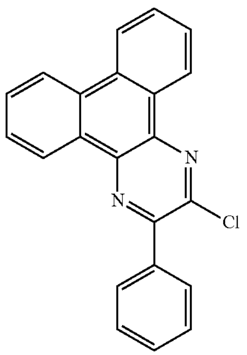 [SMILES: Clc1nc2c3ccccc3c3ccccc3c2nc1-c1ccccc1] | 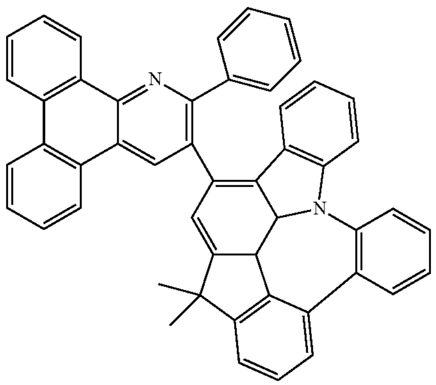 308 | 57.3 | 662.2 |

TABLE 21-continued
| Preparation Example | Reactant I | Reactant J | Compound X | Yield (%) | MS $[M+H]^+$ |
|---|---|---|---|---|---|
| 36 | 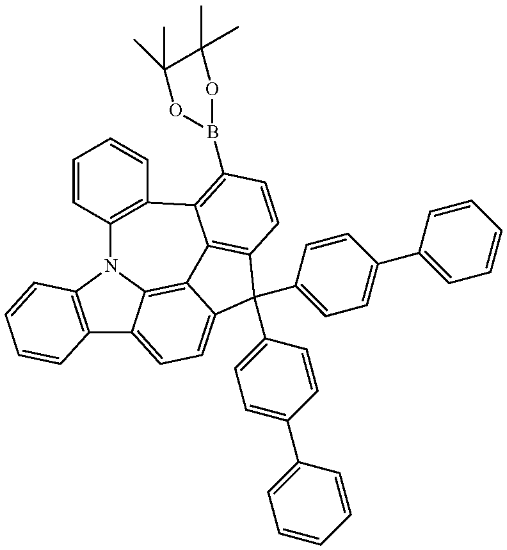 B-8-3 | 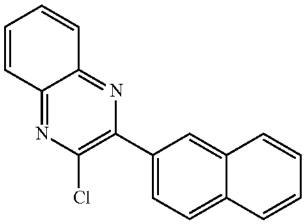 [SMILES: Clc1nc2ccccc2nc1-c1ccc2ccccc2c1] | 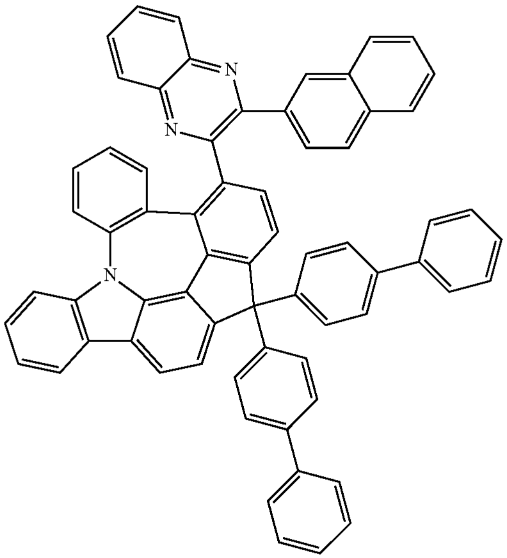 309 | 72.5 | 888.3 |

TABLE 21-continued
| Preparation Example | Reactant I | Reactant J | Compound X | Yield (%) | MS [M + H]+ |
| --- | --- | --- | --- | --- | --- |
| 37 | 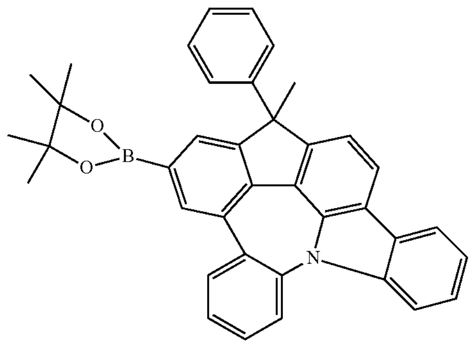 B-8-8 | 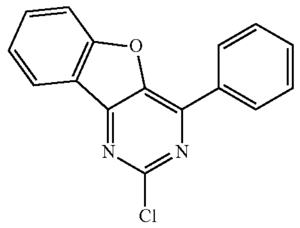 [SMILES: Clc1nc(-c2ccccc2)c2oc3ccccc3c2n1] | 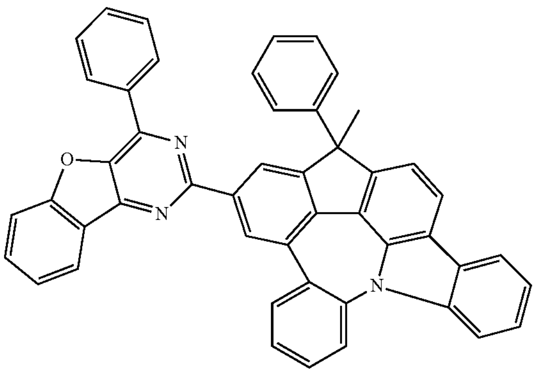 310 | 63.4 | 664.2 |
| 38 | 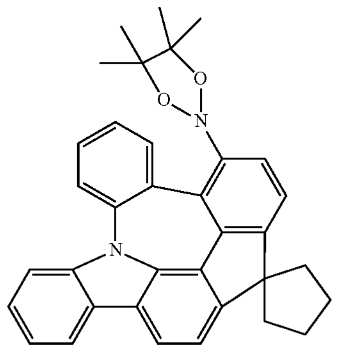 B-8-15 | 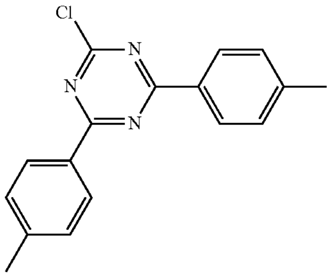 [SMILES: Cc1ccc(-c2nc(Cl)nc(-c3ccc(C)cc3)n2)cc1] | 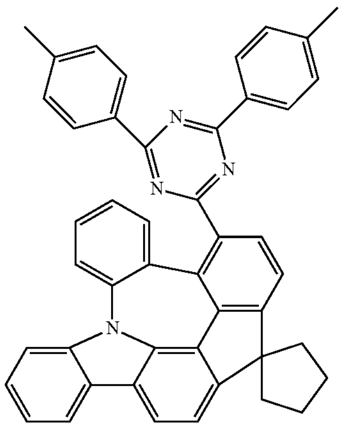 311 | 67.2 | 643.3 |

TABLE 21-continued
| Preparation Example | Reactant I | Reactant J | Compound X | Yield (%) | MS [M + H]+ |
| --- | --- | --- | --- | --- | --- |
| 39 | 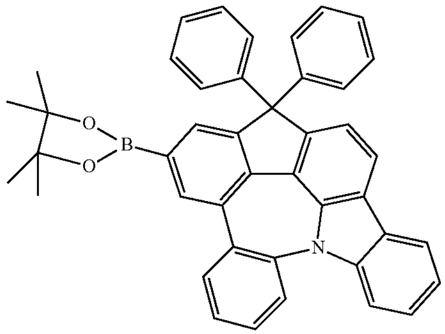 B-8-1 | 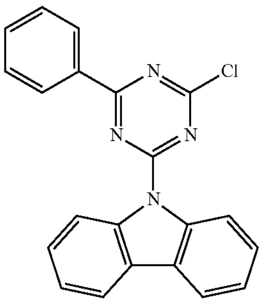 [SMILES: Clc1nc(-c2ccccc2)nc(-n2c3ccccc3c3ccccc32)n1] | 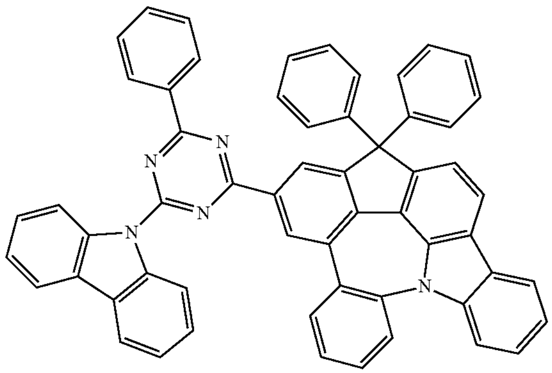 312 | 61.2 | 802.3 |
| 40 | 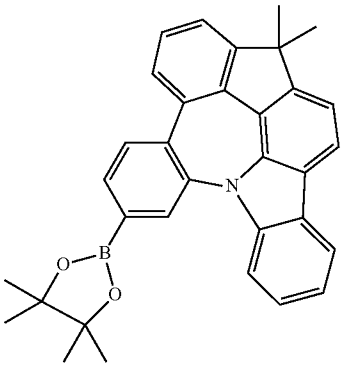 A-10-12 | 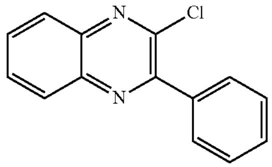 [SMILES: Clc1nc2ccccc2nc1-c1ccccc1] | 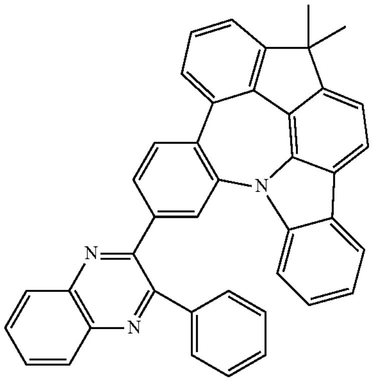 313 | 72.2 | 562.2 |

TABLE 21-continued
| Preparation Example | Reactant I | Reactant J | Compound X | Yield (%) | MS $[M + H]^+$ |
|---|---|---|---|---|---|
| 41 | 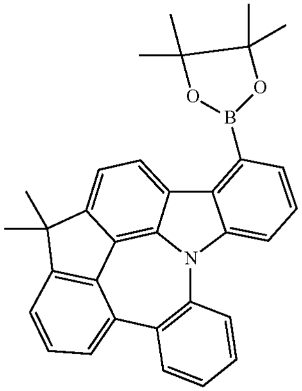 A-10-6 | 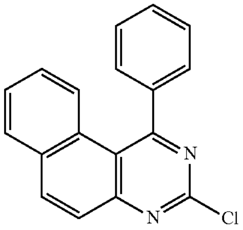 [SMILES: Clc1nc(-c2ccccc2)c2c(ccc3ccccc32)n1] | 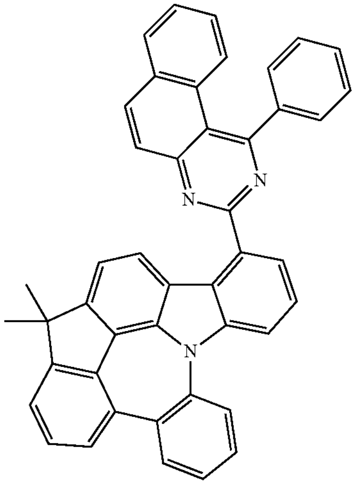 314 | 63.1 | 612.2 |

TABLE 21-continued
| Preparation Example | Reactant I | Reactant J | Compound X | Yield (%) | MS [M + H]+ |
|---|---|---|---|---|---|
| 42 | 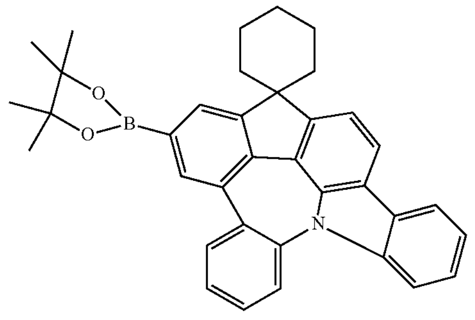 B-8-13 | 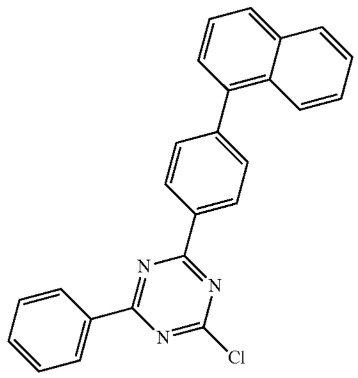 [SMILES: Clc1nc(-c2ccccc2)nc(-c2ccc(-c3cccc4ccccc34)cc2)n1] | 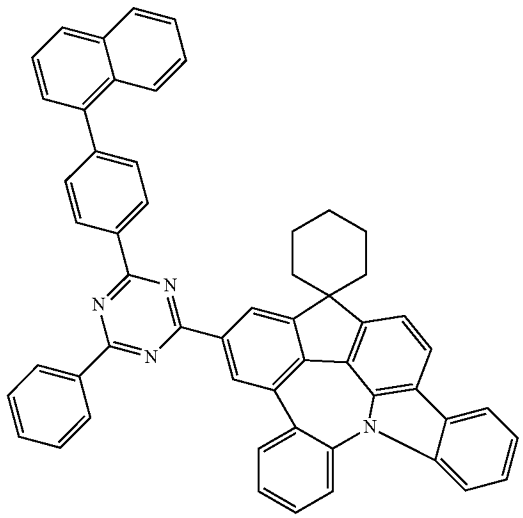 315 | 63.2 | 755.3 |

TABLE 21-continued
| Preparation Example | Reactant I | Reactant J | Compound X | Yield (%) | MS [M + H]+ |
|---|---|---|---|---|---|
| 43 | 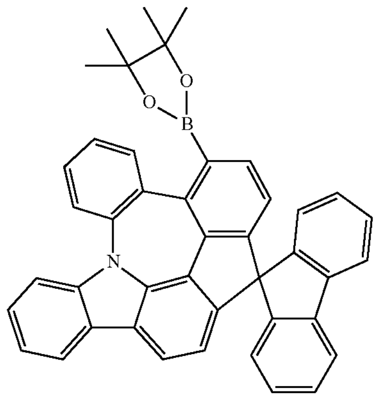 B-8-20 | 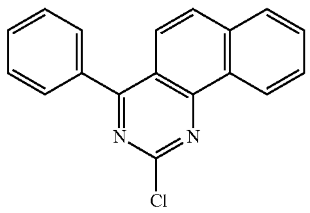 [SMILES: Clc1nc(-c2ccccc2)c2ccc3ccccc3c2n1] | 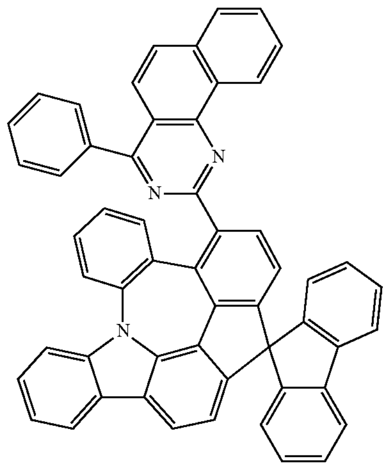 316 | 66.3 | 734.2 |

TABLE 21-continued
| Preparation Example | Reactant I | Reactant J | Compound X | Yield (%) | MS [M + H]$^+$ |
| --- | --- | --- | --- | --- | --- |
| 44 | 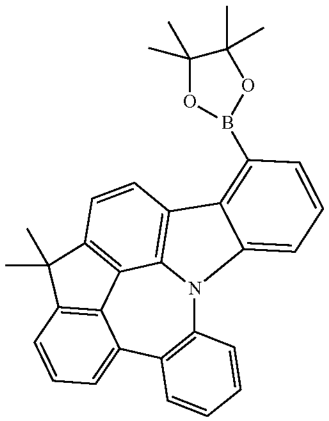 A-10-6 | 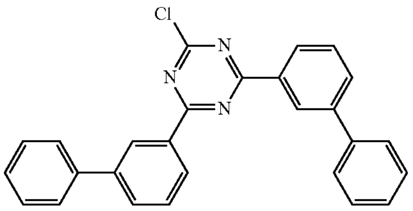 [SMILES: Clc1nc(-c2cccc(-c3ccccc3)c2)nc(-c2cccc(-c3ccccc3)c2)n1] | 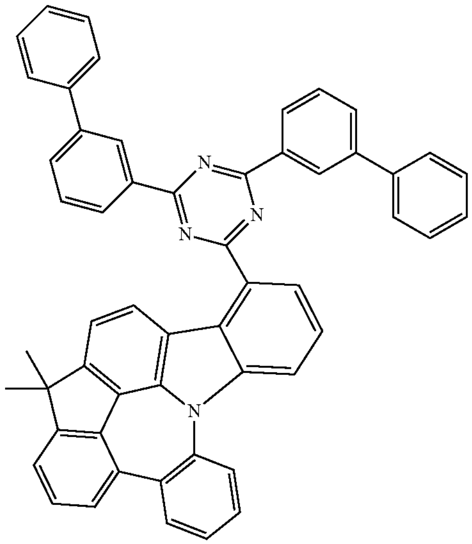 317 | 62.9 | 741.3 |

TABLE 21-continued
| Preparation Example | Reactant I | Reactant J | Compound X | Yield (%) | MS [M + H]+ |
|---|---|---|---|---|---|
| 45 | 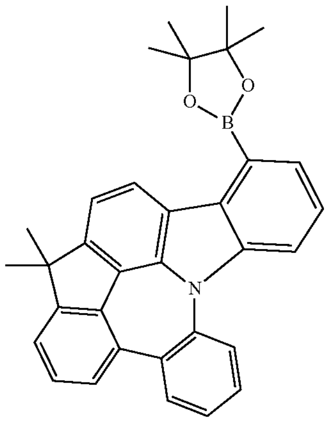 A-10-6 | 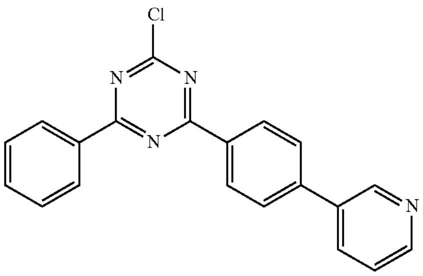 [SMILES: Clc1nc(-c2ccccc2)nc(-c2ccc(-c3cccnc3)cc2)n1] | 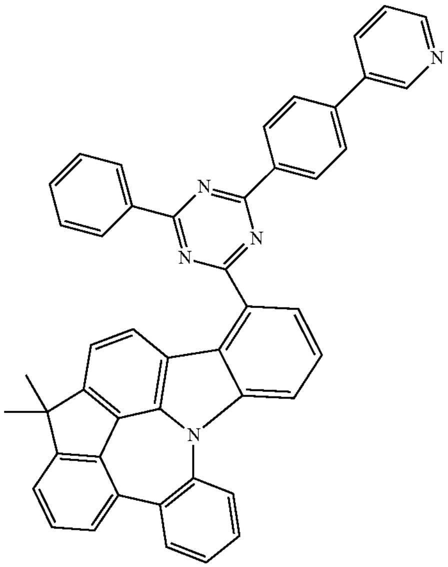 318 | 70.3 | 666.3 |

Example 1: Red Light-Emitting OLED

An anode was produced by the following process: An ITO substrate with a thickness of 1,500 Å (manufactured by Corning) was cut into a size of 40 mm×40 mm×0.7 mm, then the substrate was processed through photolithography into an experimental substrate with cathode, anode, and insulating layer patterns, and the experimental substrate was subjected to a surface treatment with ultraviolet (UV)-ozone and $O_2$:$N_2$ plasma to increase a work function of the anode (experimental substrate) and remove scums.

F4-TCNQ was vacuum-evaporated on the experimental substrate (anode) to form an HIL with a thickness of 105 Å.

NPB was vacuum-evaporated on the HIL to form a first HTL (HTL-1) with a thickness of 1,000 Å, and PAPB was vacuum-deposited on the first HTL to form a hole adjustment layer with a thickness of 850 Å.

The compound 1 and $Ir(piq)_2(acac)$ were co-evaporated on the hole adjustment layer in a film thickness ratio of 97%:3% to form a red light-emitting layer (R-EML) with a thickness of 450 Å.

ET-06 and LiQ were mixed in a weight ratio of 1:1 and then deposited to form an ETL with a thickness of 300 Å, then LiQ was evaporated on the ETL to form an EIL with a thickness of 10 Å, and magnesium (Mg) and silver (Ag) were mixed in a ratio of 1:9 and then vacuum-evaporated on the EIL to form a cathode with a thickness of 115 Å.

CP-05 was evaporated on the cathode to form an organic capping layer (CPL) with a thickness of 650 Å, thereby completing the fabrication of the OLED.

Examples 2 to 45

OLEDs were each preparated by the same method as in Example 1, except that the compounds X listed in Table 22 were each used instead of the compound 1 in Example 1 during the formation of a red light-emitting layer.

Comparative Example 1

An OLED was prepared by the same method as in Example 1, except that a compound A was used instead of the compound 1 in Example 1 during the formation of a red light-emitting layer.

Comparative Example 2

An OLED was prepared by the same method as in Example 1, except that a compound B was used instead of the compound 1 in Example 1 during the formation of a red light-emitting layer.

Comparative Example 3

An OLED was prepared by the same method as in Example 1, except that a compound C was used instead of the compound 1 in Example 1 during the formation of a red light-emitting layer.

Comparative Example 4

An OLED was prepared by the same method as in Example 1, except that a compound D was used instead of the compound 1 in Example 1 during the formation of a red light-emitting layer.

Comparative Example 5

An OLED was prepared by the same method as in Example 1, except that a compound E was used instead of the compound 1 in Example 1 during the formation of a red light-emitting layer.

The structural formulas of the materials used in Examples 1 to 45 and Comparative Examples 1 to 5 were shown in Table 22.

TABLE 22

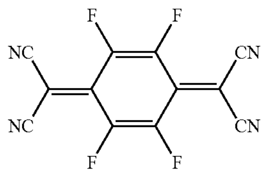

F4-TCNQ

TABLE 22-continued
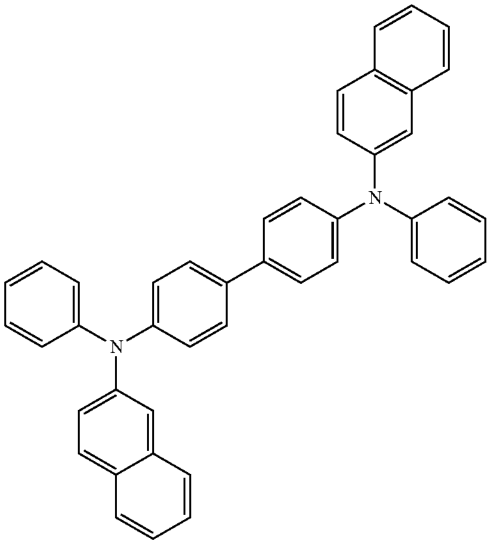
NPB
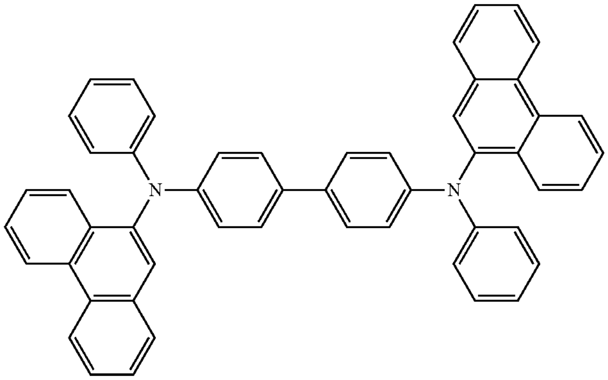
PAPB
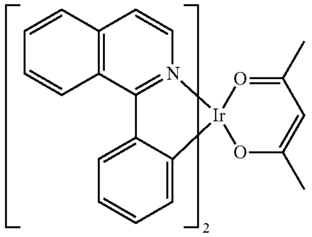
$Ir(piq)_2(acac)$ TABLE 22-continued
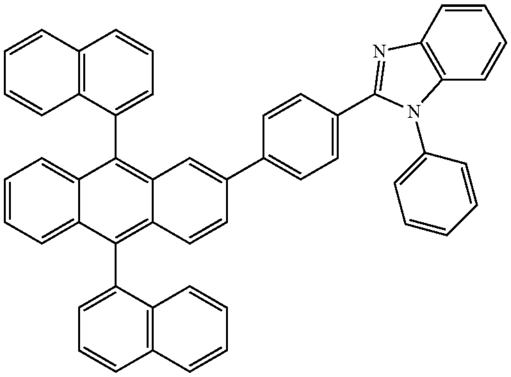
ET-06
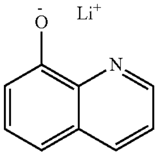 [SMILES: [Li+] ; Oc1cccc2cccnc12]
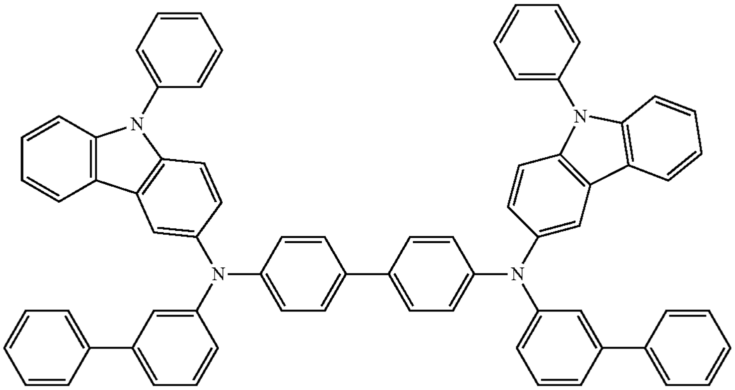
CP-05
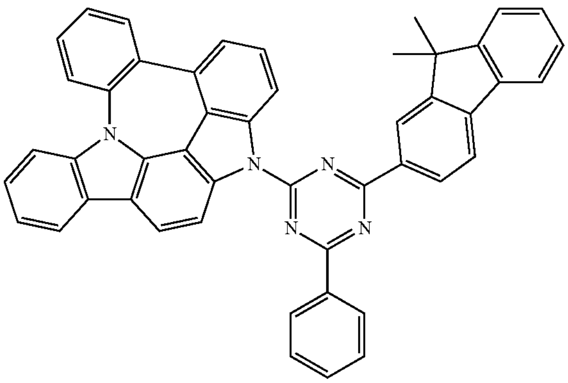
Compound A TABLE 22-continued
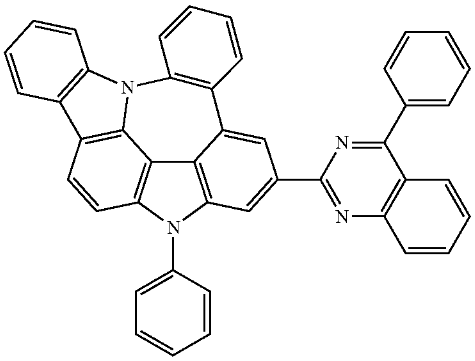
Compound B
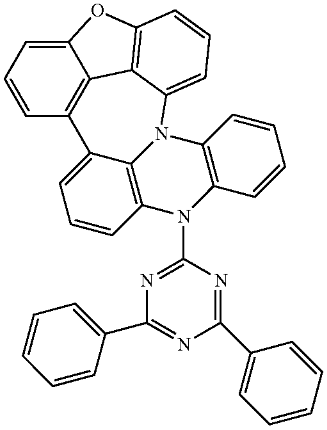
Compound C
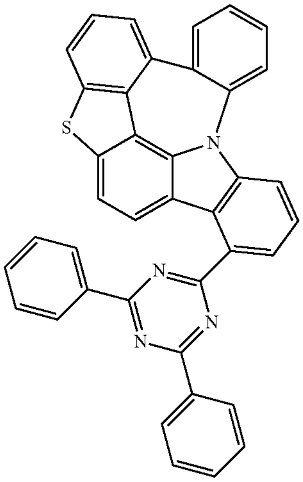
Compound D TABLE 22-continued

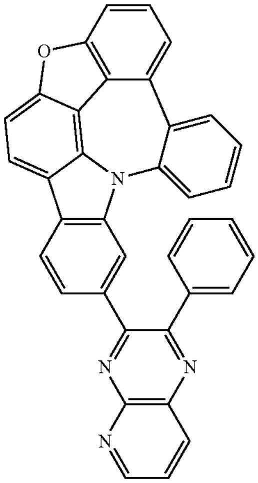

Compound E

The OLEDs fabricated above were subjected to performance analysis at 15 $mA/cm^2$, and results were shown in Table 23 below.

TABLE 23

| Example | Compound | Volt (V) | Cd/A | lm/W | CIEx | CIEy | T95(hrs) @15 $mA/cm^2$ |
|---|---|---|---|---|---|---|---|
| Example 1 | Compound 1 | 3.79 | 39.8 | 31.9 | 0.680 | 0.330 | 594 |
| Example 2 | Compound 43 | 3.73 | 39.0 | 31.0 | 0.680 | 0.330 | 597 |
| Example 3 | Compound 33 | 3.78 | 39.5 | 31.7 | 0.680 | 0.330 | 599 |
| Example 4 | Compound 50 | 3.76 | 39.9 | 32.3 | 0.680 | 0.330 | 598 |
| Example 5 | Compound 85 | 3.71 | 39.5 | 31.2 | 0.680 | 0.330 | 528 |
| Example 6 | Compound 80 | 3.78 | 39.0 | 31.0 | 0.680 | 0.330 | 525 |
| Example 7 | Compound 69 | 3.76 | 39.5 | 31.6 | 0.680 | 0.330 | 539 |
| Example 8 | Compound 79 | 3.77 | 39.5 | 31.7 | 0.680 | 0.330 | 524 |
| Example 9 | Compound 100 | 3.70 | 39.9 | 32.1 | 0.680 | 0.330 | 585 |
| Example 10 | Compound 122 | 3.79 | 39.4 | 31.5 | 0.680 | 0.330 | 586 |
| Example 11 | Compound 140 | 3.79 | 39.7 | 31.9 | 0.680 | 0.330 | 521 |
| Example 12 | Compound 107 | 3.71 | 39.6 | 31.6 | 0.680 | 0.330 | 520 |
| Example 13 | Compound 154 | 3.77 | 39.8 | 32.0 | 0.680 | 0.330 | 610 |
| Example 14 | Compound 97 | 3.75 | 39.7 | 31.8 | 0.680 | 0.330 | 592 |
| Example 15 | Compound 129 | 3.73 | 39.7 | 31.8 | 0.680 | 0.330 | 587 |
| Example 16 | Compound 211 | 3.73 | 39.8 | 31.9 | 0.680 | 0.330 | 608 |
| Example 17 | Compound 225 | 3.77 | 39.1 | 31.1 | 0.680 | 0.320 | 591 |
| Example 18 | Compound 195 | 3.78 | 39.9 | 32.1 | 0.680 | 0.330 | 597 |
| Example 19 | Compound 228 | 3.75 | 39.3 | 31.2 | 0.680 | 0.330 | 590 |
| Example 20 | Compound 111 | 3.77 | 39.9 | 32.0. | 0.680 | 0.330 | 522 |
| Example 21 | Compound 117 | 3.73 | 35.4 | 29.7 | 0.680 | 0.330 | 586 |
| Example 22 | Compound 147 | 3.70 | 35.2 | 29.5 | 0.680 | 0.330 | 514 |
| Example 23 | Compound 96 | 3.73 | 39.3 | 31.6 | 0.680 | 0.330 | 527 |
| Example 24 | Compound 168 | 3.76 | 35.5 | 29.8 | 0.680 | 0.320 | 526 |
| Example 25 | Compound 136 | 3.72 | 39.1 | 31.8 | 0.680 | 0.330 | 535 |
| Example 26 | Compound 104 | 3.78 | 39.1 | 31.4 | 0.680 | 0.330 | 530 |

TABLE 23-continued

| Example | Compound | Volt (V) | Cd/A | lm/W | CIEx | CIEy | T95(hrs) @15 mA/cm$^2$ |
|---|---|---|---|---|---|---|---|
| Example 27 | Compound 128 | 3.78 | 39.1 | 31.4 | 0.680 | 0.330 | 529 |
| Example 28 | Compound 232 | 3.75 | 39.4 | 31.8 | 0.680 | 0.320 | 522 |
| Example 29 | Compound 200 | 3.71 | 39.3 | 31.1 | 0.680 | 0.330 | 599 |
| Example 30 | Compound 242 | 3.75 | 35.3 | 29.7 | 0.680 | 0.330 | 599 |
| Example 31 | Compound 181 | 3.79 | 39.4 | 31.5 | 0.680 | 0.330 | 521 |
| Example 32 | Compound 305 | 3.71 | 40.2 | 32.8 | 0.680 | 0.330 | 601 |
| Example 33 | Compound 306 | 3.72 | 40.0 | 32.6 | 0.680 | 0.330 | 607 |
| Example 34 | Compound 307 | 3.73 | 35.3 | 29.7 | 0.680 | 0.330 | 589 |
| Example 35 | Compound 308 | 3.72 | 34.8 | 29.1 | 0.680 | 0.320 | 592 |
| Example 36 | Compound 309 | 3.78 | 34.9 | 29.1 | 0.680 | 0.330 | 596 |
| Example 37 | Compound 310 | 3.72 | 34.8 | 29.1 | 0.680 | 0.330 | 598 |
| Example 38 | Compound 311 | 3.74 | 40.1 | 32.7 | 0.680 | 0.330 | 602 |
| Example 39 | Compound 312 | 3.72 | 39.8 | 31.9 | 0.680 | 0.330 | 604 |
| Example 40 | Compound 313 | 3.76 | 34.7 | 29.0 | 0.680 | 0.330 | 587 |
| Example 41 | Compound 314 | 3.78 | 34.7 | 29.0 | 0.680 | 0.330 | 586 |
| Example 42 | Compound 315 | 3.71 | 39.7 | 31.8 | 0.680 | 0.320 | 607 |
| Example 43 | Compound 316 | 3.79 | 34.8 | 29.1 | 0.680 | 0.330 | 592 |
| Example 44 | Compound 317 | 3.72 | 39.6 | 31.7 | 0.680 | 0.330 | 599 |
| Example 45 | Compound 318 | 3.71 | 40.3 | 32.9 | 0.680 | 0.330 | 597 |
| Comparative Example 1 | Compound A | 3.89 | 31.3 | 25.3 | 0.680 | 0.330 | 364 |
| Comparative Example 2 | Compound B | 3.90 | 28.2 | 23.1 | 0.680 | 0.320 | 362 |
| Comparative Example 3 | Compound C | 3.93 | 31.2 | 24.1 | 0.680 | 0.330 | 360 |
| Comparative Example 4 | Compound D | 3.92 | 31.0 | 24.9 | 0.680 | 0.330 | 380 |
| Comparative Example 5 | Compound E | 3.91 | 28.3 | 23.3 | 0.680 | 0.330 | 389 |

It can be seen from the results in Table 23 that, compared with the OLEDs corresponding to well-known compounds exhibited in Comparative Examples 1 to 5, the OLEDs with the organic compound of the present application as a red light-emitting layer exhibited in Examples 1 to 45 have a driving voltage reduced by at least 0.1 V, a current efficiency (Cd/A) increased by at least 10.9%, and a life span increased by at least 32%.

Preferred embodiments of the present application are described above in detail with reference to the accompanying drawings, but the present application is not limited to specific details in the above embodiments. Various simple variations can be made to the technical solutions of the present application without departing from the technical ideas of the present application, and these simple variations fall within the protection scope of the present application.

What is claimed is:

1. An organic compound with a structure shown in formula 1:

formula 1

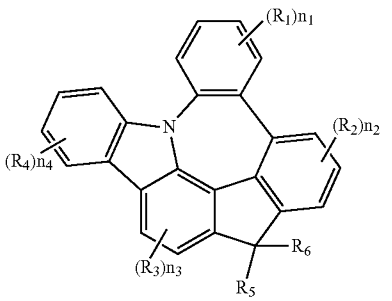

wherein $R_5$ and $R_6$ are the same or different, and are each independently selected from the group consisting of alkyl with 1 to 6 carbon atoms, haloalkyl with 1 to 6 carbon atoms, cycloalkyl with 3 to 10 carbon atoms, substituted or unsubstituted aryl with 6 to 15 carbon atoms, and substituted or unsubstituted heteroaryl with 3 to 12 carbon atoms; or $R_5$ and $R_6$ are optionally connected to form a 5- to 18-membered aliphatic ring or a substituted or unsubstituted 5- to 18-membered aromatic ring together with the carbon atom to which they are jointly connected, and a substituent on the 5- to 18-membered aromatic ring is selected from the group consisting of deuterium, halogen, and alkyl with 1 to 6 carbon atoms;

$R_1$, $R_2$, $R_3$, and $R_4$ are the same or different, and are each independently selected from the group consisting of a group shown in formula 2, aryl with 6 to 20 carbon atoms, heteroaryl with 3 to 20 carbon atoms, hydrogen, deuterium, halogen, cyano, alkyl with 1 to 10 carbon atoms, haloalkyl with 1 to 10 carbon atoms, deuterated alkyl with 1 to 10 carbon atoms, alkoxy with 1 to 10 carbon atoms, cycloalkyl with 3 to 10 carbon atoms, and trialkylsilyl with 3 to 12 carbon atoms, and any one or two of $R_1$, $R_2$, $R_3$, and $R_4$ are the group shown in formula 2, formula 2

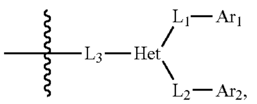

wherein Het is electron-deficient 6- to 18-membered nitrogen-containing heteroarylene;

$L_1$, $L_2$, and $L_3$ are each independently selected from the group consisting of a single bond, substituted or unsubstituted arylene with 6 to 30 carbon atoms, and substituted or unsubstituted heteroarylene with 3 to 30 carbon atoms;

$Ar_1$ and $Ar_2$ are the same or different, and are each independently selected from the group consisting of hydrogen, deuterium, substituted or unsubstituted aryl with 6 to 30 carbon atoms, and substituted or unsubstituted heteroaryl with 3 to 30 carbon atoms;

$n_1$ and $n_4$ are the same or different, represent a number of $R_1$ and a number of $R_4$ respectively, and are each independently selected from the group consisting of 1, 2, 3, and 4; $n_3$ represents a number of $R_3$ and is selected from the group consisting of 1 and 2; and $n_2$ represents a number of $R_2$ and is selected from the group consisting of 1, 2, and 3;

substituents in $L_1$, $L_2$, $L_3$, $Ar_1$, $Ar_2$, $R_5$, and $R_6$ are the same or different, and are each independently selected from the group consisting of deuterium, cyano, halogen, alkyl with 1 to 10 carbon atoms, haloalkyl with 1 to 10 carbon atoms, deuterated alkyl with 1 to 10 carbon atoms, cycloalkyl with 3 to 10 carbon atoms, aryl with 6 to 20 carbon atoms, heteroaryl with 3 to 20 carbon atoms, alkoxy with 1 to 10 carbon atoms, alkylthio with 1 to 10 carbon atoms, trialkylsilyl with 1 to 12 carbon atoms, arylsilyl with 6 to 18 carbon atoms, aryloxy with 6 to 20 carbon atoms, and arylthio with 6 to 20 carbon atoms; and optionally, in $Ar_1$ and $Ar_2$, any two adjacent substituents connected to form a substituted or unsubstituted 5- to 15-membered ring, and a substituent on the 5 to 15-membered ring is independently selected from the group consisting of deuterium, cyano, halogen, alkyl with 1 to 4 carbon atoms, haloalkyl with 1 to 4 carbon atoms, deuterated alkyl with 1 to 4 carbon atoms, trialkylsilyl with 3 to 6 carbon atoms, aryl with 6 to 12 carbon atoms, and heteroaryl with 5 to 12 carbon atoms.

2. The organic compound according to claim 1, wherein $R_5$ and $R_6$ are each independently selected from the group consisting of methyl, ethyl, n-propyl, isopropyl, tert-butyl, trifluoromethyl, trideuteromethyl, phenyl, naphthyl, biphenyl, fluorenyl, dimethylfluorenyl, anthracenyl, phenanthryl, pyridyl, dibenzothienyl, dibenzofuranyl, and carbazolyl; or $R_5$ and $R_6$ are connected to form a fluorene ring, cyclopentane, cyclohexane, or

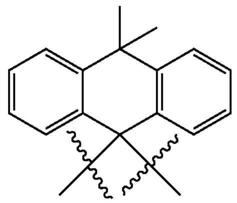 [SMILES: *C1(*)c2ccccc2C(C)(C)c2ccccc21]

together with the carbon atom to which they are jointly connected.

3. The organic compound according to claim 1, wherein the Het is selected from the group consisting of triazinylene, pyridylene, pyrimidinylene, quinolinylene, quinoxalinylene, quinazolinylene, isoquinolinylene, benzimidazolylene, benzothiazolylene, benzoxazolylene, phenanthrolinylene, benzoquinazolinylene, phenanthroimidazolylene, benzofuranopyrimidinylene, benzothienopyrimidinylene, and the following groups:

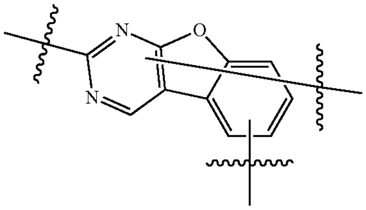

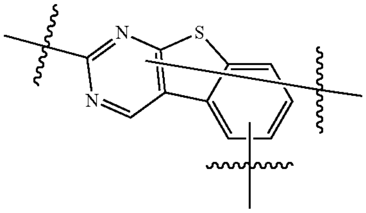

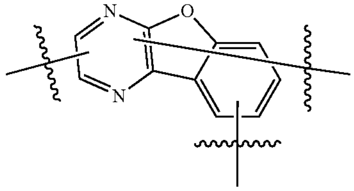

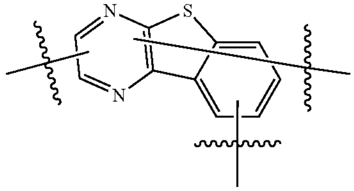

-continued

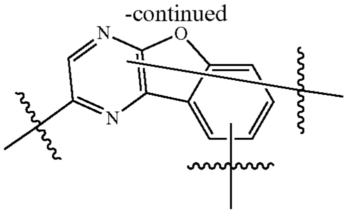

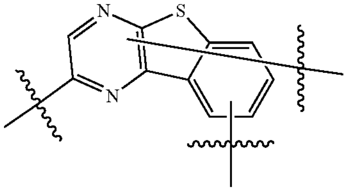

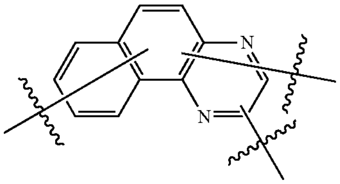

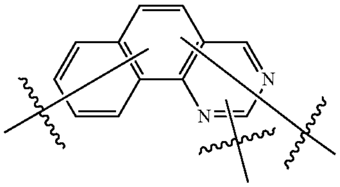

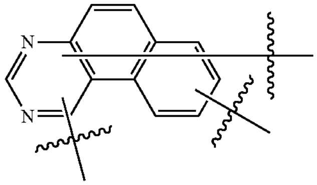

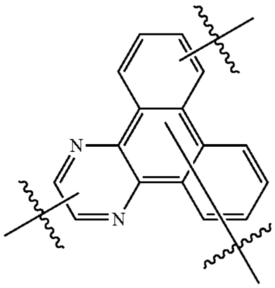

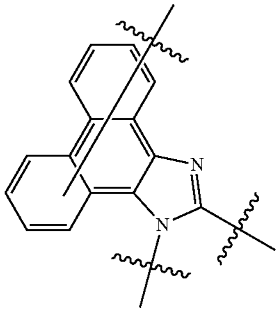

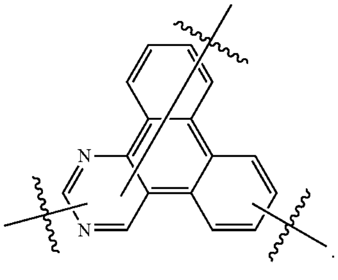

4. The organic compound according to claim 1, wherein $L_1$, $L_2$, and $L_3$ are each independently selected from the group consisting of a single bond, substituted or unsubstituted arylene with 6 to 18 carbon atoms, and substituted or unsubstituted heteroarylene with 5 to 12 carbon atoms; and optionally, substituents in $L_1$, $L_2$, and $L_3$ are each independently selected from the group consisting of deuterium, cyano, fluorine, alkyl with 1 to 5 carbon atoms, haloalkyl with 1 to 5 carbon atoms, deuterated alkyl with 1 to 5 carbon atoms, aryl with 6 to 12 carbon atoms, and pyridyl.

5. The organic compound according to claim 1, wherein $L_1$, $L_2$, and $L_3$ are each independently selected from the group consisting of a single bond, substituted or unsubstituted phenylene, substituted or unsubstituted naphthylene, substituted or unsubstituted biphenylene, substituted or unsubstituted anthracenylene, substituted or unsubstituted phenanthrylene, substituted or unsubstituted fluorenylene, substituted or unsubstituted dibenzothienylene, substituted or unsubstituted dibenzofuranylene, and substituted or unsubstituted carbazolylene; and substituents in $L_1$, $L_2$, and $L_3$ are each independently selected from the group consisting of deuterium, cyano, fluorine, methyl, ethyl, n-propyl, isopropyl, n-butyl, tert-butyl, trifluoromethyl, trideuteromethyl, phenyl, naphthyl, and pyridyl.

6. The organic compound according to claim 1, wherein $L_1$, $L_2$, and $L_3$ are each independently selected from the group consisting of a single bond and a substituted or unsubstituted group W; an unsubstituted group W is selected from the group consisting of the following groups:

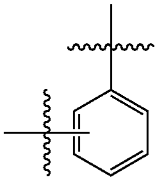

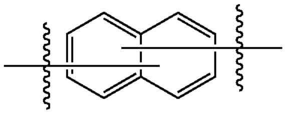

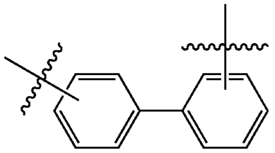

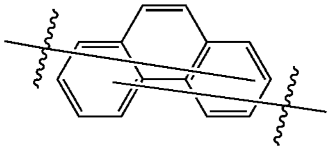

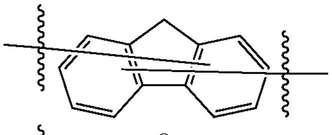

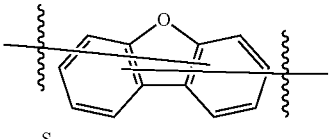

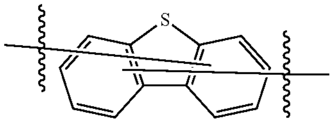

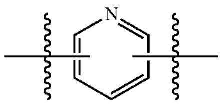

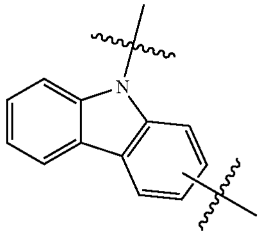

-continued

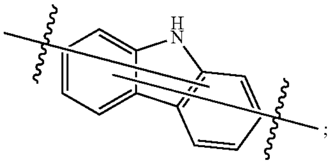

wherein

represents a chemical bond; when the group W is substituted by one or more substituents, the one or more substituents are each independently selected from the group consisting of deuterium, fluorine, cyano, methyl, ethyl, n-propyl, isopropyl, n-butyl, tert-butyl, trifluoromethyl, trideuteromethyl, phenyl, naphthyl, and pyridyl.

7. The organic compound according to claim 1, wherein $L_1$, $L_2$, and $L_3$ are each independently selected from the group consisting of a single bond and the following groups:

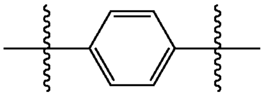
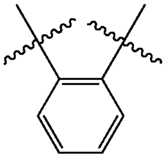
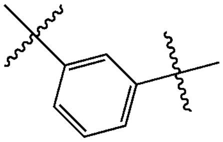
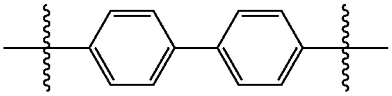
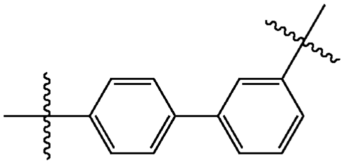
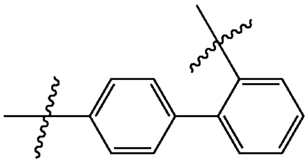
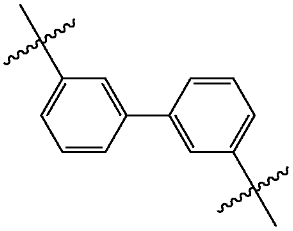

-continued

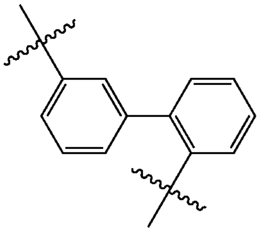
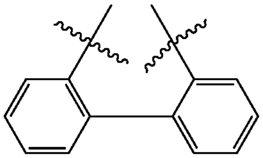
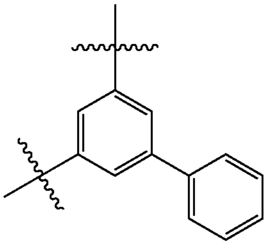
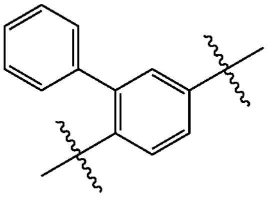
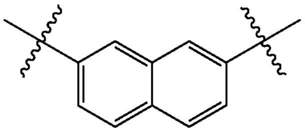
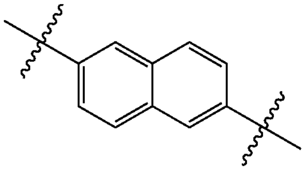
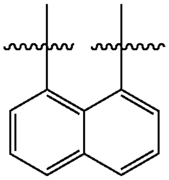
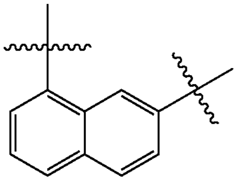
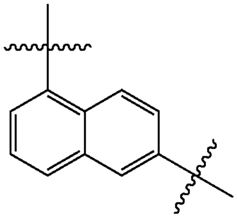
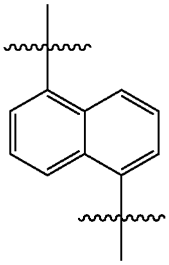
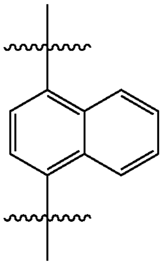
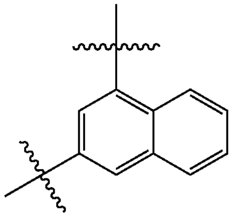
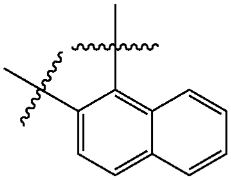

-continued
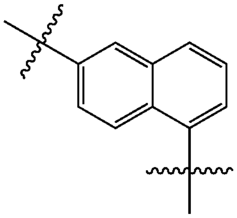
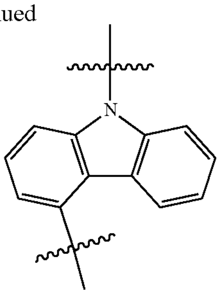
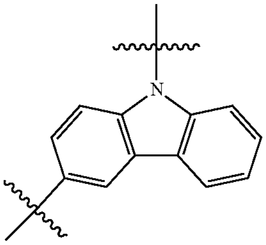
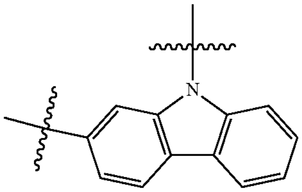
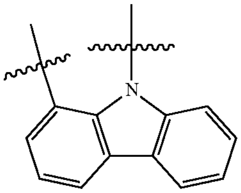
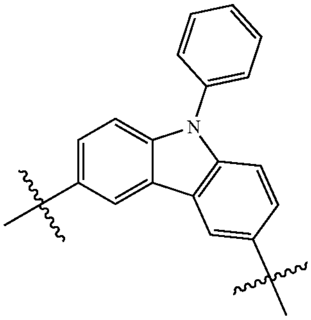
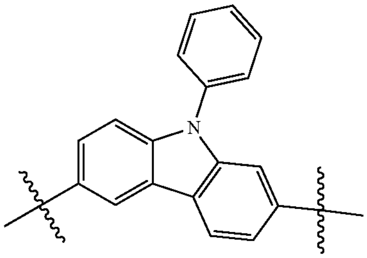
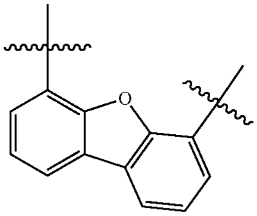
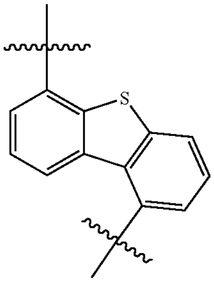
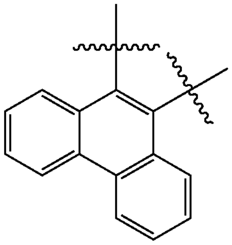
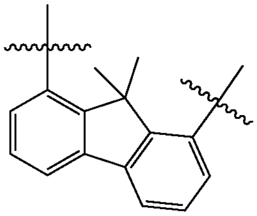
-continued
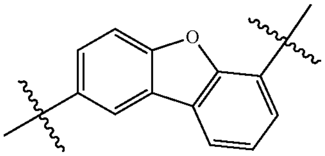
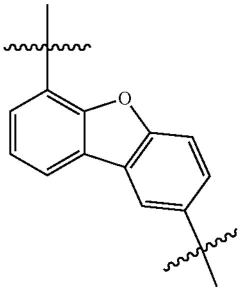
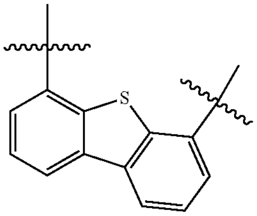
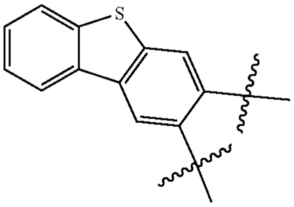
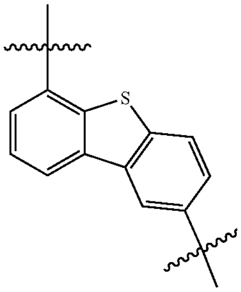
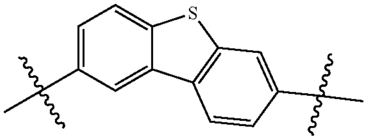
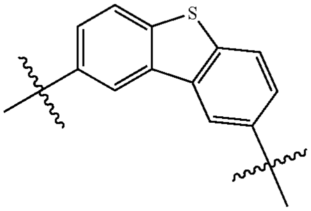
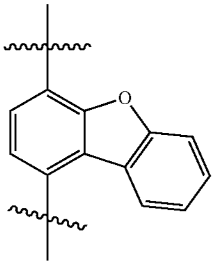
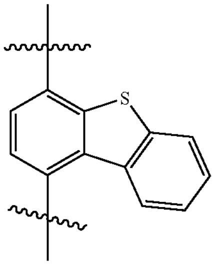
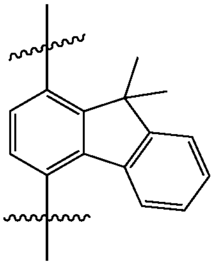
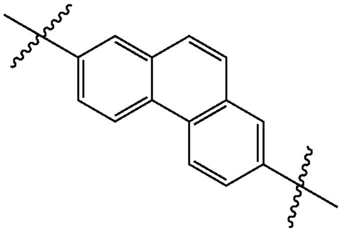

-continued

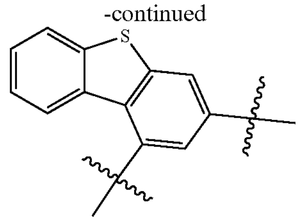

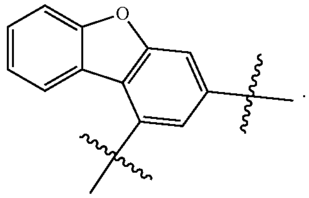

8. The organic compound according to claim 1, wherein $Ar_1$ and $Ar_2$ are the same or different, and are each independently selected from the group consisting of hydrogen, deuterium, substituted or unsubstituted aryl with 6 to 25 carbon atoms, and substituted or unsubstituted heteroaryl with 5 to 20 carbon atoms;

optionally, substituents in $Ar_1$ and $Ar_2$ are each independently selected from the group consisting of deuterium, cyano, fluorine, alkyl with 1 to 5 carbon atoms, haloalkyl with 1 to 5 carbon atoms, deuterated alkyl with 1 to 5 carbon atoms, aryl with 6 to 15 carbon atoms, and heteroaryl with 5 to 12 carbon atoms; and optionally, in $Ar_1$ and $Ar_2$, any two adjacent substituents connected to form a substituted or unsubstituted 5- to 13-membered ring, and a substituent on the 5- to 13-membered ring is selected from the group consisting of deuterium, cyano, halogen, alkyl with 1 to 4 carbon atoms, haloalkyl with 1 to 4 carbon atoms, deuterated alkyl with 1 to 4 carbon atoms, trialkylsilyl with 3 to 6 carbon atoms, aryl with 6 to 12 carbon atoms, and heteroaryl with 5 to 12 carbon atoms.

9. The organic compound according to claim 1, wherein $Ar_1$ and $Ar_2$ are the same or different, and are each independently selected from the group consisting of hydrogen, deuterium, substituted or unsubstituted phenyl, substituted or unsubstituted biphenyl, substituted or unsubstituted naphthyl, substituted or unsubstituted terphenyl, substituted or unsubstituted fluorenyl, substituted or unsubstituted pyrenyl, substituted or unsubstituted perylenyl, substituted or unsubstituted anthracenyl, substituted or unsubstituted phenanthryl, substituted or unsubstituted pyridyl, substituted or unsubstituted dibenzothienyl, substituted or unsubstituted dibenzofuranyl, substituted or unsubstituted carbazolyl, and substituted or unsubstituted spirobifluorenyl; and substituents in $Ar_1$ and $Ar_2$ are the same or different, and are each independently selected from the group consisting of methyl, ethyl, n-propyl, isopropyl, n-butyl, tert-butyl, trifluoromethyl, trideuteromethyl, phenyl, naphthyl, dibenzothienyl, dibenzofuranyl, carbazolyl, and pyridyl.

10. The organic compound according to claim 1, wherein $Ar_1$ and $Ar_2$ are the same or different, and are each independently selected from the group consisting of hydrogen, deuterium, and a substituted or unsubstituted group Y; an unsubstituted group Y is selected from the group consisting of the following groups:

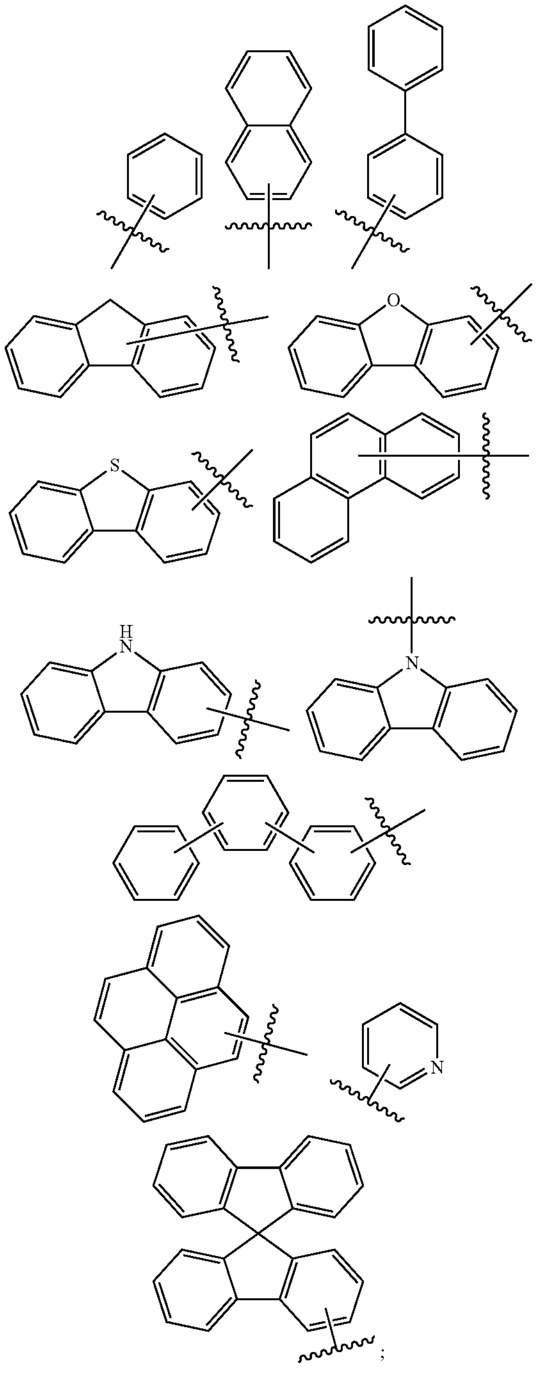

;

wherein

represents a chemical bond; and when the group Y is substituted by one or more substituents, the one or more substituents are each independently selected from the group consisting of deuterium, cyano, fluorine, methyl, ethyl, n-propyl, isopropyl, n-butyl, tert-butyl, trifluoromethyl, trideuteromethyl, trimethylsilyl, phenyl, naphthyl, and pyridyl.
11. The organic compound according to claim 1, wherein $Ar_1$ and $Ar_2$ are the same or different, and are each independently selected from the group consisting of hydrogen, deuterium, and the following groups:
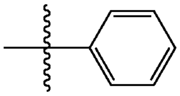
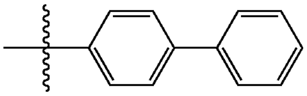
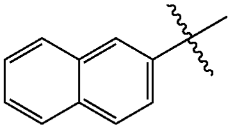
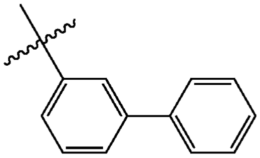
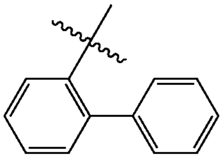
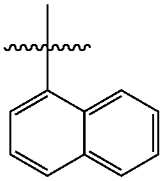
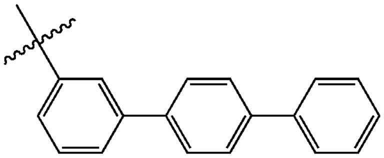
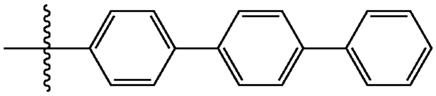
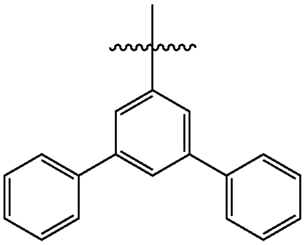
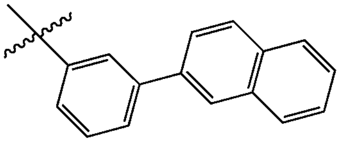
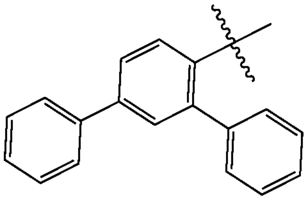
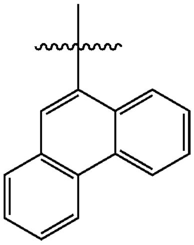
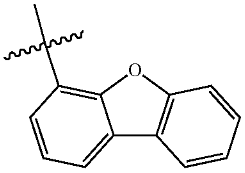
-continued
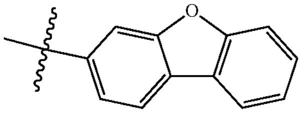
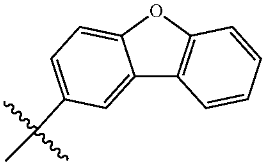
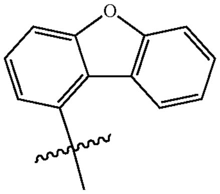
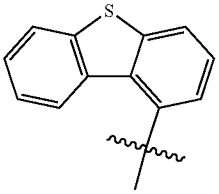
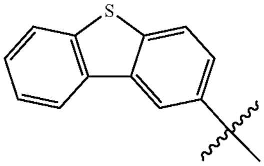
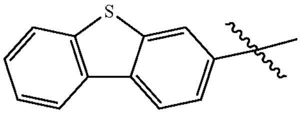
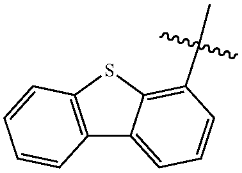
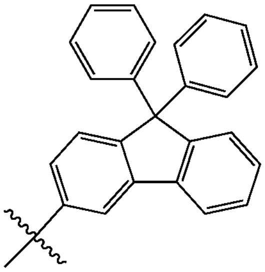
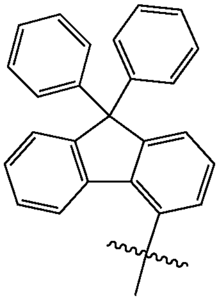
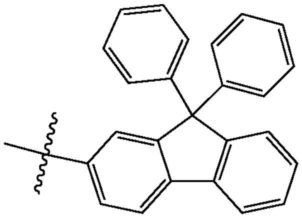
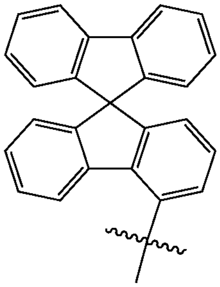
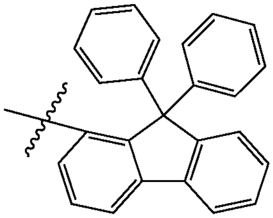
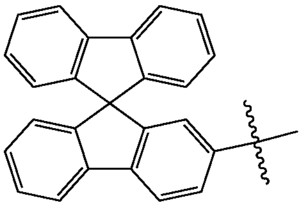

-continued
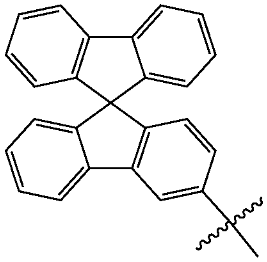
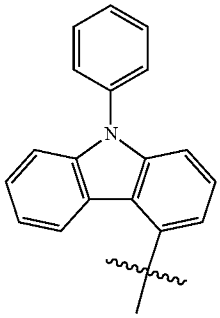
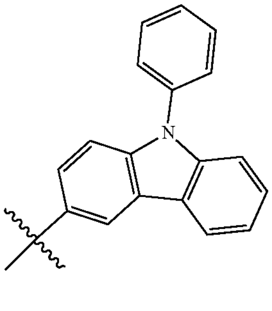
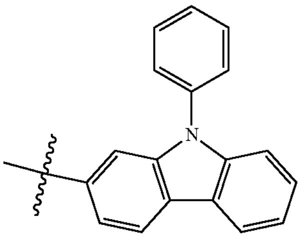
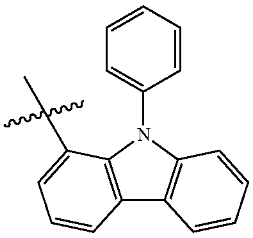
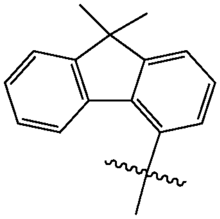
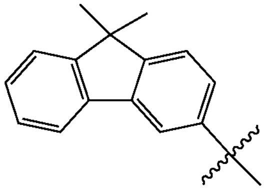
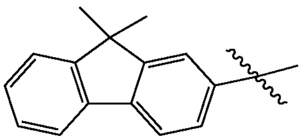
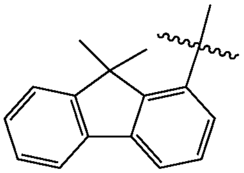
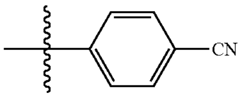
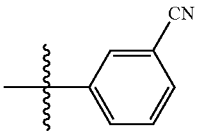
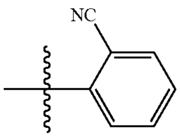
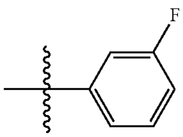
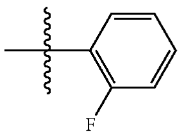
-continued
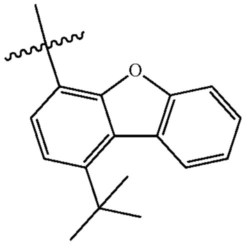
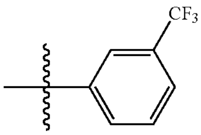
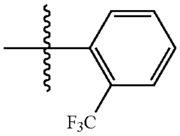
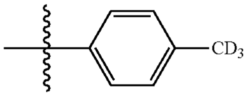
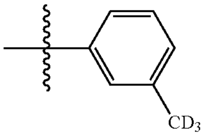
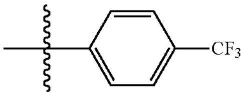
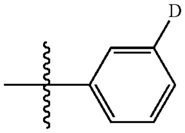
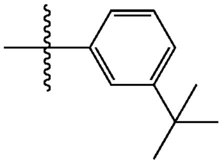
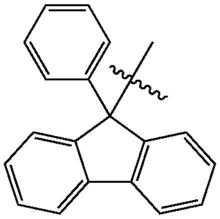
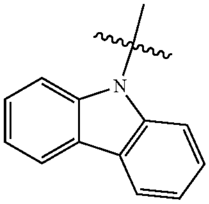
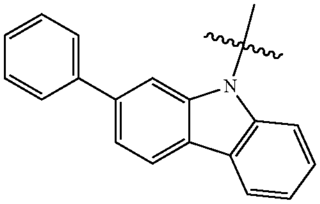
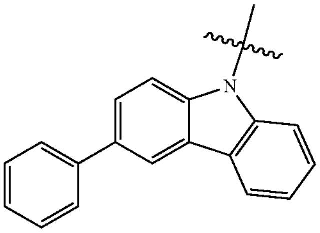
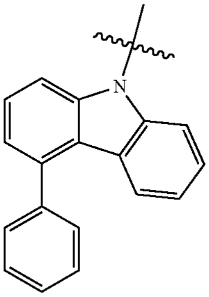
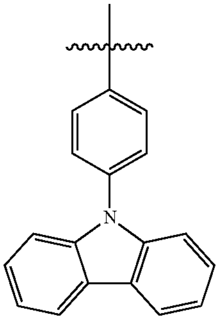

-continued
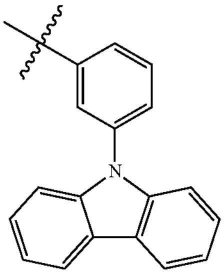
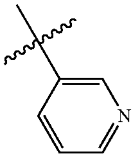
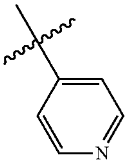
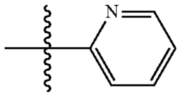
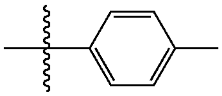
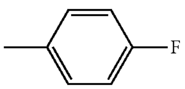
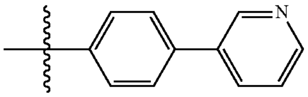
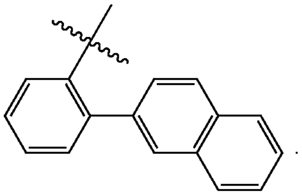
12. The organic compound according to claim 1, wherein the
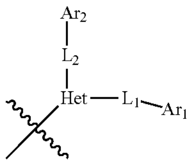
is selected from the group consisting of the following structures:
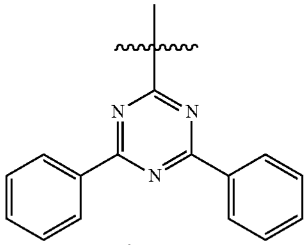
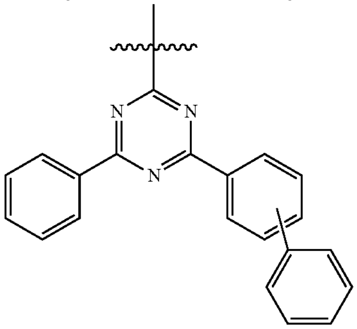
-continued
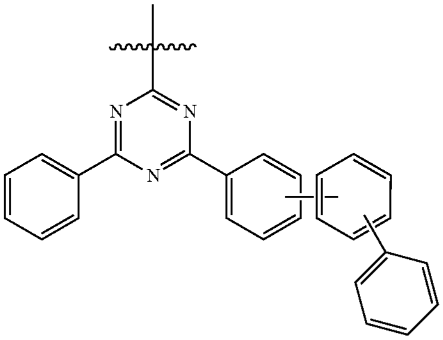
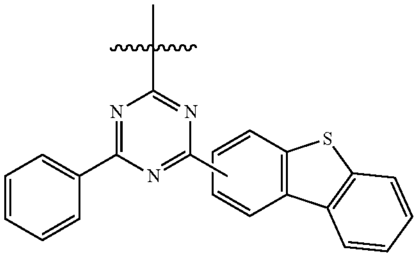
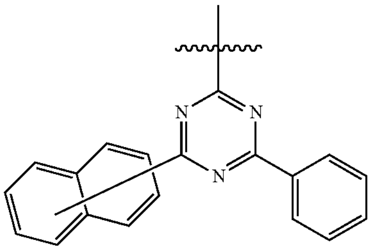
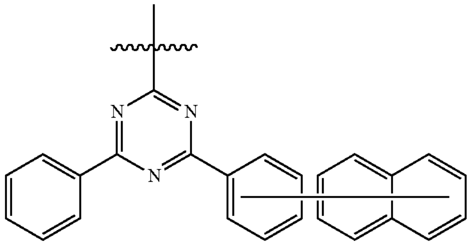
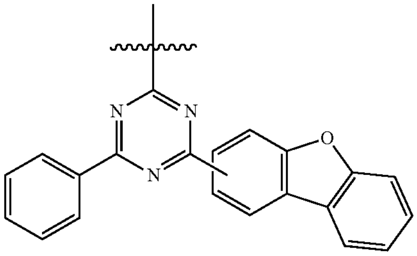
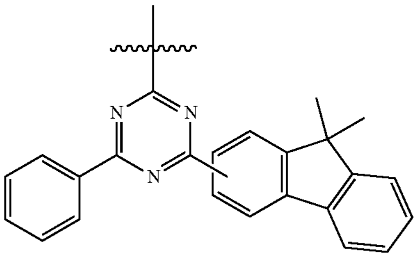

-continued
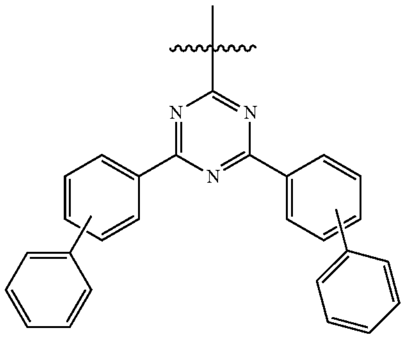
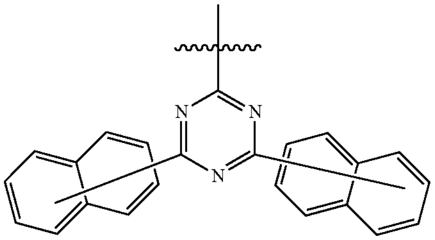
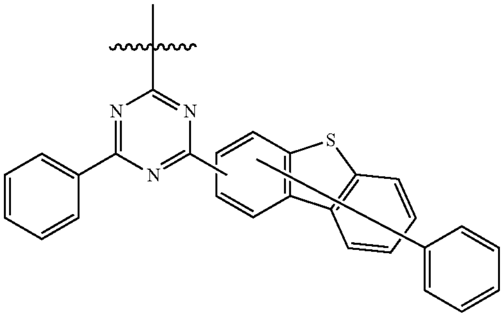
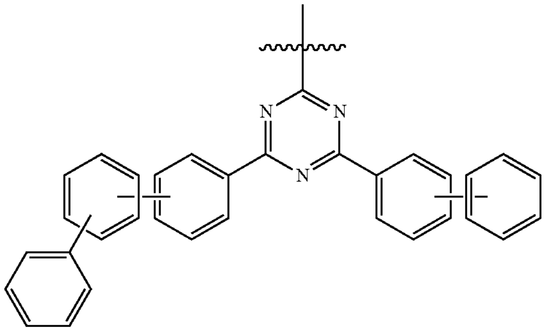
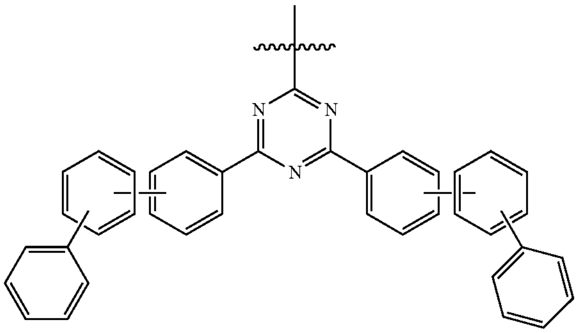
-continued
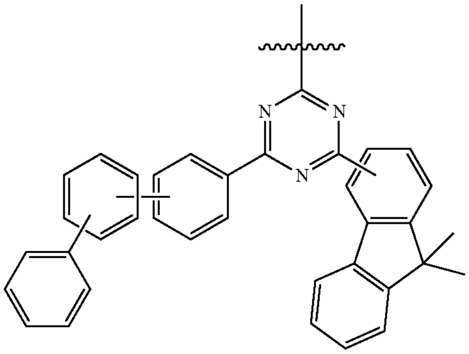
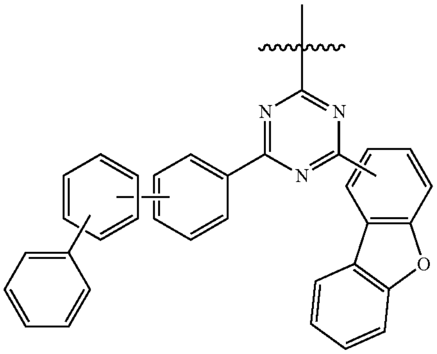
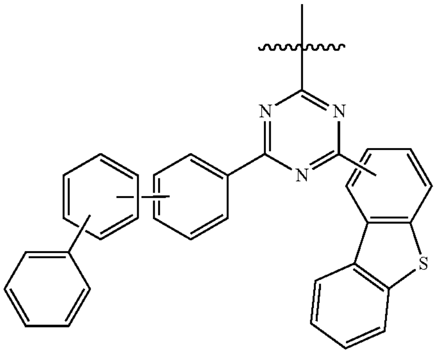
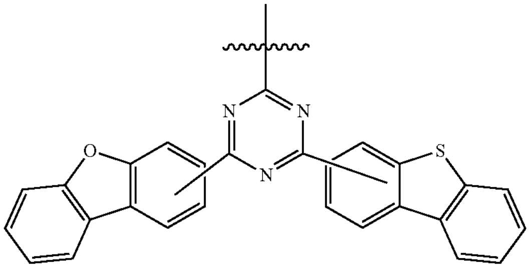
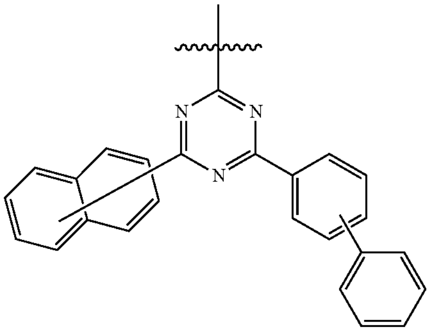

-continued
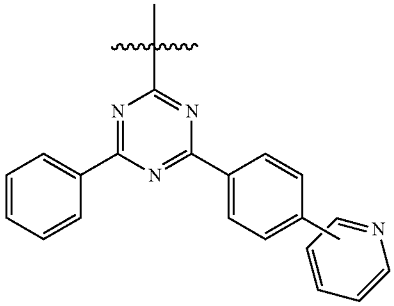
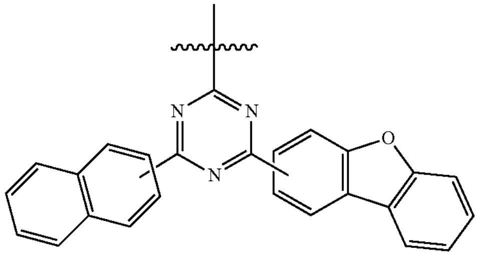
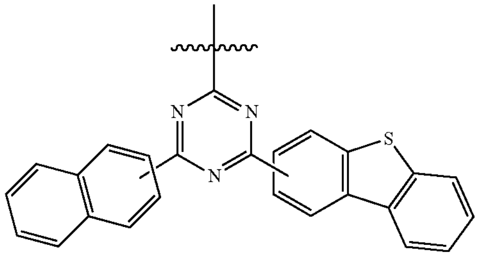
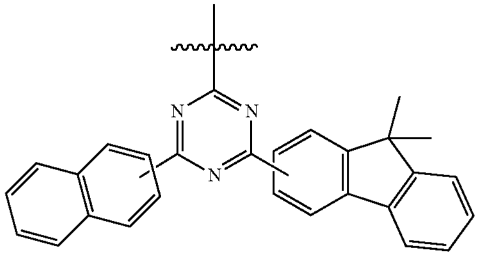
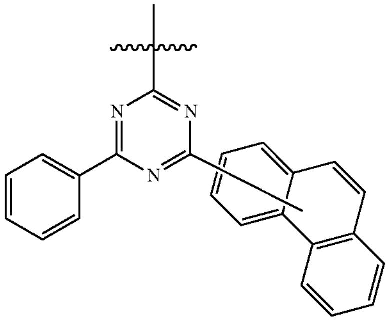
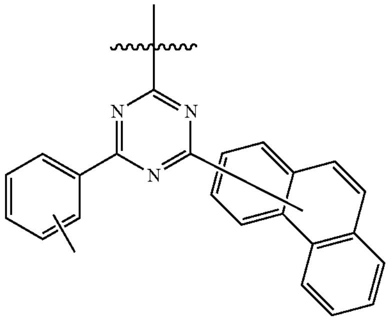
-continued
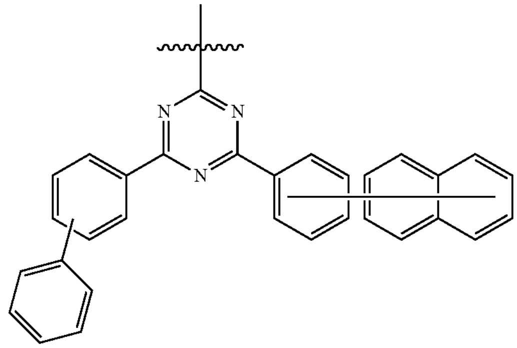
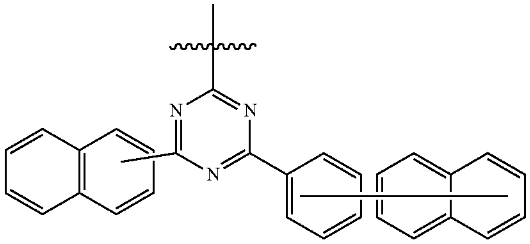
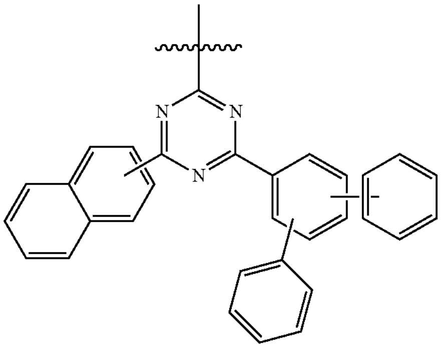
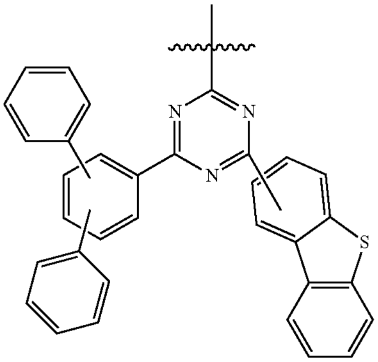
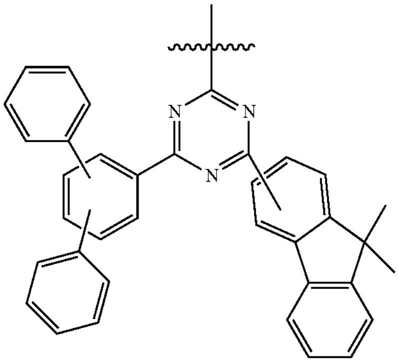

-continued
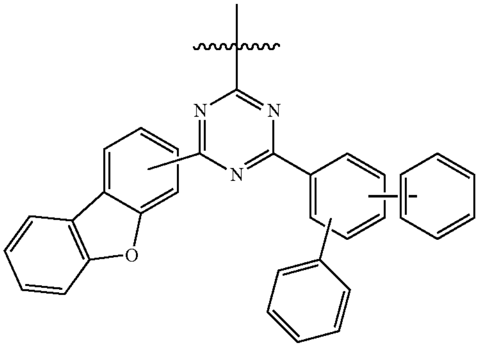
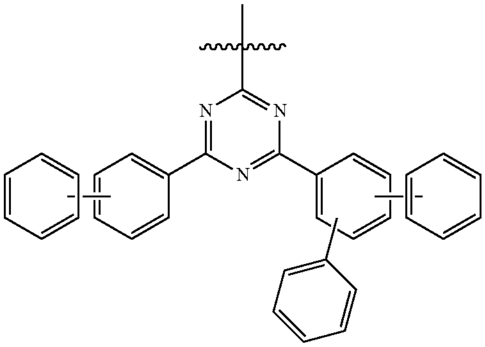
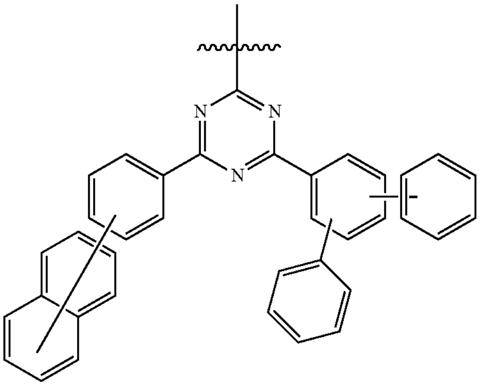
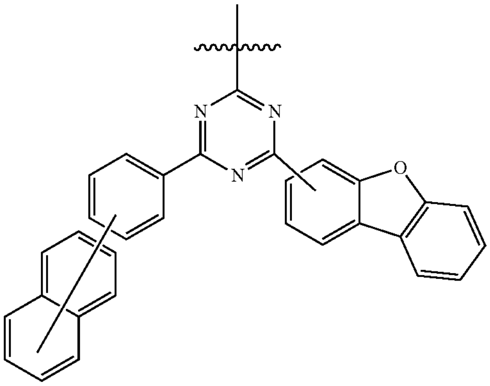
-continued
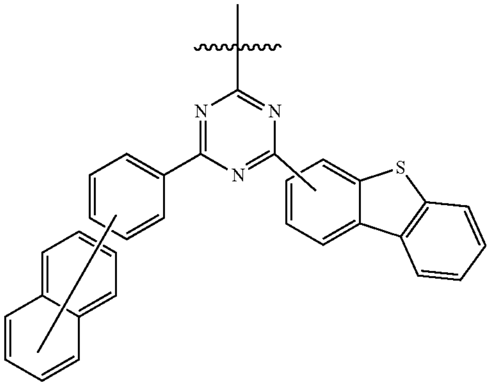
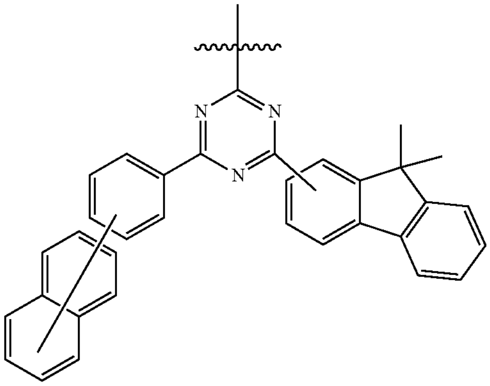
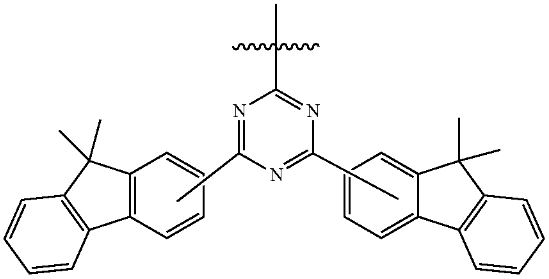
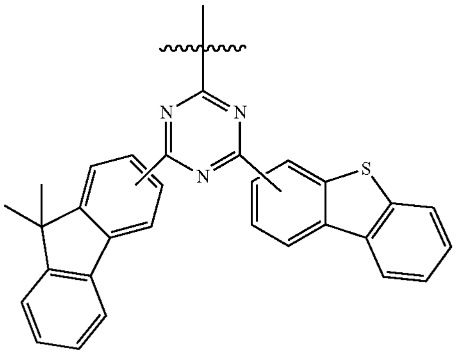

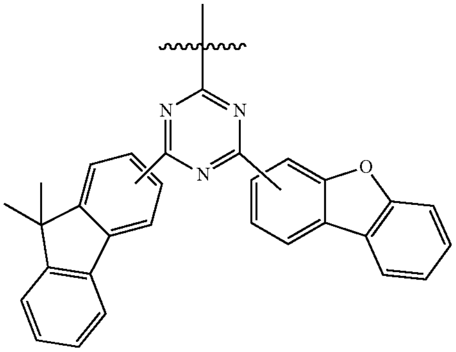
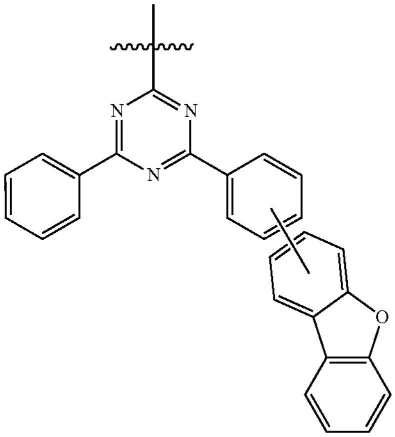
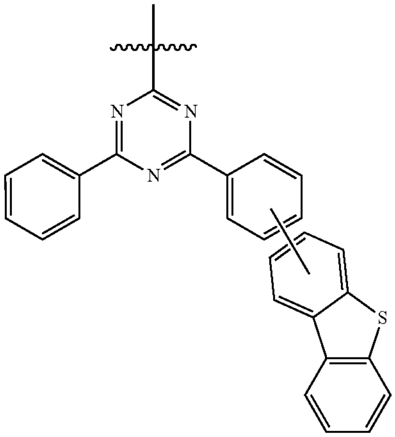
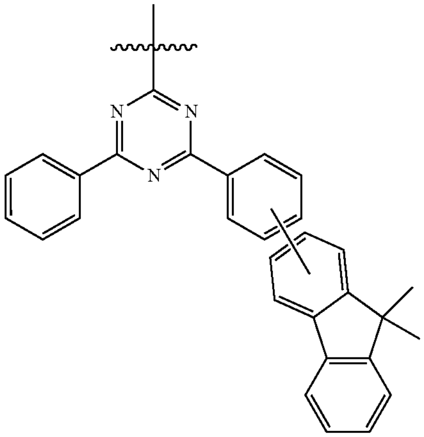
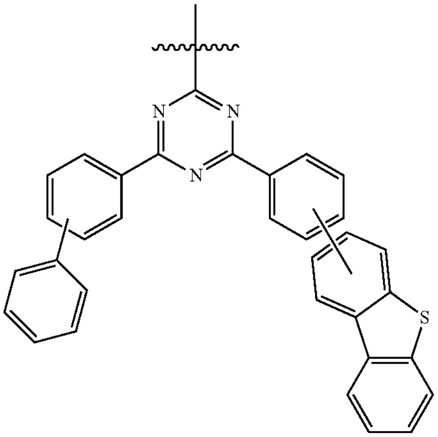
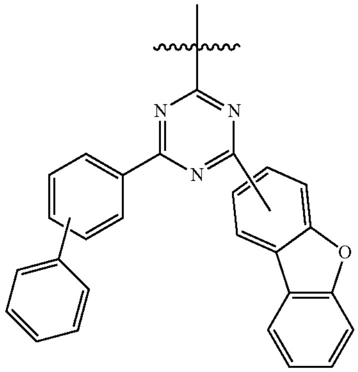
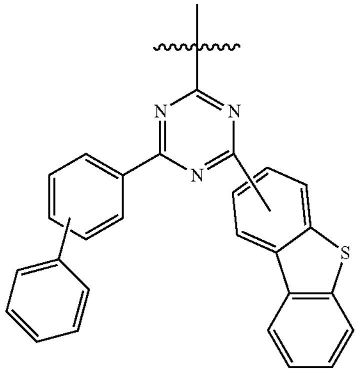
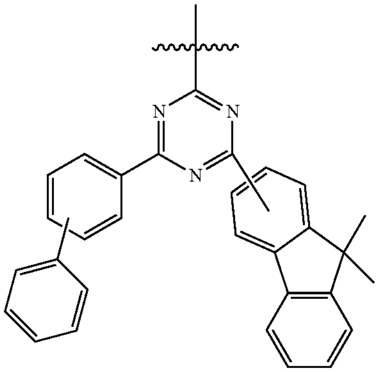

-continued
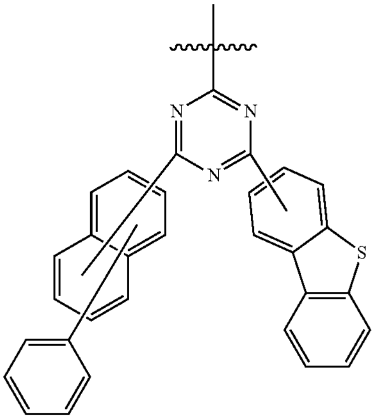
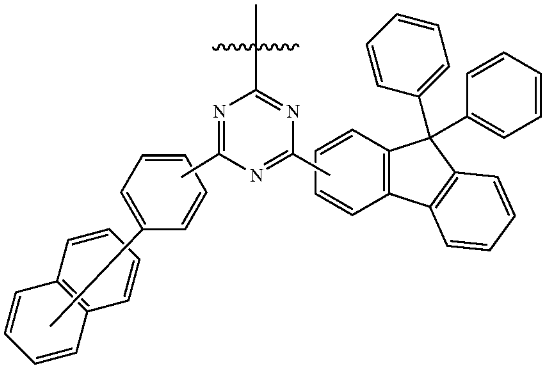
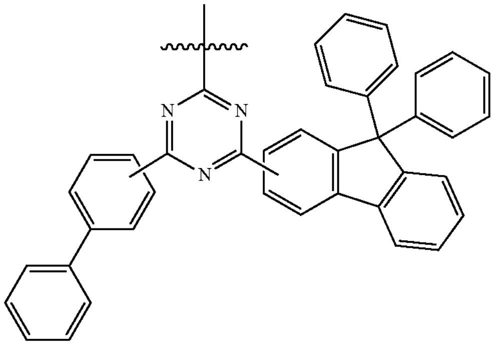
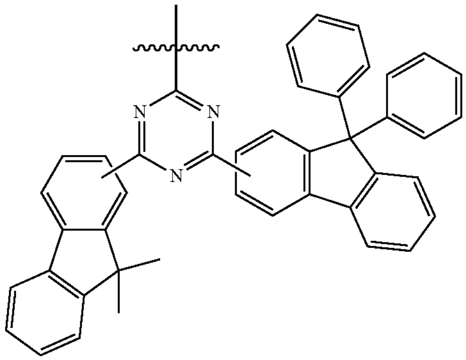
-continued
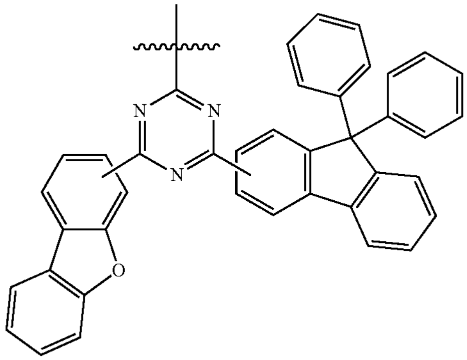
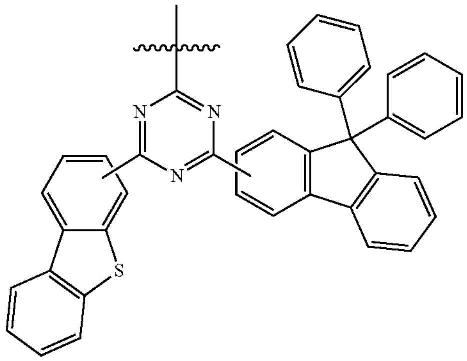
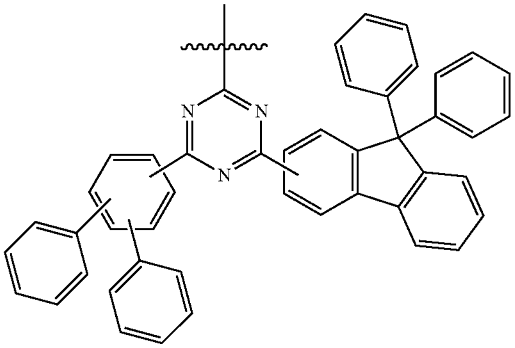
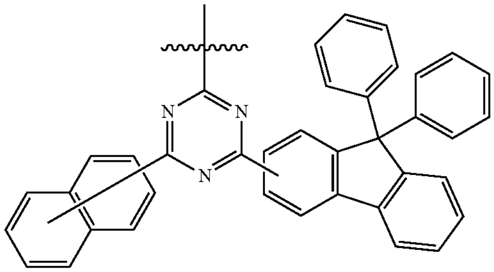
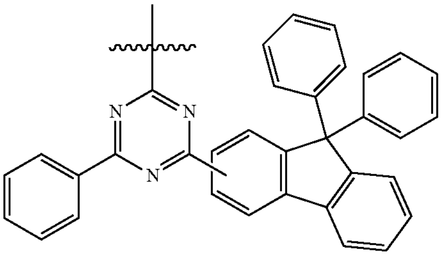

-continued
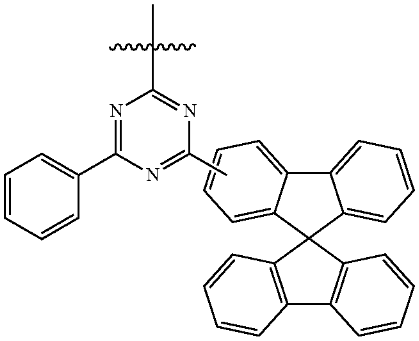
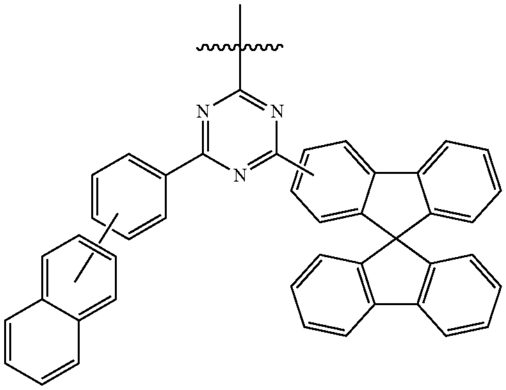
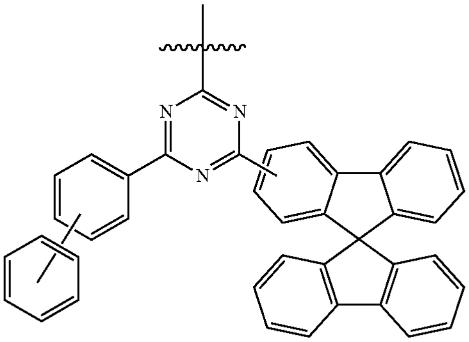
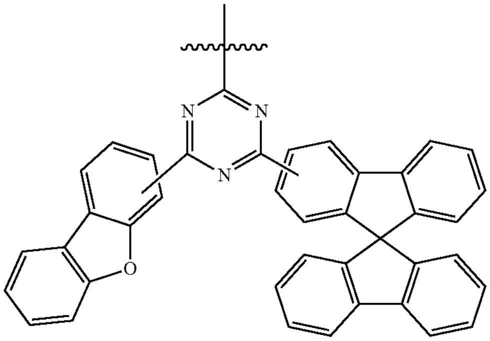
-continued
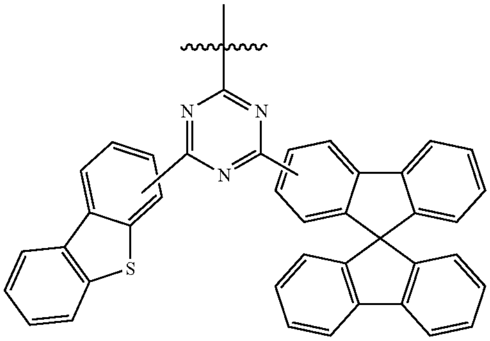
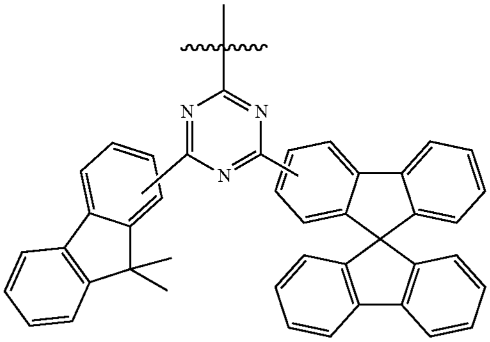
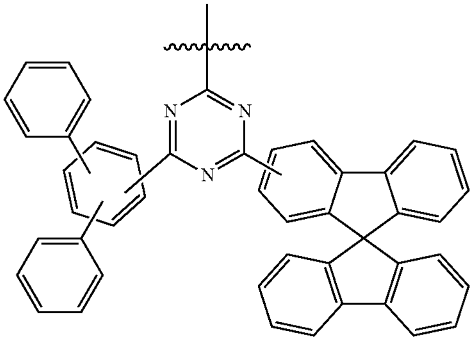
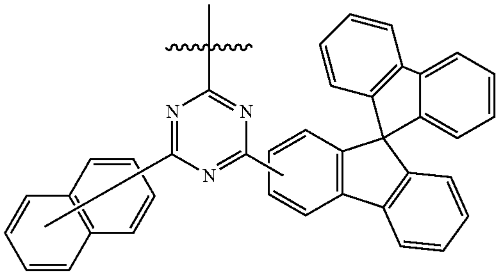
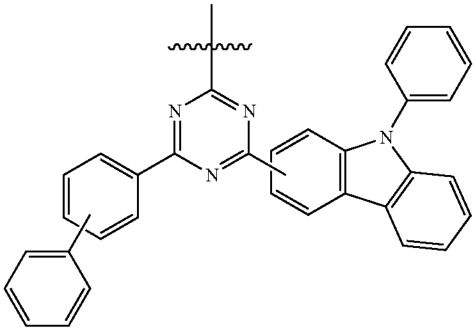

-continued
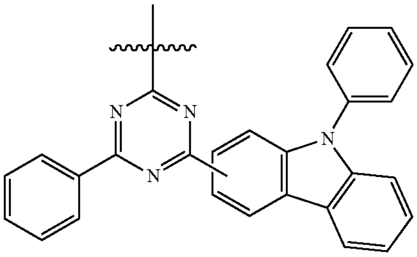
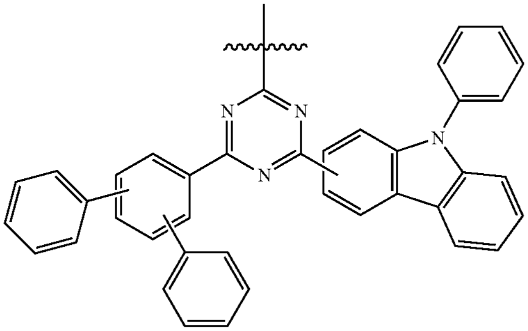
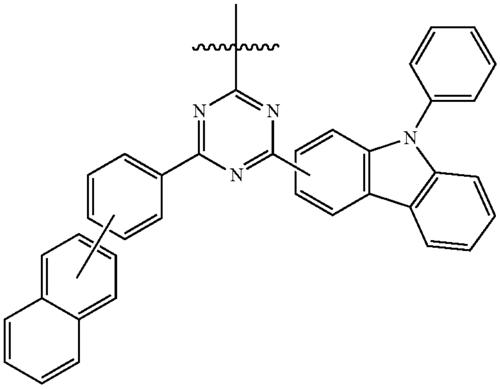
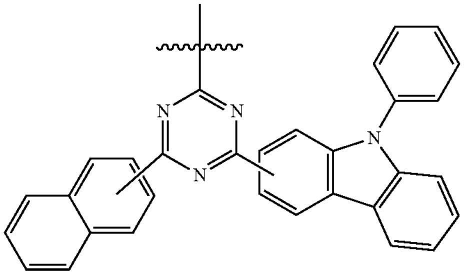
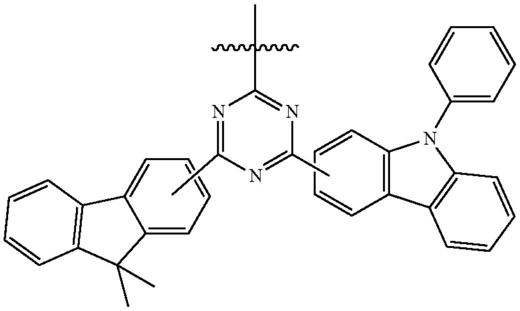
-continued
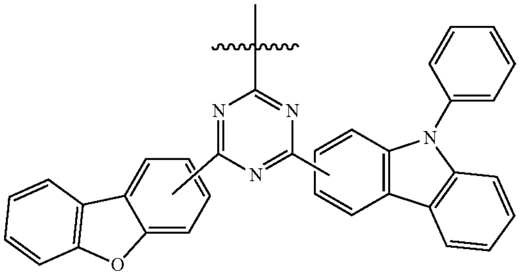
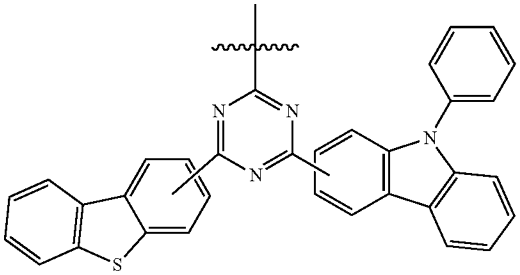
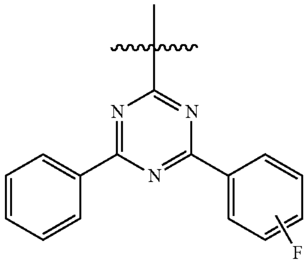
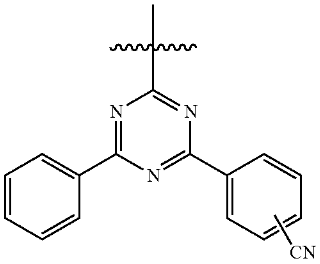
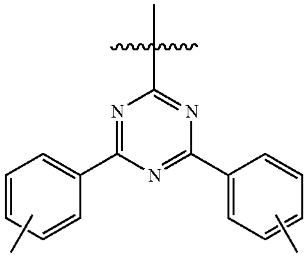
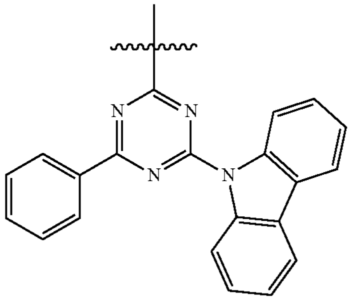

-continued
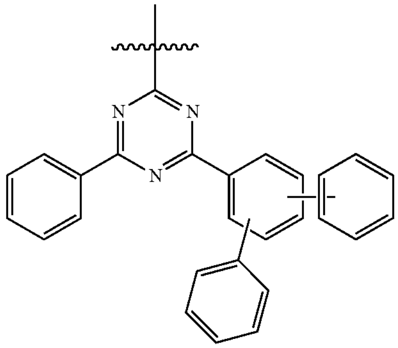
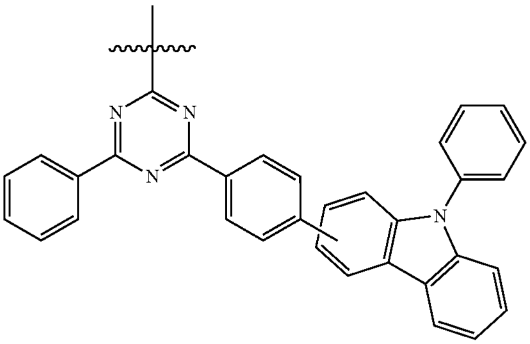
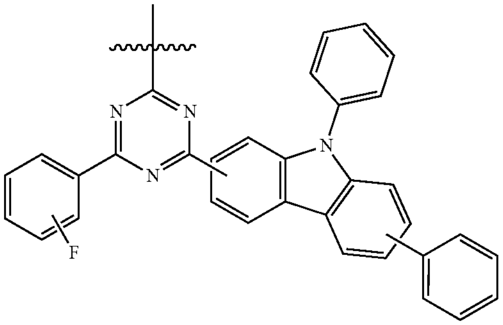
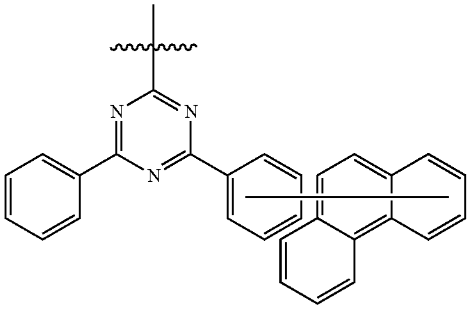
-continued
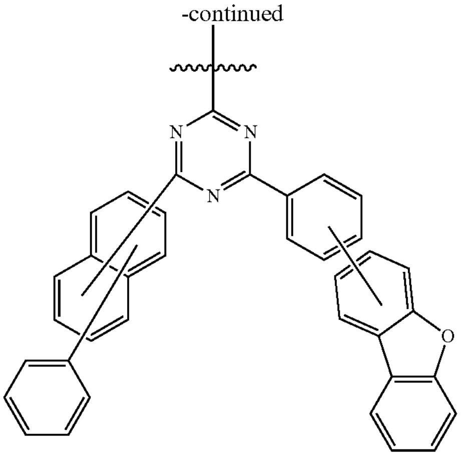
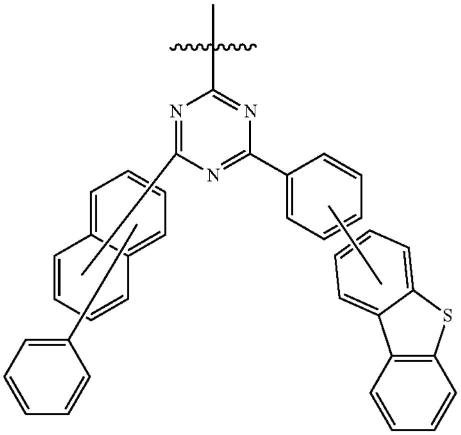
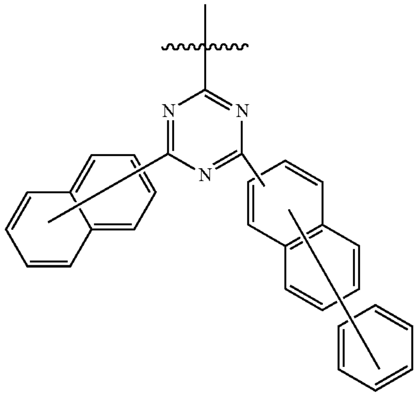
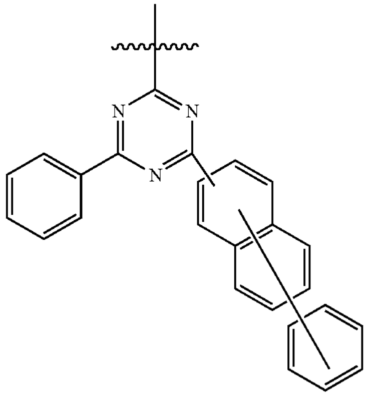

-continued
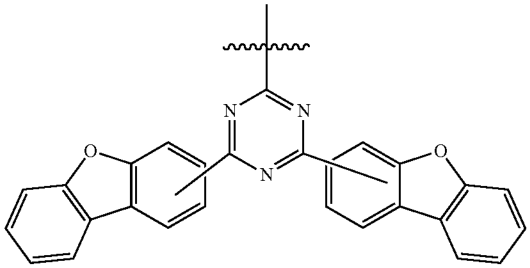
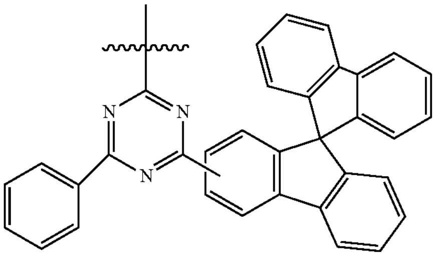
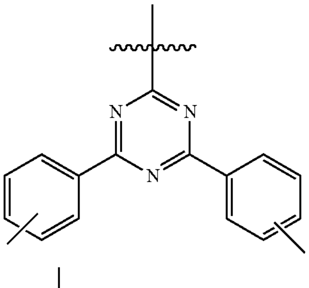
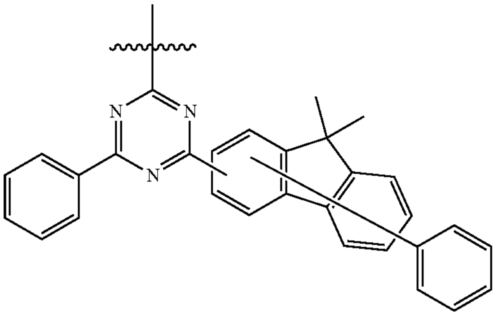
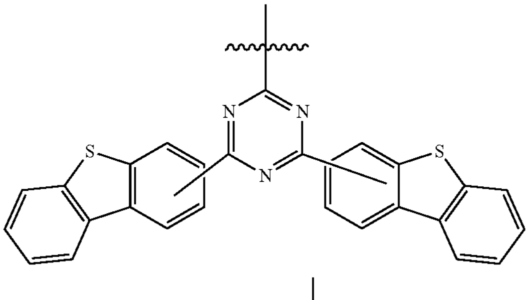
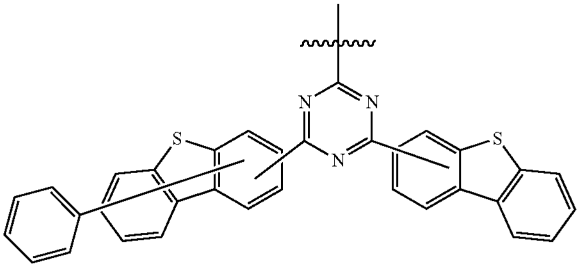
-continued
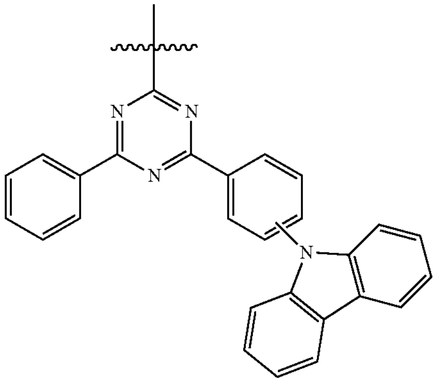
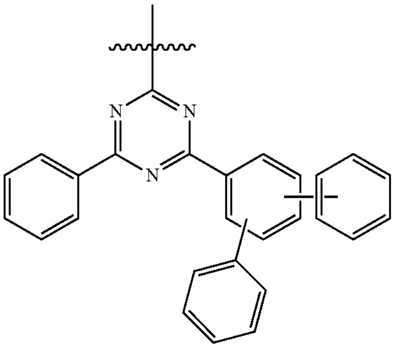
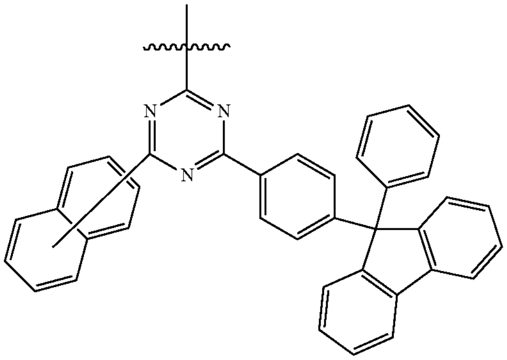
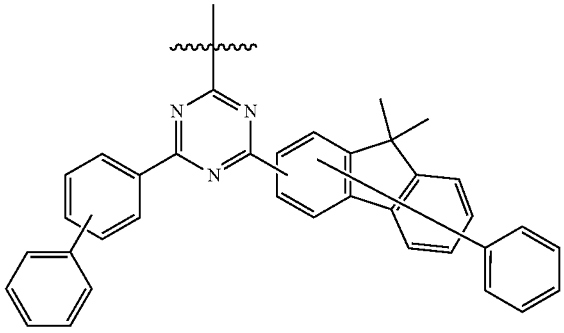
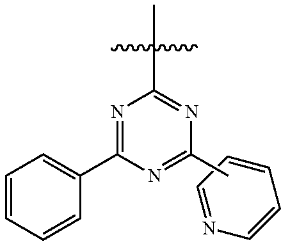

-continued
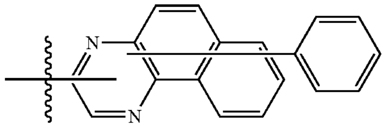
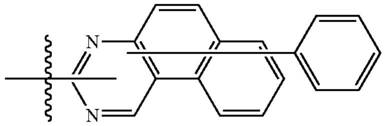
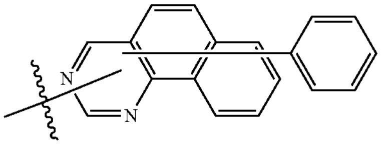
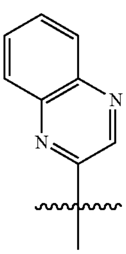
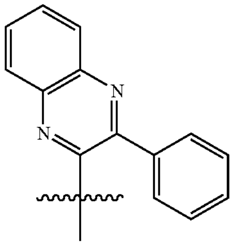
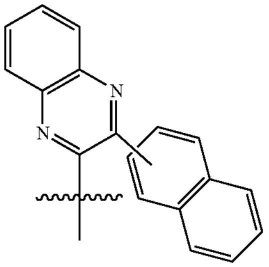
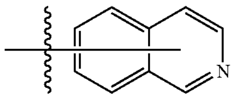
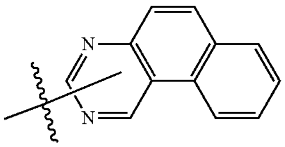
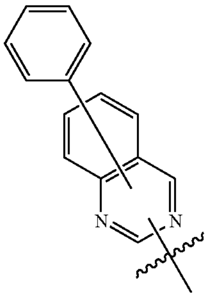
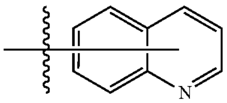
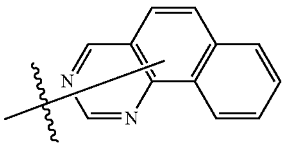
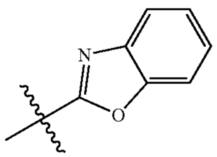
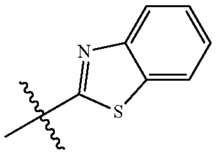
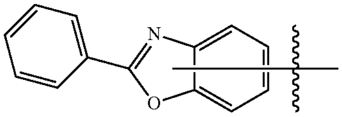
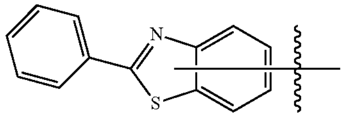
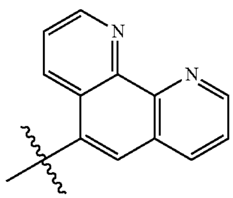
-continued
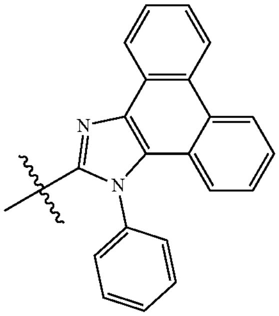
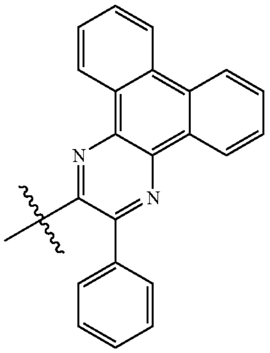
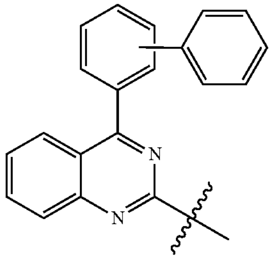
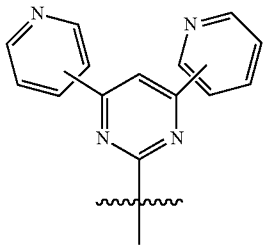
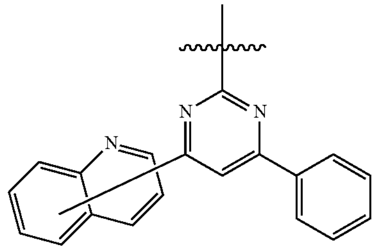
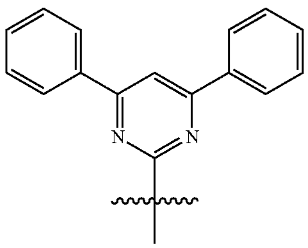
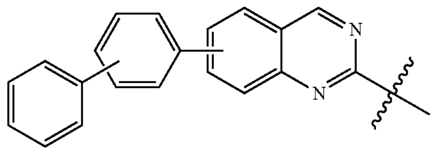
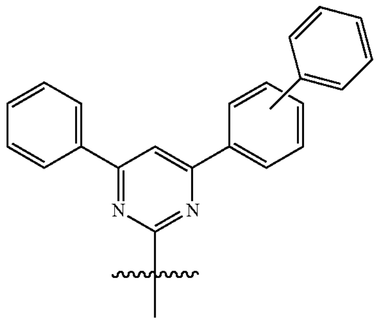

-continued
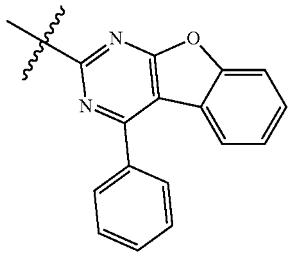
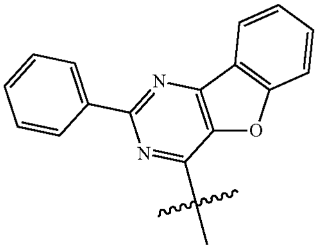
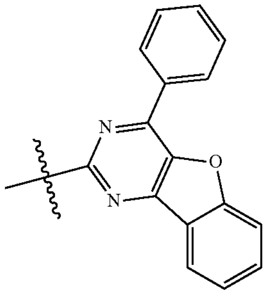
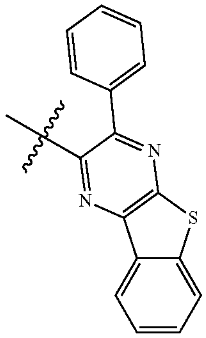
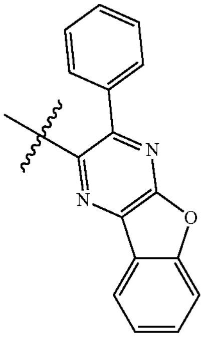
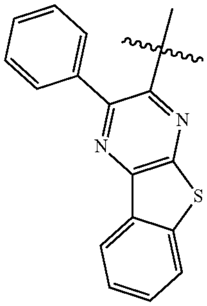
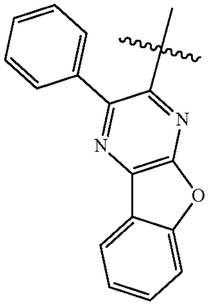
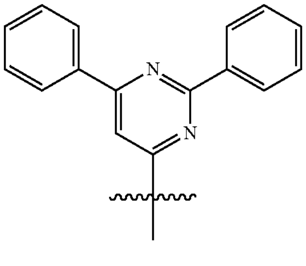
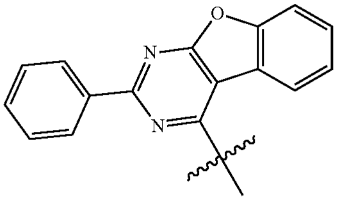
-continued
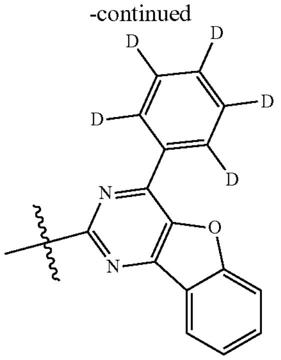
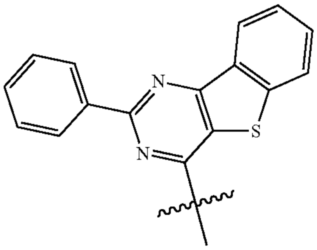
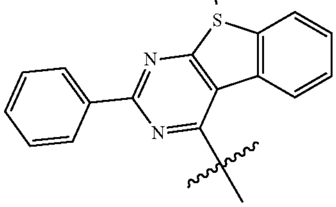
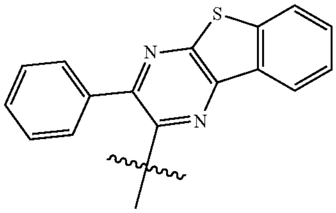
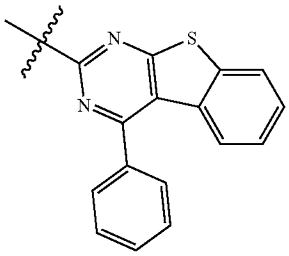
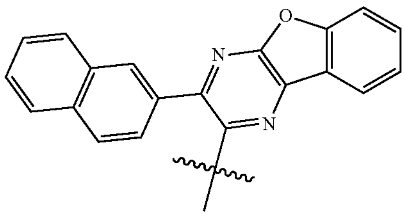
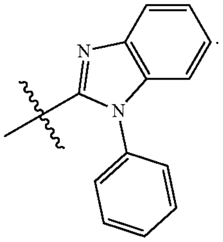

13. The organic compound according to claim 1, wherein $R_5$ and $R_6$ are each independently selected from the group consisting of methyl and the following groups:

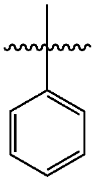

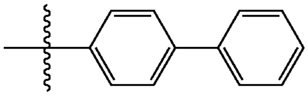

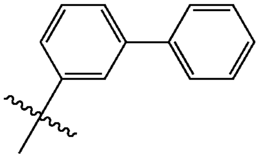

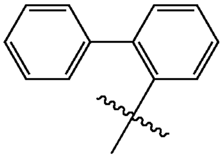

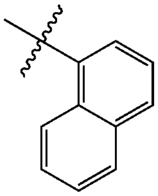

-continued

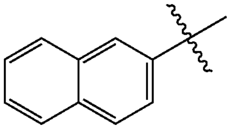

;

or $R_5$ and $R_6$ are linked to form one selected from the group consisting of the following spiro-rings together with carbon atoms attached to the two:

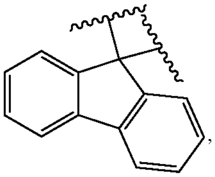

,

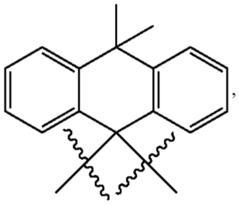

,

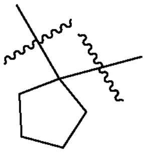

, and

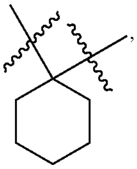

,

14. The organic compound according to claim 1, wherein the organic compound is selected from the group consisting of the following organic compounds:

1

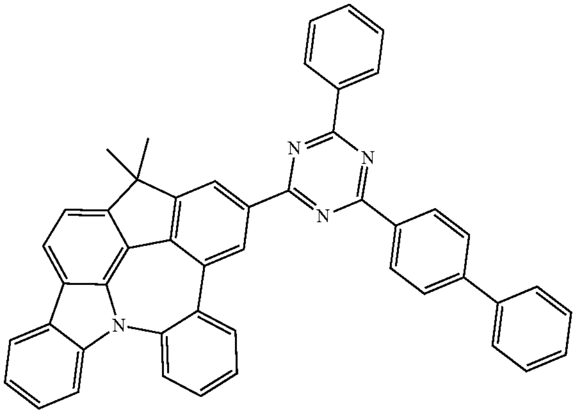

2

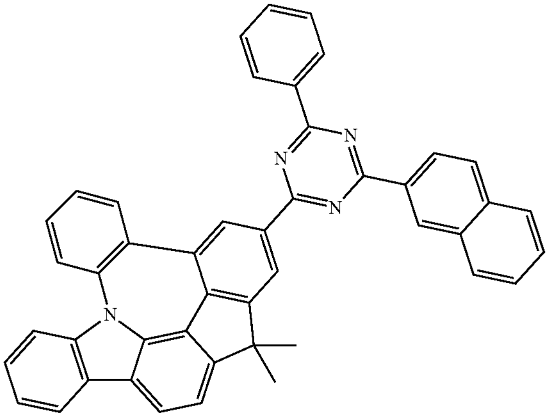

-continued
3
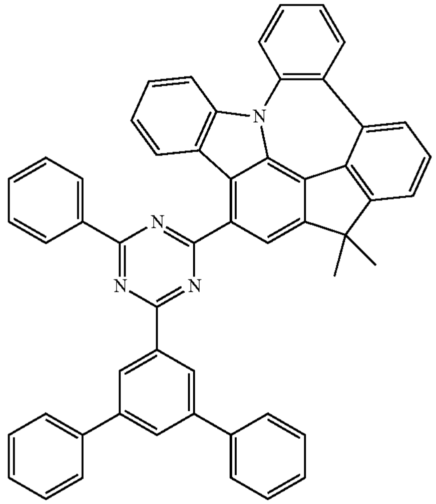
4
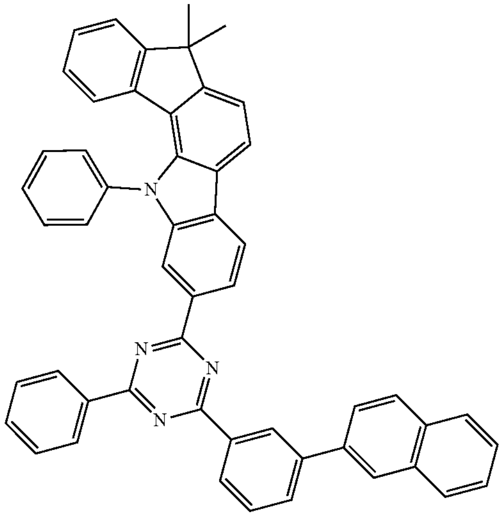
5
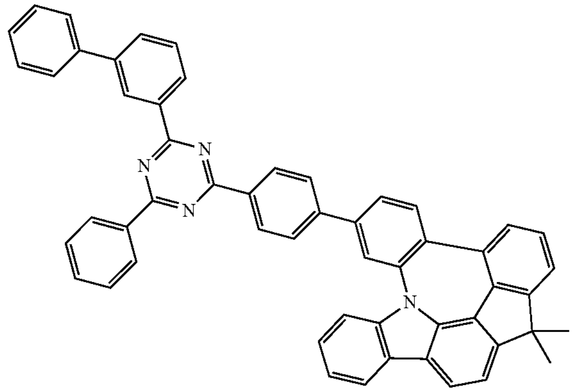
6
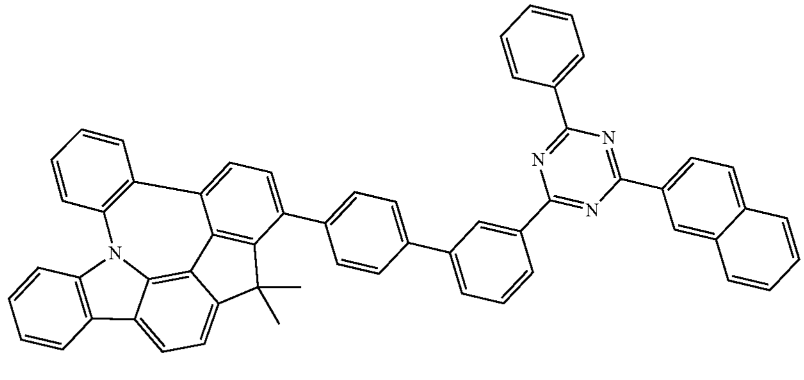

-continued
7
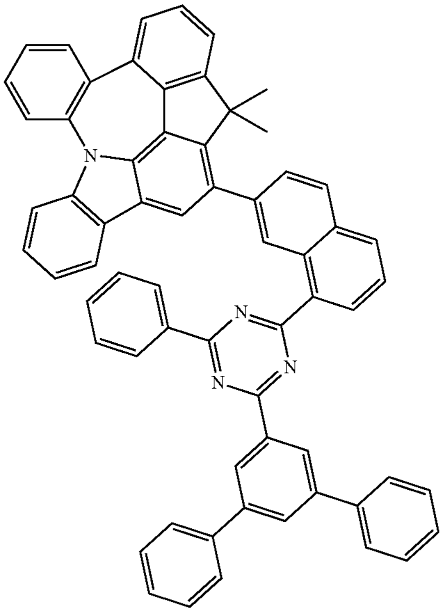
8
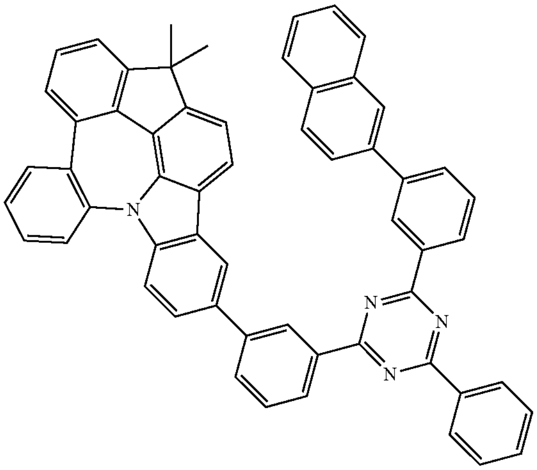
9
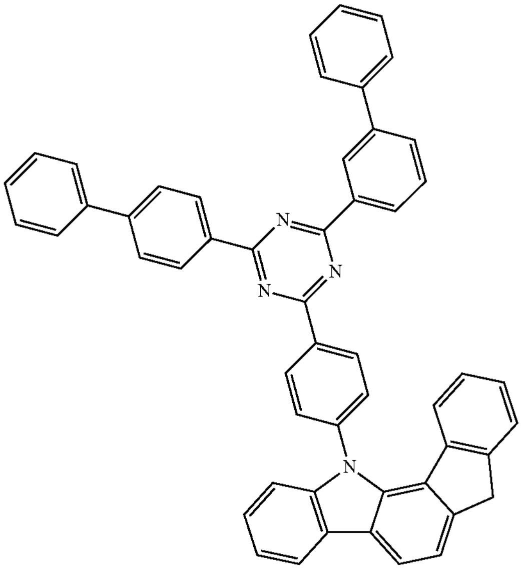
10
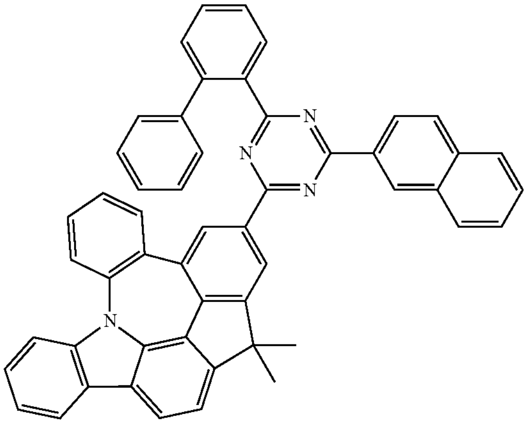

-continued
11
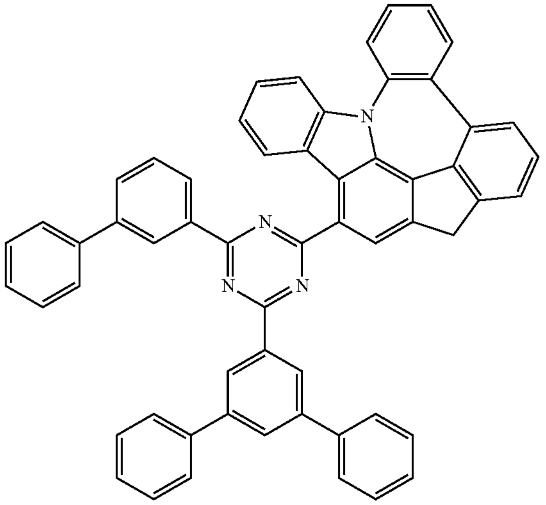
12
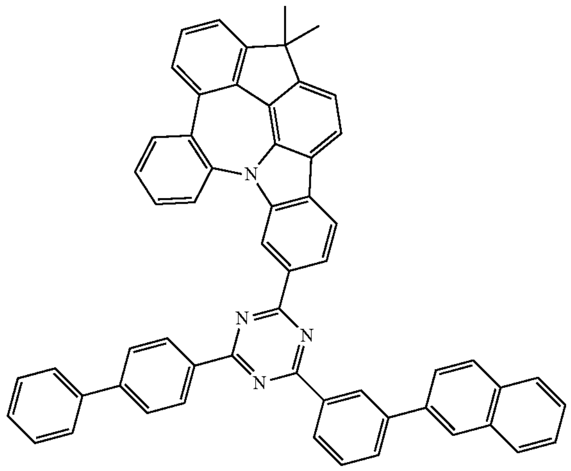
13
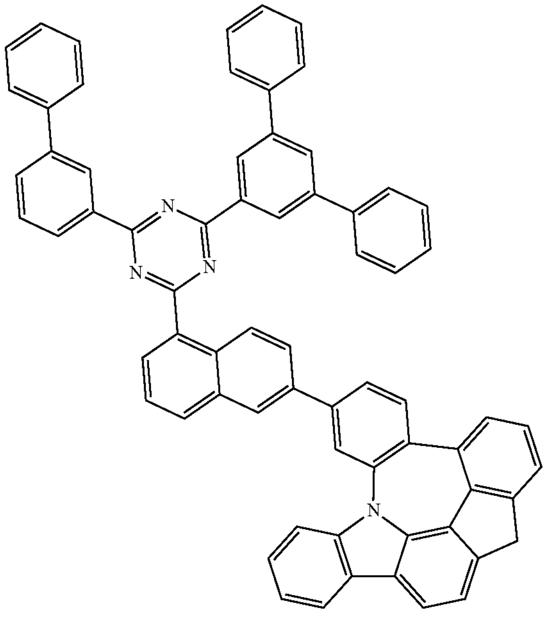
14
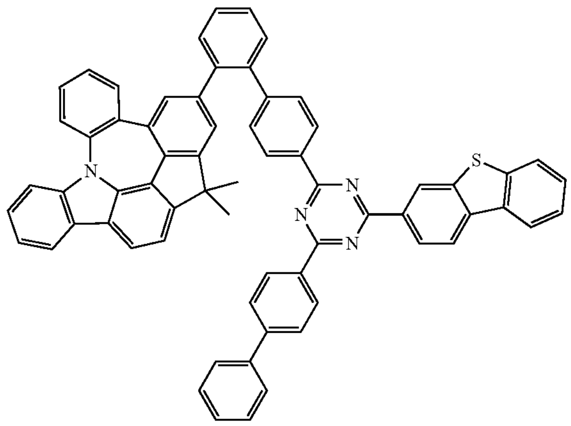

-continued
15
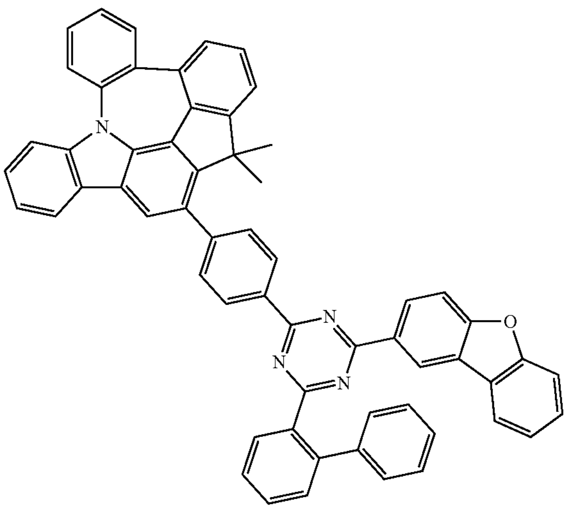
16
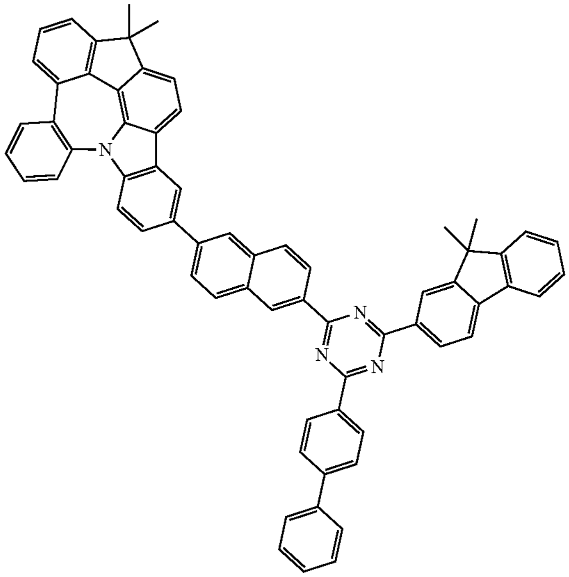
17
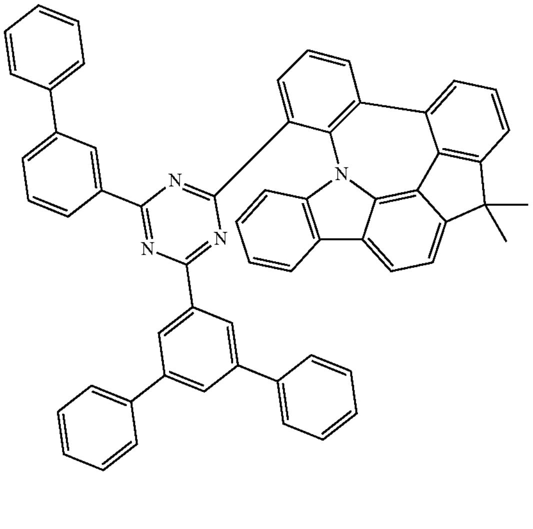
18
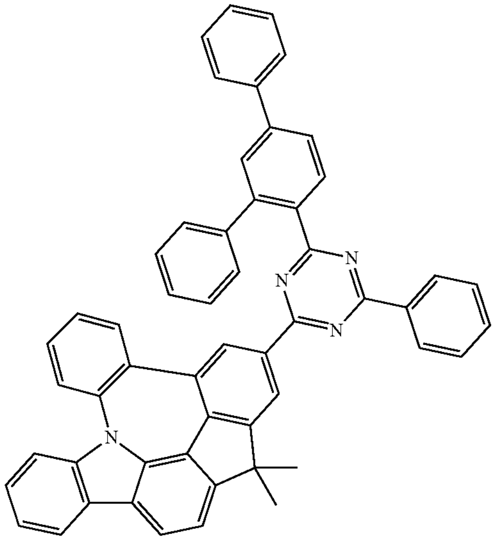

-continued
19
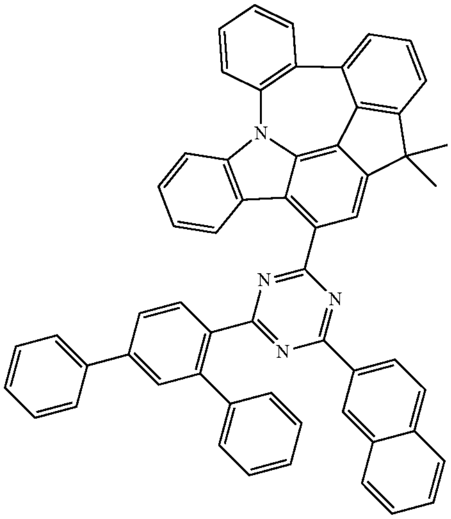
20
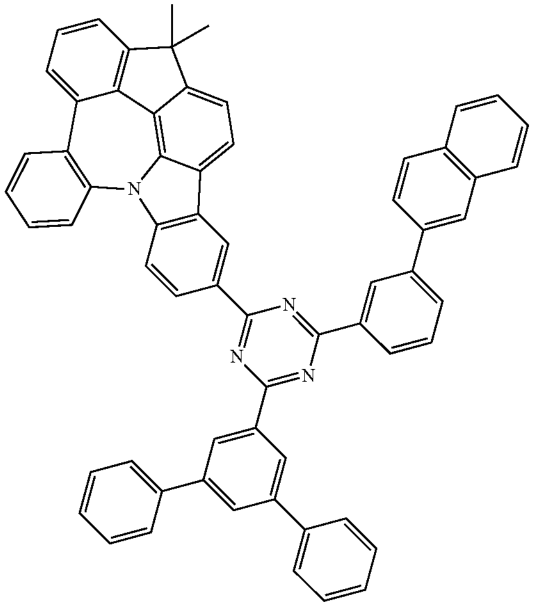
21
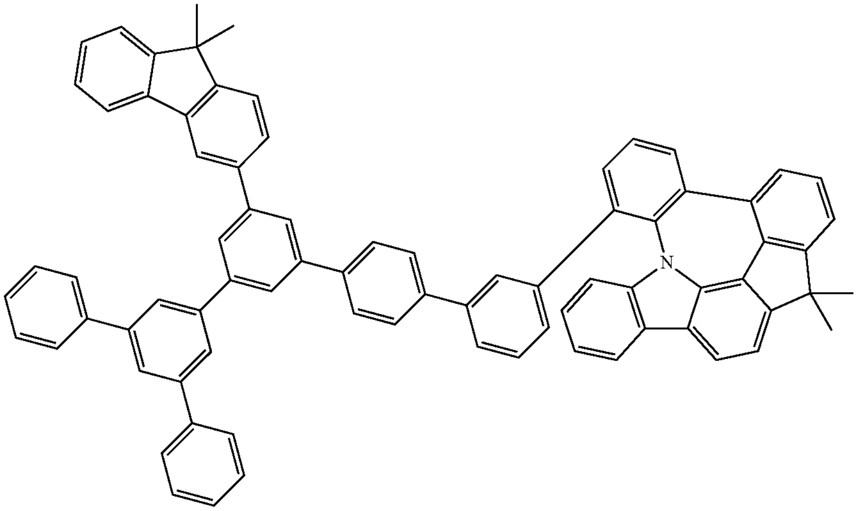
22
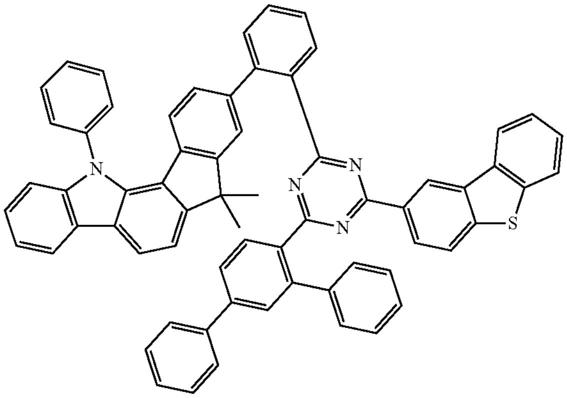
23
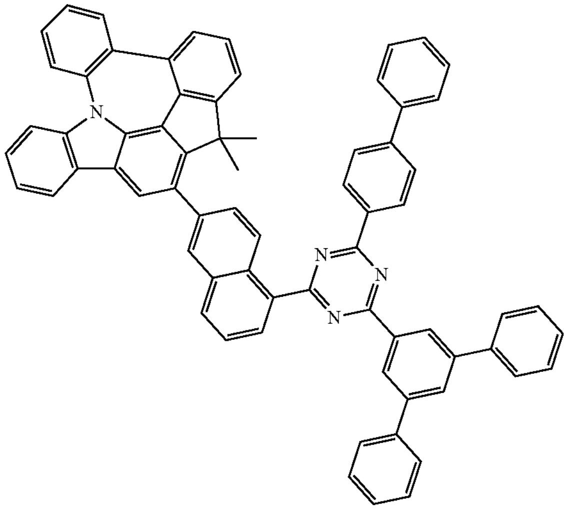

-continued
24
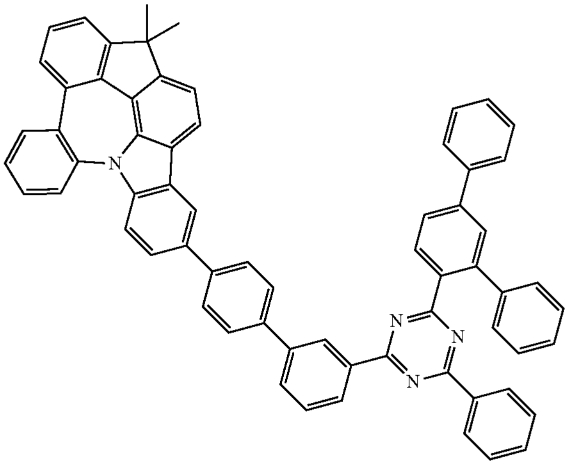
25
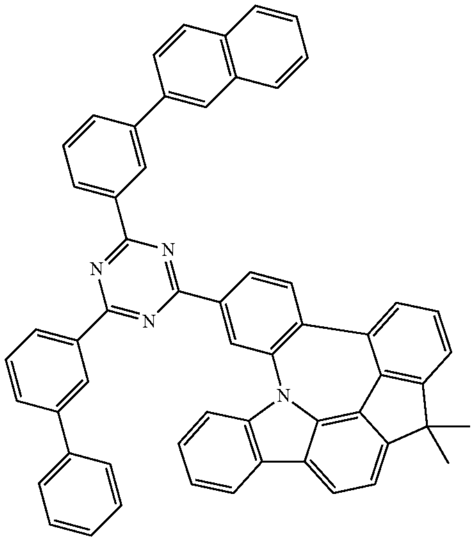
26
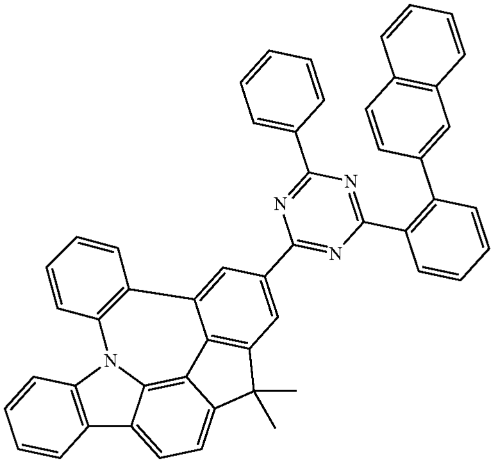
27
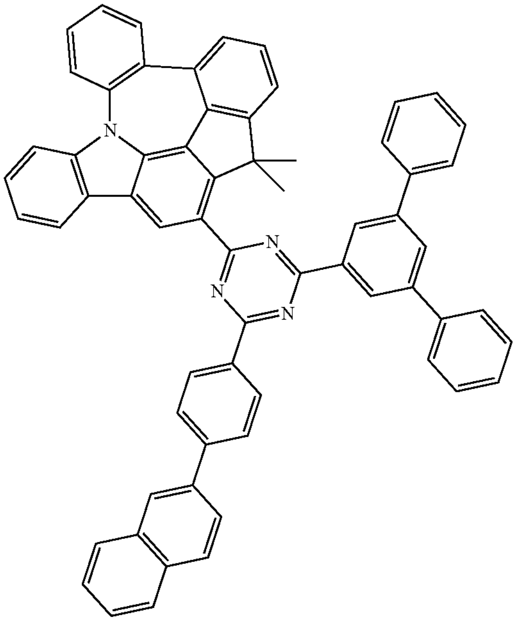

-continued
28
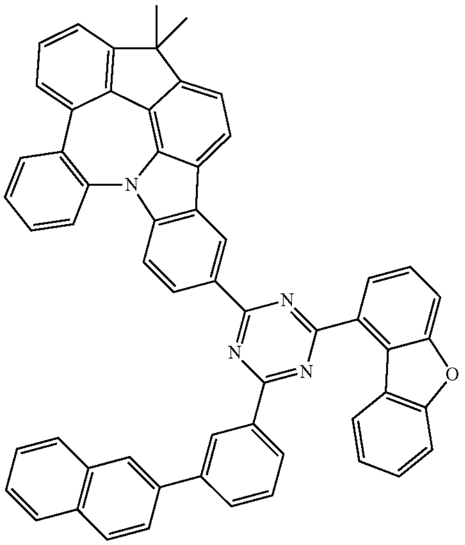
29
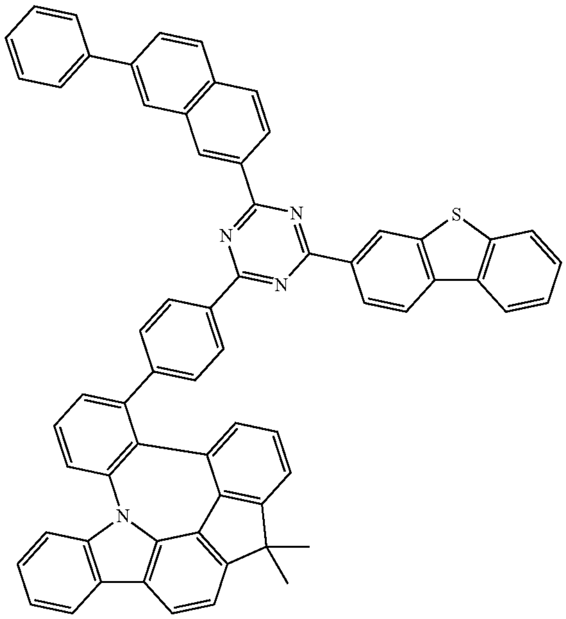
30
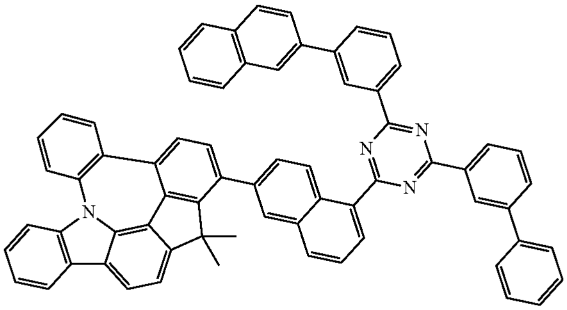
31
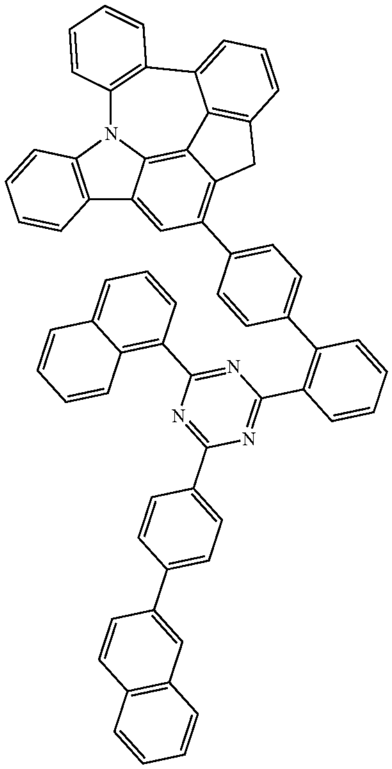

-continued
32
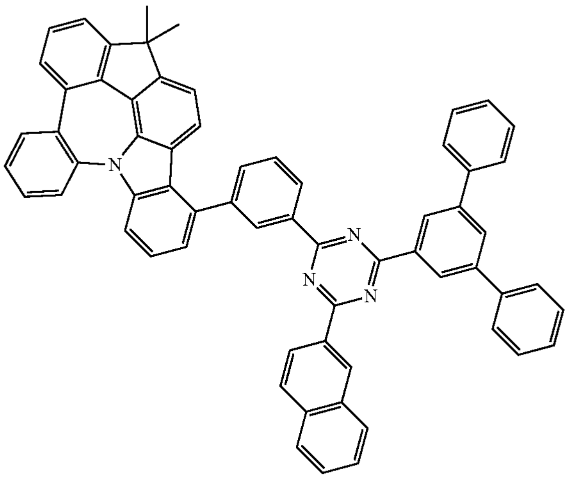
33
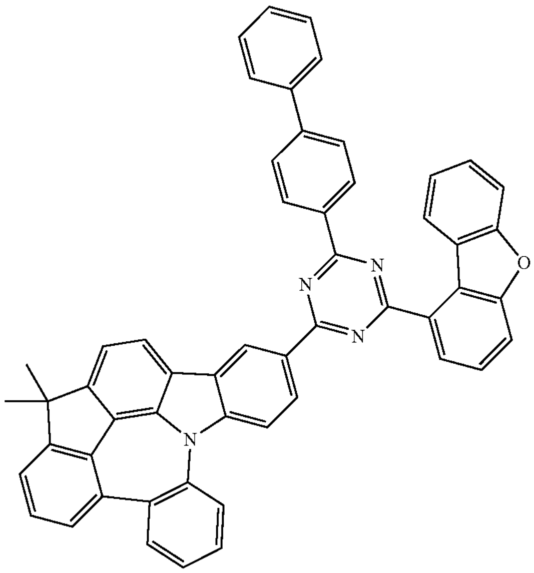
34
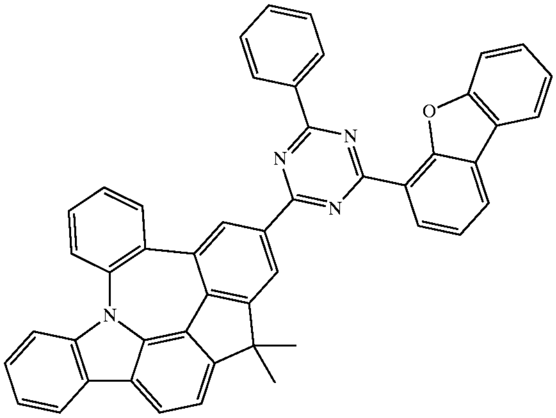
35
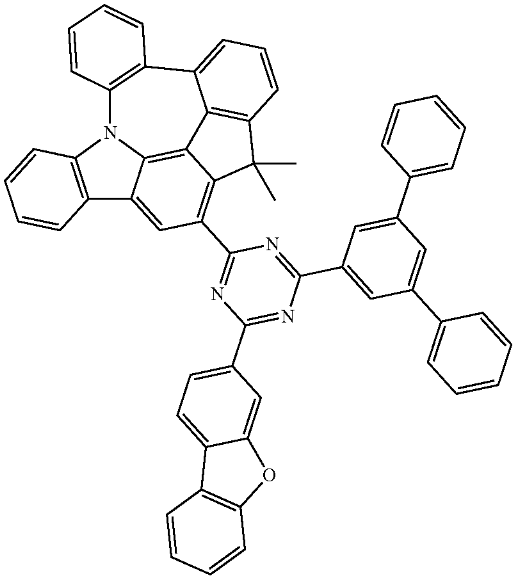

-continued
36
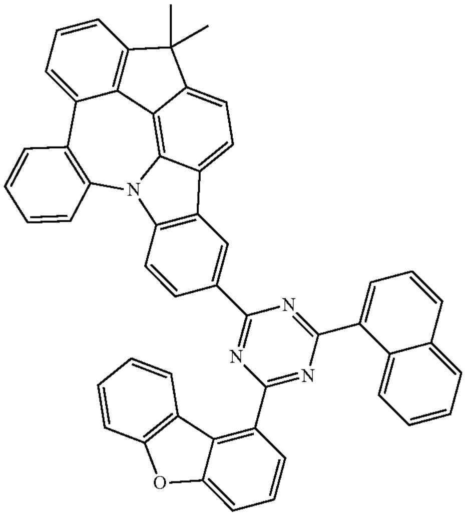
37
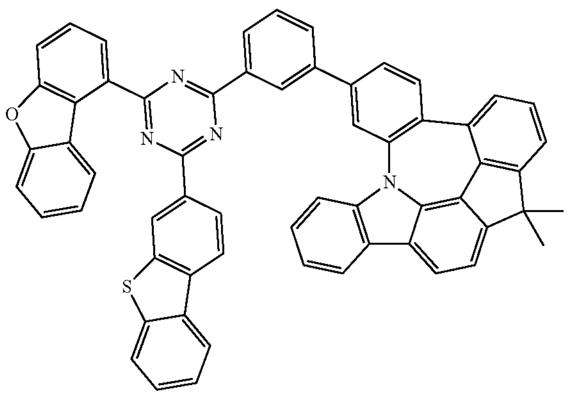
38
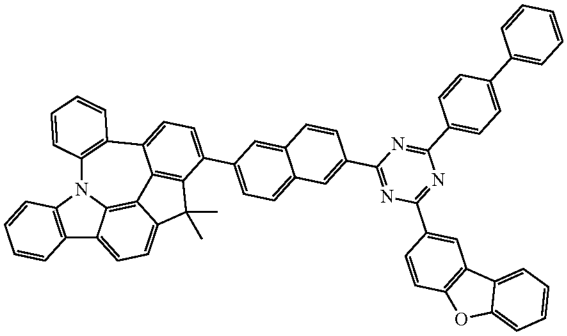
39
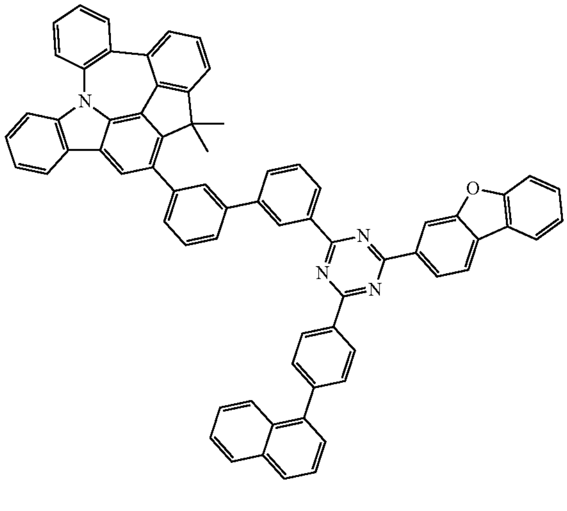

-continued
40
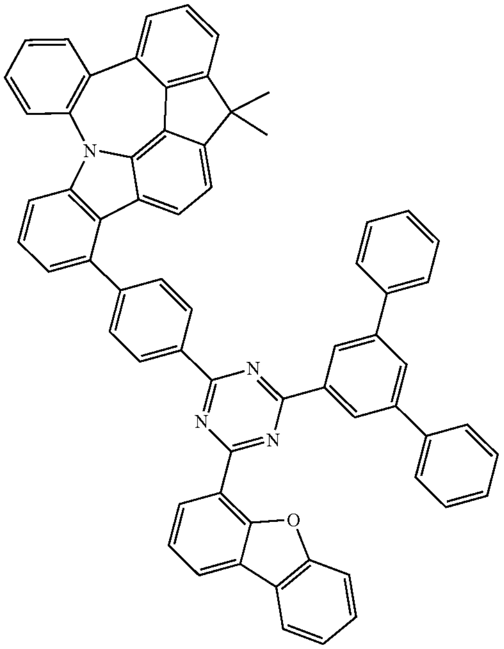
41
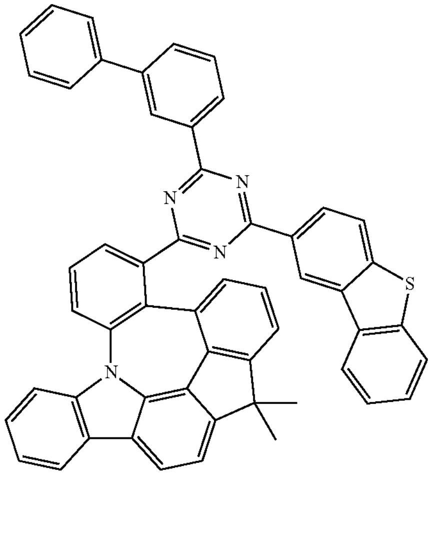
42
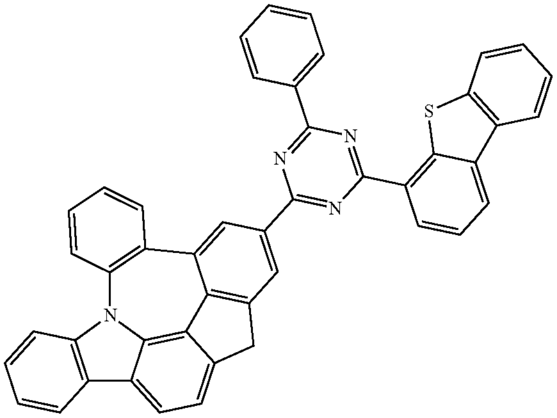
43
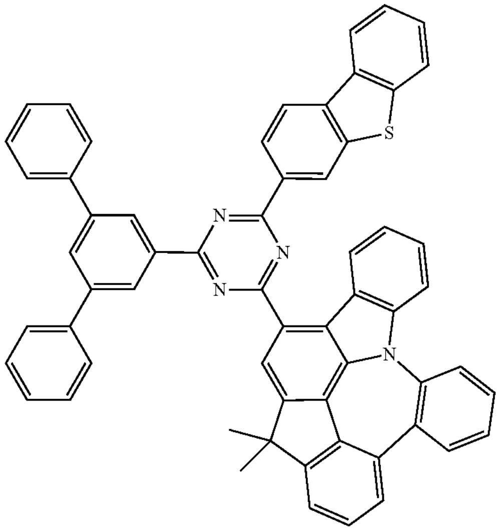

-continued
44
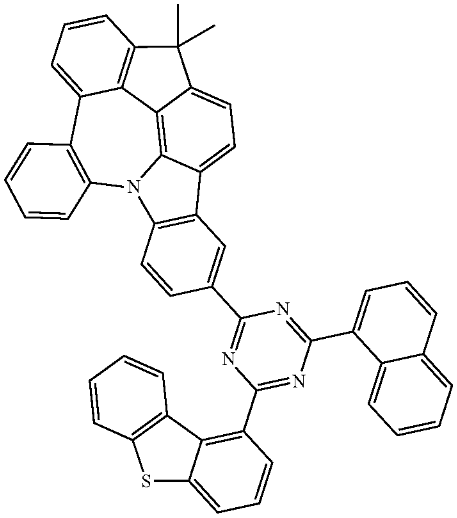
45
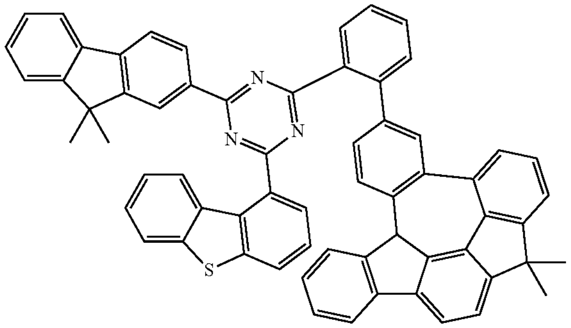
46
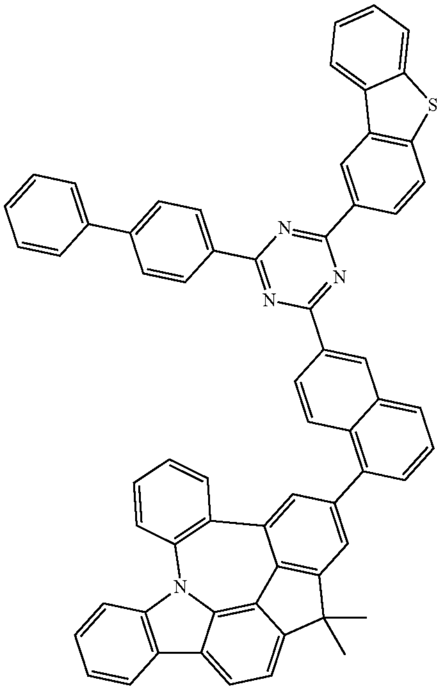
47
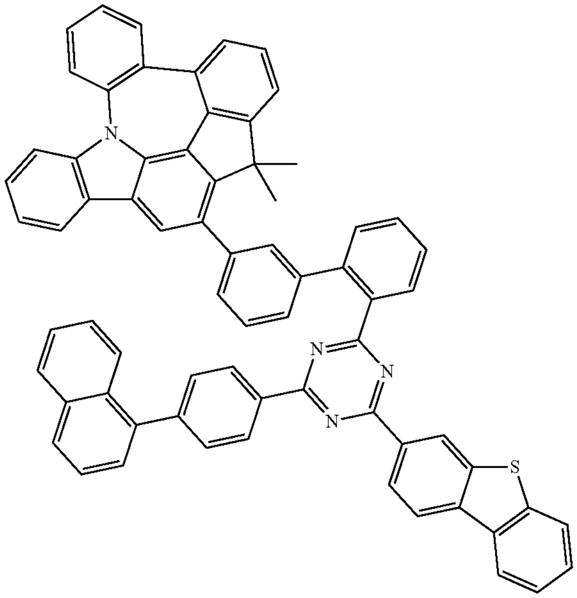

-continued
48
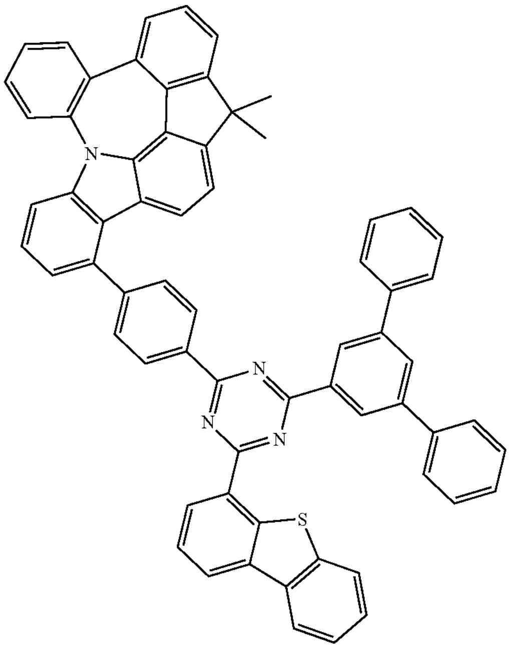
49
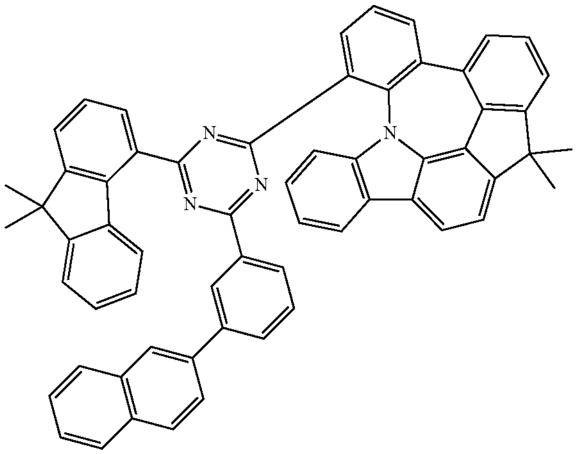
50
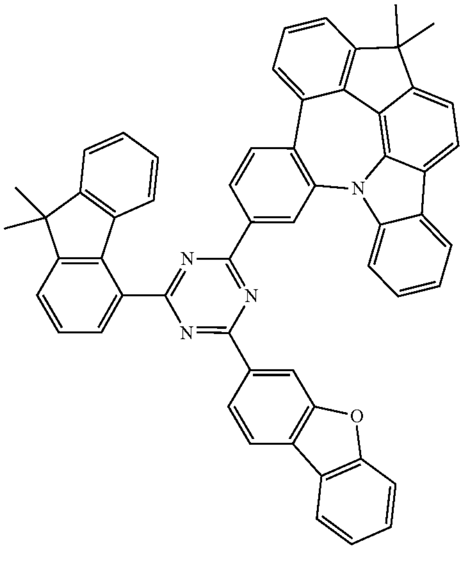
51
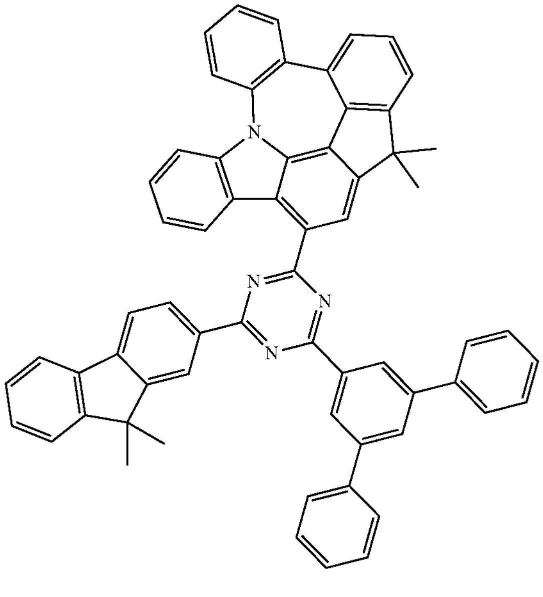

-continued
52
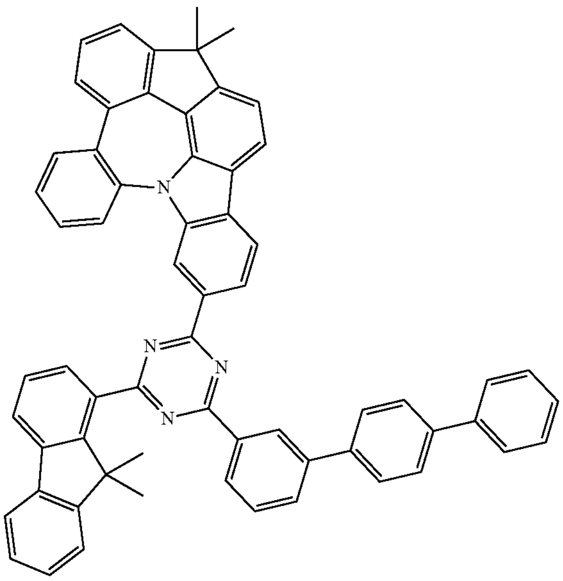
53
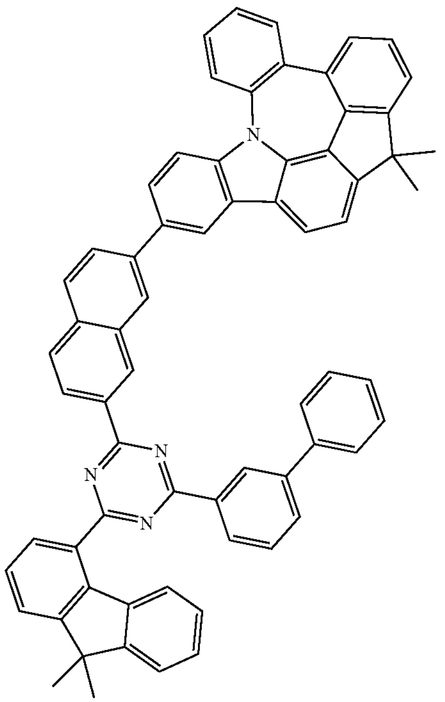
54
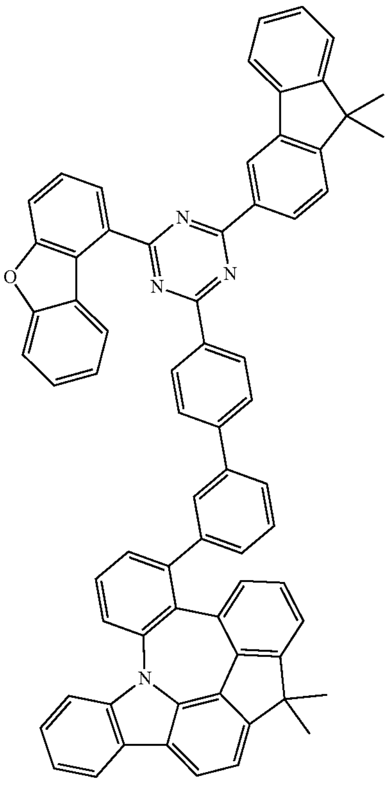
55
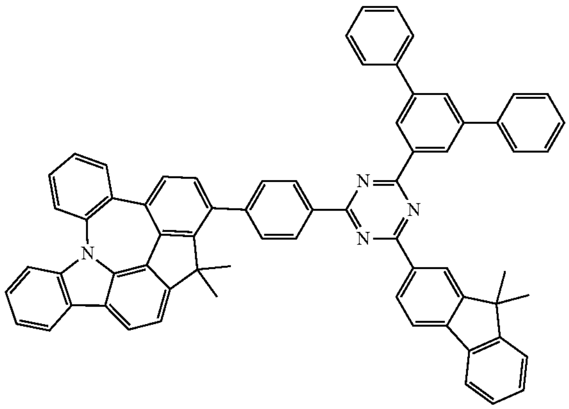

-continued
56
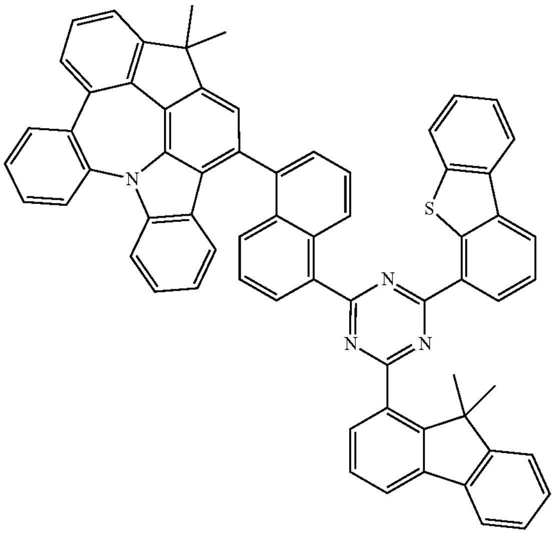
57
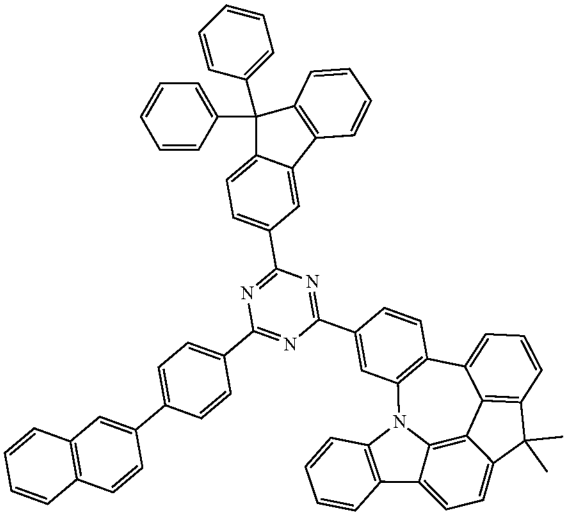
58
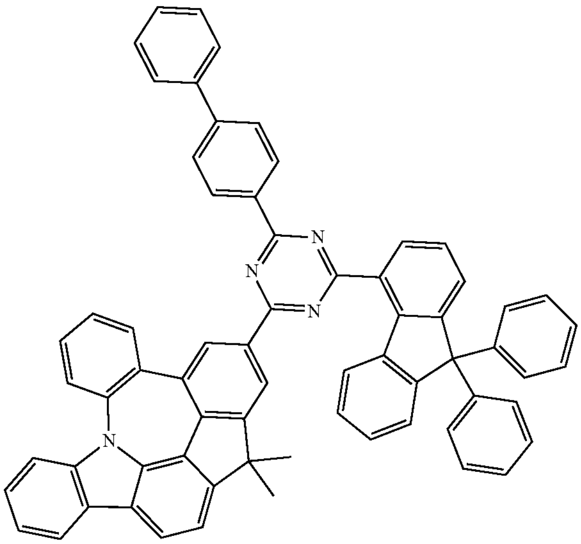
59
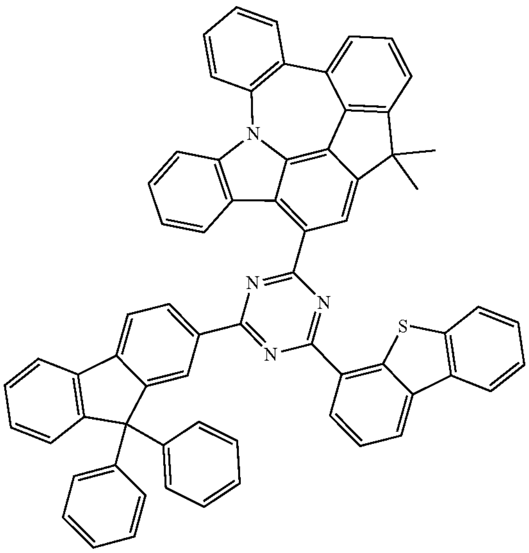

-continued
60
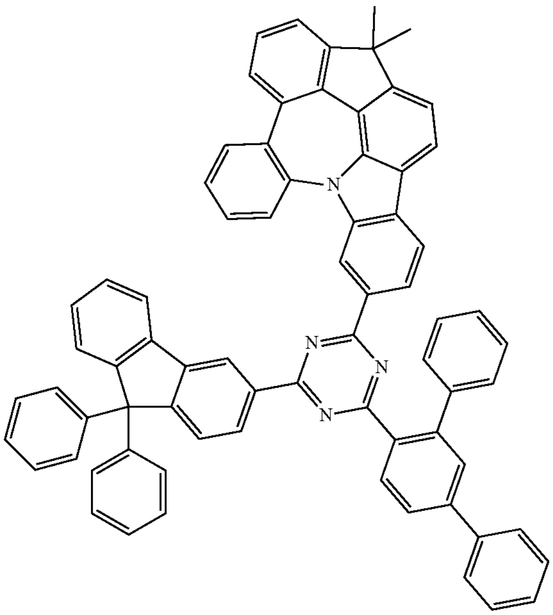
61
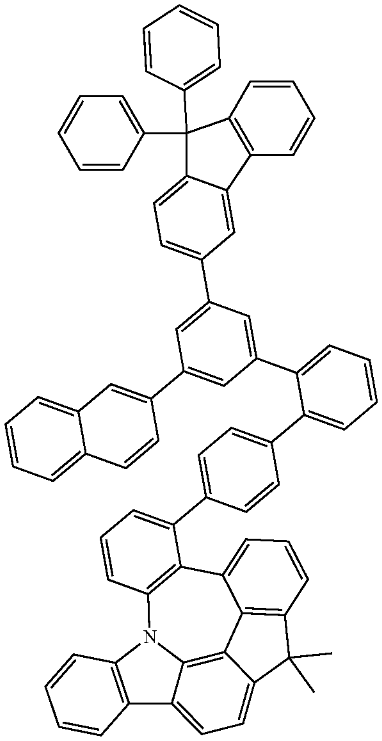
62
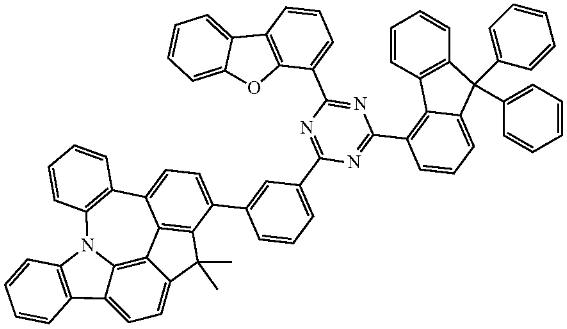
63
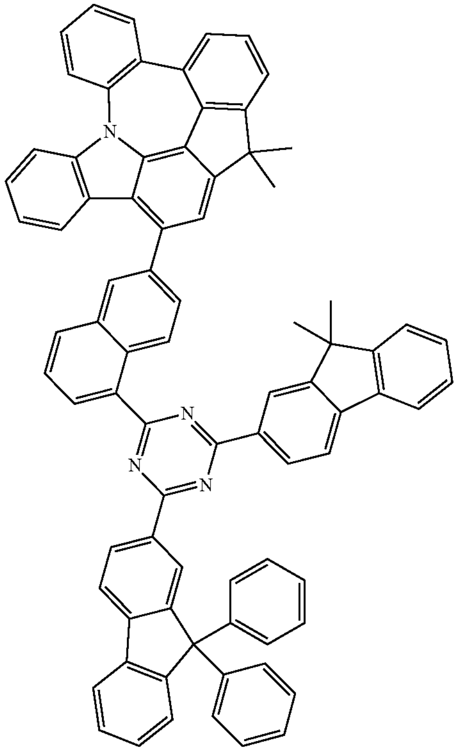

-continued
64
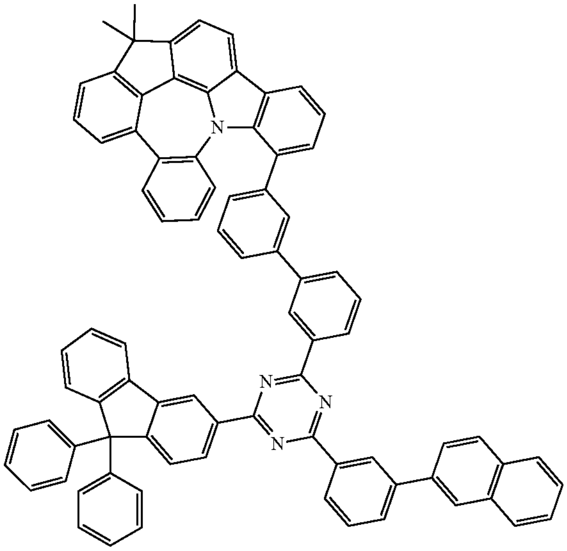
65
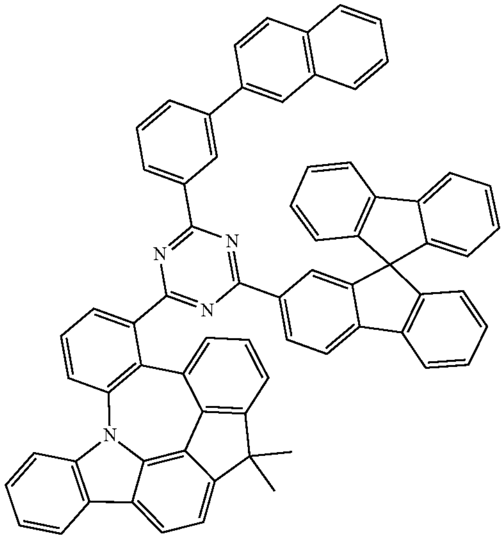
66
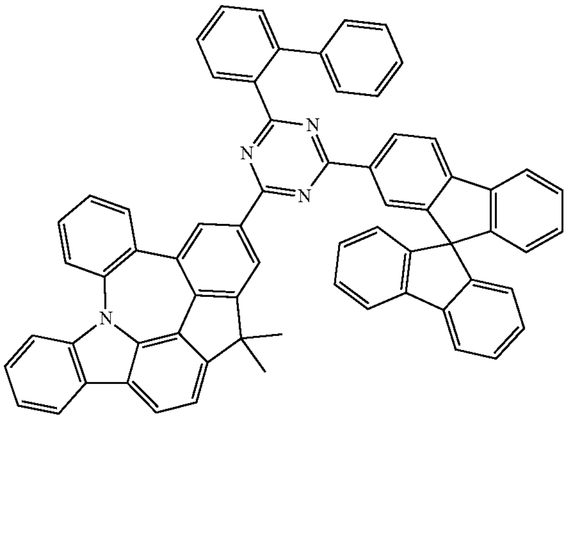
67
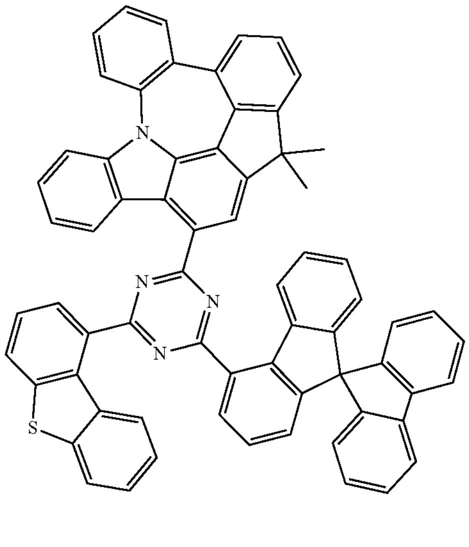

-continued
68
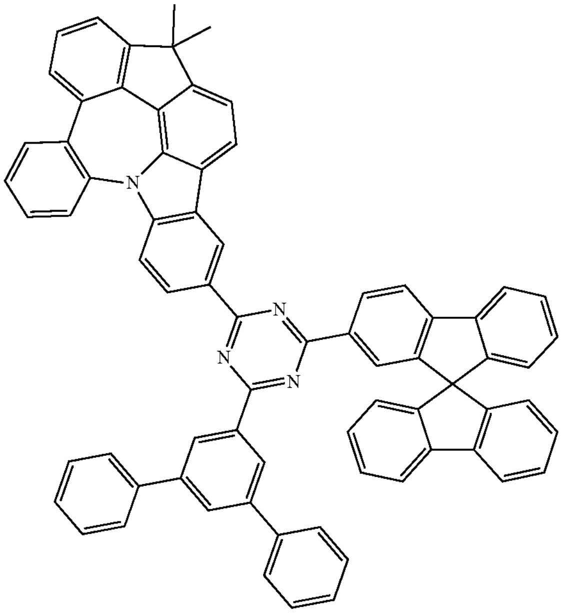
69
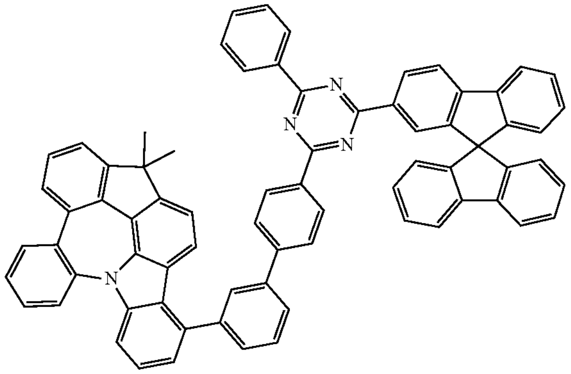
70
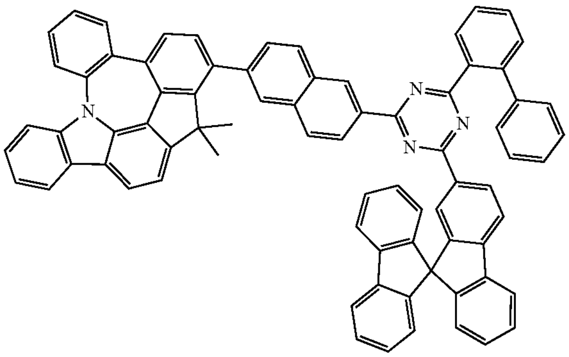
71
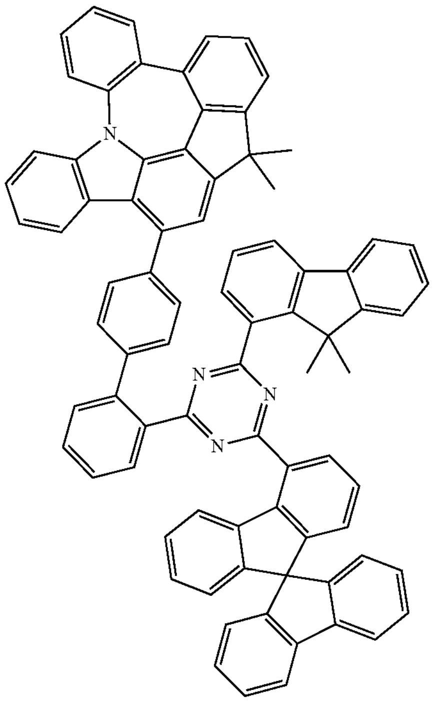

-continued
72
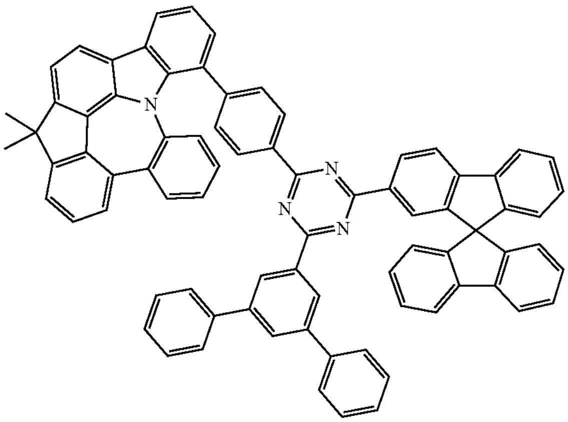
73
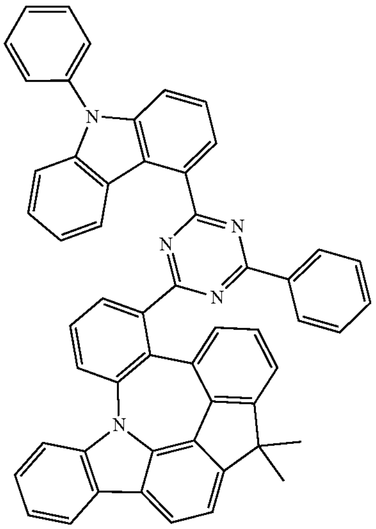
74
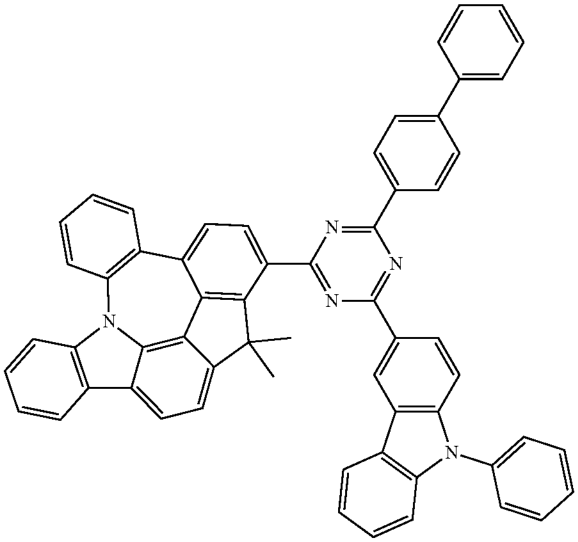
75
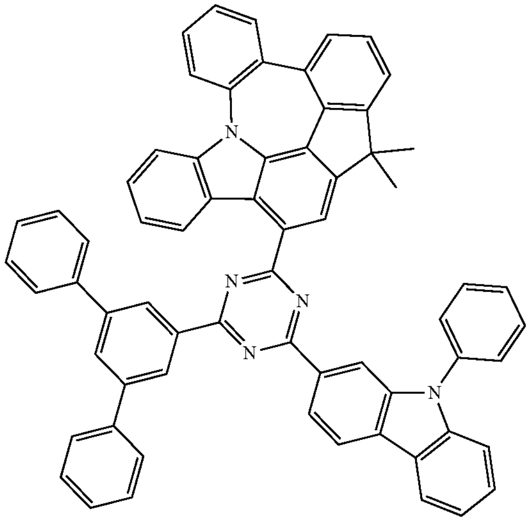

-continued
76
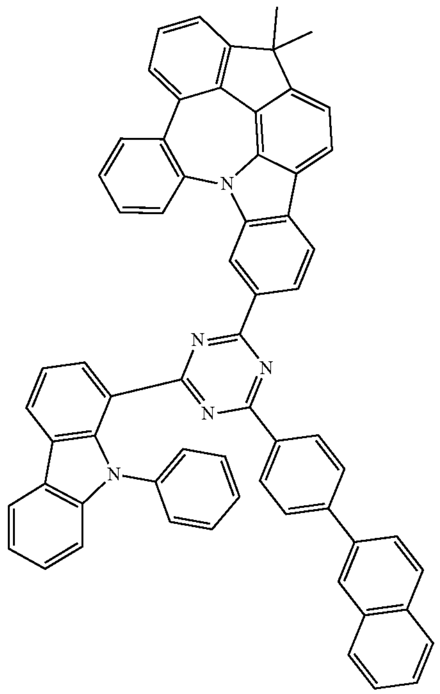
77
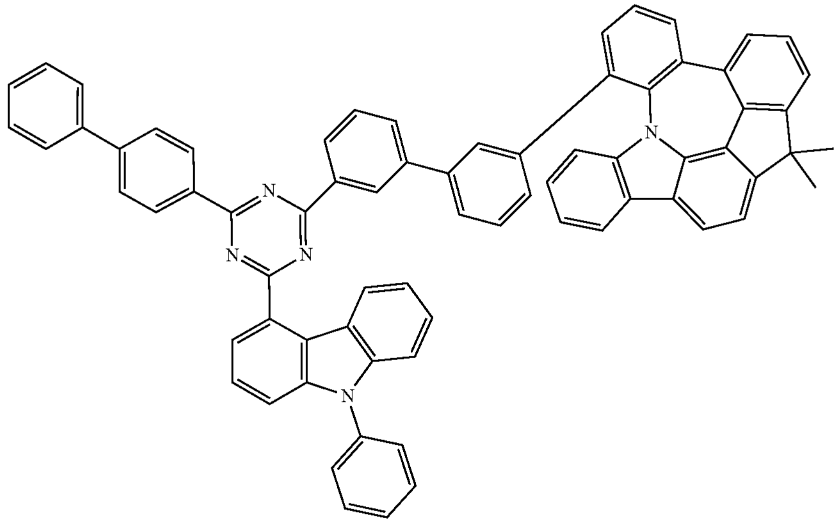

-continued
78
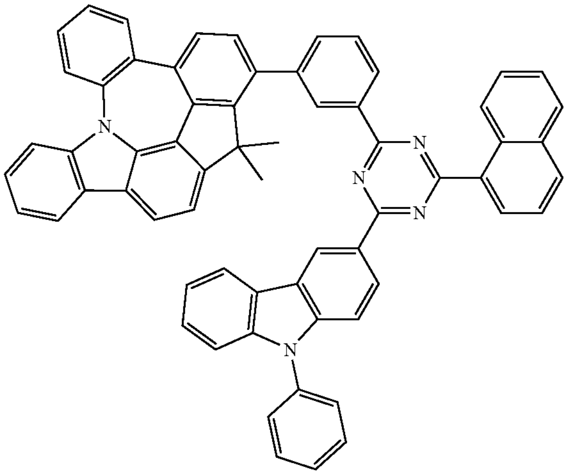
79
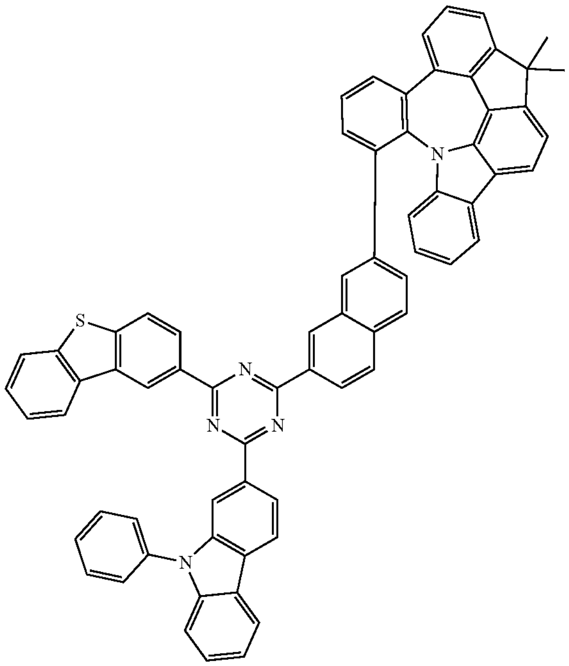
80
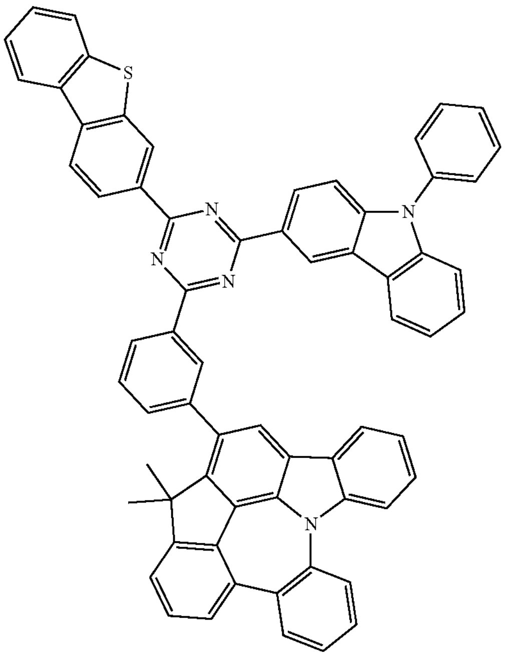

-continued
81
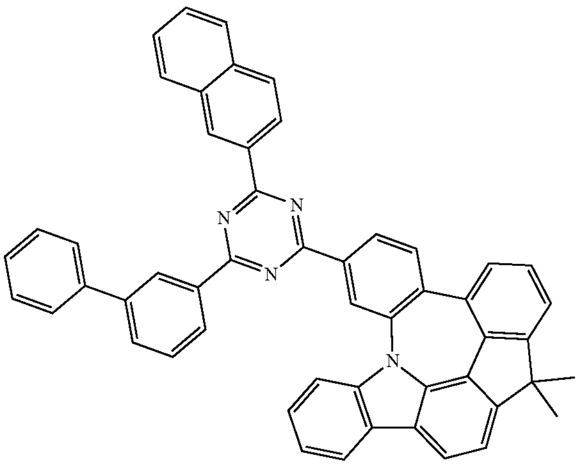
82
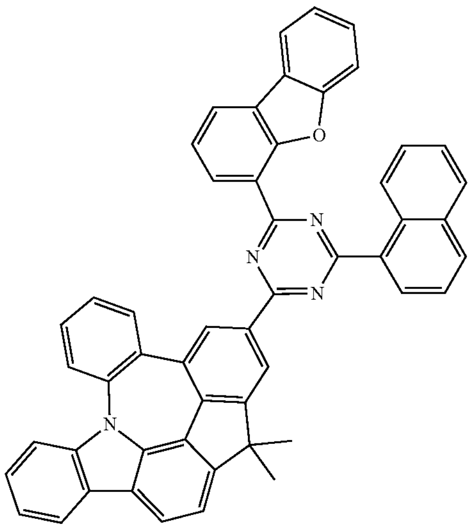
83
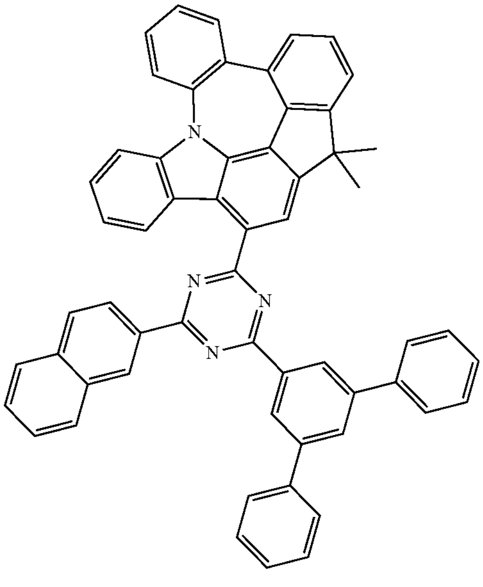
84
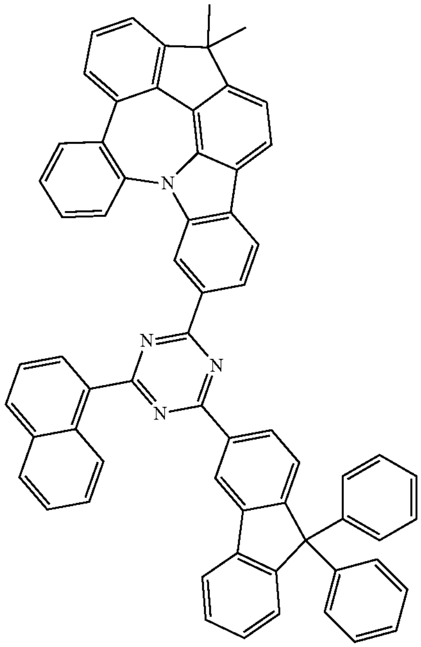

-continued
85
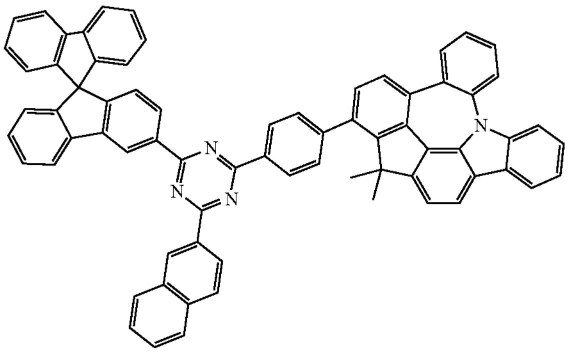
86
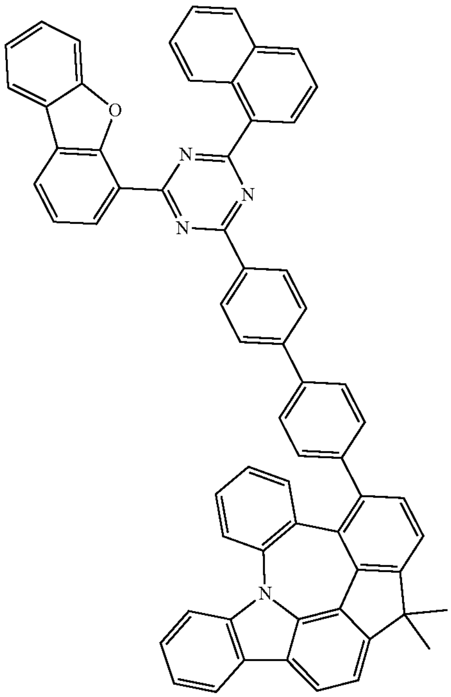
87
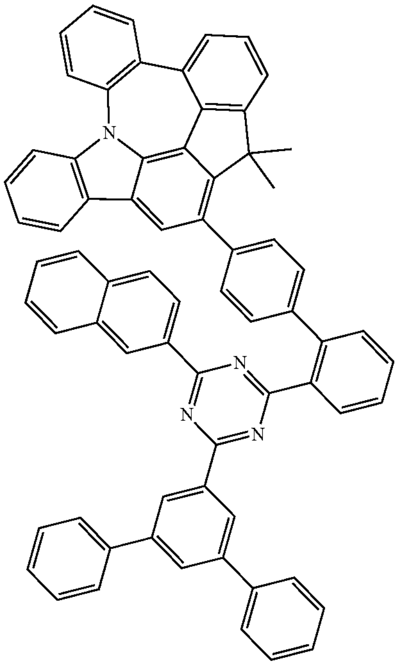
88
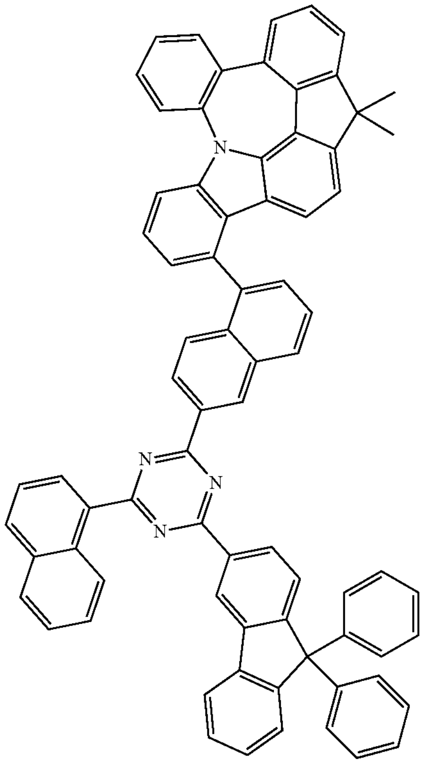

-continued
168
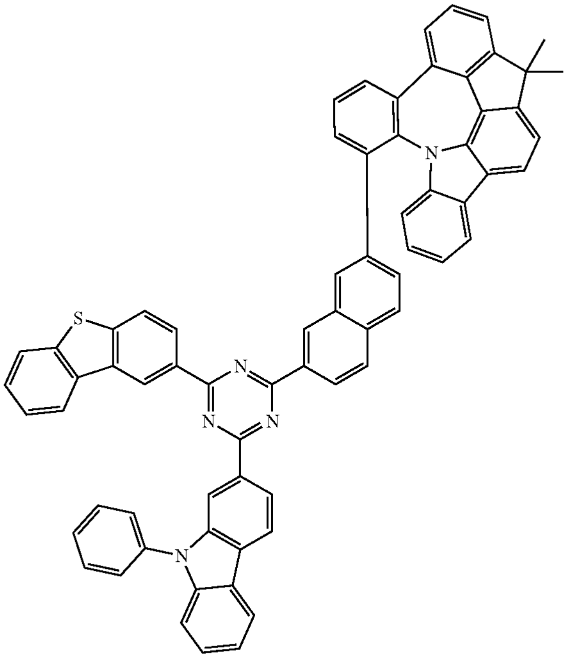
173
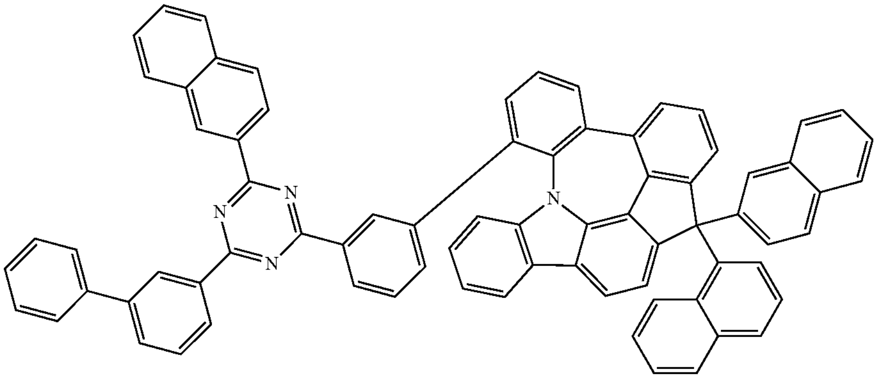

-continued
174
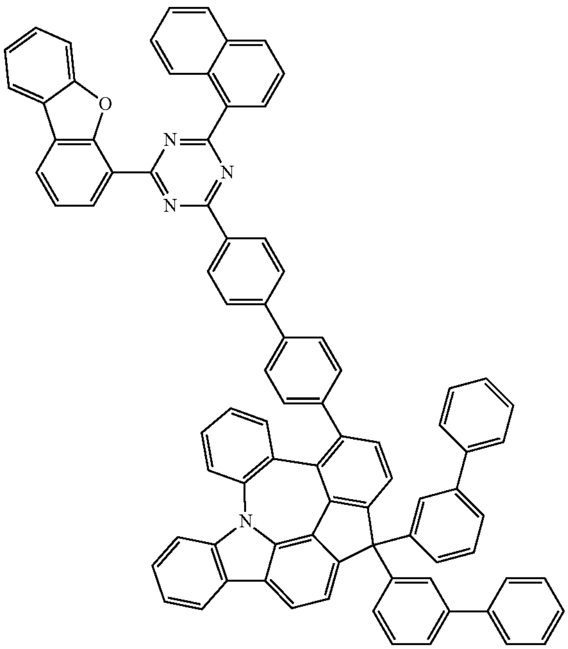
175
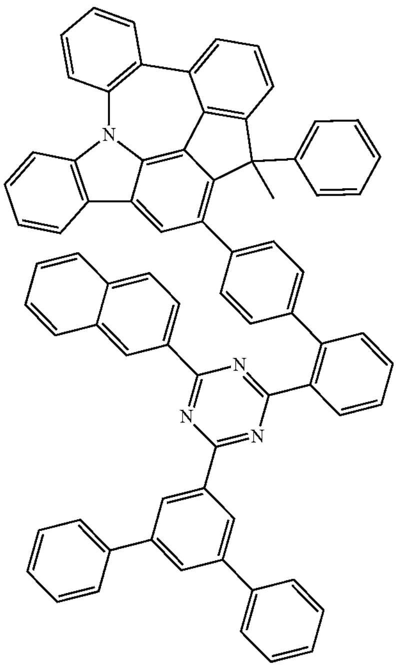
176
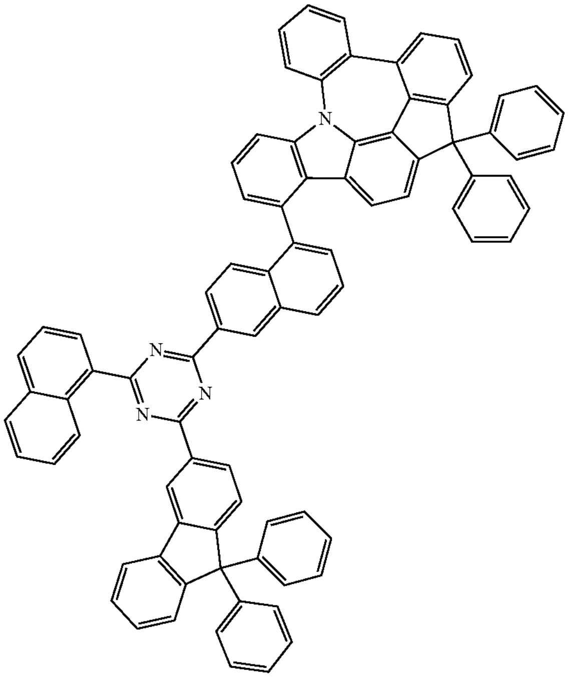

-continued
185
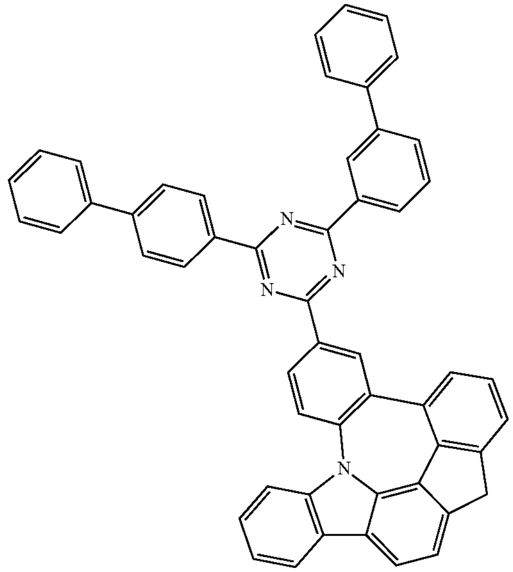
197
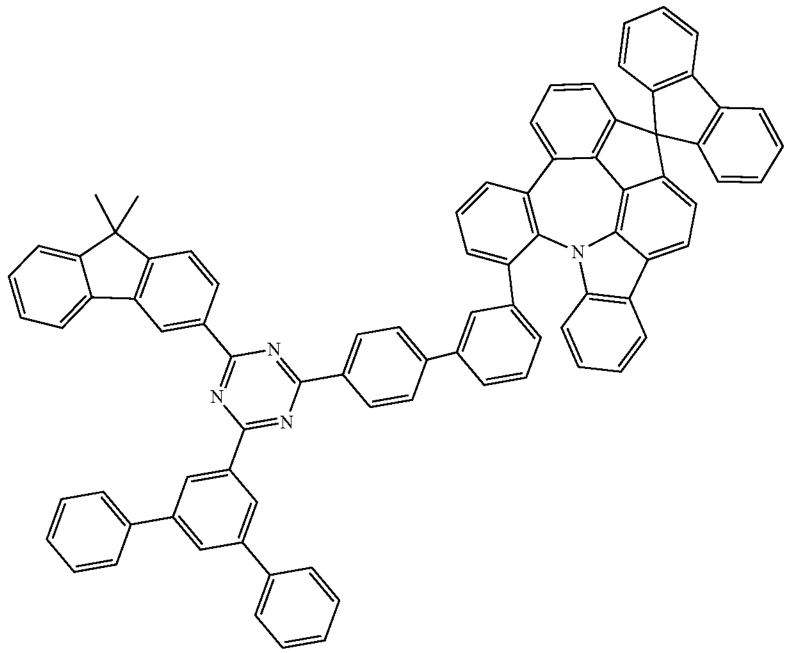

-continued
198
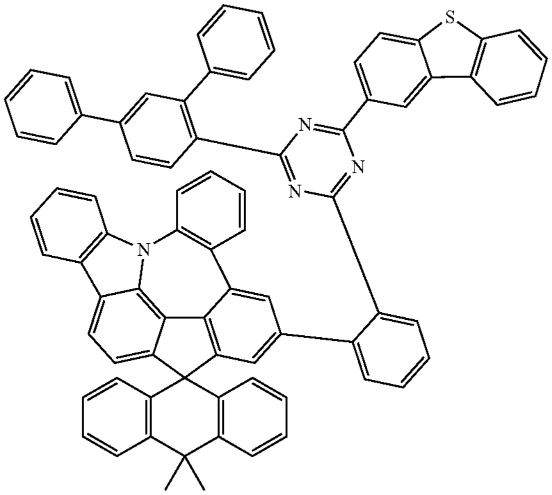
199
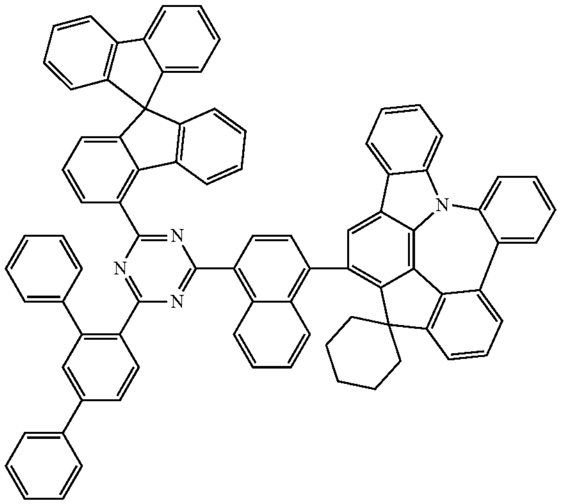
200
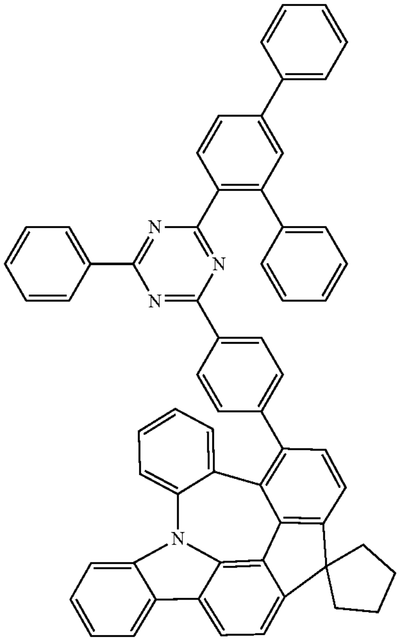
249
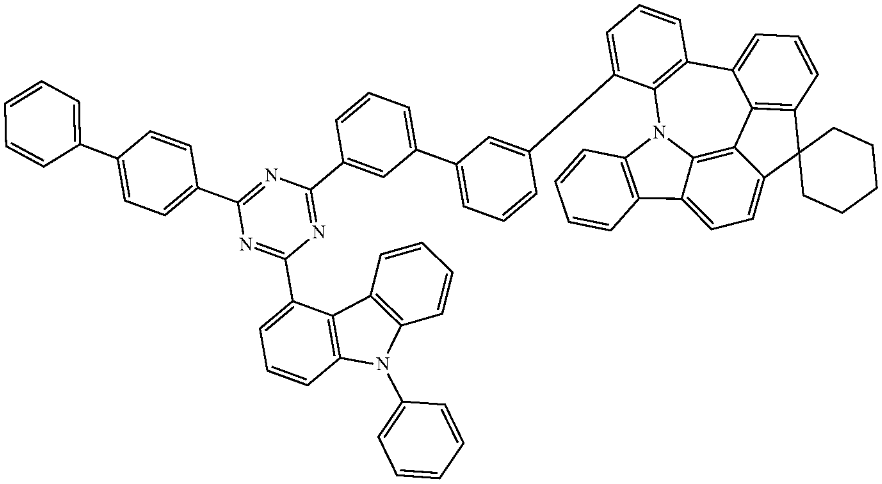

-continued
250
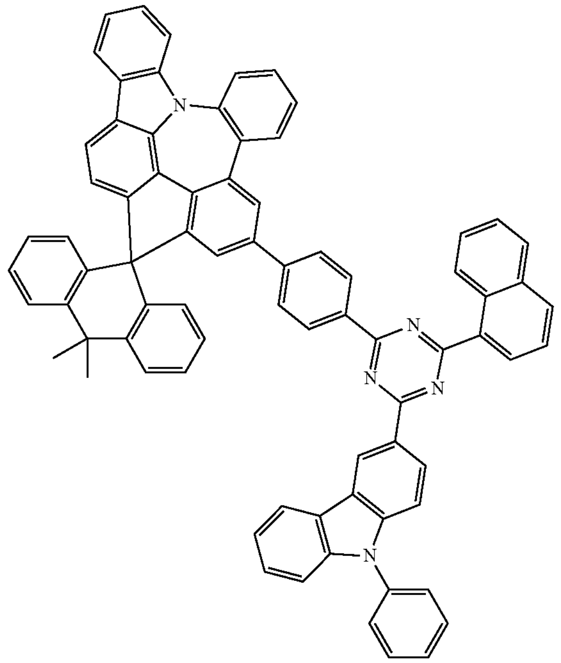
251
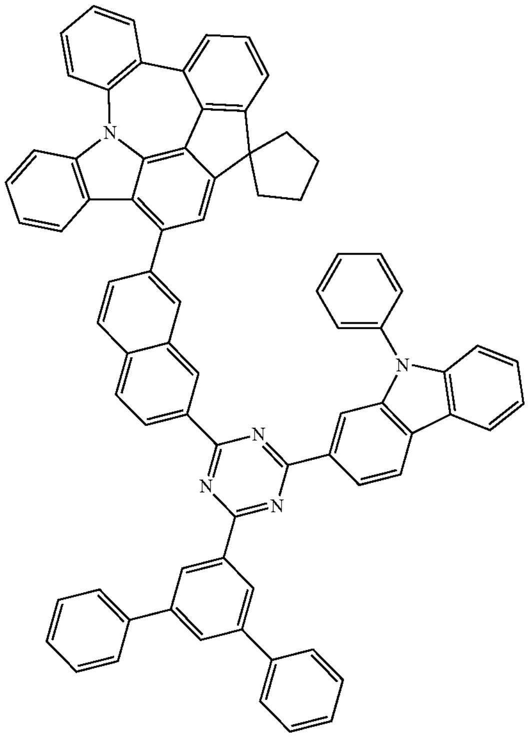
252
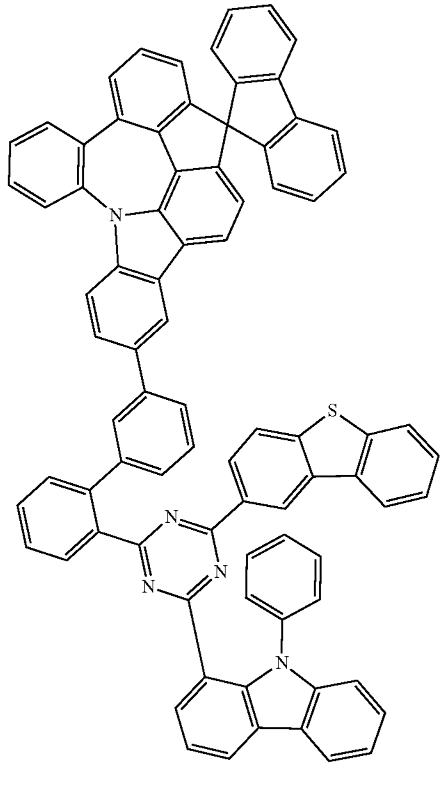

-continued
305
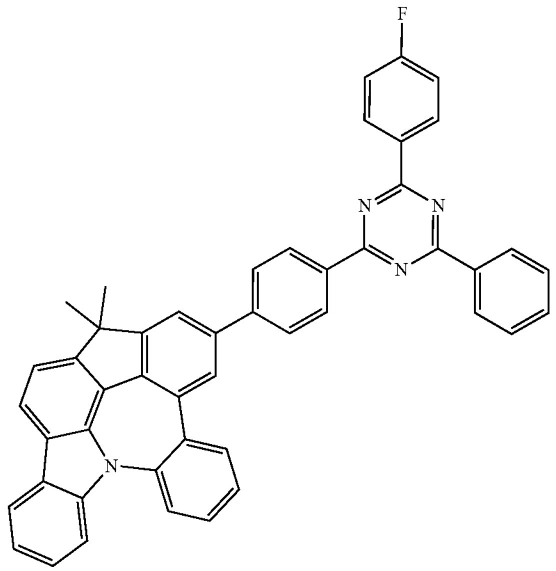
306
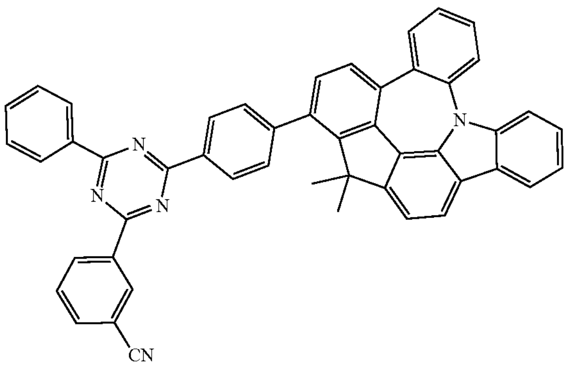
307
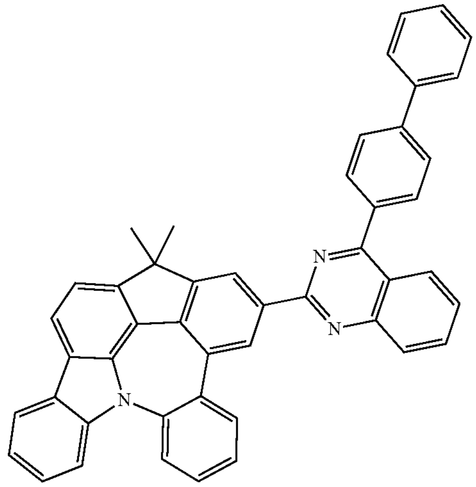
308
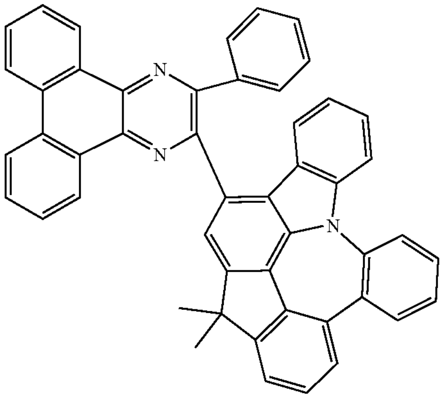
309
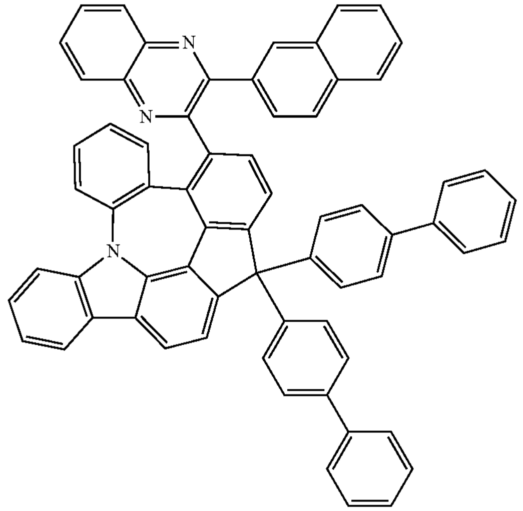
310
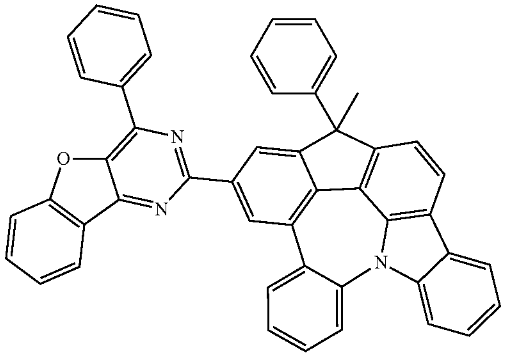

-continued
311
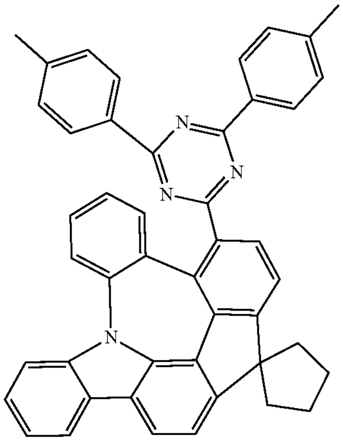
312
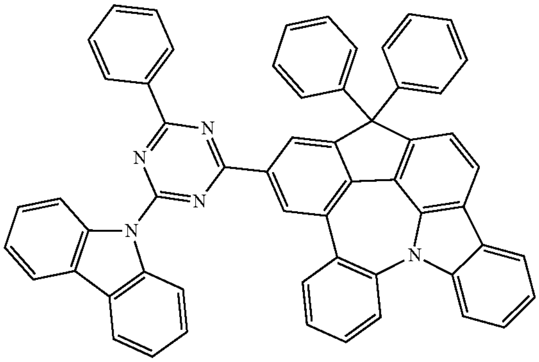
313
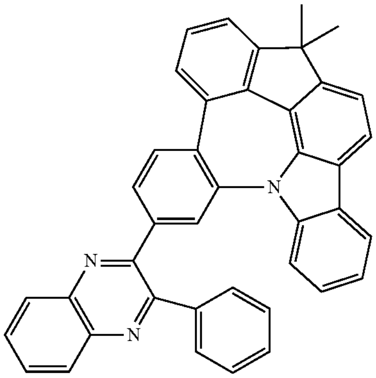
314
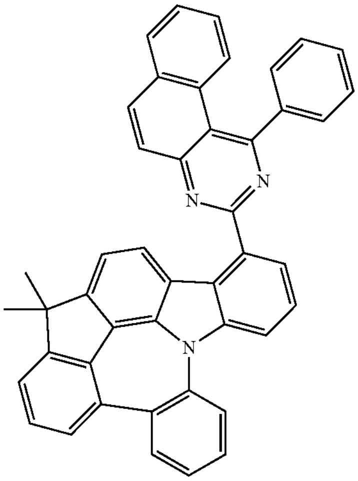
315
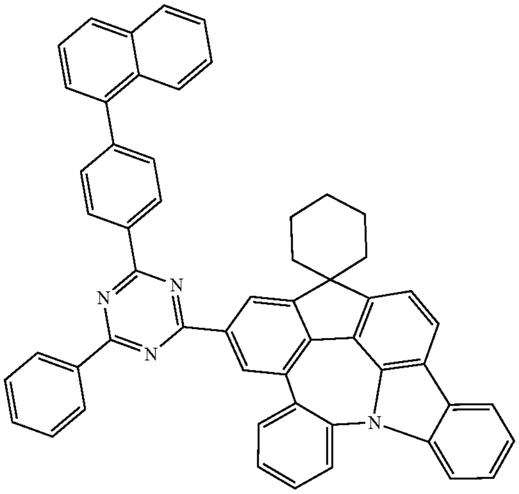
316
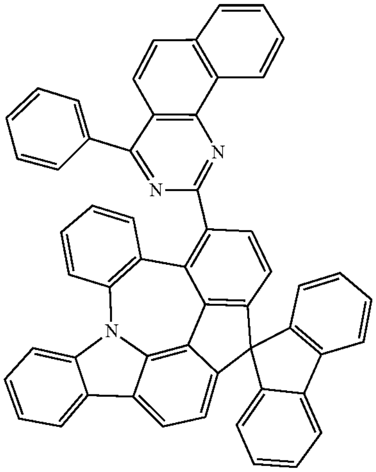

-continued
317
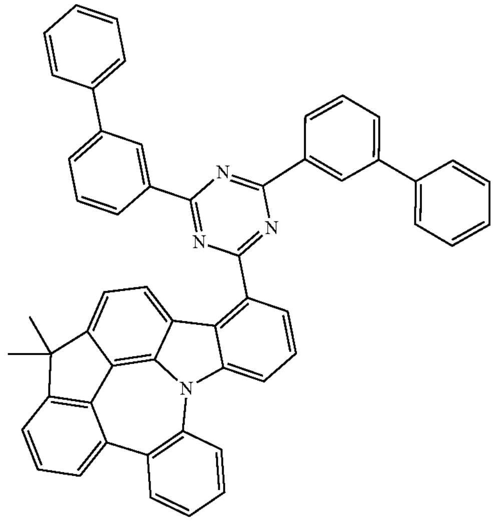
318
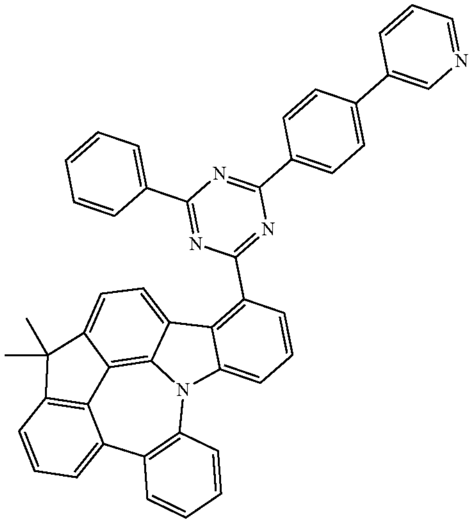
319
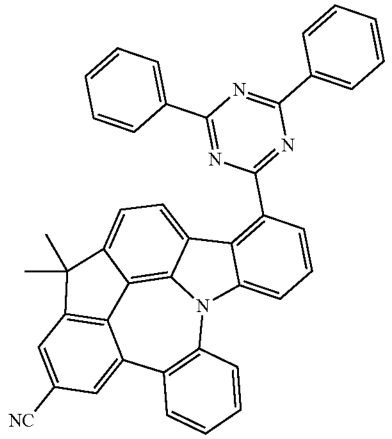
320
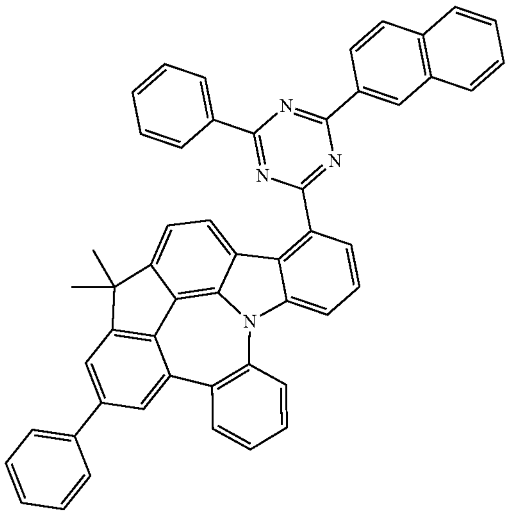
321
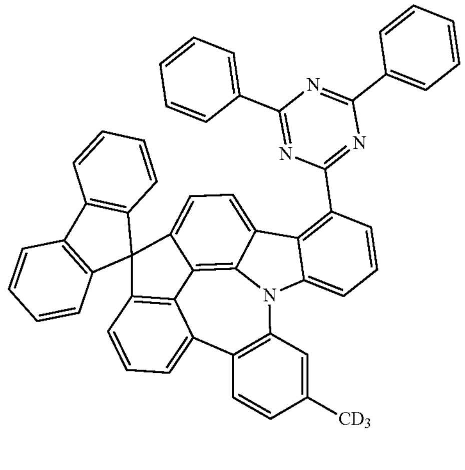
322
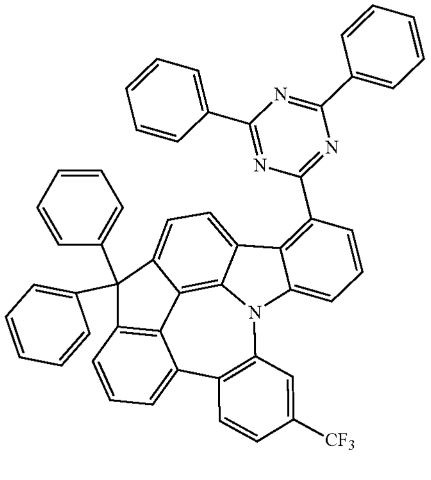

-continued

323

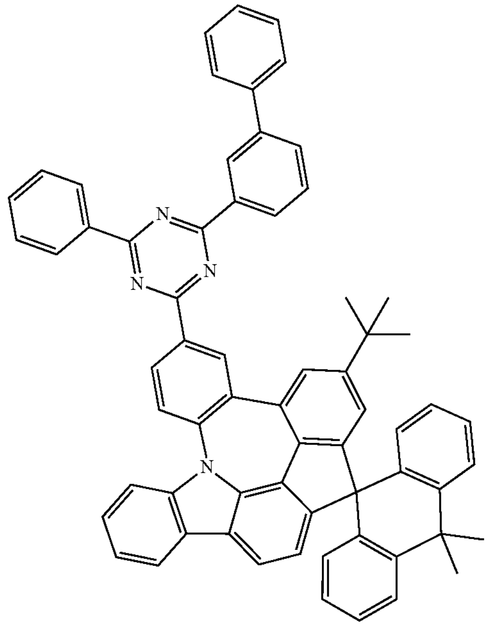

324

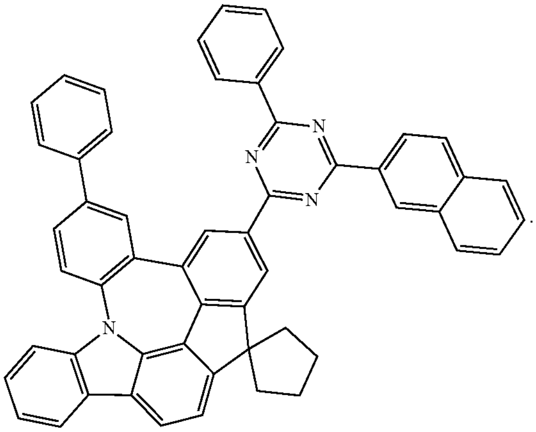

15. An organic light-emitting device (OLED), comprising: an anode and a cathode that are arranged oppositely, and a functional layer arranged between the anode and the cathode, wherein the functional layer comprises the organic compound according to claim 1; and optionally, the functional layer comprises an electron transport layer (ETL) and/or a light-emitting layer, and the ETL and/or the light-emitting layer comprises the organic compound.

16. An electronic apparatus comprising the OLED according to claim 15.

* * * * *